United States Patent
Suzuki et al.

(10) Patent No.: US 11,896,634 B2
(45) Date of Patent: *Feb. 13, 2024

(54) ONCOLYTIC VIROTHERAPY WITH HELPER-DEPENDENT ADENOVIRAL-BASED VECTORS EXPRESSING IMMUNOMODULATORY MOLECULES

(71) Applicant: Baylor College of Medicine, Houston, TX (US)

(72) Inventors: Masataka Suzuki, Houston, TX (US); Amanda Rosewell Shaw, Pearland, TX (US); Caroline Elaine Porter, Houston, TX (US); Norihiro Watanabe, Houston, TX (US); Malcolm K. Brenner, Bellaire, TX (US)

(73) Assignee: Baylor College Of Medicine, Houston, TX (US)

( * ) Notice: Subject to any disclaimer, the term of this patent is extended or adjusted under 35 U.S.C. 154(b) by 1018 days.

This patent is subject to a terminal disclaimer.

(21) Appl. No.: 16/607,066

(22) PCT Filed: Apr. 20, 2018

(86) PCT No.: PCT/US2018/028577
§ 371 (c)(1),
(2) Date: Oct. 21, 2019

(87) PCT Pub. No.: WO2018/195427
PCT Pub. Date: Oct. 25, 2018

(65) Prior Publication Data
US 2020/0323932 A1 Oct. 15, 2020

Related U.S. Application Data

(60) Provisional application No. 62/488,181, filed on Apr. 21, 2017.

(51) Int. Cl.
| | | |
|---|---|---|
| *A61P 35/00* | (2006.01) | |
| *A61K 35/761* | (2015.01) | |
| *A61K 38/20* | (2006.01) | |
| *A61K 39/395* | (2006.01) | |
| *A61K 38/16* | (2006.01) | |
| *C12N 15/86* | (2006.01) | |
| *A61K 35/17* | (2015.01) | |
| *A61K 38/43* | (2006.01) | |
| *A61K 38/17* | (2006.01) | |
| *C12N 15/861* | (2006.01) | |
| *C07K 14/54* | (2006.01) | |
| *C07K 16/28* | (2006.01) | |
| *C07K 16/32* | (2006.01) | |
| *C07K 14/705* | (2006.01) | |
| *C07K 14/725* | (2006.01) | |

(52) U.S. Cl.
CPC ............ *A61K 35/761* (2013.01); *A61K 35/17* (2013.01); *A61K 38/1774* (2013.01); *A61K 38/208* (2013.01); *A61K 38/43* (2013.01); *A61K 39/3955* (2013.01); *A61P 35/00* (2018.01); *C12N 15/861* (2013.01); *C07K 14/5434* (2013.01); *C07K 14/7051* (2013.01); *C07K 14/70521* (2013.01); *C07K 16/2818* (2013.01); *C07K 16/32* (2013.01); *C07K 2317/24* (2013.01); *C07K 2317/565* (2013.01); *C07K 2317/622* (2013.01); *C07K 2317/73* (2013.01); *C07K 2319/03* (2013.01); *C07K 2319/33* (2013.01); *C12N 15/86* (2013.01); *C12N 2710/10343* (2013.01)

(58) Field of Classification Search
CPC .................. A61K 35/76; A61K 35/761; A61K 39/39558; C07K 16/32
See application file for complete search history.

(56) References Cited

U.S. PATENT DOCUMENTS

| | | | |
|---|---|---|---|
| 5,919,676 A | 7/1999 | Graham et al. | |
| 6,080,569 A | 6/2000 | Graham et al. | |
| 6,566,128 B1 | 5/2003 | Graham et al. | |
| 6,730,507 B1 | 5/2004 | Graham et al. | |
| 7,045,347 B2 | 5/2006 | Graham et al. | |
| 10,716,818 B2 * | 7/2020 | Suzuki .................. | A61K 35/17 |
| 2003/0073072 A1 | 4/2003 | Havenga et al. | |
| 2006/0275262 A1 | 12/2006 | Mathis et al. | |

(Continued)

FOREIGN PATENT DOCUMENTS

| | | |
|---|---|---|
| CN | 106831986 A | 6/2017 |
| CN | 106831987 A | 6/2017 |

(Continued)

OTHER PUBLICATIONS

Wang et al, 2014. Blood blood. 124(21): 5808.*
Yu et al (2017. Exp Hematol Oncol. 6:31; 15 pages as printed).*
Koneru et al., IL-12 secreting tumor-targeted chimeric antigen receptor T cells eradicate ovarian tumors in vivo. Oncoimmunology. Jan. 23, 2015;4(3):e994446. doi: 10.4161/2162402X.2014.994446. eCollection Mar. 2015.
International Search Report and Written Opinion for Application No. PCT/US2018/028577, dated Jan. 28, 2019.
International Preliminary Report on Patentability for Application No. PCT/US2018/028577, dated Oct. 31, 2019.

(Continued)

*Primary Examiner* — Zachary C Howard
(74) *Attorney, Agent, or Firm* — Wolf, Greenfield & Sacks, P.C.

(57) ABSTRACT

The present disclosure concerns combination therapy for cancer that utilizes (i) an oncolytic virus; (ii) a virus comprising nucleic acid encoding an immunomodulatory factor; and (iii) at least one cell comprising a chimeric antigen receptor (CAR) specific for a cancer cell antigen. In particular embodiments, the virus comprises nucleic acid encoding an immunomodulatory factor comprises nucleic acid encoding IL-12 and/or antagonist anti-PD-L1 antibody.

13 Claims, 44 Drawing Sheets

Specification includes a Sequence Listing.

(56) References Cited

U.S. PATENT DOCUMENTS

| | | |
|---|---|---|
| 2007/0059287 A1 | 3/2007 | Yun et al. |
| 2015/0232811 A1 | 8/2015 | Ranki et al. |
| 2019/0374589 A1 | 12/2019 | Suzuki et al. |

FOREIGN PATENT DOCUMENTS

| | | |
|---|---|---|
| WO | WO 1994/018992 A1 | 1/1994 |
| WO | WO 1995/000655 A1 | 1/1995 |
| WO | WO 1998/013508 A1 | 4/1998 |
| WO | WO 2005/086922 A2 | 9/2005 |
| WO | WO 2010/072900 A1 | 7/2010 |
| WO | WO 2012/038606 A1 | 3/2012 |
| WO | WO 2012/038607 A1 | 3/2012 |
| WO | WO 2013/114199 A1 | 8/2013 |
| WO | WO 2014/115022 A1 | 7/2014 |
| WO | WO 2014/153204 A1 | 9/2014 |

OTHER PUBLICATIONS

Ajina et al., Prospects for combined use of oncolytic viruses and CAR T-cells. J Immunother Cancer. Nov. 21, 2017;5(1):90. doi:10.1186/s40425-017-0294-6.

Attwood, Genomics. The Babel of bioinformatics. Science. Oct. 20, 2000;290(5491):471-3.

Baker, Protein structure prediction and structural genomics. Science. Oct. 5, 2001;294(5540):93-6.

Barker et al., Adenovirus proteins from both E1B reading frames are required for transformation of rodent cells by viral infection and DNA transfection. Virology. Jan. 1987;156(1):107-21. Erratum in: Virology May 1987;158(1):263.

Butte et al., Programmed death-1 ligand 1 interacts specifically with the B7-1 costimulatory molecule to inhibit T cell responses. Immunity. Jul. 2007;27(1):111-22. Epub Jul. 12, 2007.

Chiocca et al., Oncolytic viruses and their application to cancer immunotherapy. Cancer Immunol Res. Apr. 2014;2(4):295-300. doi:10.1158/2326-6066.CIR-14-0015. Review. Erratum in: Cancer Immunol Res. Jul. 2014;2(7):699.

Economopoulou et al., The emerging role of immunotherapy in head and neck squamous cell carcinoma (HNSCC): anti-tumor immunity and clinical applications. Ann Transl Med. May 2016;4(9):173. doi:10.21037/atm.2016.03.34.

Farzad et al., Combinatorial treatment with oncolytic adenovirus and helper-dependent adenovirus augments adenoviral cancer gene therapy. Mol Ther Oncolytics. Dec. 17, 2014;1:14008. doi: 10.1038/mto.2014.8. eCollection 2014.

Fueyo et al., A mutant oncolytic adenovirus targeting the Rb pathway produces anti-glioma effect in vivo. Oncogene. Jan. 6, 2000;19(1):2-12. Erratum in: Oncogene Oct. 12, 2000;19(43):5038.

Gottschalk et al., Harnessing the immune system to potentiate oncolytics. Mol Ther. Feb. 2014;22(2):239-240. doi: 10.1038/mt.2013.295.

Lee et al., Enhanced antitumor effect of oncolytic adenovirus expressing interleukin-12 and B7-1 in an immunocompetent murine model. Clin Cancer Res. Oct. 1, 2006;12(19):5859-68.

Malekshah et al., Enzyme/Prodrug Systems for Cancer Gene Therapy. Curr Pharmacol Rep. Dec. 2016;2(6):299-308. doi: 10.1007/s40495-016-0073-y. Epub Oct. 19, 2016.

Morgenstern, Combining Oncolytic Adenovirus (OncAd) with Tumor Directed, Adenovirus-specific T-cells for the Treatment of Neuroblastoma: Effects of OncAds on Immunosuppressive Myeloid Cells. 2016. Retrieved from https://www.alexslemonade.org/grantee/ari-morgenstern on Aug. 21, 2018.

Nishino et al., Adenovirus-mediated gene therapy specific for small cell lung cancer cells using a Myc-Max binding motif. Int J Cancer. Mar. 15, 2001;91(6):851-6.

Nishio et al., Armed oncolytic virus enhances immune functions of chimeric antigen receptor-modified T cells in solid tumors. Cancer Res. Sep. 15, 2014;74(18):5195-205. doi: 10.1158/0008-5472.CAN-14-0697. Epub Jul. 24, 2014.

Rojas et al., Minimal RB-responsive E1A promoter modification to attain potency, selectivity, and transgene-arming capacity in oncolytic adenoviruses. Mol Ther. Nov. 2010;18(11):1960-71. doi: 10.1038/mt.2010.173. Epub Aug. 31, 2010.

Rosewell Shaw et al., Adenovirotherapy Delivering Cytokine and Checkpoint Inhibitor Augments CAR T Cells against Metastatic Head and Neck Cancer. Mol Ther. Nov. 1, 2017;25(11):2440-2451. doi: 10.1016/j.ymthe.2017.09.010. Epub Sep. 14, 2017.

Rosewell Shaw et al., Armed-Ad Gene Therapy Expressing PDL1 Minibody Enhances the Anti-Tumor Effect of Adoptively Transferred Chimeric Antigen Receptor T-Cells for Solid Tumor Treatment. Mol. Ther. May 2016;24(1):S204-S205.

Rosewell Shaw et al., Combinatorial Treatment of "armed" oncolytic adenovirus expressing checkpoint inhibitor and cytokine with chimeric antigen receptor t-cells leads to superior anti-tumor effects inhead and neck cancer. Mol Ther. May 2017;25(5S1):6-7. Abstract 12.

Sun et al., Early transduction produces highly functional chimeric antigen receptor-modified virus-specific T-cells with central memory markers: a Production Assistant for Cell Therapy (PACT) translational application. J Immunother Cancer. Feb. 18, 2015;3:5. doi: 10.1186/s40425-015-0049-1. eCollection 2015.

Tanaka et al., Vaccination Targeting Native Receptors to Enhance the Function and Proliferation of Chimeric Antigen Receptor (CAR)-Modified T Cells. Clin Cancer Res. Jul. 15, 2017;23(14):3499-3509. doi: 10.1158/1078-0432.CCR-16-2138. Epub Feb. 9, 2017.

Tanque et al., Armed Oncolytic Adenovirus-Expressing PD-L1 Mini-Body Enhances Antitumor Effects of Chimeric Antigen Receptor T Cells in Solid Tumors. Cancer Res. Apr. 15, 2017;77(8):2040-2051. doi: 10.1158/0008-5472.CAN-16-1577. Epub Feb. 24, 2017.

Waknine, International Approvals: Procoralan, H101, AP2573. Nov. 21, 2005. Medscape Medical News. Retrieved from http://www.medscape.com/viewarticle/517543_print on Dec. 4, 2017.

Abate-Daga et al., CAR models: next-generation CAR modifications for enhanced T-cell function. Mol Ther Oncolytics. May 18, 2016;3:16014. doi: 10.1038/mto.2016.14. eCollection 2016.

Ji et al., Oncolytic adenovirus delivering herpes simplex virus thymidine kinase suicide gene reduces the growth of human retinoblastoma in an in vivo mouse model. Exp Eye Res. Aug. 2009;89(2):193-9. doi: 10.1016/j.exer.2009.03.007. Epub Mar. 27, 2009.

Shaw et al., Recent advances in oncolytic adenovirus therapies for cancer. Curr Opin Virol. Dec. 2016;21:9-15. doi: 10.1016/j.coviro.2016.06.009. Epub Jul. 2, 2016.

\* cited by examiner

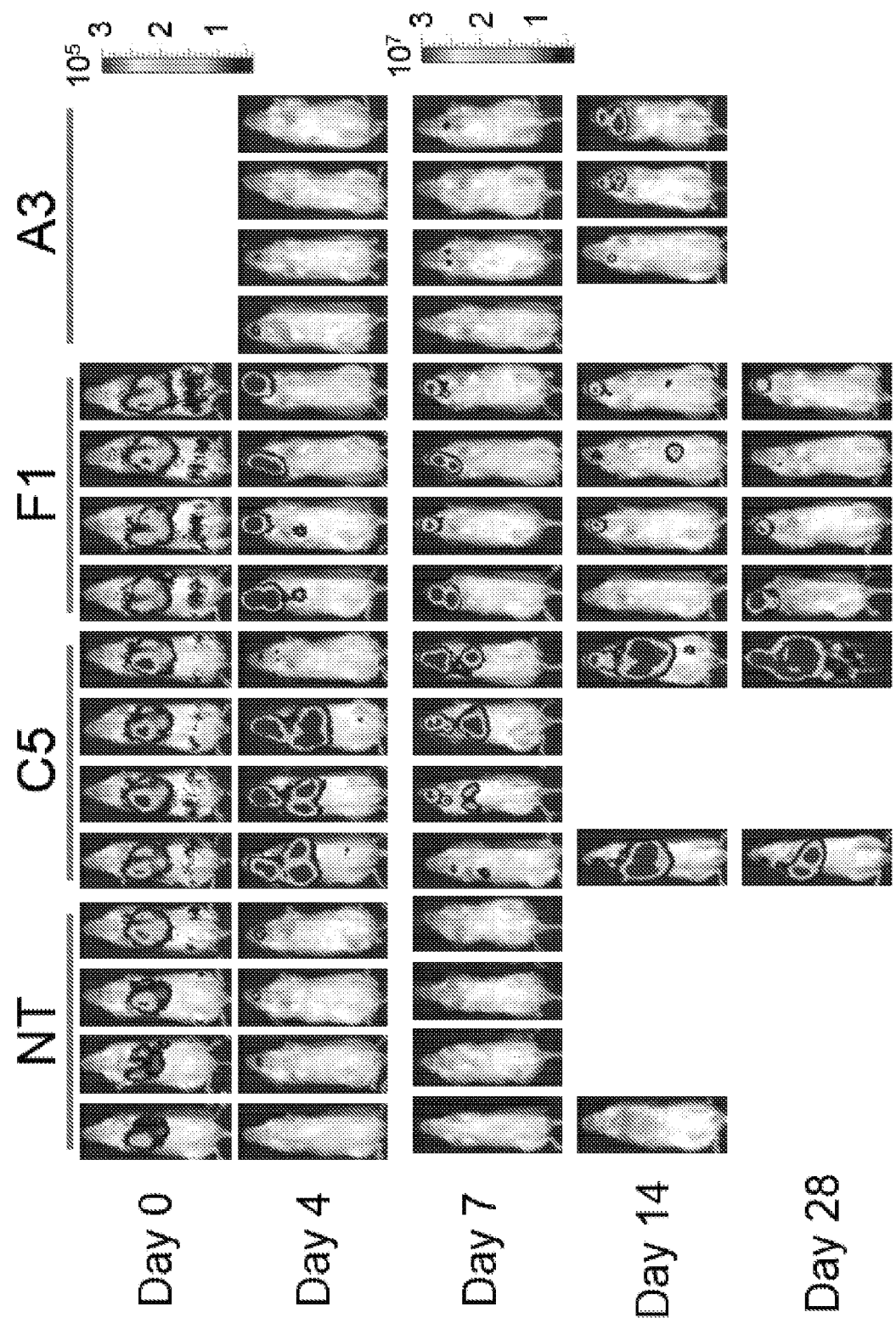

SEQUENCE LISTING

<160> NUMBER OF SEQ ID NOS: 64

<210> SEQ ID NO 1
<211> LENGTH: 469
<212> TYPE: PRT
<213> ORGANISM: Artificial Sequence
<220> FEATURE:
<223> OTHER INFORMATION: HER2(C5)-CD28TM,ICD-CD3Z CAR

<400> SEQUENCE: 1

Met Thr Arg Ala Met Asp Trp Ile Trp Arg Ile Leu Phe Leu Val Gly
1               5                   10                  15

Ala Ala Thr Gly Ala His Ser Gln Val Gln Leu Gln Glu Ser Gly Pro
            20                  25                  30

Gly Leu Val Lys Pro Ser Glu Thr Leu Ser Leu Thr Cys Thr Val Ser
        35                  40                  45

Gly Gly Ser Ile Ser Ser Ser Ser Tyr Tyr Trp Gly Trp Ile Arg Gln
    50                  55                  60

Pro Pro Gly Lys Gly Leu Glu Trp Ile Gly Ser Ile Tyr Tyr Ser Gly
65                  70                  75                  80

Ser Thr Tyr Tyr Asn Pro Ser Leu Lys Ser Arg Val Thr Ile Ser Val
                85                  90                  95

Asp Thr Ser Lys Asn Gln Phe Ser Leu Lys Leu Ser Ser Val Thr Ala
            100                 105                 110

Ala Asp Thr Ala Val Tyr Tyr Cys Ala Arg Tyr Ala Pro Asp Ser Ser
        115                 120                 125

Gly Tyr Leu Val Ala Phe Asp Ile Trp Gly Gln Gly Thr Met Val Thr
    130                 135                 140

Val Ser Ser Gly Gly Gly Gly Ser Gly Gly Gly Gly Ser Gly Gly Gly
145                 150                 155                 160

Gly Ser Gln Thr Val Val Thr Gln Glu Pro Ser Phe Ser Val Ser Pro
                165                 170                 175

Gly Gly Thr Val Thr Leu Thr Cys Gly Leu Ser Ser Gly Ser Val Ser
            180                 185                 190

Thr Gly Tyr Tyr Pro Ser Trp Tyr Gln Gln Thr Pro Gly Gln Ala Pro

```
                195                 200                 205
Arg Thr Leu Ile Tyr Ser Thr Asn Ser Arg Ser Ser Gly Val Pro Asp
    210                 215                 220

Arg Phe Ser Gly Ser Ile Leu Gly Asn Lys Ala Ala Leu Thr Ile Thr
225                 230                 235                 240

Gly Ala Gln Ala Asp Asp Glu Ser Asp Tyr Tyr Cys Val Leu Tyr Met
                245                 250                 255

Gly Ser Gly Ile Ser Val Phe Gly Gly Gly Thr Lys Leu Thr Val Leu
                260                 265                 270

Gly Ser Glu Pro Lys Ser Cys Asp Lys Thr His Thr Cys Pro Thr Arg
                275                 280                 285

Phe Trp Val Leu Val Val Val Gly Gly Val Leu Ala Cys Tyr Ser Leu
290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
                340                 345                 350

Ala Tyr Arg Ser Arg Val Lys Phe Ser Arg Ser Ala Asp Ala Pro Ala
                355                 360                 365

Tyr Gln Gln Gly Gln Asn Gln Leu Tyr Asn Glu Leu Asn Leu Gly Arg
370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
                420                 425                 430

Met Lys Gly Glu Arg Arg Arg Gly Lys Gly His Asp Gly Leu Tyr Gln
                435                 440                 445

Gly Leu Ser Thr Ala Thr Lys Asp Thr Tyr Asp Ala Leu His Met Gln
450                 455                 460

Ala Leu Pro Pro Arg
465

<210> SEQ ID NO 2
<211> LENGTH: 467
<212> TYPE: PRT
<213> ORGANISM: Artificial Sequence
<220> FEATURE:
<223> OTHER INFORMATION: HER2(E4)-CD28TM,ICD-CD3Z CAR

<400> SEQUENCE: 2

Met Thr Arg Ala Met Asp Trp Ile Trp Arg Ile Leu Phe Leu Val Gly
1               5                   10                  15

Ala Ala Thr Gly Ala His Ser Gln Val Gln Leu Gln Gln Trp Gly Ala
                20                  25                  30

Gly Leu Leu Lys Pro Ser Glu Thr Leu Ser Leu Thr Cys Ala Val Tyr
            35                  40                  45

Gly Gly Ser Phe Ser Gly Tyr Tyr Trp Ser Trp Ile Arg Gln Pro Pro
        50                  55                  60

Gly Lys Gly Leu Glu Trp Ile Gly Glu Ile Asn His Ser Gly Ser Thr
65                  70                  75                  80

Asn Tyr Asn Pro Ser Leu Lys Ser Arg Val Thr Ile Ser Val Asp Thr
```

85                  90                  95
Ser Lys Asn Gln Phe Ser Leu Lys Leu Ser Ser Val Thr Thr Ala Asp
                100                 105                 110

Thr Ala Val Tyr Tyr Cys Ala Arg Met Gly Ile Asn Ser Gly Gly Tyr
                115                 120                 125

Leu Tyr Gly Met Asp Val Trp Gly Gln Gly Thr Thr Val Thr Val Ser
            130                 135                 140

Ser Gly Gly Gly Ser Gly Gly Gly Ser Gly Gly Gly Gly Ser
145                 150                 155                 160

Gln Thr Val Val Thr Gln Glu Pro Ser Phe Ser Val Ser Pro Gly Gly
                165                 170                 175

Thr Val Thr Leu Thr Cys Gly Leu Ser Ser Gly Ser Val Ser Thr Ser
            180                 185                 190

Tyr Tyr Pro Ser Trp Tyr Gln Gln Ile Pro Gly Gln Ala Pro Arg Thr
            195                 200                 205

Leu Ile Tyr Thr Thr Asn Ile Arg Ser Ser Gly Val Pro Asp Arg Phe
            210                 215                 220

Gly Gly Ser Ile Leu Gly Asn Lys Ala Ala Leu Thr Ile Thr Gly Ala
225                 230                 235                 240

Gln Ala Glu Asp Glu Ser Asp Tyr Tyr Cys Met Leu Tyr Met Gly Ser
                245                 250                 255

Gly Ile Trp Val Phe Gly Gly Gly Thr Lys Leu Thr Val Leu Gly Ser
            260                 265                 270

Glu Pro Lys Ser Cys Asp Lys Thr His Thr Cys Pro Thr Arg Phe Trp
            275                 280                 285

Val Leu Val Val Val Gly Gly Val Leu Ala Cys Tyr Ser Leu Leu Val
290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
                340                 345                 350

Arg Ser Arg Val Lys Phe Ser Arg Ser Ala Asp Ala Pro Ala Tyr Gln
            355                 360                 365

Gln Gly Gln Asn Gln Leu Tyr Asn Glu Leu Asn Leu Gly Arg Arg Glu
            370                 375                 380

Glu Tyr Asp Val Leu Asp Lys Arg Arg Gly Arg Asp Pro Glu Met Gly
385                 390                 395                 400

Gly Lys Pro Gln Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
                420                 425                 430

Gly Glu Arg Arg Arg Gly Lys Gly His Asp Gly Leu Tyr Gln Gly Leu
            435                 440                 445

Ser Thr Ala Thr Lys Asp Thr Tyr Asp Ala Leu His Met Gln Ala Leu
            450                 455                 460

Pro Pro Arg
465

<210> SEQ ID NO 3
<211> LENGTH: 468
<212> TYPE: PRT
<213> ORGANISM: Artificial Sequence

<220> FEATURE:
<223> OTHER INFORMATION: HER2(F1)-CD28TM,ICD-CD3Z CAR

<400> SEQUENCE: 3

```
Met Thr Arg Ala Met Asp Trp Ile Trp Arg Ile Leu Phe Leu Val Gly
1               5                   10                  15

Ala Ala Thr Gly Ala His Ser Gln Val Gln Leu Val Glu Ser Gly Pro
            20                  25                  30

Gly Leu Val Lys Pro Ser Gly Thr Leu Ser Leu Thr Cys Ala Val Ser
        35                  40                  45

Gly Gly Ser Ile Ser Ser Asn Trp Trp Ser Trp Val Arg Gln Pro
    50                  55                  60

Pro Gly Lys Gly Leu Glu Trp Ile Gly Glu Ile Tyr His Ser Gly Ser
65              70                  75                  80

Thr Asn Tyr Asn Pro Ser Leu Lys Ser Arg Val Thr Ile Ser Val Asp
            85                  90                  95

Thr Ser Lys Asn Gln Phe Ser Leu Lys Leu Ser Ser Val Thr Ala Ala
        100                 105                 110

Asp Thr Ala Val Tyr Tyr Cys Ala Arg Met Gly Ala Asn Ser Gly Gly
    115                 120                 125

Tyr Leu Tyr Gly Met Asp Val Trp Gly Gln Gly Thr Thr Val Thr Val
130                 135                 140

Ser Ser Gly Gly Gly Gly Ser Gly Gly Gly Gly Ser Gly Gly Gly Gly
145                 150                 155                 160

Ser Gln Thr Val Val Thr Gln Glu Pro Ser Phe Ser Val Ser Pro Gly
            165                 170                 175

Gly Thr Val Thr Leu Thr Cys Gly Leu Ser Ser Gly Ser Val Ser Thr
        180                 185                 190

Ser Tyr Tyr Pro Ser Trp Tyr Gln Gln Thr Pro Gly Gln Ala Pro Arg
    195                 200                 205

Thr Leu Ile Tyr Ser Thr Asn Thr Arg Ser Ser Gly Val Pro Asp Arg
210                 215                 220

Phe Ser Gly Ser Ile Leu Gly Asn Lys Ala Ala Leu Thr Ile Thr Gly
225                 230                 235                 240

Ala Gln Ala Asp Asp Glu Ser Asp Tyr Tyr Cys Val Leu Tyr Met Gly
            245                 250                 255

Ser Gly Ile Trp Val Phe Gly Gly Gly Thr Lys Leu Thr Val Leu Gly
        260                 265                 270

Ser Glu Pro Lys Ser Cys Asp Lys Thr His Thr Cys Pro Thr Arg Phe
    275                 280                 285

Trp Val Leu Val Val Val Gly Gly Val Leu Ala Cys Tyr Ser Leu Leu
290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
            325                 330                 335

Thr Arg Lys His Tyr Gln Pro Tyr Ala Pro Pro Arg Asp Phe Ala Ala
        340                 345                 350

Tyr Arg Ser Arg Val Lys Phe Ser Arg Ser Ala Asp Ala Pro Ala Tyr
    355                 360                 365

Gln Gln Gly Gln Asn Gln Leu Tyr Asn Glu Leu Asn Leu Gly Arg Arg
370                 375                 380

Glu Glu Tyr Asp Val Leu Asp Lys Arg Arg Gly Arg Asp Pro Glu Met
385                 390                 395                 400
```

```
Gly Gly Lys Pro Gln Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 4
<211> LENGTH: 27
<212> TYPE: PRT
<213> ORGANISM: Artificial Sequence
<220> FEATURE:
<223> OTHER INFORMATION: CD28 TMD

<400> SEQUENCE: 4

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 5
<211> LENGTH: 41
<212> TYPE: PRT
<213> ORGANISM: Artificial Sequence
<220> FEATURE:
<223> OTHER INFORMATION: CD28 ICD

<400> SEQUENCE: 5

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 6
<211> LENGTH: 113
<212> TYPE: PRT
<213> ORGANISM: Artificial Sequence
<220> FEATURE:
<223> OTHER INFORMATION: CD3Z ICD

<400> SEQUENCE: 6

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95
```

```
Ala Thr Lys Asp Thr Tyr Asp Ala Leu His Met Gln Ala Leu Pro Pro
            100                 105                 110
Arg

<210> SEQ ID NO 7
<211> LENGTH: 15
<212> TYPE: PRT
<213> ORGANISM: Artificial Sequence
<220> FEATURE:
<223> OTHER INFORMATION: (G4S)3 linker

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 19
<212> TYPE: PRT
<213> ORGANISM: Artificial Sequence
<220> FEATURE:
<223> OTHER INFORMATION: huIgG H leader

<400> SEQUENCE: 8

Met Asp Trp Ile Trp Arg Ile Leu Phe Leu Val Gly Ala Ala Thr Gly
1               5                   10                  15

Ala His Ser

<210> SEQ ID NO 9
<211> LENGTH: 14
<212> TYPE: PRT
<213> ORGANISM: Artificial Sequence
<220> FEATURE:
<223> OTHER INFORMATION: Hinge

<400> SEQUENCE: 9

Glu Pro Lys Ser Cys Asp Lys Thr His Thr Cys Pro Thr Arg
1               5                   10

<210> SEQ ID NO 10
<211> LENGTH: 14
<212> TYPE: PRT
<213> ORGANISM: Artificial Sequence
<220> FEATURE:
<223> OTHER INFORMATION: HER2(C5) LC-CDR1

<400> SEQUENCE: 10

Gly Leu Ser Ser Gly Ser Val Ser Thr Gly Tyr Tyr Pro Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: HER2(C5) LC-CDR2

<400> SEQUENCE: 11

Ser Thr Asn Ser Arg Ser Ser
1               5

<210> SEQ ID NO 12
<211> LENGTH: 10
<212> TYPE: PRT
<213> ORGANISM: Artificial Sequence
<220> FEATURE:
<223> OTHER INFORMATION: HER2(C5) LC-CDR3
```

```
<400> SEQUENCE: 12

Val Leu Tyr Met Gly Ser Gly Ile Ser Val
1               5                   10

<210> SEQ ID NO 13
<211> LENGTH: 7
<212> TYPE: PRT
<213> ORGANISM: Artificial Sequence
<220> FEATURE:
<223> OTHER INFORMATION: HER2(C5) HC-CDR1

<400> SEQUENCE: 13

Ser Ser Ser Tyr Tyr Trp Gly
1               5

<210> SEQ ID NO 14
<211> LENGTH: 16
<212> TYPE: PRT
<213> ORGANISM: Artificial Sequence
<220> FEATURE:
<223> OTHER INFORMATION: HER2(C5) HC-CDR2

<400> SEQUENCE: 14

Ser Ile Tyr Tyr Ser Gly Ser Thr Tyr Tyr Asn Pro Ser Leu Lys Ser
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: HER2(C5) HC-CDR3

<400> SEQUENCE: 15

Tyr Ala Pro Asp Ser Ser Gly Tyr Leu Val Ala Phe Asp Ile
1               5                   10

<210> SEQ ID NO 16
<211> LENGTH: 112
<212> TYPE: PRT
<213> ORGANISM: Artificial Sequence
<220> FEATURE:
<223> OTHER INFORMATION: HER2(C5) VL

<400> SEQUENCE: 16

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Gly
                20                  25                  30

Tyr Tyr Pro Ser Trp Tyr Gln Gln Thr Pro Gly Gln Ala Pro Arg Thr
            35                  40                  45

Leu Ile Tyr Ser Thr Asn Ser Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Ser Val Phe Gly Gly Gly Thr Lys Leu Thr Val Leu Gly Ser
            100                 105                 110

<210> SEQ ID NO 17
<211> LENGTH: 124
```

```
<212> TYPE: PRT
<213> ORGANISM: Artificial Sequence
<220> FEATURE:
<223> OTHER INFORMATION: HER2(C5) VH

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Tyr Ala Pro Asp Ser Ser Gly Tyr Leu Val Ala Phe Asp
        100                 105                 110

Ile Trp Gly Gln Gly Thr Met Val Thr Val Ser Ser
        115                 120

<210> SEQ ID NO 18
<211> LENGTH: 14
<212> TYPE: PRT
<213> ORGANISM: Artificial Sequence
<220> FEATURE:
<223> OTHER INFORMATION: HER2(E4) LC-CDR1

<400> SEQUENCE: 18

Gly Leu Ser Ser Gly Ser Val Ser Thr Ser Tyr Tyr Pro Ser
1               5                   10

<210> SEQ ID NO 19
<211> LENGTH: 7
<212> TYPE: PRT
<213> ORGANISM: Artificial Sequence
<220> FEATURE:
<223> OTHER INFORMATION: HER2(E4) LC-CDR2

<400> SEQUENCE: 19

Thr Thr Asn Ile Arg Ser Ser
1               5

<210> SEQ ID NO 20
<211> LENGTH: 10
<212> TYPE: PRT
<213> ORGANISM: Artificial Sequence
<220> FEATURE:
<223> OTHER INFORMATION: HER2(E4) LC-CDR3

<400> SEQUENCE: 20

Met Leu Tyr Met Gly Ser Gly Ile Trp Val
1               5                   10

<210> SEQ ID NO 21
<211> LENGTH: 6
<212> TYPE: PRT
<213> ORGANISM: Artificial Sequence
<220> FEATURE:
<223> OTHER INFORMATION: HER2(E4) HC-CDR1

<400> SEQUENCE: 21
```

```
Ser Gly Tyr Tyr Trp Ser
1               5

<210> SEQ ID NO 22
<211> LENGTH: 16
<212> TYPE: PRT
<213> ORGANISM: Artificial Sequence
<220> FEATURE:
<223> OTHER INFORMATION: HER2(E4) HC-CDR2

<400> SEQUENCE: 22

Glu Ile Asn His Ser Gly Ser Thr Asn Tyr Asn Pro Ser Leu Lys Ser
1               5                   10                  15

<210> SEQ ID NO 23
<211> LENGTH: 14
<212> TYPE: PRT
<213> ORGANISM: Artificial Sequence
<220> FEATURE:
<223> OTHER INFORMATION: HER2(E4) HC-CDR3

<400> SEQUENCE: 23

Met Gly Ile Asn Ser Gly Gly Tyr Leu Tyr Gly Met Asp Val
1               5                   10

<210> SEQ ID NO 24
<211> LENGTH: 112
<212> TYPE: PRT
<213> ORGANISM: Artificial Sequence
<220> FEATURE:
<223> OTHER INFORMATION: HER2(E4) VL

<400> SEQUENCE: 24

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Ile Pro Gly Gln Ala Pro Arg Thr
        35                  40                  45

Leu Ile Tyr Thr Thr Asn Ile Arg Ser Ser Gly Val Pro Asp Arg Phe
    50                  55                  60

Gly Gly Ser Ile Leu Gly Asn Lys Ala Ala Leu Thr Ile Thr Gly Ala
65                  70                  75                  80

Gln Ala Glu Asp Glu Ser Asp Tyr Tyr Cys Met Leu Tyr Met Gly Ser
                85                  90                  95

Gly Ile Trp Val Phe Gly Gly Gly Thr Lys Leu Thr Val Leu Gly Ser
            100                 105                 110

<210> SEQ ID NO 25
<211> LENGTH: 122
<212> TYPE: PRT
<213> ORGANISM: Artificial Sequence
<220> FEATURE:
<223> OTHER INFORMATION: HER2(E4) VH

<400> SEQUENCE: 25

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45
```

Gly Glu Ile Asn His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Thr Ala Asp Thr Ala Val Tyr Tyr Cys Ala
                85                  90                  95

Arg Met Gly Ile Asn Ser Gly Gly Tyr Leu Tyr Gly Met Asp Val Trp
            100                 105                 110

Gly Gln Gly Thr Thr Val Thr Val Ser Ser
            115                 120

<210> SEQ ID NO 26
<211> LENGTH: 14
<212> TYPE: PRT
<213> ORGANISM: Artificial Sequence
<220> FEATURE:
<223> OTHER INFORMATION: HER2(F1) LC-CDR1

<400> SEQUENCE: 26

Gly Leu Ser Ser Gly Ser Val Ser Thr Ser Tyr Tyr Pro Ser
1               5                   10

<210> SEQ ID NO 27
<211> LENGTH: 7
<212> TYPE: PRT
<213> ORGANISM: Artificial Sequence
<220> FEATURE:
<223> OTHER INFORMATION: HER2(F1) LC-CDR2

<400> SEQUENCE: 27

Ser Thr Asn Thr Arg Ser Ser
1               5

<210> SEQ ID NO 28
<211> LENGTH: 10
<212> TYPE: PRT
<213> ORGANISM: Artificial Sequence
<220> FEATURE:
<223> OTHER INFORMATION: HER2(F1) LC-CDR3

<400> SEQUENCE: 28

Val Leu Tyr Met Gly Ser Gly Ile Trp Val
1               5                   10

<210> SEQ ID NO 29
<211> LENGTH: 6
<212> TYPE: PRT
<213> ORGANISM: Artificial Sequence
<220> FEATURE:
<223> OTHER INFORMATION: HER2(F1) HC-CDR1

<400> SEQUENCE: 29

Ser Ser Asn Trp Trp Ser
1               5

<210> SEQ ID NO 30
<211> LENGTH: 16
<212> TYPE: PRT
<213> ORGANISM: Artificial Sequence
<220> FEATURE:
<223> OTHER INFORMATION: HER2(F1) HC-CDR2

<400> SEQUENCE: 30

Glu Ile Tyr His Ser Gly Ser Thr Asn Tyr Asn Pro Ser Leu Lys Ser

<210> SEQ ID NO 31
<211> LENGTH: 14
<212> TYPE: PRT
<213> ORGANISM: Artificial Sequence
<220> FEATURE:
<223> OTHER INFORMATION: HER2(F1) HC-CDR3

<400> SEQUENCE: 31

```
Met Gly Ala Asn Ser Gly Gly Tyr Leu Tyr Gly Met Asp Val
1               5                   10
```

<210> SEQ ID NO 32
<211> LENGTH: 112
<212> TYPE: PRT
<213> ORGANISM: Artificial Sequence
<220> FEATURE:
<223> OTHER INFORMATION: HER2(F1) VL

<400> SEQUENCE: 32

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Trp Val Phe Gly Gly Gly Thr Lys Leu Thr Val Leu Gly Ser
            100                 105                 110
```

<210> SEQ ID NO 33
<211> LENGTH: 123
<212> TYPE: PRT
<213> ORGANISM: Artificial Sequence
<220> FEATURE:
<223> OTHER INFORMATION: HER2(F1) VH

<400> SEQUENCE: 33

```
Gln Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Gly Ala Asn Ser Gly Gly Tyr Leu Tyr Gly Met Asp Val
            100                 105                 110

Trp Gly Gln Gly Thr Thr Val Thr Val Ser Ser
        115                 120
```

-continued

```
<210> SEQ ID NO 34
<211> LENGTH: 281
<212> TYPE: PRT
<213> ORGANISM: Artificial Sequence
<220> FEATURE:
<223> OTHER INFORMATION: Ad2 E1Adelta24

<400> SEQUENCE: 34
```

Met Arg His Ile Ile Cys His Gly Gly Val Ile Thr Glu Glu Met Ala
1               5                  10                 15

Ala Ser Leu Leu Asp Gln Leu Ile Glu Glu Val Leu Ala Asp Asn Leu
            20                  25                  30

Pro Pro Pro Ser His Phe Glu Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Glu Ser Val Met Leu Ala Val Gln Glu Gly Ile Asp Leu
65                  70                  75                  80

Phe Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Pro Pro Ser Asp Asp Glu Asp
        115                 120                 125

Glu Glu Gly Glu Glu Phe Val Leu Asp Tyr Val Glu His Pro Gly His
    130                 135                 140

Gly Cys Arg Ser Cys His Tyr His Arg Arg Asn Thr Gly Asp Pro Asp
145                 150                 155                 160

Ile Met Cys Ser Leu Cys Tyr Met Arg Thr Cys Gly Met Phe Val Tyr
                165                 170                 175

Ser Pro Val Ser Glu Pro Glu Pro Glu Pro Glu Pro Glu Pro Glu Pro
            180                 185                 190

Ala Arg Pro Thr Arg Arg Pro Lys Leu Val Pro Ala Ile Leu Arg Arg
        195                 200                 205

Pro Thr Ser Pro Val Ser Arg Glu Cys Asn Ser Ser Thr Asp Ser Cys
    210                 215                 220

Asp Ser Gly Pro Ser Asn Thr Pro Pro Glu Ile His Pro Val Val Pro
225                 230                 235                 240

Leu Cys Pro Ile Lys Pro Val Ala Val Arg Val Gly Gly Arg Arg Gln
                245                 250                 255

Ala Val Glu Cys Ile Glu Asp Leu Leu Asn Glu Ser Gly Gln Pro Leu
            260                 265                 270

Asp Leu Ser Cys Lys Arg Pro Arg Pro
        275                 280

```
<210> SEQ ID NO 35
<211> LENGTH: 536
<212> TYPE: PRT
<213> ORGANISM: Artificial Sequence
<220> FEATURE:
<223> OTHER INFORMATION: huIL-12p70

<400> SEQUENCE: 35
```

Met Gly His Gln Gln Leu Val Ile Ser Trp Phe Ser Leu Val Phe Leu
1               5                  10                 15

Ala Ser Pro Leu Val Ala Ile Trp Glu Leu Lys Lys Asp Val Tyr Val

-continued

```
                20                  25                  30
Val Glu Leu Asp Trp Tyr Pro Asp Ala Pro Gly Glu Met Val Val Leu
             35                  40                  45
Thr Cys Asp Thr Pro Glu Glu Asp Gly Ile Thr Trp Thr Leu Asp Gln
         50                  55                  60
Ser Ser Glu Val Leu Gly Ser Gly Lys Thr Leu Thr Ile Gln Val Lys
65                  70                  75                  80
Glu Phe Gly Asp Ala Gly Gln Tyr Thr Cys His Lys Gly Gly Glu Val
                 85                  90                  95
Leu Ser His Ser Leu Leu Leu His Lys Lys Glu Asp Gly Ile Trp
             100                 105                 110
Ser Thr Asp Ile Leu Lys Asp Gln Lys Glu Pro Lys Asn Lys Thr Phe
         115                 120                 125
Leu Arg Cys Glu Ala Lys Asn Tyr Ser Gly Arg Phe Thr Cys Trp Trp
         130                 135                 140
Leu Thr Thr Ile Ser Thr Asp Leu Thr Phe Ser Val Lys Ser Ser Arg
145                 150                 155                 160
Gly Ser Ser Asp Pro Gln Gly Val Thr Cys Gly Ala Ala Thr Leu Ser
                 165                 170                 175
Ala Glu Arg Val Arg Gly Asp Asn Lys Glu Tyr Glu Tyr Ser Val Glu
             180                 185                 190
Cys Gln Glu Asp Ser Ala Cys Pro Ala Ala Glu Glu Ser Leu Pro Ile
         195                 200                 205
Glu Val Met Val Asp Ala Val His Lys Leu Lys Tyr Glu Asn Tyr Thr
         210                 215                 220
Ser Ser Phe Phe Ile Arg Asp Ile Ile Lys Pro Asp Pro Pro Lys Asn
225                 230                 235                 240
Leu Gln Leu Lys Pro Leu Lys Asn Ser Arg Gln Val Glu Val Ser Trp
                 245                 250                 255
Glu Tyr Pro Asp Thr Trp Ser Thr Pro His Ser Tyr Phe Ser Leu Thr
             260                 265                 270
Phe Cys Val Gln Val Gln Gly Lys Ser Lys Arg Glu Lys Lys Asp Arg
         275                 280                 285
Val Phe Thr Asp Lys Thr Ser Ala Thr Val Ile Cys Arg Lys Asn Ala
         290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser Val Pro Gly Val Gly Val Pro Gly
                 325                 330                 335
Val Gly Ala Arg Asn Leu Pro Val Ala Thr Pro Asp Pro Gly Met Phe
             340                 345                 350
Pro Cys Leu His His Ser Gln Asn Leu Leu Arg Ala Val Ser Asn Met
         355                 360                 365
Leu Gln Lys Ala Arg Gln Thr Leu Glu Phe Tyr Pro Cys Thr Ser Glu
         370                 375                 380
Glu Ile Asp His Glu Asp Ile Thr Lys Asp Lys Thr Ser Thr Val Glu
385                 390                 395                 400
Ala Cys Leu Pro Leu Glu Leu Thr Lys Asn Glu Ser Cys Leu Asn Ser
                 405                 410                 415
Arg Glu Thr Ser Phe Ile Thr Asn Gly Ser Cys Leu Ala Ser Arg Lys
             420                 425                 430
Thr Ser Phe Met Met Ala Leu Cys Leu Ser Ser Ile Tyr Glu Asp Leu
         435                 440                 445
```

```
Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
                500                 505                 510

Cys Ile Leu Leu His Ala Phe Arg Ile Arg Ala Val Thr Ile Asp Arg
            515                 520                 525

Val Met Ser Tyr Leu Asn Ala Ser
    530                 535

<210> SEQ ID NO 36
<211> LENGTH: 376
<212> TYPE: PRT
<213> ORGANISM: Artificial Sequence
<220> FEATURE:
<223> OTHER INFORMATION: HSV1 TK

<400> SEQUENCE: 36

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Pro Glu Gln Lys Met Pro Thr
            35                  40                  45

Leu Leu Arg Val Tyr Ile Asp Gly Pro His Gly Met Gly Lys Thr Thr
50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Thr Ala Val Pro Pro Gln Gly Ala
                260                 265                 270
```

-continued

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Ile Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 37
<211> LENGTH: 9
<212> TYPE: PRT
<213> ORGANISM: Artificial Sequence
<220> FEATURE:
<223> OTHER INFORMATION: HA tag

<400> SEQUENCE: 37

Tyr Pro Tyr Asp Val Pro Asp Tyr Ala
1               5

<210> SEQ ID NO 38
<211> LENGTH: 534
<212> TYPE: PRT
<213> ORGANISM: Artificial Sequence
<220> FEATURE:
<223> OTHER INFORMATION: PD-L1(H12_g1) minibody

<400> SEQUENCE: 38

Met Asp Trp Ile Trp Arg Ile Leu Phe Leu Val Gly Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Arg Ile Ile Pro Ile Leu Gly Ile Ala Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Gly His Gly Tyr Ser Tyr Gly Ala Phe Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Gly Ala Pro Gly Gln Arg Val Thr Ile Ser
                165                 170                 175

Cys Thr Gly Ser Ser Ser Asn Ile Gly Ala Gly Tyr Asp Val His Trp

-continued

```
            180                 185                 190
Tyr Gln Gln Leu Pro Gly Thr Ala Pro Lys Leu Leu Ile Tyr Gly Asn
        195                 200                 205

Ser Asn Arg Pro Ser Gly Val Pro Asp Arg Phe Ser Gly Ser Lys Ser
    210                 215                 220

Gly Thr Ser Ala Ser Leu Ala Ile Thr Gly Leu Gln Ala Glu Asp Glu
225                 230                 235                 240

Ala Asp Tyr Tyr Cys Gln Ser Tyr Asp Ser Ser Leu Ser Gly Ser Tyr
                245                 250                 255

Val Val Phe Gly Gly Gly Thr Lys Leu Thr Val Leu Glu Ala Lys Ser
            260                 265                 270

Cys Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys Gly Gly Gly Ser Tyr Pro Tyr Asp Val Pro Asp
            500                 505                 510

Tyr Ala Gly Tyr Pro Tyr Asp Val Pro Asp Tyr Ala Gly Tyr Pro Tyr
        515                 520                 525

Asp Val Pro Asp Tyr Ala
    530
```

<210> SEQ ID NO 39
<211> LENGTH: 14
<212> TYPE: PRT
<213> ORGANISM: Artificial Sequence
<220> FEATURE:
<223> OTHER INFORMATION: PD-L1(H12_gl) LC-CDR1

<400> SEQUENCE: 39

Thr Gly Ser Ser Ser Asn Ile Gly Ala Gly Tyr Asp Val His

-continued

```
<210> SEQ ID NO 40
<211> LENGTH: 7
<212> TYPE: PRT
<213> ORGANISM: Artificial Sequence
<220> FEATURE:
<223> OTHER INFORMATION: PD-L1(H12_gl) LC-CDR2

<400> SEQUENCE: 40

Gly Asn Ser Asn Arg Pro Ser
1               5

<210> SEQ ID NO 41
<211> LENGTH: 13
<212> TYPE: PRT
<213> ORGANISM: Artificial Sequence
<220> FEATURE:
<223> OTHER INFORMATION: PD-L1(H12_gl) LC-CDR3

<400> SEQUENCE: 41

Gln Ser Tyr Asp Ser Ser Leu Ser Gly Ser Tyr Val Val
1               5                   10

<210> SEQ ID NO 42
<211> LENGTH: 5
<212> TYPE: PRT
<213> ORGANISM: Artificial Sequence
<220> FEATURE:
<223> OTHER INFORMATION: PD-L1(H12_gl) HC-CDR1

<400> SEQUENCE: 42

Ser Tyr Ala Ile Ser
1               5

<210> SEQ ID NO 43
<211> LENGTH: 17
<212> TYPE: PRT
<213> ORGANISM: Artificial Sequence
<220> FEATURE:
<223> OTHER INFORMATION: PD-L1(H12_gl) HC-CDR2

<400> SEQUENCE: 43

Arg Ile Ile Pro Ile Leu Gly Ile Ala Asn Tyr Ala Gln Lys Phe Gln
1               5                   10                  15
Gly

<210> SEQ ID NO 44
<211> LENGTH: 12
<212> TYPE: PRT
<213> ORGANISM: Artificial Sequence
<220> FEATURE:
<223> OTHER INFORMATION: PD-L1(H12_gl) HC-CDR3

<400> SEQUENCE: 44

Ser Gly His Gly Tyr Ser Tyr Gly Ala Phe Asp Tyr
1               5                   10

<210> SEQ ID NO 45
<211> LENGTH: 113
<212> TYPE: PRT
<213> ORGANISM: Artificial Sequence
<220> FEATURE:
<223> OTHER INFORMATION: PD-L1(H12_gl) VL

<400> SEQUENCE: 45
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Tyr Val Val Phe Gly Gly Gly Thr Lys Leu Thr Val
            100                 105                 110

Leu

<210> SEQ ID NO 46
<211> LENGTH: 121
<212> TYPE: PRT
<213> ORGANISM: Artificial Sequence
<220> FEATURE:
<223> OTHER INFORMATION: PD-L1(H12_g1) VH

<400> SEQUENCE: 46

Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly His Gly Tyr Ser Tyr Gly Ala Phe Asp Tyr Trp Gly
            100                 105                 110

Gln Gly Thr Leu Val Thr Val Ser Ser
        115                 120

<210> SEQ ID NO 47
<211> LENGTH: 3750
<212> TYPE: DNA
<213> ORGANISM: Artificial Sequence
<220> FEATURE:
<223> OTHER INFORMATION: HER2(C5)-CD28TM,ICD-CD3Z CAR

<400> SEQUENCE: 47
aagttcagat caaggtcagg aacagatgga acagctgaat atgggccaaa caggatatct        60
gtggtaagca gttcctgccc cggctcaggg ccaagaacag atggaacagc tgaatatggg       120
ccaaacagga tatctgtggt aagcagttcc tgccccggct cagggccaag aacagatggt       180
ccccagatgc ggtccagccc tcagcagttt ctagagaacc atcagatgtt tccagggtgc       240
cccaaggacc tgaaatgacc ctgtgcctta tttgaactaa ccaatcagtt cgcttctcgc       300
ttctgttcgc gcgcttctgc tccccgagct caataaaaga gcccacaacc cctcactcgg       360

```
cgcgccagtc ctccgattga ctgagtcgcc cgggtacccg tgtatccaat aaaccctctt    420
gcagttgcat ccgacttgtg gtctcgctgt tccttgggag ggtctcctct gagtgattga    480
ctacccgtca gcgggggtct ttcatttggg ggctcgtccg ggatcgggag acccctgccc    540
agggaccacc gacccaccac cgggaggtaa gctggccagc aacttatctg tgtctgtccg    600
attgtctagt gtctatgact gattttatgc gcctgcgtcg gtactagtta gctaactagc    660
tctgtatctg gcggacccgt ggtggaactg acgagttcgg aacacccggc cgcaaccctg    720
ggagacgtcc cagggacttc gggggccgtt tttgtggccc gacctgagtc ctaaaatccc    780
gatcgtttag gactctttgg tgcacccccc ttagaggagg gatatgtggt tctggtagga    840
gacgagaacc taaaacagtt cccgcctccg tctgaatttt tgctttcggt ttgggaccga    900
agccgcgccg cgcgtcttgt ctgctgcagc atcgttctgt gttgtctctg tctgactgtg    960
tttctgtatt tgtctgaaaa tatgggcccg ggctagcctg ttaccactcc cttaagtttg   1020
accttaggtc actggaaaga tgtcgagcgg atcgctcaca accagtcggt agatgtcaag   1080
aagagacgtt gggttacctt ctgctctgca gaatggccaa cctttaacgt cggatggccg   1140
cgagacggca cctttaaccg agacctcatc acccaggtta agatcaaggt cttttcacct   1200
ggcccgcatg gacacccaga ccaggtcccc tacatcgtga cctgggaagc cttggctttt   1260 gaccccctc cctgggtcaa gccctttgta caccctaagc ctccgcctcc tcttcctcca   1320 tccgcccgt ctctccccct tgaacctcct cgttcgaccc cgcctcgatc ctccctttat    1380
ccagccctca ctccttctct aggcgccccc atatggccat atgagatctt atatggggca   1440 ccccgcccc ttgtaaactt ccctgaccct gacatgacaa gagttactaa cagcccctct   1500
ctccaagctc acttacaggc tctctactta gtccagcacg aagtctggag acctctggcg   1560
gcagcctacc aagaacaact ggaccgaccg gtggtacctc acccttaccg agtcggcgac   1620
acagtgtggg tccgccgaca ccagactaag aacctagaac ctcgctggaa aggaccttac   1680
acagtcctgc tgaccacccc caccgccctc aaagtagacg gcatcgcagc ttggatacac   1740 gccgccacg tgaaggctgc cgaccccggg ggtggaccat gactcgagcc atggattgga   1800
tctggcgcat cctgtttctc gtgggagctg ccacaggcgc ccattctcag gttcagctgc   1860
aagagtctgg ccctggcctg gtcaagccta gcgaaacact gagcctgacc tgtaccgtgt   1920
ctggcggcag catcagcagc agctcttact actgggggctg gatcagacag cctcctggca   1980
aaggcctgga atggatcggc tccatctact acagcggcag cacctactac aaccccagcc   2040
tgaagtccag agtgaccatc agcgtggaca ccagcaagaa ccagttctcc ctgaagctga   2100
gcagcgtgac agccgccgat acagccgtgt actactgtgc cagatacgcc cctgatagca   2160
gcggctacct ggtggccttt gatatctggg gccaggcac aatggtcacc gtttctagcg   2220
gaggcggagg ttctggtggc ggaggaagtg gcggcggagg atctcagaca gtggtcacac   2280
aagagcccag cttctccgtg tctcctggcg gaacagtgac cctgacatgt ggccttagct   2340
ctggctctgt gtccaccggc tactaccccca gctggtatca gcagacacct ggacaggccc   2400
ctcggacact gatctacagc accaacagca gatccagcgg cgtgcccgat agattcagcg   2460
gctctatcct gggcaacaag gccgcactga caatcacagg cgctcaggcc gatgacgaga   2520
gcgactacta ctgcgtgctg tacatgggca gcggcatctc cgttttggc ggaggcacaa   2580 agctgaccgt gctgggatcc gaaccaaaga gttgcgacaa aacacacacc tgccctacgc   2640 gttttttgggt gctcgtggtg gtgggtgcg tgctcgcttg ctactcactt ctggtgaccg   2700
tagcgtttat cattttttgg gtcaggagca agcgatcccg cctattgcac agcgactaca   2760
```

```
tgaacatgac cccccggcgc cccgggccaa cccggaagca ctaccagcca tatgcgcctc    2820
cccgcgattt cgcagcgtat cggtcccggg tcaaattttc acggtccgct gacgcccgg     2880 cctatcaaca gggccagaat cagctgtata atgaattaaa cctcggtaga cgcgaggagt    2940
acgacgtcct cgacaagaga aggggcgcg acccagagat gggaggcaaa ccgcagcgca     3000
ggaagaatcc acaggagggc ctgtacaacg aattacagaa ggacaagatg cagaggcct     3060 acagcgagat aggaatgaag ggtgaaaggc gtcgtggaaa gggccacgat gggctttacc    3120
agggcctaag tactgccaca aaagatacgt atgacgcgct gcatatgcaa gccctcccc     3180 ccaggtaagc atgcaacctc gatccggatt agtccaattt gttaaagaca ggatatcagt    3240
ggtccaggct ctagttttga ctcaacaata tcaccagctg aagcctatag agtacgagcc    3300
atagataaaa taaagatttt tatttagtct ccagaaaaag gggggaatga agaccccac     3360 ctgtaggttt ggcaagctag cttaagtaac gccatttgc aaggcatgga aaatacata      3420 actgagaata gagaagttca gatcaaggtc aggaacagat ggaacagctg aatatgggcc    3480
aaacaggata tctgtggtaa gcagttcctg ccccggctca gggccaagaa cagatggaac    3540
agctgaatat gggccaaaca ggatatctgt ggtaagcagt tcctgccccg gctcagggcc    3600
aagaacagat ggtccccaga tgcggtccag ccctcagcag tttctagaga accatcagat    3660
gtttccaggg tgccccaagg acctgaaatg accctgtgcc ttatttgaac taaccaatca    3720
gttcgcttct cgcttctgtt cgcgcgcttc                                     3750

<210> SEQ ID NO 48
<211> LENGTH: 3744
<212> TYPE: DNA
<213> ORGANISM: Artificial Sequence
<220> FEATURE:
<223> OTHER INFORMATION: HER2(E4)-CD28TM,ICD-CD3Z CAR

<400> SEQUENCE: 48
aagttcagat caaggtcagg aacagatgga acagctgaat atgggccaaa caggatatct     60
gtggtaagca gttcctgccc cggctcaggg ccaagaacag atggaacagc tgaatatggg    120
ccaaacagga tatctgtggt aagcagttcc tgccccggct cagggccaag aacagatggt    180
ccccagatgc ggtccagccc tcagcagttt ctagagaacc atcagatgtt tccagggtgc    240
cccaaggacc tgaaatgacc ctgtgcctta tttgaactaa ccaatcagtt cgcttctcgc    300
ttctgttcgc gcgcttctgc tccccgagct caataaaaga gcccacaacc cctcactcgg    360
cgcgccagtc tccgattga ctgagtcgcc cgggtacccg tgtatccaat aaaccctctt    420
gcagttgcat ccgacttgtg gtctcgctgt tccttgggag gtctcctct gagtgattga    480 ctacccgtca gcgggggtct ttcatttggg ggctcgtccg ggatcgggag accctgccc     540 agggaccacc gacccaccac cgggaggtaa gctggccagc aacttatctg tgtctgtccg    600
attgtctagt gtctatgact gatttatgc gcctgcgtcg gtactagtta gctaactagc     660
tctgtatctg gcggacccgt ggtggaactg acgagttcgg aacacccggc cgcaaccctg    720
ggagacgtcc cagggacttc gggggccgtt tttgtggccc gacctgagtc ctaaaatccc    780
gatcgtttag gactctttgg tgcacccccc ttagaggagg gatatgtggt tctggtagga    840
gacgagaacc taaaacagtt cccgcctccg tctgaatttt gctttcggt ttgggaccga    900 agccgcgccg cgcgtcttgt ctgctgcagc atcgttctgt gttgtctctg tctgactgtg    960
tttctgtatt tgtctgaaaa tatgggcccg ggctagcctg ttaccactcc cttaagtttg    1020
```

-continued

```
accttaggtc actggaaaga tgtcgagcgg atcgctcaca accagtcggt agatgtcaag    1080
aagagacgtt gggttacctt ctgctctgca gaatggccaa cctttaacgt cggatggccg    1140
cgagacggca cctttaaccg agacctcatc acccaggtta agatcaaggt cttttcacct    1200
ggcccgcatg gacacccaga ccaggtcccc tacatcgtga cctgggaagc cttggctttt    1260
gacccccctc cctgggtcaa gcccttttgta caccctaagc ctccgcctcc tcttcctcca    1320
tccgccccgt ctctcccect tgaacctcct cgttcgaccc cgcctcgatc ctcccttat     1380 ccagccctca ctccttctct aggcgccccc atatggccat atgagatctt atatggggca    1440
cccccgcccc ttgtaaactt ccctgaccct gacatgacaa gagttactaa cagcccctct    1500
ctccaagctc acttacaggc tctctactta gtccagcacg aagtctggag acctctggcg    1560
gcagcctacc aagaacaact ggaccgaccg gtggtacctc acccttaccg agtcggcgac    1620
acagtgtggg tccgccgaca ccagactaag aacctagaac ctcgctggaa aggaccttac    1680
acagtcctgc tgaccacccc caccgccctc aaagtagacg gcatcgcagc ttggatacac    1740
gccgcccacg tgaaggctgc cgaccccggg ggtggaccat gactcgagcc atggattgga    1800
tctggcgcat cctgtttctc gtgggagctg ccacaggcgc ccattctcag gttcagctgc    1860
aacagtgggg agccggactg ctgaagccta gcgaaacact gagcctgacc tgtgccgtgt    1920
acggcggcag cttttagcggc tactactggt cctggatcag acagcctcct ggcaaaggcc    1980
tggaatggat cggcgagatc aatcacagcg gcagcaccaa ctacaacccc agcctgaagt    2040
ccagagtgac catcagcgtg gacaccagca gaaccagtt ctccctgaag ctgagcagcg     2100
tgaccacagc cgataccgcc gtgtactact gtgcccggat gggcatcaat agcggcggct    2160
acctgtacgg catggatgtg tggggacagg gcaccaccgt gacagtttct agcggaggcg    2220
gaggttctgg tggcgaggga gtggcggcg gaggatctca gacagtggtc acacaagagc     2280
ccagcttctc cgtgtctcct ggcggaacag tgaccctgac atgtggcctt agcagcggct    2340
ctgtgtccac cagctactac cctagctggt atcagcagat ccccggacag gcccctcgga    2400
cactgatcta caccaccaac atcagatcca gcggcgtgcc cgatagattc ggcggatcta    2460
tcctgggcaa caaggccgca ctgacaatca caggtgccca ggccgaggac gagtccgact    2520
actactgcat gctgtacatg ggcagcggca tctgggtttt cggcggaggc acaaagctga    2580
ccgttctggg atccgaacca aagagttgcg acaaaacaca cacctgccct acgcgttttt    2640
gggtgctcgt ggtggtgggt ggcgtgctcg cttgctactc acttctggtg accgtagcgt    2700
ttatcatttt tgggtcagg agcaagcgat cccgcctatt gcacagcgac tacatgaaca    2760 tgacccccg gcgccccggg ccaacccgga agcactacca gccatatgcg cctccccgcg    2820
atttcgcagc gtatcggtcc cgggtcaaat tttcacggtc cgctgacgcc ccggcctatc    2880
aacagggcca gaatcagctg tataatgaat taaacctcgg tagacgcgag gagtacgacg    2940
tcctcgacaa gagaagggg cgcgaccag agatgggagg caaaccgcag cgcaggaaga     3000
atccacagga gggcctgtac aacgaattac agaaggacaa gatggcagag gcctacagcg    3060
agataggaat gaagggtgaa aggcgtcgtg gaaagggcca cgatgggctt taccagggcc    3120
taagtactgc cacaaaagat acgtatgacg cgctgcatat gcaagccctc cccccaggt    3180 aagcatgcaa cctcgatccg gattagtcca atttgttaaa gacaggatat cagtggtcca    3240
ggctctagtt ttgactcaac aatatcacca gctgaagcct atagagtacg agccatagat    3300
aaaataaaag attttattta gtctccagaa aaaggggga atgaaagacc ccacctgtag    3360
gtttggcaag ctagcttaag taacgccatt ttgcaaggca tggaaaaata cataactgag    3420
```

-continued

```
aatagagaag ttcagatcaa ggtcaggaac agatggaaca gctgaatatg ggccaaacag    3480
gatatctgtg gtaagcagtt cctgccccgg ctcagggcca agaacagatg gaacagctga    3540
atatgggcca acaggatatc tgtggtaagc agttcctgcc ccggctcagg gccaagaac     3600 agatggtccc cagatgcggt ccagccctca gcagtttcta gagaaccatc agatgtttcc    3660
agggtgcccc aaggacctga atgaccctg tgccttattt gaactaacca atcagttcgc     3720
ttctcgcttc tgttcgcgcg cttc                                           3744
```

<210> SEQ ID NO 49
<211> LENGTH: 3747
<212> TYPE: DNA
<213> ORGANISM: Artificial Sequence
<220> FEATURE:
<223> OTHER INFORMATION: HER2(F1)-CD28TM,ICD-CD3Z CAR

<400> SEQUENCE: 49

```
aagttcagat caaggtcagg aacagatgga acagctgaat atgggccaaa caggatatct      60
gtggtaagca gttcctgccc cggctcaggg ccaagaacag atggaacagc tgaatatggg     120
ccaaacagga tatctgtggt aagcagttcc tgccccggct cagggccaag aacagatggt     180
ccccagatgc ggtccagccc tcagcagttt ctagagaacc atcagatgtt tccagggtgc     240
cccaaggacc tgaaatgacc ctgtgcctta tttgaactaa ccaatcagtt cgcttctcgc     300
ttctgttcgc gcgcttctgc tccccgagct caataaaaga gcccacaacc cctcactcgg     360
cgcgccagtc ctccgattga ctgagtcgcc cgggtacccg tgtatccaat aaaccctctt     420
gcagttgcat ccgacttgtg gtctcgctgt tccttgggag ggtctcctct gagtgattga     480
ctacccgtca gcgggggtct ttcatttggg ggctcgtccg ggatcgggag acccctgccc     540
agggaccacc gacccaccac cgggaggtaa gctggccagc aacttatctg tgtctgtccg     600
attgtctagt gtctatgact gattttatgc gcctgcgtcg gtactagtta gctaactagc     660
tctgtatctg gcggacccgt ggtggaactg acgagttcgg aacacccggc cgcaaccctg     720
ggagacgtcc cagggacttc gggggccgtt tttgtggccc gacctgagtc ctaaaatccc     780
gatcgtttag gactctttgg tgcaccccc ttagaggagg gatatgtggt tctggtagga     840
gacgagaacc taaaacagtt cccgcctccg tctgaatttt tgctttcggt ttgggaccga     900
agccgcgccg cgcgtcttgt ctgctgcagc atcgttctgt gttgtctctg tctgactgtg     960
tttctgtatt tgtctgaaaa tatgggcccg gctagcctg ttaccactcc cttaagtttg    1020
accttaggtc actggaaaga tgtcgagcgg atcgctcaca accagtcggt agatgtcaag    1080
aagagacgtt gggttacctt ctgctctgca gaatggccaa cctttaacgt cggatggccg    1140
cgagacggca cctttaaccg agacctcatc acccaggtta agatcaaggt cttttcacct    1200
ggcccgcatg gacacccaga ccaggtcccc tacatcgtga cctgggaagc cttggctttt    1260
gacccccctc cctgggtcaa gcccttgta cacctaagc ctccgcctcc tcttcctcca    1320
tccgccccgt ctctcccct tgaacctcct cgttcgaccc cgcctcgatc ctccctttat    1380
ccagccctca ctccttctct aggcgcccc atatggccat atgagatctt atatgggca    1440 cccccgcccc ttgtaaactt ccctgaccct gacatgacaa gagttactaa cagcccctct    1500
ctccaagctc acttacaggc tctctactta gtccagcacg aagtctggag acctctggcg    1560
gcagcctacc aagaacaact ggaccgaccg gtggtacctc acccttaccg agtcggcgac    1620
acagtgtggg tccgccgaca ccagactaag aacctagaac ctcgctggaa aggaccttac    1680
```

| | |
|---|---|
| acagtcctgc tgaccacccc caccgccctc aaagtagacg gcatcgcagc ttggatacac | 1740 |
| gccgcccacg tgaaggctgc cgaccccggg ggtggaccat gactcgagcc atggattgga | 1800 |
| tctggcgcat cctgtttctc gtgggagctg ccacaggcgc ccattctcag gttcagctgg | 1860 |
| tggaatctgg ccctggcctg gttaagccta gcggcacact gtctctgacc tgtgctgtgt | 1920 |
| ctggcggcag catcagcagc agcaattggt ggtcttgggt ccgacagcct cctggcaaag | 1980 |
| gcctggaatg gatcggcgag atctaccaca cggcagcac caactacaac cccagcctga | 2040 |
| agtccagagt gaccatcagc gtggacacca gcaagaacca gttctccctg aagctgagca | 2100 |
| gcgtgacagc cgccgataca gccgtgtact actgtgccag aatgggagcc aatagcggcg | 2160 |
| gctacctgta cggcatggat gtgtggggac agggcaccac cgtgacagtt tctagcggag | 2220 |
| gcggaggttc tggtggcgga ggaagtggcg cggaggatc tcagacagtg gtcacacaag | 2280 |
| agcccagctt ctccgtgtct cctggcggaa cagtgaccct gacatgtggc cttagcagcg | 2340 |
| gctctgtgtc taccagctac tacccctcct ggtatcagca gacccctgga caggctcccc | 2400 |
| ggacactgat ctactccacc aacaccagat ccagcggcgt gcccgataga ttctccggct | 2460 |
| ctatcctggg caacaaggcc gcactgacaa tcacaggcgc tcaggccgat gacgagagcg | 2520 |
| actactactg cgtgctgtac atgggcagcg gcatctgggt tttcggcgga ggcacaaagc | 2580 |
| tgaccgttct gggatccgaa ccaaagagtt gcgacaaaac acacacctgc cctacgcgtt | 2640 |
| tttgggtgct cgtggtggtg ggtggcgtgc tcgcttgcta ctcacttctg gtgaccgtag | 2700 |
| cgtttatcat ttttttgggtc aggagcaagc gatcccgcct attgcacagc gactacatga | 2760 |
| acatgacccc ccgcgcccc gggccaaccc ggaagcacta ccagccatat gcgcctcccc | 2820 |
| gcgatttcgc agcgtatcgg tcccgggtca aattttcacg gtccgctgac gccccggcct | 2880 |
| atcaacaggg ccagaatcag ctgtataatg aattaaaccct cggtagacgc gaggagtacg | 2940 |
| acgtcctcga caagagaagg gggcgcgacc cagagatggg aggcaaaccg cagcgcagga | 3000 |
| agaatccaca ggagggcctg tacaacgaat tacagaagga caagatggca gaggcctaca | 3060 |
| gcgagatagg aatgaagggt gaaaggcgtc gtggaaaggg ccacgatggg ctttaccagg | 3120 |
| gcctaagtac tgccacaaaa gatacgtatg acgcgctgca tatgcaagcc ctcccccca | 3180 |
| ggtaagcatg caacctcgat ccggattagt ccaatttgtt aaagacagga tatcagtggt | 3240 |
| ccaggctcta gttttgactc aacaatatca ccagctgaag cctatagagt acgagccata | 3300 |
| gataaaataa aagatttat ttagtctcca gaaaagggg ggaatgaaag accccacctg | 3360 |
| taggtttggc aagctagctt aagtaacgcc attttgcaag gcatggaaaa atacataact | 3420 |
| gagaatagag aagttcagat caaggtcagg aacagatgga acagctgaat atgggccaaa | 3480 |
| caggatatct gtggtaagca gttcctgccc cggctcaggg ccaagaacag atggaacagc | 3540 |
| tgaatatggg ccaaacagga tatctgtggt aagcagttcc tgccccggct cagggccaag | 3600 |
| aacagatggt ccccagatgc ggtccagccc tcagcagttt ctagagaacc atcagatgtt | 3660 |
| tccagggtgc cccaaggacc tgaaatgacc ctgtgcctta tttgaactaa ccaatcagtt | 3720 |
| cgcttctcgc ttctgttcgc gcgcttc | 3747 |

<210> SEQ ID NO 50
<211> LENGTH: 30590
<212> TYPE: DNA
<213> ORGANISM: Artificial Sequence
<220> FEATURE:
<223> OTHER INFORMATION: HDAdIL12p70_TK_aPD-L1

<400> SEQUENCE: 50

```
aaacatcatc aataatatac cttattttgg attgaagcca atatgataat gagggggtgg      60
agtttgtgac gtggcgcggg gcgtgggaac ggggcgggtg acgtagtagt gtggcggaag     120
tgtgatgttg caagtgtggc ggaacacatg taagcgacgg atgtggcaaa agtgacgttt     180
ttggtgtgcg ccggtgtaca caggaagtga caatttcgc gcggttttag gcggatgttg      240
tagtaaattt gggcgtaacc gagtaagatt tggccatttt cgcgggaaaa ctgaataaga     300
ggaagtgaaa tctgaataat tttgtgttac tcatagcgcg taatatttgt ctagggccgc     360
ggggactttg accgtttacg tggagactcg cccaggtgtt tttctcaggt gttttccgcg     420
ttccgggtca aagttggcgt tttgatatca agcttatcga taccgtaaac aagtctttaa     480
ttcaagcaag actttaacaa gttaaaagga gcttatgggt aggaagtagt gttatgatgt     540
atgggcataa agggttttaa tgggatagtg aaaatgtcta taataatact taaatggctg     600
cccaatcacc tacaggattg atgtaaacat ggaaaaggtc aaaaacttgg gtcactaaaa     660
tagatgatta atggagagga tgaggttgat agttaaatgt agataagtgg tcttattctc     720
aataaaaatg tgaacataag gcgagtttct acaaagatgg acaggactca ttcatgaaac     780
agcaaaaact ggacatttgt tctaatcttt gaagagtatg aaaaattcct attttaaagg     840
taaaacagta actcacagga ataccaacc caacataaaa tcagaaacaa tagtctaaag      900
taataaaaat caaacgtttg cacgatcaaa ttatgaatga aattcactac taaaattcac     960
actgattttg tttcatccac agtgtcaatg ttgtgatgca tttcaattgt gtgacacagg    1020
cagactgtgg atcaaaagtg gtttctggtg cgacttactc tcttgagtat acctgcagtc    1080 cccttttctta agtgtgttaa aaaaaaggg ggatttcttc aattcgccaa tactctagct    1140
ctccatgtgc tttctaggaa acaagtgtta acccacctta tttgtcaaac ctagctccaa    1200
aggactttgt actccccaca aaccgatgta gctcaagaga gggtatctgt caccagtatg    1260
tatagtgaaa aaagtatccc aagtcccaac agcaattcct aaaaggagtt tatttaaaaa    1320
accacacaca cctgtaaaat aagtatatat cctccaaggt gactagtttt aaaaaaacag    1380
tattggcttt gatgtaaagt actagtgaat atgttagaaa atctcactg taaccaagtg    1440 aaatgaaagc aagtatggtt tgcagagatt caaagaaaat ataagaaaac ctactgttgc    1500
cactaaaaag aatcatatat taaatatact cacacaatag ctcttcagtc tgataaaatc    1560
tacagtcata ggaatggatc tatcactatt tctattcagt gctttgatgt aatccagcag    1620
gtcagcaaag aatttatagc ccccttgag cacacagagg gctacaatgt gatggcctcc     1680
catctccttc atcacatctc gagcaagacg ttcagtccta cagaaataaa atcaggaatt    1740
taatagaaag tttcatacat taaacttttat aacaaacacc tcttagtcat taaacttcca    1800
caccaacctg gcaatatag tgagaccca tgcctgcaaa aaaaaaaaa ttagccaggc        1860 atggtagcat gtacctgtag tcccagctac ttgagaggtg aggtgggaaa atcactttag    1920
tgcaggatgt tgaggctgga gtgaactgtg attgtgccac tgcactccag cctggacaat    1980
agagcaagac cttgtctcaa aaaatgcat taaaaatttt ttttaaatct tccacgtatc    2040
acatcctttg ccctcatgtt tcataaggta aaaaatttga taccttcaaa aaaaccaagc    2100
ataccactat cataatttt tttaaatgca aataaaaaca agataccatt ttcacctatc     2160
agactggcag gttctgatta aatgaaattt tctggataat atacaatatt aagagagact    2220
gtagaaactg ggccagtggc tcatgcctgt aatcccagca ctttgggagg ctgggtaaca    2280
tggcgaaccc tgtttctaca aaataaaaat attagctggg agtggtggcg cacacctata    2340
```

```
gtcccagcta ctcaggaggc tgaggtggaa ggatcgcttg aacccaggag gttgagactg    2400
cagtgaactg tgatcattct gctgcactgc accccagcct gggcaacaga gaccttgtct    2460
caaaaaaaaa aaaaaaagag acaaattgtg aagagaaagg tactctcata taacatcagg    2520
agtataaaat gattcaactt cttagaggaa aatttggcaa taccaaaata ttcaataaac    2580
tctttcccct tgacccagaa attccacttg aataaagctg aacaagtacc aaacatgtaa    2640
aagaatgttt cttctagtac agtcggtaag aacaaaatag tgtctatcaa tagtggactg    2700
gttaaatcag ttatggtatc tccataagac agaatgctat gcaaccttta aaatatatta    2760
gatagctcta gacacactaa tattaaaagt gtccaataac atttaaaact atactcatac    2820
gttaaaatat aaatgtatat atgtactttt gcatatagta tacatgcata ggccagtgct    2880
tgagaagaaa tgtgtacaga aggctgaaag gagagaactt tagtcttctt gtttatggcc    2940
tccatagtta gaatatttta taacacaaat attttgatat tataatttta aaataaaaac    3000
acagaatagc cagacataca atgcaagcat tcaataccag gtaaggtttt tcactgtaat    3060
tgacttaaca gaaaattttc aagctagatg tgcataataa taaaaatctg accttgcctt    3120
catgtgattc agccccagtc cattaccctg tttaggactg agaaatgcaa gactctggct    3180
agagttcctt cttccatctc ccttcaatgt ttactttgtt ctggtcccta cagagtccca    3240
ctataccaca actgtactaa gtaattagt aaggccctcc tcttttattt ttaataaaga    3300
agattttaga aagcatcagt tatttaataa gttggcctag tttatgttca aatagcaagt    3360
actcagaaca gctgctgatg tttgaaatta acacaagaaa aagtaaaaaa cctcattta    3420 agatcttact tacctgtcca taattagtcc atgaggaata acacccttt ccaaatcctc    3480 agcataatga ttaggtatgc aaaataaatc aaggtcataa cctggttcat catcactaat    3540
ctgaaaaaga aatatagctg tttcaatgag agcattacag gatacaaaca tttgattgga    3600
ttaagatgtt aaaaaataac cttagtctat cagagaaatt taggtgtaag atgatattag    3660
taactgttaa ctttgtaggt atgataatga attatgtaag aaaacaacag gccgggcggg    3720
ttggttcaca cgtgtaatcc cagcactttg ggaggctgag gcaggcagac tgcctgagct    3780
caggagttcg agaccagcct gggcaacacg gtgaaatccc gtctctacta aaaatacaaa    3840
aaaattagcc gggtgtggtg acacatgcct gtagtcccag ctacttggga ggctgaggca    3900
ggagaatcac ttgaacctgg gaggtgaagg ttgcagtgag ccaagatggc accacttcac    3960
tccagcctgg gaaacagagc aagactctgt ctctgagctg agatggcacc acttcactcc    4020
agcctgggaa acagagcaag actctgtctc aaaaaaaaca aaacacacaa acaaaaaaac    4080
aggctgggcg cggtggctca cgcctgtaat cccagcactt gggaggccga ggcgggtgg    4140 atcacctgag gtcaggagtt ccagaccagc cttgtcaaca tggtgaaacc tccccccgcc    4200
gtctctacta aaaatacaaa aattagccag gcgtggtggc aggagcctgt aatcccagct    4260
acttgggagg ctgaggcagg agaatcgctt gtacccagaa ggcagaggtt gcactgagct    4320
gagatggcac cattgcactc cagcctgggg acaagagcg agatttcgtc tttaaaaaac    4380 aaaacaaaa caaaaaacca tgtaactata tgtcttagtc atcttagtca agaatgtaga    4440
agtaaagtga taagatatgg aatttccttt aggtcacaaa gagaaaaaga aaattttaa    4500 agagctaaga caaacgcagc aaaatcttta tatttaataa tattctaaac atgggtgatg    4560
aacatacggg tattcattat actattctct ccacttttga gtatgtttga aaatttagta    4620
aaacaagttt taacacactg tagtctaaca agataaaata tcacactgaa caggaaaaac    4680
tggcatggtg tggtggctca cacttgtaat cccagtgctt tgggaggctg agacaggaga    4740
```

```
gttgcttgag gccaggagtt caagaccgac atggggaatg tagcaagacc ccgtccctac    4800
aaaaaacttt gtaaaatttt gccaggtatg gtggtgcata cctgtagtcc cagctactcg    4860
ggaggcggag gcagaaggaa tcacttgagc ccaggagttt gaggctgcag tgagctacga    4920
tcataccaca gcactccagc gtggacaaca gagtaagacc ctatctcaaa acaaaacaa     4980 aacaaaacaa acaaaaaaaa ccacaagaaa aactgctggc tgatgcagcg gctcatgcct    5040
gtaatcccag tattttggga ggcccaggtg ggcgtatcac ctgaggtcag gagttagaga    5100
ccagcctggc caacatggtg aaacccccatc tctactaaaa atacaaaatt agccaggcat    5160
gtggcacgcg cctgtagtcc cagttactgg gaggctgaag caggaggatc acctgagccc    5220
gggaggtgga ggttgcagtg agccgagatc acaccactgc actccagcct gggtgacaca    5280
gcaataccct acctcaaaat aaaaagaaa aagaaaagaa aagttgctgt ccccgctacc      5340
ccaatcccaa atccaaacag cctctctcat ctcacagtaa gggggaaaaa tcacccaaaa    5400
aagctaagtg atcttttgaa acccaaaact cttagaagtc taagattatt atagtcaact    5460
catgaagtgt catcataaaa gatactctaa tattatttaa gtagaaccac atattggttg    5520
tcttggtatg tctagcccct ggcatacaaa atatttaata acactgatat ggtacctgtg    5580
atgtgaaaat gtactatgag tacagcttta taaatactat atatgtacct atatacagaa    5640
aaaaatacaa caaatcata aaagcactta tctttgaaag aggagttaca gcaattttat       5700
ttagttcttt attgctttgc tatatattct aaattttttt caatgaatat atatcacttt      5760
taaaaaaatt caatggtctt tcttataaat tatctttggc agcatgcgtt tttatatata      5820
catataaaat gtatgggaaa tttttaaagg atacattaaa ttaaagcaaa atatacaaac     5880
aaaaaatcag aatacaaaaa gataaaaaga ttgggaaggg agggagggag taaggaggaa    5940
gggtgggtgg gtatagagaa ataccaaaa taatggtaag aagtggggtc ttgacacttt     6000
ctacactttt tttaaataaa aaaaatttt ttctctctct tttttttttt tagagacgaa    6060
gtctcgctat gttgcccagg ctggtcttga actcctggga tcaagagatc ctcctgcctc    6120
agcctcccaa ggtgcttgga ttacaggtgt gagccaccac gcctggtcac tttctcacct     6180
ttaatatata tatttttttca ttttcaatgt cattttttatt agttaattta taatacccat    6240
tcaccattat attcaaagtc tatttgaaga aataaaccag aaagaatgaa atactctagc    6300
tcacatgcta ttcaatacta aattacccttt caaatcacat tcaagaagct gatgatttaa    6360
gctttggcgg tttccaataa atattggtca aaccataatt aaatctcaat atatcagtta    6420
gtacctattg agcatctcct tttacaacct aagcattgta ttaggtgctt aaaatacaagc   6480 agcttgactt ttaatacatt taaaaataca tatttaagac ttaaaatctt atttatggaa     6540
ttcagttata ttttgaggtt tccagtgctg agaaatttga ggtttgtgct gtctttcagt    6600
ccccaaagct cagttctgag ttctcagact ttggtggaac ttcatgtatt gtcaggttgg    6660
cccgtaatac ctgtgggaca acttcagccc ctgtgcacat ggccaggagg ctggttgcaa    6720
acattttcag gtaggtggac caggacatgc ccctggtcat ggccaggtgg aggcatagtg    6780
ctatacagca ggcagaagtc aatattgatt tgttttttaaa gaaacatgta ctactttcat    6840
aagcagaaaa aatttctatt cttgggggaa aagattatgc cagatcctct aggattaaat    6900
gctgatgcat ctgctaaacc ttcacatatc agaacatatt tactatagaa agaatgaaaa    6960
tgggacattt gtgtgtcacc tatgtgaaca ttccaaaaat attttacaac aactaagtat    7020
tttataaatt ttatgaactg aaatttagtt caagttctag gaaaatacaa accttgctag    7080
```

```
atattataaa aatgatacaa tatatattca tttcaggctc atcagaatat atctgttatc    7140
acttgacaag aatgaaaatg caccattttg tagtgcttta aaatcaggaa gatccagagt    7200
actaaaaatg acttcttcct tgaagcttac tcaccaactt cctcccagtt actcactgct    7260
tctgccacaa gcataaacta ggacccagcc agaactccct tgaaatatac acttgcaacg    7320
attactgcat ctatcaaaat ggttcagtgc ctggctacag gttctgcaga tcgactaaga    7380
atttgaaaag tcttgtttat ttcaaaggaa gcccatgtga attctgccca gagttcatcc    7440
cagatatgca gtctaagaat acagacagat cagcagagat gtattctaaa acaggaattc    7500
tggcaatata acaaattgat ttccaatcaa aacagattta cataccatac ttatgtcaag    7560
aagttgtttt gttttattgc atcctagatt ttatttttt gatttatggt ttactttaag    7620
cataaaaaat ttgtcaatac aactcttccc aaaaggcata aacaaaaatt cataaaactt    7680
gcatcacttg agatacttca ggtatgaatt cacaactttg ttacaactta ctatatatat    7740
gcacacatat atatatattt gggtatattg gggggttct aatttaagaa atgcataatt    7800
ggctatagac agacagttgt ctggaatgaa atcaatact tttgctataa tcgattactg    7860
aaataatttt actttccagt aaaactggca ttataatttt ttttaatttt taaaacttca    7920
taattttttg ccagactgac ccatgtaaac atacaaatta ctaataatta tgcacgtcac    7980
atctgtaata atggccttca tgtaaacatt tttgtggttt acacataaaa tctctaatta    8040
caaagctata ttatctaaaa ttacagtaag caagaaaatt aatccaagct aagacaaatac   8100
ttgcaacatc aattcatcat ctgtgacaag gactgcttaa gtctctttgt ggttaaaaag    8160
gaaaaaaaaa aaaagacat gttggccaga tgcggtggct cacacctgta atcccagcac    8220
tttgggaggc tgaggtgggc ggatcacccc tggcctgccc aacatggtga accccgtct    8280
ctactaaaaa cacaaaaatt agctgggcgt ggtggcgggc gcctgtaatt ccagctactc    8340
gggaggctga ggcaggagaa ttgctagaac ccaggaggca gagattgcag tgagctgaga    8400
ttgcaccatt gcactacagt ctgggcaaca aaagtgaaac tccatcttaa aaaaaaaag    8460
acaatgttcg tgggtccaaa caagacttaa tggaagtgag tctaaaaatg agctatgtgg    8520
gccaggcgta gtggctccca cctgtaatcc cagcactttg ggaggccgaa gcaggcagat    8580
catgaggtca ggagatggag accatcctgg ccaacacggt gaaatcctgt ctctacaaaa    8640
attagctggg cgtggtggtg cctgcctgta atcccagcta ctcagaaggc tcaggcagga    8700
gaatcgcttg aaccagggag tcggtggcta gagtgagccg agatttgcat cactgcactc    8760
ctgcctggtg acagagcaag actccatctc aaaaaaaaca aacaaaaata aaagataaaa    8820
atgagctatg tgaattaaaa gaggtataac aatagataaa ccatatttta tttaattcct    8880
agtaatgagt aatatttcca aacttctgga atgggcagaa attgctagtt ggcatatttt    8940
taccttttat attcagatac attaaaattc tcaaaaaaaa acacctcaaa gcagatgatc    9000
cgccatctcc ttggataatt tgtgttaact caggataaca gaaaaccaaa attatgagtt    9060
actgatgcaa tattcctaaa tgtaaaaata attaaagcta atagtagatt catcttccaa    9120
tttcatatca gtcttacaaa taaactacat atataacttg cttgccttcc cttctgaggg    9180
ataaagctgt tagaagaatt aaaatcagca ttccttgacta ttcaaccaag ggagggataa    9240
attattactc attctaggga catgggctca taactactac atgtgtaagg acatgaattt    9300
acccaatatt acaattttc cttttattag tgtgtacagt ggaagaatag acatgttcac    9360
tctgacaaa aaaaaaatta tacttatcag ttatcagaag cacaatgctg aagacagtag    9420
ttccataaca atttgaagta tgtgatcgaa ctagtagatt atcttagtag tagtgaatta    9480
```

| | |
|---|---|
| ttgtaaatgt tagtaatttg gcagccactg ggcagaaaaa taagaattga ggctcaatat | 9540 |
| tgatattaat ggtggtgatt gacacataaa ttttatcaag tctacacaat ataaaattac | 9600 |
| agaaaggtag aagagtatac cagtacaact tcaacatatc ttcactacaa gggagtaaaa | 9660 |
| tgacatggcc tagttactat ctaatgaact gcagaaaact aaaagaaaac tccaaggcaa | 9720 |
| ctcttctctg ctgatctggt tggtcctttt cctaccttt gcaataccca gatacaaaca | 9780 |
| atggatagaa aacaaagtag acttgtagta tgcaggtcac agtgctaaat tcacagaaag | 9840 |
| aaaccctga actgaactgc tctatttcct ggtggtcaca aagagtaatt ctggtttaca | 9900 |
| cctacagatt gatgtcaatc tacaccctgt tgataacagt gtggccaagg acaaaaaaaa | 9960 |
| ggtgctccgt tttaccaatt ctgtaaaaaa ttattggcag ggtaagctcg gctagggcag | 10020 |
| gattacattt ctaggactac catccccgaa atttagaaga tattatatcc acataaagca | 10080 |
| tatctttcac attaatttgc aaaaatctaa aagcttttc ttagctcaag tgtgtccaag | 10140 |
| tttaccctgg cagtttaaaa cgatagttac aagcagcatg ggttgtatca gacacatttg | 10200 |
| agggccaatt tcatgtaagt gatattgggc aagttacttc aactatctgt gcctccaagg | 10260 |
| tcatactagt gtttatttac ctaaagggta cctgttatgt aactttaggg tgtttacatt | 10320 |
| agataatgcc tgcaaaatat ttacttcaac gcctaaaaca tagttaagta ttcaataaat | 10380 |
| acctactatt gtcactacta acttaaaagt ttagagatta agagcagaat ctggggtgag | 10440 |
| acaaacttag gttcaaatcc tagtattgtt gggtaatctt gggcaagtta cttaacctct | 10500 |
| ctgatttgtg taatttaaaa aattagttaa tatacataac agggcttaga agagtatcta | 10560 |
| gcacatagca ccatttaagc atttgttatt gctaacatgc aaacaattta agggaaagaa | 10620 |
| attttttaaa aaggaagagg gatttgcaaa ctaaaaacaa tgagtatctt atgttcaaag | 10680 |
| aaaactaaca aacagccagc tctagcaata attaaattca ctatatactg gggcaggcat | 10740 |
| cacaccccaa agctaaaagc gtctacctag gccaggcacg gtggctcatg cctgtaatcc | 10800 |
| cagcactttg ggaagcagag gcgggcagat cgcttgagct caggagttca agaccagcct | 10860 |
| ggacaacatg gcaaaacacc atctctacaa aaaatacaaa tattaggccg ggcgcagtgg | 10920 |
| ctcacgcctg taatcccagc actttgggag gccaaggcgg gtggatcacc tgagatcagg | 10980 |
| agttcgagag tagcctggcc aacatggtga aacctcgtct ctattaaaaa tacaaaaaat | 11040 |
| tagccaggca tggtggcagg cgcctgtaat cccagctact caggggggatg aggtaggaga | 11100 |
| atcgcttgaa cccgggaggc agaggttgca ctgagccgag atcatgccac tgtactccag | 11160 |
| cccgggcaac aagagcgaaa ctccatctca aaaataaat aataaataa ataaaataaa | 11220 |
| gtacaaatat tagccaggga tggtggtgcg cacctgtagt cccagctact gggaggctg | 11280 |
| aagtgggaga tcccctgag cctggggaga atcacccgag cccgggaagt cgaggctgca | 11340 |
| gtgagcagtg attgtgccac tgcactccat cctaggtgac agagtgagac cctgtctcaa | 11400 |
| aaaaagaaa ttggcagaat taagtaagtt gatgtttaga gatgaaaaat caacattttt | 11460 |
| tcctcagcaa ctgaataaaa acaacagcca ctaccatttt tttgagtacc tatttgtagc | 11520 |
| ctatttttta actggtatta ctcgagagag agagagctag gttcgagaca gagctccttc | 11580 |
| tcttaataac tgtatgacct agggtatgtc tgttagcctc tctgaggctt caaaggttcc | 11640 |
| tcatctgtaa aatggtaata atcataccat tgctacaggg ctgttttgaa gactaattag | 11700 |
| gactatgtaa gtaaacatga tgatggctat tattactgtt ccccgccagg ggccatgcaa | 11760 |
| gggttgctga ttcacataga ctgtcttata atcctctcaa taactccaag aggtagccag | 11820 |

```
cacctcagat atacataaaa tgacttaagc ccagagaggt gaagtaagtt gcccacagcc    11880
acacaactag taaatagccc aaacaagctg gattcccagt tagactccgt taatagcact    11940
gctctttacc ttaagtcatt acaatgccta atatgaaata gaatcgcttc tttcttaggg    12000
ttcaagtggt taattattta atgtattcat tcaacaaacc atcatcgagg acctcttaca    12060
agccaagtac tgtgctaagt gctagagtta cggcggtgat tcctgcccct aaaaagtttt    12120
agtgggagaa acaacaggta accaggtcat tgccaaaaca acaaaaataa tcataataaa    12180
gcaggctaaa gcatatttaa ctggccgggg ttttgactat tttagcaagc atgatcagaa    12240
cggttgagga gggaggccag cagcttggcc ggttcaacaa acaagaaaaa accagtgagg    12300
gtggagctaa gataccagag gctgattacg gttaagaatg ttcttgaagg taaggaccag    12360
attctcattt tctatatcct ggggcatcgg tcagcatgga atctggattc tagcacatgt    12420
gaatttcggc ttgaaatgac ctaatgcctt ttccctagtt ccttcgtgtg tcaaatacgc    12480
atggttaccg ctaccagagc tgtagtgggg cttcaatgag gccatgagca tctccataaa    12540
gatgaactac agtgtgtgca aaactaaagg caaaacctgg tccccacacg ccctcccagg    12600
tggtcgcttt ccgtgccgag gcccctccag aggtgccccg agaacctcac catcgcaccc    12660
caaacttcca gggaagggcc tctcccgaga aagcccccac gccccaccc cgcgccatca    12720 ttcccgaatc tgccctcggc ccctccccgc agcacgctcg caggcggcac atgtcaacca    12780
aaacgccatt tccaccttct cttcccacac gcagtcctct tttcccaggg ctcccccgag    12840
gagggaccca ccccaaaccc cgccattccg tcctccctgc cgccctcgcg tgacgtaaag    12900
ccgaacccgg gaaactggcc gccccgcct gcggggttcc ctgggcccgg ccgctctaga    12960
actagtggat cccaattgaa ggcctggtct aaatgactcc aaaatcacca cttaattcaa    13020
gagactgatt tccctgagtc aggcccctta agcagctat ttcaatggga cagggaaaca    13080
accctaggat ctggattaga atcacttggg ggctgccaca ccccagggc tctgatcctg    13140 cccttctccc acacgcacat tcacatactg ctgcagtgac cttccatttc taatgggttc    13200
ctgggccatc tgtcaggtat agggaatgga aaaggggttg gggaggctct gcttcagaaa    13260
gtttgtgtca ggggctccca gagcctccac agatagatag caggggtccc caccctacca    13320
tggcagctat aaatgtgatc aacatttatt ggcctaggat acagcagtta gcaaaatgcc    13380
tgatgtagtt cccactccgt ggaggttgca ggctagctct ttcctaatga gctttacagc    13440
agaagctgtt ttatcgttaa gtgccccaca gagacacttt accaggaggc tgggagagtt    13500
ctccagattt gggagaggcg cagagacagt gtgtgagccg agccctgtct cagcaatcca    13560
cctggaggag ctagagtatc ctcctccctt taccattcag accgagagaa aaagcccagc    13620
ttgtgtgcac cctcgtgggg ttaaggcgag ctgttcctgg tttaaagcct ttcagtattt    13680
gttttgatgt aaggctctgt ggtttgggg gaacatctg taaacattat tagttgattt    13740
ggggtttgtc tttgatggtt tctatctgca attatcgtca tgtatattta agtgtctgtt    13800
atagaaaacc cacacccact gtcctgtaaa ctttttctcag tgtccagact ttctgtaatc    13860 acatttttaat tgccacctcg tatttcacct ctacatttga aatctggcgt ctgtttcaag    13920
ccagtgtgtt ttttcttcgt tctgtaataa acagccagga gaaagtgcc tctatgtttt    13980 tatttttcaa gggagtattc agtacctaca aacccaagtc aggaagcctg ctagtggctt    14040
tggttctttc agaggctgct cgatgccttg tgtgtcagaa agaaagattc agcagttttg    14100
catcatggca aagaagcctg ttattttggg gctcagcccc tcatttata gaggatgaaa    14160 cagaggggga tgggaggtca caaagacaac tgccccggga gcaggtgtgg gggagacttg    14220
```

```
ccctgagggt ctagacgctc tgcaccaccg tcctgtctcc cttgctgaag accacacatg   14280
cccttctttg accagaccct gccacctgat aggccaggac ctggtaggcg ggtacccagg   14340
tttcatggat ggaaccacat ctccccaaaa gtggggaggt agctactggg atgcacgcct   14400
cccgccatgt gctataggag agcagctgaa gcaacagttg ggatcagatg tagtcacaat   14460
tgaatgcatc atcacattta tccctctaag tggctgggag agttgatatc ctcatcccta   14520
aggtacaaaa tgttccaatt tgatcagtgg ctttcaggag ctgagaaagg catgtgctct   14580
gaggcagagc tgttatgtcc cgcagagcct aaaaatgctc taagaacatg ctccctgcca   14640
aaattctcaa tggctgtgac aagggacaac gatcgaccaa tgggggtgga agcagacctc   14700
cgcagtccag gggccagagc taggacagag gggtcggaga aagagtcatt tcccaacac    14760 tccagctctt ggccagtcct cacacagtcc cctcctgctt cctgctgaga gagatatcct   14820
cataggtctg ggtaaagtcc ttcagtcagc tttcattccc tgtcaccaac tttgtctctg   14880
ttctccctgc ccgtctcagg cagcactcct caggaaacct ctccaagagc cagcctcact   14940
gcagcgccca ctattgtccc tctgcctcaa gtgtcccatc catgccaggc cccaggcagg   15000
ctgcagcttt ccctcagggc cacaccaaag cacttgggct cagctgtgct gtcccctcc    15060 atcactgagc tcagggcag caggggtggg gtgccaggag gcccattcac ccttctctgg    15120
ctctgtgttg gacccacctg cccagccact gctgcttaga acctacccgc tgggaaaatg   15180
aagccctccc ggaggggcca cctcaacctg agagcctcac ggatcacagt tgtccccact   15240
cagctctgcc agccctcaga gacccataga taaaagctga gcttggctcg cagagctggt   15300
tccatcttcc attcccagag ggttcaactt cctaccccaa ccacacaggg aacctcaagg   15360
ctgagccagt gtgggctgca gtgcagacca gcttcctgga cacgtcctgc cacctgaccc   15420
caggctggcc tcactgcccc tggcactcct gaccctatcc tcattcctcc tggcagtgcg   15480
tgttctgcca ttccgctttc ccttagctgt cctctcactg tactgtcagc ttctcctttt   15540
ccaggtgccc cccaggggct ttccacatga ccctgtcacc ccacagccca tccagcacca   15600
attccagctc tctgccaccc ttcaaaggag tgacagtgcc ctgcttcacc tcccactcac   15660
ccctcaaccc agagcaatct ggctccagtc ttgcctcctt ccccctaagt actctagtca   15720
cagttccaaa ttcctcctgg tcataaagcc aaatgaagct tcctggtcct cagcggactt   15780
gccacttcag cagtactgga ctctctcctc ccagaaacct gtttcccctt ggctcctgga   15840
gcccacactc tgctggaatc cttctgcctc tctggcctgt agcctggccc tctctcccaa   15900
cctgaggtcc attctctcct gctcctccac aagatgttgc tccttccatt acttcctccc   15960
tctcaaccaa agctccttca ttagctcttt atcttctggt ttcttcccct gggcagacga   16020
atggattcaa gagcctgtgg cccagcagcc cagcactcca ggatctcagc acttcagcat   16080
cccagtaccc tagcatctca ataccccagc accccagcac catagtattc cagcaccca    16140 ttgtccaagc atctcagcac tccagcatcc cagcacccca acactccagc agcccagaat   16200
ctcagcaccc tagcactgca gcatctcagg accccagcac ttcagcatcc cagcacacta   16260
gtactccagc atctcggcac cccagcacct aggcatccca acaccagca ccccagcact    16320 taagcatccc accactacag tatctcaaca ctccagcacc ccagcaccat agtgttccag   16380
caccccagca tcccaacacc ccagcactta agcatcccaa cacctcggca tcccaacacc   16440
ccagcactgc agcatctcag caccttagca tcccagtgcc ctagcatctc aatgctccag   16500
cacaccagta ctacagtatt ccagcacccc agcactccag catctcagca ctgcagcact   16560
```

```
gcagcactcc agcatcccaa aatcccagca tcccaacacc ccagcagacc agcagaccag    16620
catctcagca ccgcagcatc caaggactat cccagcatcc cagcaaccca gcacctcagc    16680
atcccaacac cccagcattt cagcatggca acaccccagt accccagcac ttcagcaccc    16740
cagtatccca gcatctcagc gacccagtat cacaaaacct cagcatccta gcaccccagc    16800
accccagcac cttagcacct tagcatccca gcatctcagc gcctcagcat cttgatattc    16860
tggctgaggt cagcgtggtg tatctagtca gggtcctaac tttcacttcg cagggaaatg    16920
ctgctggact gggtctcatg ttgggctgaa gctctctaga ccccttgaag acagcataaa    16980
agagcttgga gacgctgggt gtcccccatg gaagagttca ctctcatcct gctttgacaa    17040
cagccttctc tggggtccct cacgggcccc tctttcttac tgcaagtttg tctctgagaa    17100
gactgtgatg cagaagtcac tcagctgcct gtggctcctg aagagctgaa ggtgaggcc     17160 tgtaggcctc cctatgagag gcgcagaaaa aaccatgatt gctagtgggg aggtgctccc    17220
tctacaaccc actccataat ctgccccgc ccagctctga ggccagcccc aggggaaaat     17280
gccagatccc cagggaggtg tgtgagacct caggggctcc ctcctcccctt acagcaggct   17340 caggcccctg ggggcctcag ggccaaggtc tgtgggtaag ctactatctc tcacttgtcc    17400
tctagccaca aaagccaggg agatctggca atggacatga ggttctgaag aagcacatat    17460
gactggcttc ctaatgcgtg gttgttcagt gattcaataa acacgcatgg gccaggcatg    17520
gggaaataga caaacatgat ccccaacctc tcccagagtg aactgggagg gaggagtgtt   17580
catccctcag gattacacca gagaaacaaa ccagcaggag atatatatgg ttttgggggg    17640
tcaagaaaga ggaaaaacct ggcaaggcaa gtccaaaatc ataggacagg ctgtcaggaa    17700
gggcagcctg gaacctctca agcaggagct gatgctgcag tccacaggca gaatttcttc    17760
ttcctcgggg aaatctcagc tttgttctta aggcctttca actgattggc tgaggtctgc    17820
cccttccccc acattctcca ggataatctt ccttacttaa agtcaactat taatcacagc    17880
tacaaaatcc cttcacagct acacatagat cagtgtttga ttgacgaaca gccctacag    17940 cctagccaag ttgacacata aaactaacca tcacagggg acaaatgatg taaacacatc    18000
aacaaataaa acagtaacaa gttaaggtct atggaaaaaa cacagaaggg gcagagagaa    18060
agaaagcaag aaggagagtc ccagtttgct agggcttgtg ggaagtgggg agcagttctc    18120
tttagctagg atatttggga aaggcatatc tgaaggagtg atatttgagc ttagattaaa    18180
agatgggaag gagcaagcca tgcaaagagc taggatgttc caagcagaga cggaacagca    18240
agtgcaaatg tcaggaggaa tagaaggagg ctggtgggtg gggtccagtg agcaagagga    18300
gggcaggcag gagagggggat ggggaggtgg gcaggcccag accacccagg gccctggaga    18360
ctatcctgat ccaacaaggg aagccttgag tcacttcagt gtccatgtgg agaatggacc    18420
tcagactgaa tgagggaggc agtaaggagg gcctctacct ccagggcttc gccctgtgga    18480
ctgcgcatag acatctccaa ctcagaaagt ctgaaccaaa cttttccatag ttcccccaag   18540 tctgggcatc ctcctactca gtgaaaggca gccatcacac ctccctgccc tgctcccgga    18600
tgccccaaat cctcttggtc tccaagtcca gaacctgaga cttgtccttg atgtttgtct    18660
ttccctcacc ctttctgtat tctgggaaga tgggttttttt tccccagat gaatctgtaa    18720 aacttctgtg atcacaataa aaattctggc agtattattt tctggaacat gacaaagtga    18780
ttcaaaatta tttatctgga agactacaaa acaagaatag ccaggaaatt tctaaaaaga    18840
aagaagaagg aggaggagaa agaaggagga ggaaaaggag gagaagaaga aaagaaaaag    18900
aaccaagaaa gggttctagc tctaccaaat attaaaacat atcatgaagc tatttaaaac    18960
```

```
aatatggttg tggatactga aaaagatgtg aataaagtgg aaggaaaata aatagaaatg    19020
cacatgggga ttgagactgt gaaaaaggca gcatctcaca tcagtgaggg atgttcaaca    19080
cctggtgttg ggaaaactgg ctagtcattt aaaccaaaca actgggtcct ctacctcact    19140
cctgacatta agatacattt agatgattca aagagtaaga cagaaaaaat aacacgtgaa    19200
aacactatca gaaacaacg tgggccaggt gtggtgggtc acgcctgtaa tcccagcact     19260
ttgggaggcc gaggcagaca gatcacctga ggtggggagt tcaagaccag cctgaccaac    19320
atggtgaaat cctgtctcta ctaaaaatac aaaattagct gagcgtggtg gcgcatgcct    19380
gtaatcccag ctactcagga ggccgaggca ggagaatcac ttgaacctgg gaggcagagg    19440
ttgtggtgag ccgagatcac gccattgcac tccagcctgg gcaacaagag tgaaaatcca    19500
tctaaaaaaa aaaaaaaaag ccaaggtgga tattttata gtatcagggt agatcaagct     19560
tctccaatca tgacatgaaa cccagaaacc ataaagaaa agaatgataa aattgcccac     19620
gtaaagtaaa aagcttgcac acagaaaaac accatacagg ttacaagatg agcagcaaaa    19680
tcagagaaaa aacattgcaa ttcaggacac acagaggcta ttgttcctaa tatttaaaaa    19740 taaagtagt ggattgtcta caaaaagatg aagacaagaa tttcagaaaa ccaaatactg      19800
catgttttca cttacaagtg gaagctaaac actgagtaca cgtgtacaca aagaatggaa    19860
ccataggcca ggcaccgtgg ctcacgcctg taatcccagt actttgcgag gccgaagcgg    19920
gcggatcacc tgaggtgagg agttcgagac catcctggcc aacatggtga aacccagtct    19980
ctactaaaaa tacaaaaatt agccgggcgt ggtggtgggt gcctgtaatc ccagctactc    20040
gggaggctgc ggcagtagaa tcgcttgaac cctggaggtg gaccttgcag tgagccgaga    20100
tcgcaccact gcactccagc ctgggcaaca gagtgagact ccatctcaaa aaaaaaaaaa    20160
aggaatagaa caatagacac tggggcctac ttgagggagg agggtgagga tcaaaaacct    20220
gcctatcagg tactatgctt attacctggg tggtgaaata atctgtacac caaaccccag    20280
tgacatgcaa tttaccgatg taacaaacct gcccatgtac ccgctgaacc taaaataaaa    20340
gttggaaaaa aatatagaaa ttttctttgt aatagccaaa aactgcaaac agcccaggtg    20400
tctattagta gaatgcataa acaaactcgg gcatgttcat acaatgtaaa actactcatc    20460
aataaaaagt gatacttctc agcaatgaaa agaaactagc tactgatacc agctacaaca    20520
tggatggatt tcaagtgctt tatgatgaga gcaagaagcc agacacaaaa gtgtctatat    20580
atatatacag tatatatacg tatatataca catatataca gtatatatat acatatacat    20640
gtatatatat actgtatata tactgtatat atatacacag tatatatata catatataca    20700
gtgtatatat actgtgtata tacatgtta tatactgt gtatatatac atgtatatat       20760
actgtgtata tacatgtta tatatactgt gtatatatac atgtatatat atgtatactg     20820
tatatatact gtatatatat atacacatat atacagtata tatatacagt atatactgta    20880
tatatacagt atatacgtgt atatatacat atatacagta tatgtaaaa tatacatata     20940 tacagtatat atgtaaatat acatatatac atgtatatat atacactata tatatacata    21000
tatagtgtat atatacatat atacatgtat atatttacta tatgattcca tttatataaa    21060
gtgccaaaac agtcaaaaat aatctatgtg gaaaaaatca acaaagggat cccccgggct    21120
gcaggaattc gatggcgcgc cgacgtcgca tgcagttagg gataacaggg taatacgacc    21180
atggcatgtc ctctagactc gagcggccgc aataaaaat ctttatttc attacatctg      21240 tgtgttggtt ttttgtgtga atcgtaacta acatacgctc tccatcaaaa caaacgaaa     21300
```

```
caaaacaaac tagcaaaata ggctgtcccc agtgcaagtg caggtgccag aacatttctc   21360
tatcgaagga tctgcgatcg ctccggtgcc cgtcagtggg cagagcgcac atcgcccaca   21420
gtccccgaga agttgggggg aggggtcggc aattgaaccg gtgcctagag aaggtggcgc   21480
ggggtaaact gggaaagtga tgtcgtgtac tggctccgcc ttttcccga gggtggggga    21540 gaaccgtata taagtgcagt agtcgccgtg aacgttcttt ttcgcaacgg gtttgccgcc   21600
agaacacagc tgaagcttcg aggggctcgc atctctcctt cacgcgcccg ccgcctacc    21660 tgaggccgcc atccacgccg gttgagtcgc gttctgccgc ctcccgcctg tggtgcctcc   21720
tgaactgcgt ccgccgtcta ggtaagttta agctcaggt cgagaccggg cctttgtccg    21780
gcgctccctt ggagcctacc tagactcagc cggctctcca cgctttgcct gaccctgctt   21840
gctcaactct acgtctttgt ttcgttttct gttctgcgcc gttacagatc caagctgtga   21900
ccggcgccta cgtaagtgat atctactaga tttatcaaaa agagtgttga cttgtgagcg   21960
ctcacaattg atacttagat tcatcgagag ggacacgtcg actactaacc ttcttctctt   22020
tcctacagct gagatcaccg gcgaaggagg gccaccatgg gtcaccagca gttggtcatc   22080
tcttggtttt ccctggtttt tctggcatct cccctcgtgg ccatatggga actgaagaaa   22140
gatgtttatg tcgtagaatt ggattggtat ccggatgccc ctggagaaat ggtggtcctc   22200
acctgtgaca cccctgaaga agatggtatc acctggacct tggaccagag cagtgaggtc   22260
ttaggctctg gcaaaacccct gaccatccaa gtcaaagagt ttggagatgc tggccagtac   22320
acctgtcaca aaggaggcga ggttctaagc cattcgctcc tgctgcttca caaaaaggaa   22380
gatgaatttg gtccactga tatttaaag gaccagaaag aacccaaaaa taagacctttt   22440 ctaagatgcg aggccaagaa ttattctgga cgtttcacct gctggtggct gacgacaatc   22500
agtactgatt tgacattcag tgtcaaaagc agcagaggct cttctgaccc caagggggtg   22560
acgtgcggag ctgctacact ctctgcagag agagtcagag gggacaacaa ggagtatgag   22620
tactcagtgg agtgccagga ggacagtgcc tgcccagctg ctgaggagag tctgcccatt   22680
gaggtcatgg tggatgccgt tcacaagctc aagtatgaaa actacaccag cagcttcttc   22740
atcagggaca tcatcaaacc tgacccaccc aagaacttgc agctgaagcc attaaagaat   22800
tctcggcagg tggaggtcag ctgggagtac cctgacacct ggagtactcc acattcctac   22860
ttctccctga cattctgcgt tcaggtccag ggcaagagca agagagaaaa gaagatagaa   22920
gtcttcacgg acaagacctc agccacggtc atctgccgca aaaatgccag cattagcgtg   22980
cgggcccagg accgctacta tagctcatct tggagcgaat gggcatctgt gcctgcagt    23040 gttcctggag taggggtacc tggggtgggc gccagaaacc tccccgtggc cactccagac   23100
ccaggaatgt tccatgcct tcaccactcc caaaacctgc tgagggccgt cagcaacatg   23160
ctccagaagg ccagacaaac tctagaattt taccctttgca cttctgaaga gattgatcat   23220
gaagatatca caaagataa aaccagcaca gtggaggcct gtttaccatt ggaattaacc   23280
aagaatgaga gttgcctaaa ttccagagag acctctttca taactaatgg gagttgcctg   23340
gcctccagaa agacctcttt tatgatggcc ctgtgcctta gtagtattta tgaagacttg   23400
aagatgtacc aggtggagtt caagaccatg aatgcaaagc tgctgatgga tcctaagagg   23460
cagatctttc tagatcaaaa catgctggca gttattgatg agctgatgca ggccctgaat   23520
ttcaacagtg agactgtgcc acaaaaatcc tcccttgaag aaccggattt ttataaaact   23580
aaaatcaagc tctgcatact tcttcatgct ttcagaattc gggcagtgac tattgataga   23640
gtgatgagct atctgaatgc ttcctaaaaa gcgaggtccc tccaaaccgt tgtcattttt   23700
```

```
ataaaacttt gaaatgagga aactttgata ggatgtggat taagaactag ggaggggcta    23760
gctcgacatg ataagataca ttgatgagtt tggacaaacc acaactagaa tgcagtgaaa    23820
aaaatgcttt atttgtgaaa tttgtgatgc tattgctttta tttgtgaaat ttgtgatgct    23880
attgctttat ttgtaaccat tataagctgc aataaacaag ttaacaacaa caattgcatt    23940
cattttatgt ttcaggttca gggggaggtg tgggaggttt tttaaagcaa gtaaaacctc    24000
tacaaatgtg gtagatccat ttattagcta ggagtttcag aaaaggggc ctgagtggcc      24060 cctttttttca acttaattaa cctgcagggc ctgaaataac ctctgaaaga ggaacttggt    24120
taggtacctt ctgaggctga agaaccagc tgtggaatgt gtgtcagtta gggtgtggaa      24180
agtccccagg ctccccagca ggcagaagta tgcaaagcat gcatctcaat tagtcagcaa    24240
ccaggtgtgg aaagtcccca ggctccccag caggcagaag tatgcaaagc atgcatctca    24300
attagtcagc aaccatagtc ccactagttt catcaccacc gccaccccc cgccccccg       24360 ccatctgaaa gggttctagg ggatttgcaa cctctctcgt gtgtttcttc tttccgagaa    24420
gcgccgccac acgagaaagc tggccgcgaa agtcgtgctg gaatcacttc caacgaaacc    24480
ccaggcatag atgggaaagg gtgaagaaca cgttgtcatg gctaccgttt ccccggtcac    24540
ggaataaacg ctctctagga tccggaagta gttccgccgc gacctctcta aaaggatgga    24600
tgtgttctct gcttacattc attggacgtt ttcccttaga ggccaaggcc gcccaggcaa     24660
aggggcggtc ccacgcgtga ggggcccgcg gagccatttg attggagaaa agctgcaaac    24720
cctgaccaat cggaaggagc cacgcttcgg gcatcggtca ccgcacctgg acagctccga    24780
ttggtggact tccgcccccc ctcacgaatc ctcattgggt gccgtgggtg cgtggtgcgg    24840
cgcgattggt gggttcatgt ttcccgtccc ccgcccgcga gaagtggggg tgaaaagcgg    24900
cccgacctgc ttggggtgta gtgggcggac cgcgcggctg gaggtgtgag gatccgaacc    24960
caggggtggg gggtggaggc ggctcctgcg atcgaagggg acttgagact caccggtcgc    25020
acgtcatgaa tctagaacca tggcttcgta ccccggccat cagcacgcgt ctgcgttcga    25080
ccaggctgcg cgttctcgcg gccatagcaa ccgacgtacg gcgttgcgcc ctcgccggca    25140
gcaagaagcc acggaagtcc gcccggagca gaaaatgccc acgctactgc gggtttatat    25200
agacggtccc cacgggatgg ggaaaaccac caccacgcaa ctgctggtgg ccctgggttc    25260
gcgcgacgat atcgtctacg tacccgagcc gatgacttac tggcgggtgc tgggggcttc    25320
cgagacaatc gcgaacatct acaccacaca acaccgcctt gaccagggtg agatatcggc    25380
cggggacgcg cgcgtggtaa tgacaagcgc ccagataaca atgggcatgc cttatgccgt    25440
gaccgacgcc gttctggctc ctcatatcgg gggggaggct gggagctcac atgccccgcc    25500
cccgcccctc accctcatct tcgaccgcca tcccatcgcc gccctcctgt gctaccggc     25560 cgcgcgatac cttatgggca gcatgacccc ccaggccgtg ctggcgttcg tggccctcat    25620
cccgccgacc ttgcccggca caaacatcgt gttgggggcc cttccggagg acagacacat    25680
cgaccgcctg gccaaacgcc agcgcccgg cgagcggctt gacctggcta tgctggccgc     25740
gattcgccgc gtttacgggc tgcttgccaa tacggtgcgg tatctgcagg cggcgggtc     25800 gtggcgggag gattggggac agcttcggg gacggccgtg ccgccccagg gtgccgagcc     25860
ccagagcaac gcgggcccac gaccccatat cggggacacg ttatttaccc tgtttcgggc    25920
ccccgagttg ctgccccca acggcgacct gtacaacgtg tttgcctggg ccttggacgt     25980
cttggccaaa cgcctccgtc ccatgcacgt ctttatcctg gattacgacc aatcgcccgc    26040
```

```
cggctgccgg gacgccctgc tgcaacttac ctccgggatg atccagaccc acgtcaccac   26100
cccaggctcc ataccgacga tctgcgacct ggcgcgcacg tttgcccggg agatggggga   26160
ggctaactga gtatacccta ggattatccc taatacctgc caccccactc ttaatcagtg   26220
gtggaagaac ggtctcagaa ctgtttgttt caattggcca tttaagttta gtagtaaaag   26280
actggttaat gataacaatg catcgtaaaa ccttcagaag gaaggagaa tgttttgtgg    26340 accactttgg ttttcttttt tgcgtgtggc agttttaagt tattagtttt taaaatcagt   26400 acttttaat ggaaacaact tgaccaaaaa tttgtcacag aattttgaga cccattaaaa    26460
aagttaaatg agaaacctgt gtgttccttt ggtcaacacc gagacattta ggtgaaagac   26520
atctaattct ggttttacga atctggaaac ttcttgaaaa tgtaattctt gagttaacac   26580
ttctgggtgg agaataggdt tgttttcccc ccacataatt ggaagggaa ggaatatcat    26640 ttaaagctat gggagggttt ctttgattac aacactggag agaaatgcag catgttgctg   26700
attgcctgtc actaaaacag gccaaaaact gagtccttgg gttgcataga aagctgcctg   26760
caggcgttac ataacttacg gtaaatggcc cgcctggctg accgcccaac gaccccgcc    26820 cattgacgtc aataatgacg tatgttccca tagtaacgcc aatagggact ttccattgac   26880
gtcaatgggt ggagtattta cggtaaactg cccacttggc agtacatcaa gtgtatcata   26940
tgccaagtac gccccctatt gacgtcaatg acggtaaatg gcccgcctgg cattatgccc   27000
agtacatgac cttatgggac tttcctactt ggcagtacat ctacgtatta gtcatcgcta   27060
ttaccatgat gatgcggttt tggcagtaca tcaatgggcg tggatagcgg tttgactcac   27120
ggggatttcc aagtctccac cccattgacg tcaatgggag tttgttttga ctagttaccg   27180
gcggaaacgg tctcggttg agaggtcacc cgagggacag gcagctgctg aaccaatagg    27240
accggcgcac agggcggatg ctgcccctca ttggcggccg ttgagagtga ccaagagcca   27300
atgagtcagc ccggggggcg tagcagtgac gtaagttgcg gaggaggccg cttcgaatcg   27360
gcagcggcca gcttggtggc atggaccaat cagcgtcctc caacgaggag cgccttcgcc   27420
aatcggaggc ctccacgacg gggctggggg gagggtatat aagccgagtc ggcggcggcg   27480
cgctccacac gggccgagac cacagcgacg ggagcgtctg cctctgcggg gccgagaggt   27540
aagcgccgcg gcctgcccttc tccaggccaa ctcggagccc gtctcgtggc tccgcctgat   27600
cgggggctcc tgtcgccctc agatcggtcg gaacgccgtc gcgctcccgggg actacaagcc   27660 tgttgctggg cccggagact gccgaaggac cgctgagcac tgtcctcagc gccggcacca   27720
tggattggat ctggcggatc ctgttccttg tgggagctgc cacaggcgcc cattctgaag   27780
ttcagctggt tcagtctggc gccgaagtga agaaacctgg cgcctctgtg aaggtgtcct   27840
gcaaagcttc tggcggcacc ttcagcagct acgccatctc ttgggttcga caggcccctg   27900
gacaaggcct ggaatggatg gcagaatca tccccatcct gggaatcgcc aactacgccc    27960
agaaattcca gggcagagtg accatcaccg ccgacaagag cacaagcacc gcctacatgg   28020
aactgagcag cctgagaagc gaggacaccg ccgtgtacta ctgtgccaga agcggccacg   28080
gctacagcta cggcgccttt gattattggg gccagggcac cctggtcacc gtttctagcg   28140
gaggcggagg tagtggtggc ggaggttcag gcggcggagg atctcaatct gtgctgacac   28200
agcctccaag cgtgtcaggt gctcctggcc agagagtgac aatcagctgt acaggcagca   28260
gcagcaacat cggagccggc tatgacgtgc actggtatca gcagctgcct ggcacagccc   28320
ctaaactgct gatctacggc aacagcaaca gacccagcgg cgtgcccgat agattttccg   28380
gctctaagag cggcacaagc gccagcctgg ctattactgg actgcaggcc gaggacgagg   28440
```

```
ccgactacta ctgtcagagc tacgacagca gcctgtccgg cagctacgtt gtgtttggcg    28500
gcggaacaaa gctgaccgtg ctggaagcca agagctgcga caagacccac acctgtcctc    28560
catgtcctgc tccagaactg ctcggcggac cttccgtgtt cctgtttcct ccaaagccta    28620
aggacaccct gatgatcagc agaaccctg aagtgacctg cgtggtggtg gatgtgtccc     28680
acgaggaccc agaagtgaag ttcaattggt acgtggacgg cgtggaagtg cacaacgcca    28740
agaccaagcc tagagaggaa cagtacaaca gcacctacag agtggtgtcc gtgctgacag    28800
tgctgcacca ggattggctg aacggcaaag agtacaagtg caaggtgtcc aacaaggccc    28860
tgcctgctcc tatcgagaaa accatcagca aggccaaggg ccagcctagg gaaccccagg    28920
tttacacact gccacctagc agggacgagc tgaccaagaa tcaggtgtcc ctgacctgcc    28980
tggtcaaggg cttctaccct tccgatatcg ccgtggaatg ggagagcaat ggccagccag    29040
agaacaacta caagacaacc cctcctgtgc tggacagcga cggctcattc ttcctgtact    29100
ccaagctgac tgtggacaag agccgtggc agcagggcaa tgtgttcagc tgtagcgtga    29160
tgcacgaggc cctgcacaac cactacacac agaagtccct gtctctgagc cccggaaaag    29220
gtggcggtgg ctcttaccct tacgacgtgc cagattacgc cggctatccc tacgatgtgc    29280
ctgactatgc tggctacccc tatgacgtcc ccgactacgc ttaactagct acggaattcc    29340
ggctagctgg ccagacatga taagatacat tgatgagttt ggacaaacca caactagaat    29400
gcagtgaaaa aaatgcttta tttgtgaaat ttgtgatgct attgctttat ttgtaaccat    29460
tataagctgc aataaacaag ttaacaacaa caattgcatt cattttatgt ttcaggttca    29520
gggggaggtg tgggaggttt tttaaagcaa gtaaaacctc tacaaatgtg gtatggaaat    29580
gttaattaac tagccatgac caaaatccct taacgtgagt tttcgttcca ctgagcgtca    29640
gaccccgtag aaaagatcaa aggatcttct tgagatcctt ttttttctgcg cgtaatctgc    29700 tgcttgcaaa caaaaaaacc accgctacca gcggtggttt gtttgccgga tcaagagcta    29760
ccaactcttt ttccgaaggt aactggcttc agcagagcgc agataccaaa tactgttctt    29820
ctagtgtagc cgtagttagg ccaccacttc aagaactctg tagcaccgcc tacatacctc    29880
gctctgctaa tcctgttacc agtggctgct gccagtggcg ataagtcgtg tcttaccggg    29940
ttggactcaa gacgatagtt accggataag gcgcagcggt cgggctgaac ggggggttcg    30000
tgcacacagc ccagcttgga gcgaacgacc tacaccgaac tgagatacct acagcgtgag    30060
ctatgagaaa gcgccacgct tcccgaaggg agaaaggcgg acaggtatcc ggtaagcggc    30120
agggtcggaa caggagagcg cacgagggag cttccagggg gaaacgcctg gtatctttat    30180
agtcctgtcg ggtttcgcca cctctgactt gagcgtcgat ttttgtgatg ctcgtcaggg    30240
gggcggagcc tatggaaaaa cgccagcaac gcggccttt tacggttcct ggccttttgc    30300
tggccttttg ctcagggttc gaaatcgata agcttggatc cggagagctc ccaacgcgtc    30360
ggctagctag tagggataac agggtaataa gcgtcgacgg cgcgcccta ggggccggc     30420 ttaattaaat caagcttatc gataccgtcg aacctcgagg gggggcatca ctccgcccta    30480
aaacctacgt cacccgcccc gttcccacgc cccgcgccac gtcacaaact ccacccctc     30540 attatcatat tggcttcaat ccaaaataag gtatattatt gatgatgttt              30590
```

<210> SEQ ID NO 51
<211> LENGTH: 39752
<212> TYPE: DNA
<213> ORGANISM: Artificial Sequence
<220> FEATURE:

```
<223> OTHER INFORMATION: ICOSTAT
<220> FEATURE:
<221> NAME/KEY: misc_feature
<222> LOCATION: (5915)..(5917)
<223> OTHER INFORMATION: n is a, c, g, or t
<220> FEATURE:
<221> NAME/KEY: misc_feature
<222> LOCATION: (32912)..(32912)
<223> OTHER INFORMATION: n is a, c, g, or t
<220> FEATURE:
<221> NAME/KEY: misc_feature
<222> LOCATION: (34601)..(34601)
<223> OTHER INFORMATION: n is a, c, g, or t
<220> FEATURE:
<221> NAME/KEY: misc_feature
<222> LOCATION: (38163)..(38168)
<223> OTHER INFORMATION: n is a, c, g, or t

<400> SEQUENCE: 51
taacatcatc aattatacct tccattttgg attgaagcca atatgataat gaggggtgg      60 agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccgtgtaca caggaagtga caattttcgc gcggttttag gcggatgttg     240
tagtaaattt gggcgtaacc gagtaagatt tggccatttt cgcgggaaaa ctgaataaga    300
ggaagtgaaa tctgaataat tttgtgttac tcatagcgcg taatatttgt ctagggccgc    360
ggggactttg accgtttacg tggagactcg cccaggtgtt tttctcaggt gttttccgcg    420
tacgtcggcg gctcgtggct cttccgggaa aaggattctc ggaaagtggt tcgagtacgt    480
cggcggctcg tggctcttcc gggaaaagga ttctcggaaa gtggttcgaa gtacgtcgac    540
cacaaacccc gcccagcgtc ttgtcattgg cgtcgacgct gtacgggtc aaagttggcg     600 ttttattatt atagtcagct gacgtgtagt gtatttatac ccgtgagtt cctcaagagg     660 ccactcttga gtgccagcga gtagagtttt ctcctccgag ccgctccgac accgggactg    720
aaaatgagac atattatctg ccacggaggt gttattaccg aagaaatggc cgccagtctt    780
ttggaccagc tgatcgaaga ggtactggct gataatcttc cacctcctag ccatttgaa     840 ccacctaccc ttcacgaact gtatgattta gacgtgacgg ccccccgaaga tcccaacgag   900 gaggcggttt cgcagatttt tcccgactct gtaatgttgg cggtgcagga agggattgac    960
ttactcactt ttccgccggc gcccggttct ccggagccgc ctcacctttc ccggcagccc   1020
gagcagccgg agcagagagc cttgggtccg gtttctatgc caaaccttgt accggaggtg   1080
atcgatccac ccagtgacga cgaggatgaa gagggtgagg agtttgtgtt agattatgtg   1140
gagcaccccg ggcacggttg caggtcttgt cattatcacc ggaggaatac gggggaccca   1200
gatattatgt gttcgctttg ctatatgagg acctgtggca tgtttgtcta cagtaagtga   1260
aaattatggg cagtgggtga tagagtggtg ggtttggtgt ggtaattttt tttttaattt   1320 ttacagttt gtggttaa gaattttgta ttgtgatttt tttaaaggt cctgtgtctg       1380 aacctgagcc tgagcccgag ccagaaccgg agcctgcaag acctacccgc cgtcctaaaa   1440
tggcgcctgc tatcctgaga cgcccgacat cacctgtgtc tagagaatgc aatagtagta   1500
cggatagctg tgactccggt ccttctaaca cacctcctga gatacacccg gtggtcccgc   1560
tgtgccccat taaccagtt gccgtgagag ttggtgggcg tcgccaggct gtggaatgta    1620
tcgaggactt gcttaacgag cctgggcaac ctttggactt gagctgtaaa cgccccaggc   1680
cataaggtgt aaacctgtga ttgcgtgtgt ggttaacgcc tttgtttgct gaatgagttg   1740
atgtaagttt aataaagggt gagataatgt ttaacttgca tggcgtgtta aatggggcgg   1800
```

```
ggcttaaagg gtatataatg cgccgtgggc taatcttggt tacatctgac ctcatggagg   1860
cttgggagtg tttggaagat ttttctgctg tgcgtaactt gctggaacag agctctaaca   1920
gtacctcttg gttttggagg tttctgtggg gctcatccca ggcaaagtta gtctgcagaa   1980
ttaaggagga ttacaagtgg gaatttgaag agcttttgaa atcctgtggt gagctgtttg   2040
attctttgaa tctgggtcac caggcgcttt tccaagagaa ggtcatcaag actttggatt   2100
tttccacacc ggggcgcgct gcggctgctg ttgctttttt gagttttata aaggataaat   2160
ggagcgaaga aacccatctg agcgggggt acctgctgga ttttctggcc atgcatctgt    2220
ggagagcggt tgtgagacac aagaatcgcc tgctactgtt gtcttccgtc cgcccggcga   2280
taataccgac ggaggagcag cagcagcagc aggaggaagc caggcggcgg cggcaggagc   2340
agagcccatg gaacccgaga gccggcctgg accctcggga atgaatgttg tacaggtggc   2400
tgaactgtat ccagaactga gacgcatttt gacaattaca gaggatgggc aggggctaaa   2460
gggggtaaag agggagcggg gggcttgtga ggctacagag gaggctagga atctagcttt   2520
tagcttaatg accagacacc gtcctgagtg tattactttt caacagatca aggataattg   2580
cgctaatgag cttgatctgc tggcgcagaa gtattccata gagcagctga ccacttactg   2640
gctgcagcca ggggatgatt ttgaggaggc tattagggta tatgcaaagg tggcacttag   2700
gccagattgc aagtacaaga tcagcaaaact tgtaaatatc aggaattgtt gctacatttc   2760
tgggaacggg gccgaggtgg agatagatac ggaggatagg gtggccttta gatgtagcat   2820
gataaatatg tggccggggg tgcttggcat ggacgggtg gttattatga atgtaaggtt    2880
tactggcccc aattttagcg gtacggtttt cctggccaat accaacctta tcctacacgg   2940
tgtaagcttc tatgggttta acaatacctg tgtggaagcc tggaccgatg taagggttcg   3000
gggctgtgcc ttttactgct gctggaaggg ggtggtgtgt cgccccaaaa gcagggcttc   3060
aattaagaaa tgcctctttg aaaggtgtac cttgggtatc ctgtctgagg gtaactccag   3120
ggtgcgccac aatgtggcct ccgactgtgg ttgcttcatg ctagtgaaaa gcgtggctgt   3180
gattaagcat aacatggtat gtggcaactg cgaggacagg gcctctcaga tgctgacctg   3240
ctcggacggc aactgtcacc tgctgaagac cattcacgta gccagccact ctcgcaaggc   3300
ctggccagtg tttgagcata acatactgac ccgctgttcc ttgcatttgg gtaacaggag   3360
gggggtgttc ctaccttacc aatgcaattt gagtcacact aagatattgc ttgagcccga   3420
gagcatgtcc aaggtgaacc tgaacggggt gtttgacatg accatgaaga tctggaaggt   3480
gctgaggtac gatgagaccc gcaccaggtg cagaccctgc gagtgtggcg gtaaacatat   3540
taggaaccag cctgtgatgc tggatgtgac cgaggagctg aggcccgatc acttggtgct   3600
ggcctgcacc cgcgctgagt ttggctctag cgatgaagat acagattgag gtactgaaat   3660
gtgtgggcgt ggcttaaggg tgggaaagaa tatataaggt gggggtctta tgtagttttg   3720 tatctgttt gcagcagccg ccgccgccat gagcaccaac tcgtttgatg gaagcattgt    3780
gagctcatat ttgacaacgc gcatgccccc atgggccggg gtgcgtcaga atgtgatggg   3840
ctccagcatt gatggtcgcc ccgtcctgcc cgcaaactct actaccttga cctacgagac   3900
cgtgtctgga acgccgttgg agactgcagc ctccgccgcc gcttcagccg ctgcagccac   3960
cgcccgcggg attgtgactg actttgcttt cctgagcccg cttgcaagca gtgcagcttc   4020
ccgttcatcc gcccgcgatg acaagttgac ggctctttttg gcacaattgg attctttgac   4080
ccgggaactt aatgtcgttt ctcagcagct gttggatctg cgccagcagg tttctgccct   4140
```

```
gaaggcttcc tcccctccca atgcggttta aacataaat aaaaaaccag actctgtttg    4200
gatttggatc aagcaagtgt cttgctgtct ttatttaggg gttttgcgcg cgcggtaggc    4260
ccgggaccag cggtctcggt cgttgagggt cctgtgtatt ttttccagga cgtggtaaag    4320
gtgactctgg atgttcagat acatgggcat aagcccgtct ctggggtgga ggtagcacca    4380
ctgcagagct tcatgctgcg gggtggtgtt gtagatgatc cagtcgtagc aggagcgctg    4440
ggcgtggtgc ctaaaaatgt cttttcagtag caagctgatt gccaggggca ggcccttggt    4500
gtaagtgttt acaaagcggt taagctggga tgggtgcata cgtggggata tgagatgcat    4560
cttggactgt attttaggt tggctatgtt cccagccata tccctccggg gattcatgtt    4620
gtgcagaacc accagcacag tgtatccggt gcacttggga aatttgtcat gtagcttaga    4680
aggaaatgcg tggaagaact ggagacgcc cttgtgacct ccaagatttt ccatgcattc    4740
gtccataatg atggcaatgg gcccacgggc ggcggcctgg gcgaagatat ttctgggatc    4800
actaacgtca tagttgtgtt ccaggatgag atcgtcatag gccatttta caaagcgcgg    4860
gcggagggtg ccagactgcg gtataatggt tccatccggc ccaggggcgt agttaccctc    4920
acagatttgc atttcccacg ctttgagttc agatggggg atcatgtcta cctgcggggc    4980
gatgaagaaa acggtttccg gggtagggga gatcagctgg gaagaaagca ggttcctgag    5040
cagctgcgac ttaccgcagc cggtgggccc gtaaatcaca cctattaccg ggtgcaactg    5100
gtagttaaga gagctgcagc tgccgtcatc cctgagcagg ggggccactt cgttaagcat    5160
gtccctgact cgcatgtttt ccctgaccaa atccgccaga aggcgctcgc cgcccagcga    5220
tagcagttct tgcaaggaag caaagttttt caacggtttg agaccgtccg ccgtaggcat    5280
gcttttgagc gtttgaccaa gcagttccag gcggtcccac agctcggtca cctgctctac    5340
ggcatctcga tccagcatat ctcctcgttt cgcgggttgg ggcggctttc gctgtacggc    5400
agtagtcggt gctcgtccag acgggccagg gtcatgtctt tccacgggcg cagggtcctc    5460
gtcagcgtag tctgggtcac ggtgaagggg tgcgctccgg gctgcgcgct ggccagggtg    5520
cgcttgaggc tggtcctgct ggtgctgaag cgctgccggt cttcgccctg cgcgtcggcc    5580
aggtagcatt tgaccatggt gtcatagtcc agccctccg cggcgtggcc cttggcgcgc    5640
agcttgccct tggaggaggc gccgcacgag gggcagtgca acttttgag ggcgtagagc    5700
ttgggcgcga aaataccga ttccggggag taggcatccg cgccgcaggc cccgcagacg    5760
gtctcgcatt ccacgagcca ggtgagctct ggccgttcgg ggtcaaaaac caggtttccc    5820
ccatgctttt tgatgcgttt cttacctctg gtttccatga gccggtgtcc acgctcggtg    5880
acgaaaaggc tgtccgtgtc cccgtataca gactnnngtt ttgagaggcc tgtcctcgag    5940
cggtgttccg cggtcctcct cgtatagaaa ctcggaccac tctgagacaa aggctcgcgt    6000
ccaggccagc acgaaggagg ctaagtggga ggggtagcgg tcgttgtcca ctaggggtc     6060
cactcgctcc agggtgtgaa gacacatgtc gccctcttcg gcatcaagga aggtgattgg    6120
tttgtaggtg taggccacgt gaccgggtgt tcctgaaggg gggctataaa aggggtggg     6180
ggcgcgttcg tcctcactct cttccgcatc gctgtctgcg agggccagct gttggggtga    6240
gtactccctc tgaaaagcgg gcatgacttc tgcgctaaga ttgtcagttt ccaaaaacga    6300
ggaggatttg atattcacct ggcccgcggt gatgcctttg agggtggccg catccatctg    6360
gtcagaaaag acaatctttt tgttgtcaag cttggtggca aacgaccgt agagggcgtt    6420
ggacagcaac ttggcgatgg agcgcagggt ttggttttg tcgcgatcgg cgcgctcctt    6480
ggccgcgatg tttagctgca cgtattcgcg cgcaacgcac cgccattcgg gaaagacggt    6540
```

```
ggtgcgctcg tcgggcacca ggtgcacgcg ccaaccgcgg ttgtgcaggg tgacaaggtc    6600
aacgctggtg gctacctctc cgcgtaggcg ctcgttggtc cagcagaggc ggccgccctt    6660
gcgcgagcag aatggcggta gggggtctag ctgcgtctcg tccggggggt ctgcgtccac    6720
ggtaaagacc ccgggcagca ggcgcgcgtc gaagtagtct atcttgcatc cttgcaagtc    6780
tagcgcctgc tgccatgcgc gggcggcaag cgcgcgctcg tatgggttga gtggggacc     6840 ccatggcatg gggtgggtga gcgcggaggc gtacatgccg caaatgtcgt aaacgtagag    6900
gggctctctg agtattccaa gatatgtagg gtagcatctt ccaccgcgga tgctggcgcg    6960
cacgtaatcg tatagttcgt gcgagggagc gaggaggtcg ggaccgaggt tgctacgggc    7020
gggctgctct gctcggaaga ctatctgcct gaagatggca tgtgagttgg atgatatggt    7080
tggacgctgg aagacgttga agctggcgtc tgtgagacct accgcgtcac gcacgaagga    7140
ggcgtaggag tcgcgcagct tgttgaccag ctcggcggtg acctgcacgt ctagggcgca    7200
gtagtccagg gttccttga tgatgtcata cttatcctgt ccctttttt tccacagctc      7260 gcggttgagg acaaactctt cgcggtcttt ccagtactct tggatcggaa accgtcggc     7320 ctccgaacgg taagagccta gcatgtgaaa ctggttgacg gctggtagg cgcagcatcc     7380 cttttctacg ggtagcgcgt atgcctgcgc ggccttccgg agcgaggtgt gggtgagcgc    7440
aaaggtgtcc ctgaccatga ctttgaggta ctggtatttg aagtcagtgt cgtcgcatcc    7500
gccctgctcc cagagcaaaa agtccgtgcg ctttttggaa cgcggatttg gcagggcgaa    7560
ggtgacatcg ttgaagagta tctttcccgc gcgaggcata agttgcgtg tgatgcggaa     7620 gggtcccggc acctcggaac ggttgttaat tacctgggcg gcgagcacga tctcgtcaaa    7680
gccgttgatg ttgtggccca caatgtaaag ttccaagaag cgcgggatgc ccttgatgga    7740
aggcaatttt ttaagttcct cgtaggtgag ctcttcaggg gagctgagcc cgtgctctga    7800
aagggcccag tctgcaagat gagggttgga agcgacgaat gagctccaca ggtcacgggc    7860
cattagcatt tgcaggtggt cgcgaaaggt cctaaactgg cgacctatgg ccatttttc     7920 tggggtgatg cagtagaagg taagcgggtc ttgttcccag cggtcccatc caaggttcgc    7980
ggctaggtct cgcgcggcag tcactagagg ctcatctccg ccgaacttca tgaccagcat    8040
gaagggcacg agctgcttcc caaaggcccc catccaagta taggtctcta catcgtaggt    8100
gacaaagaga cgctcggtgc gaggatgcga gccgatcggg aagaactgga tctcccgcca    8160
ccaattggag gagtggctat tgatgtggtg aaagtagaag tccctgcgac gggccgaaca    8220
ctcgtgctgg cttttgtaaa aacgtgcgca gtactggcag cggtgcacgg gctgtacatc    8280
ctgcacgagg ttgacctgac gaccgcgcac aaggaagcag agtgggaatt tgagcccctc    8340
gcctggcggg tttggctggt ggtcttctac ttcggctgct tgtccttgac cgtctggctg    8400
ctcgagggga gttacggtgg atcggaccac cacgccgcgc gagcccaaag tccagatgtc    8460
cgcgcgcggg ggtcggagct tgatgacaac atcgcgcaga tgggagctgt ccatggtctg    8520
gagctcccgc ggcgtcaggt caggcgggag ctcctgcagg tttacctcgc atagacgggt    8580
cagggcgcgg gctagatcca ggtgatacct aatttccagg ggctggttgg tggcggcgtc    8640
gatggcttgc aagaggccgc atccccgcgg cgcgactacg gtaccgcgcg gcgggcggtg    8700
ggccgcgggg gtgtccttgg atgatgcatc taaaagcggt gacgcgggcg agccccgga    8760 ggtaggggg gctccggacc cgccgggaga ggggcaggg gcacgtcggc gccgcgcgcg     8820
ggcaggagct ggtgctgcgc gcgtaggttg ctggcgaacg cgacgacgcg gcggttgatc    8880
```

-continued

```
tcctgaatct ggcgcctctg cgtgaagacg acgggcccgg tgagcttgag cctgaaagag    8940
agttcgacag aatcaatttc ggtgtcgttg acggcggcct ggcgcaaaat ctcctgcacg    9000
tctcctgagt tgtcttgata ggcgatctcg gccatgaact gctcgatctc ttcctcctgg    9060
agatctccgc gtccggctcg ctccacggtg cggcgaggt cgttggaaat gcgggccatg     9120
agctgcgaga aggcgttgag gcctccctcg ttccagacgc ggctgtagac cacgccccct    9180
tcggcatcgc gggcgcgcat gaccacctgc gcgagattga gctccacgtg ccgggcgaag    9240
acggcgtagt ttcgcaggcg ctgaaagagg tagttgaggg tggtggcggt gtgttctgcc    9300
acgaagaagt acataaccca gcgtcgcaac gtggattcgt tgatatcccc caaggcctca    9360
aggcgctcca tggcctcgta gaagtccacg gcgaagttga aaaactggga gttgcgcgcc    9420
gacacggtta actcctcctc cagaagacgg atgagctcgg cgacagtgtc gcgcacctcg    9480
cgctcaaagg ctacaggggc ctcttcttct tcttcaatct cctcttccat aagggcctcc    9540
ccttcttctt cttctggcgg cggtggggga ggggggacac ggcggcgacg acggcgcacc    9600
gggaggcggt cgacaaagcg ctcgatcatc tccccgcgc gacggcgcat ggtctcggtg     9660
acggcgcggc cgttctcgcg ggggcgcagt tggaagacgc cgcccgtcat gtcccggtta    9720
tgggttggcg gggggctgcc atgcggcagg gatacgcgc taacgatgca tctcaacaat     9780
tgttgtgtag gtactccgcc gccgagggac ctgagcgagt ccgcatcgac cggatcggaa    9840
aacctctcga gaaaggcgtc taaccagtca cagtcgcaag gtaggctgag caccgtggcg    9900
ggcggcagcg ggcggcggtc ggggttgttt ctggcggagg tgctgctgat gatgtaatta    9960
aagtaggcgg tcttgagacg gcggatggtc gacagaagca ccatgtcctt gggtccggcc   10020
tgctgaatgc gcaggcggtc ggccatgccc caggcttcgt tttgacatcg gcgcaggtct   10080
ttgtagtagt cttgcatgag cctttctacc ggcacttctt cttctccttc ctcttgtcct   10140
gcatctcttg catctatcgc tgcggcggcg gcggagtttg gccgtaggtg gcgccctctt   10200
cctcccatgc gtgtgacccc gaagcccctc atcggctgaa gcagggctag gtcggcgaca   10260
acgcgctcgg ctaatatggc ctgctgcacc tgcgtgaggg tagactggaa gtcatccatg   10320
tccacaaagc ggtggtatgc gcccgtgttg atggtgtaag tgcagttggc cataacggac   10380
cagttaacgg tctggtgacc cggctgcgag agctcggtgt acctgagacg cgagtaagcc   10440
ctcgagtcaa atacgtagtc gttgcaagtc cgcaccaggt actggtatcc caccaaaaag   10500
tgcggcggcg gctggcggta gaggggccag cgtagggtgg ccggggctcc ggggcgaga    10560
tcttccaaca taaggcgatg atatccgtag atgtacctgg acatccaggt gatgccggcg   10620
gcggtggtgg aggcgcgcgg aaagtcgcgg acgcggttcc agatgttgcg cagcggcaaa   10680
aagtgctcca tggtcgggac gctctggccg gtcaggcgcg cgcaatcgtt gacgctctac   10740
cgtgcaaaag gagagcctgt aagcgggcac tcttccgtgg tctggtggat aaattcgcaa   10800
gggtatcatg gcggacgacc ggggttcgag cccgtatcc ggccgtccgc cgtgatccat    10860
gcggttaccg cccgcgtgtc gaacccaggt gtgcgacgtc agacaacggg ggagtgctcc   10920
ttttggcttc cttccaggcg cggcggctgc tgcgctagct ttttttggcca ctggccgcgc   10980
gcagcgtaag cggttaggct ggaaagcgaa agcattaagt ggctcgctcc ctgtagccgg   11040
agggttattt tccaagggtt gagtcgcggg acccccggtt cgagtctcgg accggccgga   11100
ctgcggcgaa cggggggtttg cctccccgtc atgcaagacc ccgcttgcaa attcctccgg  11160
aaacagggac gagccccttt tttgcttttc ccagatgcat ccggtgctgc ggcagatgcg   11220
ccccccctcct cagcagcggc aagagcaaga gcagcggcag acatgcaggg caccctcccc   11280
```

```
tcctcctacc gcgtcaggag gggcgacatc cgcggttgac gcggcagcag atggtgatta   11340 cgaaccccg  cggcgccggg cccggcacta cctggacttg gaggagggcg agggcctggc   11400
gcggctagga gcgccctctc ctgagcggta cccaagggtg cagctgaagc gtgatacgcg   11460
tgaggcgtac gtgccgcggc agaacctgtt tcgcgaccgc gagggagagg agcccgagga   11520
gatgcgggat cgaaagttcc acgcagggcg cgagctgcgg catggcctga tcgcgagcg    11580 gttgctgcgc gaggaggact ttgagcccga cgcgcgaacc gggattagtc ccgcgcgcgc   11640
acacgtggcg gccgccgacc tggtaaccgc atacgagcag acggtgaacc aggagattaa   11700
ctttcaaaaa agctttaaca accacgtgcg tacgcttgtg gcgcgcgagg aggtggctat   11760
aggactgatg catctgtggg actttgtaag cgcgctggag caaaacccaa atagcaagcc   11820
gctcatggcg cagctgttcc ttatagtgca gcacagcagg acaacgagg  cattcaggga   11880 tgcgctgcta acatagtag  agcccgaggg ccgctggctg ctcgatttga taaacatcct   11940
gcagagcata gtggtgcagg agcgcagctt gagcctggct gacaaggtgg ccgccatcaa   12000
ctattccatg cttagcctgg gcaagtttta cgcccgcaag atataccata ccccttacgt   12060
tcccatagac aaggaggtaa agatcgaggg gttctacatg cgcatggcgc tgaaggtgct   12120
taccttgagc gacgacctgg gcgtttatcg caacgagcgc atccacaagg ccgtgagcgt   12180
gagccggcgg cgcgagctca gcgaccgcga gctgatgcac agcctgcaaa gggccctggc   12240
tggcacgggc agcggcgata gagaggccga gtcctacttt gacgcgggcg ctgacctgcg   12300
ctgggcccca gccgacgcg  ccctggaggc agctggggcc ggacctgggc tggcggtggc   12360
acccgcgcgc gctggcaacg tcggcggcgt ggaggaatat gacgaggacg atgagtacga   12420
gccagaggac ggcgagtact aagcggtgat gtttctgatc agatgatgca agacgcaacg   12480
gacccggcgg tgcgggcggc gctgcagagc cagccgtccg gccttaactc cacggacgac   12540
tggcgccagg tcatggaccg catcatgtcg ctgactgcgc gcaatcctga cgcgttccgg   12600
cagcagccgc aggccaaccg gctctccgca attctggaag cggtggtccc ggcgcgcgca   12660
aaccccacgc acgagaaggt gctggcgatc gtaaacgcgc tggccgaaaa cagggccatc   12720
cggcccgacg aggccggcct ggtctacgac gcgctgcttc agcgcgtggc tcgttacaac   12780
agcggcaacg tgcagaccaa cctggaccgg ctggtggggg atgtgcgcga ggccgtggcg   12840
cagcgtgagc gcgcgcagca gcagggcaac ctgggctcca tggttgcact aaacgccttc   12900
ctgagtacac agcccgccaa cgtgccgcgg ggacaggagg actacaccaa ctttgtgagc   12960
gcactgcggc taatggtgac tgagacaccg caaagtgagg tgtaccagtc tgggccagac   13020
tattttttcc agaccagtag acaaggcctg cagaccgtaa acctgagcca ggctttcaaa   13080
aacttgcagg gctgtgtggg ggtgcgggct cccacaggcg accgcgcgac cgtgtctagc   13140
ttgctgacgc ccaactcgcg cctgttgctg ctgctaatag cgcccttcac ggacagtggc   13200
agcgtgtccc gggacacata cctaggtcac ttgctgacac tgtaccgcga ggccataggt   13260
caggcgcatg tggacgagca tactttccag gagattacaa gtgtcagccg cgcgctgggg   13320
caggaggaca cgggcagcct ggaggcaacc ctaaactacc tgctgaccaa ccggcggcag   13380
aagatcccct cgttgcacag tttaaacagc gaggaggagc gcattttgcg ctacgtgcag   13440
cagagcgtga gccttaacct gatgcgcgac ggggtaacgc ccagcgtggc gctggacatg   13500
accgcgcgca acatggaacc gggcatgtat gcctcaaacc ggccgtttat caaccgccta   13560
atggactact tgcatcgcgc ggccgccgtg aaccccgagt atttcaccaa tgccatcttg   13620
```

```
aacccgcact ggctaccgcc ccctggtttc tacaccgggg gattcgaggt gcccgagggt    13680
aacgatggat tcctctggga cgacatagac gacagcgtgt tttccccgca accgcagacc    13740
ctgctagagt tgcaacagcg cgagcaggca gaggcggcgc tgcgaaagga aagcttccgc    13800
aggccaagca gcttgtccga tctaggcgct gcggccccgc ggtcagatgc tagtagccca    13860
tttccaagct tgatagggtc tcttaccagc actcgcacca cccgcccgcg cctgctgggc    13920
gaggaggagt acctaaacaa ctcgctgctg cagccgcagc gcgaaaaaaa cctgcctccg    13980
gcatttccca acaacgggat agagagccta gtggacaaga tgagtagatg gaagacgtac    14040
gcgcaggagc acagggacgt gccaggcccg cgcccgccca cccgtcgtca aaggcacgac    14100
cgtcagcggg gtctggtgtg ggaggacgat gactcggcag acgacagcag cgtcctggat    14160
ttgggaggga gtggcaaccc gtttgcgcac cttcgcccca ggctggggag aatgttttaa    14220
aaaaaaaaaa gcatgatgca aaataaaaaa ctcaccaagg ccatggcacc gagcgttggt    14280
tttcttgtat tccccttagt atgcggcgcg cggcgatgta tgaggaaggt cctcctccct    14340
cctacgagag tgtggtgagc gcggcgcag tggcggcggc gctgggttct cccttcgatg     14400 ctccctgga cccgccgttt gtgcctccgc ggtacctgcg gcctaccggg gggagaaaca    14460
gcatccgtta ctctgagttg gcaccccctat tcgacaccac ccgtgtgtac ctggtggaca   14520
acaagtcaac ggatgtggca tccctgaact accagaacga ccacagcaac tttctgacca    14580
cggtcattca aaacaatgac tacagcccgg gggaggcaag cacacagacc atcaatcttg    14640
acgaccggtc gcactggggc ggcgacctga aaaccatcct gcataccaac atgccaaatg    14700
tgaacgagtt catgtttacc aataagttta aggcgcgggt gatggtgtcg cgcttgccta    14760
ctaaggacaa tcaggtggag ctgaaatacg agtgggtgga gttcacgctg cccgagggca    14820
actactccga gaccatgacc atagacctta tgaacaacgc gatcgtggag cactacttga    14880
aagtgggcag acagaacggg gttctggaaa gcgacatcgg ggtaaagttt gacacccgca    14940
acttcagact ggggtttgac cccgtcactg gtcttgtcat gcctgggta tatacaaacg     15000 aagccttcca tccagacatc attttgctgc caggatgcgg ggtggacttc acccacagcc    15060
gcctgagcaa cttgttgggc atccgcaagc ggcaacccct tccaggagggc tttaggatca   15120 cctacgatga tctgagggt ggtaacattc ccgcactgtt ggatgtggac gcctaccagg    15180
cgagcttgaa agatgacacc gaacagggcg ggggtggcgc aggcggcagc aacagcagtg    15240
gcagcggcgc ggaagagaac tccaacgcgg cagccgcggc aatgcagccg gtggaggaca    15300
tgaacgatca tgccattcgc ggcgacacct ttgccacacg ggctgaggag aagcgcgctg    15360
aggccgaagc agcggccgaa gctgccgccc ccgctgcgca acccgaggtc gagaagcctc    15420
agaagaaacc ggtgatcaaa cccctgacag aggacagcaa gaaacgcagt tacaacctaa    15480
taagcaatga cagcacctts acccagtacc gcagctggta ccttgcatac aactacggcg    15540
accctcagac cggaatccgc tcatggaccc tgctttgcac tcctgacgta acctgcggct    15600
cggagcaggt ctactggtcg ttgccagaca tgatgcaaga ccccgtgacc ttccgctcca    15660
cgcgccagat cagcaacttt ccggtggtgg gcgccgagct gttgcccgtg cactccaaga    15720
gcttctacaa cgaccaggcc gtctactccc aactcatccg ccagtttacc tctctgaccc    15780
acgtgttcaa tcgcttccc gagaaccaga ttttggcgcg cccgccagcc cccaccatca    15840
ccaccgtcag tgaaaacgtt cctgctctca cagatcacgg gacgctaccg ctgcgcaaca    15900
gcatcggagg agtccagcga gtgaccatta ctgacgccag acgccgcacc tgcccctacg    15960
tttacaaggc cctgggcata gtctcgccgc gcgtcctatc gagccgcact ttttgagcaa    16020
```

```
gcatgtccat ccttatatcg cccagcaata acacaggctg gggcctgcgc ttcccaagca    16080
agatgtttgg cggggccaag aagcgctccg accaacaccc agtgcgcgtg cgcgggcact    16140
accgcgcgcc ctgggcgcg cacaaacgcg gccgcactgg gcgcaccacc gtcgatgacg     16200
ccatcgacgc ggtggtggag gaggcgcgca actacacgcc cacgccgcca ccagtgtcca    16260
cagtggacgc ggccattcag accgtggtgc gcggagcccg cgctatgct aaaatgaaga     16320 gacggcggag gcgcgtagca cgtcgccacc gccgccgacc cggcactgcc gcccaacgcg    16380
cggcggcggc cctgcttaac cgcgcacgtc gcaccggccg acgggcggcc atgcgggccg    16440
ctcgaaggct ggccgcgggt attgtcactg tgcccccag gtccaggcga cgagcggccg     16500
ccgcagcagc cgcggccatt agtgctatga ctcagggtcg caggggcaac gtgtattggg    16560
tgcgcgactc ggttagcggc ctgcgcgtgc ccgtgcgcac ccgccccccg cgcaactaga    16620
ttgcaagaaa aaactactta gactcgtact gttgtatgta tccagcggcg gcggcgcgca    16680
acgaagctat gtccaagcgc aaaatcaaag aagagatgct ccaggtcatc gcgcggaga    16740 tctatggccc cccgaagaag gaagagcagg attacaagcc ccgaaagcta aagcgggtca    16800
aaaagaaaaa gaaagatgat gatgatgaac ttgacgacga ggtggaactg ctgcacgcta    16860
ccgcgcccag gcgacgggta cagtggaaag gtcgacgcgt aaaacgtgtt ttgcgacccg    16920
gcaccaccgt agtctttacg cccggtgagc gctccaccg cacctacaag cgcgtgtatg     16980
atgaggtgta cggcgacgag gacctgcttg agcaggccaa cgagcgcctc ggggagtttg    17040
cctacgaaaa gcggcataag gacatgctgg cgttgccgct ggacgagggc aacccaacac    17100
ctagcctaaa gcccgtaaca ctgcagcagg tgctgcccgc gcttgcaccg tccgaagaaa    17160
agcgcggcct aaagcgcgag tctggtgact ggcacccac cgtgcagctg atggtaccca    17220
agcgccagcg actggaagat gtcttggaaa aaatgaccgt ggaacctggg ctggagcccg    17280
aggtccgcgt gcggccaatc aagcaggtgg cgccggact gggcgtgcag accgtggacg     17340
ttcagatacc cactaccagt agcaccagta ttgccaccgc cacagagggc atggagacac    17400
aaacgtcccc ggttgcctca gcggtggcgg atgccgcgt gcaggcggtc gctgcggccg     17460
cgtccaagac ctctacggag gtgcaaacgg accgtggat gtttcgcgtt tcagccccc     17520 ggcgcccgcg cggttcgagg aagtacggcg ccgccagcgc gctactgccc gaatatgccc    17580
tacatccttc cattgcgcct accccggct atcgtggcta cacctaccgc cccagaagac    17640
gagcaactac ccgacgccga accaccactg gaacccgccg ccgccgtcgc cgtcgccagc    17700
ccgtgctggc cccgatttcc gtgcgcaggg tggctcgcga aggaggcagg accctggtgc    17760
tgccaacagc gcgctaccac cccagcatcg tttaaaagcc ggtctttgtg gttcttgcag    17820
atatggccct cacctgccgc ctccgtttcc cggtgccggg attccgagga agaatgcacc    17880
gtaggagggg catggccggc cacggcctga cgggcggcat gcgtcgtgcg caccaccggc    17940
ggcggcgcgc gtcgcaccgt cgcatgcgcg gcggtatcct gcccctcctt attccactga    18000
tcgccgcggc gattggcgcc gtgcccggaa ttgcatccgt ggccttgcag gcgcagagac    18060
actgattaaa acaagttgc atgtggaaaa atcaaaataa aaagtctgga ctctcacgct    18120
cgcttggtcc tgtaactatt ttgtagaatg gaagacatca actttgcgtc tctggccccg    18180
cgacacggct cgcgcccgtt catgggaaac tggcaagata tcggcaccag caatatgagc    18240
ggtggcgcct tcagctgggg ctcgctgtgg agcggcatta aaaatttcgg ttccaccgtt    18300
aagaactatg gcagcaaggc ctggaacagc agcacaggcc agatgctgag ggataagttg    18360
```

```
aaagagcaaa atttccaaca aaaggtggta gatggcctgg cctctggcat tagcggggtg    18420
gtggacctgg ccaaccaggc agtgcaaaat aagattaaca gtaagcttga tccccgccct    18480
cccgtagagg agcctccacc ggccgtggag acagtgtctc cagaggggcg tggcgaaaag    18540
cgtccgcgcc ccgacaggga agaaactctg gtgacgcaaa tagacgagcc tccctcgtac    18600
gaggaggcac taaagcaagg cctgcccacc acccgtccca tcgcgcccat ggctaccgga    18660
gtgctgggcc agcacacacc cgtaacgctg gacctgcctc cccccgccga cacccagcag    18720
aaacctgtgc tgccaggccc gaccgccgtt gttgtaaccc gtcctagccg cgcgtccctg    18780
cgccgcgccg ccagcggtcc gcgatcgttg cggcccgtag ccagtggcaa ctggcaaagc    18840
acactgaaca gcatcgtggg tctggggtg caatccctga agcgccgacg atgcttctga    18900
atagctaacg tgtcgtatgt gtgtcatgta tgcgtccatg tcgccgccag aggagctgct    18960
gagccgccgc gcgcccgctt tccaagatgg ctaccccttc gatgatgccg cagtggtctt    19020
acatgcacat ctcgggccag gacgcctcgg agtacctgag cccgggctg gtgcagtttg    19080 cccgcgccac cgagacgtac ttcagcctga ataacaagtt tagaaacccc acggtggcgc    19140
ctacgcacga cgtgaccaca gaccggtccc agcgtttgac gctgcggttc atccctgtgg    19200
accgtgagga tactgcgtac tcgtacaagg cgcggttcac cctagctgtg ggtgataacc    19260
gtgtgctgga catggcttcc acgtactttg acatccgcgg cgtgctggac aggggcccta    19320
cttttaagcc ctactctggc actgcctaca acgccctggc tcccaagggt gccccaaatc    19380
cttgcgaatg ggatgaagct gctactgctc ttgaaataaa cctagaagaa gaggacgatg    19440
acaacgaaga cgaagtagac gagcaagctg agcagcaaaa aactcacgta tttgggcagg    19500
cgccttattc tggtataaat attacaaagg agggtattca aataggtgtc gaaggtcaaa    19560
cacctaaata tgccgataaa acatttcaac ctgaacctca aataggagaa tctcagtggt    19620
acgaaactga aattaatcat gcagctggga gagtccttaa aaagactacc ccaatgaaac    19680
catgttacgt tcatatgca aaacccacaa atgaaaatgg agggcaaggc attcttgtaa    19740
agcaacaaaa tggaaagcta gaaagtcaag tggaaatgca ttttttctca actactgagg    19800
cgaccgcagg caatggtgat aacttgactc ctaaagtggt attgtacagt gaagatgtag    19860
atatagaaac cccagacact catatttctt acatgcccac tattaaggaa ggtaactcac    19920
gagaactaat gggccaacaa tctatgccca acaggcctaa ttacattgct tttagggaca    19980
attttattgg tctaatgtat tacaacagca cgggtaatat gggtgttctg gcgggccaag    20040
catcgcagtt gaatgctgtt gtagatttgc aagacagaaa cacagagctt tcataccagc    20100
ttttgcttga ttccattggt gatagaacca ggtactttc tatgtggaat caggctgttg    20160
acagctatga tccagatgtt agaattattg aaaatcatgg aactgaagat gaacttccaa    20220
attactgctt tccactggga ggtgtgatta atacagagac tcttaccaag gtaaaaccta    20280
aaacaggtca ggaaaatgga tgggaaaaag atgctacaga attttcagat aaaaatgaaa    20340
taagagttgg aaataatttt gccatggaaa tcaatctaaa tgccaacctg tggagaaatt    20400
tcctgtactc caacatagcg ctgtatttgc ccgacaagct aaagtacagt ccttccaacg    20460 taaaatttc tgataaccca aacacctacg actacatgaa caagcgagtg gtggctcccg    20520
ggttagtgga ctgctacatt aaccttggag cacgctggtc ccttgactat atggacaacg    20580
tcaacccatt taaccaccac cgcaatgctg gcctgcgcta ccgctcaatg ttgctgggca    20640
atggtcgcta tgtgcccttc cacatccagg tgcctcagaa gttctttgcc attaaaaacc    20700
tccttctcct gccgggctca tacacctacg agtggaactt caggaaggat gttaacatgg    20760
```

```
ttctgcagag ctccctagga aatgacctaa gggttgacgg agccagcatt aagtttgata  20820
gcatttgcct ttacgccacc ttcttcccca tggcccacaa caccgcctcc acgcttgagg  20880
ccatgcttag aaacgacacc aacgaccagt cctttaacga ctatctctcc gccgccaaca  20940
tgctctaccc tatacccgcc aacgctacca acgtgcccat atccatcccc tcccgcaact  21000
gggcggcttt ccgcggctgg gccttcacgc gccttaagac taaggaaacc ccatcactgg  21060
gctcgggcta cgacccttat tacacctact ctggctctat accctaccta gatgaaacct  21120
tttacctcaa ccacacctt aagaaggtgg ccattacctt tgactcttct gtcagctggc  21180
ctggcaatga ccgcctgctt accccaacg agtttgaaat taagcgctca gttgacgggg  21240
agggttacaa cgttgcccag tgtaacatga ccaaagactg gttcctggta caaatgctag  21300
ctaactacaa cattggctac cagggcttct atatcccaga gagctacaag gaccgcatgt  21360
actccttctt tagaaacttc cagcccatga gccgtcaggt ggtggatgat actaaataca  21420
aggactacca acaggtgggc atcctacacc aacacaacaa ctctggatttt gttggctacc  21480
ttgcccccac catgcgcgaa ggacaggcct accctgctaa cttcccctat ccgcttatag  21540
gcaagaccgc agttgacagc attacccaga aaaagtttct ttgcgatcgc accctttggc  21600
gcatcccatt ctccagtaac tttatgtcca tgggcgcact cacagacctg gccaaaaacc  21660
ttctctacgc caactccgcc cacgcgctag acatgacttt tgaggtggat cccatggacg  21720
agcccaccct tctttatgtt ttgtttgaag tctttgacgt ggtccgtgtg caccggccgc  21780
accgcggcgt catcgaaacc gtgtacctgc gcacgccctt ctcggccggc aacgccacaa  21840
cataaagaag caagcaacat caacaacagc tgccgccatg ggctccagtg agcaggaact  21900
gaaagccatt gtcaaagatc ttggttgtgg gccatatttt ttgggcacct atgacaagcg  21960
ctttccaggc tttgtttctc cacacaagct cgcctgcgcc atagtcaata cggccggtcg  22020
cgagactggg ggcgtacact ggatggcctt tgcctggaac ccgcactcaa aaacatgcta  22080
cctctttgag ccctttggct tttctgacca gcgactcaag caggtttacc agtttgagta  22140
cgagtcactc ctgcgccgta gcgccattgc ttcttccccc gaccgctgta taacgctgga  22200
aaagtccacc caaagcgtac aggggcccaa ctcgccgcc tgtggactat tctgctgcat  22260
gtttctccac gcctttgcca actggcccca aactcccatg gatcacaacc ccaccatgaa  22320
ccttattacc ggggtaccca actccatgct caacagtccc caggtacagc ccaccctgcg  22380
tcgcaaccag gaacagctct acagcttcct ggagcgccac tcgccctact tccgcagcca  22440
cagtgcgcag attaggagcg ccacttcttt ttgtcacttg aaaaacatgt aaaaataatg  22500
tactagagac actttcaata aaggcaaatg ctttttatttg tacactctcg ggtgattatt  22560
tacccccacc cttgccgtct gcgccgttta aaaatcaaag gggttctgcc gcgcatcgct  22620
atgcgccact ggcagggaca cgttgcgata ctggtgttta gtgctccact taaactcagg  22680
cacaaccatc cgcggcagct cggtgaagtt ttcactccac aggctgcgca ccatcaccaa  22740
cgcgtttagc aggtcgggcg ccgatatctt gaagtcgcag ttggggcctc cgccctgcgc  22800
gcgcgagttg cgatacacag ggttgcagca ctggaacact atcagcgccg ggtggtgcac  22860
gctggccagc acgctcttgt cggagatcag atccgcgtcc aggtcctccg cgttgctcag  22920
ggcgaacgga gtcaactttg gtagctgcct tcccaaaaag ggcgcgtgcc caggctttga  22980
gttgcactcg caccgtagtg gcatcaaaag gtgaccgtgc ccggtctggg cgttaggata  23040
cagcgcctgc ataaaagcct tgatctgctt aaaagccacc tgagcctttg cgccttcaga  23100
```

```
gaagaacatg ccgcaagact tgccggaaaa ctgattggcc ggacaggccg cgtcgtgcac    23160
gcagcacctt gcgtcggtgt tggagatctg caccacattt cggccccacc ggttcttcac    23220
gatcttggcc ttgctagact gctccttcag cgcgcgctgc ccgttttcgc tcgtcacatc    23280
catttcaatc acgtgctcct tatttatcat aatgcttccg tgtagacact taagctcgcc    23340
ttcgatctca gcgcagcggt gcagccacaa cgcgcagccc gtgggctcgt gatgcttgta    23400
ggtcacctct gcaaacgact gcaggtacgc ctgcaggaat cgccccatca tcgtcacaaa    23460
ggtcttgttg ctggtgaagg tcagctgcaa cccgcggtgc tcctcgttca gccaggtctt    23520
gcatacggcc gccagagctt ccacttggtc aggcagtagt ttgaagttcg ctttttagatc    23580 gttatccacg tggtacttgt ccatcagcgc gcgcgcagcc tccatgccct tctcccacgc    23640
agacacgatc ggcacactca gcgggttcat caccgtaatt tcactttccg cttcgctggg    23700
ctcttcctct tcctcttgcg tccgcatacc acgccact gggtcgtctt cattcagccg    23760
ccgcactgtg cgcttacctc ctttgccatg cttgattagc accggtgggt tgctgaaacc    23820
caccatttgt agcgccacat cttctctttc ttcctcgctg tccacgatta cctctggtga    23880
tggcgggcgc tcgggcttgg gagaaggggcg cttctttttc ttcttgggcg caatggccaa    23940
atccgccgcc gaggtcgatg gccgcgggct gggtgtgcgc ggcaccagcg cgtcttgtga    24000
tgagtcttcc tcgtcctcgg actcgatacg ccgcctcatc cgctttttttg ggggcgcccg    24060 gggaggcggc ggcgacgggg acggggacga cacgtcctcc atggttgggg gacgtcgcgc    24120
cgcaccgcgt ccgcgctcgg gggtggtttc gcgctgctcc tcttccccgac tggccatttc    24180 cttctccctat aggcagaaaa agatcatgga gtcagtcgag aagaaggaca gcctaaccgc    24240
cccctctgag ttcgccacca ccgcctccac cgatgccgcc aacgcgccta ccaccttccc    24300
cgtcgaggca cccccgcttg aggaggagga agtgattatc gagcaggacc caggttttgt    24360
aagcgaagac gacgaggacc gctcagtacc aacagaggat aaaaagcaag accaggacaa    24420
cgcagaggca aacgaggaac aagtcgggcg ggggacgaa aggcatggcg actacctaga    24480
tgtgggagac gacgtgctgt tgaagcatct gcagcgccag tgcgccatta tctgcgacgc    24540
gttgcaagag cgcagcgatg tgcccctcgc catagcggat gtcagccttg cctacgaacg    24600
ccacctattc tcaccgcgcg tacccccccaa acgccaagaa aacggcacat gcgagcccaa    24660
cccgcgcctc aacttctacc ccgtatttgc cgtgccagag gtgcttgcca cctatcacat    24720 cttttttccaa aactgcaaga taccctatc ctgccgtgcc aaccgcagcc gagcggacaa    24780
gcagctggcc ttgcggcagg gcgctgtcat acctgatatc gcctcgctca acgaagtgcc    24840
aaaaatcttt gagggtcttg gacgcgacga gaagcgcgcg gcaaacgctc tgcaacagga    24900
aaacagcgaa aatgaaagtc actctggagt gttggtggaa ctcgagggtg acaacgcgcg    24960
cctagccgta ctaaaacgca gcatcgaggt cacccacttt gcctacccgg cacttaacct    25020 acccccccaag gtcatgagca cagtcatgag tgagctgatc gtgcgccgtg cgcagccccct    25080 ggagagggat gcaaatttgc aagaacaaac agaggagggc ctacccgcag ttggcgacga    25140
gcagctagcg cgctggcttc aaacgcgcga gcctgccgac ttggaggagc gacgcaaact    25200
aatgatggcc gcagtgctcg ttaccgtgga gcttgagtgc atgcagcggt tctttgctga    25260
cccggagatg cagcgcaagc tagaggaaac attgcactac acctttcgac agggctacgt    25320
acgccaggcc tgcaagatct ccaacgtgga gctctgcaac ctggtctcct accttggaat    25380
tttgcacgaa aaccgccttg ggcaaaacgt gcttcattcc acgctcaagg gcgaggcgcg    25440
ccgcgactac gtccgcgact gcgtttactt atttctatgc tacacctggc agacggccat    25500
```

```
gggcgtttgg cagcagtgct tggaggagtg caacctcaag gagctgcaga aactgctaaa   25560
gcaaaacttg aaggacctat ggacggcctt caacgagcgc tccgtggccg cgcacctggc   25620
ggacatcatt ttccccgaac gcctgcttaa acccctgcaa cagggtctgc cagacttcac   25680
cagtcaaagc atgttgcaga actttaggaa ctttatccta gagcgctcag gaatcttgcc   25740
cgccacctgc tgtgcacttc ctagcgactt tgtgcccatt aagtaccgcg aatgccctcc   25800
gccgctttgg ggccactgct accttctgca gctagccaac taccttgcct accactctga   25860
cataatggaa gacgtgagcg gtgacggtct actggagtgt cactgtcgct gcaacctatg   25920
caccccgcac cgctccctgg tttgcaattc gcagctgctt aacgaaagtc aaattatcgg   25980 taccttgag ctgcagggtc cctcgcctga cgaaaagtcc gcggctccgg ggttgaaact   26040
cactccgggg ctgtggacgt cggcttacct tcgcaaattt gtacctgagg actaccacgc   26100
ccacgagatt aggttctacg aagaccaatc ccgcccgcca aatgcggagc ttaccgcctg   26160
cgtcattacc cagggccaca ttcttggcca attgcaagcc atcaacaaag cccgccaaga   26220
gtttctgcta cgaaagggac gggggttta cttggacccc cagtccggcg aggagctcaa   26280
cccaatcccc ccgccgccgc agccctatca gcagcagccg cgggcccttg cttcccagga   26340
tggcacccaa aaagaagctg cagctgccgc cgccacccac ggacgaggag gaatactggg   26400
acagtcaggc agaggaggtt ttggacgagg aggaggagga catgatggaa gactgggaga   26460
gcctagacga ggaagcttcc gaggtcgaag aggtgtcaga cgaaacaccg tcaccctcgg   26520
tcgcattccc ctcgccggcg ccccagaaat cggcaaccgg ttccagcatg gctacaacct   26580
ccgctcctca ggcgccgccg gcactgcccg ttcgccgacc caaccgtaga tgggacacca   26640
ctggaaccag ggccggtaag tccaagcagc cgccgccgtt agcccaagag caacaacagc   26700
gccaaggcta ccgctcatgg cgcgggcaca agaacgccat agttgcttgc ttgcaagact   26760 gtggggcaa catctccttc gcccgccgct ttcttctcta ccatcacggc gtggccttcc   26820
cccgtaacat cctgcattac taccgtcatc tctacagccc atactgcacc ggcggcagcg   26880
gcagcggcag caacagcagc ggccacacag aagcaaaggc gaccggatag caagactctg   26940
acaaagccca agaaatccac agcggcggca gcagcaggag gaggagcgct gcgtctggcg   27000
cccaacgaac ccgtatcgac ccgcgagctt agaaacagga ttttccccac tctgtatgct   27060
atatttcaac agagcagggg ccaagaacaa gagctgaaaa taaaaaacag gtctctgcga   27120
tccctcaccc gcagctgcct gtatcacaaa agcgaagatc agcttcggcg cacgctggaa   27180
gacgcggagg ctctcttcag taaatactgc gcgctgactc ttaaggacta gtttcgcgcc   27240
ctttctcaaa tttaagcgcg aaaactacgt catctccagc ggccacaccc ggcgccagca   27300
cctgtcgtca gcgccattat gagcaaggaa attcccacgc cctacatgtg gagttaccag   27360
ccacaaatgg gacttgcggc tggagctgcc caagactact caacccgaat aaactacatg   27420
agcgcgggac cccacatgat atcccgggtc aacggaatcc gcgcccaccg aaaccgaatt   27480
ctcttggaac aggcggctat taccaccaca cctcgtaata accttaatcc ccgtagttgg   27540
cccgctgccc tggtgtacca ggaaagtccc gctcccacca ctgtggtact tcccagagac   27600
gcccaggccg aagttcagat gactaactca ggggcgcagc ttgcgggcgg ctttcgtcac   27660
agggtgcggt cgcccgggca gggtataact cacctgacaa tcagagggcg aggtattcag   27720
ctcaacgacg agtcggtgag ctcctcgctt ggtctccgtc cggacgggac atttcagatc   27780
ggcggcgccg gccgctcttc attcacgcct cgtcaggcaa tcctaactct gcagacctcg   27840
```

```
tcctctgagc cgcgctctgg aggcattgga actctgcaat ttattgagga gtttgtgcca   27900
tcggtctact ttaaccccct tctcgggacct cccggccact atccggatca atttattcct   27960
aactttgacg cggtaaagga ctcggcggat ggctacgact gaatgttaag tggagaggca   28020
gagcaactgc gcctgaaaca cctggtccac tgtcgccgcc acaagtgctt tgcccgcgac   28080
tccggtgagt tttgctactt tgaattgccc gaggatcata tcgagggccc ggcgcacggc   28140
gtccggctta ccgcccaggg agagcttgcc cgtagcctga ttcgggagtt tacccagcgc   28200
cccctgctag ttgagcggga caggggaccc tgtgttctca ctgtgatttg caactgtcct   28260
aaccctggat tacatcaaga tctttgttgc catctctgtg ctgagtataa taaatacaga   28320
aattaaaata tactggggct cctatcgcca tcctgtaaac gccaccgtct tcacccgccc   28380
aagcaaacca aggcgaacct tacctggtac ttttaacatc tctccctctg tgatttacaa   28440
cagtttcaac ccagacggag tgagtctacg agagaacctc tccgagctca gctactccat   28500
cagaaaaaac accaccctcc ttacctgccg ggaacgtacg acctagggat aacagggtaa   28560
taagcaattg actctatgtg ggatatgctc cagcgctaca accttgaagt caggcttcct   28620
ggatgtcagc atctgacttt ggccagcacc tgtcccgcgg atttgttcca gtccaactac   28680
agcgacccac cctaacagag atgaccaaca caaccaacgc ggccgccgct accggactta   28740
catctaccac aaatacaccc caagtttctg cctttgtcaa taactgggat aacttgggca   28800
tgtggtggtt ctccatagcg cttatgtttg tatgccttat tattatgtgg ctcatctgct   28860
gcctaaagcg caaacgcgcc cgaccaccca tctatagtcc catcattgtg ctacacccaa   28920
acaatgatgg aatccataga ttggacggac tgaaacacat gttctttttct cttacagtat   28980
gattaaatga gacatgattc ctcgagtttt tatattactg acccttgttg cgcttttttg   29040
tgcgtgctcc acattggctg cggtttctca catcgaagta gactgcattc cagccttcac   29100
agtctatttg ctttacggat ttgtcaccct cacgctcatc tgcagcctca tcactgtggt   29160
catcgccttt atccagtgca ttgactgggt ctgtgtgcgc tttgcatatc tcagacacca   29220
tccccagtac agggacagga ctatagctga gcttcttaga attctttaat tatgaaattt   29280
actgtgactt ttctgctgat tatttgcacc ctatctgcgt tttgttcccc gacctccaag   29340
cctcaaagac atatatcatg cagattcact cgtatatgga atattccaag ttgctacaat   29400
gaaaaaagcg atctttccga agcctggtta tatgcaatca tctctgttat ggtgttctgc   29460
agtaccatct tagccctagc tatatatccc taccttgaca ttggctggaa acgaatagat   29520
gccatgaacc acccaacttt ccccgcgccc gctatgcttc cactgcaaca agttgttgcc   29580
ggcggctttg tcccagccaa tcagcctcgc cccacttctc ccacccccac tgaaatcagc   29640
tactttaatc taacaggagg agatgactga caccctagat ctagaaatgg acggaattat   29700
tacagagcag cgcctgctag aaagacgcag ggcagcggcc gagcaacagc gcatgaatca   29760
agagctccaa gacatggtta acttgcacca gtgcaaaagg ggtatctttt gtctggtaaa   29820
gcaggccaaa gtcacctacg acagtaatac caccggacac cgccttagct acaagttgcc   29880
aaccaagcgt cagaaattgg tggtcatggt gggagaaaag cccattacca aactcagca   29940
ctcggtagaa accgaaggct gcattcactc accttgtcaa ggacctgagg atctctgcac   30000
ccttattaag accctgtgcg gtctcaaaga tcttattccc tttaactaat aaaaaaaaat   30060
aataaagcat cacttactta aaatcagtta gcaaatttct gtccagttta ttcagcagca   30120
cctccttgcc ctcctcccag ctctggtatt gcagcttcct cctggctgca aacttttctcc   30180
acaatctaaa tggaatgtca gtttcctcct gttcctgtcc atccgcaccc actatcttca   30240
```

```
tgttgttgca gatgaagcgc gcaagaccgt ctgaagatac cttcaacccc gtgtatccat   30300
atgacacgga aaccggtcct ccaactgtgc cttttcttac tcctcccttt gtatccccca   30360
atgggtttca agagagtccc cctggggtac tctctttgcg cctatccgaa cctctagtta   30420
cctccaatgg catgcttgcg ctcaaaatgg caacggcct ctctctggac gaggccggca    30480
accttacctc ccaaaatgta accactgtga gcccacctct caaaaaaacc aagtcaaaca   30540
taaacctgga aatatctgca cccctcacga ttacctcaga agccctaact gtggctgccg   30600
ccgcacctct aatggtcgcg ggcaacacac tcaccatgca atcacaggcc ccgctaaccg   30660
tgcacgactc caaacttagc attgccaccc aaggacccct cacagtgtca gaaggaaagc   30720
tagccctgca aacatcaggc cccctcacca ccaccgatag cagtaccctt actatcactg   30780
cctcaccccc tctaactact gccactggta gcttgggcat tgacttgaaa gagcccattt   30840
atacacaaaa tggaaaacta ggactaaagt acggggctcc tttgcatgta acagacgacc   30900
taaacacttt gaccgtagca actggtccag gtgtgactat taataatact tccttgcaaa   30960
ctaaagttac tggagccttg ggttttgatt cacaaggcaa tatgcaactt aatgtagcag   31020
gaggactaag gattgattct caaaacagac gccttatact tgatgttagt tatccgtttg   31080
atgctcaaaa ccaactaaat ctaagactag gacagggccc tctttttata aactcagccc   31140
acaacttgga tattaactac aacaaaggcc tttacttgtt tacagcttca aacaattcca   31200
aaaagcttga ggttaaccta agcactgcca aggggttgat gtttgacgct acagccatag   31260
ccattaatgc aggagatggg cttgaatttg gttcacctaa tgcaccaaac acaaatcccc   31320
tcaaaacaaa aattggccat ggcctagaat ttgattcaaa caaggctatg gttcctaaac   31380
taggaactgg ccttagtttt gacagcacag gtgccattac agtaggaaac aaaaataatg   31440
ataagctaac cctatggaca ggtccaaaac cagaagccaa ctgcataatt gaatacggga   31500
aacaaacccc agatagcaaa ctaactttaa tccttgtaaa aaatggagga attgttaatg   31560
gatatgtaac gctaatggga gcctcagact acgttaacac cttatttaaa aacaaaaatg   31620
tctccattaa tgtagaacta tactttgatg ccactggtca tatattacca gactcatctt   31680
ctcttaaaac agatctagaa ctaaaataca agcaaaccgc tgactttagt gcaagaggtt   31740
ttatgccaag tactcagcg tatccatttg tccttcctaa tgcgggaaca cataatgaaa    31800
attatatttt tggtcaatgc tactacaaag caagcgatgg tgccctttt ccgttggaag     31860 ttactgttat gcttaataaa cgcctgccag atagtcgcac atcctatgtt atgacttttt   31920
tatggtcctt gaatgctggt ctagctccag aaactactca ggcaaccctc ataacctccc   31980
catttacctt ttcctatatt agagaagatg actaataaac tctaaagaat cgtttgtgtt   32040
atgtttcaac gtgtttattt ttcaattgca gaaaatttca agtcattttt cattcagtag   32100
tatagcccca ccaccacata gcttatacag atcaccgtac cttaatcaaa ctcacagaac   32160
cctagtattc aacctgccac ctccctccca acacacagag tacacagtcc tttctccccg   32220
gctggcctta aaaagcatca tatcatgggt aacagacata ttcttaggtg ttatattcca   32280
cacggtttcc tgtcgagcca aacgctcatc aagtgatatt aataaactcc ccgggcagct   32340
cacttaagtt catgtcgctg tccagctgct gagccacagg ctgctgtcca acttgcggtt   32400
gcttaacggg cggcgaagga gaagtccacg cctacatggg gggagagtca taatcgtgca   32460
tcaggatagg gcggtggtgc tgcagcagcg cgcgaataaa ctgctgccgc cgccgctccg   32520
tcctgcagga atacaacatg gcagtggtct cctcagcgat gattcgcacc gcccgcagca   32580
```

```
taaggcgctt gtcctccggg cacagcagcg caccctgatc tcacttaaat cagcacagta    32640
actgcagcac agcaccacaa tattgttcaa aatcccacag tgcaaggcgc tgtatccaaa    32700
gctcatggcg gggaccacag aacccacgtg gccatcatac cacaagcgca ggtagattaa    32760
gtggcgaccc ctcataaaca cgctggacat aaacattacc tcttttggca tgttgtaatt    32820
caccacctcc cggtaccata taaacctctg attaaacatg gcgccatcca ccaccatcct    32880
aaaccagctg gccaaaacct gccccgccgg gntatacact gcaggaacc gggacttgga     32940 caatgacaag tgggagagcc caggactcgt aaccatggat catcatgctc gtcatgatat    33000
caatgttggc acaacacagg cacacgtgca tacacttcct caggattaca agctcctccc    33060
gcgttagaac catatcccag ggaacaaccc attcctgaat cagcgtaaat cccacactgc    33120
agggaagacc tcgcacgtaa ctcacgttgt gcattgtcaa agtgttacat tcggcagca    33180 gcggatgatc ctccagtatg gtagcgcggg tttctgtctc aaaaggaggt agacgatccc    33240
tactgtacgg agtgcgccga gacaaccgag atcgtgttgg tcgtagtgtc atgccaaatg    33300
gaacgccgga cgtagtcata tttcctgaag caaaaccagg tgcgggcgtg acaaacagat    33360
ctgcgtctcc ggtctcgccg cttagatcgc tctgtgtagt agttgtagta tatccactct    33420
ctcaaagcat ccaggcgccc cctggcttcg ggttctatgt aaactccttc atgcgccgct    33480
gccctgataa catccaccac cgcagaataa gccacaccca gccaacctac acattcgttc    33540
tgcgagtcac acacggggagg agcgggaaga gctggaagaa ccatgttttt tttttattc     33600 caaaagatta tccaaaaccct caaaatgaag atctattaag tgaacgcgct cccctccggt    33660
ggcgtggtca aactctacag ccaaagaaca gataatggca tttgtaagat gttgcacaat    33720
ggcttccaaa aggcaaacgg ccctcacgtc caagtggacg taaaggctaa acccttcagg    33780
gtgaatctcc tctataaaca ttccagcacc ttcaaccatg cccaaataat tctcatctcg    33840
ccaccttctc aatatatctc taagcaaatc ccgaatattt aagtccgggc cattgtaaaa    33900
aatttggctc cagagcgccc tccaccttca gcctcaagca gcgaatcatg attgcaaaaa    33960
ttcaggttcc tcacagacct gtataagatt caaaagcgga acattaacaa aaataccgcg    34020
atcccgtagg tcccttcgca gggccagctg aacataatcg tgcaggtctg cacgaccag     34080 cgcggccact tccccgccag gaaccatgac aaaagaaccc acactgatta tgacacgcat    34140
actcggagct atgctaacca gcgtagcccc gatgtaagct tgttgcatgg gcggcgatat    34200
aaaatgcaag gtgctgctca aaaatcagg caaagcctcg cgcaaaaaag aaagcacatc     34260
gtagtcatgc tcatgcagat aaaggcaggt aagctccgga accaccacag aaaaagacac    34320 cattttctc tcaaacatgt ctgcgggttt ctgcataaac acaaataaa ataacaaaaa      34380 aacatttaaa cattagaagc ctgtcttaca acaggaaaaa caacccttat aagcataaga    34440
cggactacgg ccatgccggc gtgaccgtaa aaaaactggt caccgtgatt aaaaagcacc    34500
accgacagct cctcggtcag tccggagtca taatgtaaga ctcggtaaac acatcaggtt    34560
gattcacatc ggtcagtgtt aaaaagcgac cgaaatagcc nggggaata caatacccgc     34620 aggcgtagag acaacattac agcccccata ggaggtataa caaaattaat aggagagaaa    34680
aacacataaa cacctgaaaa accctcctgc ctaggcaaaa tagcacccte ccgctccaga    34740 acaacataca gcgcttccac agcggcagcc ataacagtca gccttaccag taaaaagaa    34800 aacctattaa aaaacaccca ctcgacacgg caccagctca atcagtcaca gtgtaaaaaa    34860
gggccaagtg cagagcgagt atatatagga ctaaaaaatg acggtaacgg ttaaagtcca    34920
caaaaaacac ccagaaaacc gcacgcgaac ctacgcccag aaacgaaagc caaaaaaccc    34980
```

| | | | | |
|---|---|---|---|---|
| acaacttcct | caaatcgtca | cttccgtttt | cccacgttac | gtcacttccc | attttaagaa | 35040 |
| aactacaatt | cccaacacat | acaagttact | ccgccctaaa | acctacgtca | cccgccccgt | 35100 |
| tcccacgccc | cgcgccacgt | cacaaactcc | accccctcat | tatcatattg | gcttcaatcc | 35160 |
| aaaataaggt | atattattga | tgatgttaat | taacatgcat | ggatcctcgt | ctcgacgatg | 35220 |
| cccttgagag | ccttcaaccc | agtcagctcc | ttccggtggg | cgcggggcat | gactatcgtc | 35280 |
| gccgcactta | tgactgtctt | ctttatcatg | caactcgtag | gacaggtgcc | ggcagcgctc | 35340 |
| tgggtcattt | tcggcgagga | ccgctttcgc | tggagcgcga | cgatgatcgg | cctgtcgctt | 35400 |
| gcggtattcg | gaatcttgca | cgccctcgct | caagccttcg | tcactggtcc | cgccaccaaa | 35460 |
| cgtttcggcg | agaagcaggc | cattatcgcc | ggcatggcgg | ccgacgcgct | gggctacgtc | 35520 |
| ttgctggcgt | tcgcgacgcg | aggctggatg | gccttcccca | ttatgattct | tctcgcttcc | 35580 |
| ggcggcatcg | ggatgcccgc | gttgcaggcc | atgctgtcca | ggcaggtaga | tgacgaccat | 35640 |
| cagggacagc | ttcaaggatc | gctcgcggct | cttaccagcc | taacttcgat | cactggaccg | 35700 |
| ctgatcgtca | cggcgattta | tgccgcctcg | gcgagcacat | ggaacgggtt | ggcatggatt | 35760 |
| gtaggcgccg | ccctatacct | tgtctgcctc | ccgcgttgc | gtcgcggtgc | atggagccgg | 35820 |
| gccacctcga | cctgaatgga | agccggcggc | acctcgctaa | cggattcacc | actccaagaa | 35880 |
| ttggagccaa | tcaattcttg | cggagaactg | tgaatgcgca | aaccaaccct | tggcagaaca | 35940 |
| tatccatcgc | gtccgccatc | tccagcagcc | gcacgcggcg | catctcgggc | agcgttgggt | 36000 |
| cctggccacg | ggtgcgcatg | atcgtgctcc | tgtcgttgag | gacccggcta | ggctggcggg | 36060 |
| gttgccttac | tggttagcag | aatgaatcac | cgatacgcga | gcgaacgtga | agcgactgct | 36120 |
| gctgcaaaac | gtctgcgacc | tgagcaacaa | catgaatggt | cttcggtttc | cgtgtttcgt | 36180 |
| aaagtctgga | aacgcggaag | tcagcgccct | gcaccattat | gttccggatc | tgcatcgcag | 36240 |
| gatgctgctg | gctaccctgt | ggaacaccta | catctgtatt | aacgaagcgc | tggcattgac | 36300 |
| cctgagtgat | ttttctctgg | tcccgccgca | tccataccgc | cagttgttta | ccctcacaac | 36360 |
| gttccagtaa | ccgggcatgt | tcatcatcag | taacccgtat | cgtgagcatc | ctctctcgtt | 36420 |
| tcatcggtat | cattaccccc | atgaacagaa | attccccctt | acacggaggc | atcaagtgac | 36480 |
| caaacaggaa | aaaaccgccc | ttaacatggc | ccgctttatc | agaagccaga | cattaacgct | 36540 |
| tctgagaaa | ctcaacgagc | tggacgcgga | tgaacaggca | gacatctgtg | aatcgcttca | 36600 |
| cgaccacgct | gatgagcttt | accgcagctg | cctcgcgcgt | ttcggtgatg | acggtgaaaa | 36660 |
| cctctgacac | atgcagctcc | cggagacggt | cacagcttgt | ctgtaagcgg | atgccgggag | 36720 |
| cagacaagcc | cgtcagggcg | cgtcagcggg | tgttggcggg | tgtcggggcg | cagccatgac | 36780 |
| ccagtcacgt | agcgatagcg | gagtgtatac | tggcttaact | atgcggcatc | agagcagatt | 36840 |
| gtactgagag | tgcaccatat | gcggtgtgaa | ataccgcaca | gatgcgtaag | gagaaaatac | 36900 |
| cgcatcaggc | gctcttccgc | ttcctcgctc | actgactcgc | tgcgctcggt | cgttcggctg | 36960 |
| cggcgagcgg | tatcagctca | ctcaaaggcg | gtaatacggt | tatccacaga | atcaggggat | 37020 |
| aacgcaggaa | agaacatgtg | agcaaaaggc | cagcaaaagg | ccaggaaccg | taaaaaggcc | 37080 |
| gcgttgctgg | cgtttttcca | taggctccgc | cccccctgacg | agcatcacaa | aaatcgacgc | 37140 |
| tcaagtcaga | ggtggcgaaa | cccgacagga | ctataaagat | accaggcgtt | tccccctgga | 37200 |
| agctccctcg | tgcgctctcc | tgttccgacc | ctgccgctta | ccggatacct | gtccgccttt | 37260 |
| ctcccttcgg | gaagcgtggc | gctttctcaa | tgctcacgct | gtaggtatct | cagttcggtg | 37320 |

```
taggtcgttc gctccaagct gggctgtgtg cacgaacccc ccgttcagcc cgaccgctgc   37380
gccttatccg gtaactatcg tcttgagtcc aacccggtaa gacacgactt atcgccactg   37440
gcagcagcca ctggtaacag gattagcaga gcgaggtatg taggcggtgc tacagagttc   37500
ttgaagtggt ggcctaacta cggctacact agaaggacag tatttggtat ctgcgctctg   37560
ctgaagccag ttaccttcgg aaaaagagtt ggtagctctt gatccggcaa acaaaccacc   37620
gctggtagcg gtggtttttt tgtttgcaag cagcagatta cgcgcagaaa aaaggatct    37680 caagaagatc ctttgatctt ttctacgggg tctgacgctc agtggaacga aaactcacgt   37740
taagggattt tggtcatgag attatcaaaa aggatcttca cctagatcct tttaaattaa   37800
aaatgaagtt ttaaatcaat ctaaagtata tatgagtaaa cttggtctga cagttaccaa   37860
tgcttaatca gtgaggcacc tatctcagcg atctgtctat ttcgttcatc catagttgcc   37920
tgactccccg tcgtgtagat aactacgata cgggagggct taccatctgg ccccagtgct   37980
gcaatgatac cgcgagaccc acgctcaccg gctccagatt tatcagcaat aaaccagcca   38040
gccggaaggg ccgagcgcag aagtggtcct gcaactttat ccgcctccat ccagtctatt   38100
aattgttgcc gggaagctag agtaagtagt tcgccagtta atagtttgcg caacgttggt   38160
tgnnnnnnaa aaaggatctt cacctagatc cttttcacgt agaaagccag tccgcagaaa   38220
cggtgctgac cccggatgaa tgtcagctac tgggctatct ggacaaggga aaacgcaagc   38280
gcaaagagaa agcaggtagc ttgcagtggg cttacatggc gatagctaga ctgggcggtt   38340
ttatggacag caagcgaacc ggaattgcca gctggggcgc cctctggtaa ggttgggaag   38400
ccctgcaaag taaactggat ggcttttctg ccgccaagga tctgatgcgc aggggatca    38460 agctctgatc aagagacagg atgaggatcg tttcgcatga ttgaacaaga tggattgcac   38520
gcaggttctc cggccgcttg ggtggagagg ctattcggct atgactgggc acaacagaca   38580
atcggctgct ctgatgccgc cgtgttccgg ctgtcagcgc aggggcgccc ggttcttttt   38640
gtcaagaccg acctgtccgg tgccctgaat gaactgcaag acgaggcagc gcggctatcg   38700
tggctggcca cgacgggcgt tccttgcgca gctgtgctcg acgttgtcac tgaagcggga   38760
agggactggc tgctattggg cgaagtgccg gggcaggatc tcctgtcatc tcaccttgct   38820
cctgccgaga aagtatccat catggctgat gcaatgcggc ggctgcatac gcttgatccg   38880
gctacctgcc cattcgacca ccaagcgaaa catcgcatcg agcgagcacg tactcggatg   38940
gaagccggtc ttgtcgatca ggatgatctg gacgaagagc atcagggct cgcgccagcc    39000 gaactgttcg ccaggctcaa ggcgagcatg cccgacggcg aggatctcgt cgtgacccat   39060
ggcgatgcct gcttgccgaa tatcatggtg aaaatggcc gcttttctgg attcatcgac    39120
tgtggccggc tgggtgtggc ggaccgctat caggacatag cgttggctac ccgtgatatt   39180
gctgaagagc ttggcggcga atgggctgac cgcttcctcg tgctttacgg tatcgccgct   39240
cccgattcgc agcgcatcgc cttctatcgc cttcttgacg agttcttctg aattttgtta   39300 aaattttttgt taaatcagct cattttttaa ccaataggcc gaaatcggca acatccctta   39360
taaatcaaaa gaatagaccg cgatagggtt gagtgttgtt ccagtttgga acaagagtcc   39420
actattaaag aacgtggact ccaacgtcaa agggcgaaaa accgtctatc agggcgatgg   39480
cccactacgt gaaccatcac ccaaatcaag ttttttgcgg tcgaggtgcc gtaaagctct   39540
aaatcggaac cctaaaggga gccccgatt tagagcttga cggggaaagc cggcgaacgt    39600
ggcgagaaag gaagggaaga agcgaaagg agcgggcgct agggcgctgg caagtgtagc    39660
ggtcacgctg cgcgtaacca ccacacccgc cgcgcttaatg cgccgctaca gggcgcgtcc   39720
```

```
attcgccatt caggatcgaa ttaattctta at                                    39752

<210> SEQ ID NO 52
<211> LENGTH: 8
<212> TYPE: PRT
<213> ORGANISM: Artificial Sequence
<220> FEATURE:
<223> OTHER INFORMATION: Amino acids 121-128 of Ad E1A protein

<400> SEQUENCE: 52

Leu Thr Cys His Glu Ala Cys Phe
1               5

<210> SEQ ID NO 53
<211> LENGTH: 9
<212> TYPE: PRT
<213> ORGANISM: Artificial Sequence
<220> FEATURE:
<223> OTHER INFORMATION: STAT1 binding site (1)

<400> SEQUENCE: 53

Thr Thr Cys Cys Gly Gly Gly Ala Ala
1               5

<210> SEQ ID NO 54
<211> LENGTH: 9
<212> TYPE: PRT
<213> ORGANISM: Artificial Sequence
<220> FEATURE:
<223> OTHER INFORMATION: STAT1 binding site (2)

<400> SEQUENCE: 54

Thr Thr Cys Thr Cys Gly Gly Ala Ala
1               5

<210> SEQ ID NO 55
<211> LENGTH: 35010
<212> TYPE: DNA
<213> ORGANISM: Artificial Sequence
<220> FEATURE:
<223> OTHER INFORMATION: Ad5/3Ad2E1Adelta24

<400> SEQUENCE: 55
taacatcatc aataatatac cttatttttgg attgaagcca atatgataat gagggggtgg     60
agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatatttgt ctagggccgc    360
ggggactttg accgtttacg tggagactcg cccaggtgtt tttctcaggt gttttccgcg    420
ttccgggtca agttggcgt tttattatta gtcagctg acgtgtagtg tatttatacc    480
cggtgagttc ctcaagaggc cactcttgag tgccagcgag tagagttttc tcctccgagc    540
cgctccgaca ccgggactga aaatgagaca tattatctgc cacggaggtg ttattaccga    600
agaaatggcc gccagtcttt tggaccagct gatcgaagag gtactggctg ataatcttcc    660
acctcctagc cattttgaac cacctaccct tcacgaactg tatgatttag acgtgacggc    720
ccccgaagat cccaacgagg aggcggtttc gcagattttt cccgagtctg taatgttggc    780
ggtgcaggaa gggattgact tattcacttt tccgccggcg cccggttctc cggagccgcc    840
```

```
tcacctttcc cggcagcccg agcagccgga gcagagagcc ttgggtccgg tttctatgcc    900
aaaccttgtg ccggaggtga tcgatccacc cagtgacgac gaggatgaag agggtgagga    960
gtttgtgtta gattatgtgg agcaccccgg gcacggttgc aggtcttgtc attatcaccg   1020
gaggaatacg ggggacccag atattatgtg ttcgctttgc tatatgagga cctgtggcat   1080
gtttgtctac agtaagtgaa aattatgggc agtcggtgat agagtggtgg gtttggtgtg   1140
gtaattttt tttaatttt acagttttgt ggtttaaaga attttgtatt gtgattttt    1200
aaaaggtcct gtgtctgaac ctgagcctga gcccgagcca gaaccggagc ctgcaagacc   1260
tacccggcgt cctaaattgg tgcctgctat cctgagacgc ccgacatcac ctgtgtctag   1320
agaatgcaat agtagtacgg atagctgtga ctccggtcct tctaacacac ctcctgagat   1380
acacccggtg gtcccgctgt gccccattaa accagttgcc gtgagagttg gtgggcgtcg   1440
ccaggctgtg gaatgtatcg aggacttgct taacgagtct gggcaacctt tggacttgag   1500
ctgtaaacgc cccaggccat aaggtgtaaa cctgtgattg cgtgtgtggt taacgccttt   1560
gtttgctgaa tgagttgatg taagtttaat aaagggtgag ataatgttta acttgcatgg   1620
cgtgttaaat ggggcgggc ttaaagggta tataatgcgc cgtgggctaa tcttggttac   1680
atctgacctc atggaggctt gggagtgttt ggaagatttt tctgctgtgc gtaacttgct   1740
ggaacagagc tctaacagta cctcttggtt ttggaggttt ctgtggggct catcccaggc   1800
aaagttagtc tgcagaatta aggaggatta caagtgggaa tttgaagagc ttttgaaatc   1860
ctgtggtgag ctgtttgatt ctttgaatct gggtcaccag gcgcttttcc aagagaaggt   1920
catcaagact ttggattttt ccacaccggg gcgcgctgcg gctgctgttg cttttttgag   1980
ttttataaag gataaatgga gcgaagaaac ccatctgagc gggggtacc tgctggattt   2040
tctggccatg catctgtgga gagcggttgt gagacacaag aatcgcctgc tactgttgtc   2100
ttccgtccgc ccggcgataa taccgacgga ggagcagcag cagcagcagg aggaagccag   2160
gcggcggcgg caggagcaga gcccatggaa cccgagagcc ggcctggacc ctcgggaatg   2220
aatgttgttc aggtggctga actgtatcca gaactgagac gcattttgac aattacagag   2280
gatgggcagg ggctaaaggg ggtaaagagg gagcgggggg cttgtgaggc tacagaggag   2340
gctaggaatc tagcttttag cttaatgacc agacaccgtc ctgagtgtat tacttttcaa   2400
cagatcaagg ataattgcgc taatgagctt gatctgctgg cgcagaagta ttccatagag   2460
cagctgacca cttactggct gcagccaggg gatgattttg aggaggctat tagggtatat   2520
gcaaaggtgg cacttaggcc agattgcaag tacaagatca gcaaacttgt aaatatcagg   2580
aattgttgct acatttctgg gaacggggcc gaggtggaga tagatacgga ggatagggtg   2640
gcctttagat gtagcatgat aaatatgtgg ccggggggtgc ttggcatgga cggggtggtt   2700
attatgaatg taaggtttac tggccccaat tttagcggta cggttttcct ggccaatacc   2760
aaccttatcc tacacggtgt aagcttctat gggtttaaca ataccgtgt ggaagcctgg   2820
accgatgtaa gggttcgggg ctgtgccttt tactgctgct ggaaggggt ggtgtgtcgc   2880
cccaaaagca gggcttcaat taagaaatgc ctcttgaaa ggtgtacctt gggtatcctg   2940
tctgaggta actccaggt gcgccacaat gtggcctccg actgtggttg cttcatgcta   3000
gtgaaaagcg tggctgtgat taagcataac atggtatgtg gcaactgcga ggacagggcc   3060
tctcagatgc tgacctgctc ggacggcaac tgtcaccttc tgaagaccat tcacgtagcc   3120
agccactctc gcaaggcctg gccagtgttt gagcataaca tactgacccg ctgttccttg   3180
```

```
catttgggta acaggagggg ggtgttccta ccttaccaat gcaatttgag tcacactaag    3240
atattgcttg agcccgagag catgtccaag gtgaacctga acggggtgtt tgacatgacc    3300
atgaagatct ggaaggtgct gaggtacgat gagacccgca ccaggtgcag accctgcgag    3360
tgtggcggta acatattag gaaccagcct gtgatgctgg atgtgaccga ggagctgagg    3420
cccgatcact tggtgctggc ctgcacccgc gctgagtttg gctctagcga tgaagataca    3480
gattgaggta ctgaaatgtg tgggcgtggc ttaagggtgg gaaagaatat ataaggtggg    3540
ggtcttatgt agttttgtat ctgttttgca gcagccgccg ccgccatgag caccaactcg    3600
tttgatggaa gcattgtgag ctcatatttg acaacgcgca tgcccccatg ggccggggtg    3660
cgtcagaatg tgatgggctc cagcattgat ggtcgccccg tcctgcccgc aaactctact    3720
accttgacct acgagaccgt gtctggaacg ccgttggaga ctgcagcctc cgccgccgct    3780
tcagccgctg cagccaccgc ccgcgggatt gtgactgact ttgctttcct gagcccgctt    3840
gcaagcagtg cagcttcccg ttcatccgcc cgcgatgaca agttgacggc tcttttggca    3900
caattggatt ctttgacccg ggaacttaat gtcgtttctc agcagctgtt ggatctgcgc    3960
cagcaggttt ctgccctgaa ggcttcctcc cctcccaatg cggtttaaaa cataaataaa    4020
aaaccagact ctgtttggat ttggatcaag caagtgtctt gctgtctta tttaggggtt     4080
ttgcgcgcgc ggtaggcccg ggaccagcgg tctcggtcgt tgagggtcct gtgtattttt    4140
tccaggacgt ggtaaaggtg actctggatg ttcagataca tgggcataag cccgtctctg    4200
gggtggaggt agcaccactg cagagcttca tgctgcgggg tggtgttgta gatgatccag    4260
tcgtagcagg agcgctgggc gtggtgccta aaaatgtctt tcagtagcaa gctgattgcc    4320
aggggcaggc ccttggtgta agtgtttaca aagcggttaa gctgggatgg gtgcatacgt    4380
ggggatatga gatgcatctt ggactgtatt tttaggttgg ctatgttccc agccatatcc    4440
ctccggggat tcatgttgtg cagaaccacc agcacagtgt atccggtgca cttgggaaat    4500
ttgtcatgta gcttagaagg aaatgcgtgg aagaacttgg agacgccctt gtgacctcca    4560
agatttccca tgcattcgtc cataatgatg gcaatgggcc cacgggcggc ggcctgggcg    4620
aagatatttc tgggatcact aacgtctag ttgtgttcca ggatgagatc gtcataggcc      4680
attttttacaa agcgcgggcg gagggtgcca gactgcggta taatggttcc atccggccca    4740
ggggcgtagt taccctcaca gatttgcatt tcccacgctt tgagttcaga tgggggatc     4800
atgtctacct gcgggcgat gaagaaaacg gtttccgggg taggggagat cagctgggaa      4860
gaaagcaggt tcctgagcag ctgcgactta ccgcagccgg tgggcccgta aatcacacct    4920
attaccgggt gcaactggta gttaagagag ctgcagctgc cgtcatccct gagcaggggg    4980
gccacttcgt taagcatgtc cctgactcgc atgttttccc tgaccaaatc cgccagaagg    5040
cgctcgccgc ccagcgatag cagttcttgc aaggaagcaa agtttttcaa cggtttgaga    5100
ccgtccgccg taggcatgct tttgagcgtt tgaccaagca gttccaggcg gtcccacagc    5160
tcggttacct gctctacggc atctcgatcc agcatatctc ctcgtttcgc gggttgggc      5220
ggctttcgct gtacggcagt agtcggtgct cgtccagacg ggccagggtc atgtctttcc    5280
acgggcgcag ggtcctcgtc agcgtagtct gggtcacggt gaaggggtgc gctccgggct    5340
gcgcgctggc cagggtgcgc ttgaggctgg tcctgctggt gctgaagcgc tgccggtctt    5400
cgccctgcgc gtcggccagg tagcatttga ccatggtgtc atagtccagc ccctccgcgg    5460
cgtggccctt ggcgcgcagc ttgcccttgg aggaggcgcc gcacgagggg cagtgcagac    5520
ttttgagggc gtagagcttg ggcgcgagaa ataccgattc cggggagtag gcatccgcgc    5580
```

```
cgcaggcccc gcagacggtc tcgcattcca cgagccaggt gagctctggc cgttcggggt    5640
caaaaaccag gtttccccca tgcttttga tgcgtttctt acctctggtt tccatgagcc     5700
ggtgtccacg ctcggtgacg aaaaggctgt ccgtgtcccc gtatacagac ttgagaggcc    5760
tgtcctcgag cggtgttccg cggtcctcct cgtatagaaa ctcggaccac tctgagacaa    5820
aggctcgcgt ccaggccagc acgaaggagg ctaagtggga ggggtagcgg tcgttgtcca    5880 ctaggggtc  cactcgctcc agggtgtgaa gacacatgtc gccctcttcg gcatcaagga    5940
aggtgattgg tttgtaggtg taggccacgt gaccgggtgt tcctgaaggg gggctataaa    6000 aggggggtggg ggcgcgttcg tcctcactct cttccgcatc gctgtctgcg agggccagct   6060
gttggggtga gtactccctc tgaaaagcgg gcatgacttc tgcgctaaga ttgtcagttt    6120
ccaaaaacga ggaggattg  atattcacct ggcccgcgt  gatgcctttg agggtggccg    6180
catccatctg gtcagaaaag acaatctttt tgttgtcaag cttggtggca aacgacccgt    6240
agagggcgtt ggacagcaac ttggcgatgg agcgcagggt ttggttttg  tcgcgatcgg    6300 cgcgctcctt ggccgcgatg tttagctgca cgtattcgcg cgcaacgcac cgccattcgg    6360
gaaagacggt ggtgcgctcg tcgggcacca ggtgcacgcg ccaaccgcgg ttgtgcaggg    6420
tgacaaggtc aacgctggtg gctacctctc cgcgtaggcg ctcgttggtc cagcagaggc    6480
ggccgccctt gcgcgagcag aatgcgggta gggggtctag ctgcgtctcg tccgggggt    6540 ctgcgtccac ggtaaagacc ccgggcagca ggcgcgcgtc gaagtagtct atcttgcatc    6600
cttgcaagtc tagcgcctgc tgccatgcgc gggcggcaag cgcgcgctcg tatgggttga    6660 gtggggggacc ccatggcatg gggtgggtga gcgcggaggc gtacatgccg caaatgtcgt    6720
aaacgtagag gggctctctg agtattccaa gatatgtagg gtagcatctt ccaccgcgga    6780
tgctggcgcg cacgtaatcg tatagttcgt gcgagggagc gaggaggtcg ggaccgaggt    6840
tgctacgggc gggctgctct gctcggaaga ctatctgcct gaagatggca tgtgagttgg    6900
atgatatggt tggacgctgg aagacgttga agctggcgtc tgtgagacct accgcgtcac    6960
gcacgaagga ggcgtaggag tcgcgcagct tgttgaccag ctcggcggtg acctgcacgt    7020
ctagggcgca gtagtccagg gtttccttga tgatgtcata cttatcctgt ccctttttt    7080 tccacagctc gcggttgagg acaaactctt cgcggtcttt ccagtactct tggatcggaa    7140
acccgtcggc ctccgaacgg taagagccta gcatgtagaa ctggttgacg gcctggtagg    7200
cgcagcatcc ctttttctacg ggtagcgcgt atgcctgcgc ggccttccgg agcgaggtgt    7260
gggtgagcgc aaaggtgtcc ctgaccatga ctttgaggta ctggtatttg aagtcagtgt    7320
cgtcgcatcc gccctgctcc cagagcaaaa agtccgtgcg cttttttggaa cgcggatttg    7380 gcagggcgaa ggtgacatcg ttgaagagta tctttcccgc gcgaggcata agttgcgtg    7440 tgatgcggaa gggtcccggc acctcggaac ggttgttaat tacctgggcg gcgagcacga    7500
tctcgtcaaa gccgttgatg ttgtggccca aatgtaaag  ttccaagaag cgcgggatgc    7560
ccttgatgga aggcaatttt ttaagttcct cgtaggtgag ctcttcaggg gagctgagcc    7620
cgtgctctga aagggcccag tctgcaagat gagggttgga agcgacgaat gagctccaca    7680
ggtcacgggc cattagcatt tgcaggtggt cgcgaaaggt cctaaactgg cgacctatgg    7740 ccatttttc  tggggtgatg cagtagaagg taagcgggtc ttgttcccag cggtcccatc    7800
caaggttcgc ggctaggtct cgcgcggcag tcactagagg ctcatctccg ccgaacttca    7860
tgaccagcat gaagggcacg agctgcttcc caaaggcccc catccaagta taggtctcta    7920
```

```
catcgtaggt gacaaagaga cgctcggtgc gaggatgcga gccgatcggg aagaactgga   7980
tctcccgcca ccaattggag gagtggctat tgatgtggtg aaagtagaag tccctgcgac   8040
gggccgaaca ctcgtgctgg cttttgtaaa aacgtgcgca gtactggcag cggtgcacgg   8100
gctgtacatc ctgcacgagg ttgacctgac gaccgcgcac aaggaagcag agtgggaatt   8160
tgagcccctc gcctggcggg tttggctggt ggtcttctac ttcggctgct tgtccttgac   8220
cgtctggctg ctcgaggga gttacggtgg atcggaccac cacgccgcgc gagcccaaag    8280
tccagatgtc cgcgcgcggc ggtcggagct tgatgacaac atcgcgcaga tgggagctgt   8340
ccatggtctg gagctcccgc ggcgtcaggt caggcgggag ctcctgcagg tttacctcgc   8400
atagacgggt cagggcgcgg gctagatcca ggtgatacct aatttccagg ggctggttgg   8460
tggcggcgtc gatggcttgc aagaggccgc atccccgcgg cgcgactacg gtaccgcgcg   8520
gcgggcggtg ggccgcgggg gtgtccttgg atgatgcatc taaaagcggt gacgcgggcg   8580
agcccccgga ggtagggggg gctccggacc cgccggaga gggggcaggg gcacgtcggc    8640
gccgcgcgcg ggcaggagct ggtgctgcgc gcgtaggttg ctggcgaacg cgacgacgcg   8700
gcggttgatc tcctgaatct ggcgcctctg cgtgaagacg acgggcccgg tgagcttgag   8760
cctgaaagag agttcgacag aatcaatttc ggtgtcgttg acgcggcct ggcgcaaaat    8820
ctcctgcacg tctcctgagt tgtcttgata ggcgatctcg gccatgaact gctcgatctc   8880
ttcctcctgg agatctccgc gtccggctcg ctccacggtg gcggcgaggt cgttggaaat   8940
gcgggccatg agctgcgaga aggcgttgag gcctccctcg ttccagacgc ggctgtagac   9000
cacgccccct tcggcatcgc gggcgcgcat gaccacctgc gcgagattga gctccacgtg   9060
ccgggcgaag acggcgtagt ttcgcaggcg ctgaaagagg tagttgaggg tggtggcggt   9120
gtgttctgcc acgaagaagt acataaccca gcgtcgcaac gtggattcgt tgatatcccc   9180
caaggcctca aggcgctcca tggcctcgta gaagtccacg gcgaagttga aaaactggga   9240
gttgcgcgcc gacacggtta actcctcctc cagaagacgg atgagctcgg cgacagtgtc   9300
gcgcacctcg cgctcaaagg ctacagggc ctcttcttct tcttcaatct cctcttccat    9360
aagggcctcc ccttcttctt cttctggcgg cggtgggga gggggacac ggcggcgacg     9420
acggcgcacc gggaggcggt cgacaaagcg ctcgatcatc tccccgcggc gacggcgcat   9480
ggtctcggtg acgcgcggc cgttctcgcg ggggcgcagt tggaagacgc cgcccgtcat    9540
gtcccggtta tgggttggcg ggggctgcc atgcggcagg gatacggcgc taacgatgca    9600
tctcaacaat tgttgtgtag gtactccgcc gccgagggac ctgagcgagt ccgcatcgac   9660
cggatcggaa aacctctcga gaaaggcgtc taaccagtca cagtcgcaag gtaggctgag   9720
caccgtggcg ggcggcagcg ggcggcggtc ggggttgttt ctggcggagg tgctgctgat   9780
gatgtaatta aagtaggcgg tcttgagacg gcggatggtc gacagaagca ccatgtcctt   9840
gggtccggcc tgctgaatgc gcaggcggtc ggccatgccc caggcttcgt tttgacatcg   9900
gcgcaggtct ttgtagtagt cttgcatgag cctttctacc ggcacttctt cttctccttc   9960
ctcttgtcct gcatctcttg catctatcgc tgcggcggcg gcggagtttg gccgtaggtg  10020
gcgccctctt cctcccatgc gtgtgacccc gaagcccctc atcggctgaa gcagggctag  10080
gtcggcgaca acgcgctcgg ctaatatggc ctgctgcacc tgcgtgaggg tagactggaa  10140
gtcatccatg tccacaaagc ggtggtatgc gcccgtgttg atggtgtaag tgcagttggc  10200
cataacggac cagttaacgg tctggtgacc cggctgcgag agctcggtgt acctgagacg  10260
cgagtaagcc ctcgagtcaa atacgtagtc gttgcaagtc cgcaccaggt actggtatcc  10320
```

```
caccaaaaag tgcggcggcg gctggcggta gaggggccag cgtagggtgg ccggggctcc   10380
gggggcgaga tcttccaaca taaggcgatg atatccgtag atgtacctgg acatccaggt   10440
gatgccggcg gcggtggtgg aggcgcgcgg aaagtcgcgg acgcggttcc agatgttgcg   10500
cagcggcaaa aagtgctcca tggtcggac gctctggccg tcaggcgcg cgcaatcgtt    10560
gacgctctag accgtgcaaa aggagagcct gtaagcgggc actcttccgt ggtctggtgg   10620
ataaattcgc aagggtatca tggcggacga ccggggttcg agccccgtat ccggccgtcc   10680
gccgtgatcc atgcggttac cgcccgcgtg tcgaacccag gtgtgcgacg tcagacaacg   10740
ggggagtgct cctttttggct tccttccagg cgcggcggct gctgcgctag cttttttggc   10800
cactggccgc gcgcagcgta agcggttagg ctggaaagcg aaagcattaa gtggctcgct   10860
ccctgtagcc ggagggttat tttccaaggg ttgagtcgcg ggaccccgg ttcgagtctc    10920
ggaccggccg gactgcggcg aacggggggtt tgcctccccg tcatgcaaga cccgcttgc   10980
aaattcctcc ggaaacaggg acgagcccct tttttgcttt tcccagatgc atccggtgct   11040
gcggcagatg cgccccctc ctcagcagcg gcaagagcaa gagcagcggc agacatgcag    11100
ggcaccctcc cctcctccta ccgcgtcagg aggggcgaca tccgcggttg acgcggcagc   11160
agatggtgat tacgaacccc cgcggcgccg ggcccggcac tacctggact tggaggaggg   11220
cgagggcctg gcgcggctag gagcgccctc tcctgagcgg tacccaaggg tgcagctgaa   11280
gcgtgatacg cgtgaggcgt acgtgccgcg gcagaacctg tttcgcgacc gcgagggaga   11340
ggagcccgag gagatgcggg atcgaaagtt ccacgcaggg cgcgagctgc ggcatggcct   11400
gaatcgcgag cggttgctgc gcgaggagga cttgagccc gacgcgcgaa ccgggattag    11460
tcccgcgcgc gcacacgtgg cggccgccga cctggtaacc gcatacgagc agacggtgaa   11520
ccaggagatt aactttcaaa aaagctttaa caaccacgtg cgtacgcttg tggcgcgcga   11580
ggaggtggct ataggactga tgcatctgtg ggactttgta agcgcgctgg agcaaaaccc   11640
aaatagcaag ccgctcatgg cgcagctgtt ccttatagtg cagcacagca gggacaacga   11700
ggcattcagg gatgcgctgc taaacatagt agagcccgag ggccgctggc tgctcgattt   11760
gataaacatc ctgcagagca tagtggtgca ggagcgcagc ttgagcctgg ctgacaaggt   11820
ggccgccatc aactattcca tgcttagcct gggcaagttt tacgcccgca agatatacca   11880
tacccccttac gttcccatag acaaggaggt aaagatcgag gggttctaca tgcgcatggc   11940
gctgaaggtg cttaccttga gcgacgacct gggcgtttat cgcaacgagc gcatccacaa   12000
ggccgtgagc gtgagccggc ggcgcgagct cagcgaccgc gagctgatgc acagcctgca   12060
aagggccctg gctggcacgg gcagcggcga tagagaggcc gagtcctact ttgacgcggg   12120
cgctgacctg gcgctgggcc caagccgacg cgccctggag gcagctgggg ccggacctgg   12180
gctggcggtg gcacccgcgc gcgctggcaa cgtcggcggc gtggaggaat atgacgagga   12240
cgatgagtac gagccagagg acggcgagta ctaagcggtg atgtttctga tcagatgatg   12300
caagacgcaa cggacccggc ggtgcgggcg cgctgcaga gccagccgtc cggccttaac    12360
tccacggacg actggcgcca ggtcatggac cgcatcatgt cgctgactgc gcgcaatcct   12420
gacgcgttcc ggcagcagcc gcaggccaac cggctctccg caattctgga agcggtggtc   12480
ccggcgcgcg caaaccccac gcacgagaag gtgctggcga tcgtaaacgc gctggccgaa   12540
aacagggcca tccggcccga cgaggccggc ctggtctacg acgcgctgct tcagcgcgtg   12600
gctcgttaca acagcggcaa cgtgcagacc aacctggacc ggctggtggg ggatgtgcgc   12660
```

-continued

```
gaggccgtgg cgcagcgtga gcgcgcgcag cagcagggca acctgggctc catggttgca    12720
ctaaacgcct tcctgagtac acagcccgcc aacgtgccgc ggggacagga ggactacacc    12780
aactttgtga gcgcactgcg gctaatggtg actgagacac cgcaaagtga ggtgtaccag    12840
tctgggccag actattttt ccagaccagt agacaaggcc tgcagaccgt aaacctgagc     12900
caggctttca aaaacttgca ggggctgtgg ggggtgcggg ctcccacagg cgaccgcgcg    12960
accgtgtcta gcttgctgac gcccaactcg cgcctgttgc tgctgctaat agcgccttc     13020
acggacagtg gcagcgtgtc ccgggacaca tacctaggtc acttgctgac actgtaccgc    13080
gaggccatag gtcaggcgca tgtggacgag catactttcc aggagattac aagtgtcagc    13140
cgcgcgctgg ggcaggagga cacgggcagc ctggaggcaa ccctaaacta cctgctgacc    13200
aaccggcggc agaagatccc ctcgttgcac agtttaaaca gcgaggagga gcgcattttg    13260
cgctacgtgc agcagagcgt gagccttaac ctgatgcgcg acggggtaac gcccagcgtg    13320
gcgctggaca tgaccgcgcg caacatggaa ccgggcatgt atgcctcaaa ccggccgttt    13380
atcaaccgcc taatggacta cttgcatcgc gcggccgccg tgaaccccga gtatttcacc    13440
aatgccatct tgaacccgca ctggctaccc cccctggtt tctacaccgg gggattcgag     13500
gtgcccgagg gtaacgatgg attcctctgg acgacatag cgacagcgt gttttcccccg    13560
caaccgcaga ccctgctaga gttgcaacag cgcgagcagg cagaggcggc gctgcgaaag    13620
gaaagcttcc gcaggccaag cagcttgtcc gatctaggcg ctgcggcccc cgcggtcagat    13680
gctagtagcc catttccaag cttgataggg tctcttacca gcactcgcac cacccgcccg    13740
cgcctgctgg gcgaggagga gtacctaaac aactcgctgc tgcagccgca gcgcgaaaaa    13800
aacctgcctc cggcatttcc caacaacggg atagagagcc tagtggacaa gatgagtaga    13860
tggaagacgt acgcgcagga gcacagggac gtgccaggcc cgcgcccgcc caccgtcgt     13920
caaaggcacg accgtcagcg gggtctggtg tgggaggacg atgactcggc agacgacagc    13980
agcgtcctgg atttggggagg gagtggcaac ccgtttgcgc accttcgccc caggctgggg    14040
agaatgttt aaaaaaaaa aagcatgatg caaaataaaa aactcaccaa ggccatggca      14100
ccgagcgttg gttttcttgt attcccctta gtatgcggcg cgcggcgatg tatgaggaag    14160
gtcctcctcc ctcctacgag agtgtggtga gcgcggcgcc agtggcggcg cgctgggtt     14220
ctcccttcga tgctcccctg gacccgccgt ttgtgcctcc gcggtacctg cggcctaccg    14280
ggggagaaa cagcatccgt tactctgagt tggcaccct attcgacacc accccgtgtgt     14340
acctggtgga caacaagtca acggatgtgg catccctgaa ctaccagaac gaccacagca    14400
actttctgac cacggtcatt caaaacaatg actacagccc gggggaggca agcacacaga    14460
ccatcaatct tgacgaccgg tcgcactggg gcggcgacct gaaaaccatc ctgcatacca    14520
acatgccaaa tgtgaacgag ttcatgttta ccaataagtt taaggcgcgg gtgatggtgt    14580
cgcgcttgcc tactaaggac aatcaggtgg agctgaaata cgagtgggtg gagttcacgc    14640
tgcccgaggg caactactcc gagaccatga ccatagacct tatgaacaac gcgatcgtgg    14700
agcactactt gaaagtgggc agacagaacg gggttctgga aagcgacatc ggggtaaagt    14760
ttgacacccg caacttcaga ctggggttg accccgtcac tggtcttgtc atgcctgggg    14820
tatatacaaa cgaagccttc catccagaca tcattttgct gccaggatgc ggggtggact    14880
tcacccacag ccgcctgagc aacttgttgg gcatccgcaa gcggcaaccc ttccaggagg    14940
gctttaggat cacctacgat gatctggagg gtggtaacat tccccgcactg ttggatgtgg   15000
acgcctacca ggcgagcttg aaagatgaca ccgaacaggg cggggtggc gcaggcggca     15060
```

```
gcaacagcag tggcagcggc gcggaagaga actccaacgc ggcagccgcg gcaatgcagc    15120
cggtggagga catgaacgat catgccattc gcggcgacac ctttgccaca cgggctgagg    15180
agaagcgcgc tgaggccgaa gcagcggccg aagctgccgc ccccgctgcg caacccgagg    15240
tcgagaagcc tcagaagaaa ccggtgatca accccctgac agaggacagc aagaaacgca    15300
gttacaacct aataagcaat gacagcacct tcacccagta ccgcagctgg taccttgcat    15360
acaactacgg cgaccctcag accggaatcc gctcatggac cctgctttgc actcctgacg    15420
taacctgcgg ctcggagcag gtctactggt cgttgccaga catgatgcaa gaccccgtga    15480
ccttccgctc cacgcgccag atcagcaact ttccggtggt gggcgccgag ctgttgcccg    15540
tgcactccaa gagcttctac aacgaccagg ccgtctactc ccaactcatc cgccagttta    15600
cctctctgac ccacgtgttc aatcgctttc ccgagaacca gattttggcg cgcccgccag    15660
cccccaccat caccaccgtc agtgaaaacg ttcctgctct cacagatcac gggacgctac    15720
cgctgcgcaa cagcatcgga ggagtccagc gagtgaccat tactgacgcc agacgccgca    15780
cctgcccctacgtttacaag gccctgggca tagtctcgcc gcgcgtccta tcgagccgca    15840
cttttttgagc aagcatgtcc atccttatat cgcccagcaa taacacaggc tggggcctgc    15900
gcttcccaag caagatgttt ggcggggcca agaagcgctc cgaccaacac ccagtgcgcg    15960
tgcgcgggca ctaccgcgcg ccctgggggcg cgcacaaacg cggccgcact gggcgcacca    16020
ccgtcgatga cgccatcgac gcggtggtgg aggaggcgcg caactacacg cccacgccgc    16080
caccagtgtc cacagtggac gcggccattc agaccgtggt gcgcggagcc cggcgctatg    16140
ctaaaatgaa gagacggcgg aggcgcgtag cacgtcgcca ccgccgccga cccggcactg    16200
ccgcccaacg cgcggcggcg gccctgctta accgcgcacg tcgcaccggc cgacgggcgg    16260
ccatgcgggc cgctcgaagg ctggccgcgg gtattgtcac tgtgcccccc aggtccaggc    16320
gacgagcggc cgccgcagca gccgcggcca ttagtgctat gactcagggt cgcaggggca    16380
acgtgtattg ggtgcgcgac tcggttagcg gcctgcgcgt gcccgtgcgc acccgccccc    16440
cgcgcaacta gattgcaaga aaaaactact tagactcgta ctgttgtatg tatccagcgg    16500
cggcggcgcg caacgaagct atgtccaagc gcaaaatcaa agaagagatg ctccaggtca    16560
tcgcgccgga gatctatggc ccccccgaaga aggaagagca ggattacaag ccccgaaagc    16620
taaagcgggt caaaaagaaa aagaaagatg atgatgatga acttgacgac gaggtggaac    16680
tgctgcacgc taccgcgccc aggcgacggg tacagtggaa aggtcgacgc gtaaaacgtg    16740
tttttgcgacc cggcaccacc gtagtctttta cgcccggtga gcgctccacc cgcacctaca    16800
agcgcgtgta tgatgaggtg tacggcgacg aggacctgct tgagcaggcc aacgagcgcc    16860
tcggggagtt tgcctacgga aagcggcata aggacatgct ggcgttgccg ctggacgagg    16920
gcaacccaac acctagccta aagcccgtaa cactgcagca ggtgctgccc gcgcttgcac    16980
cgtccgaaga aaagcgcggc ctaaagcgcg agtctggtga cttggcaccc accgtgcagc    17040
tgatggtacc caagcgccag cgactggaag atgtcttgga aaaaatgacc gtggaacctg    17100
ggctggagcc cgaggtccgc gtgcggccaa tcaagcaggt ggcgccggga ctgggcgtgc    17160
agaccgtgga cgttcagata cccactacca gtagcaccag tattgccacc gccacagagg    17220
gcatggagac acaaacgtcc ccggttgcct cagcggtggc ggatgccgcg gtgcaggcgg    17280
tcgctgcggc cgcgtccaag acctctacgg aggtgcaaac ggaccgtggg atgtttcgcg    17340
tttcagcccc ccggcgcccg cgcggttcga ggaagtacgg cgccgccagc gcgctactgc    17400
```

| | |
|---|---|
| ccgaatatgc cctacatcct tccattgcgc ctaccccggg ctatcgtggc tacacctacc | 17460 |
| gccccagaag acgagcaact acccgacgcc gaaccaccac tggaacccgc cgccgccgtc | 17520 |
| gccgtcgcca gcccgtgctg gccccgattt ccgtgcgcag ggtggctcgc gaaggaggca | 17580 |
| ggaccctggt gctgccaaca gcgcgctacc accccagcat cgtttaaaag ccggtctttg | 17640 |
| tggttcttgc agatatggcc ctcacctgcc gcctccgttt cccggtgccg ggattccgag | 17700 |
| gaagaatgca ccgtaggagg ggcatggccg gccacggcct gacgggcggc atgcgtcgtg | 17760 |
| cgcaccaccg gcggcggcgc gcgtcgcacc gtcgcatgcg cggcggtatc ctgcccctcc | 17820 |
| ttattccact gatcgccgcg gcgattggcg ccgtgcccgg aattgcatcc gtggccttgc | 17880 |
| aggcgcagag acactgatta aaaacaagtt gcatgtggaa aaatcaaaat aaaaagtctg | 17940 |
| gactctcacg ctcgcttggt cctgtaacta ttttgtagaa tggaagacat caactttgcg | 18000 |
| tctctggccc cgcgacacgg ctcgcgcccg ttcatgggaa actggcaaga tatcggcacc | 18060 |
| agcaatatga gcggtggcgc cttcagctgg ggctcgctgt ggagcggcat taaaaatttc | 18120 |
| ggttccaccg ttaagaacta tggcagcaag gcctggaaca gcagcacagg ccagatgctg | 18180 |
| agggataagt tgaaagagca aaatttccaa caaaaggtgg tagatggcct ggcctctggc | 18240 |
| attagcgggg tggtggacct ggccaaccag gcagtgcaaa ataagattaa cagtaagctt | 18300 |
| gatccccgcc ctcccgtaga ggagcctcca ccggccgtgg agacagtgtc tccagagggg | 18360 |
| cgtggcgaaa agcgtccgcg ccccgacagg gaagaaactc tggtgacgca aatagacgag | 18420 |
| cctccctcgt acgaggaggc actaaagcaa ggcctgccca ccaccgtcc catcgcgccc | 18480 |
| atggctaccg gagtgctggg ccagcacaca cccgtaacgc tggacctgcc tcccccgcc | 18540 |
| gacacccagc agaaacctgt gctgccaggc ccgaccgccg ttgttgtaac ccgtcctagc | 18600 |
| cgcgcgtccc tgccgcgcgc cgccagcggt ccgcgatcgt gcggccgt agccagtggc | 18660 |
| aactggcaaa gcacactgaa cagcatcgtg ggtctggggg tgcaatccct gaagcgccga | 18720 |
| cgatgcttct gaatagctaa cgtgtcgtat gtgtgtcatg tatgcgtcca tgtcgccgcc | 18780 |
| agaggagctg ctgagccgcc gcgcgcccgc tttccaagat ggctacccct tcgatgatgc | 18840 |
| cgcagtggtc ttacatgcac atctcgggcc aggacgcctc ggagtacctg agccccgggc | 18900 |
| tggtgcagtt tgcccgcgcc accgagacgt acttcagcct gaataacaag tttagaaacc | 18960 |
| ccacggtggc gcctacgcac gacgtgacca cagaccggtc ccagcgtttg acgctgcggt | 19020 |
| tcatccctgt ggaccgtgag gatactgcgt actcgtacaa ggcgcggttc accctagctg | 19080 |
| tgggtgataa ccgtgtgctg gacatggctt ccacgtactt tgacatccgc ggcgtgctgg | 19140 |
| acaggggccc tactttttaag ccctactctg gcactgccta caacgccctg gctcccaagg | 19200 |
| gtgccccaaa tccttgcgaa tgggatgaag ctgctactgc tcttgaaata aacctagaag | 19260 |
| aagaggacga tgacaacgaa gacgaagtag acagcaagc tgagcagcaa aaaactcacg | 19320 |
| tatttgggca ggcgccttat tctggtataa atattacaaa ggagggtatt caaataggtg | 19380 |
| tcgaaggtca aacacctaaa tatgccgata aaacatttca acctgaacct caaataggag | 19440 |
| aatctcagtg gtacgaaact gaaattaatc atgcagctgg gagagtcctt aaaaagacta | 19500 |
| ccccaatgaa accatgttac ggttcatatg caaacccac aaatgaaaat ggagggcaag | 19560 |
| gcattcttgt aaagcaacaa atggaaagc tagaaagtca agtggaaatg caattttct | 19620 |
| caactactga ggcgaccgca ggcaatggtg ataacttgac tcctaaagtg gtattgtaca | 19680 |
| gtgaagatgt agatatagaa accccagaca ctcatatttc ttacatgccc actattaagg | 19740 |
| aaggtaactc acgagaacta atgggccaac aatctatgcc caacaggcct aattacattg | 19800 |

```
cttttaggga caattttatt ggtctaatgt attacaacag cacgggtaat atgggtgttc    19860
tggcgggcca agcatcgcag ttgaatgctg ttgtagattt gcaagacaga aacacagagc    19920
tttcatacca gcttttgctt gattccattg gtgatagaac caggtacttt tctatgtgga    19980
atcaggctgt tgacagctat gatccagatg ttagaattat tgaaaatcat ggaactgaag    20040
atgaacttcc aaattactgc tttccactgg gaggtgtgat taatacagag actcttacca    20100
aggtaaaacc taaacaggt caggaaaatg gatgggaaaa agatgctaca gaattttcag     20160
ataaaaatga aataagagtt ggaaataatt ttgccatgga aatcaatcta aatgccaacc    20220
tgtggagaaa tttcctgtac tccaacatag cgctgtattt gcccgacaag ctaaagtaca    20280
gtccttccaa cgtaaaaatt tctgataacc caaacaccta cgactacatg aacaagcgag    20340
tggtggctcc cggttagtg gactgctaca ttaaccttgg agcacgctgg tcccttgact     20400
atatggacaa cgtcaaccca tttaaccacc accgcaatgc tggcctgcgc taccgctcaa    20460
tgttgctggg caatggtcgc tatgtgccct tccacatcca ggtgcctcag aagttctttg    20520
ccattaaaaa cctccttctc ctgccgggct catacaccta cgagtggaac ttcaggaagg    20580
atgttaacat ggtctgcag agctccctag gaaatgacct aagggttgac ggagccagca     20640
ttaagtttga tagcatttgc ctttacgcca ccttcttccc catggcccac aacaccgcct    20700
ccacgcttga ggccatgctt agaaacgaca ccaacgacca gtcctttaac gactatctct    20760
ccgccgccaa catgctctac cctataccg ccaacgctac caacgtgccc atatccatcc     20820
cctcccgcaa ctgggcggct ttccgcggct gggccttcac gcgccttaag actaaggaaa    20880
ccccatcact gggctcgggc tacgaccctt attcaccta ctctggctct atacccacc      20940 tagatggaac cttttacctc aaccacacct ttaagaaggt ggccattacc tttgactctt    21000
ctgtcagctg gcctggcaat gaccgcctgc ttaccccaa cgagtttgaa attaagcgct     21060
cagttgacgg ggagggttac aacgttgccc agtgtaacat gaccaaagac tggttcctgg    21120
tacaaatgct agctaactac aacattggct accagggctt ctatatccca gagagctaca    21180
aggaccgcat gtactccttc tttagaaact tccagcccat gagccgtcag gtggtggatg    21240
atactaaata caaggactac caacaggtgg gcatcctaca ccaacacaac aactctggat    21300
ttgttggcta ccttgccccc accatgcgcg aaggacaggc ctaccctgct aacttcccct    21360 atcgcttat aggcaagacc gcagttgaca gcattaccca gaaaagttt ctttgcgatc      21420 gcacctttg gcgcatccca ttctccagta actttatgtc catgggcgca ctcacagacc    21480
tgggccaaaa ccttctctac gccaactccg cccacgcgct agacatgact tttgaggtgg    21540
atcccatgga cgagcccacc cttctttatg ttttgtttga agtctttgac gtggtccgtg    21600
tgcaccggcc gcaccgcggc gtcatcgaaa ccgtgtacct cgcacgcgcc ttctcggccg    21660
gcaacgccac aacataaaga agcaagcaac atcaacaaca gctgccgcca tgggctccag    21720
tgagcaggaa ctgaaagcca ttgtcaaaga tcttggttgt gggccatatt tttttgggcac   21780 ctatgacaag cgcttccag gctttgtttc tccacacaag ctcgcctgcg ccatagtcaa     21840
tacggccggt cgcgagactg ggggcgtaca ctggatggcc tttgcctgga acccgcactc    21900
aaaaacatgc tacctctttg agcccttggg cttttctgac cagcgactca gcaggttta    21960 ccagtttgag tacgagtcac tcctgcgccg tagcgccatt gcttcttccc ccgaccgctg    22020
tataacgctg gaaaagtcca cccaaagcgt acagggccc aactcggccg cctgtggact     22080
attctgctgc atgtttctcc acgcctttgc caactggccc caaactccca tggatcacaa    22140
```

```
ccccaccatg aaccttatta ccggggtacc caactccatg ctcaacagtc cccaggtaca    22200 gcccacccctg cgtcgcaacc aggaacagct ctacagcttc ctggagcgcc actcgccct a   22260 cttccgcagc cacagtgcgc agattaggag cgccacttct ttttgtcact tgaaaaacat    22320
gtaaaaataa tgtactagag acactttcaa taaaggcaaa tgcttttatt tgtacactct    22380
cgggtgatta tttaccccca cccttgccgt ctgcgccgtt taaaaatcaa aggggttctg    22440
ccgcgcatcg ctatgcgcca ctggcaggga cacgttgcga tactggtgtt tagtgctcca    22500
cttaaactca ggcacaacca tccgcggcag ctcggtgaag ttttcactcc acaggctgcg    22560
caccatcacc aacgcgttta gcaggtcggg cgccgatatc ttgaagtcgc agttggggcc    22620
tccgccctgc gcgcgcgagt tgcgatacac agggttgcag cactggaaca ctatcagcgc    22680
cgggtggtgc acgctggcca gcacgctctt gtcggagatc agatccgcgt ccaggtcctc    22740
cgcgttgctc agggcgaacg gagtcaactt tggtagctgc cttcccaaaa agggcgcgtg    22800
cccaggcttt gagttgcact cgcaccgtag tggcatcaaa aggtgaccgt gcccggtctg    22860
ggcgttagga tacagcgcct gcataaaagc cttgatctgc ttaaaagcca cctgagcctt    22920
tgcgccttca gagaagaaca tgccgcaaga cttgccggaa aactgattgg ccggacaggc    22980
cgcgtcgtgc acgcagcacc ttgcgtcggt gttggagatc tgcaccacat ttcggcccca    23040
ccggttcttc acgatcttgg ccttgctaga ctgctccttc agcgcgcgct gcccgttttc    23100
gctcgtcaca tccatttcaa tcacgtgctc cttatttatc ataatgcttc cgtgtagaca    23160
cttaagctcg ccttcgatct cagcgcagcg gtgcagccac aacgcgcagc ccgtgggctc    23220
gtgatgcttg taggtcacct ctgcaaacga ctgcaggtac gcctgcagga atcgccccat    23280
catcgtcaca aaggtcttgt tgctggtgaa ggtcagctgc aacccgcggt gctcctcgtt    23340
cagccaggtc ttgcatacgg ccgccagagc ttccacttgg tcaggcagta gtttgaagtt    23400
cgcctttaga tcgttatcca cgtggtactt gtccatcagc gcgcgcgcag cctccatgcc    23460
cttctcccac gcagacacga tcggcacact cagcgggttc atcaccgtaa tttcactttc    23520
cgcttcgctg ggctcttcct cttcctcttg cgtccgcata ccacgcgcca ctgggtcgtc    23580
ttcattcagc cgccgcactg tgcgcttacc tcctttgcca tgcttgatta gcaccggtgg    23640
gttgctgaaa cccaccattt gtagcgccac atcttctctt tcttcctcgc tgtccacgat    23700
tacctctggt gatggcgggc gctcgggctt gggagaaggg cgcttctttt tcttcttggg    23760
cgcaatggcc aaatccgccg ccgaggtcga tggccgcggg ctgggtgtgc gcggcaccag    23820
cgcgtcttgt gatgagtctt cctcgtcctc ggactcgata cgccgcctca tccgcttttt    23880
tgggggcgcc cggggaggcg gcggcgacgg ggacggggac gacacgtcct ccatggttgg    23940
gggacgtcgc gccgcaccgc gtccgcgctc ggggtggtt tcgcgctgct cctcttcccg    24000
actggccatt tccttctcct ataggcagaa aaagatcatg gagtcagtcg agaagaagga    24060
cagcctaacc gccccctctg agttcgccac caccgcctcc accgatgccg ccaacgcgcc    24120
taccaccttc cccgtcgagg caccccgct tgaggaggag gaagtgatta tcgagcagga    24180
cccaggtttt gtaagcgaag acgacgagga ccgctcagta ccaacagagg ataaaaagca    24240
agaccaggac aacgcagagg caaacgagga acaagtcggg cgggggacg aaaggcatgg    24300 cgactaccta gatgtgggag acgacgtgct gttgaagcat ctgcagcgcc agtgcgccat    24360
tatctgcgac gcgttgcaag agcgcagcga tgtgccccctc gccatagcgg atgtcagcct    24420
tgcctacgaa cgccacctat tctcaccgcg cgtaccccc aaacgccaag aaaacggcac    24480
atgcgagccc aacccgcgcc tcaacttcta ccccgtattt gccgtgccag aggtgcttgc    24540
```

```
cacctatcac atcttttcc aaaactgcaa gatacccta tcctgccgtg ccaaccgcag   24600
ccgagcggac aagcagctgg ccttgcggca gggcgctgtc atacctgata tcgcctcgct   24660
caacgaagtg ccaaaaatct ttgagggtct tggacgcgac gagaagcgcg cggcaaacgc   24720
tctgcaacag gaaaacagcg aaaatgaaag tcactctgga gtgttggtgg aactcgaggg   24780
tgacaacgcg cgcctagccg tactaaaacg cagcatcgag gtcacccact ttgcctaccc   24840
ggcacttaac ctaccccca aggtcatgag cacagtcatg agtgagctga tcgtgcgccg   24900
tgcgcagccc ctggagaggg atgcaaattt gcaagaacaa acagaggagg gcctacccgc   24960
agttggcgac gagcagctag cgcgctggct tcaaacgcgc gagcctgccg acttggagga   25020
gcgacgcaaa ctaatgatgg ccgcagtgct cgttaccgtg gagcttgagt gcatgcagcg   25080
gttctttgct gacccggaga tgcagcgcaa gctagaggaa acattgcact acaccttccg   25140
acagggctac gtacgccagg cctgcaagat ctccaacgtg gagctctgca acctggtctc   25200
ctaccttgga attttgcacg aaaaccgcct tgggcaaaac gtgcttcatt ccacgctcaa   25260
gggcgaggcg cgccgcgact acgtccgcga ctgcgtttac ttatttctat gctacacctg   25320
gcagacggcc atgggcgttt ggcagcagtg cttggaggag tgcaacctca aggagctgca   25380
gaaactgcta aagcaaaact tgaaggacct atggacggcc ttcaacgagc gctccgtggc   25440
cgcgcacctg gcggacatca ttttcccga acgcctgctt aaaaccctgc aacagggtct   25500
gccagacttc accagtcaaa gcatgttgca gaactttagg aactttatcc tagagcgctc   25560
aggaatcttg cccgccacct gctgtgcact tcctagcgac tttgtgccca ttaagtaccg   25620
cgaatgccct ccgccgcttt ggggccactg ctaccttctg cagctagcca actaccttgc   25680
ctaccactct gacataatgg aagacgtgag cggtgacggt ctactggagt gtcactgtcg   25740
ctgcaaccta tgcacccgc accgctccct ggtttgcaat tcgcagctgc ttaacgaaag   25800
tcaaattatc ggtaccttg agctgcaggg tccctcgcct gacgaaaagt ccgcggctcc   25860
ggggttgaaa ctcactccgg ggctgtggac gtcggcttac cttcgcaaat ttgtacctga   25920
ggactaccac gcccacgaga ttaggttcta cgaagaccaa tcccgcccgc caaatgcgga   25980
gcttaccgcc tgcgtcatta cccagggcca cattcttggc caattgcaag ccatcaacaa   26040
agcccgccaa gagtttctgc tacgaaaggg acgggggggt tacttggacc cccagtccgg   26100
cgaggagctc aacccaatcc ccccgccgcc gcagccctat cagcagcagc cgcgggccct   26160
tgcttcccag gatggcaccc aaaaagaagc tgcagctgcc gccgccaccc acggacgagg   26220
aggaatactg ggacagtcag gcagaggagg ttttggacga ggaggaggag gacatgatgg   26280
aagactggga gagcctagac gaggaagctt ccgaggtcga agaggtgtca gacgaaacac   26340
cgtcaccctg gtcgcattc ccctcgccgg cgccccagaa atcggcaacc ggttccagca   26400
tggctacaac ctccgctcct caggcgccgc cggcactgcc cgttcgccga cccaaccgta   26460
gatgggacac cactgaacc agggccggta agtccaagca gccgccgccg ttagcccaag   26520
agcaacaaca gcgccaaggc taccgctcat ggcgcgggca caagaacgcc atagttgctt   26580
gcttgcaaga ctgtggggc aacatctcct tcgcccgccg cttcttctc taccatcacg   26640
gcgtggcctt cccccgtaac atcctgcatt actaccgtca tctctacagc ccatactgca   26700
ccggcggcag cggcagcggc agcaacagca gcggccacac agaagcaaag gcgaccggat   26760
agcaagactc tgacaaagcc caagaaatcc acagcggcgg cagcagcagg aggaggagc   26820
ctgcgtctgg cgcccaacga acccgtatcg acccgcgagc ttagaaacag gattttccc   26880
```

```
actctgtatg ctatatttca acagagcagg ggccaagaac aagagctgaa aataaaaaac    26940
aggtctctgc gatccctcac ccgcagctgc ctgtatcaca aaagcgaaga tcagcttcgg    27000
cgcacgctgg aagacgcgga ggctctcttc agtaaatact gcgcgctgac tcttaaggac    27060
tagtttcgcg ccctttctca aatttaagcg cgaaaactac gtcatctcca gcggccacac    27120
ccggcgccag cacctgtcgt cagcgccatt atgagcaagg aaattcccac gccctacatg    27180
tggagttacc agccacaaat gggacttgcg gctggagctg cccaagacta ctcaacccga    27240
ataaactaca tgagcgcggg accccacatg atatcccggg tcaacggaat ccgcgcccac    27300
cgaaaccgaa ttctcttgga acaggcggct attaccacca cacctcgtaa taaccttaat    27360
ccccgtagtt ggcccgctgc cctggtgtac caggaaagtc ccgctcccac cactgtggta    27420
cttcccagag acgcccaggc cgaagttcag atgactaact caggggcgca gcttgcgggc    27480
ggctttcgtc acagggtgcg gtcgcccggg cagggtataa ctcacctgac aatcagaggg    27540
cgaggtattc agctcaacga cgagtcggtg agctcctcgc ttggtctccg tccggacggg    27600
acatttcaga tcggcggcgc cggccgctct tcattcacgc ctcgtcaggc aatcctaact    27660
ctgcagacct cgtcctctga gccgcgctct ggaggcattg gaactctgca atttattgag    27720
gagtttgtgc catcggtcta ctttaacccc ttctcgggac ctcccggcca ctatccggat    27780
caatttattc ctaactttga cgcggtaaag gactcggcgg atggctacga ctgaatgtta    27840
agtggagagg cagagcaact gcgcctgaaa cacctggtcc actgtcgccg ccacaagtgc    27900
tttgcccgcg actccggtga gttttgctac tttgaattgc ccgaggatca tatcgagggc    27960
ccggcgcacg gcgtccggct taccgcccag ggagagcttg cccgtagcct gattcgggag    28020
tttacccagc gccccctgct agttgagcgg gacaggggac cctgtgttct cactgtgatt    28080
tgcaactgtc ctaaccctgg attacatcaa gatctttgtt gccatctctg tgctgagtat    28140
aataaataca gaaattaaaa tatactgggg ctcctatcgc catcctgtaa acgccaccgt    28200
cttcacccgc ccaagcaaac caaggcgaac cttacctggt acttttaaca tctctccctc    28260
tgtgatttac aacagtttca acccagacgg agtgagtcta cgagagaacc tctccgagct    28320
cagctactcc atcagaaaaa acaccaccct ccttacctgc cgggaacgta cgacctaggg    28380
ataacagggt aataagcaat tgactctatg tgggatatgc tccagcgcta caaccttgaa    28440
gtcaggcttc ctggatgtca gcatctgact ttggccagca cctgtcccgc ggatttgttc    28500
cagtccaact acagcgaccc accctaacag agatgaccaa cacaaccaac gcggccgccg    28560
ctaccggact tacatctacc acaaatacac cccaagtttc tgcctttgtc aataactggg    28620
ataacttggg catgtggtgg ttctccatag cgcttatgtt tgtatgcctt attattatgt    28680
ggctcatctg ctgcctaaag cgcaaacgcg cccgaccacc catctatagt cccatcattg    28740
tgctacaccc aaacaatgat ggaatccata gattggacgg actgaaacac atgttctttt    28800
ctcttacagt atgattaaat gagacatgat tcctcgagtt tttatattac tgacccttgt    28860
tgcgcttttt tgtgcgtgct ccacattggc tgcggtttct cacatcgaag tagactgcat    28920
tccagccttc acagtctatt tgctttacgg atttgtcacc ctcacgctca tctgcagcct    28980
catcactgtg gtcatcgcct ttatccagtg cattgactgg gtctgtgtgc ctttgcata    29040 tctcagacac catccccagt acagggacag gactatagct gagcttctta gaattcttta    29100
attatgaaat ttactgtgac ttttctgctg attatttgca ccctatctgc gttttgttcc    29160
ccgacctcca agcctcaaag acatatatca tgcagattca ctcgtatatg gaatattcca    29220
agttgctaca atgaaaaaag cgatctttcc gaagcctggt tatatgcaat catctctgtt    29280
```

```
atggtgttct gcagtaccat cttagccta  gctatatatc cctaccttga cattggctgg   29340
aaacgaatag atgccatgaa ccacccaact ttccccgcgc ccgctatgct tccactgcaa   29400
caagttgttg ccggcggctt tgtcccagcc aatcagcctc gccccacttc tcccaccccc   29460
actgaaatca gctactttaa tctaacagga ggagatgact gacaccctag atctagaaat   29520
ggacggaatt attacagagc agcgcctgct agaaagacgc agggcagcgg ccgagcaaca   29580
gcgcatgaat caagagctcc aagacatggt taacttgcac cagtgcaaaa ggggtatctt   29640
ttgtctggta aagcaggcca aagtcaccta cgacagtaat accaccggac accgccttag   29700
ctacaagttg ccaaccaagc gtcagaaatt ggtggtcatg gtgggagaaa agcccattac   29760
cataactcag cactcggtag aaaccgaagg ctgcattcac tcaccttgtc aaggacctga   29820
ggatctctgc acccttatta agaccctgtg cggtctcaaa gatcttattc cctttaacta   29880
ataaaaaaaa ataataaagc atcacttact taaaatcagt tagcaaattt ctgtccagtt   29940
tattcagcag caccctcctt ccctcctccc agctctggta ttgcagcttc ctcctggctg   30000
caaactttct ccacaatcta aatggaatgt cagtttcctc ctgttcctgt ccatccgcac   30060
ccactatctt catgttgttg cagatgaagc gcgcaagacc gtctgaagat accttcaacc   30120
ccgtgtatcc atatgacacg gaaaccggtc ctccaactgt gccttttctt actcctccct   30180
ttgtatcccc caatgggttt caagagagtc ccctgggt  actctctttg cgcctatccg   30240
aacctctagt tacctccaat ggcatgcttg cgctcaaaat gggcaacggc ctctctctgg   30300
acgaggccgg caaccttacc tcccaaaatg taaccactgt gagcccacct ctcaaaaaaa   30360
ccaagtcaaa cataaacctg gaaatatctg caccctcac  agttacctca gaagccctaa   30420
ctgtggctgc cgccgcacct ctaatggtcg cgggcaacac actcaccatg caatcacagg   30480
ccccgctaac cgtgcacgac tccaaactta gcattgccac ccaaggaccc ctcacagtgt   30540
cagaaggaaa gctagccctg caaacatcag gcccctcac  caccaccgat agcagtaccc   30600
ttactatcac tgcctcaccc cctctaacta ctgccactgg tagcttgggc attgacttga   30660
aagagcccat ttatacacaa aatggaaaac taggactaaa gtacggggct cctttgcatg   30720
taacagacga cctaaacact ttgaccgtag caactggtcc aggtgtgact attaataata   30780
cttccttgca aactaaagtt actggagcct gggttttga  ttcacaaggc aatatgcaac   30840
ttaatgtagc aggaggacta aggattgatt ctcaaaacag acgccttata cttgatgtta   30900
gttatccgtt tgatgctcaa aaccaactaa atctaagact aggacagggc cctctttta   30960 taaactcagc ccacaacttg gatattaact acaacaaagg cctttacttg tttacagctt   31020
caaacaattc caaaaagctt gaggttaacc taagcactgc caaggggttg atgtttgacg   31080
ctacagccat agccattaat gcaggagatg ggcttgaatt tggttcacct aatgcaccaa   31140
acacaaatcc cctcaaaaca aaaattggcc atggcctaga atttgattca aacaaggcta   31200
tggttcctaa actaggaact ggccttagtt ttgacagcac aggtgccatt acagtaggaa   31260
acaaaaataa tgataagcta accctatgga caggtccaaa accagaagcc aactgcataa   31320
ttgaatacgg gaaacaaaac ccagatagca aactaacttt aatccttgta aaaaatggag   31380
gaattgttaa tggatatgta acgctaatgg gagcctcaga ctacgttaac accttattta   31440
aaaacaaaaa tgtctccatt aatgtagaac tatactttga tgccactggt catatattac   31500
cagactcatc ttctcttaaa acagatctag aactaaaata caagcaaacc gctgacttta   31560
gtgcaagagg ttttatgcca agtactacag cgtatccatt tgtccttcct aatgcgggaa   31620
```

```
cacataatga aaattatatt tttggtcaat gctactacaa agcaagcgat ggtgcccttt    31680
ttccgttgga agttactgtt atgcttaata aacgcctgcc agatagtcgc acatcctatg    31740
ttatgacttt tttatggtcc ttgaatgctg gtctagctcc agaaactact caggcaaccc    31800
tcataacctc cccatttacc ttttcctata ttagagaaga tgactaataa actctaaaga    31860
atcgtttgtg ttatgtttca acgtgtttat ttttcaattg cagaaaattt caagtcattt    31920
ttcattcagt agtatagccc caccaccaca tagcttatac agatcaccgt accttaatca    31980
aactcacaga accctagtat tcaacctgcc acctccctcc caacacacag agtacacagt    32040
cctttctccc cggctggcct taaaaagcat catatcatgg gtaacagaca tattcttagg    32100
tgttatattc cacacggttt cctgtcgagc caaacgctca tcagtgatat taataaactc    32160
cccgggcagc tcacttaagt tcatgtcgct gtccagctgc tgagccacag gctgctgtcc    32220
aacttgcggt tgcttaacgg gcggcgaagg agaagtccac gcctacatgg gggtagagtc    32280
ataatcgtgc atcaggatag ggcggtggtg ctgcagcagc gcgcgaataa actgctgccg    32340
ccgccgctcc gtcctgcagg aatacaacat ggcagtggtc tcctcagcga tgattcgcac    32400
cgcccgcagc ataaggcgcc ttgtcctccg ggcacagcag cgcaccctga tctcacttaa    32460
atcagcacag taactgcagc acagcaccac aatattgttc aaaatcccac agtgcaaggc    32520
gctgtatcca aagctcatgg cggggaccac agaacccacg tggccatcat accacaagcg    32580
caggtagatt aagtggcgac ccctcataaa cacgctggac ataaacatta cctcttttgg    32640
catgttgtaa ttcaccacct cccggtacca tataaacctc tgattaaaca tggcgccatc    32700
caccaccatc ctaaaccagc tggccaaaac ctgcccgccg gctatacact gcagggaacc    32760
gggactggaa caatgacagt ggagagccca ggactcgtaa ccatggatca tcatgctcgt    32820
catgatatca atgttggcac aacacaggca cacgtgcata cacttcctca ggattacaag    32880
ctcctcccgc gttagaacca tatcccaggg aacaacccat tcctgaatca gcgtaaatcc    32940
cacactgcag ggaagacctc gcacgtaact cacgttgtgc attgtcaaag tgttacattc    33000
gggcagcagc ggatgatcct ccagtatggt agcgcgggtt tctgtctcaa aaggaggtag    33060
acgatcccta ctgtacggag tgcgccgaga caaccgagat cgtgttggtc gtagtgtcat    33120
gccaaatgga acgccggacg tagtcatatt tcctgaagca aaaccaggtg cgggcgtgac    33180
aaacagatct gcgtctccgg tctcgccgct tagatcgctc tgtgtagtag ttgtagtata    33240
tccactctct caaagcatcc aggcgccccc tggcttcggg ttctatgtaa actccttcat    33300
gcgccgctgc cctgataaca tccaccaccg cagaataagc cacacccagc caacctacac    33360
attcgttctg cgagtcacac acgggaggag cgggaagagc tggaagaacc atgtttttt    33420 tttattcca aaagattatc caaaacctca aaatgaagat ctattaagtg aacgcgctcc    33480
cctccggtgg cgtggtcaaa ctctacagcc aaagaacaga taatggcatt tgtaagatgt    33540
tgcacaatgg cttccaaaag gcaaacggcc ctcacgtcca agtggacgta aaggctaaac    33600
ccttcagggt gaatctcctc tataaacatt ccagcacctt caaccatgcc caaataattc    33660
tcatctcgcc accttctcaa tatatctcta agcaaatccc gaatattaag tccggccatt    33720
gtaaaaatct gctccagagc gccctccacc ttcagcctca agcagcgaat catgattgca    33780
aaaattcagg ttcctcacag acctgtataa gattcaaaag cggaacatta acaaaaatac    33840
cgcgatcccg taggtccctt cgcagggcca gctgaacata atcgtgcagg tctgcacgga    33900
ccagcgcggc cacttccccg ccaggaacct tgacaaaaga acccacactg attatgcac    33960 gcatactcgg agctatgcta accagcgtag ccccgatgta agctttgttg catgggcggc    34020
```

-continued

```
gatataaaat gcaaggtgct gctcaaaaaa tcaggcaaag cctcgcgcaa aaagaaagc    34080
acatcgtagt catgctcatg cagataaagg caggtaagct ccggaaccac cacagaaaaa    34140
gacaccattt ttctctcaaa catgtctgcg ggtttctgca taaacacaaa ataaaataac    34200
aaaaaaacat ttaaacatta gaagcctgtc ttacaacagg aaaaacaacc cttataagca    34260
taagacggac tacggccatg ccggcgtgac cgtaaaaaaa ctggtcaccg tgattaaaaa    34320
gcaccaccga cagctcctcg gtcatgtccg gagtcataat gtaagactcg gtaaacacat    34380
caggttgatt catcggtcag tgctaaaaag cgaccgaaat agcccggggg aatacatacc    34440
cgcaggcgta gagacaacat tacagccccc ataggaggta taacaaaatt aataggagag    34500
aaaaacacat aaacacctga aaaaccctcc tgcctaggca aaatagcacc ctcccgctcc    34560
agaacaacat acagcgcttc acagcggcag cctaacagtc agccttacca gtaaaaaaga    34620
aaacctatta aaaaaacacc actcgacacg gcaccagctc aatcagtcac agtgtaaaaa    34680
agggccaagt gcagagcgag tatatatagg actaaaaaat gacgtaacgg ttaaagtcca    34740
caaaaaacac ccagaaaacc gcacgcgaac ctacgcccag aaacgaaagc caaaaaaccc    34800
acaacttcct caaatcgtca cttccgtttt cccacgttac gtaacttccc attttaagaa    34860
aactacaatt cccaacacat acaagttact ccgccctaaa acctacgtca cccgccccgt    34920
tcccacgccc cgcgccacgt cacaaactcc acccccctcat tatcatattg gcttcaatcc    34980
aaaataaggt atattattga tgatgttaat                                      35010
```

<210> SEQ ID NO 56
<211> LENGTH: 464
<212> TYPE: PRT
<213> ORGANISM: Artificial Sequence
<220> FEATURE:
<223> OTHER INFORMATION: HER2(A3)-CD28TM,ICD-CD3Z CAR

<400> SEQUENCE: 56

```
Met Thr Arg Ala Met Asp Trp Ile Trp Arg Ile Leu Phe Leu Val Gly
1               5                   10                  15

Ala Ala Thr Gly Ala His Ser Glu Val Gln Leu Val Gln Ser Gly Thr
            20                  25                  30

Glu Val Lys Lys Pro Gly Ala Ser Val Arg Val Ser Cys Lys Ser Ser
        35                  40                  45

Gly Tyr Thr Phe Thr Ser Tyr Tyr Ile His Trp Val Arg Gln Ala Pro
    50                  55                  60

Gly Gln Gly Leu Glu Trp Met Ala Ile Ile Asn Pro Gly Asn Gly Asp
65                  70                  75                  80

Thr Asn Tyr Ala Gln Arg Phe Gln Gly Arg Val Thr Met Thr Arg Asp
                85                  90                  95

Thr Ser Thr Ser Thr Val Tyr Met Glu Leu Arg Ser Leu Arg Ser Asp
            100                 105                 110

Asp Thr Ala Val Tyr Phe Cys Ala Arg Glu Ile Ala Ser Tyr Ser Gly
        115                 120                 125

Ser Tyr Tyr Asp Tyr Trp Gly Gln Gly Thr Leu Val Thr Val Ser Ser
    130                 135                 140

Gly Gly Gly Gly Ser Gly Gly Gly Ser Gly Gly Gly Gly Ser Gln
145                 150                 155                 160

Ala Val Val Leu Gln Glu Pro Ser Leu Ser Val Ser Pro Gly Gly Thr
                165                 170                 175

Val Thr Leu Thr Cys Gly Leu Ser Ser Gly Ser Val Ser Thr Gly His
```

```
                180             185             190
Tyr Ala Ser Trp Tyr Gln Gln Thr Pro Gly Gln Ala Pro Arg Thr Leu
            195                 200                 205
Phe Tyr Asn Thr Asn Thr Arg Ser Ser Gly Val Pro Asp Arg Phe Ser
            210                 215                 220
Gly Ser Ile Val Gly Asn Lys Ala Ala Leu Thr Ile Thr Gly Ala Gln
225                 230                 235                 240
Ala Asp Asp Glu Ser Asp Tyr Tyr Cys Val Leu Tyr Val Gly Asp Gly
                245                 250                 255
Ile Trp Val Phe Gly Gly Gly Thr Lys Leu Thr Val Leu Glu Pro Lys
            260                 265                 270
Ser Cys Asp Lys Thr His Thr Cys Pro Thr Arg Phe Trp Val Leu Val
            275                 280                 285
Val Val Gly Gly Val Leu Ala Cys Tyr Ser Leu Leu Val Thr Val Ala
            290                 295                 300
Phe Ile Ile Phe Trp Val Arg Ser Lys Arg Ser Arg Leu Leu His Ser
305                 310                 315                 320
Asp Tyr Met Asn Met Thr Pro Arg Arg Pro Gly Pro Thr Arg Lys His
                325                 330                 335
Tyr Gln Pro Tyr Ala Pro Pro Arg Asp Phe Ala Ala Tyr Arg Ser Arg
            340                 345                 350
Val Lys Phe Ser Arg Ser Ala Asp Ala Pro Ala Tyr Gln Gln Gly Gln
            355                 360                 365
Asn Gln Leu Tyr Asn Glu Leu Asn Leu Gly Arg Arg Glu Glu Tyr Asp
            370                 375                 380
Val Leu Asp Lys Arg Arg Gly Arg Asp Pro Glu Met Gly Gly Lys Pro
385                 390                 395                 400
Gln Arg Arg Lys Asn Pro Gln Glu Gly Leu Tyr Asn Glu Leu Gln Lys
                405                 410                 415
Asp Lys Met Ala Glu Ala Tyr Ser Glu Ile Gly Met Lys Gly Glu Arg
            420                 425                 430
Arg Arg Gly Lys Gly His Asp Gly Leu Tyr Gln Gly Leu Ser Thr Ala
            435                 440                 445
Thr Lys Asp Thr Tyr Asp Ala Leu His Met Gln Ala Leu Pro Pro Arg
            450                 455                 460

<210> SEQ ID NO 57
<211> LENGTH: 14
<212> TYPE: PRT
<213> ORGANISM: Artificial Sequence
<220> FEATURE:
<223> OTHER INFORMATION: HER2(A3) LC-CDR1

<400> SEQUENCE: 57

Gly Leu Ser Ser Gly Ser Val Ser Thr Gly His Tyr Ala Ser
1               5                   10

<210> SEQ ID NO 58
<211> LENGTH: 7
<212> TYPE: PRT
<213> ORGANISM: Artificial Sequence
<220> FEATURE:
<223> OTHER INFORMATION: HER2(A3) LC-CDR2

<400> SEQUENCE: 58

Asn Thr Asn Thr Arg Ser Ser
1               5
```

```
<210> SEQ ID NO 59
<211> LENGTH: 10
<212> TYPE: PRT
<213> ORGANISM: Artificial Sequence
<220> FEATURE:
<223> OTHER INFORMATION: HER2(A3) LC-CDR3

<400> SEQUENCE: 59

Val Leu Tyr Val Gly Asp Gly Ile Trp Val
1               5                   10

<210> SEQ ID NO 60
<211> LENGTH: 10
<212> TYPE: PRT
<213> ORGANISM: Artificial Sequence
<220> FEATURE:
<223> OTHER INFORMATION: HER2(A3) HC-CDR1

<400> SEQUENCE: 60

Ser Tyr Tyr Ile His Trp Val Arg Gln Ala
1               5                   10

<210> SEQ ID NO 61
<211> LENGTH: 17
<212> TYPE: PRT
<213> ORGANISM: Artificial Sequence
<220> FEATURE:
<223> OTHER INFORMATION: HER2(A3) HC-CDR2

<400> SEQUENCE: 61

Ile Ile Asn Pro Gly Asn Gly Asp Thr Asn Tyr Ala Gln Arg Phe Gln
1               5                   10                  15

Gly

<210> SEQ ID NO 62
<211> LENGTH: 12
<212> TYPE: PRT
<213> ORGANISM: Artificial Sequence
<220> FEATURE:
<223> OTHER INFORMATION: HER2(A3) HC-CDR3

<400> SEQUENCE: 62

Glu Ile Ala Ser Tyr Ser Gly Ser Tyr Tyr Asp Tyr
1               5                   10

<210> SEQ ID NO 63
<211> LENGTH: 110
<212> TYPE: PRT
<213> ORGANISM: Artificial Sequence
<220> FEATURE:
<223> OTHER INFORMATION: HER2(A3) VL

<400> SEQUENCE: 63

Gln Ala Val Val Leu Gln Glu Pro Ser Leu Ser Val Ser Pro Gly Gly
1               5                   10                  15

Thr Val Thr Leu Thr Cys Gly Leu Ser Ser Gly Ser Val Ser Thr Gly
                20                  25                  30

His Tyr Ala Ser Trp Tyr Gln Gln Thr Pro Gly Gln Ala Pro Arg Thr
            35                  40                  45

Leu Phe Tyr Asn Thr Asn Thr Arg Ser Ser Gly Val Pro Asp Arg Phe
        50                  55                  60

Ser Gly Ser Ile Val Gly Asn Lys Ala Ala Leu Thr Ile Thr Gly Ala
65                  70                  75                  80
```

```
Gln Ala Asp Asp Glu Ser Asp Tyr Tyr Cys Val Leu Tyr Val Gly Asp
                85                  90                  95

Gly Ile Trp Val Phe Gly Gly Gly Thr Lys Leu Thr Val Leu
            100                 105                 110

<210> SEQ ID NO 64
<211> LENGTH: 121
<212> TYPE: PRT
<213> ORGANISM: Artificial Sequence
<220> FEATURE:
<223> OTHER INFORMATION: HER2(A3) VH

<400> SEQUENCE: 64

Glu Val Gln Leu Val Gln Ser Gly Thr Glu Val Lys Lys Pro Gly Ala
1               5                   10                  15

Ser Val Arg Val Ser Cys Lys Ser Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Ala Ile Ile Asn Pro Gly Asn Gly Asp Thr Asn Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Arg Ser Leu Arg Ser Asp Asp Thr Ala Val Tyr Phe Cys
                85                  90                  95

Ala Arg Glu Ile Ala Ser Tyr Ser Gly Ser Tyr Tyr Asp Tyr Trp Gly
            100                 105                 110

Gln Gly Thr Leu Val Thr Val Ser Ser
            115                 120
```

ONCOLYTIC VIROTHERAPY WITH HELPER-DEPENDENT ADENOVIRAL-BASED VECTORS EXPRESSING IMMUNOMODULATORY MOLECULES

RELATED APPLICATIONS

This application is a national stage filing under 35 U.S.C. § 371 of international application number PCT/US2018/028577, filed Apr. 20, 2018, which claims priority under 35 USC 119(e) of U.S. provisional application No. 62/488,181, filed Apr. 21, 2017, each of which is herein incorporated by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Nov. 12, 2019, is named T082470003US00-SEQ-AWW and is 200 kilobytes in size.

TECHNICAL FIELD

The present disclosure relates at least to the fields of cell biology, molecular biology, immunology, virology, and medicine, including cancer therapy. In particular embodiments the disclosure relates to combination treatments involving the use of oncolytic virotherapy and immunotherapy.

BACKGROUND

Oncolytic Virotherapy for Squamous Cell Carcinoma of the Head and Neck (HNSCC)

HNSCC is the sixth leading cancer by incidence worldwide. Treatment of locally advanced, recurrent and metastatic HNSCC is often limited by an unfavorable efficacy to toxicity ratio and median survival for patients with metastatic disease remains less than one year (Zandberg and Strome, Oral Oncology (2014) 50: 627-632). Since HNSCC is a locoregional disease that presents at or close to the surface of the body, it is amenable to initial intratumoral injection of adenoviral vectors (Ads) to prompt a locoregional and even a systemic anti-tumor immune response (Liu et al., Nature Clinical Practice Oncology (2007) 4: 101-117). Several clinical trials of conditionally-replicating Ads (OncAds) or replication-deficient Ads encoding a therapeutic transgene have demonstrated the safety and feasibility of Ad gene therapy for HNSCC, but failed to show improved overall survival since intensive local treatment, even when combined with chemo/radiotherapy, did not prevent metastasis to distant sites (Liu et al., supra). OncAds are generally administered intratumorally, and poorly re-target to metastasized tumors (Koksi et al., Molecular Therapy: The Journal of the American Society of Gene Therapy (2015) 23:1641-1652).

OncAd with Helper-Dependent Ad (HDAd) Expressing Immunomodulatory Molecules

Adenoviral-based vectors (Ads) can infect a range of malignant cells and express high levels of lytic antigens and immunogenic transgenes, making them attractive as agents for cancer gene therapy (Cerullo et al., Advances in Cancer Research (2012) 115, 265-318). OncAds selectively replicate in cancer cells and are commonly used Ad-based vectors in clinical trials for cancer gene therapy. However, OncAds have a limited coding capacity for transgenes (~1.5 kb). Helper-dependent Ads (HDAds) are devoid of viral coding sequences, enabling a cargo capacity of up to 34 kb for insertion of multiple transgenes in a single vector (Suzuki et al., Human Gene Therapy (2010) 21; 120-126). Since HDAd vector DNA encodes packaging signals, the OncAd replication machinery acts in trans to replicate and package both OncAd and HDAd within infected tumor cells, leading to multiple cycles of production and release of both the oncolytic virus and the transgenes encoded by the HDAd (combinatorial adenoviral vectors: CAd-VEC; Farzad et al., Molecular Therapy—Oncolytics (2014) 1, 14008).

CAR T-Cell Therapy

The use of T-cells as agents for cancer therapy has recently been facilitated by the expression of cancer cell antigen-directed chimeric antigen receptors (CARs; reviewed in Kershaw et al., Nature (2013) 13: 525-541). CAR-modified T-cells have shown promise for the treatment of hematological malignancies (Garfall et al., The New England Journal of Medicine (2015) 373:1040-1047), but have been less effective in treating solid tumors, which may in part be a consequence of the highly immunosuppressive nature of the solid tumor microenvironment (Quail et al., Nature Medicine (2013) 19:1423-1437). Due to immunosuppressive mechanisms at tumor site CAR T-cells fail to expand and persist long term despite the expression of one or two costimulatory endodomains. The present disclosure provides a solution to a long-felt need for effective cancer therapies, including combinatorial cancer therapies.

BRIEF SUMMARY

In one aspect, the present disclosure provides a method of treating a cancer, comprising administering to a subject:
(i) an oncolytic virus;
(ii) a virus comprising nucleic acid encoding an immunomodulatory factor; and
(iii) at least one cell comprising a chimeric antigen receptor (CAR) specific for a cancer cell antigen.

Also provided is a combination of (i) an oncolytic virus, (ii) a virus comprising nucleic acid encoding an immunomodulatory factor, and (iii) at least one cell comprising a chimeric antigen receptor (CAR) specific for a cancer cell antigen, for use in a method of treating a cancer.

Also provided is the use of (i) an oncolytic virus, (ii) a virus comprising nucleic acid encoding an immunomodulatory factor, and (iii) at least one cell comprising a chimeric antigen receptor (CAR) specific for a cancer cell antigen, in the manufacture of a medicament for use in a method of treating a cancer.

Also provided is a method of treating a cancer, comprising administering to a subject:
(i) an oncolytic virus; and
(ii) at least one cell comprising a chimeric antigen receptor (CAR) specific for a cancer cell antigen.

Also provided is a combination of (i) an oncolytic virus, and (ii) at least one cell comprising a chimeric antigen receptor (CAR) specific for a cancer cell antigen, for use in a method of treating a cancer.

Also provided is the use of (i) an oncolytic virus, and (ii) at least one cell comprising a chimeric antigen receptor (CAR) specific for a cancer cell antigen, in the manufacture of a medicament for use in a method of treating a cancer.

In some embodiments the cell comprising a CAR is specific for the oncolytic virus.

Also provided is a method of treating a cancer, comprising administering to a subject:
(i) an oncolytic virus; and
(ii) at least one immune cell specific for the oncolytic virus.

Also provided is a combination of (i) an oncolytic virus, and (ii) at least one immune cell specific for the oncolytic virus, for use in a method of treating a cancer.

Also provided is the use of (i) an oncolytic virus, and (ii) at least one immune cell specific for the oncolytic virus, in the manufacture of a medicament for use in a method of treating a cancer.

In some embodiments, the oncolytic virus is an oncolytic adenovirus (OncAd). In some embodiments, the oncolytic virus is derived from adenovirus 5 (Ad5). In some embodiments, the oncolytic virus encodes an E1A protein which displays reduced binding to Rb protein as compared to E1A protein encoded by Ad5. In some embodiments, the oncolytic virus encodes an E1A protein lacking the amino acid sequence LTCHEACF (SEQ ID NO:52). In some embodiments, the oncolytic virus encodes an E1A protein comprising, or consisting of or consisting essentially of, the amino acid sequence SEQ ID NO:34. In some embodiments, the oncolytic virus comprises nucleic acid having one or more binding sites for one or more transcription factors. In some embodiments, the oncolytic virus comprises nucleic acid having one or more binding sites for STAT1.

In some embodiments, the virus comprising nucleic acid encoding an immunomodulatory factor is a helper-dependent adenovirus (HDAd). In some embodiments, the immunomodulatory factor is selected from: an agonist of an effector immune response or antagonist of an immunoregulatory response. In some embodiments, the virus comprising nucleic acid encoding an immunomodulatory factor comprises nucleic acid encoding IL-12 and/or antagonist anti-PD-L1 antibody. In some embodiments, the virus comprising nucleic acid encoding an immunomodulatory factor comprises nucleic acid encoding an enzyme capable of catalysing conversion of a non-toxic factor to a cytotoxic form. In some embodiments, the enzyme is selected from: thymidine kinase, cytosine deaminase, nitroreductase, cytochrome P450, carboxypeptidase G2, purine nucleoside phosphorylase, horseradish peroxidase and carboxylesterase. In some embodiments, the virus comprising nucleic acid encoding an immunomodulatory factor comprises nucleic acid encoding a thymidine kinase.

In some embodiments, the at least one cell comprising a CAR specific for a cancer cell antigen is a T cell. In some embodiments, the CAR comprises an antigen binding domain capable of specific binding to HER2. In some embodiments, the CAR comprises an antigen binding domain comprising:
a VL domain comprising:
  LC-CRD1: SEQ ID NO:10;
  LC-CRD2: SEQ ID NO:11;
  LC-CRD3: SEQ ID NO:12;
and a VH domain comprising:
  HC-CRD1: SEQ ID NO:13;
  HC-CRD2: SEQ ID NO:14;
  HC-CRD3: SEQ ID NO:15;
or
a VL domain comprising:
  LC-CRD1: SEQ ID NO:18;
  LC-CRD2: SEQ ID NO:19;
  LC-CRD3: SEQ ID NO:20;
and a VH domain comprising:
  HC-CRD1: SEQ ID NO:21;
  HC-CRD2: SEQ ID NO:22;
  HC-CRD3: SEQ ID NO:23;
or
a VL domain comprising:
  LC-CRD1: SEQ ID NO:26;
  LC-CRD2: SEQ ID NO:27;
  LC-CRD3: SEQ ID NO:28;
and a VH domain comprising:
  HC-CRD1: SEQ ID NO:29;
  HC-CRD2: SEQ ID NO:30;
  HC-CRD3: SEQ ID NO:31;
or
a VL domain comprising:
  LC-CRD1: SEQ ID NO:57;
  LC-CRD2: SEQ ID NO:58;
  LC-CRD3: SEQ ID NO:59;
and a VH domain comprising:
  HC-CRD1: SEQ ID NO:60;
  HC-CRD2: SEQ ID NO:61;
  HC-CRD3: SEQ ID NO:62.

In some embodiments, the CAR comprises an antigen binding domain comprising:
a VL comprising, or consisting of or consisting essentially of, an amino acid sequence having at least 75%, 80%, 85%, 90%, 95% or greater sequence identity to SEQ ID NO:16 and a VH comprising, or consisting of or consisting essentially of, an amino acid sequence having at least 75%, 80%, 85%, 90%, 95% or greater sequence identity to SEQ ID NO:17;
or
a VL comprising, or consisting of or consisting essentially of, an amino acid sequence having at least 75%, 80%, 85%, 90%, 95% or greater sequence identity to SEQ ID NO:24 and a VH comprising, or consisting of or consisting essentially of, an amino acid sequence having at least 75%, 80%, 85%, 90%, 95% or greater sequence identity to SEQ ID NO:25;
or
a VL comprising, or consisting of or consisting essentially of, an amino acid sequence having at least 75%, 80%, 85%, 90%, 95% or greater sequence identity to SEQ ID NO:32 and a VH comprising, or consisting of or consisting essentially of, an amino acid sequence having at least 75%, 80%, 85%, 90%, 95% or greater sequence identity to SEQ ID NO:33;
or
a VL comprising, or consisting of, an amino acid sequence having at least 75% sequence identity to SEQ ID NO:63 and a VH comprising, or consisting of, an amino acid sequence having at least 75% sequence identity to SEQ ID NO:64.

In some embodiments, the method additionally comprises:
(a) isolating at least one cell from a subject, and in specific embodiments the cell is an immune cell;
(b) modifying the at least one cell to express or comprise a CAR specific for a cancer cell antigen, or a nucleic acid encoding a CAR specific for a cancer cell antigen,
(c) optionally expanding the modified at least one cell, and;
(d) administering the modified at least one cell to a subject; in specific embodiments the modified cell upon administration is provided to the subject with one or more other agents for cancer therapy.

In some embodiments, the method of treating a cancer comprises:
(a) isolating at least one cell from a subject;
(b) modifying the at least one cell to express or comprise a CAR specific for a cancer cell antigen, or a nucleic acid encoding a CAR specific for a cancer cell antigen,
(c) optionally expanding the modified at least one cell, and;
(d) administering the modified at least one cell to a subject.

In some embodiments, the method of treating a cancer comprises:
(a) isolating immune cells from a subject;
(b) generating or expanding a population of immune cells specific for an oncolytic virus by a method comprising: stimulating the immune cells by culture in the presence of antigen presenting cells (APCs) presenting a peptide of the oncolytic virus, and;
(c) administering at least one immune cell specific for the oncolytic virus to a subject.

In some embodiments, the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

The present disclosure also provides an oncolytic adenovirus (OncAd) encoding an E1A protein comprising, or consisting of or consisting essentially of, the amino acid sequence SEQ ID NO:34.

The present disclosure also provides an oncolytic adenovirus (OncAd) comprising nucleic acid having one or more binding sites for STAT1. In some embodiments, the OncAd comprises a nucleic acid sequence having at least 60%, 65%, 70%, 75%, 80%, 85%, 90%, 95% or greater sequence identity to SEQ ID NO:51 or an equivalent sequence as a result of codon degeneracy.

Also provided is an OncAd comprising a nucleic acid sequence having at least 60%, 65%, 70%, 75%, 80%, 85%, 90%, 95% or greater sequence identity to SEQ ID NO:55 or an equivalent sequence as a result of codon degeneracy. In some embodiments the OncAd encodes an E1A protein comprising, or consisting of or consisting essentially of, the amino acid sequence SEQ ID NO:34.

The present disclosure also provides a helper-dependent adenovirus (HDAd) comprising nucleic acid encoding IL-12 and/or antagonist anti-PD-L1 antibody. In some embodiments the HDAd additionally comprises nucleic acid encoding an enzyme capable of catalysing conversion of a non-toxic factor to a cytotoxic form. In some embodiments the enzyme is selected from: thymidine kinase, cytosine deaminase, nitroreductase, cytochrome P450, carboxypeptidase G2, purine nucleoside phosphorylase, horseradish peroxidase and carboxylesterase.

In some embodiments, the HDAd additionally comprises nucleic acid encoding a thymidine kinase. In cases wherein the HDAd nucleic acid encodes IL-12 and anti-PD-L1 antibody, the respective expression sequences may or may not be regulated by the same regulatory sequence. In such cases wherein the HDAd nucleic acid encodes both IL-12 and anti-PD-L1 antibody, the positioning on the HDAd nucleic acid may be of any suitable configuration, such as in a 5' to 3' direction the nucleic acid region encoding IL-12 being either upstream or downstream of the nucleic acid region encoding anti-PD-L1 antibody.

The present disclosure also provides a chimeric antigen receptor (CAR) comprising an antigen binding domain comprising:

a VL domain comprising:
LC-CRD1: SEQ ID NO:10;
LC-CRD2: SEQ ID NO:11;
LC-CRD3: SEQ ID NO:12;
and a VH domain comprising:
HC-CRD1: SEQ ID NO:13;
HC-CRD2: SEQ ID NO:14;
HC-CRD3: SEQ ID NO:15;
or
a VL domain comprising:
LC-CRD1: SEQ ID NO:18;
LC-CRD2: SEQ ID NO:19;
LC-CRD3: SEQ ID NO:20;
and a VH domain comprising:
HC-CRD1: SEQ ID NO:21;
HC-CRD2: SEQ ID NO:22;
HC-CRD3: SEQ ID NO:23;
or
a VL domain comprising:
LC-CRD1: SEQ ID NO:26;
LC-CRD2: SEQ ID NO:27;
LC-CRD3: SEQ ID NO:28;
and a VH domain comprising:
HC-CRD1: SEQ ID NO:29;
HC-CRD2: SEQ ID NO:30;
HC-CRD3: SEQ ID NO:31;
or
a VL domain comprising:
LC-CRD1: SEQ ID NO:57;
LC-CRD2: SEQ ID NO:58;
LC-CRD3: SEQ ID NO:59;
and a VH domain comprising:
HC-CRD1: SEQ ID NO:60;
HC-CRD2: SEQ ID NO:61;
HC-CRD3: SEQ ID NO:62.

In some embodiments, the CAR comprises an antigen binding domain comprising:
a VL comprising, or consisting of or consisting essentially of, an amino acid sequence having at least 75%, 80%, 85%, 90%, 95% or greater sequence identity to SEQ ID NO:16 and a VH comprising, or consisting of or consisting essentially of, an amino acid sequence having at least 75%, 80%, 85%, 90%, 95% or greater sequence identity to SEQ ID NO:17;
or
a VL comprising, or consisting of, an amino acid sequence having at least 75%, 80%, 85%, 90%, 95% or greater sequence identity to SEQ ID NO:24 and a VH comprising, or consisting of or consisting essentially of, an amino acid sequence having at least 75%, 80%, 85%, 90%, 95% or greater sequence identity to SEQ ID NO:25;
or
a VL comprising, or consisting of, an amino acid sequence having at least 75%, 80%, 85%, 90%, 95% or greater sequence identity to SEQ ID NO:32 and a VH comprising, or consisting of or consisting essentially of, an amino acid sequence having at least 75%, 80%, 85%, 90%, 95% sequence identity to SEQ ID NO:33;
or
a VL comprising, or consisting of, an amino acid sequence having at least 75%, 80%, 85%, 90%, 95% or greater sequence identity to SEQ ID NO:63 and a VH comprising, or consisting of or consisting essentially of, an amino acid sequence having at least 75%, 80%, 85%, 90%, 95% sequence identity to SEQ ID NO:64.

The present disclosure also provides a nucleic acid, or a plurality of nucleic acids, optionally isolated, encoding the oncolytic adenovirus (OncAd), the helper-dependent adenovirus (HDAd), or the chimeric antigen receptor (CAR) according to the present disclosure.

The present disclosure also provides a cell comprising the oncolytic adenovirus (OncAd), the helper-dependent adenovirus (HDAd), the chimeric antigen receptor (CAR), or the nucleic acid or plurality of nucleic acids according to the present disclosure.

The present disclosure also provides a pharmaceutical composition comprising the oncolytic adenovirus (OncAd), the helper-dependent adenovirus (HDAd), the chimeric antigen receptor (CAR); the nucleic acid or plurality of nucleic acids or the cell according to the present disclosure may be associated with or comprised in a pharmaceutically acceptable carrier, diluent, excipient or adjuvant.

The present disclosure also provides a method of treating cancer comprising administering to a subject the oncolytic adenovirus (OncAd), the helper-dependent adenovirus (HDAd), the chimeric antigen receptor (CAR), the nucleic acid or plurality of nucleic acids, the cell or the pharmaceutical composition according to the present disclosure.

The present disclosure also provides the oncolytic adenovirus (OncAd), the helper-dependent adenovirus (HDAd), the chimeric antigen receptor (CAR), the nucleic acid or plurality of nucleic acids, the cell or the pharmaceutical composition according to the present disclosure for use in a method of treating a cancer.

The present disclosure also provides the use of the oncolytic adenovirus (OncAd), the helper-dependent adenovirus (HDAd), the chimeric antigen receptor (CAR), the nucleic acid or plurality of nucleic acids, the cell or the pharmaceutical composition according to the present disclosure in the manufacture of a medicament for treating a cancer.

In some embodiments in accordance with various aspects of the present disclosure, the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

The present disclosure also provides a kit of parts comprising a predetermined quantity of the oncolytic adenovirus (OncAd), the helper-dependent adenovirus (HDAd), the chimeric antigen receptor (CAR), the nucleic acid or plurality of nucleic acids, the cell or the pharmaceutical composition according to the present disclosure.

DETAILED DESCRIPTION

The present disclosure is concerned with the combined use of multiple therapeutic agents for the treatment of cancer. In particular, (i) oncolytic virus, (ii) virus providing immunomodulatory factor(s) and (iii) CAR-bearing immune cells (such as T cells) specific for a cancer cell antigen are used in combination as a cancer therapy. The therapeutic agents are combined to provide an improved treatment effect as compared to the effect seen when any one of the agents is used alone. In certain embodiments, at least two of the three therapeutic agents act in an additive manner to treat the cancer, whereas in other embodiments at least two of the three different therapeutic agents act synergisitically to treat the cancer.

Without wishing to be bound by any particular theory, the improved treatment effect is thought to be achieved by combining the advantageous features of oncolytic virotherapy (e.g. effective treatment of solid tumours) and CAR-T cell therapy (e.g. effective treatment of diffuse/metastatic cancer), in conjunction with providing a favourable immune environment for CAR-T cell proliferation and activity.

Oncolytic Virus

The present disclosure employs oncolytic virus. Oncolytic viruses and their use to treat cancer is reviewed, for example, in Chiocca and Rabkin Cancer Immunol Res (2014) 2(4): 295-300, which is hereby incorporated by reference in its entirety.

Oncolytic viruses replicate in, and cause lysis of, cancer cells. Often they are selective for cancer cells over non-cancerous cells; for example, oncolytic viruses commonly replicate in dividing cells in preference to non-dividing cells. Oncolytic viruses are therefore useful to selectively kill cancer cells and destroy tumours, without causing substantial damage to normal, non-cancerous cells/tissue.

Oncolytic virotherapy is associated with several advantages features. Oncolytic viruses often target several oncogenic pathways and use multiple mechanisms for cytotoxicity, minimising the chances of resistance arising. As noted above, because oncolytic viruses replicate selectively in tumours and are non-pathogenic they display minimal toxicity. Virus dose in the tumour also increases over time due to replication of the virus, and the oncolytic viruses can also be manipulated genetically to improve safety, e.g. by engineering sensitivity to a drug.

There are two main classes of oncolytic virus:
(i) viruses that naturally replicate preferentially in cancer cells, and which are non-pathogenic in humans often due to elevated sensitivity to innate antiviral signalling or dependence on oncogenic signalling pathways, including autonomous parvoviruses, myxoma virus (MYXV; poxvirus), Newcastle disease virus (NDV; paramyxovirus), reovirus, and Seneca valley virus (SVV; picornavirus); and
(ii) viruses that are genetically-manipulated, e.g. with mutations/deletions in genes required for replication in normal, but not cancer cells, including adenovirus (Ad), herpes simplex virus (HSV), vaccinia virus (VV), and vesicular stomatitis virus (VSV; rhabdovirus); or viruses that are genetically-manipulated for use as vaccine vectors including measles virus (MV; paramyxovirus), poliovirus (PV; picornavirus), and VV (poxvirus).

Genetic manipulation can include insertion/alteration of functional sequences to provide enhanced selectivity for cancer cells, safety, and/or to modify virus tropism.

For example, oncolytic virus may by genetically engineered to introduce tissue-specific internal ribosome entry sites (IRESs) only permitting viral translation in target cells, and/or to introduce miRNAs/miRNA response elements (MREs); differential miRNA expression between healthy cells or certain tissues vs. tumor cells allows viruses to be detargeted from healthy cells/tissues. Oncolytic virus may also by engineered to place transcription of the viral genome under the control of a cell- or tissue-specific regulatory region, such as promoter/enhancers (e.g. tumour cell-specific promoter). In some embodiments, the oncolytic virus according to the present disclosure may comprise one or more modifications for such purpose.

Virus may also be modified for transductional targeting, e.g. through modification of virus receptors/coat proteins to target tumour cells and/or detarget healthy cells/tissues.

Oncolytic viruses may be administered in such a way as to minimise anti-oncolytic virus responses (e.g. neutralisation by anti-virus antibodies) in the subject and sequestration in the liver, and to maximise tumour delivery, as described in Chiocca and Rabkin, supra. For example, oncolytic virus may be administered in a cell carrier, e.g. in mesenchymal stromal cells, myeloid-derived suppressor cells (MDSCs), neural stem cells, T cells, cytokine-induced killer cells, or irradiated tumor cells, or can be coated in nanoparticles.

In some embodiments, the oncolytic virus of the present disclosure is, or is derived from, an adenovirus (Ad), herpes simplex virus (HSV), vaccinia virus (VV), vesicular stomatitis virus (VSV); autonomous parvovirus, myxoma virus (MYXV), Newcastle disease virus (NDV), reovirus, Seneca valley virus (SVV) morbillivirus virus, retrovirus, influenza virus, Sindbis virus (SINV) or poxvirus, as examples. In some embodiments, the oncolytic virus is not vaccinia virus. In some embodiments, the oncolytic virus is not vaccinia virus JX-594.

As used herein, an oncolytic virus which is "derived from" a reference virus comprises a nucleic acid sequence or amino acid sequence which is possessed by the reference virus. In some embodiments an oncolytic virus which is "derived from" a reference virus comprises one or more genes possessed by the reference virus. In some embodiments an oncolytic virus which is "derived from" encodes one or more proteins encoded by the reference virus.

In some embodiments, an oncolytic virus which is derived from a reference virus may comprise nucleic acid sequence encoding one or more functional elements of the reference virus. A "functional element" may e.g. be a transcriptional regulator (e.g. a promoter/enhancer), a regulator of post-transcriptional processing, a translational regulator, a regulator of post-transcriptional processing, a response element, a repeat sequence, or a viral protein. In some embodiments, an oncolytic virus which is derived from a reference virus may comprise one or more genes of, or proteins encoded by, the reference virus.

In some embodiments the oncolytic virus of the present disclosure is, or is derived from, an adenovirus (OncAd). OncAds are reviewed e.g. in Larson et al., Oncotarget. (2015) 6(24): 19976-19989, which is hereby incorporated by reference in its entirety.

In some embodiments the OncAd is, or is derived from, a species A, B, C, D, E, F or G human adenovirus (i.e. HAdV-A, HAdV-B, HAdV-C, HAdV-D, HAdV-E, HAdV-F or HAdV-G). In some embodiments the OncAd is, or is derived from, a species C human adenovirus. In some embodiments the OncAd is, or is derived from, Ad5, Ad2, Ad1, Ad6 or Ad57.

In some embodiments the OncAd is a conditionally replicating adenovirus (or CRAd).

In some embodiments the OncAd has reduced ability to infect, replicate in and/or lyse non-cancerous cells (as compared to the ability to infect/replicate in and/or lyse equivalent cancerous cells), for example as a consequence of a genetic modification of the adenovirus from which the OncAd is derived.

In some embodiments the oncolytic virus comprises a modification to one or more protein encoding sequences. In some embodiments, the modification alters the production or activity of the encoded protein. In some embodiments, the modification is a truncation or deletion of the protein.

In some embodiments, the OncAd comprises modification to an adenovirus early protein. In some embodiments, the modification is to the region encoding E1A protein. In some embodiments, the OncAd encodes an E1A protein having reduced ability to bind to Rb protein as compared to wild-type E1A protein (e.g. E1A encoded by the adenovirus from which the OncAd is derived). In some embodiments the OncAd encodes an E1A protein lacking the amino acid sequence LTCHEACF (SEQ ID NO:52). An example of an OncAd comprising encodes an E1A protein lacking the amino acid sequence LTCHEACF (SEQ ID NO:52) is Onc5/3Ad2E1Δ24 shown in SEQ ID NO:55.

In some embodiments the oncolytic virus encodes an E1A protein comprising, or consisting of or consisting essentially of, an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:34.

In some embodiments, the oncolytic virus comprises a nucleic acid sequence providing one or more binding sites for one or more transcription factors. In some embodiments, the transcription factor is an activating transcription factor (i.e. a transcriptional activator). The one or more binding sites for one or more transcription factors are preferably provided upstream of (i.e. 5' to) nucleic acid sequence encoding one or more functional elements (e.g. viral proteins).

In some embodiments, the transcription factor is a transcription factor having increased expression, or increased activity, in cancerous cells as compared to comparable non-cancerous cells (e.g. non-cancerous cells derived from the same tissue/cell type).

Herein, "expression" may refer to gene expression or protein expression. Gene expression can be measured by various means known to those skilled in the art, for example by measuring levels of mRNA by quantitative real-time PCR (qRT-PCR), or by reporter-based methods. Similarly, protein expression can be measured by various methods well known in the art, e.g. by antibody-based methods, for example by western blot, immunohistochemistry, immunocytochemistry, flow cytometry, ELISA, ELISPOT, or reporter-based methods.

An example of an OncAd comprising one or more binding sites for one or more transcription factors is ICOVIR15 described in Rojas et al. 2010 Mol Ther 18 1960-1971, which is hereby incorporated by reference its entirety. ICOVIR15 comprises 8 binding sites for the transcription factor E2F.

In some embodiments the oncolytic virus comprises one or more binding sites for a transcription factor whose gene or protein expression, or activity in a cell, is upregulated in response to a factor produced or expressed by an immune cell. In some embodiments, a factor produced or expressed by an immune cell may at least one cytokine/chemokine produced by, or a protein expressed at the cell surface of, an effector immune cell, e.g. CD8+ cytotoxic T lymphocyte (CTL), CD4+T helper 1 ($T_H1$) cell, natural killer (NK) cell or natural killer T (NKT) cell.

In some embodiments, the oncolytic virus of the present disclosure comprises one or more binding sites for a STAT transcription factor. In some embodiments, the oncolytic virus comprises one or more binding sites for a STAT1. An ICOSTAT OncAd described herein possesses 8 binding sites for STAT1, and STAT1 is known to be upregulated by IFNγ. In particular embodiments, ICOSTAT is a particularly effective treatment for a cancer because the host's immune response to the cancer cells will promote the replication of the oncolytic virus in situ.

In some embodiments, the oncolytic virus comprises more than one binding site for a STAT1, e.g. at least 2, 3, 4, 5, 6, 7, 8, 9, or 10 binding sites for STAT1. In some embodiments, a binding site for STAT1 may comprise or consist of or consist essentially of the sequence TTCCGGGAA (SEQ ID NO:53), or TTCTCGGAA (SEQ ID NO:54).

In some embodiments, the oncolytic virus of the present disclosure comprises one or more copies of the sequence TTCCGGGAA (SEQ ID NO:53) or TTCTCGGAA (SEQ ID NO:54).

In some embodiments the oncolytic virus according to the present disclosure comprises, or consists of, or consists essentially of, a nucleic acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:51 or an equivalent sequence as a result of codon degeneracy.

In some embodiments the oncolytic virus according to the present disclosure comprises, or consists of, or consists essentially of, a nucleic acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:55 or an equivalent sequence as a result of codon degeneracy.

In some embodiments the oncolytic virus according to the present disclosure encodes the same proteins as the proteins encoded by an oncolytic virus comprising, consisting of, or consisting essentially of, the nucleic acid shown in SEQ ID NO:55. In some embodiments the oncolytic virus according to the present disclosure encodes the same proteins as the proteins encoded by an oncolytic virus comprising, consisting of, or consisting essentially of, the nucleic acid shown in SEQ ID NO:51.

Virus Comprising Nucleic Acid Encoding an Immunomodulatory Factor

The present disclosure employs a virus comprising nucleic acid encoding an immunomodulatory factor. The virus acts as a vector for delivering the immunomodulatory factor. In certain embodiments, the virus comprises nucleic acid encoding more than one immunomodulatory factor(s).

Any virus capable of introducing the nucleic acid encoding an immunomodulatory factor into a cell (e.g. a primary human immune cell) may be used. Suitable viruses include gammaretrovirus (e.g. murine Leukemia virus (MLV)-derived vectors), lentivirus, adenovirus, adeno-associated virus, vaccinia virus and herpesvirus, e.g. as described in Maus et al., Annu Rev Immunol (2014) 32:189-225 or Morgan and Boyerinas, Biomedicines 2016 4, 9, which are both hereby incorporated by reference in its entirety. In some embodiments, the virus comprising nucleic acid encoding an immunomodulatory factor is, or is derived from, an adenovirus, lentivirus, retrovirus, or herpesvirus.

In some embodiments, the virus comprising nucleic acid encoding at least one immunomodulatory factor is an oncolytic virus comprising nucleic acid encoding at least one immunomodulatory factor.

An immunomodulatory factor(s) encoded by the virus comprising nucleic acid encoding the immunomodulatory factor(s) according to the present disclosure are preferably selected to facilitate the immune response to a cancer in a subject, in particular the cell-mediated immune response. In one embodiment, the immunomodulatory factor(s) provide favourable conditions for the activation, recruitment, proliferation, activity and/or survival of effector immune cells (e.g. CTLs, $T_H1$ cells, NK cells or NKT cells).

In some embodiments, the immunomodulatory factor may be an agonist of an effector immune response, e.g. a cytokine or chemokine promoting activation, recruitment, proliferation, activity and/or survival of effector immune cells (e.g. IL-2, IL-7, IL-17, IL-12, IL-21, IL-15, MIP-1a or RANTES), agonist antibody for a costimulatory receptor (e.g. 4-1 BB, OX40, CD28, CD27, ICOS, CD30 or GITR), or ligand for a costimulatory receptor (e.g. 4-1 BBL, OX40L, CD80, CD86, CD70, ICOSL, CD30L or GITRL).

In some embodiments, the agonist of an effector immune response may be an antagonist of an immune checkpoint inhibitor, or an antagonist of ligand for immune checkpoint inhibitor, e.g. antagonist antibody to PD-L1, PD-L2, PD-1, CTLA-4, LAG-3, TIM-3, Gal-9, TIGIT, VISTA or BTLA, or an antagonist of a cytokine/chemokine which is an antagonist of an effector immune response, e.g. TGFβ (i.e. antagonist anti-TGFβ antibody or soluble/decoy TGFβ receptor).

In some embodiments, an agonist of an effector immune response may be a molecule for engaging and co-opting bystander effector immune cells such as T cells and NK cells.

In some embodiments, the immunomodulatory factor may be an antagonist of an immunoregulatory response, e.g. an antagonist of a cytokine/chemokine promoting activation, recruitment, proliferation, activity and/or survival of immunoregulatory cells such as regulatory T cells (Tregs) and/or myeloid-derived suppressor cells (MDSCs), e.g. CCL9, CXCL10, CCL20, CCL22.

In some embodiments the virus comprising nucleic acid encoding an immunomodulatory factor may additionally comprise nucleic acid encoding further functional sequence(s). For example, the virus may comprise nucleic acid encoding a protein(s) for reducing growth/proliferation/survival of infected cells, or protein(s) for rendering infected cells sensitive to treatment with a given agent, or protein(s) for disrupting tumour structure (e.g. enzymes for digesting tumour matrix) to facilitate immune cell infiltration.

In some embodiments the virus comprising nucleic acid encoding an immunomodulatory factor additionally comprises nucleic acid encoding an enzyme capable of catalysing conversion of a non-toxic factor to a cytotoxic form. The enzyme may catalyse conversion of a non-toxic prodrug into its active, cytotoxic form.

Enzyme/prodrug systems are well known in the art and include those described in Malekshah et al. Curr Pharmacol Rep. (2016) 2(6): 299-308 which is hereby incorporated by reference in its entirety. Examples of non-toxic prodrugs, their active cytotoxic forms and enzymes capable of catalysing conversion of the non-toxic prodrugs to their active cytotoxic forms are shown in FIG. 2 of Malekshah et al.

In some embodiments the virus comprising nucleic acid encoding an immunomodulatory factor additionally comprises nucleic acid encoding a thymidine kinase, cytosine deaminase, nitroreductase, cytochrome P450, carboxypeptidase G2, purine nucleoside phosphorylase, horseradish peroxidase and/or carboxylesterase.

For example, the virus may comprise nucleic acid encoding thymidine kinase for rendering cells expressing the virus sensitive to treatment with ganciclovir (GCV), aciclovir (ACV) and/or valaciclovir. The virus may comprise nucleic acid encoding cytosine deaminase for rendering cells expressing the virus sensitive to treatment with 5-fluorocytosine (5-FC), which is converted by cytosine deaminase to 5-fluorouracil (5-FU). The virus may comprise nucleic acid encoding nitroreductase for rendering cells expressing the virus sensitive to treatment with CB1954, nitro-CBI-DEI and/or PR-104A. The virus may comprise nucleic acid encoding cytochrome P450 for rendering cells expressing the virus sensitive to treatment with oxazaphosphorine (e.g. cyclophosphamide or ifosfamide). The virus may comprise nucleic acid encoding carboxypeptidase G2 for rendering cells expressing the virus sensitive to treatment with nitrogen mustard based drugs (e.g. CMDA or ZD2767P). The virus may comprise nucleic acid encoding purine nucleoside phosphorylase for rendering cells expressing the virus sensitive to treatment with 6-methylpurine 2-deoxyriboside and/or fludarabine (e.g. 6-methylpurine-2'-deoxyriboside (MeP-dR), 2-F-2'-deoxyadenosine (F-dAdo) or arabinofuranosyl-2-F-adenine monophosphate (F-araAMP). The virus may comprise nucleic acid encoding horseradish peroxidase for rendering cells expressing the virus sensitive to treatment with indole-3-acetic acid (IAA). The virus may comprise nucleic acid encoding carboxylesterase for rendering cells expressing the virus sensitive to treatment with irinotecan.

In some embodiments the virus may comprise nucleic acid encoding antagonist of a growth factor.

In some embodiments, the virus may be a helper-dependent adenovirus (HDAd). HDAds are reviewed, for example, in Rosewell et al., J Genet Syndr Gene Ther (2011) Suppl 5:001, which is hereby incorporated by reference in its entirety.

HDAds are devoid of viral protein coding sequences, and therefore possess a large capacity (up to 37 Kb) for transduction of a coding sequence of interest. HDAds are non-integrating, and are able to efficiently transduce a wide variety of cell types independently of the cell cycle, and mediate long-term transgene expression without chronic toxicity.

HDAds comprise only the cis acting viral elements required for genomic replication (inverted terminal repeats (ITRs)) and encapsidation (ψ), and are therefore dependent on helper virus for propagation. When a cell is infected with both the helper virus and the HDAd, the helper virus replication machinery acts in trans to replicate and package HDAd.

In particular embodiments of the present disclosure, the oncolytic virus is an OncAd and the virus comprising nucleic acid encoding an immunomodulatory factor is a HDAd, and the OncAd and HDAd are able to co-infect and replicate in cells of a cancer.

Dependence of the HDAd on help from the OncAd provides highly localised expression of the immunomodulatory factor(s). That is, because the HDAd is only able to propagate in cells co-infected with the OncAd, and in turn because the OncAd is selective for replication in cancerous cells, expression of the factor(s) encoded by the HDAd is restricted to cancerous cells/tissue, minimising side effects.

Furthermore, because the OncAd and HDAd efficiently target and infect tumour cells, expression of the immunomodulatory factor(s) in those cells can change the normally immunosuppressive tumour microenvironment to provide conditions promoting the activation, recruitment (i.e. tumour penetration/infiltration), proliferation, activity and/or survival of effector immune cells.

In particular, in the context of the present disclosure wherein the methods of treatment employ the use of CAR-T cells, expression of the immunomodulatory factor(s) encoded by the HDAd provide for enhanced activation, recruitment, proliferation, activity and/or survival of the CAR-T cells.

In particular embodiments herein the virus comprising nucleic acid encoding an immunomodulatory factor is a HDAd comprising nucleic acid encoding IL-12p70, HSV-1 thymidine kinase and an antagonist anti-PD-L1 minibody.

In some embodiments, the virus comprising nucleic acid encoding an immunomodulatory factor according to the present disclosure encodes IL-12. In some embodiments the virus comprising nucleic acid encoding an immunomodulatory factor comprises nucleic acid encoding an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:35.

In some embodiments, the virus comprising nucleic acid encoding an immunomodulatory factor according to the present disclosure encodes an antagonist of PD-1/PD-L1 signalling. In some embodiments the antagonist of PD-1/PD-L1 signalling is an anti-PD-L1 antibody.

In some embodiments the anti-PD-L1 antibody comprises an antigen binding domain comprising a VL domain comprising:
  LC-CRD1: SEQ ID NO:39;
  LC-CRD2: SEQ ID NO:40;
  LC-CRD3: SEQ ID NO:41;
and a VH domain comprising:
  HC-CRD1: SEQ ID NO:42;
  HC-CRD2: SEQ ID NO:43;
  HC-CRD3: SEQ ID NO:44.

In some embodiments the anti-PD-L1 antibody comprises a VL comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:45 and a VH comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:46.

In some embodiments the virus comprising nucleic acid encoding an immunomodulatory factor comprises nucleic acid encoding an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:38.

In some embodiments, the virus comprising nucleic acid encoding an immunomodulatory factor according to the present disclosure comprises an amino acid sequence encoding a thymidine kinase. In some embodiments the virus comprising nucleic acid encoding an immunomodulatory factor comprises nucleic acid encoding an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:36.

In some embodiments, the virus comprising nucleic acid encoding an immunomodulatory factor according to the present disclosure comprises, or consists of or consist essentially of, a nucleic acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:50 or an equivalent sequence as a result of codon degeneracy.

Chimeric Antigen Receptors (CARs) and CAR-Expressing Cells

The present disclosure employs immune cells comprising a chimeric antigen receptor (CAR).

Chimeric Antigen Receptors (CARs) are recombinant receptors that provide both antigen-binding and immune cell activating functions. CAR structure and engineering is reviewed, for example, in Dotti et al., Immunol Rev (2014)

257(1), hereby incorporated by reference in its entirety. CARs comprise an antigen-binding region linked to a cell membrane anchor region and a signaling region. An optional hinge region may provide separation between the antigen-binding region and cell membrane anchor region, and may act as a flexible linker.

The antigen-binding region of a CAR may be based on the antigen-binding region of an antibody which is specific for the antigen to which the CAR is targeted, or other agent capable of binding to the target. For example, the antigen-binding domain of a CAR may comprise amino acid sequences for the complementarity-determining regions (CDRs) or complete light chain and heavy chain variable region amino acid sequences of an antibody which binds specifically to the target protein. Antigen-binding domains of CARs may target antigen based on other protein:protein interaction, such as ligand:receptor binding; for example an IL-13Ra2-targeted CAR has been developed using an antigen-binding domain based on IL-13 (see e.g. Kahlon et al. 2004 Cancer Res 64(24): 9160-9166).

The CAR of the present disclosure comprises an antigen-binding region specific for a cancer cell antigen. The antigen binding region of the CAR may be provided with any suitable format, e.g. scFv, Fab, etc. In some embodiments, the antigen binding region of the CAR comprises or consists of a cancer cell antigen binding scFv.

A cancer cell antigen is an antigen which is expressed by a cancer cell. A cancer cell antigen may be any peptide/polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response.

In some embodiments, the antigen is expressed at the cell surface of the cancer cell (i.e. the cancer cell antigen is a cancer cell surface antigen). In some embodiments, the part of the antigen which is bound by the bispecific antigen binding polypeptide of the present disclosure is displayed on the external surface of the cancer cell (i.e. is extracellular). In some embodiments, the antigen is anchored to the cell membrane, e.g. via a transmembrane domain or other membrane anchor (e.g. a lipid anchor such as a GPI anchor). In some embodiments, the cancer cell antigen is expressed at the cell surface (i.e. is expressed in or at the cell membrane) of a cancerous cell, but may be expressed inside the cell (i.e. is expressed inside comparable non-cancerous cells).

The cancer cell antigen may be a cancer-associated antigen. In some embodiments the cancer cell antigen is an antigen whose expression is associated with the development, progression and/or severity of symptoms of a cancer. The cancer-associated antigen may be associated with the cause or pathology of the cancer, or may be expressed abnormally as a consequence of the cancer. In some embodiments, the antigen is an antigen whose expression is upregulated (e.g. at the RNA and/or protein level) by cells of a cancer, e.g. as compared to the level of expression of by comparable non-cancerous cells (e.g. non-cancerous cells derived from the same tissue/cell type).

In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

Cancer cell antigens are reviewed by Zarour H M, DeLeo A, Finn O J, et al. Categories of Tumor Antigens. In: Kufe D W, Pollock R E, Weichselbaum R R, et al., editors. Holland-Frei Cancer Medicine. 6th edition. Hamilton (ON): BC Decker; 2003. Cancer cell antigens include oncofetal antigens: CEA, Immature laminin receptor, TAG-72; oncoviral antigens such as HPV E6 and E7; overexpressed proteins: BING-4, calcium-activated chloride channel 2, cyclin-B1, 9D7, Ep-CAM, EphA3, HER2/neu, telomerase, mesothelin, SAP-1, surviving; cancer-testis antigens: BAGE, CAGE, GAGE, MAGE, SAGE, XAGE, CT9, CT10, NY-ESO-1, PRAME, SSX-2; lineage restricted antigens: MART1, Gp100, tyrosinase, TRP-1/2, MC1R, prostate specific antigen; mutated antigens: β-catenin, BRCA1/2, CDK4, CML66, Fibronectin, MART-2, p53, Ras, TGF-βRII; post-translationally altered antigens: MUC1, idiotypic antigens: Ig, TCR. Other cancer cell antigens include heat-shock protein 70 (HSP70), heat-shock protein 90 (HSP90), glucose-regulated protein 78 (GRP78), vimentin, nucleolin, feto-acinar pancreatic protein (FAPP), alkaline phosphatase placental-like 2 (ALPPL-2), siglec-5, stress-induced phosphoprotein 1 (STIP1), protein tyrosine kinase 7 (PTK7), and cyclophilin B.

In some embodiments, the cancer cell antigen is HER2. In some embodiments, the CAR of the present disclosure comprises an antigen binding domain capable of specific binding to HER2. In some embodiments, the CAR comprises an antigen binding domain comprising the CDRs of an antibody capable of specific binding to HER2. In some embodiments, the CAR comprises an antigen binding domain comprising the VL and VH regions of an antibody capable of specific binding to HER2.

In particular embodiments, the cell expressing the CAR comprises two, separate CARs each that target different cancer cell antigens, and in particular aspects at least one of the CARs targets HER2. In some cases, the CAR is bispecific for two different cancer cell antigens, one of which may be HER2.

In some embodiments the CAR comprises an antigen binding domain comprising a VL domain comprising:
 LC-CRD1: SEQ ID NO:10, SEQ ID NO:18, SEQ ID NO:26 or SEQ ID NO: 57;
 LC-CRD2: SEQ ID NO:11, SEQ ID NO:19, SEQ ID NO:27 or SEQ ID NO: 58;
 LC-CRD3: SEQ ID NO:12, SEQ ID NO:20, SEQ ID NO:28 or SEQ ID NO: 59;
and a VH domain comprising:
 HC-CRD1: SEQ ID NO:13, SEQ ID NO:21, SEQ ID NO:29 or SEQ ID NO: 60;
 HC-CRD2: SEQ ID NO:14, SEQ ID NO:22, SEQ ID NO:30 or SEQ ID NO: 61;
 HC-CRD3: SEQ ID NO:15, SEQ ID NO:23, SEQ ID NO:31 or SEQ ID NO: 62.

In some embodiments the CAR comprises an antigen binding domain comprising a VL domain comprising:
 LC-CRD1: SEQ ID NO:10;
 LC-CRD2: SEQ ID NO:11;
 LC-CRD3: SEQ ID NO:12;
and a VH domain comprising:
 HC-CRD1: SEQ ID NO:13;
 HC-CRD2: SEQ ID NO:14;
 HC-CRD3: SEQ ID NO:15.

In some embodiments the CAR comprises an antigen binding domain comprising a VL domain comprising:
LC-CRD1: SEQ ID NO:18;
LC-CRD2: SEQ ID NO:19;
LC-CRD3: SEQ ID NO:20;
and a VH domain comprising:
HC-CRD1: SEQ ID NO:21;
HC-CRD2: SEQ ID NO:22;
HC-CRD3: SEQ ID NO:23.

In some embodiments the CAR comprises an antigen binding domain comprising a VL domain comprising:
LC-CRD1: SEQ ID NO:26;
LC-CRD2: SEQ ID NO:27;
LC-CRD3: SEQ ID NO:28;
and a VH domain comprising:
HC-CRD1: SEQ ID NO:29;
HC-CRD2: SEQ ID NO:30;
HC-CRD3: SEQ ID NO:31.

In some embodiments the CAR comprises an antigen binding domain comprising a VL domain comprising:
a VL domain comprising:
LC-CRD1: SEQ ID NO:57;
LC-CRD2: SEQ ID NO:58;
LC-CRD3: SEQ ID NO:59;
and a VH domain comprising:
HC-CRD1: SEQ ID NO:60;
HC-CRD2: SEQ ID NO:61;
HC-CRD3: SEQ ID NO:62.

In some embodiments the CAR comprises an antigen binding domain comprising a light chain variable region (VL) comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:16, 24, 32 or 63.

In some embodiments the CAR comprises an antigen binding domain comprising a heavy chain variable region (VH) comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:17, 25, 33 or 64.

In some embodiments the CAR comprises an antigen binding domain comprising a VL comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:16 and a VH comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:17. In some embodiments the CAR comprises an antigen binding domain comprising a VL comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:24 and a VH comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:25. In some embodiments the CAR comprises an antigen binding domain comprising a VL comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:32 and a VH comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:33. In some embodiments the CAR comprises an antigen binding domain comprising a VL comprising, consisting of, or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:63 and a VH comprising, consisting of. or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:64.

In some embodiments, the CAR of the present disclosure comprises an antigen binding region which comprises or consists of or consists essentially of an antibody/antigen binding fragment according to the present disclosure.

The cell membrane anchor region is provided between the antigen-binding region and the signalling region of the CAR. The cell membrane anchor region provides for anchoring the CAR to the cell membrane of a cell expressing a CAR, with the antigen-binding region in the extracellular space, and signalling region inside the cell. Suitable transmembrane domains include transmembrane region derived from CD28, CD4 or CD8.

In some embodiments the cell membrane anchor region comprises, or consists of or consists essentially of, an amino acid sequence having at least 80%, 85%, 90%, 91%, 92%, 93%, 94%, 95%, 96%, 97%, 98%, 99% or 100% sequence identity to SEQ ID NO:4.

The signalling region of a CAR allows for activation of the T cell. The CAR signalling regions may comprise the amino acid sequence of the intracellular domain of CD3-ζ, which provides immunoreceptor tyrosine-based activation motifs (ITAMs) for phosphorylation and activation of the CAR-expressing T cell. Signalling regions comprising sequences of other ITAM-containing proteins have also been employed in CARs, such as domains comprising the ITAM containing region of FcγRI (Haynes et al., 2001 J Immunol 166(1):182-187). CARs comprising a signalling region derived from the intracellular domain of CD3-ζ are often referred to as first generation CARs.

In some embodiments the cell membrane anchor region comprises, or consists of or consists essentially of, an amino acid sequence having at least 80%, 85%, 90%, 91%, 92%, 93%, 94%, 95%, 96%, 97%, 98%, 99% or 100% sequence identity to SEQ ID NO:6.

Signalling regions of CARs may also comprise co-stimulatory sequences derived from the signalling region of co-stimulatory molecules, to facilitate activation of CAR-expressing T cells upon binding to the target protein. Suitable co-stimulatory molecules include at least CD28, OX40, 4-1 BB, ICOS and CD27. CARs having a signalling region including additional co-stimulatory sequences are often referred to as second generation CARs.

In some cases CARs are engineered to provide for co-stimulation of different intracellular signalling pathways. For example, signalling associated with CD28 costimulation preferentially activates the phosphatidylinositol 3-kinase (P13K) pathway, whereas the 4-1 BB-mediated signalling is through TNF receptor associated factor (TRAF) adaptor proteins. Signalling regions of CARs therefore sometimes contain co-stimulatory sequences derived from signalling regions of more than one co-stimulatory molecule. CARs comprising a signalling region with multiple co-stimulatory sequences are often referred to as third generation CARs.

In some embodiments, the CAR of the present disclosure comprises one or more co-stimulatory sequences comprising or consisting of or consisting essentially of an amino acid sequence which comprises, consists of or consists essentially of, or is derived from, the amino acid sequence of the intracellular domain of one or more of CD28, OX40, 4-1 BB, ICOS and CD27.

In some embodiments the cell membrane anchor region comprises, or consists of or consists essentially of, an amino acid sequence having at least 80%, 85%, 90%, 91%, 92%, 93%, 94%, 95%, 96%, 97%, 98%, 99% or 100% sequence identity to SEQ ID NO:5.

An optional hinge region may provide separation between the antigen-binding domain and the transmembrane domain, and may act as a flexible linker. Hinge regions may be flexible domains allowing the binding moiety to orient in different directions. Hinge regions may be derived from IgG1 or the $CH_2CH_3$ region of immunoglobulin. In some embodiments, the CAR of the present disclosure comprises a hinge region comprising or consisting of or consisting essentially of an amino acid sequence which comprises, consists of or consists essentially of, or is derived from, the amino acid sequence of the hinge region of IgG1 or the $CH_2CH_3$ region of immunoglobulin.

In some embodiments the cell membrane anchor region comprises, or consists of or consists essentially of, an amino acid sequence having at least 85%, 90%, 91%, 92%, 93%, 94%, 95%, 96%, 97%, 98%, 99% or 100% sequence identity to SEQ ID NO:9.

In some embodiments the CAR comprises, or consists of or consists essentially of, an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:1, 2, 3 or 56.

The present disclosure also provides a cell comprising or expressing a CAR according to the present disclosure. Also provided is a cell comprising or expressing a nucleic acid encoding a CAR according to the disclosure. Engineering of CARs into T cells may be performed during culture, in vitro, for transduction and expansion, such as happens during expansion of T cells for adoptive T cell therapy. Methods for engineering immune cells to express CARs are known to the skilled person and are described e.g. in Wang and Rivière Mol Ther Oncolytics. (2016) 3:16015, which is hereby incorporated by reference in its entirety. It will be appreciated that "at least one cell" encompasses plural cells, e.g. populations of such cells.

The cell comprising or expressing a CAR according to the present disclosure may be a eukaryotic cell, e.g. a mammalian cell. The mammal may be a human, or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

In some embodiments, the cell may be from, or may have been obtained from, a human subject. Where the CAR-expressing cell is to be used in the treatment of a subject, the cell may be from the subject to be treated with the CAR-expressing cell (i.e. the cell may be autologous), or the cell may be from a different subject (i.e. the cell may be allogeneic).

The cell may be an immune cell. The cell may be a cell of hematopoietic origin, e.g. a neutrophil, eosinophil, basophil, dendritic cell, lymphocyte, or monocyte. The lymphocyte may be e.g. a T cell, B cell, NK cell, NKT cell or innate lymphoid cell (ILC), or a precursor thereof. The cell may express e.g. CD3 polypeptides (e.g. CD3γ CD3ε CD3ζ or CD3β), TCR polypeptides (TCRα or TCRβ), CD27, CD28, CD4 or CD8.

In some embodiments, the cell is a T cell. In some embodiments, the T cell is a CD3+ T cell. In some embodiments, the T cell is a CD3+, CD8+ T cell. In some embodiments, the T cell is a cytotoxic T cell (e.g. a cytotoxic T lymphocyte (CTL)).

The use of CAR T-cells is associated with advantages that they can be systemically administered, and will home to both primary and metastasized tumors (Manzo et al., Human Molecular Genetics (2015) R67-73).

In some embodiments, the cell is an antigen-specific T cell. In embodiments herein, an "antigen-specific" T cell is a cell which displays certain functional properties of a T cell in response to the antigen for which the T cell is specific, or a cell expressing said antigen. In some embodiments, the properties are functional properties associated with effector T cells, e.g. cytotoxic T cells.

In some embodiments, an antigen-specific T cell may display one or more of the following properties: cytotoxicity, e.g. to a cell comprising/expressing antigen for which the T cell is specific; proliferation, IFNγ expression, CD107a expression, IL-2 expression, TNFα expression, perforin expression, granzyme expression, granulysin expression, and/or FAS ligand (FASL) expression, e.g. in response to antigen for which the T cell is specific or a cell comprising/expressing antigen for which the T cell is specific. Antigen-specific T cells comprise a TCR capable of recognising a peptide of the antigen for which the T cell is specific when presented by the appropriate MHC molecule. Antigen-specific T cells may be CD4+ T cells and/or CD8+ T cells.

In some embodiments, the antigen for which the T cell is specific may be a peptide or polypeptide of a virus, e.g. Adenovirus, Cytomegalovius (CMV), Epstein-Barr virus (EBV), human papilloma virus (HPV), influenza virus, measles virus, hepatitis B virus (HBV), hepatitis C virus (HCV), human immunodeficiency virus (HIV), lymphocytic choriomeningitis virus (LCMV), or herpes simplex virus (HSV).

A T cell which is specific for an antigen of a virus may be referred to herein as a virus-specific T cell (VST). VSTs may be CD4+ T cells (e.g. $T_H$ cells) and/or CD8+ T cells (e.g. CTLs). A T cell which is specific for an antigen of a particular virus may be described as being being specific for the relevant virus; for example, a T cell which is specific for an antigen of an Adenovris may be referred to as an Adenovirus-specific T cell, or "AdVST". The use of virus-specific T cells for the generation of CAR-T cells is associated with the advantage that whilst naïve T cells may have limited long-term persistence after infusion, virus-specific T-cells (VSTs) derived from the memory compartment, and genetically-modified VSTs have been shown to persist for over 10 years after infusion in stem cell transplant recipients (Cruz et al., Cytotherapy (2010) 12:743-749). For example, VSTs expressing GD2.CARs have been shown to persist long-term after infusion and produce complete tumor responses in patients with low tumor burden (Sun et al., Journal for Immunotherapy of Cancer (2015) 3:5 and Pule et al., Nature Medicine (2008) 14: 1264-1270).

In some embodiments the cell comprising/expressing the CAR is a virus-specific T cell (VST, e.g. a virus-specific CD4+ T cell (e.g. $T_H$ cell) and/or a virus-specific CD8+ T cell (e.g. CTL). In some embodiments the CAR-expressing cell is an Adenovirus-specific T cell (AdVST), Cytomegalovius-specific T cell (CMVST), Epstein-Barr virus-specific T cell (EBVST), influenza virus-specific T cell, measles virus-specific T cell, hepatitis B virus-specific T cell (HBVST), hepatitis C virus-specific T cell (HCVST), human immunodeficiency virus-specific T cell (HIVST), lymphocytic choriomeningitis virus-specific T cell (LCMVST), Herpes simplex virus-specific T cell (HSVST) or human papilloma virus (HPVST).

In some embodiments the cell comprising/expressing the CAR is an oncolytic virus-specific immune cell (e.g. an oncolytic virus-specific T cell), e.g. as described herein.

Any cells of the disclosure may be included in an isolated population of cells that may or may not be homogeneous. In specific embodiments, the cell population has a majority of cells that are immune cells specific for an oncolytic virus and/or that express a CAR. The cells in the cell population may comprise an oncolytic adenovirus (OncAd), a helper-dependent adenovirus (HDAd), a chimeric antigen receptor (CAR) and/or nucleic acid or plurality of nucleic acids that encodes one or more of the OncAd, HDAd, and/or CAR. In particular embodiments, the cell population has at least 70, 75, 80, 85, 90, 91, 92, 93, 94, 95, 96, 97, 98, or 99% of cells that comprise an oncolytic adenovirus (OncAd), a helper-dependent adenovirus (HDAd), a chimeric antigen receptor (CAR) and/or nucleic acid or plurality of nucleic acids that encodes one or more of the OncAd, HDAd, and/or CAR.

Oncolytic Virus-Specific Immune Cells

Aspects of the present disclosure provide oncolytic virus-specific immune cells (also referred to herein as immune cells specific for an oncolytic virus). Oncolytic virus-specific immune cells express/comprise a receptor capable of recognising a peptide of an antigen of an oncolytic virus (e.g. when presented by an MHC molecule). The immune cell may express/comprise such a receptor as a result of expression of endogenous nucleic acid encoding such antigen receptor, or as a result of having been engineered to express such a receptor.

In some embodiments an oncolytic virus-specific immune cell may be a cell of hematopoietic origin, e.g. a neutrophil, eosinophil, basophil, dendritic cell, lymphocyte, or monocyte. The lymphocyte may be e.g. a T cell, B cell, NK cell, NKT cell or innate lymphoid cell (ILC), or a precursor thereof. The cell may express e.g. CD3 polypeptides (e.g. CD3γ CD3ε CD3ζ or CD3δ), TCR polypeptides (TCRα or TCRβ), CD27, CD28, CD4 or CD8. In some embodiments, the oncolytic virus-specific immune cell is a T cell, e.g. a CD3+ T cell. In some embodiments, the T cell is a CD3+, CD4+ T cell. In some embodiments, the T cell is a CD3+, CD8+ T cell. In some embodiments, the T cell is a T helper cell ($T_H$ cell)). In some embodiments, the T cell is a cytotoxic T cell (e.g. a cytotoxic T lymphocyte (CTL)).

The oncolytic virus-specific immune cell (e.g. oncolytic virus-specific T cell) may be specific for an oncolytic virus as described herein. That is to say, the oncolytic virus-specific immune cell may be specific for one or more antigens of an oncolytic virus described herein.

Methods for generating/expanding populations of immune cells specific for antigen(s) of interest and/or a virus of interest are well known in the art, and are described e.g. in Wang and Rivière Cancer Gene Ther. (2015) 22(2):85-94, which is hereby incorporated by reference in its entirety.

Such methods may involve contacting heterogeneous populations of immune cells (e.g. peripheral blood mononuclear cells (PBMCs), peripheral blood lymphocytes (PBLs) tumor-infiltrating lymphocytes (TILs)) with one or more peptides of the antigen(s) of interest, or cells comprising/expressing the antigen(s)/peptides. Cells comprising/expressing the antigen(s)/peptides may do so as a consequence of infection with the virus comprising/encoding the antigen(s), uptake by the cell of the antigen(s)/peptides thereof or expression of the antigen(s)/peptides thereof. The presentation is typically in the context of an MHC molecule at the cell surface of the antigen-presenting cell.

Cells comprising/expressing the antigen(s)/peptides may have been contacted ("pulsed") with peptides of the antigen(s) according to methods well known to the skilled person. Antigenic peptides may be provided in a library of peptide mixtures (corresponding to one or more antigens), which may be referred to as pepmixes. Peptides of pepmixes may e.g. be overlapping peptides of 8-20 amino acids in length, and may cover all or part of the amino acid sequence of the relevant antigen.

Cells within the population of immune cells comprising receptors specific for the peptide(s) may be activated (and stimulated to proliferate), following recognition of peptide(s) of the antigen(s) presented by antigen-presenting cells (APCs) in the context of appropriate costimulatory signals. It will be appreciated that "an immune cell specific for an oncolytic virus" encompasses plural cells, e.g. populations of such cells. Such populations may be generated/expanded in vitro and/or ex vivo.

In some embodiments, an immune cell specific for an oncolytic virus is specific for an oncolytic adenovirus (OncAd), e.g. an OncAd as described herein. In some embodiments, an immune cell specific for an oncolytic virus is specific for an antigen of an OncAd. In some embodiments, the antigen is, or is derived from, an OncAd protein, e.g. a protein encoded by an early gene (e.g. E1 (e.g. E1A, E1B), E2 (e.g. E2A, E2B), E3 or E4), a protein encoded by a late gene (e.g. L1, L2, L3, L4 or L5), a protein encoded by IX, or a protein encoded by IVa2. In some embodiments, the antigen is, or is derived from, an OncAd hexon and/or penton.

In some embodiments in accordance with various aspects of the present disclosure an immune cell specific for a virus may be generated/expanded (or may have been generated/expanded) by a method comprising: stimulating a population of immune cells by culture in the presence of antigen presenting cells (APCs) presenting a peptide of the virus.

In some embodiments an immune cell specific for an oncolytic virus according to the present disclosure is prepared by a method employing a PepMix comprising a mixture of overlappying peptides corresponding to Human Adenovirus 3 hexon and/or a PepMix comprising a mixture of overlappying peptides corresponding to Human Adenovirus 5 penton.

In some embodiments the oncolytic virus-specific immune cell expresses/comprises a CAR, e.g. a CAR as described herein. The oncolytic virus-specific immune cell may be engineered to express a CAR e.g. by transfection/ transduction of the oncolytic virus-specific immune cell with nucleic acid encoding a CAR.

Combinations of the Disclosure

Aspects of the present invention include compositions and methods comprising/employing (i) an oncolytic virus; (ii) a virus comprising nucleic acid encoding an immunomodulatory factor; and (iii) at least one cell comprising a chimeric antigen receptor (CAR) specific for a cancer cell antigen.

Also provided are compositions and methods comprising/employing (i) an oncolytic virus; and (ii) at least one cell comprising a chimeric antigen receptor (CAR) specific for a cancer cell antigen (i.e. without necessarily also employing a virus comprising nucleic acid encoding an immunomodulatory factor).

Also provided are compositions and methods comprising/employing (i) an oncolytic virus; and (ii) an immune cell specific for the oncolytic virus.

In some embodiments in accordance with various aspects described herein the cell comprising/expressing the CAR is specific for the oncolytic virus employed (e.g. comprises antigen receptor (e.g. TCR) specific for an antigen of the oncolytic virus). That is to say, in some embodiments the oncolytic virus and the specificity of the cell comprising/expressing the CAR are matched. By way of example, in some embodiments the oncolytic virus is an adenovirus, and the CAR-expressing cell comprising/expressing a CAR is an Adenovirus-specific T cell.

Similarly, in various aspects described herein an oncolytic virus is employed in combination with an immune cell specific for the oncolytic virus (i.e. the same oncolytic virus).

"Combinations" as referred to herein encompass products and compositions (e.g. pharmaceutical compositions) comprising the components of the combination. "Combinations" also encompass therapeutic regimens employing the the components of the combination.

In some embodiments the components of a combination are provided in separate compositions. In some embodiments more than one component of a combination is provided in a composition. In some embodiments the components of a combination are provided in one composition.

Similarly, in some embodiments the components of a combination are administered separately. In some embodiments a component of a combination is administered with another component of the combination. In some embodiments the components of a combination are administered together.

By way of illustration, in the example of a combination comprising an oncolytic virus, a virus comprising nucleic acid encoding an immunomodulatory factor and at least one cell comprising a CAR specific for a cancer cell antigen, the oncolytic virus and the virus comprising nucleic acid encoding an immunomodulatory factor may be administered together, and the at least one cell comprising a CAR specific for a cancer cell antigen may be administered separately (e.g. subsequently).

Where components of a combination are administered together administration may be simultaneous administration as described hereinbelow. Where components of a combination are administered separately, administration may be simultaneous administration or sequential administration, as described hereinbelow. In cases wherein components of a combination are administered separately, the administration of the separate components may or may not be administered via the same administration routes Functional Properties The agents of the present disclosure may be defined by reference to one of more functional properties. The agents may be evaluated for the functional properties, for example, by analysis as described in the experimental examples. Similarly, the combinations and methods of the present disclosure may be defined by reference to one or more functional properties and/or effects, and may be evaluated for such properties/effects e.g. by analysis as described in the experimental examples.

In some embodiments, an oncolytic virus according to the present disclosure may possess one or more of the following functional properties:
 ability to replicate in, and/or cause cell killing of, cancer cells;
 reduced ability to replicate in and/or cause cell killing of, non-cancerous cells as compared to the ability to replicate in, and/or cause cell killing of, cancer cells;
 comparable or improved ability to cause cell killing of cancer cells as compared to the ability of one or more oncolytic viruses known in the art;
 ability to help replication of helper-dependent adenovirus (HDAd);
 comparable or improved ability to replicate in cancer cells as compared to the ability of one or more oncolytic viruses known in the art.

In some embodiments, a cell comprising a chimeric antigen receptor (CAR) specific for a cancer cell antigen according to the present disclosure may possess one or more of the following functional properties:
 ability to bind to HER2;
 ability to bind to HER2-expressing cells;
 ability to cause cell killing of HER2-expressing cells;
 reduced ability to cause cell killing of cell not expressing HER2 as compared to the ability to cause cell killing of HER2-expressing cells.

In some embodiments the combination of an oncolytic virus, a virus comprising nucleic acid encoding an immunomodulatory and at least one cell comprising a CAR specific for a cancer cell antigen may possess one or more of the following functional properties:
 improved ability to cause cell killing of cancer cells as compared to the ability to cause cell killing of cancer cells by any one of the components use alone, or by any two of the components used in combination.
 ability to cause cell killing of cancer cells which is synergistic (i.e. super-additive) as compared to the ability to cause cell killing of cancer cells by the components used alone.

In some embodiments the combination of an oncolytic virus and at least one cell comprising a CAR specific for a cancer cell antigen may possess one or more of the following functional properties:
 improved ability to cause cell killing of cancer cells as compared to the ability to cause cell killing of cancer cells by either component used alone.
 ability to cause cell killing of cancer cells which is synergistic (i.e. super-additive) as compared to the ability to cause cell killing of cancer cells by the components used alone.

In some embodiments the combination of an oncolytic virus and an immune cell specific for the oncolytic virus may possess one or more of the following functional properties:
 improved ability to cause cell killing of cancer cells as compared to the ability to cause cell killing of cancer cells by either component used alone.

ability to cause cell killing of cancer cells which is synergistic (i.e. super-additive) as compared to the ability to cause cell killing of cancer cells the components used alone.

Analysis of the ability to cause cell killing of cancer cells may be assessed e.g. in vitro, by analysis of number/viability of cancer cells. Analysis of the ability to cause cell killing of cancer cells may also be analysed in vivo in an appropriate model, e.g. by analysis of number of cancer cells, tumor size/volume and/or some other correlate of the number of cancer cells (e.g. disease progression, severity of symptoms of the cancer etc.).

Therapeutic Applications

Aspects of the present disclosure are concerned in particular with the use of an oncolytic virus, a virus comprising nucleic acid encoding an immunomodulatory factor and at least one T cell comprising a chimeric antigen receptor (CAR) specific for a cancer cell antigen, in the treatment of a cancer in a subject.

Accordingly, the present disclosure provides a method of treating a cancer, comprising administering to a subject: an oncolytic virus; a virus comprising nucleic acid encoding an immunomodulatory factor; and at least one T cell comprising a chimeric antigen receptor (CAR) specific for a cancer cell antigen.

The present disclosure also provides an oncolytic virus; a virus comprising nucleic acid encoding an immunomodulatory factor; and at least one T cell comprising a chimeric antigen receptor (CAR) specific for a cancer cell antigen; for use in a method of treating a cancer. Also provided is the use of an oncolytic virus; a virus comprising nucleic acid encoding an immunomodulatory factor; and at least one T cell comprising a chimeric antigen receptor (CAR) specific for a cancer cell antigen; in the manufacture of a medicament for treating a cancer.

The present disclosure also provides a method of treating a cancer, comprising administering to a subject: (i) an oncolytic virus; and (ii) at least one cell comprising a chimeric antigen receptor (CAR) specific for a cancer cell antigen. Also provided is (i) an oncolytic virus; and (ii) at least one cell comprising a chimeric antigen receptor (CAR) specific for a cancer cell antigen for use in a method of treating a cancer. Also provided is the use of (i) an oncolytic virus; and (ii) at least one cell comprising a chimeric antigen receptor (CAR) specific for a cancer cell antigen in the manufacture of a medicament for use in a method of treating a cancer.

The present disclosure also provides a method of treating a cancer, comprising administering to a subject: (i) an oncolytic virus; and (ii) an immune cell specific for the oncolytic virus. Also provided is (i) an oncolytic virus; and (ii) an immune cell specific for the oncolytic virus for use in a method of treating a cancer. Also provided is the use of (i) an oncolytic virus; and (ii) an immune cell specific for the oncolytic virus in the manufacture of a medicament for use in a method of treating a cancer.

Also provided are methods for treating cancer comprising administering the OncAds, HDAds, CARs, nucleic acids/plurality of nucleic acids, cells and pharmaceutical compositions of the present disclosure to a subject. Also provided are the OncAds, HDAds, CARs, nucleic acids/plurality of nucleic acids, cells and pharmaceutical compositions of the present disclosure for use in methods for treating cancer. Also provided are the use of the OncAds, HDAds, CARs, nucleic acids/plurality of nucleic acids, cells and pharmaceutical compositions of the present disclosure in the manufacture of a medicament for treating cancer.

'Treatment' may, for example, be reduction in the development or progression of a cancer, alleviation of the symptoms of a cancer or reduction in the pathology of a cancer. Treatment or alleviation of a cancer may be effective to prevent progression of the cancer, e.g. to prevent worsening of the condition or to slow the rate of development of a more severe disease state. In some embodiments treatment or alleviation may lead to an improvement in the cancer, e.g. a reduction in the symptoms of the cancer or reduction in some other correlate of the severity/activity of the cancer. Prevention of a cancer may refer to prevention of a worsening of the condition or prevention of the development of the cancer, e.g. preventing an early stage cancer developing to a later stage.

In some embodiments, the treatment may be aimed at reducing the number of cells of the cancer or the amount of tissue comprising cancerous cells in the subject. In some embodiments, the treatment may be aimed at reducing the size of and/or preventing the growth of at least one tumor in the subject.

In some embodiments, the treatment comprises administering an oncolytic virus according to the present disclosure to the subject. In some embodiments, the treatment may comprise administering to a subject a cell or population of cells comprising or encoding an oncolytic virus according to the present disclosure. In some embodiments, the treatment comprises administering an oncolytic virus and a virus encoding an immunomodulatory factor according to the present disclosure to the subject. In some embodiments, the treatment may comprise administering to a subject a cell or population of cells comprising or encoding an oncolytic virus and/or virus encoding an immunomodulatory factor according to the present disclosure.

In some embodiments, the treatment may comprise modifying a cell or population of cells to comprise/express a CAR according to the present disclosure. In some embodiments, the treatment may comprise administering to a subject a cell or population of cells modified to comprise/express a CAR of the present disclosure. In some embodiments, the treatment is aimed at providing the subject with an immune cell or population of immune cells which having specificity for a cancer cell antigen, e.g. by administering a CAR-expressing cell according to the present disclosure, or generating a CAR-expressing cell according to the present disclosure.

In some embodiments, the treatment may comprise administering to a subject an immune cell/population of immune cells specific for an oncolytic virus according to the present disclosure. In some embodiments, the treatment is aimed at providing the subject with an immune cell/population of immune cells having specificity for an oncolytic virus. In some embodiments, the treatment may comprise generating/expanding a population of immune cells specific for an oncolytic virus according to the present disclosure.

In some embodiments, the treatment may comprise administering to a subject an immune cell/population of immune cells specific for an oncolytic virus according to the present disclosure, modified to comprise/express a CAR according to the present disclosure. In some embodiments, the treatment is aimed at providing the subject with an immune cell/population of immune cells having specificity for an oncolytic virus also having specificity for a cancer cell antigen. In some embodiments, the treatment may comprise generating/expanding a population of immune cells specific for an oncolytic virus according to the present disclosure, and modifying a cell or cells of the population to comprise/express a CAR according to the present disclosure.

The subject to be treated may be any animal or human. The subject is preferably mammalian, more preferably human. The subject may be a non-human mammal, but is more preferably human. The subject may be male or female or of any gender. The subject may be a patient. A subject may have been diagnosed with a cancer requiring treatment, may be suspected of having such a cancer, or may be at risk of developing such a cancer.

In some embodiments, the cancer to be treated comprises cells expressing a cancer cell antigen, e.g. a cancer cell antigen as described herein (e.g. HER2). In some embodiments, the cells express the cancer cell antigen (e.g. HER2) at the cell surface.

In some embodiments, the cancer to be treated comprises cells expressing a cancer cell antigen for which the CAR is specific. In some embodiments, the CAR comprises a cancer cell antigen binding domain, and the cancer to be treated comprises cells expressing the cancer cell antigen, e.g. cells expressing the cancer cell antigen at the cell surface.

In some embodiments, the cancer over-expresses the cancer cell antigen. Overexpression of a cancer cell antigen can be determined by detection of a level of expression of the cancer cell antigen which is greater than the level of expression by equivalent non-cancerous cells/non-tumor tissue.

In some embodiments the cancer is a cancer expressing HER2, e.g. a cancer expressing HER2 at the cell surface. In some embodiments, the cancer over-expresses HER2. Overexpression of HER2 can be determined by detection of a level of expression of HER2 which is greater than the level of expression of HER2 by equivalent non-cancerous cells/non-tumor tissue.

In some embodiments, the subject to be treated according to the present disclosure is selected for treatment on the basis detection of expression/overexpression of the cancer cell antigen by a cancer cell or tumour obtained from the subject.

Expression of a given cancer cell antigen may be determined by any suitable means. Expression may be gene expression or protein expression. Gene expression can be determined e.g. by detection of mRNA encoding the cancer cell antigen, for example by quantitative real-time PCR (qRT-PCR). Protein expression can be determined e.g. by detection of the cancer cell antigen, for example by antibody-based methods, for example by western blot, immunohistochemistry, immunocytochemistry, flow cytometry, or ELISA.

The cancer to be treated/prevented in accordance with the present disclosure may be any unwanted cell proliferation (or any disease manifesting itself by unwanted cell proliferation), neoplasm or tumor. The cancer may be benign or malignant and may be primary or secondary (metastatic). The cancer may be resistant (initially or following treatment) and/or the cancer may be recurring. A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

The cancer to be treated/prevented may be any kind of cancer, including any one of an acute lymphoblastic leukemia (ALL), acute myeloid leukemia (AML), adrenocortical carcinoma, AIDS-related cancer (e.g. Kaposi sarcoma, AIDS-related lymphoma, primary CNS lymphoma), anal cancer, appendix cancer, astrocytoma, basal cell carcinoma of the skin, bile duct cancer (e.g. cholangiocarcinoma), bladder cancer, bone cancer (e.g. Ewing sarcoma, osteosarcoma, malignant fibrous histiocytoma), brain tumor, breast cancer, bronchial tumor, Burkitt lymphoma, carcinoid tumor, carcinoma of unknown primary, cardiac tumor, central nervous system cancer (e.g. atypical teratoid/rhabdoid tumor, embryonal tumor, germ cell tumor, primary CNS lymphoma), cervical cancer, chordoma, chronic lymphocytic leukemia (CLL), chronic myelogenous leukemia (CML), chronic myeloproliferative neoplasm, colorectal cancer, craniopharyngioma, cutaneous T-cell lymphoma (e.g. mycosis fungoides, Sézary syndrome), ductal carcinoma in situ (DCIS), endometrial cancer (uterine cancer), ependymoma, esophageal cancer, esthesioneuroblastoma, extracranial germ cell tumor, extragonadal germ cell tumor, eye cancer (e.g. intraocular melanoma, retinoblastoma) fallopian tube cancer, malignant fibrous histiocytoma of bone, gallbladder cancer, gastric (stomach) cancer, gastrointestinal carcinoid tumor, gastrointestinal stromal tumor (GIST), ovarian germ cell tumor, testicular cancer, gestational trophoblastic disease, hairy cell leukemia, head and neck cancer, heart tumor, hepatocellular (liver) cancer, histiocytosis, Langerhans cell, Hodgkin lymphoma, hypopharyngeal cancer, islet cell tumor (pancreatic neuroendocrine tumor), kidney (renal cell) cancer, laryngeal cancer, papillomatosis, leukemia, lip and oral cavity cancer, lung cancer (non-small cell lung cancer (NSCLC) and small cell lung cancer (SCLC)) lymphoma, male breast cancer, melanoma, Merkel cell carcinoma, mesothelioma, metastatic cancer, metastatic squamous neck cancer with occult primary, midline tract carcinoma involving NUT gene, mouth cancer, multiple endocrine neoplasia syndromes, multiple myeloma/plasma cell neoplasms, mycosis fungoides, myelodysplastic syndrome, myelodysplastic/myeloproliferative neoplasm, myelogenous leukemia, chronic myeloid leukemia, acute myeloid leukemia (AML), nasal cavity and paranasal sinus cancer, nasopharyngeal cancer, neuroblastoma, non-Hodgkin lymphoma, oral cancer, lip and oral cavity cancer, oropharyngeal cancer, osteosarcoma, ovarian cancer, pancreatic cancer, papillomatosis, paraganglioma, paranasal sinus cancer, nasal cavity cancer, parathyroid cancer, penile cancer, pharyngeal cancer, pheochromocytoma, pituitary tumor, plasma cell neoplasm/multiple myeloma, pleuropulmonary blastoma, pregnancy and breast cancer, primary peritoneal cancer, prostate cancer, rectal cancer, recurrent cancer, retinoblastoma, rhabdomyosarcoma, salivary gland cancer, vascular tumor, uterine sarcoma, skin cancer, small intestine cancer, squamous cell carcinoma of the skin, T-cell lymphoma, throat cancer, thymoma, thymic carcinoma, thyroid cancer, transitional cell cancer of the renal pelvis and ureter, urethral cancer, vaginal cancer, vulvar cancer or Wilms tumor.

In some embodiments, the cancer to be treated is one or more of nasopharyngeal carcinoma (NPC; e.g. Epstein-Barr Virus (EBV)-positive NPC), cervical carcinoma (CC; e.g. human papillomavirus (HPV)-positive CC), oropharyngeal carcinoma (OPC; e.g. HPV-positive OPC), gastric carcinoma (GC; e.g. EBV-positive GC), hepatocellular carcinoma (HCC; e.g. Hepatitis B Virus (HBV)-positive HCC), lung cancer (e.g. non-small cell lung cancer (NSCLC)) and head and neck cancer (e.g. cancer originating from tissues of the lip, mouth, nose, sinuses, pharynx or larynx, e.g. head and neck squamous cell carcinoma (HNSCC)).

In some embodiments the cancer is associated with, or caused by, a virus. In some embodiments the cancer is an EBV-positive cancer. In some embodiments the cancer is an HPV-positive cancer.

In some embodiments, the cancer is one of a head and neck cancer, nasopharyngeal carcinoma (NPC), oropharyngeal cancer (OPC), cervical cancer (CC), gastric/stomach cancer, gastric carcinoma or lung cancer.

Methods of medical treatment may also involve in vivo, ex vivo, and adoptive immunotherapies, including those using autologous and/or heterologous cells or immortalized cell lines.

Administration

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the condition to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Viruses, CARs, nucleic acids, and cells according to the present disclosure may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion. Suitable formulations may comprise the viruses, CARs, nucleic acids, or cells in sterile or isotonic medium. Medicaments and pharmaceutical compositions may be formulated in fluid, including gel, form. Fluid formulations may be formulated for administration by injection or infusion (e.g. via catheter) to a selected region of the human or animal body.

The oncolytic virus and/or the virus comprising nucleic acid encoding an immunomodulatory factor may be formulated for intratumoral administration. In some embodiments, the methods may comprise intratumoral administration of the oncolytic virus and/or the virus comprising nucleic acid encoding an immunomodulatory factor.

The cell comprising a CAR and/or the immune cell specific for an oncolytic virus may be formulated for intravenous administration. In some embodiments, the methods may comprise intravenous administration of the cell comprising a CAR and/or the immune cell specific for an oncolytic virus.

Administration of the components of combinations of the present disclosure (e.g. oncolytic virus, virus comprising nucleic acid encoding an immunomodulatory factor; at least one T cell comprising a CAR specific for a cancer cell antigen; immune cell specific for an oncolytic virus in accordance with the present disclosure) may be simultaneous or sequential. The present disclosure also contemplates simultaneous or sequential administration of the OncAds, HDAds, CARs, nucleic acids/plurality of nucleic acids, cells and pharmaceutical compositions of the present disclosure.

Simultaneous administration refers to administration of the agents together, for example as a pharmaceutical composition containing the agents (i.e. a combined preparation), or immediately after each other and optionally via the same route of administration, e.g. to the same artery, vein or other blood vessel. In particular embodiments, the oncolytic virus and virus comprising nucleic acid encoding an immunomodulatory factor may be administered simultaneously in a combined preparation. In certain embodiments upon simultaneous administration the two or more of the agents may be administered via different routes of administration. In some embodiments simultaneous administration refers to administration at the same time, or within e.g. 1 hr, 2 hrs, 3 hrs, 4 hrs, 5 hrs, 6 hrs, 8 hrs, 12 hrs, 24 hrs, 36 hrs or 48 hrs.

Sequential administration refers to administration of one or more of the agents followed after a given time interval by separate administration of another of the agents. It is not required that the two agents are administered by the same route, although this is the case in some embodiments.

The time interval may be any time interval, including hours, days, weeks, months, or years. In some embodiments sequential administration refers to administrations separated by a time interval of one of at least 10 min, 30 min, 1 hr, 6 hrs, 8 hrs, 12 hrs, 24 hrs, 36 hrs, 48 hrs, 3 days, 4 days, 5 days, 6 days, 1 week, 2 weeks, 3 weeks, 1 month, 6 weeks, 2 months, 3 months, 4 months, 5 months or 6 months.

In some embodiments, the treatment may further comprise other therapeutic or prophylactic intervention, e.g. chemotherapy, immunotherapy, radiotherapy, surgery, vaccination and/or hormone therapy. Such other therapeutic or prophylactic intervention may occur before, during and/or after the therapies encompassed by the disclosure, and the deliveries of the other therapeutic or prophylactic interventions may occur via different administration routes as the therapies of the disclosure. Chemotherapy and radiotherapy respectively refer to treatment of a cancer with a drug or with ionising radiation (e.g. radiotherapy using X-rays or γ-rays). The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a predetermined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs and biologics may be selected from: alkylating agents such as cisplatin, carboplatin, mechlorethamine, cyclophosphamide, chlorambucil, ifosfamide; purine or pyrimidine anti-metabolites such as azathiopurine or mercaptopurine; alkaloids and terpenoids, such as *vinca* alkaloids (e.g. vincristine, vinblastine, vinorelbine, vindesine), podophyllotoxin, etoposide, teniposide, taxanes such as paclitaxel (Taxol™), docetaxel; topoisomerase inhibitors such as the type I topoisomerase inhibitors camptothecins irinotecan and topotecan, or the type II topoisomerase inhibitors amsacrine, etoposide, etoposide phosphate, teniposide; antitumor antibiotics (e.g. anthracyline antibiotics) such as dactinomycin, doxorubicin (Adriamycin™), epirubicin, bleomycin, rapamycin; antibody based agents, such as anti-PD-1 antibodies, anti-PD-L1 antibodies, anti-TIM-3 antibodies, anti-CTLA-4, anti-4-1 BB, anti-GITR, anti-CD27, anti-BLTA, anti-OX43, anti-VEGF, anti-TNFα, anti-IL-2, antiGpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab; EGFR inihibitors such as erlotinib, cetuximab and gefitinib; anti-angiogenic agents such as bevacizumab (Avastin®); cancer vaccines such as Sipuleucel-T (Provenge®).

Further chemotherapeutic drugs may be selected from: 13-cis-Retinoic Acid, 2-Chlorodeoxyadenosine, 5-Azacitidine 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Deni leukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleevec™, Gliadel® Wafer, Goserelin, Granulocyte—Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin -2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

In embodiments of the present disclosure wherein a nucleic acid/virus encoding an enzyme capable of catalysing conversion of a non-toxic factor to a cytotoxic form is employed, the method may further comprise administration with a prodrug substrate for the enzyme. The prodrug may be administered simultaneously or sequentially to administration of the nucleic acid/virus encoding an enzyme capable of catalysing conversion of a non-toxic factor to a cytotoxic form.

In some embodiments the prodrug is selected from ganciclovir (GCV), aciclovir (ACV) and/or valaciclovir, e.g. where the nucleic acid/virus encodes a thymidine kinase. In some embodiments the prodrug is 5-fluorocytosine (5-FC), e.g. where the nucleic acid/virus encodes a cytosine deaminase. In some embodiments the prodrug is selected from CB1954, nitro-CBI-DEI and/or PR-104A, e.g. where the nucleic acid/virus encodes a nitroreductase. In some embodiments the prodrug is oxazaphosphorine (e.g. cyclophosphamide or ifosfamide), e.g. where the nucleic acid/virus encodes a cytochrome P450. In some embodiments the prodrug is a nitrogen mustard based drug (e.g. CMDA or ZD2767P), e.g. where the nucleic acid/virus encodes a carboxypeptidase G2. In some embodiments the prodrug is 6-methylpurine 2-deoxyriboside and/or fludarabine (e.g. 6-methylpurine-2'-deoxyriboside (MeP-dR), 2-F-2'-deoxyadenosine (F-dAdo) or arabinofuranosyl-2-F-adenine monophosphate (F-araAMP), e.g. where the nucleic acid/virus encodes a purine nucleoside phosphorylase. In some embodiments the prodrug is indole-3-acetic acid (IAA), e.g. where the nucleic acid/virus encodes a horseradish peroxidase. In some embodiments the prodrug is irinotecan, e.g. where the nucleic acid/virus encodes a carboxylesterase.

Multiple doses of the agents (e.g. viruses (OncAds, HdAds), CARs, nucleic acids/plurality of nucleic acids, vectors, cells, compositions, combinations, prodrugs) of the present disclosure may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, or more hours or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Adoptive Transfer

In embodiments of the present disclosure, the methods of treatment comprise adoptive transfer of immune cells. Adoptive cell transfer (ACT) generally refers to a process by which cells (e.g. immune cells) are obtained from a subject, typically by drawing a blood sample from which the cells are isolated. The cells are then typically treated or altered in some way, and then administered either to the same subject (adoptive transfer is of autologous cells) or to a different subject (adoptive transfer is of allogeneic cells). The treatment is typically aimed at providing population of cells with certain desired characteristics to a subject, or increasing the frequency of cells with such characteristics in that subject. In the present disclosure, adoptive transfer may be performed with the aim of introducing a cell or population of cells into a subject, and/or increasing the frequency of a cell or population of cells in a subject.

In some embodiments, the subject from which the cell is isolated is the subject administered with the modified cell (i.e., adoptive transfer is of autologous cells). In some embodiments, the subject from which the cell is isolated is a different subject to the subject to which the modified cell is administered (i.e., adoptive transfer is of allogeneic cells).

Adoptive transfer of T cells is described, for example, in Kalos and June 2013, Immunity 39(1): 49-60, which is hereby incorporated by reference in its entirety. Adoptive transfer of NK cells is described, for example, in Davis et al. 2015, Cancer J. 21(6): 486-491, which is hereby incorporated by reference in its entirety.

The cell may e.g. be a neutrophil, eosinophil, basophil, dendritic cell, lymphocyte, or monocyte. The lymphocyte may be e.g. a T cell, B cell, NK cell, NKT cell or innate lymphoid cell (ILC), or a precursor thereof. In some embodiments, the cell is a T cell. In some embodiments, the T cell is a CD3+ T cell. In some embodiments, the T cell is a CD3+, CD4+ T cell. In some embodiments, the T cell is a CD3+, CD8+ T cell. In some embodiments, the T cell is a T helper cell ($T_H$ cell)). In some embodiments, the T cell is a cytotoxic T cell (e.g. a cytotoxic T lymphocyte (CTL)). In some embodiments, the T cell is a virus-specific T cell. In some embodiments, the T cell is specific for EBV, HPV, HBV, HCV or sHIV.

In some embodiments the cell is an immune cell specific for an oncolytic virus, as described herein. Accordingly, in some embodiments the methods comprise administration of at least one immune cell specific for an oncolytic virus to a subject. In some embodiments, the methods of the disclosure comprise generating/expanding a population of immune cells specific for an oncolytic virus, and administering at least one immune cell specific for the oncolytic virus to a subject.

In some embodiments, the methods comprise:
(a) isolating immune cells from a subject;
(b) generating or expanding a population of immune cells specific for an oncolytic virus by a method comprising: stimulating the immune cells by culture in the presence of antigen presenting cells (APCs) presenting a peptide of the oncolytic virus, and;
(c) administering at least one immune cell specific for the oncolytic virus to a subject.

In some embodiments the method steps for production of an immune cell specific for an oncolytic virus may comprise one or more of: taking a blood sample from a subject; isolating PBMCs from the blood sample; generating/expanding a population of immune cells specific for an oncolytic virus (e.g. by culturing PBMCs in the presence of cells (e.g. APCs) comprising/expressing antigen(s)/peptide(s) of the oncolytic virus); culturing immune cells specific for an oncolytic virus in in vitro or ex vivo cell culture; collecting immune cells specific for an oncolytic virus; mixing immune cells specific for an oncolytic virus with an adjuvant, diluent, or carrier; administering the modified cell to a subject.

The present disclosure also provides methods of treating a cancer in a subject comprising administering at least one cell comprising a chimeric antigen receptor (CAR) specific for a cancer cell antigen. In connection with this feature of the disclosure, in some embodiments, the method additionally comprises steps for production of the at least one cell comprising a chimeric antigen receptor (CAR) specific for a cancer cell antigen. The CAR may be a first generation, second generation or third or subsequent generation CAR. The CAR may comprise one, two, three, or more costimulatory domains, for example.

In some embodiments, the methods comprise modifying at least one cell obtained from a subject to express or comprise a CAR according to the disclosure, optionally expanding the modified at least one cell, and administering the modified at least one cell to a subject.

In some embodiments, the methods comprise:
(a) isolating at least one cell from a subject;
(b) modifying the at least one cell to express or comprise a CAR according to the present disclosure, or a nucleic acid encoding a CAR according to the present disclosure,
(c) optionally expanding the modified at least one cell, and;
(d) administering the modified at least one cell to a subject.

In some embodiments the cell comprising/expressing a CAR specific for a cancer cell antigen is an immune cell specific for an oncolytic virus, as described herein. In some embodiments, the methods comprise modifying an immune cell specific for an oncolytic virus to express or comprise a CAR according to the disclosure, optionally expanding the modified immune cell specific for an oncolytic virus, and administering the modified immune cell specific for an oncolytic virus to a subject.

In some embodiments, the methods comprise:
(a) isolating immune cells from a subject;
(b) generating or expanding a population of immune cells specific for an oncolytic virus by a method comprising: stimulating the immune cells by culture in the presence of antigen presenting cells (APCs) presenting a peptide of the oncolytic virus;
(c) modifying at least one immune cell specific for an oncolytic virus to express or comprise a CAR according to the present disclosure, or a nucleic acid encoding a CAR according to the present disclosure,
(d) optionally expanding the modified at least one immune cell specific for an oncolytic virus, and;
(e) administering the modified at least one immune cell specific for an oncolytic virus to a subject.

The at least one cell modified according to the present disclosure can be modified to comprise/express a CAR according to methods well known to the skilled person. The modification may comprise nucleic acid transfer for permanent or transient expression of the transferred nucleic acid. Any suitable genetic engineering platform may be used to modify a cell according to the present disclosure. Suitable methods for modifying a cell include the use of genetic engineering platforms such as gammaretroviral vectors, lentiviral vectors, adenovirus vectors, DNA transfection, transposon-based gene delivery and RNA transfection, for example as described in Maus et al., Annu Rev Immunol (2014) 32:189-225, incorporated by reference hereinabove.

In some embodiments the method steps for production of the at least one cell comprising a chimeric antigen receptor (CAR) specific for a cancer cell antigen may comprise one or more of: taking a blood sample from a subject; isolating and/or expanding at least one cell from the blood sample; culturing the at least one cell in in vitro or ex vivo cell culture; introducing into the at least one cell a CAR as described herein, or a nucleic acid encoding a CAR as described herein, thereby modifying the at least one cell; expanding the at least one modified cell; collecting the at least one modified cell; mixing the modified cell with an adjuvant, diluent, or carrier; administering the modified cell to a subject.

In some embodiments, the methods may additionally comprise treating the cell to induce/enhance expression of the CAR or nucleic acid encoding the CAR. For example, the nucleic acid may comprise a control element for inducible upregulation of expression of the CAR from the nucleic acid in response to treatment with a particular agent. In some embodiments, treatment may be in vivo by administration of the agent to a subject having been administered with a modified cell according to the disclosure. In some embodiments, treatment may be ex vivo or in vitro by administration of the agent to cells in culture ex vivo or in vitro.

The skilled person is able to determine appropriate reagents and procedures for adoptive transfer of cells according to the present disclosure, for example by reference to Dai et al., 2016 J Nat Cancer Inst 108(7): djv439, which is incorporated by reference in its entirety.

In a related aspect, the present disclosure provides a method of preparing a modified cell, the method comprising introducing into a cell a CAR according to the present disclosure or a nucleic acid encoding a CAR according to the present disclosure, thereby modifying the at least one cell. The method is preferably performed in vitro or ex vivo.

Compositions/Products/Kits

The present disclosure also provides an oncolytic virus as described herein, optionally isolated. Also provided is a nucleic acid encoding the oncolytic virus, optionally isolated. Also provided is a cell comprising the oncolytic virus, or comprising nucleic acid encoding the oncolytic virus, optionally isolated.

The present disclosure also provides a virus comprising nucleic acid encoding an immunomodulatory factor as described herein, optionally isolated. Also provided is a nucleic acid encoding the virus, optionally isolated. Also provided is a cell comprising the virus, or comprising nucleic acid encoding the virus, optionally isolated.

The present disclosure also provides a chimeric antigen receptor (CAR) as described herein, optionally isolated. Also provided is a nucleic acid encoding the CAR, optionally isolated. Also provided is a cell comprising the CAR, or comprising nucleic acid encoding the CAR, optionally isolated.

The present disclosure also provides compositions comprising an oncolytic virus, a virus comprising nucleic acid encoding an immunomodulatory factor, a chimeric antigen receptor, a nucleic acid/plurality of nucleic acids, or a cell according to the disclosure.

The oncolytic virus, virus comprising nucleic acid encoding an immunomodulatory factor, chimeric antigen receptor, nucleic acid/plurality of nucleic acids or cell according to the present disclosure may be formulated as pharmaceutical compositions for clinical use and may comprise a pharmaceutically acceptable carrier, diluent, excipient or adjuvant. Combinations of the present disclosure may be provided in a single composition, or may be provided as plural compositions comprising the components of the combination.

In accordance with the present disclosure methods are also provided for the production of pharmaceutically useful compositions, such methods of production may comprise one or more steps selected from: isolating an oncolytic virus, a virus comprising nucleic acid encoding an immunomodulatory factor, a chimeric antigen receptor, a nucleic acid/plurality of nucleic acids, or a cell as described herein; and/or mixing an oncolytic virus, a virus comprising nucleic acid encoding an immunomodulatory factor, a chimeric antigen receptor, a nucleic acid/plurality of nucleic acids, or a cell as described herein with a pharmaceutically acceptable carrier, adjuvant, excipient or diluent.

For example, a further aspect of the present disclosure relates to a method of formulating or producing a medicament or pharmaceutical composition for use in the treatment of a cancer, the method comprising formulating a pharmaceutical composition or medicament by mixing an oncolytic virus, a virus comprising nucleic acid encoding an immunomodulatory factor, a chimeric antigen receptor, a nucleic acid/plurality of nucleic acids, or a cell as described herein with a pharmaceutically acceptable carrier, adjuvant, excipient or diluent.

The present disclosure also provides a kit of parts comprising one or more of an oncolytic virus, a virus comprising nucleic acid encoding an immunomodulatory factor, a chimeric antigen receptor, a nucleic acid, a cell or a composition according to the present disclosure.

In some embodiments the kit may have at least one container having a predetermined quantity of an oncolytic virus, a virus comprising nucleic acid encoding an immunomodulatory factor, a chimeric antigen receptor, a nucleic acid/plurality of nucleic acids, or a cell according to the disclosure or a composition according to the present disclosure. The kit may have containers containing individual components of the combinations of the present disclosure, or may have containers containing combinations of the components of the combinations of the present disclosure.

The kit may provide the oncolytic virus, virus comprising nucleic acid encoding immunomodulatory factor, CAR, nucleic acid, cell or composition with instructions for administration to a patient in order to treat a specified cancer. The oncolytic virus, virus comprising nucleic acid encoding immunomodulatory factor, CAR, nucleic acid/plurality of nucleic acids, cell or composition may be formulated so as to be suitable for injection or infusion to a tumor or to the blood.

In some embodiments the kit may comprise materials for producing a cell according to the present disclosure. For example, the kit may comprise materials for modifying a cell to express or comprise a virus or an antigen/peptide thereof, CAR or nucleic acid/plurality of nucleic acids according to the present disclosure, or materials for introducing into a cell the virus or an antigen/peptide thereof or nucleic acid/plurality of nucleic acids according to the present disclosure. The kit may comprise materials for producing an immune cell specific for an oncolytic virus; for example, the kit may comprise pepmixes of one or more antigens of the oncolytic virus.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the cancer. The therapeutic agent may also be formulated so as to be suitable for injection or infusion to a tumor or to the blood.

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Soding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | HER2(C5)-CD28TM, ICD-CD3Z CAR | MTRAMDWIWRILFLVGAATGAHSQVQLQESGPGLVKPSETLSLTCTVSGGSIS SSSYYWGWIRQPPGKGLEWIGSIYYSGSTYYNPSLKSRVTISVDTSKNQFSLKL SSVTAADTAVYYCARYAPDSSGYLVAFDIWGQGTMVTVSSGGGGSGGGGSG GGGGSQTVVTQEPSFSVSPGGTVTLTCGLSSGSVSTGYYPSWYQQTPGQAPR TLIYSTNSRSSGVPDRFSGSILGNKAALTITGAQADDESDYYCVLYMGSGISVF GGGTKLTVLGSEPKSCDKTHTCPTRFWVLVVVGGVLACYSLLVTVAFIIFWVRS KRSRLLHSDYMNMTPRRPGPTRKHYQPYAPPRDFAAYRSRVKFSRSADAPAY QQGQNQLYNELNLGRREEYDVLDKRRGRDPEMGGKPQRRKNPQEGLYNEL QKDKMAEAYSEIGMKGERRRGKGHDGLYQGLSTATKDTYDALHMQALPPR |
| 2 | HER2(E4)-CD28TM, ICD-CD3Z CAR | MTRAMDWIWRILFLVGAATGAHSQVQLQQWGAGLLKPSETLSLTCAVYGGSF SGYYWSWIRQPPGKGLEWIGEINHSGSTNYNPSLKSRVTISVDTSKNQFSLKL SSVTTADTAVYYCARMGINSGGYLYGMDVWGQGTTVTVSSGGGGSGGGGS GGGGSQTVVTQEPSFSVSPGGTVTLTCGLSSGSVSTSYYPSWYQQIPGQAPR TLIYTTNIRSSGVPDRFGGSILGNKAALTITGAQAEDESDYYCMLYMGSGIWVF GGGTKLTVLGSEPKSCDKTHTCPTRFWVLVVVGGVLACYSLLVTVAFIIFWVRS KRSRLLHSDYMNMTPRRPGPTRKHYQPYAPPRDFAAYRSRVKFSRSADAPAY QQGQNQLYNELNLGRREEYDVLDKRRGRDPEMGGKPQRRKNPQEGLYNEL QKDKMAEAYSEIGMKGERRRGKGHDGLYQGLSTATKDTYDALHMQALPPR |
| 3 | HER2(F1)-CD28TM, ICD-CD3Z CAR | MTRAMDWIWRILFLVGAATGAHSQVQLVESGPGLVKPSGTLSLTCAVSGGSIS SSNWWSWVRQPPGKGLEWIGEIYHSGSTNYNPSLKSRVTISVDTSKNQFSLKL SSVTAADTAVYYCARMGANSGGYLYGMDVWGQGTTVTVSSGGGGSGGGGS GGGGSQTVVTQEPSFSVSPGGTVTLTCGLSSGSVSTSYYPSWYQQTPGQAP RTLIYSTNTRSSGVPDRFSGSILGNKAALTITGAQADDESDYYCVLYMGSGIWV FGGGTKLTVLGSEPKSCDKTHTCPTRFWVLVVVGGVLACYSLLVTVAFIIFWVR SKRSRLLHSDYMNMTPRRPGPTRKHYQPYAPPRDFAAYRSRVKFSRSADAPA YQQGQNQLYNELNLGRREEYDVLDKRRGRDPEMGGKPQRRKNPQEGLYNEL QKDKMAEAYSEIGMKGERRRGKGHDGLYQGLSTATKDTYDALHMQALPPR |
| 4 | CD28 TMD | FWVLVVVGGVLACYSLLVTVAFIIFWV |
| 5 | CD28 ICD | RSKRSRLLHSDYMNMTPRRPGPTRKHYQPYAPPRDFAAYRS |
| 6 | CD3Z ICD | RVKFSRSADAPAYQQGQNQLYNELNLGRREEYDVLDKRRGRDPEMGGKPQR RKNPQEGLYNELQKDKMAEAYSEIGMKGERRRGKGHDGLYQGLSTATKDTYD ALHMQALPPR |
| 7 | (G4S)3 linker | GGGGSGGGGSGGGGS |
| 8 | huIgGH leader | MDWIWRILFLVGAATGAHS |
| 9 | Hinge | EPKSCDKTHTCPTR |

| SEQ ID NO: | DESCRIPTION | SEQUENCE |
|---|---|---|
| 10 | HER2(C5) LC-CDR1 | GLSSGSVSTGYYPS |
| 11 | HER2(C5) LC-CDR2 | STNSRSS |
| 12 | HER2(C5) LC-CDR3 | VLYMGSGISV |
| 13 | HER2(C5) HC-CDR1 | SSSYYWG |
| 14 | HER2(C5) HC-CDR2 | SIYYSGSTYYNPSLKS |
| 15 | HER2(C5) HC-CDR3 | YAPDSSGYLVAFDI |
| 16 | HER2(C5) VL | QTVVTQEPSFSVSPGGTVTLTCGLSSGSVSTGYYPSWYQQTPGQAPRTLIYSTNSRSSGVPDRFSGSILGNKAALTITGAQADDESDYYCVLYMGSGISVFGGGTKLTVLGS |
| 17 | HER2(C5) VH | QVQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCARYAPDSSGYLVAFDIWGQGTMVTVSS |
| 18 | HER2(E4) LC-CDR1 | GLSSGSVSTSYYPS |
| 19 | HER2(E4) LC-CDR2 | TTNIRSS |
| 20 | HER2(E4) LC-CDR3 | MLYMGSGIWV |
| 21 | HER2(E4) HC-CDR1 | SGYYWS |
| 22 | HER2(E4) HC-CDR2 | EINHSGSTNYNPSLKS |
| 23 | HER2(E4) HC-CDR3 | MGINSGGYLYGMDV |
| 24 | HER2(E4) VL | QTVVTQEPSFSVSPGGTVTLTCGLSSGSVSTSYYPSWYQQIPGQAPRTLIYTTNIRSSGVPDRFGGSILGNKAALTITGAQAEDESDYYCMLYMGSGIWVFGGGTKLTVLGS |
| 25 | HER2(E4) VH | QVQLQQWGAGLLKPSETLSLTCAVYGGSFSGYYWSWIRQPPGKGLEWIGEINHSGSTNYNPSLKSRVTISVDTSKNQFSLKLSSVTTADTAVYYCARMGINSGGYLYGMDVWGQGTTVTVSS |
| 26 | HER2(F1) LC-CDR1 | GLSSGSVSTSYYPS |
| 27 | HER2(F1) LC-CDR2 | STNTRSS |
| 28 | HER2(F1) LC-CDR3 | VLYMGSGIWV |
| 29 | HER2(F1) HC-CDR1 | SSNWWS |
| 30 | HER2(F1) HC-CDR2 | EIYHSGSTNYNPSLKS |
| 31 | HER2(F1) HC-CDR3 | MGANSGGYLYGMDV |
| 32 | HER2(F1) VL | QTVVTQEPSFSVSPGGTVTLTCGLSSGSVSTSYYPSWYQQTPGQAPRTLIYSTNTRSSGVPDRFSGSILGNKAALTITGAQADDESDYYCVLYMGSGIWVFGGGTKLTVLGS |

-continued

| SEQ ID NO: | DESCRIPTION | SEQUENCE |
|---|---|---|
| 33 | HER2(F1) VH | QVQLVESGPGLVKPSGTLSLTCAVSGGSISSSNWWSWVRQPPGKGLEWIGEI YHSGSTNYNPSLKSRVTISVDTSKNQFSLKLSSVTAADTAVYYCARMGANSGG YLYGMDVWGQGTTVTVSS |
| 34 | Ad2 E1AΔ24 | MRHIICHGGVITEEMAASLLDQLIEEVLADNLPPPSHFEPPTLHELYDLDVTAPE DPNEEAVSQIFPESVMLAVQEGIDLFTFPPAPGSPEPPHLSRQPEQPEQRALG PVSMPNLVPEVIDPPSDDEDEEGEEFVLDYVEHPGHGCRSCHYHRRNTGDPD IMCSLCYMRTCGMFVYSPVSEPEPEPEPEPEPEPARPTRRPKLVPAILRRPTSPV SRECNSSTDSCDSGPSNTPPEIHPVVPLCPIKPVAVRVGGRRQAVECIEDLLNE SGQPLDLSCKRPRP |
| 35 | huIL-12p70 | MGHQQLVISWFSLVFLASPLVAIWELKKDVYVVELDWYPDAPGEMVVLTCDTP EEDGITWTLDQSSEVLGSGKTLTIQVKEFGDAGQYTCHKGGEVLSHSLLLLHK KEDGIWSTDILKDQKEPKNKTFLRCEAKNYSGRFTCWWLTTISTDLTFSVKSSR GSSDPQGVTCGAATLSAERVRGDNKEYEYSVECQEDSACPAAEESLPIEVMV DAVHKLKYENYTSSFFIRDIIKPDDPPKNLQLKPLKNSRQVEVSWEYPDTWSTPH SYFSLTFCVQVQGKSKREKKDRVFTDKTSATVICRKNASISVRAQDRYYSSSW SEWASVPCSVPGVGVPGVGARNLPVATPDPGMFPCLHHSQNLLRAVSNMLQ KARQTLEFYPCTSEEIDHEDITKDKTSTVEACLPLELTKNESCLNSRETSFITNG SCLASRKTSFMMALCLSSIYEDLKMYQVEFKTMNAKLLMDPKRQIFLDQNMLA VIDELMQALNFNSETVPQKSSLEEPDFYKTKIKLCILLHAFRIRAVTIDRVMSYLN AS |
| 36 | HSV1 TK | MASYPGHQHASAFDQAARSRGHSNRRTALRPRRQQEATEVRPEQKMPTLLR VYIDGPHGMGKTTTTQLLVALGSRDDIVYVPEPMTYWRVLGASETIANIYTTQH RLDQGEISAGDAAVVMTSAQITMGMPYAVTDAVLAPHIGGEAGSSHAPPPALT LIFDRHPIAALLCYPAARYLMGSMTPQAVLAFVALIPPTLPGTNIVLGALPEDRHI DRLAKRQRPGERLDLAMLAAIRRVYGLLANTVRYLQGGGSWREDWGQLSGT AVPPQGAEPQSNAGPRPHIGDTLFTLFRAPELLAPNGDLYNVFAWALDVLAKR LRPMHVFILDYDQSPAGCRDALLQLTSGMIQTHVTTPGSIPTICDLARTFAREM GEAN |
| 37 | HA tag | YPYDVPDYA |
| 38 | PD-L1(H12_g1) minibody | MDWIWRILFLVGAATGAHSEVQLVQSGAEVKKPGASVKVSCKASGGTFSSYAI SWVRQAPGQGLEWMGRIIPILGIANYAQKFQGRVTITADKSTSTAYMELSSLRS EDTAVYYCARSGHGYSYGAFDYWGQGTLVTVSSGGGGSGGGGSGGGGSQS VLTQPPSVSGAPGQRVTISCTGSSSNIGAGYDVHWYQQLPGTAPKLLIYGNSN RPSGVPDRFSGSKSGTSASLAITGLQAEDEADYYCQSYDSSLSGSYVVFGGG TKLTVLEAKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGN VFSCSVMHEALHNHYTQKSLSLSPGKGGGGSYPYDVPDYAGYPYDVPDYAG YPYDVPDYA |
| 39 | PD-L1(H12_g1) LC-CDR1 | TGSSSNIGAGYDVH |
| 40 | PD-L1(H12_g1) LC-CDR2 | GNSNRPS |
| 41 | PD-L1(H12_g1) LC-CDR3 | QSYDSSLSGSYVV |
| 42 | PD-L1(H12_g1) HC-CDR1 | SYAIS |
| 43 | PD-L1(H12_g1) HC-CDR2 | RIIPILGIANYAQKFQG |
| 44 | PD-L1(H12_g1) HC-CDR3 | SGHGYSYGAFDY |
| 45 | PD-L1(H12_g1) VL | QSVLTQPPSVSGAPGQRVTISCTGSSSNIGAGYDVHWYQQLPGTAPKLLIYGN SNRPSGVPDRFSGSKSGTSASLAITGLQAEDEADYYCQSYDSSLSGSYVVFG GGTKLTVL |
| 46 | PD-L1(H12_g1) VH | EVQLVQSGAEVKKPGASVKVSCKASGGTFSSYAISWVRQAPGQGLEWMGRII PILGIANYAQKFQGRVTITADKSTSTAYMELSSLRSEDTAVYYCARSGHGYSYG AFDYWGQGTLVTVSS |

| SEQ ID NO: | DESCRIPTION | SEQUENCE |
|---|---|---|
| 47 | HER2(C5)-CD28TM, ICD-CD3Z CAR | AAGTTCAGATCAAGGTCAGGAACAGATGGAACAGCTGAATATGGGCCAAAC AGGATATCTGTGGTAAGCAGTTCCTGCCCCGGCTCAGGGCCAAGAACAGA TGGAACAGCTGAATATGGGCCAAACAGGATATCTGTGGTAAGCAGTTCCTG CCCCGGCTCAGGGCCAAGAACAGATGGTCCCCAGATGCGGTCCAGCCCTC AGCAGTTTCTAGAGAACCATCAGATGTTTCCAGGGTGCCCCAAGGACCTGA AATGACCCTGTGCCTTATTTGAACTAACCAATCAGTTCGCTTCTCGCTTCTG TTCGCGCGCTTCTGCTCCCCGAGCTCAATAAAAGAGCCCACAACCCCTCAC TCGGCGCGCCAGTCCTCCGATTGACTGAGTCGCCCGGGTACCCGTGTATC CAATAAACCCTCTTGCAGTTGCATCCGACTTGTGGTCTCGCTGTTCCTTGG GAGGGTCTCCTCTGAGTGATTGACTACCCGTCAGCGGGGGTCTTTCATTTG GGGGCTCGTCCGGGATCGGGAGACCCCTGCCCAGGGACCACCGACCCAC CACCGGGAGGTAAGCTGGCCAGCAACTTATCTGTGTCTGTCCGATTGTCTA GTGTCTATGACTGATTTTATGCGCCTGCGTCGGTACTAGTTAGCTAACTAGC TCTGTATCTGGCGGACCCGTGGTGGAACTGACGAGTTCGGAACACCCGGC CGCAACCCTGGGAGACGTCCCAGGGACTTCGGGGCCGTTTTTGTGGCCC GACCTGAGTCCTAAAATCCCGATCGTTTAGGACTCTTTGGTGCACCCCCCT TAGAGGAGGGATATGTGGTTCTGGTAGGAGACGAGAACCTAAAACAGTTCC CGCCTCCGTCTGAATTTTTGCTTTCGGTTTGGGACCGAAGCCGCGCCGCG CGTCTTGTCTGCTGCAGCATCGTTCTGTGTTGTCTCGTCTGACTGTGTTTC TGTATTTGTCTGAAAATATGGGCCCGGGCTAGCCTGTTACCACTCCCTTAA GTTTGACCTTAGGTCACTGGAAAGATGTCGAGCGGATCGCTCACAACCAGT CGGTAGATGTCAAGAAGAGACGTTGGGTTACCTTCTGCTCTGCAGAATGGC CAACCTTTAACGTCGGATGGCCGCGAGACGGCACCTTTAACCGAGACCTC ATCACCCAGGTTAAGATCAAGGTCTTTTCACCTGGCCCGCATGGACACCCA GACCAGGTCCCCTACATCGTGACCTGGGAAGCCTTGGCTTTTGACCCCCCT CCCTGGGTCAAGCCCTTTGTACACCCTAAGCCTCCGCCTCCTCTTCCTCCA TCCGCCCCGTCTCTCCCCCTTGAACCTCCTCGTTCGACCCCGCCTCGATCC TCCCTTTATCCAGCCCTCACTCCTTCTCTAGGCGCCCCCATATGGCCATAT GAGATCTTATATGGGCACCCCCGCCCCTTGTAAACTTCCCTGACCCTGAC ATGACAAGAGTTACTAACAGCCCCTCTCTCCAAGCTCACTTACAGGCTCTCT ACTTAGTCCAGCACGAAGTCTGGAGACCTCTGGCGGCAGCCTACCAAGAA CAACTGGACCGACCGGTGGTACCTCACCCTTACCGAGTCGGCGACACAGT GTGGGTCCGCCGACACCAGACTAAGAACCTAGAACCTCGCTGGAAAGGAC CTTACACAGTCCTGCTGACCACCCCCACCGCCCTCAAAGTAGACGGCATC GCAGCTTGGATACACGCCGCCCACGTGAAGGCTGCCGACCCCGGGGGTG GACCATGACTCGAGCCATGGATTGGATCTGGCGCATCCTGTTTCTCGTGGG AGCTGCCAGGCGCCCATTCTCAGGTTCAGCTGCAAGAGTCTGGCCCTG GCCTGGTCAAGCCTAGCGAAACACTGAGCCTGACCTGTACCGTGTCTGGC GGCAGCATCAGCAGCAGCTCTTACTACTGGGGCTGGATCAGACAGCCTCC TGGCAAAGGCCTGGAATGGATCGGCTCCATCTACTACAGCGGCAGCACCT ACTACAACCCCAGCCTGAAGTCCAGAGTGACCATCAGCGTGGACACCAGC AAGAACCAGTTCTCCCTGAAGCTGAGCAGCGTGACAGCCGCCGATACAGC CGTGTACTACTGTGCCAGATACGCCCCTGATAGCAGCGGCTACTGGTGG CCTTTTGATATCTGGGGCCAGGGCACAATGGTCACCGTTTCTAGCGGAGGC GGAGGTTCTGGTGGCGGAGGAAGTGGCGGCGGAGGATCTCAGACAGTGG TCACACAAGAGCCCAGCTTCTCCGTGTCTCCTGGCGGAACAGTGACCCTG ACATGTGGCCTTAGCTCTGGCTCTGTGTCCACCGGCTACTACCCCAGCTGG TATCAGCAGACACCTGGACAGGCCCCTCGGACACTGATCTACAGCACCAA CAGCAGATCCAGCGGCGTGCCCGATAGATTCAGCGGCTCTATCCTGGGCA ACAAGGCCGCACTGACAATCACAGGCGCTCAGGCCGATGACGAGAGCGAC TACTACTGCGTGCTGTACATGGGCAGCGGCATCTCCGTTTTTGGCGGAGG CACAAAGCTGACCGTGCTGGGATCCGAACCAAAGAGTTGCGACAAAACAC ACACCTGCCCTACGCGTTTTTGGGTGCTCGTGGTGGTGGGTGGCGTGCTC GCTTGCTACTCACTTCTGGTGACCGTAGCGTTTATCATTTTTTGGGTCAGGA GCAAGCGATCCCGCCTATTGCACAGCGACTACATGAACATGACCCCCCGG CGCCCCGGGCCAACCCGGAAGCACTACCAGCCATATGCGCCTCCCCGCG ATTTCGCAGCGTATCGGTCCCGGGTCAAATTTTCACGGTCCGCTGACGCCC CGGCCTATCAACAGGGCCAGAATCAGCTGTATAATGAATTAAACCTCGGTA GACGCGAGGAGTACGACGTCCTCGACAAGAGAAGGGGGCGCGACCCAGA GATGGGAGGCAAACCGCAGCGCAGGAAGAATCCACAGGAGGGCCTGTAC AACGAATTACAGAAGGACAAGATGGCAGAGGCCTACAGCGAGATAGGAAT GAAGGGTGAAAGGCGTCGTGGAAAGGGCCACGATGGGCTTTACCAGGGC CTAAGTACTGCCACAAAAGATACGTATGACGCGCTGCATATGCAAGCCCTC CCCCCAGGTAAGCATGCAACCTCGATCCGGATTAGTCCAATTTGTTAAAG ACAGGATATCAGTGGTCCAGGCTCTAGTTTTGACTCAACAATATCACCAGCT GAAGCCTATAGAGTACGAGCCATAGATAAAATAAAAGATTTTATTTAGTCTC CAGAAAAAGGGGGAATGAAAGACCCCACCTGTAGGTTTGGCAAGCTAGC TTAAGTAACGCCATTTTGCAAGGCATGGAAAAATACATAACTGAGAATAGAG AAGTTCAGATCAAGGTCAGGAACAGATGGAACAGCTGAATATGGGCCAAAC AGGATATCTGTGGTAAGCAGTTCCTGCCCCGGCTCAGGGCCAAGAACAGA TGGAACAGCTGAATATGGGCCAAACAGGATATCTGTGGTAAGCAGTTCCTG CCCCGGCTCAGGGCCAAGAACAGATGGTCCCCAGATGCGGTCCAGCCCTC AGCAGTTTCTAGAGAACCATCAGATGTTTCCAGGGTGCCCCAAGGACCTGA |

| SEQ ID NO: | DESCRIPTION | SEQUENCE |
|---|---|---|
| | | AATGACCCTGTGCCTTATTTGAACTAACCAATCAGTTCGCTTCTCGCTTCTG TTCGCGCGCTTC |
| 48 | HER2(E4)- CD28TM, ICD- CD3Z CAR | AAGTTCAGATCAAGGTCAGGAACAGATGGAACAGCTGAATATGGGCCAAAC AGGATATCTGTGGTAAGCAGTTCCTGCCCCGGCTCAGGGCCAAGAACAGA TGGAACAGCTGAATATGGGCCAAACAGGATATCTGTGGTAAGCAGTTCCTG CCCCGGCTCAGGGCCAAGAACAGATGGTCCCCAGATGCGGTCCAGCCCTC AGCAGTTTCTAGAGAACCATCAGATGTTTCCAGGGTGCCCCAAGGACCTGA AATGACCCTGTGCCTTATTTGAACTAACCAATCAGTTCGCTTCTCGCTTCTG TTCGCGCGCTTCTGCTCCCCGAGCTCAATAAAAGAGCCCACAACCCCTCAC TCGGCGCGCCAGTCCTCCGATTGACTGAGTCGCCCGGGTACCCGTGTATC CAATAAACCCTCTTGCAGTTGCATCCGACTTGTGGTCTCGCTGTTCCTTGG GAGGGTCTCCTCTGAGTGATTGACTACCCGTCAGCGGGGGTCTTTCATTTG GGGGCTCGTCCGGGATCGGGAGACCCTGCCCAGGGACCACCGACCCAC CACCGGGAGGTAAGCTGGCCAGCAACTTATCTGTGTCTGTCCGATTGTCTA GTGTCTATGACTGATTTTATGCGCCTGCGTCGGTACTAGTTAGCTAACTAGC TCTGTATCTGGCGGACCCGTGGTGGAACTGACGAGTTCGGAACACCCGGC CGCAACCCTGGGAGACGTCCCAGGGACTTCGGGGGCCGTTTTTGTGGCCC GACCTGAGTCCTAAAATCCCGATCGTTTAGGACTCTTTGGTGCACCCCCCT TAGAGGAGGGATATGTGGTTCTGGTAGGAGACGAGAACCTAAAACAGTTCC CGCCTCCGTCTGAATTTTTGCTTTCGGTTTGGGACCGAAGCCGCGCCGCG CGTCTTGTCTGCTGCAGCATCGTTCTGTGTTGTCTCTGTCTGACTGTGTTTC TGTATTTGTCTGAAAATATGGGCCCGGGCTAGCTGTTACCACTCCCTTAA GTTTGACCTTAGGTCACTGGAAAGATGTCGAGCGGATCGCTCACAACCAGT CGGTAGATGTCAAGAAGAGACGTTGGGTTACCTTCTGCTCTGCAGAATGGC CAACCTTTAACGTCGGATGGCCGCGAGACGGCACCTTTAACCGAGACCTC ATCACCCAGGTTAAGATCAAGGTCTTTTCACCTGGCCCGCATGGACACCCA GACCAGGTCCCCTACATCGTGACCTGGGAAGCCTTGGCTTTTGACCCCCCT CCCTGGGTCAAGCCCTTTGTACACCCTAAGCCTCCGCCTCCTCTTCCTCCA TCCGCCCCGTCTCTCCCCCTTGAACCTCCTCGTTCGACCCCGCCTCGATCC TCCCTTTATCCAGCCCTCACTCCTTCTCTAGGCGCCCCCATATGGCCATAT GAGATCTTATATGGGGCACCCCCGCCCCTTGTAAACTTCCCTGACCCTGAC ATGACAAGAGTTACTAACAGCCCCTCTCTCCAAGCTCACTTACAGGCTCTCT ACTTAGTCCAGCACGAAGTCTGGAGACCTCTGGCGGCAGCCTACCAAGAA CAACTGGACCGACCGGTGGTACCTCACCCTTACCGAGTCGGCGACACAGT GTGGGTCCGCCGACACCAGACTAAGAACCTAGAACCTCGCTGGAAAGGAC CTTACACAGTCCTGCTGACCACCCCCACCGCCCTCAAAGTAGACGGCATC GCAGCTTGGATACACGCCGCCCACGTGAAGGCTGCCGACCCCGGGGGTG GACCATGACTCGAGCCATGGATTGGATCTGGCGCATCCTGTTTCTCGTGGG AGCTGCCACAGGCGCCCATTCTCAGGTTCAGCTGCAACAGTGGGGAGCCG GACTGCTGAAGCCTAGCGAAACACTGAGCCTGACCTGTGCCGTGTACGGC GGCAGCTTTAGCGGCTACTACTGGTCCTGGATCAGACAGCCTCCTGGCAA AGGCCTGGAATGGATCGGCGAGATCAATCACAGCGGCAGCACCAACTACA ACCCCAGCCTGAAGTCCAGAGTGACCATCAGCGTGGACACCAGCAAGAAC CAGTTCTCCCTGAAGCTGAGCAGCGTGACCACAGCCGATACCGCCGTGTA CTACTGTGCCCGGATGGGCATCAATAGCGGCGGCTACCTGTACGGCATGG ATGTGTGGGGACAGGGCACCACCGTGACAGTTTCTAGCGGAGGCGGAGGT TCTGGTGGCGGAGGAAGTGGCGGCGGAGGATCTCAGACAGTGGTCACAC AAGAGCCCAGCTTCTCCGTGTCTCCTGGCGGAACAGTGACCCTGACATGT GGCCTTAGCAGCGGCTCTGTGTCCACCAGCTACTACCCTAGCTGGTATCAG CAGATCCCCGGACAGGCCCCTCGGACACTGATCTACACCACCAACATCAG ATCCAGCGGCGTGCCCGATAGATTCGGCGGATCTATCCTGGGCAACAAGG CCGCACTGACAATCACAGGTGCCCAGGCCGAGGACGAGTCCGACTACTAC TGCATGCTGTACATGGGCAGCGGCATCTGGGTTTTCGGCGGAGGCACAAA GCTGACCGTTCTGGGATCCGAACCAAAGAGTTGCGACAAAACACACACCTG CCCTACGCGTTTTTGGGTGCTCGTGGTGGTGGGTGGCGTGCTCGCTTGCT ACTCACTTCTGGTGACCGTAGCGTTTATCATTTTTGGGTCAGGAGCAAGC GATCCCGCCTATTGCACAGCGACTACATGAACATGACCCCCCGGCGCCCC GGGCCAACCCGGAAGCACTACCAGCCATATGCGCCTCCCCGCGATTTCGC AGCGTATCGGTCCCGGGTCAAATTTTCACGGTCCGCTGACGCCCCGGCCT ATCAACAGGGCCAGAATCAGCTGTATAATGAATTAAACCTCGGTAGACGCG AGGAGTACGACGTCCTCGACAAGAGAAGGGGGCGCGACCCAGAGATGGG AGGCAAACCGCAGCGCAGGAAGAATCCACAGGAGGGCCTGTACAACGAAT TACAGAAGGACAAGATGGCAGAGGCCTACAGCGAGATAGGAATGAAGGGT GAAAGGCGTCGTGGAAAGGGCCACGATGGGCTTTACCAGGGCCTAAGTAC TGCCACAAAAGATACGTATGACGCGCTGCATATGCAAGCCCTCCCCCCCAG GTAAGCATGCAACCTCGATCCGGATTAGTCCAATTTGTTAAAGACAGGATAT CAGTGGTCCAGGCTCTAGTTTTGACTCAACAATATCACCAGCTGAAGCCTA TAGAGTACGAGCCATAGATAAAATAAAAGATTTTATTTAGTCTCCAGAAAAA GGGGGGAATGAAAGACCCCACCTGTAGGTTTGGCAAGCTAGCTTAAGTAA CGCCATTTTGCAAGGCATGGAAAATACATAACTGAGAATAGAGAAGTTCA GATCAAGGTCAGGAACAGATGGAACAGCTGAATATGGGCCAAACAGGATAT CTGTGGTAAGCAGTTCCTGCCCCGGCTCAGGGCCAAGAACAGATGGAACA GCTGAATATGGGCCAAACAGGATATCTGTGGTAAGCAGTTCCTGCCCCGG |

| SEQ ID NO: | DESCRIPTION | SEQUENCE |
|---|---|---|
| | | CTCAGGGCCAAGAACAGATGGTCCCCAGATGCGGTCCAGCCCTCAGCAGT<br>TTCTAGAGAACCATCAGATGTTTCCAGGGTGCCCCAAGGACCTGAAATGAC<br>CCTGTGCCTTATTTGAACTAACCAATCAGTTCGCTTCTCGCTTCTGTTCGCG<br>CGCTTC |
| 49 | HER2(F1)-<br>CD28TM, ICD-<br>CD3Z CAR | AAGTTCAGATCAAGGTCAGGAACAGATGGAACAGCTGAATATGGGCCAAAC<br>AGGATATCTGTGGTAAGCAGTTCCTGCCCCGGCTCAGGGCCAAGAACAGA<br>TGGAACAGCTGAATATGGGCCAAACAGGATATCTGTGGTAAGCAGTTCCTG<br>CCCCGGCTCAGGGCCAAGAACAGATGGTCCCCAGATGCGGTCCAGCCCTC<br>AGCAGTTTCTAGAGAACCATCAGATGTTTCCAGGGTGCCCCAAGGACCTGA<br>AATGACCCTGTGCCTTATTTGAACTAACCAATCAGTTCGCTTCTCGCTTCTG<br>TTCGCGCGCTTCTGCTCCCCGAGCTCAATAAAAGAGCCCACAACCCCTCAC<br>TCGGCGCGCCAGTCCTCCGATTGACTGAGTCGCCCGGGTACCCGTGTATC<br>CAATAAACCCTCTTGCAGTTGCATCCGACTTGTGGTCTCGCTGTTCCTTGG<br>GAGGGTCTCCTCTGAGTGATTGACTACCCGTCAGCGGGGGTCTTTCATTTG<br>GGGGCTCGTCCGGGATCGGGAGACCCCTGCCCAGGGACCACCGACCCAC<br>CACCGGGAGGTAAGCTGGCCAGCAACTTATCTGTGTCTGTCCGATTGTCTA<br>GTGTCTATGACTGATTTTATGCGCCTGCGTCGGTACTAGTTAGCTAACTAGC<br>TCTGTATCTGGCGGACCCGTGGTGGAACTGACGAGTTCGGAACACCCGGC<br>CGCAACCCTGGGAGACGTCCCAGGGACTTCGGGGGCCGTTTTTGTGGCCC<br>GACCTGAGTCCTAAAATCCCGATCGTTTAGGACTCTTTGGTGCACCCCCCT<br>TAGAGGAGGGATATGTGGTTCTGGTAGGAGACGAGAACCTAAAACAGTTCC<br>CGCCTCCGTCTGAATTTTTGCTTTCGGTTTGGGACCGAAGCCGCGCCGCG<br>CGTCTTGTCTGCTGCAGCATCGTTCTGTGTTGTCTCTGTCTGACTGTGTTTC<br>TGTATTTGTCTGAAAATATGGGCCCGGGCTAGCTGTTACCACTCCCTTAA<br>GTTTGACCTTAGGTCACTGGAAAGATGTCGAGCGGATCGCTCACAACCAGT<br>CGGTAGATGTCAAGAAGAGACGTTGGGTTACCTTCTGCTCTGCAGAATGGC<br>CAACCTTTAACGTCGGATGGCCGCGAGACGGCACCTTTAACCGAGACCTC<br>ATCACCCAGGTTAAGATCAAGGTCTTTTCACCTGGCCCGCATGGACACCCA<br>GACCAGGTCCCCTACATCGTGACCTGGGAAGCCTTGGCTTTTGACCCCCCT<br>CCCTGGGTCAAGCCCTTTGTACACCCTAAGCCTCCGCCTCCTCTTCCTCCA<br>TCCGCCCCGTCTCTCCCCCTTGAACCTCCTCGTTCGACCCCGCCTCGATCC<br>TCCCTTTATCCAGCCCTCACTCCTTCTCTAGGCGCCCCCATATGGCCATAT<br>GAGATCTTATATGGGGCACCCCCGCCCCTTGTAAACTTCCCTGACCCTGAC<br>ATGACAAGAGTTACTAACAGCCCCTCTCTCCAAGCTCACTTACAGGCTCTCT<br>ACTTAGTCCAGCACGAAGTCTGGAGACCTCTGGCGGCAGCCTACCAAGAA<br>CAACTGGACCGACCGGTGGTACCTCACCCTTACCGAGTCGGCGACACAGT<br>GTGGGTCCGCCGACACCAGACTAAGAACCTAGAACCTCGCTGGAAAGGAC<br>CTTACACAGTCCTGCTGACCACCCCCACCGCCCTCAAAGTAGACGGCATC<br>GCAGCTTGGATACACGCCGCCCACGTGAAGGCTGCCGACCCCGGGGGTG<br>GACCATGACTCGAGCCATGGATTGGATCTGGCGCATCCTGTTTCTCGTGGG<br>AGCTGCCACAGGCGCCCATTCTCAGGTTCAGCTGGTGGAATCTGGCCCTG<br>GCCTGGTTAAGCCTAGCGGCACACTGTCTCTGACCTGTGCTGTGTCTGGC<br>GGCAGCATCAGCAGCAGCAATTGGTGGTCTTGGGTCCGACAGCCTCCTGG<br>CAAAGGCCTGGAATGGATCGGCGAGATCTACCACAGCGGCAGCACCAACT<br>ACAACCCCAGCCTGAAGTCCAGAGTGACCATCAGCGTGGACACCAGCAAG<br>AACCAGTTCTCCCTGAAGCTGAGCAGCGTGACAGCCGCCGATACAGCCGT<br>GTACTACTGTGCCAGAATGGGAGCCAATAGCGGCGGCTACCTGTACGGCA<br>TGGATGTGTGGGGACAGGGCACCACCGTGACAGTTTCTAGCGGAGGCGGA<br>GGTTCTGGTGGCGGAGGAAGTGGCGGCGGAGGATCTCAGACAGTGGTCA<br>CACAAGAGCCCAGCTTCTCCGTGTCTCCTGGCGGAACAGTGACCCTGACA<br>TGTGGCCTTAGCAGCGGCTCTGTGTCTACCAGCTACTACCCCTCCTGGTAT<br>CAGCAGACCCCTGGACAGGCTCCCCGGACACTGATCTACTCCACCAACAC<br>CAGATCCAGCGGCGTGCCCGATAGATTCTCCGGCTCTATCTGGGCAACA<br>AGGCCGCACTGACAATCACAGGCGCTCAGGCCGATGACGAGAGCGACTAC<br>TACTGCGTGCTGTACATGGGCAGCGGCATCTGGGTTTTCGGCGGAGGCAC<br>AAAGCTGACCGTTCTGGGATCCGAACCAAAGAGTTGCGACAAAACACACAC<br>CTGCCCTACGCGTTTTGGGTGCTCGTGGTGGTGGGTGGCGTGCTCGCTT<br>GCTACTCACTTCTGGTGACCGTAGCGTTTATCATTTTTGGGTCAGGAGCAA<br>GCGATCCCGCCTATTGCACAGCGACTACATGAACATGACCCCCCGGCGCC<br>CCGGGCCAACCCGGAAGCACTACCAGCCATATGCGCCTCCCCGCGATTTC<br>GCAGCGTATCGGTCCCGGGTCAAATTTTCACGGTCCGCTGACGCCCCGGC<br>CTATCAACAGGGCCAGATCAGCTGTATAATGAATTAAACCTCGGTAGACG<br>CGAGGAGTACGACGTCCTCGACAAGAGAAGGGGGCGCGACCCAGAGATG<br>GGAGGCAAACCGCAGCGCAGGAAGAATCCACAGGAGGGCCTGTACAACG<br>AATTACAGAAGGACAAGATGGCAGAGGCCTACAGCGAGATAGGAATGAAG<br>GGTGAAAGGCGTCGTGGAAGGGCCACGATGGGCTTTACCAGGGCCTAAG<br>TACTGCCACAAAAGATACGTATGACGCGCTGCATATGCAAGCCCTCCCCCC<br>CAGGTAAGCATGCAACCTCGATCCGGATTAGTCCAATTTGTTAAAGACAGG<br>ATATCAGTGGTCCAGGCTCTAGTTTTGACTCAACAATATCACCAGCTGAAGC<br>CTATAGAGTACGAGCCATAGATAAAATAAAAGATTTTATTTAGTCTCCAGAA<br>AAAGGGGGGAATGAAAGACCCCACCTGTAGGTTTGGCAAGCTAGCTTAAGT<br>AACGCCATTTTGCAAGGCATGGAAAATACATAACTGAGAATAGAGAAGTTC<br>AGATCAAGGTCAGGAACAGATGGAACAGCTGAATATGGGCCAAACAGGATA |

| SEQ ID NO: | DESCRIPTION | SEQUENCE |
|---|---|---|
| | | TCTGTGGTAAGCAGTTCCTGCCCCGGCTCAGGGCCAAGAACAGATGGAAC
AGCTGAATATGGGCCAAACAGGATATCTGTGGTAAGCAGTTCCTGCCCCGG
CTCAGGGCCAAGAACAGATGGTCCCCAGATGCGGTCCAGCCCTCAGCAGT
TTCTAGAGAACCATCAGATGTTTCCAGGGTGCCCCAAGGACCTGAAATGAC
CCTGTGCCTTATTTGAACTAACCAATCAGTTCGCTTCTCGCTTCTGTTCGCG
CGCTTC |
| 50 | HDAdIL12p70_
TK_aPD-L1 | AAACATCATCAATAATATACCTTATTTTGGATTGAAGCCAATATGATAATGAG
GGGGTGGAGTTTGTGACGTGGCGCGGGGCGTGGGAACGGGGCGGGTGA
CGTAGTAGTGTGGCGGAAGTGTGATGTTGCAAGTGTGGCGGAACACATGT
AAGCGACGGATGTGGCAAAAGTGACGTTTTTGGTGTGCGCCGGTGTACAC
AGGAAGTGACAATTTTCGCGCGGTTTTAGGCGGATGTTGTAGTAAATTTGG
GCGTAACCGAGTAAGATTTGGCCATTTTCGCGGGAAAACTGAATAAGAGGA
AGTGAAATCTGAATAATTTTGTGTTACTCATAGCGCGTAATATTTGTCTAGG
GCCGCGGGGACTTTGACCGTTTACGTGGAGACTCGCCCAGGTGTTTTTCTC
AGGTGTTTTCCGCGTTCCGGGTCAAAGTTGGCGTTTTGATATCAAGCTTATC
GATACCGTAAACAAGTCTTTAATTCAAGCAAGACTTTAACAAGTTAAAAGGA
GCTTATGGGTAGGAAGTAGTGTTATGATGTATGGGCATAAAGGGTTTTAAT
GGGATAGTGAAAATGTCTATAATAATACTTAAATGGCTGCCCAATCACCTAC
AGGATTGATGTAAACATGGAAAAGGTCAAAAACTTGGGTCACTAAAATAGAT
GATTAATGGAGAGGATGAGGTTGATAGTTAAATGTAGATAAGTGGTCTTATT
CTCAATAAAAATGTGAACATAAGGCGAGTTTCTACAAAGATGGACAGGACT
CATTCATGAAACAGCAAAAACTGGACATTTGTTCTAATCTTTGAAGAGTATG
AAAAATTCCTATTTTAAAGGTAAAACAGTAACTCACAGGAAATACCAACCCA
ACATAAAATCAGAACAATAGTCTAAAGTAATAAAAATCAAACGTTTGCACG
ATCAAATTATGAATGAAATTCACTACTAAAATTCACACTGATTTTGTTTCATC
CACAGTGTCAATGTTGTGATGCATTTCAATTGTGTGACACAGGCAGACTGT
GGATCAAAAGTGGTTTCTGGTGCGACTTACTCTCTTGAGTATACCTGCAGT
CCCCTTTCTTAAGTGTGTTAAAAAAAAAGGGGGATTTCTTCAATTCGCCAAT
ACTCTAGCTCTCCATGTGCTTTCTAGGAAACAAGTGTTAACCCACCTTATTT
GTCAAACCTAGCTCCAAAGGACTTTTGACTCCCCACAAACCGATGTAGCTC
AAGAGAGGGTATCTGTCACCAGTATGTATAGTGAAAAAAGTATCCCAAGTC
CCAACAGCAATTCCTAAAAGGAGTTTATTTAAAAAACCACACACACCTGTAA
AATAAGTATATATCCTCCAAGGTGACTAGTTTTAAAAAAACAGTATTGGCTTT
GATGTAAAGTACTAGTGAATATGTTAGAAAAATCTCACTGTAACCAAGTGAA
ATGAAAGCAAGTATGGTTTGCAGAGATTCAAAGAAAATATAAGAAAACCTAC
TGTTGCCACTAAAAAGAATCATATATTAAATATACTCACACAATAGCTCTTCA
GTCTGATAAAATCTACAGTCATAGGAATGGATCTATCACTATTTCTATTCAGT
GCTTTGATGTAATCCAGCAGGTCAGCAAAGAATTTATAGCCCCCCTTGAGC
ACACAGAGGGCTACAATGTGATGGCCTCCCATCTCCTTCATCACATCTCGA
GCAAGACGTTCAGTCCTACAGAAATAAAATCAGGAATTTAATAGAAAGTTTC
ATACATTAAACTTTATAACAAACACCTCTTAGTCATTAAACTTCCACACCAAC
CTGGGCAATATAGTGAGACCCCATGCCTGCAAAAAAAAAAAAAATTAGCCAG
GCATGGTAGCATGTACCTGTAGTCCCAGCTACTTGAGAGGTGAGGTGGGA
AAATCACTTTAGTGCAGGATGTTGAGGCTGGAGTGAACTGTGATTGTGCCA
CTGCACTCCAGCCTGGACAATAGAGCAAGACCTTGTCTCAAAAAAATGCAT
TAAAAATTTTTTTTAAATCTTCCACGTATCACATCCTTTGCCCTCATGTTTCAT
AAGGTAAAAATTTGATACCTTCAAAAAAACCAAGCATACCACTATCATAATT
TTTTTAAATGCAAATAAAAACAAGATACCATTTTCACCTATCAGACTGGCAG
GTTCTGATTAAATGAAATTTTCTGGATAATATACAATATTAAGAGAGACTGTA
GAAACTGGGCCAGTGGCTCATGCCTGTAATCCCAGCACTTTGGGAGGCTG
GGTAACATGGCGAACCCTGTTTCTACAAAATAAAAATATTAGCTGGGAGTG
GTGGCGCACACCTATAGTCCCAGCTACTCAGGAGGCTGAGGTGGAAGGAT
CGCTTGAACCCAGGAGGTTGAGACTGCAGTGAACTGTGATCATTCTGCTGC
ACTGCACCCCAGCCTGGGCAACAGAGACCTTGTCTCAAAAAAAAAAAAAAA
AGAGACAAATTGTGAAGAGAAAGGTACTCTCATATAACATCAGGAGTATAAA
ATGATTCAACTTCTTAGAGGAAAATTTGGCAATACCAAAATATTCAATAAACT
CTTTCCCCTTGACCCAGAAATTCCACTTGAATAAAGCTGAACAAGTACCAAA
CATGTAAAAGAATGTTTCTTCTAGTACAGTCGGTAAGAACAAAATAGTGTCT
ATCAATAGTGGACTGGTTAAATCAGTTATGGTATCTCCATAAGACAGAATGC
TATGCAACCTTTAAAATATATTAGATAGCTCTAGACACACTAATATTAAAAGT
GTCCAATAACATTTAAAACTATACTCATACGTTAAAATATAAATGTATATATG
TACTTTTGCATATAGTATACATGCATAGGCCAGTGCTTGAGAGAAATGTGT
ACAGAAGGCTGAAAGGAGAGAACTTTAGTCTTCTTGTTTATGGCCTCCATA
GTTAGAATATTTTATAACACAAATATTTTGATATTATAATTTTAAAATAAAAAC
ACAGAATAGCCAGACATACAATGCAAGCATTCAATACCAGGTAAGGTTTTTC
ACTGTAATTGACTTAACAGAAAATTTTCAAGCTAGATGTGCATAATAATAAAA
ATCTGACCTTGCCTTCATGTGATTCAGCCCCAGTCCATTACCCTGTTTAGGA
CTGAGAAATGCAAGACTCTGGCTAGAGTTCCTTCTTCCATCTCCCTTCAATG
TTTACTTTGTTCTGGTCCCTACAGAGTCCCACTATACCACAACTGATACTAA
GTAATTAGTAAGGCCCTCCTCTTTTATTTTAATAAGAAGATTTTAGAAAGC
ATCAGTTATTTAATAAGTTGGCCTAGTTTATGTTCAAATAGCAAGTACTCAGA
ACAGCTGCTGATGTTTGAAATTAACACAAGAAAAGTAAAAAACCTCATTTT
AAGATCTTACTTACCTGTCCATAATTAGTCCATGAGGAATAAACACCCTTTC |

| SEQ ID NO: | DESCRIPTION | SEQUENCE |
|---|---|---|
| | | CAAATCCTCAGCATAATGATTAGGTATGCAAATAAATCAAGGTCATAACCT |
| | | GGTTCATCATCACTAATCTGAAAAAGAAATATAGCTGTTTCAATGAGAGCAT |
| | | TACAGGATACAAACATTTGATTGGATTAAGATGTTAAAAAATAACCTTAGTCT |
| | | ATCAGAGAAATTTAGGTGTAAGATGATATTAGTAACTGTTAACTTTGTAGGT |
| | | ATGATAATGAATTATGTAAGAAAACAACAGGCCGGGCGGGTTGGTTCACAC |
| | | GTGTAATCCCAGCACTTTGGGAGGCTGAGGCAGGCAGACTGCCTGAGCTC |
| | | AGGAGTTCGAGACCAGCCTGGGCAACACGGTGAAATCCCGTCTCTACTAAA |
| | | AATACAAAAAAATTAGCCGGGTGTGGTGACACATGCCTGTAGTCCCAGCTA |
| | | CTTGGGAGGCTGAGGCAGGAGAATCACTTGAACCTGGGAGGTGAAGGTTG |
| | | CAGTGAGCCAAGATGGCACCACTTCACTCCAGCCTGGGAAACAGAGCAAG |
| | | ACTCTGTCTCTGAGCTGAGATGGCACCACTTCACTCCAGCCTGGGAAACAG |
| | | AGCAAGACTCTGTCTCAAAAAAAACAAAACACACAAACAAAAAAACAGGCTG |
| | | GGCGCGGTGGCTCACGCCTGTAATCCCAGCACTTTGGGAGGCCGAGGCG |
| | | GGTGGATCACCTGAGGTCAGGAGTTCCAGACCAGCCTTGTCAACATGGTG |
| | | AAACCTCCCCCGCCGTCTCTACTAAAAATACAAAAATTAGCCAGGCGTGG |
| | | TGGCAGGAGCCTGTAATCCCAGCTACTTGGGAGGCTGAGGCAGGAGAATC |
| | | GCTTGTACCCAGAAGGCAGAGGTTGCACTGAGCTGAGATGGCACCATTGC |
| | | ACTCCAGCCTGGGGACAAGAGCGAGATTTCGTCTTTAAAAAACAAAAACA |
| | | AAACAAAAAACCATGTAACTATATGTCTTAGTCATCTTAGTCAAGAATGTAGA |
| | | AGTAAAGTGATAAGATATGGAATTTCCTTTAGGTCACAAAGAGAAAAAGAAA |
| | | AATTTTAAAGAGCTAAGACAAACGCAGCAAAATCTTTATATTTAATAATATTC |
| | | TAAACATGGGTGATGAACATACGGGTATTCATTATACTATTCTCTCCACTTTT |
| | | GAGTATGTTTGAAAATTTAGTAAAACAAGTTTTAACACACTGTAGTCTAACAA |
| | | GATAAAATATCACACTGAACAGGAAAAACTGGCATGGTGTGGTGGCTCACA |
| | | CTTGTAATCCCAGTGCTTTGGGAGGCTGAGACAGGAGAGTTGCTTGAGGC |
| | | CAGGAGTTCAAGACCGACATGGGGAATGTAGCAAGACCCCGTCCCTACAA |
| | | AAAACTTTGTAAAAATTTGCCAGGTATGGTGGTGCATACCTGTAGTCCCAGC |
| | | TACTCGGGAGGCGGAGGCAGAAGGAATCACTTGAGCCCAGGAGTTTGAGG |
| | | CTGCAGTGAGCTACGATCATACCACAGCACTCCAGCGTGGACAACAGAGTA |
| | | AGACCCTATCTCAAAAACAAAACAAAACAAAACAAACAAAAAAAACCACAAG |
| | | AAAAACTGCTGGCTGATGCAGCGGCTCATGCCTGTAATCCCAGTATTTTGG |
| | | GAGGCCCAGGTGGGCGTATCACCTGAGGTCAGGAGTTAGAGACCAGCCTG |
| | | GCCAACATGGTGAAACCCCATCTCTACTAAAAATACAAAATTAGCCAGGCAT |
| | | GTGGCACGCGCCTGTAGTCCCAGTTACTGGGAGGCTGAAGCAGGAGGATC |
| | | ACCTGAGCCCGGGAGGTGGAGGTTGCAGTGAGCCGAGATCACACCACTGC |
| | | ACTCCAGCCTGGGTGACACAGCAATACCCTACCTCAAAATAAAAAAGAAAA |
| | | AGAAAAGAAAAGTTGCTGTCCCCGCTACCCCAATCCCAAATCCAAACAGCC |
| | | TCTCTCATCTCACAGTAAGGGGGAAAAATCACCCAAAAAAGCTAAGTGATCT |
| | | TTTGAAAACCCAAACTCTTAGAAGTCTAAGATTATTATAGTCAACTCATGAAG |
| | | TGTCATCATAAAAGATACTCTAATATTATTTAAGTAGAACCACATATTGGTTG |
| | | TCTTGGTATGTCTAGCCCCTGGCATACAAAATATTTAATAACACTGATATGG |
| | | TACCTGTGATGTGAAAATGTACTATGAGTACAGCTTTATAAATACTATATATG |
| | | TACCTATATACAGAAAAAAATACAACAAAATCATAAAAGCACTTATCTTTGAA |
| | | AGAGGAGTTACAGCAATTTTATTTAGTTCTTTATTGCTTTGCTATATATTCTA |
| | | AATTTTTTTCAATGAATATATATCACTTTTAAAAAAATTCAATGGTCTTTCTTA |
| | | TAAATTATCTTTGGCAGCATGCGTTTTTATATATACATATAAATGTATGGGA |
| | | AATTTTTAAAGGATACATTAAATTAAAGCAAAATATACAAACAAAAAATCAGA |
| | | ATACAAAAAGATAAAAGATTGGGAAGGGAGGGAGGGAGTAAGGAGGAAG |
| | | GGTGGGTGGGTATAGAGAAATATACCAAATAATGGTAAGAAGTGGGGTCTT |
| | | GACACTTTCTACACTTTTTTTAAATAAAAAAATTTTTTTCTCTCTCTTTTTTTT |
| | | TTTTAGAGACGAAGTCTCGCTATGTTGCCCAGGCTGGTCTTGAACTCCTGG |
| | | GATCAAGAGATCCTCCTGCCTCAGCCTCCCAAGGTGCTTGGATTACAGGTG |
| | | TGAGCCACCACGCCTGGTCACTTTCTACACTTTAATATATATATTTTTTCATT |
| | | TTCAATGTCATTTTTATTAGTTAATTTATAATACCCATTCACCATTATATTCAA |
| | | AGTCTATTTGAAGAAATAAACCAGAAAGAATGAAATACTCTAGCTCACATGC |
| | | TATTCAATACTAAATTACCTTTCAAATCACATTCAAGAAGCTGATGATTTAAG |
| | | CTTTGGCGGTTTCCAATAAATATTGGTCAAACCATAATTAAATCTCAATATAT |
| | | CAGTTAGTACCTATTGAGCATCTCCTTTTACAACCTAAGCATTGTATTAGGT |
| | | GCTTAAATACAAGCAGCTTGACTTTTAATACATTTAAAAATACATATTTAAGA |
| | | CTTAAAATCTTATTTATGGAATTCAGTTATATTTTGAGGTTTCCAGTGCTGAG |
| | | AAATTTGAGGTTTGTGCTGTCTTTCAGTCCCCAAAGCTCAGTTCTGAGTTCT |
| | | CAGACTTTGGTGGAACTTCATGTATTGTCAGGTTGGCCCGTAATACCTGTG |
| | | GGACAACTTCAGCCCCTGTGCACATGGCCAGGAGGCTGGTTGCAAACATTT |
| | | TCAGGTAGGTGGACCAGGACATGCCCCTGGTCATGGCCAGGTGGAGGCAT |
| | | AGTGCTATACAGCAGGCAGAAGTCAATATTGATTTGTTTTTAAAGAAACATG |
| | | TACTACTTTCATAAGCAGAAAAAATTTCTATTCTTGGGGAAAAGATTATGC |
| | | CAGATCCTCTAGGATTAAATGCTGATGCATCTGCTAAACCTTCACATATCAG |
| | | AACATATTTACTATAGAAAGAATGAAAATGGGACATTTGTGTGTCACCTATG |
| | | TGAACATTCCAAAATATTTTACAACAACTAAGTATTTTATAAATTTTATGAAC |
| | | TGAAATTTAGTTCAAGTTCTAGGAAAATACAAACCTTGCTAGATATTATAAAA |
| | | ATGATACAATATATATTCATTTCAGGCTCATCAGATATATCTGTTATCACTT |
| | | GACAAGAATGAAAATGCACCATTTTGTAGTGCTTTAAAATCAGGAAGATCCA |
| | | GAGTACTAAAAATGACTTCTTCCTTGAAGCTTACTCACCAACTTCCTCCCAG |
| | | TTACTCACTGCTTCTGCCACAAGCATAAACTAGGACCCAGCCAGAACTCCC |

Sequences

| SEQ ID NO: | DESCRIPTION | SEQUENCE |
|---|---|---|
| | | TTGAAATATACACTTGCAACGATTACTGCATCTATCAAAATGGTTCAGTGCC |
| | | TGGCTACAGGTTCTGCAGATCGACTAAGAATTTGAAAAGTCTTGTTTATTTC |
| | | AAAGGAAGCCCATGTGAATTCTGCCCAGAGTTCATCCCAGATATGCAGTCT |
| | | AAGAATACAGACAGATCAGCAGAGATGTATTCTAAAACAGGAATTCTGGCA |
| | | ATATAACAAATTGATTTCCAATCAAAACAGATTTACATACCATACTTATGTCA |
| | | AGAAGTTGTTTTGTTTTATTGCATCCTAGATTTTATTTTTTTGATTTATGGTTT |
| | | ACTTTAAGCATAAAAAATTTGTCAATACAACTCTTCCCAAAAGGCATAAACAA |
| | | AAATTCATAAAACTTGCATCACTTGAGATACTTCAGGTATGAATTCACAACTT |
| | | TGTTACAACTTACTATATATATGCACACATATATATATATTTGGGTATATTGG |
| | | GGGGGTTCTAATTTAAGAAATGCATAATTGGCTATAGACAGACAGTTGTCTG |
| | | GAATGAAAATCAATACTTTTGCTATAATCGATTACTGAAATAATTTTACTTTC |
| | | CAGTAAAACTGGCATTATAATTTTTTTTAATTTTTAAAACTTCATAATTTTTTG |
| | | CCAGACTGACCCATGTAAACATACAAATTACTAATAATTATGCACGTCACAT |
| | | CTGTAATAATGGCCTTCATGTAAACATTTTTGTGGTTTACACATAAAATCTCT |
| | | AATTACAAAGCTATATTATCTAAAATTACAGTAAGCAAGAAAATTAATCCAAG |
| | | CTAAGACAATACTTGCAACATCAATTCATCATCTGTGACAAGGACTGCTTAA |
| | | GTCTCTTTGTGGTTAAAAAGGAAAAAAAAAAAAAAGACATGTTGGCCAGATG |
| | | CGGTGGCTCACACCTGTAATCCCAGCACTTTGGGAGGCTGAGGTGGGCGG |
| | | ATCACCCCTGGCCTGCCCAACATGGTGAAACCCCGTCTCTACTAAAAACAC |
| | | AAAAATTAGCTGGGCGTGGTGGCGGGCGCCTGTAATTCCAGCTACTCGGG |
| | | AGGCTGAGGCAGGAGAATTGCTAGAACCCAGGAGGCAGAGATTGCAGTGA |
| | | GCTGAGATTGCACCATTGCACTACAGTCTGGGCAACAAAAGTGAAACTCCA |
| | | TCTTAAAAAAAAAAGACAATGTTCGTGGGTCCAAACAAGACTTAATGGAAG |
| | | TGAGTCTAAAAATGAGCTATGTGGGCCAGGCGTAGTGGCTCCCACCTGTAA |
| | | TCCCAGCACTTTGGGAGGCCGAAGCAGGCAGATCATGAGGTCAGGAGATG |
| | | GAGACCATCCTGGCCAACACGGTGAAATCCTGTCTCTACAAAAATTAGCTG |
| | | GGCGTGGTGGTGCCTGCCTGTAATCCCAGCTACTCAGAAGGCTCAGGCAG |
| | | GAGAATCGCTTGAACCAGGGAGTCGGTGGCTAGAGTGAGCCGAGATTTGC |
| | | ATCACTGCACTCCTGCCTGGTGACAGAGCAAGACTCCATCTCAAAAAAAAC |
| | | AAACAAAAATAAAAGATAAAAATGAGCTATGTGAATTAAAAGAGGTATAACA |
| | | ATAGATAAACCATATTTTATTTAATTCCTAGTAATGAGTAATATTTCCAAACTT |
| | | CTGGAATGGGCAGAAATTGCTAGTTGGCATATTTTTACCTTTTATATTCAGA |
| | | TACATTAAAATTCTCAAAAAAAAACACCTCAAAGCAGATGATCCGCCATCTC |
| | | CTTGGATAATTTGTGTTAACTCAGGATAACAGAAAACCAAAATTATGAGTTA |
| | | CTGATGCAATATTCCTAAATGTAAAAATAATTAAAGCTAATAGTAGATTCATC |
| | | TTCCAATTTCATATCAGTCTTACAAATAAACTACATATATAACTTGCTTGCCT |
| | | TCCCTTCTGAGGGATAAAGCTGTTAGAAGAATTAAAATCAGCATTCTTGACT |
| | | ATTCAACCAAGGGAGGGATAAATTATTACTCATTCTAGGGACATGGGCTCAT |
| | | AACTACTACATGTGTAAGGACATGAATTTACCCAATATTACAATTTTTCCTTT |
| | | TATTAGTGTGTACAGTGGAAGAATAGACATGTTCACTCTGGACAAAAAAAAA |
| | | ATTATACTTATCAGTTATCAGAAGCACAATGCTGAAGACAGTAGTTCCATAA |
| | | CAATTTGAAGTATGTGATCGAACTAGTAGATTATCTTAGTAGTAGTGAATTAT |
| | | TGTAAATGTTAGTAATTTGGCAGCCACTGGGCAGAAAAATAAGAATTGAGG |
| | | CTCAATATTGATATTAATGGTGGTGATTGACACATAAATTTTATCAAGTCTAC |
| | | ACAATATAAAATTACAGAAAGGTAGAAGAGTATACCAGTACAACTTCAACAT |
| | | ATCTTCACTACAAGGGAGTAAAATGACATGGCCTAGTTACTATCTAATGAAC |
| | | TGCAGAAAACTAAAAGAAAACTCCAAGGCAACTCTTCTCTGCTGATCTGGTT |
| | | GGTCCTTTTCCTACCTTTTGCAATACCCAGATACAAACAATGGATAGAAAAC |
| | | AAAGTAGACTTGTAGTATGCAGGTCACAGTGCTAAATTCACAGAAAGAAAC |
| | | CCCTGAACTGAACTGCTCTATTTCCTGGTGGTCACAAAGAGTAATTCTGGTT |
| | | TACACCTACAGATTGATGTCAATCTACACCCTGTTGATAACAGTGTGGCCAA |
| | | GGACAAAAAAAAGGTGCTCCGTTTTACCAATTCTGTAAAAAATTATTGGCAG |
| | | GGTAAGCTCGGCTAGGGCAGGATTACATTTCTAGGACTACCATCCCCGAAA |
| | | TTTAGAAGATATTATATCCACATAAAGCATATCTTTCACATTAATTTGCAAAA |
| | | ATCTAAAAGCTTTTTCTTAGCTCAAGTGTGTCCAAGTTTACCCTGGCAGTTT |
| | | AAAACGATAGTTACAAGCAGCATGGGTTGTATCAGACACATTTGAGGGCCA |
| | | ATTTCATGTAAGTGATATTGGGCAAGTTACTTCAACTATCTGTGCCTCCAAG |
| | | GTCATACTAGTGTTTATTTACCTAAAGGGTACCTGTTATGTAACTTTAGGGT |
| | | GTTTACATTAGATAATGCCTGCAAAATATTTACTTCAACGCCTAAAACATAGT |
| | | TAAGTATTCAATAAATACCTACTATTGTCACTACTAACTTAAAAGTTTAGAGA |
| | | TTAAGAGCAGAATCTGGGGTGAGACAAACTTAGGTTCAAATCCTAGTATTGT |
| | | TGGGTAATCTTGGGCAAGTTACTTAACCTCTCTGATTTGTGTAATTTAAAAAA |
| | | TTAGTTAATATACATAACAGGGCTTAGAAGAGTATCTAGCACATAGCACCAT |
| | | TTAAGCATTTGTTATTGCTAACATGCAAACAATTTAAGGGAAAGAAATTTTTT |
| | | AAAAAGGAAGAGGGATTTGCAAACTAAAAACAATGAGTATCTTATGTTCAAA |
| | | GAAAACTAACAAACAGCCAGCTCTAGCAATAATTAAATTCACTATATACTGG |
| | | GGCAGGCATCACACCCCAAAGCTAAAAGCGTCTACCTAGGCCAGGCACGG |
| | | TGGCTCATGCCTGTAATCCCAGCACTTTGGGAAGCAGAGGCGGGCAGATC |
| | | GCTTGAGCTCAGGAGTTCAAGACCAGCCTGGACAACATGGCAAAACACCAT |
| | | CTCTACAAAAAATACAAATATTAGGCCGGGCGCAGTGGCTCACGCCTGTAA |
| | | TCCCAGCACTTTGGGAGGCCAAGGCGGGTGGATCACCTGAGATCAGGAGT |
| | | TCGAGAGTAGCCTGGCCAACATGGTGAAACCTCGTCTCTATTAAAAATACA |
| | | AAAAATTAGCCAGGCATGGTGGCAGGCGCCTGTAATCCCAGCTACTCAGG |
| | | GGGATGAGGTAGGAGAATCGCTTGAACCCGGGAGGCAGAGGTTGCACTGA |

Sequences

| SEQ ID NO: | DESCRIPTION | SEQUENCE |
|---|---|---|
| | | GCCGAGATCATGCCACTGTACTCCAGCCCGGGCAACAAGAGCGAAACTCC |
| | | ATCTCAAAAAATAAATAAATAAATAAATAAATAAAGTACAAATATTAGCCAG |
| | | GGATGGTGGTGCGCACCTGTAGTCCCAGCTACTTGGGAGGCTGAAGTGGG |
| | | AGAATCCCCTGAGCCTGGGGAGAATCACCCGAGCCCGGGAAGTCGAGGCT |
| | | GCAGTGAGCAGTGATTGTGCCACTGCACTCCATCCTAGGTGACAGAGTGA |
| | | GACCCTGTCTCAAAAAAAAGAAATTGGCAGAATTAAGTAAGTTGATGTTTAG |
| | | AGATGAAAAATCAACATTTTTTCCTCAGCAACTGAATAAAAACAACAGCCAC |
| | | TACCATTTTTTTGAGTACCTATTTGTAGCCTATTTTTTAACTGGTATTACTCG |
| | | AGAGAGAGAGAGCTAGGTTCGAGACAGAGCTCCTTCTCTTAATAACTGTAT |
| | | GACCTAGGGTATGTCTGTTAGCCTCTCTGAGGCTTCAAAGGTTCCTCATCT |
| | | GTAAAATGGTAATAATCATACCATTGCTACAGGGCTGTTTTGAAGACTAATT |
| | | AGGACTATGTAAGTAAACATGATGATGGCTATTATTACTGTTCCCCGCCAGG |
| | | GGCCATGCAAGGGTTGCTGATTCACATAGACTGTCTTATAATCCTCTCAATA |
| | | ACTCCAAGAGGTAGCCAGCACCTCAGATATACATAAAATGACTTAAGCCCA |
| | | GAGAGGTGAAGTAAGTTGCCCACAGCCACACAACTAGTAAATAGCCCAAAC |
| | | AAGCTGGATTCCCAGTTAGACTCCGTTAATAGCACTGCTCTTTACCTTAAGT |
| | | CATTACAATGCCTAATATGAAATAGAATCGCTTCTTTCTTAGGGTTCAAGTG |
| | | GTTAATTATTTAATGTATTCATTCAACAAACCATCATCGAGGACCTCTTACAA |
| | | GCCAAGTACTGTGCTAAGTGCTAGAGTTACGGCGGTGATTCCTGCCCTTAA |
| | | AAAGTTTTAGTGGGAGAAACAACAGGTAACCAGGTCATTGCCAAAACAACA |
| | | AAAATAATCATAATAAAGCAGGCTAAAGCATATTTAACTGGCCGGGGTTTTG |
| | | ACTATTTTAGCAAGCATGATCAGAACGGTTGAGGAGGGAGGCCAGCAGCTT |
| | | GGCCGGTTCAACAAACAAGAAAAAACCAGTGAGGGTGGAGCTAAGATACC |
| | | AGAGGCTGATTACGGTTAAGAATGTTCTTGAAGGTAAGGACCAGATTCTCA |
| | | TTTTCTATATCCTGGGGCATCGGTCAGCATGGAATCTGGATTCTAGCACAT |
| | | GTGAATTTCGGCTTGAAATGACCTAATGCCTTTTCCCTAGTTCCTTCGTGTG |
| | | TCAAATACGCATGGTTACCGCTACCAGAGCTGTAGTGGGGCTTCAATGAGG |
| | | CCATGAGCATCTCCATAAAGATGAACTACAGTGTGTGCAAAACTAAAGGCA |
| | | AAACCTGGTCCCCACACGCCCTCCCAGGTGGTCGCTTTCCGTGCCGAGGC |
| | | CCCTCCAGAGGTGCCCCGAGAACCTCACCATCGCACCCCAAACTTCCAGG |
| | | GAAGGGCCTCTCCCGAGAAAGCCCCCACGCCCCCACCCCGCGCCATCATT |
| | | CCCGAATCTGCCCTCGGCCCCTCCCCGCAGCACGCTCGCAGGCGGCACAT |
| | | GTCAACCAAAACGCCATTTCCACCTTCTCTTCCCACACGCGAGTCCTCTTTTC |
| | | CCAGGGCTCCCCCGAGGAGGGACCCACCCCAAACCCCGCCATTCCGTCCT |
| | | CCCTGCCGCCCTCGCGTGACGTAAAGCCGAACCCGGGAAACTGGCCGCC |
| | | CCCGCCTGCGGGGTTCCCTGGGCCCGGCCGCTCTAGAACTAGTGGATCCC |
| | | AATTGAAGGCCTGGTCTAAATGACTCCAAAATCACCACTTAATTCAAGAGAC |
| | | TGATTTCCCTGAGTCAGGCCCCTTAAAGCAGCTATTTCAATGGGACAGGGA |
| | | AACAACCCTAGGATCTGGATTAGAATCACTTGGGGGCTGCCACACCCCCAG |
| | | GGCTCTGATCCTGCCCTTCTCCCACACGCACATTCACATACTGCTGCAGTG |
| | | ACCTTCCATTTCTAATGGGTTCCTGGGCCATCTGTCAGGTATAGGGAATGG |
| | | AAAAGGGGTTGGGAGGCTCTGCTTCAGAAAGTTTGTGTCAGGGGCTCCC |
| | | AGAGCCTCCACAGATAGATAGCAGGGGTCCCCACCCTACCATGGCAGCTA |
| | | TAAATGTGATCAACATTTATTGGCCTAGGATACAGCAGTTAGCAAAATGCCT |
| | | GATGTAGTTCCCACTCCGTGGAGGTTGCAGGCTAGCTCTTTCCTAATGAGC |
| | | TTTACAGCAGAAGCTGTTTTATCGTTAAGTGCCCCACAGAGACACTTTACCA |
| | | GGAGGCTGGGAGAGTTCTCCAGATTTGGGAGAGGCGCAGAGACAGTGTGT |
| | | GAGCCGAGCCCTGTCTCAGCAATCCACCTGGAGGAGCTAGAGTATCCTCC |
| | | TCCCTTTACCATTCAGACCGAGAGAAAAAGCCCAGCTTGTGTGCACCCTCG |
| | | TGGGGTTAAGGCGAGCTGTTCCTGGTTTAAAGCCTTTCAGTATTTGTTTTGA |
| | | TGTAAGGCTCTGTGGTTTGGGGGGGAACATCTGTAAACATTATTAGTTGATT |
| | | TGGGGTTTGTCTTTGATGGTTTCTATCTGCAATTATCGTCATGTATATTTAAG |
| | | TGTCTGTTATAGAAAACCCACACCCACTGTCCTGTAAACTTTTCTCAGTGTC |
| | | CAGACTTTCTGTAATCACATTTTAATTGCCACCTCGTATTTCACCTCTACATT |
| | | TGAAATCTGGCGTCTGTTTCAAGCCAGTGTGTTTTTTCTTCGTTCTGTAATAA |
| | | ACAGCCAGGAGAAAAGTGCCTCTATGTTTTTATTTTTCAAGGGAGTATTCAG |
| | | TACCTACAAACCCAAGTCAGGAAGCCTGCTAGTGGCTTTGGTTCTTTCAGA |
| | | GGCTGCTCGATGCCTTGTGTGTCAGAAAGAAAGATTCAGCAGTTTTGCATC |
| | | ATGGCAAAGAAGCCTGTTATTTTGGGGCTCAGCCCCTCATTTTATAGAGGA |
| | | TGAAACAGAGGGGATGGGAGGTCACAAAGACAACTGCCCCGGGAGCAG |
| | | GTGTGGGGGAGACTTGCCCTGAGGGTCTAGACGCTCTGCACCACCGTCCT |
| | | GTCTCCCTTGCTGAAGACCACACATGCCCTTCTTTGACCAGACCCTGCCAC |
| | | CTGATAGGCCAGGACCTGGTAGGCGGGTACCCAGGTTTCATGGATGGAAC |
| | | CACATCTCCCCAAAAGTGGGGAGGTAGCTACTGGGATGCACGCCTCCCGC |
| | | CATGTGCTATAGGAGAGCAGCTGAAGCAACAGTTGGGATCAGATGTAGTCA |
| | | CAATTGAATGCATCATCACATTTATCCCTCTAAGTGGCTGGGAGAGTTGATA |
| | | TCCTCATCCCTAAGGTACAAAATGTTCCAATTTGATCAGTGGCTTTCAGGAG |
| | | CTGAGAAAGGCATGTGCTCTGAGGCAGAGCTGTTATGTCCCGCAGAGCCT |
| | | AAAAATGCTCTAAGAACATGCTCCCTGCCAAAATTCTCAATGGCTGTGACAA |
| | | GGGACAACGATCGACCAATGGGGGTGGAAGCAGACCTCCGCAGTCCAGG |
| | | GGCCAGAGCTAGGACAGAGGGGTCGGAGAAAGAGTCATTTTCCCAACACT |
| | | CCAGCTCTTGGCCAGTCCTCACACAGTCCCCTCCTGCTTCCTGCTGAGAGA |
| | | GATATCCTCATAGGTCTGGGTAAAGTCCTTCAGTCAGCTTTCATTCCCTGTC |
| | | ACCAACTTTGTCTCTGTTCTCCCTGCCCGTCTCAGGCAGCACTCCTCAGGA |

| SEQ ID NO: | DESCRIPTION | SEQUENCE |
|---|---|---|
| | | AACCTCTCCAAGAGCCAGCCTCACTGCAGCGCCCACTATTGTCCCTCTGCC |
| | | TCAAGTGTCCCATCCATGCCAGGCCCCAGGCAGGCTGCAGCTTTCCCTCA |
| | | GGGCCACACCAAAGCACTTGGGCTCAGCTGTGCTGTCCCCCTCCATCACT |
| | | GAGCTCAGGGGCAGCAGGGGTGGGGTGCCAGGAGGCCCATTCACCCTTC |
| | | TCTGGCTCTGTGTTGGACCCACCTGCCCAGCCACTGCTGCTTAGAACCTAC |
| | | CCGCTGGGAAAATGAAGCCCTCCCGGAGGGGCCACCTCAACCTGAGAGCC |
| | | TCACGGATCACAGTTGTCCCCACTCAGCTCTGCCAGCCCTCAGAGACCCAT |
| | | AGATAAAAGCTGAGCTTGGCTCGCAGAGCTGGTTCCATCTTCCATTCCCAG |
| | | AGGGGTTCAACTTCCTACCCCAACCACACAGGGAACCTCAAGGCTGAGCCA |
| | | GTGTGGGCTGCAGTGCAGACCAGCTTCCTGGACACGTCCTGCCACCTGAC |
| | | CCCAGGCTGGCCTCACTGCCCCTGGCACTCCTGACCCTATCCTCATTCCTC |
| | | CTGGCAGTGCGTGTTCTGCCATTCCGCTTTCCCTTAGCTGTCCTCTCACTG |
| | | TACTGTCAGCTTCTCCTTTTCCAGGTGCCCCCCAGGGGCTTTCCACATGAC |
| | | CCTGTCACCCCACAGCCCATCCAGCACCAATTCCAGCTCTCTGCCACCCTT |
| | | CAAAGGAGTGACAGTGCCCTGCTTCACCTCCCACTCACCCCTCAACCCAGA |
| | | GCAATCTGGCTCCAGTCTTGCCTCCTTCCCCCTAAGTACTCTAGTCACAGTT |
| | | CCAAATTCCTCCTGGTCATAAAGCCAAATGAAGCTTCCTGGTCCTCAGCGG |
| | | ACTTGCCACTTCAGCAGTACTGGACTCTCTCCTCCCAGAAACCTGTTTCCC |
| | | CTTGGCTCCTGGAGCCCACACTCTGCTGGAATCCTTCTGCCTCTCTGGCCT |
| | | GTAGCCTGGCCCTCTCTCCCAACCTGAGGTCCATTCTCTCCTGCTCCTCCA |
| | | CAAGATGTTGCTCCTTCCATTACTTCCTCCCTCTCAACCAAAGCTCTTCAT |
| | | TAGCTCTTTATCTTCTGGTTTCTTCCCCTGGGCAGACGAATGGATTCAAGAG |
| | | CCTGTGGCCCAGCAGCCCAGCACTCCAGGATCTCAGCACTTCAGCATCCC |
| | | AGTACCCTAGCATCTCAATACCCCAGCACCCCAGCACCATAGTATTCCAGC |
| | | ACCCCATTGTCCAAGCATCTCAGCACTCCAGCATCCCAGCACCCCAACACT |
| | | CCAGCAGCCCAGAATCTCAGCACCCTAGCACTGCAGCATCTCAGGACCCC |
| | | AGCACTTCAGCATCCCAGCACACTAGTACTCCAGCATCTCGGCACCCCAGC |
| | | ACCTAGGCATCCCAACACCCAGCACCCCAGCACTTAAGCATCCCACCACTA |
| | | CAGTATCTCAACACTCCAGCACCCCAGCACCATAGTGTTCCAGCACCCCAG |
| | | CATCCCAACACCCCAGCACTTAAGCATCCCAACACCTCGGCATCCCAACAC |
| | | CCCAGCACTGCAGCATCTCAGCACCTTAGCATCCCAGTGCCCTAGCATCTC |
| | | AATGCTCCAGCACACCAGTACTACAGTATTCCAGCACCCCAGCACTCCAGC |
| | | ATCTCAGCACTGCAGCACTGCCAGCACTCCAGCATCCCAAAATCCCAGCATC |
| | | CCAACACCCCAGCAGACCAGCAGACCAGCATCTCAGCACCGCAGCATCCA |
| | | AGGACTATCCCAGCATCCCAGCAACCCAGCACCTCAGCATCCCAACACCC |
| | | CAGCATTTCAGCATGGCAACACCCCAGTACCCCAGCACTTCAGCACCCCAG |
| | | TATCCCAGCATCTCAGCGACCCAGTATCACAAAACCTCAGCATCCTAGCAC |
| | | CCCAGCACCCCAGCACCTTAGCACCTTAGCATCCCAGCATCTCAGCGCCTC |
| | | AGCATCTTGATATTCTGGCTGAGGTCAGCGTGGTGTATCTAGTCAGGGTCC |
| | | TAACTTTCACTTCGCAGGGAAATGCTGCTGGACTGGGTCTCATGTTGGGCT |
| | | GAAGCTCTCTAGACCCCTTGAAGACAGCATAAAAGAGCTTGGAGACGCTGG |
| | | GTGTCCCCATGGAAGAGTTCACTCTCATCCTGCTTTGACAACAGCCTTCT |
| | | CTGGGGTCCCTCACGGGCCCCTCTTTCTTACTGCAAGTTTGTCTCTGAGAA |
| | | GACTGTGATGCAGAAGTCACTCAGCTGCCTGTGGCTCCTGAAGAGCTGAA |
| | | GGTGGAGGCCTGTAGGCCTCCCTATGAGAGGCGCAGAAAAAACCATGATT |
| | | GCTAGTGGGGAGGTGCTCCCTCTACAACCCACTCCATAATCTGCCCCCGC |
| | | CCAGCTCTGAGGCCAGCCCCAGGGGAAAATGCCAGATCCCCAGGGAGGT |
| | | GTGTGAGACCTCAGGGGCTCCCTCCTCCCTTACAGCAGGCTCAGGCCCCT |
| | | GGGGGCCTCAGGGCCAAGGTCTGTGGGTAAGCTACTATCTCTCACTTGTC |
| | | CTCTAGCCACAAAAGCCAGGGAGATCTGGCAATGGACATGAGGTTCTGAA |
| | | GAAGCACATATGACTGGCTTCCTAATGCGTGGTTGTTCAGTGATTCAATAAA |
| | | CACGCATGGGCCAGGCATGGGGAAATAGACAAACATGATCCCCAACCTCT |
| | | CCCAGAGTGAACTGGGAGGGAGGAGTGTTCATCCCTCAGGATTACACCAG |
| | | AGAAACAAACCAGCAGGAGATATATATGGTTTTGGGGGGTCAAGAAAGAGG |
| | | AAAAACCTGGCAAGGCAAGTCCAAAATCATAGGACAGGCTGTCAGGAAGG |
| | | GCAGCCTGGAACCTCTCAAGCAGGAGCTGATGCTGCAGTCCACAGGCAGA |
| | | ATTTCTTCTTCCTCGGGGAAATCTCAGCTTTGTTCTTAAGGCCTTTCAACTG |
| | | ATTGGCTGAGGTCTGCCCCTTCCCCCACATTCTCCAGGATAATCTTCCTTAC |
| | | TTAAAGTCAACTATTAATCACAGCTACAAAATCCCTTCACAGCTACACATAG |
| | | ATCAGTGTTTGATTGACGAACAGCCCCTACAGCCTAGCCAAGTTGACACAT |
| | | AAAACTAACCATCACAGGGGGACAAATGATGTAAACACATCAACAAATAAA |
| | | CAGTAACAAGTTAAGGTCTATGGAAAAAACACAGAAGGGGCAGAGAGAAAG |
| | | AAAGCAAGAAGGAGAGTCCCAGTTTGCTAGGGCTTGTGGGAAGTGGGGAG |
| | | CAGTTCTCTTTAGCTAGGATATTTGGGAAAGGCATATCTGAAGGAGTGATAT |
| | | TTGAGCTTAGATTAAAAGATGGGAAGGAGCAAGCCATGCAAAGAGCTAGGA |
| | | TGTTCCAAGCAGAGACGGAACAGCAAGTGCAAATGTCAGGAGGAATAGAA |
| | | GGAGGCTGGTGGGTGGGTCCAGTGAGCAAGAGGAGGGCAGGCAGGAGA |
| | | GGGGATGGGGAGGTGGGCAGGCCCAGACCACCCAGGGCCCTGGAGACTA |
| | | TCCTGATCCAACAAGGGAAGCCTTGAGTCACTTCAGTGTTCCATGTGGAGAA |
| | | TGGACCTCAGACTGAATGAGGGAGGCAGTAAGGAGGGCCTCTACCTCCAG |
| | | GGCTTCGCCCTGTGGACTGCGCATAGACATCTCCAACTCAGAAAGTCTGAA |
| | | CCAAACTTTCCATAGTTCCCCCAAGTCTGGGCATCCTCCTACTCAGTGAAA |
| | | GGCAGCCATCACACCTCCCTGCCCTGCTCCCGGATGCCCCAAATCCTCTT |
| | | GGTCTCCAAGTCCAGAACCTGAGACTTGTCCTTGATGTTTGTCTTTCCCTCA |

-continued

| SEQ ID NO: | DESCRIPTION | SEQUENCE |
|---|---|---|
| | | CCCTTTCTGTATTCTGGGAAGATGGGTTTTTTTCCCCCAGATGAATCTGTAA |
| | | AACTTCTGTGATCACAATAAAAATTCTGGCAGTATTATTTTCTGGAACATGAC |
| | | AAAGTGATTCAAAATTATTTATCTGGAAGACTACAAAACAAGAATAGCCAGG |
| | | AAATTTCTAAAAAGAAAGAAGAAGGAGGAGGAGAAAGAAGGAGGAGGAAAA |
| | | GGAGGAGAAGAAGAAAAGAAAAAGAACCAAGAAAGGGTTCTAGCTCTACCA |
| | | AATATTAAAACATATCATGAAGCTATTTAAAACAATATGGTTGTGGATACTGA |
| | | AAAAGATGTGAATAAAGTGGAAGGAAAATAAATAGAAATGCACATGGGGAT |
| | | TGAGACTGTGAAAAGGCAGCATCTCACATCAGTGAGGGATGTTCAACACC |
| | | TGGTGTTGGGAAAACTGGCTAGTCATTTAAACCAAACAACTGGGTCCTCTA |
| | | CCTCACTCCTGACATTAAGATACATTTAGATGATTCAAAGAGTAAGACAGAA |
| | | AAAATAACACGTGAAAACACTATCAGAAAACAACGTGGGCCAGGTGTGGTG |
| | | GGTCACGCCTGTAATCCCAGCACTTTGGGAGGCCGAGGCAGACAGATCAC |
| | | CTGAGGTGGGGAGTTCAAGACCAGCCTGACCAACATGGTGAAATCCTGTCT |
| | | CTACTAAAAATACAAAATTAGCTGAGCGTGGTGGCGCATGCCTGTAATCCC |
| | | AGCTACTCAGGAGGCCGAGGCAGGAGAATCACTTGAACCTGGGAGGCAGA |
| | | GGTTGTGGTGAGCCGAGATCACGCCATTGCACTCCAGCCTGGGCAACAAG |
| | | AGTGAAAATCCATCTAAAAAAAAAAAAAAAGCCAAGGTGGATATTTTTATA |
| | | GTATCAGGGTAGATCAAGCTTCTCCAATCATGACATGAAACCCAGAAACCA |
| | | TAAAAGAAAAGAATGATAAAATTGCCCACGTAAAGTAAAAGCTTGCACACA |
| | | GAAAAACACCATACAGGTTACAAGATGAGCAGCAAAATCAGAGAAAAAACA |
| | | TTGCAATTCAGGACACACAGAGGCTATTGTTCCTAATATTTAAAAATAAAAG |
| | | TAGTGGATTGTCTACAAAAAGATGAAGACAAGAATTTCAGAAAACCAAATAC |
| | | TGCATGTTTTCACTTACAAGTGGAAGCTAAACACTGAGTACACGTGTACACA |
| | | AAGAATGGAACCATAGGCCAGGCACCGTGGCTCACGCCTGTAATCCCAGT |
| | | ACTTTGCGAGGCCGAAGCGGGCGGATCACCTGAGGTGAGGAGTTCGAGAC |
| | | CATCCTGGCCAACATGGTGAAACCCAGTCTCTACTAAAAATACAAAAATTAG |
| | | CCGGGCGTGGTGGGTGCCTGTAATCCCAGCTACTCGGGAGGCTGCG |
| | | GCAGTAGAATCGCTTGAACCCGGAGGTGGACCTTGCAGTGAGCCGAGAT |
| | | CGCACCACTGCACTCCAGCCTGGGCAACAGAGTGAGACTCCATCTCAAAAA |
| | | AAAAAAAAGGAATAGAACAATAGACACTGGGGCCTACTTGAGGGAGGAG |
| | | GGTGAGGATCAAAAACCTGCCTATCAGGTACTATGCTTATTACCTGGGTGG |
| | | TGAAATAATCTGTACACCAAACCCCAGTGACATGCAATTTACCGATGTAACA |
| | | AACCTGCCCATGTACCCGCTGAACCTAAAATAAAAGTTGGAAAAAAATATAG |
| | | AAATTTTCTTTGTAATAGCCAAAAACTGCAAACAGCCCAGGTGTCTATTAGT |
| | | AGAATGCATAAACAAACTCGGGCATGTTCATACAATGTAAAACTACTCATCA |
| | | ATAAAAAGTGATACTTCTCAGCAATGAAAAGAAACTAGCTACTGATACCAGC |
| | | TACAACATGGATGGATTTCAAGTGCTTTATGATGAGAGCAAGAAGCCAGAC |
| | | ACAAAAGTGTCTATATATATATACAGTATATATACGTATATATACACATATATA |
| | | CAGTATATATATACATATACATGTATATATATACTGTATATATACTGTATATAT |
| | | ATACACAGTATATATATACATATATACAGTGTATATATACTGTGTATATATAC |
| | | ATGTATATATACTGTGTATATATACATGTATATATACTGTGTATATATACATGT |
| | | ATATATACTGTGTATATATACATGTATATATATGTATACTGTATATATACTGTA |
| | | TATATATACACATATATACAGTATATATATACAGTATATACTGTATATATAC |
| | | AGTATATACGTGTATATATACATATATACAGTATATATGTAAATATACATATAT |
| | | ACAGTATATATGTAAATATACATATATACATGTATATATATACACTATATATAT |
| | | ACATATATAGTGTATATATACATATATACATGTATATATTTACTATATGATTCC |
| | | ATTTATATAAAGTGCCAAAACAGTCAAAAATAATCTATGTGGAAAAAATCAAC |
| | | AAAGGGATCCCCCGGGCTGCAGGAATTCGATGGCGCGCCGACGTCGCAT |
| | | GCAGTTAGGGATAACAGGGTAATACGACCATGGCATGTCCTCTAGACTCGA |
| | | GCGGCCGCAATAAAATATCTTTATTTTCATTACATCTGTGTGTTGGTTTTTTG |
| | | TGTGAATCGTAACTAACATACGCTCTCCATCAAAACAAAACGAAACAAAACA |
| | | AACTAGCAAAATAGGCTGTCCCCAGTGCAAGTGCAGGTGCCAGAACATTTC |
| | | TCTATCGAAGGATCTGCGATCGCTCCGGTGCCCGTCAGTGGGCAGAGCGC |
| | | ACATCGCCACAGTCCCCGAGAAGTTGGGGGGAGGGGTCGGCAATTGAAC |
| | | CGGTGCCTAGAGAAGGTGGCGCGGGGTAAACTGGGAAAGTGATGTCGTGT |
| | | ACTGGCTCCGCCTTTTTCCCGAGGGTGGGGGAGAACCGTATATAAGTGCA |
| | | GTAGTCGCCGTGAACGTTCTTTTTCGCAACGGGTTTGCCGCCAGAACACAG |
| | | CTGAAGCTTCGAGGGGCTCGCATCTCTCCTTCACGCGCCCGCCGCCCTAC |
| | | CTGAGGCCGCCATCCACGCCGGTTGAGTCGCGTTCTGCCGCCTCCCGCCT |
| | | GTGGTGCCTCCTGAACTGCGTCCGCCGTCTAGGTAAGTTTAAAGCTCAGGT |
| | | CGAGACCGGGCCTTTGTCCGGCGCTCCCTTGGAGCCTACCTAGACTCAGC |
| | | CGGCTCTCCACGCTTTGCCTGACCCTGCTTGCTCAACTCTACGTCTTTGTTT |
| | | CGTTTTCTGTTCTGCGCCGTTACAGATCCAGCTGTGACCGGCGCCTACGT |
| | | AAGTGATATCTACTAGATTTATCAAAAAGAGTGTTGACTTGTGAGCGCTCAC |
| | | AATTGATACTTAGATTCATCGAGAGGGACACGTCGACTACTAACCTTCTTCT |
| | | CTTTCCTACAGCTGAGATCACCGGCGAAGGAGGGCCACCATGGGTCACCA |
| | | GCAGTTGGTCATCTCTTGGTTTTCCCTGGTTTTTCTGGCATCTCCCCTCGTG |
| | | GCCATATGGGAACTGAAGAAAGATGTTTATGTCGTAGAATTGGATTGGTATC |
| | | CGGATGCCCCTGGAGAAATGGTGGTCCTCACCTGTGACACCCCTGAAGAA |
| | | GATGGTATCACCTGGACCTTGGACCAGAGCAGTGAGGTCTTAGGCTCTGG |
| | | CAAAACCCTGACCATCCAAGTCAAAGAGTTTGGAGATGCTGGCCAGTACAC |
| | | CTGTCACAAAGGAGGCGAGGTTCTAAGCCATTCGCTCCTGCTGCTTCACAA |
| | | AAAGGAAGATGGAATTTGGTCCACTGATTTTAAAGGACCAGAAAGAACC |
| | | CAAAAATAAGACCTTTCTAAGATGCGAGGCCAAGAATTATTCTGGACGTTTC |

-continued

| Sequences | |
|---|---|
| SEQ ID NO: DESCRIPTION | SEQUENCE |
| | ACCTGCTGGTGGCTGACGACAATCAGTACTGATTTGACATTCAGTGTCAAA |
| | AGCAGCAGAGGCTCTTCTGACCCCCAAGGGGTGACGTGCGGAGCTGCTAC |
| | ACTCTCTGCAGAGAGAGTCAGAGGGGACAACAAGGAGTATGAGTACTCAG |
| | TGGAGTGCCAGGAGGACAGTGCCTGCCCAGCTGCTGAGGAGAGTCTGCC |
| | CATTGAGGTCATGGTGGATGCCGTTCACAAGCTCAAGTATGAAAACTACAC |
| | CAGCAGCTTCTTCATCAGGGACATCATCAAACCTGACCCACCCAAGAACTT |
| | GCAGCTGAAGCCATTAAAGAATTCTCGGCAGGTGGAGGTCAGCTGGGAGT |
| | ACCCTGACACCTGGAGTACTCCACATTCCTACTTCTCCCTGACATTCTGCGT |
| | TCAGGTCCAGGGCAAGAGCAAGAGAGAAAAGAAAGATAGAGTCTTCACGG |
| | ACAAGACCTCAGCCACGGTCATCTGCCGCAAAAATGCCAGCATTAGCGTGC |
| | GGGCCCAGGACCGCTACTATAGCTCATCTTGGAGCGAATGGGCATCTGTG |
| | CCCTGCAGTGTTCCTGGAGTAGGGGTACCTGGGGTGGGCGCCAGAAACCT |
| | CCCCGTGGCCACTCCAGACCCAGGAATGTTCCCATGCCTTCACCACTCCCA |
| | AAACCTGCTGAGGGCCGTCAGCAACATGCTCCAGAAGGCCAGACAAACTC |
| | TAGAATTTTACCCTTGCACTTCTGAAGAGATTGATCATGAAGATATCACAAA |
| | AGATAAAACCAGCACAGTGGAGGCCTGTTTACCATTGGAATTAACCAAGAA |
| | TGAGAGTTGCCTAAATTCCAGAGAGACCTCTTTCATAACTAATGGGAGTTGC |
| | CTGGCCTCCAGAAAGACCTCTTTTATGATGGCCCTGTGCCTTAGTAGTATTT |
| | ATGAAGACTTGAAGATGTACCAGGTGGAGTTCAAGACCATGAATGCAAAGC |
| | TGCTGATGGATCCTAAGAGGCAGATCTTTCTAGATCAAAACATGCTGGCAG |
| | TTATTGATGAGCTGATGCAGGCCCTGAATTTCAACAGTGAGACTGTGCCAC |
| | AAAAATCCTCCCTTGAAGAACCGGATTTTTATAAAACTAAAATCAAGCTCTG |
| | CATACTTCTTCATGCTTTCAGAATTCGGGCAGTGACTATTGATAGAGTGATG |
| | AGCTATCTGAATGCTTCCTAAAAAGCGAGGTCCCTCCAAACCGTTGTCATTT |
| | TTATAAAACTTTGAAATGAGGAAACTTTGATAGGATGTGGATTAAGAACTAG |
| | GGAGGGGCTAGCTCGACATGATAAGATACATTGATGAGTTTGGACAAACCA |
| | CAACTAGAATGCAGTGAAAAAAATGCTTTATTTGTGAAATTTGTGATGCTATT |
| | GCTTTATTTGTGAAATTTGTGATGCTATTGCTTTATTTGTAACCATTATAAGC |
| | TGCAATAAACAAGTTAACAACAACAATTGCATTCATTTTATGTTTCAGGTTCA |
| | GGGGGAGGTGTGGGAGGTTTTTTAAAGCAAGTAAAACCTCTACAAATGTGG |
| | TAGATCCATTTATTAGCTAGGAGTTTCAGAAAAGGGGGCCTGAGTGGCCCC |
| | TTTTTTCAACTTAATTAACCTGCAGGGCTGAAATAACCTCTGAAAGAGGAA |
| | CTTGGTTAGGTACCTTCTGAGGCTGAAAGAACCAGCTGTGGAATGTGTGTC |
| | AGTTAGGGTGTGGAAAGTCCCCAGGCTCCCCAGCAGGCAGAAGTATGCAA |
| | AGCATGCATCTCAATTAGTCAGCAACCAGGTGTGGAAAGTCCCCAGGCTCC |
| | CCAGCAGGCAGAAGTATGCAAAGCATGCATCTCAATTAGTCAGCAACCATA |
| | GTCCCACTAGTTTCATCACCACCGCCACCCCCCGCCCCCCCGCCATCTG |
| | AAAGGGTTCTAGGGGATTTGCAACCTCTCTCGTGTGTTTCTTCTTTCCGAGA |
| | AGCGCCGCCACACGAGAAAGCTGGCCGCGAAAGTCGTGCTGGAATCACTT |
| | CCAACGAAACCCCAGGCATAGATGGGAAAGGGTGAAGAACACGTTGTCAT |
| | GGCTACCGTTTCCCCGGTCACGGAATAAACGCTCTCTAGGATCCGGAAGTA |
| | GTTCCGCCGCGACCTCTCTAAAAGGATGGATGTGTTCTCTGCTTACATTCAT |
| | TGGACGTTTTCCCTTAGAGGCCAAGGCCGCCCAGGCAAAGGGGCGGTCCC |
| | ACGCGTGAGGGCCCGCGGAGCCATTTGATTGGAGAAAAGCTGCAAACCC |
| | TGACCAATCGGAAGGAGCCACGCTTCGGGCATCGGTCACCGCACCTGGAC |
| | AGCTCCGATTGGTGGACTTCCGCCCCCCTCACGAATCCTCATTGGGTGC |
| | CGTGGGTGCGTGGTGCGGCGCGATTGGTGGGTTCATGTTTCCCGTCCCCC |
| | GCCCGCGAGAAGTGGGGGTGAAAAGCGGCCCGACCTGCTTGGGGTGTAG |
| | TGGGCGGACCGCGCGGCTGGAGGTGTGAGGATCCGAACCCAGGGGTGGG |
| | GGGTGGAGGCGGCTCCTGCGATCGAAGGGGACTTGAGACTCACCGGTCG |
| | CACGTCATGAATCTAGAACCATGGCTTCGTACCCCGGCCATCAGCACGCGT |
| | CTGCGTTCGACCAGGCTGCGCGTTCTCGCGGCCATAGCAACCGACGTACG |
| | GCGTTGCGCCCTCGCCGGCAGCAAGAAGCACGGAAGTCCGCCCGGAGC |
| | AGAAAATGCCCACGCTACTGCGGGTTTATATAGACGGTCCCCACGGGATG |
| | GGGAAAACCACCACCACGCAACTGCTGGTGGCCCTGGGTTCGCGCGACGA |
| | TATCGTCTACGTACCCGAGCCGATGACTTACTGGCGGGTGCTGGGGGCTT |
| | CCGAGACAATCGCGAACATCTACACCACACAACACCGCCTTGACCAGGGT |
| | GAGATATCGGCCGGGGACGCGGCGGTGGTAATGACAAGCGCCCAGATAA |
| | CAATGGGCATGCCTTATGCCGTGACCGACGCCGTTCTGGCTCCTCATATCG |
| | GGGGGGAGGCTGGGAGCTCACATGCCCCGCCCCCGGCCCTCACCCTCAT |
| | CTTCGACCGCCATCCCATCGCCGCCTCCTGTGCTACCCGGCCGCGCGAT |
| | ACCTTATGGGCAGCATGACCCCCCAGGCCGTGCTGGCGTTCGTGGCCCTC |
| | ATCCCGCCGACCTTGCCCGGCACAAACATCGTGTTGGGGGCCCTTCCGGA |
| | GGACAGACACATCGACCGCCTGGCCAAACGCCAGCGCCCCGGCGAGCGG |
| | CTTGACCTGGCTATGCTGGCCGCGATTCGCCGCGTTTACGGGCTGCTTGC |
| | CAATACGGTGCGGTATCTGCAGGGCGGCGGGTCGTGGCGGGAGGATTGG |
| | GGACAGCTTTCGGGGACGGCCGTGCCGCCCCAGGGTGCCGAGCCCCAGA |
| | GCAACGCGGGCCCACGACCCCATATCGGGGACAGTTATTTACCCTGTTTC |
| | GGGCCCCCGAGTTGCTGGCCCCAACGGCGACCTGTACAACGTGTTTGCC |
| | TGGGCCTTGGACGTCTTGGCCAAACGCCTCCGTCCCATGCACGTCTTTATC |
| | CTGGATTACGACCAATCGCCCGCCGGCTGCCGGGACGCCCTGCTGCAACT |
| | TACCTCCGGGATGATCCAGACCCACGTCACCACCCCAGGCTCCATACCGA |
| | CGATCTGCGACCTGGCGCGCACGTTTGCCCGGGAGATGGGGGAGGCTAA |
| | CTGAGTATACCCTAGGATTATCCCTAATACCTGCCACCCCACTCTTAATCAG |

| SEQ ID NO: | DESCRIPTION | SEQUENCE |
|---|---|---|
| | | TGGTGGAAGAACGGTCTCAGAACTGTTTGTTTCAATTGGCCATTTAAGTTTA |
| | | GTAGTAAAAGACTGGTTAATGATAACAATGCATCGTAAAACCTTCAGAAGGA |
| | | AAGGAGAATGTTTTGTGGACCACTTTGGTTTTCTTTTTTGCGTGTGGCAGTT |
| | | TTAAGTTATTAGTTTTTAAAATCAGTACTTTTTAATGGAAACAACTTGACCAA |
| | | AAATTTGTCACAGAATTTTGAGACCCATTAAAAAAGTTAAATGAGAAACCTG |
| | | TGTGTTCCTTTGGTCAACACCGAGACATTTAGGTGAAAGACATCTAATTCTG |
| | | GTTTTACGAATCTGGAAACTTCTTGAAAATGTAATTCTTGAGTTAACACTTCT |
| | | GGGTGGAGAATAGGGTTGTTTTCCCCCCACATAATTGGAAGGGGAAGGAAT |
| | | ATCATTTAAAGCTATGGGAGGGTTTCTTTGATTACAACACTGGAGAGAAATG |
| | | CAGCATGTTGCTGATTGCCTGTCACTAAAACAGGCCAAAAACTGAGTCCTT |
| | | GGGTTGCATAGAAAGCTGCCTGCAGGCGTTACATAACTTACGGTAAATGGC |
| | | CCGCCTGGCTGACCGCCCAACGACCCCCGCCCATTGACGTCAATAATGAC |
| | | GTATGTTCCCATAGTAACGCCAATAGGGACTTTCCATTGACGTCAATGGGT |
| | | GGAGTATTTACGGTAAACTGCCCACTTGGCAGTACATCAAGTGTATCATATG |
| | | CCAAGTACGCCCCCTATTGACGTCAATGACGGTAAATGGCCCGCCTGGCAT |
| | | TATGCCCAGTACATGACCTTATGGGACTTTCCTACTTGGCAGTACATCTACG |
| | | TATTAGTCATCGCTATTACCATGATGATGCGGTTTTGGCAGTACATCAATGG |
| | | GCGTGGATAGCGGTTTGACTCACGGGGATTTCCAAGTCTCCACCCCATTGA |
| | | CGTCAATGGGAGTTTGTTTTGACTAGTTACCGGCGGAAACGGTCTCGGGTT |
| | | GAGAGGTCACCCGAGGGACAGGCAGCTGCTGAACCAATAGGACCGGCGC |
| | | ACAGGGCGGATGCTGCCCCTCATTGGCGGCCGTTGAGAGTGACCAAGAGC |
| | | CAATGAGTCAGCCCGGGGGGCGTAGCAGTGACGTAAGTTGCGGAGGAGG |
| | | CCGCTTCGAATCGGCAGCGGCCAGCTTGGTGGCATGGACCAATCAGCGTC |
| | | CTCCAACGAGGAGCGCCTTCGCCAATCGGAGGCCTCCACGACGGGGCTG |
| | | GGGGGAGGGTATATAAGCCGAGTCGGCGGCGGCGCGCTCCACACGGGCC |
| | | GAGACCACAGCGACGGGAGCGTCTGCCTCTGCGGGGCCGAGAGGTAAGC |
| | | GCCGCGGCCTGCCCTTTCCAGGCCAACTCGGAGCCCGTCTCGTGGCTCCG |
| | | CCTGATCGGGGGCTCCTGTCGCCCTCAGATCGGTCGGAACGCCGTCGCG |
| | | CTCCGGGACTACAAGCCTGTTGCTGGGCCCGGAGACTGCCGAAGGACCG |
| | | CTGAGCACTGTCCTCAGCGCCGGCACCATGGATTGGATCTGGCGGATCCT |
| | | GTTCCTTGTGGGAGCTGCCACAGGCGCCCATTCTGAAGTTCAGCTGGTTCA |
| | | GTCTGGCGCCGAAGTGAAGAAACCTGGCGCCTCTGTGAAGGTGTCCTGCA |
| | | AAGCTTCTGGCGGCACCTTCAGCAGCTACGCCATCTCTTGGGTTCGACAG |
| | | GCCCCTGGACAAGGCCTGGAATGGATGGGCAGAATCATCCCCATCCTGGG |
| | | AATCGCCAACTACGCCCAGAAATTCCAGGGCAGAGTGACCATCACCGCCG |
| | | ACAAGAGCACAAGCACCGCCTACATGGAACTGAGCAGCCTGAGAAGCGAG |
| | | GACACCGCCGTGTACTACTGTGCCAGAAGCGGCCACGGCTACAGCTACGG |
| | | CGCCTTTGATTATTGGGGCCAGGGCACCCTGGTCACCGTTTCTAGCGGAG |
| | | GCGGAGGTAGTGGTGGCGGAGGTTCAGGCGGCGGAGGATCTCAATCTGT |
| | | GCTGACACAGCCTCCAAGCGTGTCAGGTGCTCCTGGCCAGAGAGTGACAA |
| | | TCAGCTGTACAGGCAGCAGCAGCAACATCGGAGCCGGCTATGACGTGCAC |
| | | TGGTATCAGCAGCTGCCTGGCACAGCCCCTAAACTGCTGATCTACGGCAAC |
| | | AGCAACAGACCCAGCGGCGTGCCCGATAGATTTTCCGGCTCTAAGAGCGG |
| | | CACAAGCGCCAGCCTGGCTATTACTGGACTGCAGGCCGAGGACGAGGCC |
| | | GACTACTACTGTCAGAGCTACGACAGCAGCCTGTCCGGCAGCTACGTTGT |
| | | GTTTGGCGGCGGAACAAAGCTGACCGTGCTGGAAGCCAAGAGCTGCGACA |
| | | AGACCCACACCTGTCCTCCATGTCCTGCTCCAGAACTGCTCGGCGGACCTT |
| | | CCGTGTTCCTGTTTCCTCCAAAGCCTAAGGACACCCTGATGATCAGCAGAA |
| | | CCCCTGAAGTGACCTGCGTGGTGGTGGATGTGTCCCACGAGGACCCAGAA |
| | | GTGAAGTTCAATTGGTACGTGGACGGCGTGGAAGTGCACAACGCCAAGAC |
| | | CAAGCCTAGAGAGGAACAGTACAACAGCACCTACAGAGTGGTGTCCGTGC |
| | | TGACAGTGCTGCACCAGGATTGGCTGAACGGCAAAGAGTACAAGTGCAAG |
| | | GTGTCCAACAAGGCCCTGCCTGCTCCTATCGAGAAACCATCAGCAAGGC |
| | | CAAGGGCCAGCCTAGGGAACCCCAGGTTTACACACTGCCACCTAGCAGGG |
| | | ACGAGCTGACCAAGAATCAGGTGTCCCTGACCTGCCTGGTCAAGGGCTTC |
| | | TACCCTTCCGATATCGCCGTGGAATGGGAGAGCAATGGCCAGCCAGAGAA |
| | | CAACTACAAGACAACCCCTCCTGTGCTGGACAGCGACGGCTCATTCTTCCT |
| | | GTACTCCAAGCTGACTGTGGACAAGAGCCGGTGGCAGCAGGGCAATGTGT |
| | | TCAGCTGTAGCGTGATGCACGAGGCCCTGCACAACCACTACACACAGAAG |
| | | TCCCTGTCTCTGAGCCCCGGAAAAGGTGGCGGTGGCTCTTACCCTTACGA |
| | | CGTGCCAGATTACGCCGGCTATCCCTACGATGTGCCTGACTATGCTGGCTA |
| | | CCCCTATGACGTCCCCGACTACGCTTAACTAGCTACGGAATTCCGGCTAGC |
| | | TGGCCAGACATGATAAGATACATTGATGAGTTTGGACAAACCACAACTAGA |
| | | ATGCAGTGAAAAAAATGCTTTATTTGTGAAATTTGTGATGCTATTGCTTTATT |
| | | TGTAACCATTATAAGCTGCAATAAACAAGTTAACAACAACAATTGCATTCATT |
| | | TTATGTTTCAGGTTCAGGGGGAGGTGTGGGAGGTTTTTTAAAGCAAGTAAA |
| | | ACCTCTACAAATGTGGTATGGAAATGTTAATTAACTAGCCATGACCAAAATC |
| | | CCTTAACGTGAGTTTTCGTTCCACTGAGCGTCAGACCCCGTAGAAAAGATC |
| | | AAAGGATCTTCTTGAGATCCTTTTTTTCTGCGCGTAATCTGCTGCTTGCAAA |
| | | CAAAAAAACCACCGCTACCAGCGGTGGTTTGTTTGCCGGATCAAGAGCTAC |
| | | CAACTCTTTTTCCGAAGGTAACTGGCTTCAGCAGAGCGCAGATACCAAATA |
| | | CTGTTCTTCTAGTGTAGCCGTAGTTAGGCCACCACTTCAAGAACTCTGTAG |
| | | CACCGCCTACATACCTCGCTCTGCTAATCCTGTTACCAGTGGCTGCTGCCA |
| | | GTGGCGATAAGTCGTGTCTTACCGGGTTGGACTCAAGACGATAGTTACCGG |

| SEQ ID NO: | DESCRIPTION | SEQUENCE |
|---|---|---|
| | | ATAAGGCGCAGCGGTCGGGCTGAACGGGGGGTTCGTGCACACAGCCCAG<br>CTTGGAGCGAACGACCTACACCGAACTGAGATACCTACAGCGTGAGCTATG<br>AGAAAGCGCCACGCTTCCCGAAGGGAGAAAGGCGGACAGGTATCCGGTAA<br>GCGGCAGGGTCGGAACAGGAGAGCGCACGAGGGAGCTTCCAGGGGGAAA<br>CGCCTGGTATCTTTATAGTCCTGTCGGGTTTCGCCACCTCTGACTTGAGCG<br>TCGATTTTGTGATGCTCGTCAGGGGGGCGGAGCCTATGGAAAAACGCCA<br>GCAACGCGGCCTTTTTACGGTTCCTGGCCTTTTGCTGGCCTTTTGCTCAGG<br>GTTCGAAATCGATAAGCTTGGATCCGGAGAGCTCCCAACGCGTCGGCTAG<br>CTAGTAGGGATAACAGGGTAATAAGCGTCGACGGCGCGCCCCTAGGGGCC<br>GGCCTTAATTAAATCAAGCTTATCGATACCGTCGAACCTCGAGGGGGGGCA<br>TCACTCCGCCCTAAAACCTACGTCACCCGCCCCGTTCCCACGCCCCGCGC<br>CACGTCACAAACTCCACCCCCTCATTATCATATTGGCTTCAATCCAAAATAA<br>GGTATATTATTGATGATGTTT |
| 51 | ICOSTAT | TAACATCATCAATTATACCTTCCATTTTGGATTGAAGCCAATATGATAATGAG<br>GGGGTGGAGTTTGTGACGTGGCGCGGGGCGTGGGAACGGGGCGGGTGA<br>CGTAGTAGTGTGGCGGAAGTGTGATGTTGCAAGTGTGGCGGAACACATGT<br>AAGCGACGGATGTGGCAAAAGTGACGTTTTTGGTGTGCGCCGGTGTACAC<br>AGGAAGTGACAATTTTCGCGCGGTTTTAGGCGGATGTTGTAGTAAATTTGG<br>GCGTAACCGAGTAAGATTTGGCCATTTTCGCGGGAAAACTGAATAAGAGGA<br>AGTGAAATCTGAATAATTTTGTGTTACTCATAGCGCGTAATATTTGTCTAGG<br>GCCGCGGGGACTTTGACCGTTTACGTGGAGACTCGCCCAGGTGTTTTTCTC<br>AGGTGTTTTCCGCGTACGTCGGCGGCTCGTGGCTCTTCCGGGAAAAGGAT<br>TCTCGGAAAGTGGTTCGAGTACGTCGGCGGCTCGTGGCTCTTCCGGGAAA<br>AGGATTCTCGGAAAGTGGTTCGAAGTACGTCGACCACAAACCCCGCCCAG<br>CGTCTTGTCATTGGCGTCGACGCTGTACGGGGTCAAAGTTGGCGTTTTATT<br>ATTATAGTCAGCTGACGTGTAGTGTATTTATACCCGGTGAGTTCCTCAAGAG<br>GCCACTCTTGAGTGCCAGCGAGTAGAGTTTTCTCCTCCGAGCCGCTCCGA<br>CACCGGGACTGAAAATGAGACATATTATCTGCCACGGAGGTGTTATTACCG<br>AAGAAATGGCCGCCAGTCTTTTGGACCAGCTGATCGAAGAGGTACTGGCT<br>GATAATCTTCCACCTCCTAGCCATTTTGAACCACCTTACCCTTCACGAACTGT<br>ATGATTTAGACGTGACGGCCCCCGAAGATCCCAACGAGGAGGCGGTTTCG<br>CAGATTTTTCCCGACTCTGTAATGTTGGCGGTGCAGGAAGGGATTGACTTA<br>CTCACTTTTCCGCCGGCGCCCGGTTCTCCGGAGCCGCCTCACCTTTCCCG<br>GCAGCCCGAGCAGCCGGAGCAGAGAGCCTTGGGTCCGGTTTCTATGCCAA<br>ACCTTGTACCGGAGGTGATCGATCCACCCAGTGACGACGAGGATGAAGAG<br>GGTGAGGAGTTTGTGTTAGATTATGTGGAGCACCCCGGGCACGGTTGCAG<br>GTCTTGTCATTATCACCGGAGGAATACGGGGGACCCAGATATTATGTGTTC<br>GCTTTGCTATATGAGGACCTGTGGCATGTTTGTCTACAGTAAGTGAAAATTA<br>TGGGCAGTGGGTGATAGAGTGGTGGGTTTGGTGTGGTAATTTTTTTTTAAT<br>TTTTACAGTTTTGTGGTTTAAAGAATTTTGTATTGTGATTTTTTTAAAAGGTCC<br>TGTGTCTGAACCTGAGCCTGAGCCCGAGCCAGAACCGGAGCCTGCAAGAC<br>CTACCCGCCGTCCTAAAATGGCGCCTGCTATCCTGAGACGCCCGACATCA<br>CCTGTGTCTAGAGAATGCAATAGTAGTACGGATAGCTGTGACTCCGGTCCT<br>TCTAACACACCTCCTGAGATACACCCGGTGGTCCCGCTGTGCCCCATTAAA<br>CCAGTTGCCGTGAGAGTTGGTGGGCGTCGCCAGGCTGTGGAATGTATCGA<br>GGACTTGCTTAACGAGCCTGGGCAACCTTTGGACTTGAGCTGTAAACGCCC<br>CAGGCCATAAGGTGTAAACCTGTGATTGCGTGTGTGGTTAACGCCTTTGTT<br>TGCTGAATGAGTTGATGTAAGTTTAATAAAGGGTGAGATAATGTTTAACTTG<br>CATGGCGTGTTAAATGGGGCGGGGCTTAAAGGGTATATAATGCGCCGTGG<br>GCTAATCTTGGTTACATCTGACCTCATGGAGGCTTGGGAGTGTTTGGAAGA<br>TTTTTCTGCTGTGCGTAACTTGCTGGAACAGAGCTCTAACAGTACCTCTTGG<br>TTTTGGAGGTTTCTGTGGGCTCATCCCAGGCAAAGTTAGTCTGCAGAATT<br>AAGGAGGATTACAAGTGGGAATTTGAAGAGCTTTTGAAATCCTGTGGTGAG<br>CTGTTTGATTCTTTGAATCTGGGTCACCAGGCGCTTTTCCAAGAGAAGGTC<br>ATCAAGACTTTGGATTTTTCCACACCGGGGCGCGCTGCGGCTGCTGTTGCT<br>TTTTTGAGTTTTATAAAGGATAAATGGAGCGAAGAAACCCATCTGAGCGGG<br>GGGTACCTGCTGGATTTTCTGGCCATGCATCTGTGGAGAGCGGTTGTGAG<br>ACACAAGAATCGCCTGCTACTGTTGTCTTCCGTCCGCCCGGCGATAATACC<br>GACGGAGGAGCAGCAGCAGCAGGAGGAAGCCAGGCGGCGGCGGCA<br>GGAGCAGAGCCCATGAACCCGAGAGCCGGCCTGGACCCTCGGGAATGA<br>ATGTTGTACAGGTGGCTGAACTGTATCCAGAACTGAGACGCATTTTGACAA<br>TTACAGAGGATGGGCAGGGGCTAAAGGGGGTAAAGAGGGAGCGGGGGGC<br>TTGTGAGGCTACAGAGGAGGCTAGGAATCTAGCTTTTAGCTTAATGACCAG<br>ACACCGTCCTGAGTGTATTACTTTTCAACAGATCAAGGATAATTGCGCTAAT<br>GAGCTTGATCGCTGGCGCAGAAGTATTCCATAGAGCAGCTGACCACTTAC<br>TGGCTGCAGCCAGGGGATGATTTTGAGGAGGCTATTAGGGTATATGCAAAG<br>GTGGCACTTAGGCCAGATTGCAAGTACAAGATCAGCAAACTTGTAAATATC<br>AGGAATTGTTGCTACATTTCTGGGAACGGGGCCGAGGTGGAGATAGATAC<br>GGAGGATAGGGTGGCCTTTAGATGTAGCATGATAAATATGTGGCCGGGGG<br>TGCTTGGCATGGACGGGGTGGTTATTATGAATGTAAGGTTTACTGGCCCCA<br>ATTTTAGCGGTACGGTTTTCCTGGCCAATACCAACCTTATCCTACACGGTGT<br>AAGCTTCTATGGGTTTAACAATACCTGTGTGGAAGCCTGGACCGATGTAAG<br>GGTTCGGGGCTGTGCCTTTTACTGCTGCTGGAAGGGGGTGGTGTGTCGCC |

Sequences

| SEQ ID NO: | DESCRIPTION | SEQUENCE |
|---|---|---|
| | | CCAAAAGCAGGGCTTCAATTAAGAAATGCCTCTTTGAAAGGTGTACCTTGG |
| | | GTATCCTGTCTGAGGGTAACTCCAGGGTGCGCCACAATGTGGCCTCCGAC |
| | | TGTGGTTGCTTCATGCTAGTGAAAAGCGTGGCTGTGATTAAGCATAACATG |
| | | GTATGTGGCAACTGCGAGGACAGGGCCTCTCAGATGCTGACCTGCTCGGA |
| | | CGGCAACTGTCACCTGCTGAAGACCATTCACGTAGCCAGCCACTCTCGCAA |
| | | GGCCTGGCCAGTGTTTGAGCATAACATACTGACCCGCTGTTCCTTGCATTT |
| | | GGGTAACAGGAGGGGGGTGTTCCTACCTTACCAATGCAATTTGAGTCACAC |
| | | TAAGATATTGCTTGAGCCCGAGAGCATGTCCAAGGTGAACCTGAACGGGGT |
| | | GTTTGACATGACCATGAAGATCTGGAAGGTGCTGAGGTACGATGAGACCC |
| | | GCACCAGGTGCAGACCCTGCGAGTGTGGCGGTAAACATATTAGGAACCAG |
| | | CCTGTGATGCTGGATGTGACCGAGGAGCTGAGGCCCGATCACTTGGTGCT |
| | | GGCCTGCACCCGCGCTGAGTTTGGCTCTAGCGATGAAGATACAGATTGAG |
| | | GTACTGAAATGTGTGGGCGTGGCTTAAGGGTGGGAAAGAATATATAAGGTG |
| | | GGGGTCTTATGTAGTTTTGTATCTGTTTTGCAGCAGCCGCCGCCGCCATGA |
| | | GCACCAACTCGTTTGATGGAAGCATTGTGAGCTCATATTTGACAACGCGCA |
| | | TGCCCCCATGGGCCGGGGTGCGTCAGAATGTGATGGGCTCCAGCATTGAT |
| | | GGTCGCCCCGTCCTGCCCGCAAACTCTACTACCTTGACCTACGAGACCGT |
| | | GTCTGGAACGCCGTTGGAGACTGCAGCCTCCGCCGCCGCTTCAGCCGCTG |
| | | CAGCCACCGCCCGCGGGATTGTGACTGACTTTGCTTTCCTGAGCCCGCTT |
| | | GCAAGCAGTGCAGCTTCCCGTTCATCCGCCCGCGATGACAAGTTGACGGC |
| | | TCTTTTGGCACAATTGGATTCTTTGACCCGGGAACTTAATGTCGTTTCTCAG |
| | | CAGCTGTTGGATCTGCGCCAGCAGGTTTCTGCCCTGAAGGCTTCCTCCCCT |
| | | CCCAATGCGGTTTAAAACATAAATAAAAAACCAGACTCTGTTTGGATTGGA |
| | | TCAAGCAAGTGTCTTGCTGTCTTTATTTAGGGGTTTTGCGCGCGCGGTAGG |
| | | CCCGGGACCAGCGGTCTCGGTCGTTGAGGGTCCTGTGTATTTTTTCCAGG |
| | | ACGTGGTAAAGGTGACTCTGGATGTTCAGATACATGGGCATAAGCCCGTCT |
| | | CTGGGGTGGAGGTAGCACCACTGCAGAGCTTCATGCTGCGGGGTGGTGTT |
| | | GTAGATGATCCAGTCGTAGCAGGAGCGCTGGGCGTGGTGCCTAAAAATGT |
| | | CTTTCAGTAGCAAGCTGATTGCCAGGGGCAGGCCCTTGGTGTAAGTGTTTA |
| | | CAAAGCGGTTAAGCTGGGATGGGTGCATACGTGGGGATATGAGATGCATC |
| | | TTGGACTGTATTTTTAGGTTGGCTATGTTCCCAGCCATATCCCTCCGGGGAT |
| | | TCATGTTGTGCAGAACCACCAGCACAGTGTATCCGGTGCACTTGGGAAATT |
| | | TGTCATGTAGCTTAGAAGGAAATGCGTGGAAGAACTTGGAGACGCCCTTGT |
| | | GACCTCCAAGATTTTCCATGCATTCGTCCATAATGATGGCAATGGGCCCAC |
| | | GGGCGGCGGCCTGGGCGAAGATATTTCTGGGATCACTAACGTCATAGTTG |
| | | TGTTCCAGGATGAGATCGTCATAGGCCATTTTTACAAAGCGCGGGCGGAG |
| | | GGTGCCAGACTGCGGTATAATGGTTCCATCCGGCCCAGGGGCGTAGTTAC |
| | | CCTCACAGATTTGCATTTCCCACGCTTTGAGTTCAGATGGGGGATCATGT |
| | | CTACCTGCGGGGCGATGAAGAAAACGGTTTCCGGGGTAGGGGAGATCAGC |
| | | TGGGAAGAAAGCAGGTTCCTGAGCAGCTGCGACTTACCGCAGCCGGTGGG |
| | | CCCGTAAATCACACCTATTACCGGGTGCAACTGGTAGTTAAGAGAGCTGCA |
| | | GCTGCCGTCATCCCTGAGCAGGGGGGCCACTTCGTTAAGCATGTCCCTGA |
| | | CTCGCATGTTTTCCCTGACCAAATCCGCCAGAAGGCGCTCGCCGCCCAGC |
| | | GATAGCAGTTCTTGCAAGGAAGCAAAGTTTTTCAACGGTTTGAGACCGTCC |
| | | GCCGTAGGCATGCTTTTGAGCGTTTGACCAAGCAGTTCCAGGCGGTCCCA |
| | | CAGCTCGGTCACCTGCTCTACGGCATCTCGATCCAGCATATCTCCTCGTTT |
| | | CGCGGGTTGGGGCGGCTTTCGCTGTACGGCAGTAGTCGGTGCTCGTCCAG |
| | | ACGGGCCAGGGTCATGTCTTTCCACGGGCGCAGGGTCCTCGTCAGCGTAG |
| | | TCTGGGTCACGGTGAAGGGGTGCGCTCCGGGCTGCGCGCTGGCCAGGGT |
| | | GCGCTTGAGGCTGGTCCTGCTGGTGCTGAAGCGCTGCCGGTCTTCGCCCT |
| | | GCGCGTCGGCCAGGTAGCATTTGACCATGGTGTCATAGTCCAGCCCCTCC |
| | | GCGGCGTGGCCCTTGGCGCGCAGCTTGCCCTTGGAGGAGGCGCCGCACG |
| | | AGGGGCAGTGCAGACTTTTGAGGGCGTAGAGCTTGGGCGCGAGAAATACC |
| | | GATTCCGGGGAGTAGGCATCCGCGCCGCAGGCCCCGCAGACGGTCTCGC |
| | | ATTCCACGAGCCAGGTGAGCTCTGGCCGTTCGGGGTCAAAAACCAGGTTT |
| | | CCCCCATGCTTTTTGATGCGTTTCTTACCTCTGGTTTCCATGAGCCGGTGTC |
| | | CACGCTCGGTGACGAAAAGGCTGTCCGTGTCCCGTATACAGACTNNNGT |
| | | TTTGAGAGGCCTGTCCTCGAGCGGTGTTCCGCGGTCCTCCTCGTATAGAAA |
| | | CTCGGACCACTCTGAGACAAAGGCTCGCGTCCAGGCCAGCACGAAGGAGG |
| | | CTAAGTGGGAGGGGTAGCGGTCGTTGTCCACTAGGGGGTCCACTCGCTCC |
| | | AGGGTGTGAAGACACATGTCGCCCTCTTCGGCATCAAGGAAGGTGATTGG |
| | | TTTGTAGGTGTAGGCCACGTGACCGGGTGTTCCTGAAGGGGGCTATAAA |
| | | AGGGGGTGGGGCGCGTTCGTCCTCACTCTCTTCCGCATCGCTGTCTGCG |
| | | AGGGCCAGCTGTTGGGGTGAGTACTCCCTCTGAAAAGCGGGCATGACTTC |
| | | TGCGCTAAGATTGTCAGTTTCCAAAAACGAGGAGGATTTGATATTCACCTG |
| | | GCCCGCGGTGATGCCTTTGAGGGTGGCCGCATCCATCTGGTCAGAAAAGA |
| | | CAATCTTTTTGTTGTCAAGCTTGGTGGCAAACGACCCGTAGAGGGCGTTGG |
| | | ACAGCAACTTGGCGATGGAGCGCAGGGTTTGGTTTTTGTCGCGATCGGCG |
| | | CGCTCCTTGGCCGCGATGTTTAGCTGCACGTATTCGCGCGCAACGCACCG |
| | | CCATTCGGGAAAGACGGTGGTGCGCTCGTCGGGCACCAGGTGCACGCGC |
| | | CAACCGCGGTTGTGCAGGGTGACAAGGTCAACGCTGGTGGCTACCTCTCC |
| | | GCGTAGGCGCTCGTTGGTCCAGCAGAGGCGGCCGCCCTTGCGCGAGCAG |
| | | AATGGCGGTAGGGGGTCTAGCTGCGTCTCGTCCGGGGGGTCTGCGTCCA |
| | | CGGTAAAGACCCCGGGCAGCAGGCGCGCGTCGAAGTAGTCTATCTTGCAT |

Sequences

| SEQ ID NO: | DESCRIPTION | SEQUENCE |
|---|---|---|
| | | CCTTGCAAGTCTAGCGCCTGCTGCCATGCGCGGGCGGCAAGCGCGCGCT |
| | | CGTATGGGTTGAGTGGGGGACCCCATGGCATGGGTGGGTGAGCGCGGA |
| | | GGCGTACATGCCGCAAATGTCGTAAACGTAGAGGGGCTCTCTGAGTATTCC |
| | | AAGATATGTAGGGTAGCATCTTCCACCGCGGATGCTGGCGCGCACGTAAT |
| | | CGTATAGTTCGTGCGAGGGAGCGAGGAGGTCGGGACCGAGGTTGCTACG |
| | | GGCGGGCTGCTCTGCTCGGAAGACTATCTGCCTGAAGATGGCATGTGAGT |
| | | TGGATGATATGGTTGGACGCTGGAAGACGTTGAAGCTGGCGTCTGTGAGA |
| | | CCTACCGCGTCACGCACGAAGGAGGCGTAGGAGTCGCGCAGCTTGTTGAC |
| | | CAGCTCGGCGGTGACCTGCACGTCTAGGGCGCAGTAGTCCAGGGTTTCCT |
| | | TGATGATGTCATACTTATCCTGTCCCTTTTTTTTCCACAGCTCGCGGTTGAG |
| | | GACAAACTCTTCGCGGTCTTTCCAGTACTCTTGGATCGGAAACCCGTCGGC |
| | | CTCCGAACGGTAAGAGCCTAGCATGTAGAACTGGTTGACGGCCTGGTAGG |
| | | CGCAGCATCCCTTTTCTACGGGTAGCGCGTATGCCTGCGCGGCCTTCCGG |
| | | AGCGAGGTGTGGGTGAGCGCAAAGGTGTCCCTGACCATGACTTTGAGGTA |
| | | CTGGTATTTGAAGTCAGTGTCGTCGCATCCGCCCTGCTCCCAGAGCAAAA |
| | | GTCCGTGCGCTTTTTGGAACGCGGATTTGGCAGGGCGAAGGTGACATCGT |
| | | TGAAGAGTATCTTTCCCGCGCGAGGCATAAAGTTGCGTGTGATGCGGAAG |
| | | GGTCCCGGCACCTCGGAACGGTTGTTAATTACCTGGGCGGCGAGCACGAT |
| | | CTCGTCAAAGCCGTTGATGTTGTGGCCCACAATGTAAAGTTCCAAGAAGCG |
| | | CGGGATGCCCTTGATGGAAGGCAATTTTTTAAGTTCCTCGTAGGTGAGCTC |
| | | TTCAGGGGAGCTGAGCCCGTGCTCTGAAAGGGCCCAGTCTGCAAGATGAG |
| | | GGTTGGAAGCGACGAATGAGCTCCACAGGTCACGGGCCATTAGCATTTGC |
| | | AGGTGGTCGCGAAAGGTCCTAAACTGGCGACCTATGGCCATTTTTTCTGGG |
| | | GTGATGCAGTAGAAGGTAAGCGGGTCTTGTTCCCAGCGGTCCCATCCAAG |
| | | GTTCGCGGCTAGGTCTCGCGCGGCAGTCACTAGAGGCTCATCTCCGCCGA |
| | | ACTTCATGACCAGCATGAAGGGCACGAGCTGCTTCCCAAAGGCCCCCATC |
| | | CAAGTATAGGTCTCTACATCGTAGGTGACAAAGAGACGCTCGGTGCGAGG |
| | | ATGCGAGCCGATCGGGAAGAACTGGATCTCCCGCCACCAATTGGAGGAGT |
| | | GGCTATTGATGTGGTGAAAGTAGAAGTCCCTGCGACGGGCCGAACACTCG |
| | | TGCTGGCTTTTGTAAAAACGTGCGCAGTACTGGCAGCGGTGCACGGGCTG |
| | | TACATCCTGCACGAGGTTGACCTGACGACCGCGCACAAGGAAGCAGAGTG |
| | | GGAATTTGAGCCCCTCGCCTGGCGGGTTTGGCTGGTGGTCTTCTACTTCG |
| | | GCTGCTTGTCCTTGACCGTCTGGCTGCTCGAGGGGAGTTACGGTGGATCG |
| | | GACCACCACGCCGCGCGAGCCCAAAGTCCAGATGTCCGCGCGCGGCGGT |
| | | CGGAGCTTGATGACAACATCGCGCAGATGGGAGCTGTCCATGGTCTGGAG |
| | | CTCCCGCGGCGTCAGGTCAGGCGGGAGCTCCTGCAGGTTTACCTCGCATA |
| | | GACGGGTCAGGGCGCGGGCTAGATCCAGGTGATACCTAATTTCCAGGGGC |
| | | TGGTTGGTGGCGGCGTCGATGGCTTGCAAGAGGCCGCATCCCCGCGGCG |
| | | CGACTACGGTACCGCGCGGCGGGCGGTGGGCCGCGGGGTGTCCTTGGA |
| | | TGATGCATCTAAAAGCGGTGACGCGGGCGAGCCCCCGGAGGTAGGGGGG |
| | | GCTCCGGACCCGCCGGGAGAGGGGCAGGGGCACGTCGGCGCCGCGCG |
| | | CGGGCAGGAGCTGGTGCTGCGCGCGTAGGTTGCTGGCGAACGCGACGAC |
| | | GCGGCGGTTGATCTCCTGAATCTGGCGCCTCTGCGTGAAGACGACGGGCC |
| | | CGGTGAGCTTGAGCCTGAAAGAGAGTTCGACAGAATCAATTTCGGTGTCGT |
| | | TGACGGCGGCCTGGCGCAAAATCTCCTGCACGTCTCCTGAGTTGTCTTGAT |
| | | AGGCGATCTCGGCCATGAACTGCTCGATCTCTTCCTCCTGGAGATCTCCGC |
| | | GTCCGGCTCGCTCCACGGTGGCGGCGAGGTCGTTGGAAATGCGGGCCAT |
| | | GAGCTGCGAGAAGGCGTTGAGGCCTCCCTCGTTCCAGACGCGGCTGTAGA |
| | | CCACGCCCCCTTCGGCATCGCGGGCGCGCATGACCACCTGCGCGAGATT |
| | | GAGCTCCACGTGCCGGGCGAAGACGGCGTAGTTTCGCAGGCGCTGAAAG |
| | | AGGTAGTTGAGGGTGGTGGCGGTGTGTTCTGCCACGAAGAAGTACATAAC |
| | | CCAGCGTCGCAACGTGGATTCGTTGATATCCCCAAGGCCTCAAGGCGCT |
| | | CCATGGCCTCGTAGAAGTCCACGGCGAAGTTGAAAAACTGGGAGTTGCGC |
| | | GCCGACACGGTTAACTCCTCCTCCAGAAGACGGATGAGCTCGGCGACAGT |
| | | GTCGCGCACCTCGCGCTCAAAGGCTACAGGGGCCTCTTCTTCTTCTTCAAT |
| | | CTCCTCTTCCATAAGGGCCTCCCCTTCTTCTTCTTCTGGCGGCGGTGGGGG |
| | | AGGGGGGACACGGCGGCGACGACGGCGCACCGGGAGGCGGTCGACAAA |
| | | GCGCTCGATCATCTCCCCGCGGCGACGGCGCATGGTCTCGGTGACGGCG |
| | | CGGCCGTTCTCGCGGGGGCGCAGTTGGAAGACGCCGCCCGTCATGTCCC |
| | | GGTTATGGGTTGGCGGGGGCTGCCATGCGGCAGGGATACGGCGCTAAC |
| | | GATGCATCTCAACAATTGTTGTGTAGGTACTCCGCCGCCGAGGGACCTGAG |
| | | CGAGTCCGCATCGACCGGATCGGAAAACCTCTCGAGAAAGGCGTCTAACC |
| | | AGTCACAGTCGCAAGGTAGGCTGAGCACCGTGGCGGGCGGCAGCGGGCG |
| | | GCGGTCGGGGTTGTTTCTGGCGGAGGTGCTGCTGATGATGTAATTAAAGTA |
| | | GGCGGTCTTGAGACGGCGGATGGTCGACAGAAGCACCATGTCCTTGGGTC |
| | | CGGCCTGCTGAATGCGCAGGCGGTCGGCCATGCCCCAGGCTTCGTTTTGA |
| | | CATCGGCGCAGGTCTTTGTAGTAGTCTTGCATGAGCCTTTCTACCGGCACT |
| | | TCTTCTTCTCCTTCCTCTTGTCCTGCATCTCTTGCATCTATCGCTGCGGCGG |
| | | CGGCGGAGTTTGGCCGTAGGTGGCGCCCTCTTCCTCCCATGCGTGTGACC |
| | | CCGAAGCCCCTCATCGGCTGAAGCAGGGCTAGGTCGGCGACAACGCGCT |
| | | CGGCTAATATGGCCTGCTGCACCTGCGTGAGGGTAGACTGGAAGTCATCC |
| | | ATGTCCACAAAGCGGTGGTATGCGCCCGTGTTGATGGTGTAAGTGCAGTTG |
| | | GCCATAACGGACCAGTTAACGGTCTGGTGACCCGGCTGCGAGAGCTCGGT |
| | | GTACCTGAGACGCGAGTAAGCCCTCGAGTCAAATACGTAGTCGTTGCAAGT |

Sequences

| SEQ ID NO: | DESCRIPTION | SEQUENCE |
|---|---|---|
| | | CCGCACCAGGTACTGGTATCCCACCAAAAAGTGCGGCGGCGGCTGGCGGT |
| | | AGAGGGGCCAGCGTAGGGTGGCCGGGGCTCCGGGGGCGAGATCTTCCAA |
| | | CATAAGGCGATGATATCCGTAGATGTACCTGGACATCCAGGTGATGCCGGC |
| | | GGCGGTGGTGGAGGCGCGCGGAAAGTCGCGGACGCGGTTCCAGATGTTG |
| | | CGCAGCGGCAAAAAGTGCTCCATGGTCGGGACGCTCTGGCCGGTCAGGC |
| | | GCGCGCAATCGTTGACGCTCTACCGTGCAAAAGGAGAGCCTGTAAGCGGG |
| | | CACTCTTCCGTGGTCTGGTGGATAAATTCGCAAGGGTATCATGGCGGACGA |
| | | CCGGGGTTCGAGCCCCGTATCCGGCCGTCCGCCGTGATCCATGCGGTTAC |
| | | CGCCCGCGTGTCGAACCCAGGTGTGCGACGTCAGACAACGGGGGAGTGC |
| | | TCCTTTTGGCTTCCTTCCAGGCGCGGCGGCTGCTGCGCTAGCTTTTTTGGC |
| | | CACTGGCCGCGCGCAGCGTAAGCGGTTAGGCTGGAAAGCGAAAGCATTAA |
| | | GTGGCTCGCTCCCTGTAGCCGGAGGGTTATTTTCCAAGGGTTGAGTCGCG |
| | | GGACCCCCGGTTCGAGTCTCGGACCGGCCGGACTGCGGCGAACGGGGGT |
| | | TTGCCTCCCCGTCATGCAAGACCCCGCTTGCAAATTCCTCCGGAAACAGGG |
| | | ACGAGCCCTTTTTTGCTTTTCCCAGATGCATCCGGTGCTGCGGCAGATGC |
| | | GCCCCCCTCCTCAGCAGCGGCAAGAGCAAGAGCAGCGGCAGACATGCAG |
| | | GGCACCCTCCCCTCCTCCTACCGCGTCAGGAGGGGCGACATCCGCGGTTG |
| | | ACGCGGCAGCAGATGGTGATTACGAACCCCCGCGGCGCCGGGCCCGGCA |
| | | CTACCTGGACTTGGAGGAGGGCGAGGGCCTGGCGCGGCTAGGAGCGCCC |
| | | TCTCCTGAGCGGTACCCAAGGGTGCAGCTGAAGCGTGATACGCGTGAGGC |
| | | GTACGTGCCGCGGCAGAACCTGTTTCGCGACCGCGAGGGAGAGGAGCCC |
| | | GAGGAGATGCGGGATCGAAAGTTCCACGCAGGGCGCGAGCTGCGGCATG |
| | | GCCTGAATCGCGAGCGGTTGCTGCGCGAGGAGGACTTTGAGCCCGACGC |
| | | GCGAACCGGGATTAGTCCCGCGCGCGCACACGTGGCGGCCGCCGACCTG |
| | | GTAACCGCATACGAGCAGACGGTGAACCAGGAGATTAACTTTCAAAAAAGC |
| | | TTTAACAACCACGTGCGTACGCTTGTGGCGCGCGAGGAGGTGGCTATAGG |
| | | ACTGATGCATCTGTGGGACTTTGTAAGCGCGCTGGAGCAAAACCCAAATAG |
| | | CAAGCCGCTCATGGCGCAGCTGTTCCTTATAGTGCAGCACAGCAGGGACA |
| | | ACGAGGCATTCAGGGATGCGCTGCTAAACATAGTAGAGCCCGAGGGCCGC |
| | | TGGCTGCTCGATTTGATAAACATCCTGCAGAGCATAGTGGTGCAGGAGCGC |
| | | AGCTTGAGCCTGGCTGACAAGGTGGCCGCCATCAACTATTCCATGCTTAGC |
| | | CTGGGCAAGTTTTACGCCCGCAAGATATACCATACCCCTTACGTTCCCATA |
| | | GACAAGGAGGTAAAGATCGAGGGGTTCTACATGCGCATGGCGCTGAAGGT |
| | | GCTTACCTTGAGCGACGACCTGGGCGTTTATCGCAACGAGCGCATCCACA |
| | | AGGCCGTGAGCGTGAGCCGGCGGCGCGAGCTCAGCGACCGCGAGCTGAT |
| | | GCACAGCCTGCAAAGGGCCCTGGCTGGCACGGGCAGCGGCGATAGAGAG |
| | | GCCGAGTCCTACTTTGACGCGGGCGCTGACCTGCGCTGGGCCCCAAGCC |
| | | GACGCGCCCTGGAGGCAGCTGGGGCCGGACCTGGGCTGGCGGTGGCAC |
| | | CCGCGCGCGCTGGCAACGTCGGCGGCGTGGAGGAATATGACGAGGACGA |
| | | TGAGTACGAGCCAGAGGACGGCGAGTACTAAGCGGTGATGTTTCTGATCA |
| | | GATGATGCAAGACGCAACGGACCCGGCGGTGCGGGCGGCGCTGCAGAGC |
| | | CAGCCGTCCGGCCTTAACTCCAGGACGACTGGCGCCAGGTCATGGACCG |
| | | CATCATGTCGCTGACTGCGCGCAATCCTGACGCGTTCCGGCAGCAGCCGC |
| | | AGGCCAACCGGCTCTCCGCAATTCTGGAAGCGGTGGTCCCGGCGCGCGC |
| | | AAACCCCACGCACGAGAAGGTGCTGGCGATCGTAAACGCGCTGGCCGAAA |
| | | ACAGGGCCATCCGGCCCGACGAGGCCGGCCTGGTCTACGACGCGCTGCT |
| | | TCAGCGCGTGGCTCGTTACAACAGCGGCAACGTGCAGACCAACCTGGACC |
| | | GGCTGGTGGGGATGTGCGCGAGGCCGTGGCGCAGCGTGAGCGCGCGC |
| | | AGCAGCAGGGCAACCTGGGCTCCATGGTTGCACTAAACGCCTTCCTGAGT |
| | | ACACAGCCCGCCAACGTGCCGCGGGGACAGGAGGACTACACCAACTTTGT |
| | | GAGCGCACTGCGGCTAATGGTGACTGAGACACCGCAAAGTGAGGTGTACC |
| | | AGTCTGGGCCAGACTATTTTTTCCAGACCAGTAGACAAGGCCTGCAGACCG |
| | | TAAACCTGAGCCAGGCTTTCAAAAACTTGCAGGGGCTGTGGGGGGTGCGG |
| | | GCTCCCACAGGCGACCGCGCGACCGTGTCTAGCTTGCTGACGCCCAACTC |
| | | GCGCCTGTTGCTGCTGCTAATAGCGCCCTTCACGGACAGTGGCAGCGTGT |
| | | CCCGGGACACATACCTAGGTCACTTGCTGACACTGTACCGCGAGGCCATA |
| | | GGTCAGGCGCATGTGGACGAGCATACTTTCCAGGAGATTACAAGTGTCAG |
| | | CCGCGCGCTGGGGCAGGAGGACACGGGCAGCCTGGAGGCAACCCTAAAC |
| | | TACCTGCTGACCAACCGGCGGCAGAAGATCCCCTCGTTGCACAGTTTAAAC |
| | | AGCGAGGAGGAGCGCATTTTGCGCTACGTGCAGCAGAGCGTGAGCCTTAA |
| | | CCTGATGCGCGACGGGGTAACGCCCAGCGTGGCGCTGGACATGACCGCG |
| | | CGCAACATGGAACCGGGCATGTATGCCTCAAACCGGCCGTTTATCAACCG |
| | | CCTAATGGACTACTTGCATCGCGCGGCCGCCGTGAACCCCGAGTATTTCAC |
| | | CAATGCCATCTTGAACCCGCACTGGCTACCGCCCCCTGGTTTCTACACCGG |
| | | GGGATTCGAGGTGCCCGAGGGTAACGATGGATTCCTCTGGGACGACATAG |
| | | ACGACAGCGTGTTTTCCCGCAACCGCGACCCTGCTAGAGTTGCAACAG |
| | | CGCGAGCAGGCAGAGGCGGCGCTGCAAAGGAAAGCTTCCGCAGGCCAA |
| | | GCAGCTTGTCCGATCTAGGCGCTGCGGCCCCGCGGTCAGATGCTAGTAGC |
| | | CCATTTCCAAGCTTGATAGGGTCTCTTACCAGCACTCGCACCACCCGCCCG |
| | | CGCCTGCTGGGCGAGGAGGAGTACCTAAACAACTCGCTGCTGCAGCCGCA |
| | | GCGCGAAAAAAACCTGCCTCCGGCATTTCCCAACAACGGGATAGAGAGCC |
| | | TAGTGGACAAGATGAGTAGATGGAAGACGTACGCGCAGGAGCACAGGGAC |
| | | GTGCCAGGCCCGCGCCCGCCCACCCGTCGTCAAAGGCACGACCGTCAGC |
| | | GGGGTCTGGTGTGGGAGGACGATGACTCGGCAGACGACAGCAGCGTCCT |

Sequences

| SEQ ID NO: | DESCRIPTION | SEQUENCE |
|---|---|---|
| | | GGATTTGGGAGGGAGTGGCAACCCGTTTGCGCACCTTCGCCCCAGGCTGG |
| | | GGAGAATGTTTTAAAAAAAAAAAAGCATGATGCAAATAAAAAACTCACCAA |
| | | GGCCATGGCACCGAGCGTTGGTTTTCTTGTATTCCCCTTAGTATGCGGCGC |
| | | GCGGCGATGTATGAGGAAGGTCCTCCTCCCTCCTACGAGAGTGTGGTGAG |
| | | CGCGGCGCCAGTGGCGGCGGCGCTGGGTTCTCCCTTCGATGCTCCCCTG |
| | | GACCCGCCGTTTGTGCCTCCGCGGTACCTGCGGCCTACCGGGGGGAGAA |
| | | ACAGCATCCGTTACTCTGAGTTGGCACCCCTATTCGACACCACCCGTGTGT |
| | | ACCTGGTGGACAACAAGTCAACGGATGTGGCATCCCTGAACTACCAGAAC |
| | | GACCACAGCAACTTTCTGACCACGGTCATTCAAAACAATGACTACAGCCCG |
| | | GGGGAGGCAAGCACACAGACCATCAATCTTGACGACCGGTCGCACTGGGG |
| | | CGGCGACCTGAAAACCATCCTGCATACCAACATGCCAAATGTGAACGAGTT |
| | | CATGTTTACCAATAAGTTTAAGGCGCGGGTGATGGTGTCGCGCTTGCCTAC |
| | | TAAGGACAATCAGGTGGAGCTGAAATACGAGTGGGTGGAGTTCACGCTGC |
| | | CCGAGGGCAACTACTCCGAGACCATGACCATAGACCTTATGAACAACGCGA |
| | | TCGTGGAGCACTACTTGAAAGTGGGCAGACAGAACGGGGTTCTGGAAAGC |
| | | GACATCGGGGTAAAGTTTGACACCCGCAACTTCAGACTGGGGGTTTGACCCC |
| | | GTCACTGGTCTTGTCATGCCTGGGGTATATACAAACGAAGCCTTCCATCCA |
| | | GACATCATTTTGCTGCCAGGATGCGGGGTGGACTTCACCCACAGCCGCCT |
| | | GAGCAACTTGTTGGGCATCCGCAAGCGGCAACCCTTCCAGGAGGGCTTTA |
| | | GGATCACCTACGATGATCTGGAGGGTGGTAACATTCCCGCACTGTTGGATG |
| | | TGGACGCCTACCAGGCGAGCTTGAAAGATGACACCGAACAGGGCGGGGG |
| | | TGGCGCAGGCGGCAGCAACAGCAGTGGCAGCGGCGCGGAAGAGAACTCC |
| | | AACGCGGCAGCCGCGGCAATGCAGCCGGTGGAGGACATGACGATCATG |
| | | CCATTCGCGGCGACACCTTTGCCACACGGGCTGAGGAGAAGCGCGCTGAG |
| | | GCCGAAGCAGCGGCCGAAGCTGCCGCCCCGCTGCGCAACCCGAGGTCG |
| | | AGAAGCCTCAGAAGAAACCGGTGATCAAACCCCTGACAGAGGACAGCAAG |
| | | AAACGCAGTTACAACCTAATAAGCAATGACAGCACCTTCACCCAGTACCGC |
| | | AGCTGGTACCTTGCATACAACTACGGCGACCCTCAGACCGGAATCCGCTCA |
| | | TGGACCCTGCTTTGCACTCCTGACGTAACCTGCGGCTCGGAGCAGGTCTA |
| | | CTGGTCGTTGCCAGACATGATGCAAGACCCCGTGACCTTCCGCTCCACGC |
| | | GCCAGATCAGCAACTTTCCGGTGGTGGGCGCCGAGCTGTTGCCCGTGCAC |
| | | TCCAAGAGCTTCTACAACGACCAGGCCGTCTACTCCCAACTCATCCGCCAG |
| | | TTTACCTCTCTGACCCACGTGTTCAATCGCTTTCCCGAGAACCAGATTTTGG |
| | | CGCGCCCGCCAGCCCCCACCATCACCACCGTCAGTGAAAACGTTCCTGCT |
| | | CTCACAGATCACGGGACGCTACCGCTGCGCAACAGCATCGGAGGAGTCCA |
| | | GCGAGTGACCATTACTGACGCCAGACGCCGCACCTGCCCCTACGTTTACA |
| | | AGGCCCTGGGCATAGTCTCGCCGCGCGTCCTATCGAGCCGCACTTTTTGA |
| | | GCAAGCATGTCCATCCTTATATCGCCCAGCAATAACACAGGCTGGGGCCTG |
| | | CGCTTCCCAAGCAAGATGTTTGGCGGGGCCAAGAAGCGCTCCGACCAACA |
| | | CCCAGTGCGCGTGCGCGGGCACTACCGCGCGCCCTGGGGCGCGCACAAA |
| | | CGCGGCCGCACTGGGCGCACCACCGTCGATGACGCCATCGACGCGGTGG |
| | | TGGAGGAGGCGCGCAACTACACGCCCACGCCGCCACCAGTGTCCACAGT |
| | | GGACGCGGCCATTCAGACCGTGGTGCGCGGAGCCCGGCGCTATGCTAAA |
| | | ATGAAGAGACGGCGGAGGCGCGTAGCACGTCGCCACCGCCGCCGACCCG |
| | | GCACTGCCGCCCAACGCGCGGCGGCGGCCCTGCTTAACCGCGCACGTCG |
| | | CACCGGCCGACGGGCGGCCATGCGGGCCGCTCGAAGGCTGGCCGCGGG |
| | | TATTGTCACTGTGCCCCCCAGGTCCAGGCGACGAGCGGCCGCCGCAGCA |
| | | GCCGCGGCCATTAGTGCTATGACTCAGGGTCGCAGGGGCAACGTGTATTG |
| | | GGTGCGCGACTCGGTTAGCGGCCTGCGCGTGCCCGTGCGCACCCGCCCC |
| | | CCGCGCAACTAGATTGCAAGAAAAAAACTACTTAGACTCGTACTGTTGTATGT |
| | | ATCCAGCGGCGGCGGCGCGCAACGAAGCTATGTCCAAGCGCAAAATCAAA |
| | | GAAGAGATGCTCCAGGTCATCGCGCCGGAGATCTATGGCCCCCGAAGAA |
| | | GGAAGAGCAGGATTACAAGCCCCGAAAGCTAAAGCGGGTCAAAAAGAAAA |
| | | AGAAAGATGATGATGATGAACTTGACGACGAGGTGGAACTGCTGCACGCTA |
| | | CCGCGCCCAGGCGACGGGTACAGTGGAAAGGTCGACGCGTAAAACGTGTT |
| | | TTGCGACCCGGCACCACCGTAGTCTTTACGCCCGGTGAGCGCTCCACCCG |
| | | CACCTACAAGCGCGTGTATGATGAGGTGTACGGCGACGAGGACCTGCTTG |
| | | AGCAGGCCAACGAGCGCCTCGGGGAGTTTGCCTACGGAAAGCGGCATAAG |
| | | GACATGCTGGCGTTGCCGCTGGACGAGGGCAACCCAACACCTAGCCTAAA |
| | | GCCCGTAACACTGCAGCAGGTGCTGCCCGCGCTTGCACCGTCCGAAGAAA |
| | | AGCGCGGCCTAAAGCGCGAGTCTGGTGACTTGGCACCCACCGTGCAGCTG |
| | | ATGGTACCCAAGCGCCAGCGACTGGAAGATGTCTTGGAAAAAATGACCGT |
| | | GGAACCTGGGCTGGAGCCCGAGGTCCGCGTGCGGCCAATCAAGCAGGTG |
| | | GCGCCGGGACTGGGCGTGCAGACCGTGGACGTTCAGATACCCACTACCAG |
| | | TAGCACCAGTATTGCCACCGCCACAGAGGGCATGGAGACACAAACGTCCC |
| | | CGGTTGCCTCAGCGGTGGCGGATGCCGCGGTGCAGGCGGTCGCTGCGGC |
| | | CGCGTCCAAGACCTCTACGGAGGTGCAAACGGACCCGTGGATGTTTCGCG |
| | | TTTCAGCCCCCGGCGCCCGCGCGGTTCGAGGAAGTACGGCGCCGCCAG |
| | | CGCGCTACTGCCCGAATATGCCCTACATCCTTCCATTGCGCCTACCCCCGG |
| | | CTATCGTGGCTACACCTACCGCCCCAGAAGACGAGCAACTACCCGACGCC |
| | | GAACCACCACTGGAACCCGCCGCCGCCGTCGCCGTCGCCAGCCCCGTGCT |
| | | GGCCCCGATTTCCGTGCGCAGGGTGGCTCGCAAGGAGGCAGGACCCTG |
| | | GTGCTGCCAACAGCGCGCTACCACCCCAGCATCGTTTAAAAGCCGGTCTTT |
| | | GTGGTTCTTGCAGATATGGCCCTCACCTGCCGCCTCCGTTTCCCGGTGCC |

-continued

| SEQ ID NO: | DESCRIPTION | SEQUENCE |
|---|---|---|
| | | GGGATTCCGAGGAAGAATGCACCGTAGGAGGGGCATGGCCGGCCACGGC |
| | | CTGACGGGCGGCATGCGTCGTGCGCACCACCGGCGGCGGCGCGCGTCG |
| | | CACCGTCGCATGCGCGGCGGTATCCTGCCCCTCCTTATTCCACTGATCGC |
| | | CGCGGCGATTGGCGCCGTGCCCGGAATTGCATCCGTGGCCTTGCAGGCG |
| | | CAGAGACACTGATTAAAAACAAGTTGCATGTGGAAAAATCAAATAAAAAGT |
| | | CTGGACTCTCACGCTCGCTTGGTCCTGTAACTATTTTGTAGAATGGAAGAC |
| | | ATCAACTTTGCGTCTCTGGCCCCGCGACACGGCTCGCGCCCGTTCATGGG |
| | | AAACTGGCAAGATATCGGCACCAGCAATATGAGCGGTGGCGCCTTCAGCT |
| | | GGGGCTCGCTGTGGAGCGGCATTAAAAATTTCGGTTCCACCGTTAAGAACT |
| | | ATGGCAGCAAGGCCTGGAACAGCAGCACAGGCCAGATGCTGAGGGATAAG |
| | | TTGAAAGAGCAAAATTTCCAACAAAAGGTGGTAGATGGCCTGGCCTCTGGC |
| | | ATTAGCGGGGTGGTGGACCTGGCCAACCAGGCAGTGCAAAATAAGATTAA |
| | | CAGTAAGCTTGATCCCCGCCCTCCCGTAGAGGAGCCTCCACCGGCCGTGG |
| | | AGACAGTGTCTCCAGAGGGGCGTGGCGAAAAGCGTCCGCGCCCCGACAG |
| | | GGAAGAAACTCTGGTGACGCAAATAGACGAGCCTCCCTCGTACGAGGAGG |
| | | CACTAAAGCAAGGCCTGCCCACCACCCGTCCCATCGCGCCCATGGCTACC |
| | | GGAGTGCTGGGCCAGCACACACCCGTAACGCTGGACCTGCCTCCCCCCG |
| | | CCGACACCCAGCAGAAACCTGTGCTGCCAGGCCCGACCGCCGTTGTTGTA |
| | | ACCCGTCCTAGCCGCGCGTCCCTGCGCCGCGCCGCCAGCGGTCCGCGAT |
| | | CGTTGCGGCCCGTAGCCAGTGGCAACTGGCAAAGCACACTGAACAGCATC |
| | | GTGGGTCTGGGGGTGCAATCCCTGAAGCGCCGACGATGCTTCTGAATAGC |
| | | TAACGTGTCGTATGTGTGTCATGTATGCGTCCATGTCGCCGCCAGAGGAGC |
| | | TGCTGAGCCGCCGCGCGCCCGCTTTCCAAGATGGCTACCCCTTCGATGAT |
| | | GCCGCAGTGGTCTTACATGCACATCTCGGGCCAGGACGCCTCGGAGTACC |
| | | TGAGCCCCGGGCTGGTGCAGTTTGCCCGCGCCACCGAGACGTACTTCAGC |
| | | CTGAATAACAAGTTTAGAAACCCCACGGTGGCGCCTACGCACGACGTGAC |
| | | CACAGACCGGTCCCAGCGTTTGACGCTGCGGTTCATCCCTGTGGACCGTG |
| | | AGGATACTGCGTACTCGTACAAGGCGCGGTTCACCCTAGCTGTGGGTGAT |
| | | AACCGTGTGCTGGACATGGCTTCCACGTACTTTGACATCCGCGGCGTGCT |
| | | GGACAGGGGCCCTACTTTTAAGCCCTACTCTGGCACTGCCTACAACGCCCT |
| | | GGCTCCCAAGGGTGCCCCAAATCCTTGCGAATGGGATGAAGCTGCTACTG |
| | | CTCTTGAAATAAACCTAGAAGAAGAGGACGATGACAACGAAGACGAAGTAG |
| | | ACGAGCAAGCTGAGCAGCAAAAAACTCACGTATTTGGGCAGGCGCCTTATT |
| | | CTGGTATAAATATTACAAAGGAGGGTATTCAAATAGGTGTCGAAGGTCAAAC |
| | | ACCTAAATATGCCGATAAAACATTTCAACCTGAACCTCAAATAGGAGAATCT |
| | | CAGTGGTACGAAACTGAAATTAATCATGCAGCTGGGAGAGTCCTTAAAAAG |
| | | ACTACCCCAATGAAACCATGTTACGGTTCATATGCAAAACCCACAAATGAAA |
| | | ATGGAGGGCAAGGCATTCTTTGTAAAGCAACAAAATGGAAAGCTAGAAAGTC |
| | | AAGTGGAAATGCAATTTTTCTCAACTACTGAGGCGACCGCAGGCAATGGTG |
| | | ATAACTTGACTCCTAAAGTGGTATTGTACAGTGAAGATGTAGATATAGAAAC |
| | | CCCAGACACTCATATTTCTTACATGCCCACTATTAAGGAAGGTAACTCACGA |
| | | GAACTAATGGGCCAACAATCTATGCCCAACAGGCCTAATTACATTGCTTTTA |
| | | GGGACAATTTTATTGGTCTAATGTATTACAACAGCACGGGTAATATGGGTGT |
| | | TCTGGCGGGCCAAGCATCGCAGTTGAATGCTGTTGTAGATTTGCAAGACAG |
| | | AAACACAGAGCTTTCATACCAGCTTTTGCTTGATTCCATTGGTGATAGAACC |
| | | AGGTACTTTTCTATGTGGAATCAGGCTGTTGACAGCTATGATCCAGATGTTA |
| | | GAATTATTGAAAATCATGGAACTGAAGATGAACTTCCAAATTACTGCTTTCC |
| | | ACTGGGAGGTGTGATTAATACAGAGACTCTTACCAAGGTAAAACCTAAAAC |
| | | AGGTCAGGAAAATGGATGGGAAAAAGATGCTACAGAATTTTCAGATAAAAAT |
| | | GAAATAAGAGTTGGAAATAATTTTGCCATGGAAATCAATCTAAATGCCAACC |
| | | TGTGGAGAAATTTCCTGTACTCCAACATAGCGCTGTATTTGCCCGACAAGC |
| | | TAAAGTACAGTCCTTCCAACGTAAAAATTTCTGATAACCCAAACACCTACGA |
| | | CTACATGAACAAGCGAGTGGTGGCTCCCGGGTTAGTGGACTGCTACATTAA |
| | | CCTTGGAGCACGCTGGTCCCTTGACTATATGGACAACGTCAACCCCATTTAA |
| | | CCACCACCGCAATGCTGGCCTGCGCTACCGCTCAATGTTGCTGGGCAATG |
| | | GTCGCTATGTGCCCTTCCACATCCAGGTGCCTCAGAAGTTCTTTGCCATTA |
| | | AAAACCTCCTTCTCCTGCCGGGCTCATACACCTACGAGTGGAACTTCAGGA |
| | | AGGATGTTAACATGGTTCTGCAGAGCTCCCTAGGAAATGACCTAAGGGTTG |
| | | ACGGAGCCAGCATTAAGTTTGATAGCATTTGCCTTTACGCCACCTTCTTCCC |
| | | CATGGCCCACAACACCGCCTCCACGCTTGAGGCCATGCTTAGAAACGACA |
| | | CCAACGACCAGTCCTTTAACGACTATCTCCGCCGCCAACATGCTCTACC |
| | | CTATACCCGCCAACGCTACCAACGTGCCCATATCCATCCCCTCCCGCAACT |
| | | GGGCGGCTTTCCGCGGCTGGGCCTTCACGCGCCTTAAGACTAAGGAAACC |
| | | CCATCACTGGGCTCGGGCTACGACCCTTATTACACCTACTCTGGCTCTATA |
| | | CCCTACCTAGATGGAACCTTTTACCTCAACCACACCTTTAAGAAGGTGGCC |
| | | ATTACCTTTGACTCTTCTGTCAGCTGGCCTGGCAATGACCGCCTGCTTACC |
| | | CCCAACGAGTTTGAAATTAAGCGCTCAGTTGACGGGGAGGGTTACAACGTT |
| | | GCCCAGTGTAACATGACCAAAGACTGGTTCCTGGTACAAATGCTAGCTAAC |
| | | TACAACATTGGCTACCAGGGCTTCTATATCCCAGAGAGCTACAAGGACCGC |
| | | ATGTACTCCTTCTTTAGAAACTTCCAGCCCATGAGCCGTCAGGTGGTGGAT |
| | | GATACTAAATACAAGGACTACCAACAGGTGGGCATCCTACACCAACACAAC |
| | | AACTCTGGATTTGTTGGCTACCTTGCCCCCACCATGCGCGAAGGACAGGC |
| | | CTACCCTGCTAACTTCCCCTATCCGCTTATAGGCAAGACCGCAGTTGACAG |
| | | CATTACCCAGAAAAAGTTTCTTTGCGATCGCACCCTTTGGCGCATCCCATTC |

-continued

| SEQ ID NO: | DESCRIPTION | SEQUENCE |
|---|---|---|
| | | TCCAGTAACTTTATGTCCATGGGCGCACTCACAGACCTGGGCCAAAACCTT
CTCTACGCCAACTCCGCCCACGCGCTAGACATGACTTTTGAGGTGGATCCC
ATGGACGAGCCCACCCTTCTTTATGTTTTGTTTGAAGTCTTTGACGTGGTCC
GTGTGCACCGGCCGCACCGCGGCGTCATCGAAACCGTGTACCTGCGCAC
GCCCTTCTCGGCCGGCAACGCCACAACATAAAGAAGCAAGCAACATCAACA
ACAGCTGCCGCCATGGGCTCCAGTGAGCAGGAACTGAAAGCCATTGTCAA
AGATCTTGGTTGTGGGCCATATTTTTGGGCACCTATGACAAGCGCTTTCCA
GGCTTTGTTTCTCCACACAAGCTCGCCTGCGCCATAGTCAATACGGCCGGT
CGCGAGACTGGGGGCGTACACTGGATGGCCTTTGCCTGGAACCCGCACTC
AAAAACATGCTACCTCTTTGAGCCCTTTGGCTTTTCTGACCAGCGACTCAAG
CAGGTTTACCAGTTTGAGTACGAGTCACTCCTGCGCCGTAGCGCCATTGCT
TCTTCCCCCGACCGCTGTATAACGCTGGAAAAGTCCACCCAAAGCGTACAG
GGGCCCAACTCGGCCGCCTGTGGACTATTCTGCTGCATGTTTCTCCACGC
CTTTGCCAACTGGCCCCAAACTCCCATGGATCACAACCCCACCATGAACCT
TATTACCGGGGTACCCAACTCCATGCTCAACAGTCCCCAGGTACAGCCCAC
CCTGCGTCGCAACCAGGAACAGCTCTACAGCTTCCTGGAGCGCCACTCGC
CCTACTTCCGCAGCCACAGTGCGCAGATTAGGAGCGCCACTTCTTTTTGTC
ACTTGAAAACATGTAAAAATAATGTACTAGAGACACTTTCAATAAAGGCAA
ATGCTTTTATTTGTACACTCTCGGGTGATTATTTACCCCCACCCTTGCCGTC
TGCGCCGTTTAAAAATCAAAGGGGTTCTGCCGCGCATCGCTATGCGCCACT
GGCAGGGACACGTTGCGATACTGGTGTTTAGTGCTCCACTTAAACTCAGGC
ACAACCATCCGCGGCAGCTCGGTGAAGTTTTCACTCCACAGGCTGCGCAC
CATCACCAACGCGTTTAGCAGGTCGGGCGCCGATATCTTGAAGTCGCAGTT
GGGGCCTCCGCCCTGCGCGCGCGAGTTGCGATACACAGGGTTGCAGCAC
TGGAACACTATCAGCGCCGGGTGGTGCACGCTGGCCAGCACGCTCTTGTC
GGAGATCAGATCCGCGTCCAGGTCCTCCGCGTTGCTCAGGGCGAACGGAG
TCAACTTTGGTAGCTGCCTTCCCAAAAAGGGCGCGTGCCCAGGCTTTGAGT
TGCACTCGCACCGTAGTGGCATCAAAAGGTGACCGTGCCCGGTCTGGGCG
TTAGGATACAGCGCCTGCATAAAAGCCTTGATCTGCTTAAAAGCCACCTGA
GCCTTTGCGCCTTCAGAGAAGAACATGCCGCAAGCTTGCCGGAAAACTGA
TTGGCCGGACAGGCCGCGTCGTGCACGCAGCACCTTGCGTCGGTGTTGGA
GATCTGCACCACATTTCGGCCCCACCGGTTCTTCACGATCTTGGCCTTGCT
AGACTGCTCCTTCAGCGCGCGCTGCCCGTTTTCGCTCGTCACATCCATTTC
AATCACGTGCTCCTTATTTATCATAATGCTTCCGTGTAGACACTTAAGCTCG
CCTTCGATCTCAGCGCAGCGGTGCAGCCACAACGCGCAGCCCGTGGGCTC
GTGATGCTTGTAGGTCACCTCTGCAAACGACTGCAGGTACGCCTGCAGGA
ATCGCCCCATCATCGTCACAAAGGTCTTGTTGCTGGTGAAGGTCAGCTGCA
ACCCGCGGTGCTCCTCGTTCAGCCAGGTCTTGCATACGGCCGCCAGAGCT
TCCACTTGGTCAGGCAGTAGTTTGAAGTTCGCCTTTAGATCGTTATCCACGT
GGTACTTGTCCATCAGCGCGCGCGCAGCCTCCATGCCCTTCTCCCACGCA
GACACGATCGGCACACTCAGCGGGTTCATCACCGTAATTTCACTTTCCGCT
TCGCTGGGCTCTTCCTCTTCCTCTTGCGTCCGCATACCACGCGCCACTGGG
TCGTCTTCATTCAGCCGCCGCACTGTGCGCTTACCTCCTTTGCCATGCTTG
ATTAGCACCGGTGGGTTGCTGAAACCCACCATTTGTAGCGCCACATCTTCT
CTTTCTTCCTCGCTGTCCACGATTACCTCTGGTGATGGCGGGCGCTCGGGC
TTGGGAGAAGGGCGCTTCTTTTTCTTCTTGGGCGCAATGGCCAAATCCGCC
GCCGAGGTCGATGGCCGCGGGCTGGGTGTGCGCGGCACCAGCGCGTCTT
GTGATGAGTCTTCCTCGTCCTCGGACTCGATACGCCGCCTCATCCGCTTTT
TTGGGGGCGCCCGGGGAGGCGGCGGCGACGGGGACGGGGACGACACGT
CCTCCATGGTTGGGGGACGTCGCGCCGCACCGCGTCCGCGCTCGGGGGT
GGTTTCGCGCTGCTCCTCTTCCCGACTGGCCATTTCCTTCTCCTATAGGCA
GAAAAAGATCATGGAGTCAGTCGAGAAGAAGGACAGCCTAACCGCCCCCT
CTGAGTTCGCCACCACCGCCTCCACCGATGCCGCCAACGCGCCTACCACC
TTCCCCGTCGAGGCACCCCCGCTTGAGGAGGAGGAAGTGATTATCGAGCA
GGACCCAGGTTTTGTAAGCGAAGACGACGAGGACCGCTCAGTACCAACAG
AGGATAAAAAGCAAGACCAGGACAACGCAGAGGCAAACGAGGAACAAGTC
GGGCGGGGGACGAAAGGCATGGCGACTACCTAGATGTGGGAGACGACG
TGCTGTTGAAGCATCTGCAGCGCCAGTGCGCCATTATCTGCGACGCGTTG
CAAGAGCGCAGCGATGTGCCCCTCGCCATAGCGGATGTCAGCCTTGCCTA
CGAACGCCACCTATTCTCACCGCGCGTACCCCCAAACGCCAAGAAAACG
GCACATGCGAGCCCAACCCGCGCCTCAACTTCTACCCCGTATTTGCCGTG
CCAGAGGTGCTTGCCACCTATCACATCTTTTTCCAAAACTGCAAGATACCCC
TATCCTGCCGTGCCAACCGCAGCCGAGCGGACAAGCAGCTGGCCTTGCGG
CAGGGCGCTGTCATACCTGATATCGCCTCGCTCAACGAAGTGCCAAAAATC
TTTGAGGGTCTTGGACGCGACGAGAAGCGCGCGGCAAACGCTCTGCAACA
GGAAAACAGCGAAAATGAAAGTCACTCTGGAGTGTTGGTGGAACTCGAGG
GTGACAACGCGCGCCTAGCCGTACTAAAACGCAGCATCGAGGTCACCCAC
TTTGCCTACCCGGCACTTAACCTACCCCCAAGGTCATGAGCACAGTCATG
AGTGAGCTGATCGTGCGCCGTGCGCAGCCCCTGGGAGAGGGATGCAAATTT
GCAAGAACAAACAGAGGAGGGCCTACCCGCAGTTGGCGACGAGCAGCTAG
CGCGCTGGCTTCAAACGCGCGAGCCTGCCGACTTGGAGGAGCGACGCAA
ACTAATGATGGCCGCAGTGCTCGTTACCGTGGAGCTTGAGTGCATGCAGC
GGTTCTTTGCTGACCCGGAGATGCAGCGCAAGCTAGAGGAAACATTGCACT
ACACCTTTCGACAGGGCTACGTACGCCAGGCCTGCAAGATCTCCAACGTG |

-continued

| SEQ ID NO: | DESCRIPTION | SEQUENCE |
|---|---|---|
| | | GAGCTCTGCAACCTGGTCTCCTACCTTGGAATTTTGCACGAAAACCGCCTT
GGGCAAAACGTGCTTCATTCCACGCTCAAGGGCGAGGCGCGCCGCGACTA
CGTCCGCGACTGCGTTTACTTATTTCTATGCTACACCTGGCAGACGGCCAT
GGGCGTTTGGCAGCAGTGCTTGGAGGAGTGCAACCTCAAGGAGCTGCAGA
AACTGCTAAAGCAAAACTTGAAGGACCTATGGACGGCCTTCAACGAGCGCT
CCGTGGCCGCGCACCTGGCGGACATCATTTTCCCCGAACGCCTGCTTAAA
ACCCTGCAACAGGGTCTGCCAGACTTCACCAGTCAAAGCATGTTGCAGAAC
TTTAGGAACTTTATCCTAGAGCGCTCAGGAATCTTGCCCGCCACCTGCTGT
GCACTTCCTAGCGACTTTGTGCCCATTAAGTACCGCGAATGCCCTCCGCCG
CTTTGGGGCCACTGCTACCTTCTGCAGCTAGCCAACTACCTTGCCTACCAC
TCTGACATAATGGAAGACGTGAGCGGTGACGGTCTACTGGAGTGTCACTGT
CGCTGCAACCTATGCACCCCGCACCGCTCCCTGGTTTGCAATTCGCAGCT
GCTTAACGAAAGTCAAATTATCGGTACCTTTGAGCTGCAGGGTCCCTCGCC
TGACGAAAAGTCCGCGGCTCCGGGGTTGAAACTCACTCCGGGGCTGTGGA
CGTCGGCTTACCTTCGCAAATTTGTACCTGAGGACTACCACGCCCACGAGA
TTAGGTTCTACGAAGACCAATCCCGCCCGCCAAATGCGGAGCTTACCGCCT
GCGTCATTACCCAGGGCCACATTCTTGGCCAATTGCAAGCCATCAACAAAG
CCCGCCAAGAGTTTCTGCTACGAAAGGGACGGGGGGTTTACTTGGACCCC
CAGTCCGGCGAGGAGCTCAACCCAATCCCCCGCCGCCGCAGCCCTATCA
GCAGCAGCCGCGGGCCCTTGCTTCCCAGGATGGCACCCAAAAAGAAGCTG
CAGCTGCCGCCGCCACCCACGGACGAGGAGGAATACTGGGACAGTCAGG
CAGAGGAGGTTTTGGACGAGGAGGAGGAGGACATGATGGAAGACTGGGA
GAGCCTAGACGAGGAAGCTTCCGAGGTCGAAGAGGTGTCAGACGAAACAC
CGTCACCCTCGGTCGCATTCCCCTCGCCGGCGCCCCAGAAATCGGCAACC
GGTTCCAGCATGGCTACAACCTCCGCTCCTCAGGCGCCGCCGGCACTGCC
CGTTCGCCGACCCAACCGTAGATGGGACACCACTGGAACCAGGGCCGGTA
AGTCCAAGCAGCCGCCGCCGTTAGCCCAAGAGCAACAACAGCGCCAAGGC
TACCGCTCATGGCGCGGGCACAAGAACGCCATAGTTGCTTGCTTGCAAGA
CTGTGGGGCAACATCTCCTTCGCCCGCCGCTTTCTTCTCTACCATCACGG
CGTGGCCTTCCCCCGTAACATCCTGCATTACTACCGTCATCTCTACAGCCC
ATACTGCACCGGCGGCAGCGGCAGCGGCAGCAACAGCAGCGGCCACACA
GAAGCAAAGGCGACCGGATAGCAAGACTCTGACAAAGCCCAAGAAATCCA
CAGCGGCGGCAGCAGCAGGAGGAGGAGCGCTGCGTCTGGCGCCCAACGA
ACCCGTATCGACCCGCGAGCTTAGAAACAGGATTTTTCCCACTCTGTATGC
TATATTTCAACAGAGCAGGGGCCAAGAACAAGAGCTGAAAATAAAAAACAG
GTCTCTGCGATCCCTCACCCGCAGCTGCCTGTATCACAAAAGCGAAGATCA
GCTTCGGCGCACGCTGGAAGACGCGGAGGCTCTCTTCAGTAAATACTGCG
CGCTGACTCTTAAGGACTAGTTTCGCGCCCTTTCTCAAATTTAAGCGCGAAA
ACTACGTCATCTCCAGCGGCCACACCCGGCGCCAGCACCTGTCGTCAGCG
CCATTATGAGCAAGGAAATTCCCACGCCCTACATGTGGAGTTACCAGCCAC
AAATGGGACTTGCGGCTGGAGCTGCCCAAGACTACTCAACCCGAATAAACT
ACATGAGCGCGGGACCCCACATGATATCCCGGGTCAACGGAATCCGCGCC
CACCGAAACCGAATTCTCTTGGAACAGGCGGCTATTACCACCACACCTCGT
AATAACCTTAATCCCCGTAGTTGGCCCGCTGCCCTGGTGTACCAGGAAAGT
CCCGCTCCCACCACTGTGGTACTTCCCAGAGACGCCCAGGCCGAAGTTCA
GATGACTAACTCAGGGGCGCAGCTTGCGGGCGGCTTTCGTCACAGGGTGC
GGTCGCCCGGGCAGGGTATAACTCACCTGACAATCAGAGGGCGAGGTATT
CAGCTCAACGACGAGTCGGTGAGCTCCTCGCTTGGTCTCCGTCCGGACGG
GACATTTCAGATCGGCGGCGCCGGCCGCTCTTCATTCACGCCTCGTCAGG
CAATCCTAACTCTGCAGACCTCGTCCTCTGAGCCGCGCTCTGGAGGCATTG
GAACTCTGCAATTTATTGAGGAGTTTGTGCCATCGGTCTACTTTAACCCCTT
CTCGGGACCTCCCGGCCACTATCCGGATCAATTTATTCCTAACTTTGACGC
GGTAAAGGACTCGGCGGATGGCTACGACTGAATGTTAAGTGGAGAGGCAG
AGCAACTGCGCCTGAAACACCTGGTCCACTGTCGCCGCCACAAGTGCTTT
GCCCGCGACTCCGGTGAGTTTTGCTACTTTGAATTGCCCGAGGATCATATC
GAGGGCCCGGCGCACGGCGTCCGGCTTACCGCCAGGGAGAGCTTGCCC
GTAGCCTGATTCGGGAGTTTACCCAGCGCCCCTGCTAGTTGAGCGGGAC
AGGGGACCCTGTGTTCTCACTGTGATTTGCAACTGTCCTAACCCTGGATTA
CATCAAGATCTTTGTTGCCATCTCTGTGCTGAGTATAATAAATACAGAAATTA
AAATATACTGGGGCTCCTATCGCCATCCTGTAAACGCCACCGTCTTCACCC
GCCCAAGCAAACCAAGGCGAACCTTACCTGGTACTTTTAACATCTCTCCCT
CTGTGATTTACAACAGTTTCAACCCAGACGGAGTGAGTCTACGAGAGAACC
TCTCCGAGCTCAGCTACTCCATCAGAAAAAACACCACCCTCCTTACCTGCC
GGGAACGTACGACCTAGGGATAACAGGGTAATAAGCAATTGACTCTATGTG
GGATATGCTCCAGCGCTACAACCTTGAAGTCAGGCTTCCTGGATGTCAGCA
TCTGACTTTGGCCAGCACCTGTCCCGCGGATTTGTTCCAGTCCAACTACAG
CGACCCACCCTAACAGAGATGACCAACACAACCAACGCGGCCGCCGCTAC
CGGACTTACATCTACCACAAATACACCCCAAGTTTCTGCCTTTGTCAATAAC
TGGGATAACTTGGGCATGTGGTGGTTCTCCATAGCGCTTATGTTTGTATGC
CTTATTATTATGTGGCTCATCTGCTGCCTAAAGCGCAAACGCGCCCGACCA
CCCATCTATAGTCCCATCATTGTGCTACACCCAAACAATGATGGAATCCATA
GATTGGACGGACTGAAACACATGTTCTTTTCTCTTACAGTATGATTAAATGA
GACATGATTCCTCGAGTTTTTATATTACTGACCCTTGTTGCGCTTTTTTGTGC
GTGCTCCACATTGGCTGCGGTTTCTCACATCGAAGTAGACTGCATTCCAGC |

-continued

| Sequences | |
|---|---|
| SEQ ID NO: DESCRIPTION | SEQUENCE |
| | CTTCACAGTCTATTTGCTTTACGGATTTGTCACCCTCACGCTCATCTGCAGC |
| | CTCATCACTGTGGTCATCGCCTTTATCCAGTGCATTGACTGGGTCTGTGTG |
| | CGCTTTGCATATCTCAGACACCATCCCCAGTACAGGGACAGGACTATAGCT |
| | GAGCTTCTTAGAATTCTTTAATTATGAAATTTACTGTGACTTTTCTGCTGATT |
| | ATTTGCACCCTATCTGCGTTTTGTTCCCCGACCTCCAAGCCTCAAAGACATA |
| | TATCATGCAGATTCACTCGTATATGGAATATTCCAAGTTGCTACAATGAAAA |
| | AAGCGATCTTTCCGAAGCCTGGTTATATGCAATCATCTCTGTTATGGTGTTC |
| | TGCAGTACCATCTTAGCCCTAGCTATATATCCCTACCTTGACATTGGCTGGA |
| | AACGAATAGATGCCATGAACCACCCAACTTTCCCCGCGCCCGCTATGCTTC |
| | CACTGCAACAAGTTGTTGCCGGCGGCTTTGTCCCAGCCAATCAGCCTCGC |
| | CCCACTTCTCCCACCCCCACTGAAATCAGCTACTTTAATCTAACAGGAGGA |
| | GATGACTGACACCCTAGATCTAGAAATGGACGGAATTATTACAGAGCAGCG |
| | CCTGCTAGAAAGACGCAGGGCAGCGGCCGAGCAACAGCGCATGAATCAAG |
| | AGCTCCAAGACATGGTTAACTTGCACCAGTGCAAAAGGGGTATCTTTTGTC |
| | TGGTAAAGCAGGCCAAAGTCACCTACGACAGTAATACCACCGGACACCGC |
| | CTTAGCTACAAGTTGCCAACCAAGCGTCAGAAATTGGTGGTCATGGTGGGA |
| | GAAAAGCCCATTACCATAACTCAGCACTCGGTAGAAACCGAAGGCTGCATT |
| | CACTCACCTTGTCAAGGACCTGAGGATCTCTGCACCCTTATTAAGACCCTG |
| | TGCGGTCTCAAAGATCTTATTCCCTTTAACTAATAAAAAAAAAATAATAAAGCA |
| | TCACTTACTTAAAATCAGTTAGCAAATTTCTGTCCAGTTTATTCAGCAGCACC |
| | TCCTTGCCCTCCTCCCAGCTCTGGTATTGCAGCTTCCTCCTGGCTGCAAAC |
| | TTTCTCCACAATCTAAATGGAATGTCAGTTTCCTCCTGTTCCTGTCCATCCG |
| | CACCCACTATCTTCATGTTGTTGCAGATGAAGCGCGCAAGACCGTCTGAAG |
| | ATACCTTCAACCCCGTGTATCCATATGACACGGAAACCGGTCCTCCAACTG |
| | TGCCTTTTCTTACTCCTCCCTTTGTATCCCCCAATGGGTTTCAAGAGAGTCC |
| | CCCTGGGGTACTCTCTTTGCGCCTATCCGAACCTCTAGTTACCTCCAATGG |
| | CATGCTTGCGCTCAAAATGGGCAACGGCCTCTCTCTGGACGAGGCCGGCA |
| | ACCTTACCTCCCAAAATGTAACCACTGTGAGCCCACCTCTCAAAAAAACCAA |
| | GTCAAACATAAACCTGGAAATATCTGCACCCCTCACAGTTACCTCAGAAGC |
| | CCTAACTGTGGCTGCCGCCGCACCTCTAATGGTCGCGGGCAACACACTCA |
| | CCATGCAATCACAGGCCCCGCTAACCGTGCACGACTCCAAACTTAGCATTG |
| | CCACCCAAGGACCCCTCACAGTGTCAGAAGGAAAGCTAGCCCTGCAAACA |
| | TCAGGCCCCCTCACCACCACCGATAGCAGTACCCTTACTATCACTGCCTCA |
| | CCCCCTCTAACTACTGCCACTGGTAGCTTGGGCATTGACTTGAAAGAGCCC |
| | ATTTATACACAAAATGGAAAACTAGGACTAAAGTACGGGGCTCCTTTGCATG |
| | TAACAGACGACCTAAACACTTTGACCGTAGCAACTGGTCCAGGTGTGACTA |
| | TTAATAATACTTCCTTGCAAACTAAAGTTACTGGAGCCTTGGGTTTTGATTCA |
| | CAAGGCAATATGCAACTTAATGTAGCAGGAGGACTAAGGATTGATTCTCAA |
| | AACAGACGCCTTATACTTGATGTTAGTTATCCGTTTGATGCTCAAAACCAAC |
| | TAAATCTAAGACTAGGACAGGGCCCTCTTTTTATAAACTCAGCCCACAACTT |
| | GGATATTAACTACAACAAAGGCCTTTACTTGTTTACAGCTTCAAACAATTCC |
| | AAAAAGCTTGAGGTTAACCTAAGCACTGCCAAGGGGTTGATGTTTGACGCT |
| | ACAGCCATAGCCATTAATGCAGGAGATGGGCTTGAATTTGGTTCACCTAAT |
| | GCACCAAACACAAATCCCCTCAAAACAAAATTGGCCATGGCCTAGAATTT |
| | GATTCAAACAAGGCTATGGTTCCTAAACTAGGAACTGGCCTTAGTTTTGACA |
| | GCACAGGTGCCATTACAGTAGGAAACAAAAATAATGATAAGCTAACCCTAT |
| | GGACAGGTCCAAAACCAGAAGCCAACTGCATAATTGAATACGGGAAACAAA |
| | ACCCAGATAGCAAACTAACTTTAATCCTTGTAAAAAATGGAGGAATTGTTAA |
| | TGGATATGTAACGCTAATGGGAGCCTCAGACTACGTTAACACCTTATTTAAA |
| | AACAAAAATGTCTCCATTAATGTAGAACTATACTTTGATGCCACTGGTCATAT |
| | ATTACCAGACTCATCTTCTCTTAAAACAGATCTAGAACTAAATACAAGCAAA |
| | CCGCTGACTTTAGTGCAAGAGGTTTTATGCCAAGTACTACAGCGTATCCATT |
| | TGTCCTTCCTAATGCGGGAACACATAATGAAAATTATATTTTTGGTCAATGC |
| | TACTACAAAGCAAGCGATGGTGCCCTTTTTCCGTTGGAAGTTACTGTTATGC |
| | TTAATAAACGCCTGCCAGATAGTCGCACATCCTATGTTATGACTTTTTTATG |
| | GTCCTTGAATGCTGGTCTAGCTCCAGAAACTACTCAGGCAACCCTCATAAC |
| | CTCCCCATTTACCTTTTCCTATATTAGAGAAGATGACTAATAAACTCTAAAGA |
| | ATCGTTTGTGTTATGTTTCAACGTGTTTATTTTTCAATTGCAGAAAATTTCAA |
| | GTCATTTTTCATTCAGTAGTATAGCCCCACCACCACATAGCTTATACAGATC |
| | ACCGTACCTTAATCAAACTCACAGAACCCTAGTATTCAACCTGCCACCTCCC |
| | TCCCAACACACAGAGTACACAGTCCTTTCTCCCCGGCTGGCCTTAAAAAGC |
| | ATCATATCATGGGTAACAGACATATTCTTAGGTGTTATATTCCACACGGTTT |
| | CCTGTCGAGCCAAACGCTCATCAAGTGATATTAATAAACTCCCCGGGCAGC |
| | TCACTTAAGTTCATGTCGCTGTCCAGCTGCTGAGCCACAGGCTGCTGTCCA |
| | ACTTGCGGTTGCTTAACGGGCGGCGAAGGAGAAGTCCACGCCTACATGGG |
| | GGGAGAGTCATAATCGTGCATCAGGATAGGCGGTGGTGCTGCAGCAGCG |
| | CGCGAATAAACTGCTGCCGCCGCCGCTCCGTCCTGCAGGAATACAACATG |
| | GCAGTGGTCTCCTCAGCGATGATTCGCACCGCCCGCAGCATAAGGCGCTT |
| | GTCCTCCGGGCACAGCAGCGCACCCTGATCTCACTTAAATCAGCACAGTAA |
| | CTGCAGCACAGCACCACAATATTGTTCAAAATCCCACAGTGCAAGGCGCTG |
| | TATCCAAAGCTCATGGCGGGACCACAGAACCCACGTGGCCATCATACCA |
| | CAAGCGCAGGTAGATTAAGTGGCGACCCCTCATAAACACGCTGGACATAAA |
| | CATTACCTCTTTTGGCATGTTGTAATTCACCACCTCCCGGTACCATATAAAC |
| | CTCTGATTAAACATGGCGCCATCCACCACCATCCTAAACCAGCTGGCCAAA |

| SEQ ID NO: | DESCRIPTION | SEQUENCE |
|---|---|---|
| | | ACCTGCCCCGCCGGGNTATACACTGCAGGGAACCGGGACTTGGACAATGA
CAAGTGGGAGAGCCCAGGACTCGTAACCATGGATCATCATGCTCGTCATGA
TATCAATGTTGGCACAACACAGGCACACGTGCATACACTTCCTCAGGATTA
CAAGCTCCTCCCGCGTTAGAACCATATCCCAGGGAACAACCCATTCCTGAA
TCAGCGTAAATCCCACACTGCAGGGAAGACCTCGCACGTAACTCACGTTGT
GCATTGTCAAAGTGTTACATTCGGGCAGCAGCGGATGATCCTCCAGTATGG
TAGCGCGGGTTTCTGTCTCAAAAGGAGGTAGACGATCCCTACTGTACGGAG
TGCGCCGAGACAACCGAGATCGTGTTGGTCGTAGTGTCATGCCAAATGGA
ACGCCGGACGTAGTCATATTTCCTGAAGCAAAACCAGGTGCGGGCGTGAC
AAACAGATCTGCGTCTCCGGTCTCGCCGCTTAGATCGCTCTGTGTAGTAGT
TGTAGTATATCCACTCTCTCAAAGCATCCAGGCGCCCCCTGGCTTCGGGTT
CTATGTAAACTCCTTCATGCGCCGCTGCCCTGATAACATCCACCACCGCAG
AATAAGCCACACCCAGCCAACCTACACATTCGTTCTGCGAGTCACACACGG
GAGGAGCGGGAAGAGCTGGAAGAACCATGTTTTTTTTTTTATTCCAAAAGAT
TATCCAAAACCTCAAAATGAAGATCTATTAAGTGAACGCGCTCCCCTCCGGT
GGCGTGGTCAAACTCTACAGCCAAAGAACAGATAATGGCATTTGTAAGATG
TTGCACAATGGCTTCCAAAAGGCAAACGGCCCTCACGTCCAAGTGGACGTA
AAGGCTAAACCCTTCAGGGTGAATCTCCTCTATAAACATTCCAGCACCTTCA
ACCATGCCCAAATAATTCTCATCTCGCCACCTTCTCAATATATCTCTAAGCA
AATCCCGAATATTTAAGTCCGGGCCATTGTAAAAAATTTGGCTCCAGAGCG
CCCTCCACCTTCAGCCTCAAGCAGCGAATCATGATTGCAAAAATTCAGGTT
CCTCACAGACCTGTATAAGATTCAAAAGCGGAACATTAACAAAAATACCGC
GATCCCGTAGGTCCCTTCGCAGGGCAGCTGAACATAATCGTGCAGGTCT
GCACGGACCAGCGCGGCCACTTCCCCGCCAGGAACCATGACAAAAGAACC
CACACTGATTATGACACGCATACTCGGAGCTATGCTAACCAGCGTAGCCCC
GATGTAAGCTTGTTGCATGGGCGGCGATATAAAATGCAAGGTGCTGCTCAA
AAAATCAGGCAAAGCCTCGCGCAAAAAAGAAAGCACATCGTAGTCATGCTC
ATGCAGATAAAGGCAGGTAAGCTCCGGAACCACCACAGAAAAAGACACCAT
TTTTCTCTCAAACATGTCTGCGGGTTTCTGCATAAACACAAAATAAAATAACA
AAAAAACATTTAAACATTAGAAGCCTGTCTTACAACAGGAAAAACAACCCTT
ATAAGCATAAGACGGACTACGGCCATGCCGGCGTGACCGTAAAAAACTG
GTCACCGTGATTAAAAAGCACCACCGACAGCTCCTCGGTCAGTCCGGAGT
CATAATGTAAGACTCGGTAAACACATCAGGTTGATTCACATCGGTCAGTGTT
AAAAAGCGACCGAAATAGCCNGGGGGAATACAATACCCGCAGGCGTAGAG
ACAACATTACAGCCCCCATAGGAGGTATAACAAAATTAATAGGAGAGAAAA
CACATAAACACCTGAAAAACCCTCCTGCCTAGGCAAAATAGCACCCTCCCG
CTCCAGAACAACATACAGCGCTTCCACAGCGGCAGCCATAACAGTCAGCCT
TACCAGTAAAAAAGAAAACCTATTAAAAAAACACCACTCGACACGGCACCA
GCTCAATCAGTCACAGTGTAAAAAAGGGCCAAGTGCAGAGCGAGTATATAT
AGGACTAAAAAATGACGGTAACGGTTAAAGTCCACAAAAAACACCCAGAAA
ACCGCACGCGAACCTACGCCCAGAAACGAAAGCCAAAAAACCCACAACTTC
CTCAAATCGTCACTTCCGTTTTCCCACGTTACGTCACTTCCCATTTTAAGAA
AACTACAATTCCCAACACATACAAGTTACTCCGCCCTAAAACCTACGTCACC
CGCCCCGTTCCCACGCCCCGCGCCACGTCACAAACTCCACCCCCTCATTA
TCATATTGGCTTCAATCCAAAATAAGGTATATTATTGATGATGTTAATTAACA
TGCATGGATCCTCGTCTCGACGATGCCCTTGAGAGCCTTCAACCCAGTCAG
CTCCTTCCGGTGGGCGCGGGGCATGACTATCGTCGCCGCACTTATGACTG
TCTTCTTTATCATGCAACTCGTAGGACAGGTGCCGGCAGCGCTCTGGGTCA
TTTTCGGCGAGGACCGCTTTCGCTGGAGCGCGACGATGATCGGCCTGTCG
CTTGCGGTATTCGGAATCTTGCACGCCCTCGCTCAAGCCTTCGTCACTGGT
CCCGCCACCAAACGTTTCGGCGAGAAGCAGGCCATTATCGCCGGCATGGC
GGCCGACGCGCTGGGCTACGTCTTGCTGGCGTTCGCGACGCGAGGCTGG
ATGGCCTTCCCCATTATGATTCTTCTCGCTTCCGGCGGCATCGGGATGCCC
GCGTTGCAGGCCATGCTGTCCAGGCAGGTAGATGACGACCATCAGGGACA
GCTTCAAGGATCGCTCGCGGCTCTTACCAGCCTAACTTCGATCACTGGACC
GCTGATCGTCACGGCGATTTATGCCGCCTCGGCGAGCACATGGAACGGGT
TGGCATGGATTGTAGGCGCCGCCCTATACCTTGTCTGCCTCCCCGCGTTG
CGTCGCGGTGCATGGAGCCGGGCCACCTCGACCTGAATGGAAGCCGGCG
GCACCTCGCTAACGGATTCACCACTCCAAGAATTGGAGCCAATCAATTCTT
GCGGAGAACTGTGAATGCGCAAACCAACCCTTGGCAGAACATATCCATCGC
GTCCGCCATCTCCAGCAGCCGCACGCGGCGCATCTCGGGCAGCGTTGGG
TCCTGGCCACGGGTGCGCATGATCGTGCTCCTGTCGTTGAGGACCCGGCT
AGGCTGGCGGGGTTGCCTTACTGGTTAGCAGAATGAATCACCGATACGCG
AGCGAACGTGAAGCGACTGCTGCTGCAAAACGTCTGCGACCTGAGCAACA
ACATGAATGGTCTTCGGTTTCCGTGTTTCGTAAAGTCTGGAAACGCGGAAG
TCAGCGCCCTGCACCATTATGTTCCGGATCTGCATCGCAGGATGCTGCTGG
CTACCCGTGGAACACCTACATCTGTATTAACGAAGCGCTGGCATTGACCC
TGAGTGATTTTCTCTGGTCCCGCCGCATCCATACCGCCAGTTGTTTACCCT
CACAACGTTCCAGTAACCGGGCATGTTCATCATCAGTAACCCGTATCGTGA
GCATCCTCTCTCGTTTCATCGGTATCATTACCCCCATGAACAGAAATTCCCC
CTTACACGGAGGCATCAAGTGACCAAACAGGAAAAAACCGCCCTTAACATG
GCCCGCTTTATCAGAAGCCAGACATTAACGCTTCTGGAGAAACTCAACGAG
CTGGACGCGGATGAACAGGCAGACATCTGTGAATCGCTTCACGACCACGC
TGATGAGCTTTACCGCAGCTGCCTCGCGCGTTTCGGTGATGACGGTGAAAA |

| SEQ ID NO: | DESCRIPTION | SEQUENCE |
|---|---|---|
| | | CCTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGG
GTGTCGGGGCGCAGCCATGACCCAGTCACGTAGCGATAGCGGAGTGTATA
CTGGCTTAACTATGCGGCATCAGAGCAGATTGTACTGAGAGTGCACCATAT
GCGGTGTGAAATACCGCACAGATGCGTAAGGAGAAAATACCGCATCAGGC
GCTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCC
CCCTGACGAGCATCACAAAAATCGACGCTCAAGTCAGAGGTGGCGAAACC
CGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCC
CTTCGGGAAGCGTGGCGCTTTCTCAATGCTCACGCTGTAGGTATCTCAGTT
CGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCCG
GTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCC
AGTTACCTTCGGAAAAAGAGTTGGTAGCTCTTGATCCGGCAAACAAACCAC
CGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCA
GTGGAACGAAAACTCACGTTAAGGGATTTTGGTCATGAGATTATCAAAAAG
ATCTTCACCTAGATCCTTTTAAATTAAAAATGAAGTTTTAAATCAATCTAAA
GTATATATGAGTAAACTTGGTCTGACAGTTACCAATGCTTAATCAGTGAGGO
ACCTATCTCAGCGATCTGTCTATTTCGTTCATCCATAGTTGCCTGACTCCCC
GTCGTGTAGATAACTACGATACGGGAGGGCTTACCATCTGGCCCCAGTGCT
GCAATGATACCGCGAGACCCACGCTCACCGGCTCCAGATTTATCAGCAATA
AACCAGCCAGCCGGAAGGGCCGAGCGCAGAAGTGGTCCTGCAACTTTATC
CGCCTCCATCCAGTCTATTAATTGTTGCCGGGAAGCTAGAGTAAGTAGTTC
GCCAGTTAATAGTTTGCGCAACGTTGGTTGNNNNNNAAAAAGGATCTTCAC
CTAGATCCTTTTCACGTAGAAAGCCAGTCCGCAGAAACGGTGCTGACCCCG
GATGAATGTCAGCTACTGGGCTATCTGGACAAGGGAAAACGCAAGCGCAA
AGAGAAAGCAGGTAGCTTGCAGTGGGCTTACATGGCGATAGCTAGACTGG
GCGGTTTTATGGACAGCAAGCGAACCGGAATTGCCAGCTGGGGCGCCCTC
TGGTAAGGTTGGGAAGCCCTGCAAAGTAAACTGGATGGCTTTCTCGCCGC
CAAGGATCTGATGGCGCAGGGGATCAAGCTCTGATCAAGAGACAGGATGA
GGATCGTTTCGCATGATTGAACAAGATGGATTGCACGCAGGTTCTCCGGCC
GCTTGGGTGGAGAGGCTATTCGGCTATGACTGGGCACAACAGACAATCGG
CTGCTCTGATGCCGCCGTGTTCCGGCTGTCAGCGCAGGGGCGCCCGGTTC
TTTTTGTCAAGACCGACCTGTCCGGTGCCCTGAATGAACTGCAAGACGAGG
CAGCGCGGCTATCGTGGCTGGCCACGACGGGCGTTCCTTGCGCAGCTGT
GCTCGACGTTGTCACTGAAGCGGGAAGGGACTGGCTGCTATTGGGCGAAG
TGCCGGGGCAGGATCTCCTGTCATCTCACCTTGCTCCTGCCGAGAAAGTAT
CCATCATGGCTGATGCAATGCGGCGGCTGCATACGCTTGATCCGGCTACC
TGCCCATTCGACCACCAAGCGAAACATCGCATCGAGCGAGCACGTACTCG
GATGGGAAGCCGGTCTTGTCGATCAGGATGATCTGGACGAAGAGCATCAGG
GGCTCGCGCCAGCCGAACTGTTCGCCAGGCTCAAGGCGAGCATGCCCGA
CGGCGAGGATCTCGTCGTGACCCATGGCGATGCCTGCTTGCCGAATATCA
TGGTGGAAAATGGCCGCTTTTCTGGATTCATCGACTGTGGCCGGCTGGGT
GTGGCGGACCGCTATCAGGACATAGCGTTGGCTACCCGTGATATTGCTGA
AGAGCTTGGCGGCGAATGGGCTGACCGCTTCCTCGTGCTTTACGGTATCG
CCGCTCCCGATTCGCAGCGCATCGCCTTCTATCGCCTTCTTGACGAGTTCT
TCTGAATTTTGTTAAAATTTTGTTAAATCAGCTCATTTTTTAACCAATAGGC
CGAAATCGGCAACATCCCTTATAAATCAAAAGAATAGACCGCGATAGGGTT
GAGTGTTGTTCCAGTTTGGAACAAGAGTCCACTATTAAAGAACGTGGACTC
CAACGTCAAAGGGCGAAAAACCGTCTATCAGGGCGATGGCCCACTACGTG
AACCATCACCCAAATCAAGTTTTTTGCGGTCGAGGTGCCGTAAAGCTCTAA
ATCGGAACCCTAAAGGGAGCCCCCGATTTAGAGCTTGACGGGGAAAGCCG
GCGAACGTGGCGAGAAAGGAAGGGAAGAAAGCGAAAGGAGCGGGCGCTA
GGGCGCTGGCAAGTGTAGCGGTCACGCTGCGCGTAACCACCACACCCGC
GCGCTTAATGCGCCGCTACAGGGCGCGTCCATTCGCCATTCAGGATCGAA
TTAATTCTTAAT |
| 52 | Amino acids 121-128 of Ad E1A protein | LTCHEACF |
| 53 | STAT1 binding site (1) | TTCCGGGAA |
| 54 | STAT1 binding site (2) | TTCTCGGAA |
| 55 | Ad5/3Ad2E1AΔ | TAACATCATCAATAATATACCTTATTTTGGATTGAAGCCAATATGATAATGAG |

Sequences

| SEQ ID NO: | DESCRIPTION | SEQUENCE |
| --- | --- | --- |
| | 24 | GGGGTGGAGTTTGTGACGTGGCGCGGGGCGTGGGAACGGGGCGGGTGA<br>CGTAGTAGTGTGGCGGAAGTGTGATGTTGCAAGTGTGGCGGAACACATGT<br>AAGCGACGGATGTGGCAAAAGTGACGTTTTTGGTGTGCGCCGGTGTACAC<br>AGGAAGTGACAATTTTCGCGCGGTTTTAGGCGGATGTTGTAGTAAATTTGG<br>GCGTAACCGAGTAAGATTTGGCCATTTTCGCGGGAAAACTGAATAAGAGGA<br>AGTGAAATCTGAATAATTTTGTGTTACTCATAGCGCGTAATATTTGTCTAGG<br>GCCGCGGGGACTTTGACCGTTTACGTGGAGACTCGCCCAGGTGTTTTTCTC<br>AGGTGTTTTCCGCGTTCCGGGTCAAAGTTGGCGTTTTATTATTATAGTCAGC<br>TGACGTGTAGTGTATTTATACCCGGTGAGTTCCTCAAGAGGCCACTCTTGA<br>GTGCCAGCGAGTAGAGTTTTCTCCTCCGAGCCGCTCCGACACCGGGACTG<br>AAAATGAGACATATTATCTGCCACGGAGGTGTTATTACCGAAGAAATGGCC<br>GCCAGTCTTTTGGACCAGCTGATCGAAGAGGTACTGGCTGATAATCTTCCA<br>CCTCCTAGCCATTTTGAACCACCTACCCTTCACGAACTGTATGATTTAGACG<br>TGACGGCCCCCGAAGATCCCAACGAGGAGGCGGTTTCGCAGATTTTTCCC<br>GAGTCTGTAATGTTGGCGGTGCAGGAAGGGATTGACTTATTCACTTTTCCG<br>CCGGCGCCCGGTTCTCCGGAGCCGCCTCACCTTTCCCGGCAGCCCGAGC<br>AGCCGGAGCAGAGAGCCTTGGGTCCGGTTTCTATGCCAAACCTTGTGCCG<br>GAGGTGATCGATCCACCCAGTGACGACGAGGATGAAGAGGGTGAGGAGTT<br>TGTGTTAGATTATGTGGAGCACCCCGGGCACGGTTGCAGGTCTTGTCATTA<br>TCACCGGAGGAATACGGGGGACCCAGATATTATGTGTTCGCTTTGCTATAT<br>GAGGACCTGTGGCATGTTTGTCTACAGTAAGTGAAAATTATGGGCAGTCGG<br>TGATAGAGTGGTGGGTTTGGTGTGGTAATTTTTTTTTAATTTTTACAGTTTTG<br>TGGTTTAAAGAATTTTGTATTGTGATTTTTTAAAAGGTCCTGTGTCTGAACCT<br>GAGCCTGAGCCCGAGCCAGAACCGGAGCCTGCAAGACCTACCCGGCGTC<br>CTAAATTGGTGCCTGCTATCCTGAGACGCCCGACATCACCTGTGTCTAGAG<br>AATGCAATAGTAGTACGGATAGCTGTGACTCCGGTCCTTCTAACACACCTC<br>CTGAGATACACCCGGTGGTCCCGCTGTGCCCCATTAAACCAGTTGCCGTG<br>AGAGTTGGTGGGCGTCGCCAGGCTGTGGAATGTATCGAGGACTTGCTTAA<br>CGAGTCTGGGCAACCTTTGGACTTGAGCTGTAAACGCCCCAGGCCATAAG<br>GTGTAAACCTGTGATTGCGTGTGTGGTTAACGCCTTTGTTTGCTGAATGAGT<br>TGATGTAAGTTTAATAAAGGGTGAGATAATGTTTAACTTGCATGGCGTGTTA<br>AATGGGGCGGGGCTTAAAGGGTATATAATGCGCCGTGGGCTAATCTTGGTT<br>ACATCTGACCTCATGGAGGCTTGGGAGTGTTTGGAAGATTTTTCTGCTGTG<br>CGTAACTTGCTGGAACAGAGCTCTAACAGTACCTCTTGGTTTTGGAGGTTT<br>CTGTGGGGCTCATCCCAGGCAAAGTTAGTCTGCAGAATTAAGGAGGATTAC<br>AAGTGGGAATTTGAAGAGCTTTTGAAATCCTGTGGTGAGCTGTTTGATTCTT<br>TGAATCTGGGTCACCAGGCGCTTTTCCAAGAGAAGGTCATCAAGACTTTGG<br>ATTTTTCCACACCGGGGCGCGCTGCGGCTGCTGTTGCTTTTTTGAGTTTTAT<br>AAAGGATAAATGGAGCGAAGAAACCCATCTGAGCGGGGGGTACCTGCTGG<br>ATTTTCTGGCCATGCATCTGTGGAGAGCGGTTGTGAGACACAAGAATCGCC<br>TGCTACTGTTGTCTTCCGTCCGCCCGGCGATAATACCGACGGAGGAGCAG<br>CAGCAGCAGCAGGAGGAAGCCAGGCGGCGGCGGCAGGAGCAGAGCCCAT<br>GGAACCCGAGAGCCGGCCTGGACCCTCGGGAATGAATGTTGTTCAGGTGG<br>CTGAACTGTATCCAGAACTGAGACGCATTTTGACAATTACAGAGGATGGGC<br>AGGGGCTAAAGGGGGTAAAGAGGGAGCGGGGGGCTTGTGAGGCTACAGA<br>GGAGGCTAGGAATCTAGCTTTTAGCTTAATGACCAGACACCGTCCTGAGTG<br>TATTACTTTTCAACAGATCAAGGATAATTGCGCTAATGAGCTTGATCTGCTG<br>GCGCAGAAGTATTCCATAGAGCAGCTGACCACTTACTGGCTGCAGCCAGG<br>GGATGATTTTGAGGAGGCTATTAGGGTATATGCAAAGGTGGCACTTAGGCC<br>AGATTGCAAGTACAAGATCAGCAAACTTGTAAATATCAGGAATTGTTGCTAC<br>ATTTCTGGGAACGGGGCCGAGGTGGAGATAGATACGGAGGATAGGGTGGC<br>CTTTAGATGTAGCATGATAAATATGTGGCCGGGGGTGCTTGGCATGGACGG<br>GGTGGTTATTATGAATGTAAGGTTTACTGGCCCCAATTTTAGCGGTACGGTT<br>TTCCTGGCCAATACCAACCTTATCCTACACGGTGTAAGCTTCTATGGGTTTA<br>ACAATACCTGTGTGGAAGCCTGGACCGATGTAAGGGTTCGGGGCTGTGCC<br>TTTTACTGCTGCTGGAAGGGGTGGTGTGTCGCCCCAAAAGCAGGGCTTC<br>AATTAAGAAATGCCTCTTTGAAAGGTGTACCTTGGGTATCCTGTCTGAGGGT<br>AACTCCAGGGTGCGCCACAATGTGGCCTCCGACTGTGGTTGCTTCATGCTA<br>GTGAAAAGCGTGGCTGTGATTAAGCATAACATGGTATGTGGCAACTGCGAG<br>GACAGGGCCTCTCAGATGCTGACCTGCTCGGACGGCAACTGTCACCTTCT<br>GAAGACCATTCACGTAGCCAGCCACTCTCGCAAGGCCTGGCCAGTGTTTG<br>AGCATAACATACTGACCCGCTGTTCCTTGCATTTGGGTAACAGGAGGGGGG<br>TGTTCCTACCTTACCAATGCAATTTGAGTCACACTAAGATATTGCTTGAGCC<br>CGAGAGCATGTCCAAGGTGAACCTGAACGGGGTGTTTGACATGACCATGA<br>AGATCTGGAAGGTGCTGAGGTACGATGAGACCCGCACCAGGTGCAGACCC<br>TGCGAGTGTGGCGGTAAACATATTAGGAACCAGCCTGTGATGCTGGATGTG<br>ACCGAGGAGCTGAGGCCCGATCACTTGGTGCTGGCCTGCACCCGCGCTGA<br>GTTTGGCTCTAGCGATGAAGATACAGATTGAGGTACTGAAATGTGTGGGCG<br>TGGCTTAAGGGTGGGAAAGAATATATAAGGTGGGGGTCTTATGTAGTTTTG<br>TATCTGTTTTGCAGCAGCCGCCGCCGCCATGAGCACCAACTCGTTTGATGG<br>AAGCATTGTGAGCTCATATTTGACAACGCGCATGCCCCCATGGGCCGGGG<br>TGCGTCAGAATGTGATGGGCTCCAGCATTGATGGTCGCCCCGTCCTGCCC<br>GCAAACTCTACTACCTTGACCTACGAGACCGTGTCTGGAACGCCGTTGGAG<br>ACTGCAGCCTCCGCCGCCGCTTCAGCCGCTGCAGCCACCGCCCGCGGGA |

| SEQ ID NO: | DESCRIPTION | SEQUENCE |
|---|---|---|
| | | TTGTGACTGACTTTGCTTTCCTGAGCCCGCTTGCAAGCAGTGCAGCTTCCC
GTTCATCCGCCCGCGATGACAAGTTGACGGCTCTTTTGGCACAATTGGATT
CTTTTGACCCGGGAACTTAATGTCGTTTCTCAGCAGCTGTTGGATCTGCGCC
AGCAGGTTTCTGCCCTGAAGGCTTCCTCCCCTCCCAATGCGGTTTAAAACA
TAAATAAAAAACCAGACTCTGTTTGGATTTGGATCAAGCAAGTGTCTTGCTG
TCTTTATTTAGGGGTTTTGCGCGCGCGGTAGGCCCGGGACCAGCGGTCTC
GGTCGTTGAGGGTCCTGTGTATTTTTTCCAGGACGTGGTAAAGGTGACTCT
GGATGTTCAGATACATGGGCATAAGCCCGTCTCTGGGGTGGAGGTAGCAC
CACTGCAGAGCTTCATGCTGCGGGGTGGTGTTGTAGATGATCCAGTCGTA
GCAGGAGCGCTGGGCGTGGTGCCTAAAAATGTCTTTCAGTAGCAAGCTGA
TTGCCAGGGGCAGGCCCTTGGTGTAAGTGTTTACAAAGCGGTTAAGCTGG
GATGGGTGCATACGTGGGGATATGAGATGCATCTTGGACTGTATTTTTAGG
TTGGCTATGTTCCCAGCCATATCCCTCCGGGGATTCATGTTGTGCAGAACC
ACCAGCACAGTGTATCCGGTGCACTTGGGAAATTTGTCATGTAGCTTAGAA
GGAAATGCGTGGAAGAACTTGGAGACGCCCTTGTGACCTCCAAGATTTTCC
ATGCATTCGTCCATAATGATGGCAATGGGCCCACGGGCGGCGGCCTGGGC
GAAGATATTTCTGGGATCACTAACGTCATAGTTGTGTTCCAGGATGAGATC
GTCATAGGCCATTTTTACAAAGCGCGGGCGGAGGGTGCCAGACTGCGGTA
TAATGGTTCCATCCGGCCCAGGGGCGTAGTTACCCTCACAGATTTGCATTT
CCCACGCTTTGAGTTCAGATGGGGGGATCATGTCTACCTGCGGGCGATG
AAGAAAACGGTTTCCGGGGTAGGGGAGATCAGCTGGGAAGAAAGCAGGTT
CCTGAGCAGCTGCGACTTACCGCAGCCGGTGGGCCCGTAAATCACACCTA
TTACCGGGTGCAACTGGTAGTTAAGAGAGCTGCAGCTGCCGTCATCCCTGA
GCAGGGGGGCCACTTCGTTAAGCATGTCCCTGACTCGCATGTTTTCCCTGA
CCAAATCCGCAGAAGGCGCTCGCCGCCCAGCGATAGCAGTTCTTGCAAG
GAAGCAAAGTTTTTCAACGGTTTGAGACCGTCCGCCGTAGGCATGCTTTTG
AGCGTTTGACCAAGCAGTTCCAGGCGGTCCCACAGCTCGGTTACCTGCTCT
ACGGCATCTCGATCCAGCATATCTCCTCGTTTCGCGGGTTGGGGCGGCTTT
CGCTGTACGGCAGTAGTCGGTGCTCGTCCAGACGGGCCAGGGTCATGTCT
TTCCACGGGCGCAGGGTCCTCGTCAGCGTAGTCTGGGTCACGGTGAAGGG
GTGCGCTCCGGGCTGCGCGCTGGCCAGGGTGCGCTTGAGGCTGGTCCTG
CTGGTGCTGAAGCGCTGCCGGTCTTCGCCCTGCGCGTCGGCCAGGTAGCA
TTTGACCATGGTGTCATAGTCCAGCCCCTCCGCGGCGTGGCCCTTGGCGC
GCAGCTTGCCCTTGGAGGAGGCGCCGCACGAGGGGCAGTGCAGACTTTT
GAGGGCGTAGAGCTTGGGCGCGAGAAATACCGATTCCGGGGAGTAGGCAT
CCGCGCCGCAGGCCCCGCAGACGGTCTCGCATTCCACGAGCCAGGTGAG
CTCTGGCCGTTCGGGGTCAAAAACCAGGTTTCCCCCATGCTTTTTGATGCG
TTTCTTACCTCTGGTTTCCATGAGCCGGTGTCCACGCTCGGTGACGAAAAG
GCTGTCCGTGTCCCCGTATACAGACTTGAGAGGCCTGTCCTCGAGCGGTG
TTCCGCGGTCCTCCTCGTATAGAAACTCGGACCACTCTGAGACAAAGGCTC
GCGTCCAGGCCAGCACGAAGGAGGCTAAGTGGGAGGGGTAGCGGTCGTT
GTCCACTAGGGGGTCCACTCGCTCCAGGGTGTGAAGACACATGTCGCCCT
CTTCGGCATCAAGGAAGGTGATTGGTTTGTAGGTGTAGGCCACGTGACCG
GGTGTTCCTGAAGGGGGGCTATAAAAGGGGGTGGGGCGCGTTCGTCCT
CACTCTCTTCCGCATCGCTGTCTGCGAGGGCCAGCTGTTGGGGTGAGTAC
TCCCCTCTGAAAAGCGGGCATGACTTCTGCGCTAAGATTGTCAGTTTCCAAA
AACGAGGAGGATTTGATATTCACCTGGCCCGCGGTGATGCCTTTGAGGGT
GGCCGCATCCATCTGGTCAGAAAAGACAATCTTTTTGTTGTCAAGCTTGGT
GGCAAACGACCCGTAGAGGGCGTTGGACAGCAACTTGGCGATGGAGCGC
AGGGTTTGGTTTTTGTCGCGATCGGCGCGCTCCTTGGCCGCGATGTTTAGC
TGCACGTATTCGCGCGCAACGCACCGCCATTCGGGAAAGACGGTGGTGCG
CTCGTCGGGCACCAGGTGCACGCGCCAACCGCGGTTGTGCAGGGTGACA
AGGTCAACGCTGGTGGCTACCTCTCCGCGTAGGCGCTCGTTGGTCCAGCA
GAGGCGGCCGCCCTTGCGCGAGCAGAATGGCGGTAGGGGGTCTAGCTGC
GTCTCGTCCGGGGGGTCTGCGTCCACGGTAAAGACCCCGGGCAGCAGGC
GCGCGTCGAAGTAGTCTATCTTGCATCCTTGCAAGTCTAGCGCCTGCTGCC
ATGCGCGGGCGGCAAGCGCGCGCTCGTATGGGTTGAGTGGGGGACCCCA
TGGCATGGGGTGGGTGAGCGCGGAGGCGTACATGCCGCAAATGTCGTAAA
CGTAGAGGGGCTCTCTGAGTATTCCAAGATATGTAGGGTAGCATCTTCCAC
CGCGGATGCTGGCGCGACGTAATCGTATAGTTCGTGCGAGGGAGCGAG
GAGGTCGGGACCGAGGTTGCTACGGGCGGGCTGCTCTGCTCGGAAGACT
ATCTGCCTGAAGATGGCATGTGAGTTGGATGATATGGTTGGACGCTGGAAG
ACGTTGAAGCTGGCGTCTGTGAGACCTACCGCGTCACGCACGAAGGAGGC
GTAGGAGTCGCGCAGCTTGTTGACCAGCTCGGCGGTGACCTGCACGTCTA
GGGCGCAGTAGTCCAGGGTTTCCTTGATGATGTCATACTTATCCTGTCCCT
TTTTTTTCCACAGCTCGCGGTTGAGGACAAACTCTTCGCGGTCTTTCCAGTA
CTCTTGGATCGGAAACCCGTCGGCCTCCGAACGGTAAGAGCCTAGCATGT
AGAACTGGTTGACGGCCTAGTAGGCGCAGCATCCCTTTTCTACGGGTAGC
GCGTATGCCTGCGCGGCCTTCCGGAGCGAGGTGTGGGTGAGCGCAAAGG
TGTCCCTGACCATGACTTTGAGGTACTGGTATTTGAAGTCAGTGTCGTCGC
ATCCGCCCTGCTCCCAGAGCAAAAAGTCCGTGCGCTTTTTGGAACGCGGAT
TTGGCAGGGCGAAGGTGACATCGTTGAAGAGTATCTTTCCCGCGCGAGGC
ATAAAGTTGCGTGTGATGCGGAAGGGTCCCGGCACCTCGGAACGGTTGTT
AATTACCTGGGCGGCGAGCACGATCTCGTCAAAGCCGTTGATGTTGTGGC |

Sequences

| SEQ ID NO: | DESCRIPTION | SEQUENCE |
|---|---|---|
| | | CCACAATGTAAAGTTCCAAGAAGCGCGGGATGCCCTTGATGGAAGGCAATT |
| | | TTTTAAGTTCCTCGTAGGTGAGCTCTTCAGGGGAGCTGAGCCCGTGCTCTG |
| | | AAAGGGCCCAGTCTGCAAGATGAGGGTTGGAAGCGACGAATGAGCTCCAC |
| | | AGGTCACGGGCCATTAGCATTTGCAGGTGGTCGCGAAAGGTCCTAAACTG |
| | | GCGACCTATGGCCATTTTTTCTGGGGTGATGCAGTAGAAGGTAAGCGGGTC |
| | | TTGTTCCCAGCGGTCCCATCCAAGGTTCGCGGCTAGGTCTCGCGCGGCAG |
| | | TCACTAGAGGCTCATCTCCGCCGAACTTCATGACCAGCATGAAGGGCACGA |
| | | GCTGCTTCCCAAAGGCCCCCATCCAAGTATAGGTCTCTACATCGTAGGTGA |
| | | CAAAGAGACGCTCGGTGCGAGGATGCGAGCCGATCGGGAAGAACTGGATC |
| | | TCCCGCCACCAATTGGAGGAGTGGCTATTGATGTGGTGAAAGTAGAAGTCC |
| | | CTGCGACGGGCCGAACACTCGTGCTGGCTTTTGTAAAAACGTGCGCAGTA |
| | | CTGGCAGCGGTGCACGGGCTGTACATCCTGCACGAGGTTGACCTGACGAC |
| | | CGCGCACAAGGAAGCAGAGTGGGAATTTGAGCCCCTCGCCTGGCGGGTTT |
| | | GGCTGGTGGTCTTCTACTTCGGCTGCTTGTCCTTGACCGTCTGGCTGCTCG |
| | | AGGGGAGTTACGGTGGATCGGACCACCACGCCGCGGAGCCCAAAGTCC |
| | | AGATGTCCGCGCGCGGCGGTCGGAGCTTGATGACAACATCGCGCAGATGG |
| | | GAGCTGTCCATGGTCTGGAGCTCCCGCGGCGTCAGGTCAGGCGGGAGCT |
| | | CCTGCAGGTTTACCTCGCATAGACGGGTCAGGGCGCGGGCTAGATCCAGG |
| | | TGATACCTAATTTCCAGGGGCTGGTTGGTGGCGGCGTCGATGGCTTGCAA |
| | | GAGGCCGCATCCCCGCGGCGCGACTACGGTACCGCGCGGCGGGCGGTG |
| | | GGCCGCGGGGTGTCCTTGGATGATGCATCTAAAAGCGGTGACGCGGGC |
| | | GAGCCCCCGGAGGTAGGGGGGCTCCGGACCCGCCGGGAGAGGGGGCA |
| | | GGGGCACGTCGGCGCCGCGCGCGGGCAGGAGCTGGTGCTGCGCGCGTA |
| | | GGTTGCTGGCGAACGCGACGACGCGGCGGTTGATCTCCTGAATCTGGCGC |
| | | CTCTGCGTGAAGACGACGGGCCCGGTGAGCTTGAGCCTGAAAGAGAGTTC |
| | | GACAGAATCAATTTCGGTGTCGTTGACGGCGGCCTGGCGCAAAATCTCCTG |
| | | CACGTCTCCTGAGTTGTCTTGATAGGCGATCTCGGCCATGAACTGCTCGAT |
| | | CTCTTCCTCCTGGAGATCTCCGCGTCCGGCTCGCTCCACGGTGGCGGCGA |
| | | GGTCGTTGGAAATGCGGGCCATGAGCTGCGAGAAGGCGTTGAGGCCTCCC |
| | | TCGTTCCAGACGCGGCTGTAGACCACGCCCCTTCGGCATCGCGGGCGC |
| | | GCATGACCACCTGCGCGAGATTGAGCTCCACGTGCCGGGCAAGACGGC |
| | | GTAGTTTCGCAGGCGCTGAAAGAGGTAGTTGAGGGTGGTGGCGGTGTGTT |
| | | CTGCCACGAAGAAGTACATAACCCAGCGTCGCAACGTGGATTCGTTGATAT |
| | | CCCCCAAGGCCTCAAGGCGCTCCATGGCCTCGTAGAAGTCCACGGCGAAG |
| | | TTGAAAAACTGGGAGTTGCGCGCCGACACGGTTAACTCCTCCTCCAGAAGA |
| | | CGGATGAGCTCGGCGACAGTGTCGCGCACCTCGCGCTCAAAGGCTACAGG |
| | | GGCCTCTTCTTCTTTCAATCTCCTCTTCCATAAGGGCCTCCCCTTCTTCT |
| | | TCTTCTGGCGGCGGTGGGGGAGGGGGGACACGGCGGCGACGACGGCGC |
| | | ACCGGGAGGCGGTCGACAAAGCGCTCGATCATCTCCCCGCGGCGACGGC |
| | | GCATGGTCTCGGTGACGGCGCGGCCGTTCTCGCGGGGGCGCAGTTGGAA |
| | | GACGCCGCCCGTCATGTCCCGGTTATGGGTTGGCGGGGGGCTGCCATGC |
| | | GGCAGGGATACGCGCTAACGATGCATCTCAACAATTGTTGTGTAGGTACT |
| | | CCGCCGCCGAGGGACCTGAGCGAGTCCGCATCGACCGGATCGGAAAACC |
| | | TCTCGAGAAAGGCGTCTAACCAGTCACAGTCGCAAGGTAGGCTGAGCACC |
| | | GTGGCGGGCGGCAGCGGGCGGCGGTCGGGGTTGTTTCTGGCGGAGGTG |
| | | CTGCTGATGATGTAATTAAAGTAGGCGGTCTTGAGACGCGGATGGTCGAC |
| | | AGAAGCACCATGTCCTTGGGTCCGGCCTGCTGAATGCGCAGGCGGTCGGC |
| | | CATGCCCCAGGCTTCGTTTTGACATCGGCGCAGGTCTTTGTAGTAGTCTTG |
| | | CATGAGCCTTTCTACCGGCACTTCTTCTTCTCCTTCCTCTTGTCCTGCATCT |
| | | CTTGCATCTATCGCTGCGGCGGCGGCGGAGTTTGGCCGTAGGTGGCGCC |
| | | CTCTTCCTCCCATGCGTGTGACCCCGAAGCCCCTCATCGGCTGAAGCAGG |
| | | GCTAGGTCGGCGACAACGCGCTCGGCTAATATGGCCTGCTGCACCTGCGT |
| | | GAGGGTAGACTGGAAGTCATCCATGTCCACAAAGCGGTGGTATGCGCCCG |
| | | TGTTGATGGTGTAAGTGCAGTTGGCCATAACGGACCAGTTAACGGTCTGGT |
| | | GACCCGGCTGCGAGAGCTCGGTGTACCTGAGACGCGAGTAAGCCCTCGA |
| | | GTCAAATACGTAGTCGTTGCAAGTCCGCACCAGGTACTGGTATCCCACCAA |
| | | AAAGTGCGGCGGCGGCTGGCGGTAGAGGGGCCAGCGTAGGGTGGCCGG |
| | | GGCTCCGGGGGCGAGATCTTCCAACATAAGGCGATGATATCCGTAGATGT |
| | | ACCTGGACATCCAGGTGATGCCGGCGGCGGTGGTGGAGGCGCGCGGAAA |
| | | GTCGCGGACGCGGTTCCAGATGTTGCGCAGCGGCAAAAAGTGCTCCATGG |
| | | TCGGGACGCTCTGGCCGGTCAGGCGCGCGCAATCGTTGACGCTCTAGACC |
| | | GTGCAAAAGGAGAGCCTGTAAGCGGGCACTCTTCCGTGGTCTGGTGGATA |
| | | AATTCGCAAGGGTATCATGGCGGACGACCGGGGTTCGAGCCCCGTATCCG |
| | | GCCGTCCGCCGTGATCCATGCGGTTACCGCCCGCGTGTCGAACCCAGGTG |
| | | TGCGACGTCAGACAACGGGGAGTGCTCCTTTTGGCTTCCTTCCAGGCGC |
| | | GGCGGCTGCTGCGCTAGCTTTTTTGGCCACTGGCCGCGCGCAGCGTAAGC |
| | | GGTTAGGCTGGAAAGCGAAAGCATTAAGTGGCTCGCTCCCTGTAGCCGGA |
| | | GGGTTATTTTCCAAGGGTTGAGTCGCGGGACCCCGGTTCGAGTCTCGGA |
| | | CCGGCCGGACTGCGCGAACGGGGGTTTGCCTCCCCGTCATGCAAGACC |
| | | CCGCTTGCAAATTCCTCCGGAAACAGGGACGAGCCCCTTTTTTGCTTTTCC |
| | | CAGATGCATCCGGTGCTGCGGCAGATGCGCCCCCTCCTCAGCAGCGGCA |
| | | AGAGCAAGAGCAGCGGCAGACATGCAGGGCACCCTCCCCTCCTCCTACCG |
| | | CGTCAGGAGGGGCGACATCCGCGGTTGACGCGGCAGCAGATGGTGATTA |
| | | CGAACCCCCGCGGCGCCGGGCCCGGCACTACCTGGACTTGGAGGAGGGC |

Sequences

| SEQ ID NO: | DESCRIPTION | SEQUENCE |
|---|---|---|
| | | GAGGGCCTGGCGCGGCTAGGAGCGCCCTCTCCTGAGCGGTACCCAAGGG |
| | | TGCAGCTGAAGCGTGATACGCGTGAGGCGTACGTGCCGCGGCAGAACCTG |
| | | TTTCGCGACCGCGAGGGAGAGGAGCCCGAGGAGATGCGGGATCGAAAGT |
| | | TCCACGCAGGGCGCGAGCTGCGGCATGGCCTGAATCGCGAGCGGTTGCT |
| | | GCGCGAGGAGGACTTTGAGCCCGACGCGCGAACCGGGATTAGTCCCGCG |
| | | CGCGCACACGTGGCGGCCGCCGACCTGGTAACCGCATACGAGCAGACGG |
| | | TGAACCAGGAGATTAACTTTCAAAAAAGCTTTAACAACCACGTGCGTACGCT |
| | | TGTGGCGCGCGAGGAGGTGGCTATAGGACTGATGCATCTGTGGGACTTTG |
| | | TAAGCGCGCTGGAGCAAAACCCAAATAGCAAGCCGCTCATGGCGCAGCTG |
| | | TTCCTTATAGTGCAGCACAGCAGGGACAACGAGGCATTCAGGGATGCGCT |
| | | GCTAAACATAGTAGAGCCCGAGGGCCGCTGGCTGCTCGATTTGATAAACAT |
| | | CCTGCAGAGCATAGTGGTGCAGGAGCGCAGCTTGAGCCTGGCTGACAAGG |
| | | TGGCCGCCATCAACTATTCCATGCTTAGCCTGGGCAAGTTTTACGCCCGCA |
| | | AGATATACCATACCCCTTACGTTCCCATAGACAAGGAGGTAAAGATCGAGG |
| | | GGTTCTACATGCGCATGGCGCTGAAGGTGCTTACCTTGAGCGACGACCTG |
| | | GGCGTTTATCGCAACGAGCGCATCCACAAGGCCGTGAGCGTGAGCCGGC |
| | | GGCGCGAGCTCAGCGACCGCGAGCTGATGCACAGCCTGCAAAGGGCCCT |
| | | GGCTGGCACGGGCAGCGGCGATAGAGAGGCCGAGTCCTACTTTGACGCG |
| | | GGCGCTGACCTGCGCTGGGCCCCAAGCCGACGCGCCCTGGAGGCAGCTG |
| | | GGGCCGGACCTGGGCTGGCGGTGGCACCCGCGCGCGCTGGCAACGTCG |
| | | GCGGCGTGGAGGAATATGACGAGGACGATGAGTACGAGCCAGAGGACGG |
| | | CGAGTACTAAGCGGTGATGTTTCTGATCAGATGATGCAAGACGCAACGGAC |
| | | CCGGCGGTGCGGGCGGCGCTGCAGAGCCAGCCGTCCGGCCTTAACTCCA |
| | | CGGACGACTGGCGCCAGGTCATGGACCGCATCATGTCGCTGACTGCGCGC |
| | | AATCCTGACGCGTTCCGGCAGCAGCCGCAGGCCAACCGGCTCTCCGCAAT |
| | | TCTGGAAGCGGTGGTCCCGGCGCGCGCAAACCCCACGCACGAGAAGGTG |
| | | CTGGCGATCGTAAACGCGCTGGCCGAAAACAGGGCCATCCGGCCCGACG |
| | | AGGCCGGCCTGGTCTACGACGCGCTGCTTCAGCGCGTGGCTCGTTACAAC |
| | | AGCGGCAACGTGCAGACCAACCTGGACCGGCTGGTGGGGATGTGCGCG |
| | | AGGCCGTGGCGCAGCGTGAGCGCGCGCAGCAGCAGGGCAACCTGGGCTC |
| | | CATGGTTGCACTAAACGCCTTCCTGAGTACACAGCCCGCCAACGTGCCGC |
| | | GGGGACAGGAGGACTACACCAACTTTGTGAGCGCACTGCGGCTAATGGTG |
| | | ACTGAGACACCGCAAAGTGAGGTGTACCAGTCTGGGCCAGACTATTTTTC |
| | | CAGACCAGTAGACAAGGCCTGCAGACCGTAAACCTGAGCCAGGCTTTCAA |
| | | AAACTTGCAGGGGCTGTGGGGGGTGCGGGCTCCCACAGGCGACCGCGCG |
| | | ACCGTGTCTAGCTTGCTGACGCCCAACTCGCGCCTGTTGCTGCTGCTAATA |
| | | GCGCCCTTCACGGACAGTGGCAGCGTGTCCCGGGACACATACCTAGGTCA |
| | | CTTGCTGACACTGTACCGCGAGGCCATAGGTCAGGCGCATGTGGACGAGC |
| | | ATACTTTCCAGGAGATTACAAGTGTCAGCCGCGCGCTGGGGCAGGAGGAC |
| | | ACGGGCAGCCTGGAGGCAACCCTAAACTACCTGCTGACCAACCGGCGGCA |
| | | GAAGATCCCCTCGTTGCACAGTTTAAACAGCGAGGAGGAGCGCATTTTGCG |
| | | CTACGTGCAGCAGAGCGTGAGCCTTAACCTGATGCGCGACGGGGTAACGC |
| | | CCAGCGTGGCGCTGGACATGACCGCGCGCAACATGGAACCGGGCATGTAT |
| | | GCCTCAAACCGGCCGTTTATCAACCGCCTAATGGACTACTTGCATCGCGCG |
| | | GCCGCCGTGAACCCCGAGTATTTCACCAATGCCATCTTGAACCCGCACTGG |
| | | CTACCGCCCCTGGTTTCTACACCGGGGGATTCGAGGTGCCCGAGGGTAA |
| | | CGATGGATTCCTCTGGGACGACATAGACGACAGCGTGTTTTCCCCGCAACC |
| | | GCAGACCCTGCTAGAGTTGCAACAGCGCGAGCAGGCAGAGGCGGCGCTG |
| | | CGAAAGGAAAGCTTCCGCAGGCCAAGCAGCTTGTCCGATCTAGGCGCTGC |
| | | GGCCCCGCGGTCAGATGCTAGTAGCCCATTTCCAAGCTTGATAGGGTCTCT |
| | | TACCAGCACTCGCACCACCCGCCCGCGCCTGCTGGGCGAGGAGGAGTAC |
| | | CTAAACAACTCGCTGCTGCAGCCGCAGCGCGAAAAAAACCTGCCTCCGGC |
| | | ATTTCCCAACAACGGGATAGAGAGCCTAGTGGACAAGATGAGTAGATGGAA |
| | | GACGTACGCGCAGGAGCACAGGGACGTGCCAGGCCCGCGCCCGCCCACC |
| | | CGTCGTCAAAGGCACGACCGTCAGCGGGGTCTGGTGTGGGAGGACGATG |
| | | ACTCGGCAGACGACAGCAGCGTCCTGGATTTGGGAGGGAGTGGCAACCC |
| | | GTTTGCGCACCTTCGCCCCAGGCTGGGGAGAATGTTTTAAAAAAAAAAAAG |
| | | CATGATGCAAAATAAAAAACTCACCAAGGCCATGGCACCGAGCGTTGGTTT |
| | | TCTTGTATTCCCCTTAGTATGCGGCGCGCGGCGATGTATGAGGAAGGTCCT |
| | | CCTCCCTCCTACGAGAGTGTGGTGAGCGCGGCGCCAGTGGCGGCGGCGC |
| | | TGGGTTCTCCCTTCGATGCTCCCCTGGACCCGCCGTTTGTGCCTCCGCGG |
| | | TACCTGCGGCCTACCGGGGGGAGAAACAGCATCCGTTACTCTGAGTTGGC |
| | | ACCCCTATTCGACACCACCCGTGTGTACCTGGTGGACAACAAGTCAACGGA |
| | | TGTGGCATCCCTGAACTACCAGAACGACCACAGCAACTTTCTGACCACGGT |
| | | CATTCAAAACAATGACTACAGCCCGGGGGAGGCAAGCACACAGACCATCA |
| | | ATCTTGACGACCGGTCGCACTGGGGCGGCGACCTGAAAACCATCCTGCAT |
| | | ACCAACATGCCAAATGTGAACGAGTTCATGTTTACCAATAAGTTTAAGGCGC |
| | | GGGTGATGGTGTCGCGCTTGCCTACTAAGGACAATCAGGTGGAGCTGAAA |
| | | TACGAGTGGGTGGAGTTCACGCTGCCCGAGGGCAACTACTCCGAGACCAT |
| | | GACCATAGACCTTATGAACAACGCGATCGTGGAGCACTACTTGAAAGTGGG |
| | | CAGACAGAACGGGGTTCTGGAAAGCGACATCGGGGTAAAGTTTGACACCC |
| | | GCAACTTCAGACTGGGGTTTGACCCCGTCACTGGTCTTGTCATGCCTGGG |
| | | GTATATACAAACGAAGCCTTCCATCCAGACATCATTTTGCTGCCAGGATGC |
| | | GGGGTGGACTTCACCCACAGCCGCCTGAGCAACTTGTTGGGCATCCGCAA |

| SEQ ID NO: | DESCRIPTION | SEQUENCE |
|---|---|---|
| | | GCGGCAACCCTTCCAGGAGGGCTTTAGGATCACCTACGATGATCTGGAGG |
| | | GTGGTAACATTCCCGCACTGTTGGATGTGGACGCCTACCAGGCGAGCTTG |
| | | AAAGATGACACCGAACAGGGCGGGGGTGGCGCAGGCGGCAGCAACAGCA |
| | | GTGGCAGCGGCGCGGAAGAGAACTCCAACGCGGCAGCCGCGGCAATGCA |
| | | GCCGGTGGAGGACATGAACGATCATGCCATTCGCGGCGACACCTTTGCCA |
| | | CACGGGCTGAGGAGAAGCGCGCTGAGGCCGAAGCAGCGGCCGAAGCTGC |
| | | CGCCCCCGCTGCGCAACCCGAGGTCGAGAAGCCTCAGAAGAAACCGGTG |
| | | ATCAAACCCTGACAGAGGACAGCAAGAAACGCAGTTACAACCTAATAAGC |
| | | AATGACAGCACCTTCACCCAGTACCGCAGCTGGTACCTTGCATACAACTAC |
| | | GGCGACCCTCAGACCGGAATCCGCTCATGGACCCTGCTTTGCACTCCTGA |
| | | CGTAACCTGCGGCTCGGAGCAGGTCTACTGGTCGTTGCCAGACATGATGC |
| | | AAGACCCCGTGACCTTCCGCTCCACGCGCCAGATCAGCAACTTTCCGGTG |
| | | GTGGGCGCCGAGCTGTTGCCCGTGCACTCCAAGAGCTTCTACAACGACCA |
| | | GGCCGTCTACTCCCAACTCATCCGCCAGTTTACCTCTCTGACCCACGTGTT |
| | | CAATCGCTTTCCCGAGAACCAGATTTTGGCGCGCCCGCCAGCCCCCACCA |
| | | TCACCACCGTCAGTGAAAACGTTCCTGCTCTCACAGATCACGGGACGCTAC |
| | | CGCTGCGCAACAGCATCGGAGGAGTCCAGCGAGTGACCATTACTGACGCC |
| | | AGACGCCGCACCTGCCCCTACGTTTACAAGGCCCTGGGCATAGTCTCGCC |
| | | GCGCGTCCTATCGAGCCGCACTTTTTGAGCAAGCATGTCCATCCTTATATC |
| | | GCCCAGCAATAACACAGGCTGGGGCCTGCGCTTCCCAAGCAAGATGTTTG |
| | | GCGGGGCCAAGAAGCGCTCCGACCAACACCCAGTGCGCGTGCGCGGGCA |
| | | CTACCGCGCGCCCTGGGGCGCGCACAAACGCGGCCGCACTGGGCGCACC |
| | | ACCGTCGATGACGCCATCGACGCGGTGGTGGAGGAGGCGCGCAACTACA |
| | | CGCCCACGCCGCCACCAGTGTCCACAGTGGACGCGGCCATTCAGACCGTG |
| | | GTGCGCGGAGCCCGGCGCTATGCTAAAATGAAGAGACGGCGGAGGCGCG |
| | | TAGCACGTCGCCACCGCCGCCGACCCGGCACTGCCGCCCAACGCGCGGC |
| | | GGCGGCCCTGCTTAACCGCGCACGTCGCACCGGCCGACGGGCGGCCATG |
| | | CGGGCCGCTCGAAGGCTGGCCGCGGGTATTGTCACTGTGCCCCCCAGGT |
| | | CCAGGCGACGAGCGGCCGCCGCAGCAGCCGCGGCCATTAGTGCTATGAC |
| | | TCAGGGTCGCAGGGGCAACGTGTATTGGGTGCGCGACTCGGTTAGCGGC |
| | | CTGCGCGTGCCCGTGCGCACCCGCCCCCCGCGCAACTAGATTGCAAGAAA |
| | | AAACTACTTAGACTCGTACTGTTGTATGTATCCAGCGGCGGCGGCGCGCAA |
| | | CGAAGCTATGTCCAAGCGCAAAATCAAAGAAGAGATGCTCCAGGTCATCGC |
| | | GCCGGAGATCTATGGCCCCCCGAAGAAGGAAGAGCAGGATTACAAGCCCC |
| | | GAAAGCTAAAGCGGGTCAAAAAGAAAAAGAAAGATGATGATGATGAACTTG |
| | | ACGACGAGGTGGAACTGCTGCACGCTACCGCGCCCAGGCGACGGGTACA |
| | | GTGGAAAGGTCGACGCGTAAAACGTGTTTTGCGACCCGGCACCACCGTAG |
| | | TCTTTACGCCCGGTGAGCGCTCCACCCGCACCTACAAGCGCGTGTATGAT |
| | | GAGGTGTACGGCGACGAGGACCTGCTTGAGCAGGCCAACGAGCGCCTCG |
| | | GGGAGTTTGCCTACGGAAAGCGGCATAAGGACATGCTGGCGTTGCCGCTG |
| | | GACGAGGGCAACCCAACACCTAGCCTAAAGCCCGTAACACTGCAGCAGGT |
| | | GCTGCCCGCGCTTGCACCGTCCGAAGAAAAGCGCGGCCTAAAGCGCGAGT |
| | | CTGGTGACTTGGCACCCACCGTGCAGCTGATGGTACCCAAGCGCCAGCGA |
| | | CTGGAAGATGTCTTGGAAAAAATGACCGTGGAACCTGGGCTGGAGCCCGA |
| | | GGTCCGCGTGCGGCCAATCAAGCAGGTGGCGCCGGGACTGGGCGTGCAG |
| | | ACCGTGGACGTTCAGATACCCACTACCAGTAGCACCAGTATTGCCACCGCC |
| | | ACAGAGGGCATGGAGACACAAACGTCCCCGGTTGCCTCAGCGGTGGCGG |
| | | ATGCCGCGGTGCAGGCGGTCGCTGCGGCCGCGTCCAAGACCTCTACGGA |
| | | GGTGCAAACGGACCCGTGGATGTTTCGCGTTTCAGCCCCCCGGCGCCCGC |
| | | GCGGTTCGAGGAAGTACGGCGCCGCCAGCGCGCTACTGCCCGAATATGC |
| | | CCTACATCCTTCCATTGCGCCTACCCCCGGCTATCGTGGCTACACCTACCG |
| | | CCCCAGAAGACGAGCAACTACCCGACGCCGAACCACCACTGGAACCCGCC |
| | | GCCGCCGTCGCCGTCGCCAGCCCGTGCTGGCCCCGATTTCCGTGCGCAG |
| | | GGTGGCTCGCGAAGGAGGCAGGACCTGGTGCTGCCAACAGCGCGCTAC |
| | | CACCCCAGCATCGTTTAAAAGCCGGTCTTTGTGGTTCTTGCAGATATGGCC |
| | | CTCACCTGCCGCCTCCGTTTCCCGGTGCCGGGATTCCGAGGAAGAATGCA |
| | | CCGTAGGAGGGCATGGCCGGCCACGGCCTGACGGGCGGCATGCGTCGT |
| | | GCGCACCACCGGCGGCGGCGCGTCGCACCGTCGCATGCGCGGCGGT |
| | | ATCCTGCCCCTCCTTATTCCACTGATCGCCGCGGCGATTGGCGCCGTGCC |
| | | CGGAATTGCATCCGTGGCCTTGCAGGCGCAGAGACACTGATTAAAAACAAG |
| | | TTGCATGTGGAAAAATCAAAATAAAAAGTCTGGACTCTCACGCTCGCTTGGT |
| | | CCTGTAACTATTTTGTAGAATGGAAGACATCAACTTTGCGTCTCTGGCCCCG |
| | | CGACACGGCTCGCGCCCGTTCATGGGAAACTGGCAAGATATCGGCACCAG |
| | | CAATATGAGCGGTGGCGCCTTCAGCTGGGGCTCGCTGTGGAGCGGCATTA |
| | | AAAATTTCGGTTCCACCGTTAAGAACTATGGCAGCAAGGCCTGGAACAGCA |
| | | GCACAGGCCAGATGCTGAGGGATAAGTTGAAAGAGCAAAATTTCCAACAAA |
| | | AGGTGGTAGATGGCCTGGCCTCTGGCATTAGCGGGTGGTGGACCTGGC |
| | | CAACCAGGCAGTGCAAAATAAGATTAACAGTAAGCTTGATCCCCGCCCTCC |
| | | CGTAGAGGAGCCTCCACCGGCCGTGGAGACAGTGTCTCCAGAGGGGCGT |
| | | GGCGAAAAGCGTCCGCGCCCGACAGGGAAGAAACTCTGGTGACGCAAAT |
| | | AGACGAGCCTCCCTCGTACGAGGAGGCACTAAAGCAAGGCCTGCCCACCA |
| | | CCCGTCCCATCGCGCCCATGGCTACCGGAGTGCTGGGCCAGCACACACCC |
| | | GTAACGCTGGACCTGCCTCCCCCCGCCGACACCCAGCAGAAACCTGTGCT |
| | | GCCAGGCCCGACCGCCGTTGTTGTAACCCGTCCTAGCCGCGCGTCCCTGC |

-continued

Sequences

| SEQ ID NO: | DESCRIPTION | SEQUENCE |
|---|---|---|
| | | GCCGCGCCGCCAGCGGTCCGCGATCGTTGCGGCCCGTAGCCAGTGGCAA |
| | | CTGGCAAAGCACACTGAACAGCATCGTGGGTCTGGGGGTGCAATCCCTGA |
| | | AGCGCCGACGATGCTTCTGAATAGCTAACGTGTCGTATGTGTGTCATGTAT |
| | | GCGTCCATGTCGCCGCCAGAGGAGCTGCTGAGCCGCCGCGCGCCCGCTT |
| | | TCCAAGATGGCTACCCCTTCGATGATGCCGCAGTGGTCTTACATGCACATC |
| | | TCGGGCCAGGACGCCTCGGAGTACCTGAGCCCCGGGCTGGTGCAGTTTG |
| | | CCCGCGCCACCGAGACGTACTTCAGCCTGAATAACAAGTTTAGAAACCCCA |
| | | CGGTGGCGCCTACGCACGACGTGACCACAGACCGGTCCCAGCGTTTGACG |
| | | CTGCGGTTCATCCCTGTGGACCGTGAGGATACTGCGTACTCGTACAAGGC |
| | | GCGGTTCACCCTAGCTGTGGGTGATAACCGTGTGCTGGACATGGCTTCCA |
| | | CGTACTTTGACATCCGCGGCGTGCTGGACAGGGGCCCTACTTTTAAGCCCT |
| | | ACTCTGGCACTGCCTACAACGCCCTGGCTCCCAAGGGTGCCCCAAATCCTT |
| | | GCGAATGGGATGAAGCTGCTACTGCTCTTGAAATAAACCTAGAAGAAGAGG |
| | | ACGATGACAACGAAGACGAAGTAGACGAGCAAGCTGAGCAGCAAAAAACT |
| | | CACGTATTTGGGCAGGCGCCTTATTCTGGTATAAATATTACAAAGGAGGGT |
| | | ATTCAAATAGGTGTCGAAGGTCAAACACCTAAATATGCCGATAAAACATTTC |
| | | AACCTGAACCTCAAATAGGAGAATCTCAGTGGTACGAAACTGAAATTAATCA |
| | | TGCAGCTGGGAGAGTCCTTAAAAAGACTACCCCAATGAAACCATGTTACGG |
| | | TTCATATGCAAAACCCACAAATGAAAATGGAGGGCAAGGCATTCTTGTAAA |
| | | GCAACAAAATGGAAAGCTAGAAAGTCAAGTGGAAATGCAATTTTTCTCAACT |
| | | ACTGAGGCGACCGCAGGCAATGGTGATAACTTGACTCCTAAAGTGGTATTG |
| | | TACAGTGAAGATGTAGATATAGAAACCCCAGACACTCATATTTCTTACATGC |
| | | CCACTATTAAGGAAGGTAACTCACGAGAACTAATGGGCCAACAATCTATGC |
| | | CCAACAGGCCTAATTACATTGCTTTTAGGGACAATTTTATTGGTCTAATGTAT |
| | | TACAACAGCACGGGTAATATGGGTGTTCTGGCGGGCCAAGCATCGCAGTT |
| | | GAATGCTGTTGTAGATTTGCAAGACAGAAACACAGAGCTTTCATACCAGCTT |
| | | TTGCTTGATTCCATTGGTGATAGAACCAGGTACTTTTCTATGTGGAATCAGG |
| | | CTGTTGACAGCTATGATCCAGATGTTAGAATTATTGAAAATCATGGAACTGA |
| | | AGATGAACTTCCAAATTACTGCTTTCCACTGGGAGGTGTGATTAATACAGAG |
| | | ACTCTTACCAAGGTAAAACCTAAAACAGGTCAGGAAAATGGATGGGAAAAA |
| | | GATGCTACAGAATTTTCAGATAAAAATGAAATAAGAGTTGGAAATAATTTTG |
| | | CCATGGAAATCAATCTAAATGCCAACCTGTGGAGAAATTTCCTGTACTCCAA |
| | | CATAGCGCTGTATTTGCCCGACAAGCTAAAGTACAGTCCTTCCAACGTAAA |
| | | AATTTCTGATAACCCAAACACCTACGACTACATGAACAAGCGAGTGGTGGC |
| | | TCCCGGGTTAGTGGACTGCTACATTAACCTTGGAGCACGCTGGTCCCTTGA |
| | | CTATATGGACAACGTCAACCCATTTAACCACCACCGCAATGCTGGCCTGCG |
| | | CTACCGCTCAATGTTGCTGGGCAATGGTCGCTATGTGCCCTTCCACATCCA |
| | | GGTGCCTCAGAAGTTCTTTGCCATTAAAAACCTCCTTCTCCTGCCGGGCTC |
| | | ATACACCTACGAGTGGAACTTCAGGAAGGATGTTAACATGGTTCTGCAGAG |
| | | CTCCCTAGGAAATGACCTAAGGGTTGACGGAGCCAGCATTAAGTTTGATAG |
| | | CATTTGCCTTTACGCCACCTTCTTCCCCATGGCCCACAACACCGCCTCCAC |
| | | GCTTGAGGCCATGCTTAGAAACGACACCAACGACCAGTCCTTTAACGACTA |
| | | TCTCTCCGCCGCCAACATGCTCTACCCTATACCCGCCAACGCTACCAACGT |
| | | GCCCATATCCATCCCCTCCCGCAACTGGGCGGCTTTCCGCGGCTGGGCCT |
| | | TCACGCGCCTTAAGACTAAGGAAACCCCATCACTGGGCTCGGGCTACGAC |
| | | CCTTATTACACCTACTCTGGCTCTATACCCTACCTAGATGGAACCTTTTACC |
| | | TCAACCACACCTTTAAGAAGGTGGCCATTACCTTTGACTCTTCTGTCAGCTG |
| | | GCCTGGCAATGACCGCCTGCTTACCCCCAACGAGTTTGAAATTAAGCGCTC |
| | | AGTTGACGGGGAGGGTTACAACGTTGCCCAGTGTAACATGACCAAAGACT |
| | | GGTTCCTGGTACAAATGCTAGCTAACTACAACATTGGCTACCAGGGCTTCT |
| | | ATATCCCAGAGAGCTACAAGGACCGCATGTACTCCTTCTTTAGAAACTTCCA |
| | | GCCCATGAGCCGTCAGGTGGTGGATGATACTAAATACAAGGACTACCAACA |
| | | GGTGGGCATCCTACACCAACACAACAACTCTGGATTTGTTGGCTACCTTGC |
| | | CCCCACCATGCGCGAAGGACAGGCCTACCCTGCTAACTTCCCCTATCCGC |
| | | TTATAGGCAAGACCGCAGTTGACAGCATTACCCAGAAAAAGTTTCTTTGCG |
| | | ATCGCACCCTTTGGCGCATCCCATTCTCCAGTAACTTTATGTCCATGGGCG |
| | | CACTCACAGACCTGGGCCAAAACCTTCTCTACGCCAACTCCGCCCACGCG |
| | | CTAGACATGACTTTTGAGGTGGATCCCATGGACGAGCCCACCCTTCTTTAT |
| | | GTTTTGTTTGAAGTCTTTGACGTGGTCCGTGTGCACCGGCCGCACCGCGG |
| | | CGTCATCGAAACCGTGTACCTGCGCACGCCCTTCTCGGCCGGCAACGCCA |
| | | CAACATAAAGAAGCAAGCAACATCAACAACAGCTGCCGCCATGGGCTCCAG |
| | | TGAGCAGGAACTGAAAGCCATTGTCAAAGATCTTGGTTGTGGGCCATATTT |
| | | TTTGGGCACCTATGACAAGCGCTTTCCAGGCTTTGTTTCTCCACACAAGCT |
| | | CGCCTGCGCCATAGTCAATACGGCCGGTCGCGAGACTGGGGGCGTACACT |
| | | GGATGGCCTTTGCCTGGAACCCGCACTCAAAAACATGCTACCTCTTTGAGC |
| | | CCTTTGGCTTTTCTGACCAGCGACTCAAGCAGGTTTACCAGTTTGAGTACG |
| | | AGTCACTCCTGCGCCGTAGCGCCATTGCTTCTTCCCCGACCGCTGTATAA |
| | | CGCTGGAAAAGTCCACCCAAAGCGTACAGGGGCCCAACTCGGCCGCCTGT |
| | | GGACTATTCTGCTGCATGTTTCTCCACGCCTTTGCCAACTGGCCCCAAACT |
| | | CCCATGGATCACAACCCCACCATGAACCTTATTACCGGGGTACCCAACTCC |
| | | ATGCTCAACAGTCCCAGGTACAGCCCACCCTGCGTCGCAACCAGGAACA |
| | | GCTCTACAGCTTCCTGGAGCGCCACTCGCCCTACTTCCGCAGCCACAGTG |
| | | CGCAGATTAGGAGCGCCACTTCTTTTTGTCACTTGAAAACATGTAAAAATA |
| | | ATGTACTAGAGACACTTTCAATAAAGGCAAATGCTTTTATTTGTACACTCTC |

Sequences

| SEQ ID NO: | DESCRIPTION | SEQUENCE |
|---|---|---|
| | | GGGTGATTATTTACCCCCACCCTTGCCGTCTGCGCCGTTTAAAAATCAAAG |
| | | GGGTTCTGCCGCGCATCGCTATGCGCCACTGGCAGGGACACGTTGCGATA |
| | | CTGGTGTTTAGTGCTCCACTTAAACTCAGGCACAACCATCCGCGGCAGCTC |
| | | GGTGAAGTTTTCACTCCACAGGCTGCGCACCATCACCAACGCGTTTAGCAG |
| | | GTCGGGCGCCGATATCTTGAAGTCGCAGTTGGGGCCTCCGCCCTGCGCGC |
| | | GCGAGTTGCGATACACAGGGTTGCAGCACTGGAACACTATCAGCGCCGGG |
| | | TGGTGCACGCTGGCCAGCACGCTCTTGTCGGAGATCAGATCCGCGTCCAG |
| | | GTCCTCCGCGTTGCTCAGGGCGAACGGAGTCAACTTTGGTAGCTGCCTTC |
| | | CCAAAAAGGGCGCGTGCCCAGGCTTTGAGTTGCACTCGCACCGTAGTGGC |
| | | ATCAAAAGGTGACCGTGCCCGGTCTGGGCGTTAGGATACAGCGCCTGCAT |
| | | AAAAGCCTTGATCTGCTTAAAAGCCACCTGAGCCTTTGCGCCTTCAGAGAA |
| | | GAACATGCCGCAAGACTTGCCGGAAAACTGATTGGCCGGACAGGCCGCGT |
| | | CGTGCACGCAGCACCTTGCGTCGGTGTTGGAGATCTGCACCACATTTCGG |
| | | CCCCACCGGTTCTTCACGATCTTGGCCTTGCTAGACTGCTCCTTCAGCGCG |
| | | CGCTGCCCGTTTTCGCTCGTCACATCCATTTCAATCACGTGCTCCTTATTTA |
| | | TCATAATGCTTCCGTGTAGACACTTAAGCTCGCCTTCGATCTCAGCGCAGC |
| | | GGTGCAGCCACAACGCGCAGCCCGTGGGCTCGTGATGCTTGTAGGTCACC |
| | | TCTGCAAACGACTGCAGGTACGCCTGCAGGAATCGCCCCATCATCGTCACA |
| | | AAGGTCTTGTTGCTGGTGAAGGTCAGCTGCAACCCGCGGTGCTCCTCGTT |
| | | CAGCCAGGTCTTGCATACGGCCGCCAGAGCTTCCACTTGGTCAGGCAGTA |
| | | GTTTGAAGTTCGCCTTTAGATCGTTATCCACGTGGTACTTGTCCATCAGCGC |
| | | GCGCGCAGCCTCCATGCCCTTCTCCCACGCAGACACGATCGGCACACTCA |
| | | GCGGGTTCATCACCGTAATTTCACTTTCCGCTTCGCTGGGCTCTTCCTCTTC |
| | | CTCTTGCGTCCGCATACCACGCGCCACTGGGTCGTCTTCATTCAGCCGCC |
| | | GCACTGTGCGCTTACCTCCTTTGCCATGCTTGATTAGCACCGGTGGGTTGC |
| | | TGAAACCCACCATTTGTAGCGCCACATCTTCTCTTTCTTCCTCGCTGTCCAC |
| | | GATTACCTCTGGTGATGGCGGGCGCTCGGGCTTGGGAGAAGGGCGCTTCT |
| | | TTTTCTTCTTGGGCGCAATGGCCAAATCCGCCGCCGAGGTCGATGGCCGC |
| | | GGGCTGGGTGTGCGCGGCACCAGCGCGTCTTGTGATGAGTCTTCCTCGTC |
| | | CTCGGACTCGATACGCCGCCTCATCCGCTTTTTTGGGGGCGCCCGGGGAG |
| | | GCGGCGGCGACGGGACGGGGACGACACGTCCTCCATGGTTGGGGGAC |
| | | GTCGCGCCGCACCGCGTCCGCGCTCGGGGGTGGTTTCGCGCTGCTCCTC |
| | | TTCCCGACTGGCCATTTCCTTCTCCTATAGGCAGAAAAAGATCATGGAGTC |
| | | AGTCGAGAAGAAGGACAGCCTAACCGCCCCCTCTGAGTTCGCCACCACCG |
| | | CCTCCACCGATGCCGCCAACGCGCCTACCACCTTCCCCGTCGAGGCACCC |
| | | CCGCTTGAGGAGGAGGAAGTGATTATCGAGCAGGACCCAGGTTTTGTAAG |
| | | CGAAGACGACGAGGACCGCTCAGTACCAACAGAGGATAAAAAGCAAGACC |
| | | AGGACAACGCAGAGGCAAACGAGGAACAAGTCGGGCGGGGGGACGAAAG |
| | | GCATGGCGACTACCTAGATGTGGGAGACGACGTGCTGTTGAAGCATCTGC |
| | | AGCGCCAGTGCGCCATTATCTGCGACGCGTTGCAAGAGCGCAGCGATGTG |
| | | CCCCTCGCCATAGCGGATGTCAGCCTTGCCTACAACGCCACCTATTCTCA |
| | | CCGCGCGTACCCCCCAAACGCCAAGAAAACGGCACATGCGAGCCCAACCC |
| | | GCGCCTCAACTTCTACCCCGTATTTGCCGTGCCAGAGGTGCTTGCCACCTA |
| | | TCACATCTTTTTCCAAAACTGCAAGATACCCCTATCCTGCCGTGCCAACCGC |
| | | AGCCGAGCGGACAAGCAGCTGGCCTTGCGGCAGGGCGCTGTCATACCTG |
| | | ATATCGCCTCGCTCAACGAAGTGCCAAAAATCTTTGAGGGTCTTGGACGCG |
| | | ACGAGAAGCGCGCGGCAAACGCTCTGCAACAGGAAAACAGCGAAAATGAA |
| | | AGTCACTCTGGAGTGTTGGTGGAACTCGAGGGTGACAACGCGCGCCTAGC |
| | | CGTACTAAAACGCAGCATCGAGGTCACCCACTTTGCCTACCCGGCACTTAA |
| | | CCTACCCCCCAAGGTCATGAGCACAGTCATGAGTGAGCTGATCGTGCGCC |
| | | GTGCGCAGCCCCTGGAGAGGGATGCAAATTTGCAAGAACAAACAGAGGAG |
| | | GGCCTACCCGCAGTTGGCGACGAGCAGCTAGCGCGCTGGCTTCAAACGC |
| | | GCGAGCCTGCCGACTTGGAGGAGCGACGCAAACTAATGATGGCCGCAGTG |
| | | CTCGTTACCGTGGAGCTTGAGTGCATGCAGCGGTTCTTTGCTGACCCGGA |
| | | GATGCAGCGCAAGCTAGAGGAAACATTGCACTACACCTTTCGACAGGGCTA |
| | | CGTACGCCAGGCCTGCAAGATCTCCAACGTGGAGCTCTGCAACCTGGTCT |
| | | CCTACCTTGGAATTTTGCACGAAAACCGCCTTGGGCAAAACGTGCTTCATT |
| | | CCACGCTCAAGGGCGAGGCGCGCCGCGACTACGTCCGCGACTGCGTTTA |
| | | CTTATTTCTATGCTACACCTGGCAGACGGCCATGGGCGTTTGGCAGCAGTG |
| | | CTTGGAGGAGTGCAACCTCAAGGAGCTGCAGAAACTGCTAAAGCAAAACTT |
| | | GAAGGACCTATGGACGGCCTTCAACGAGCGCTCCGTGGCCGCGCACCTG |
| | | GCGGACATCATTTTCCCCGAACGCCTGCTTAAAACCCTGCAACAGGGTCTG |
| | | CCAGACTTCACCAGTCAAAGCATGTTGCAGAACTTTAGGAACTTTATCCTAG |
| | | AGCGCTCAGGAATCTTGCCCGCCACCTGCTGTGCACTTCCTAGCGACTTTG |
| | | TGCCCATTAAGTACCGCGAATGCCCTCCGCCGCTTTGGGGCCACTGCTAC |
| | | CTTCTGCAGCTAGCCAACTACCTTGCCTACCACTCTGACATAATGGAAGAC |
| | | GTGAGCGGTGACGGTCTACTGGAGTGTCACTGTCGCTGCAACCTATGCAC |
| | | CCCGCACCGCTCCCTGGTTTGCAATTCGCAGCTGCTTAACGAAAGTCAAAT |
| | | TATCGGTACCTTTGAGCTGCAGGGTCCCTCGCCTGACGAAAAGTCCGCGG |
| | | CTCGGGGTTGAAACTCACTCCGGGGCTGTGGACGTCGGCTTACCTTCGC |
| | | AAATTTGTACCTGAGGACTACCACGCCCACGAGATTAGGTTCTACGAAGAC |
| | | CAATCCCGCCCGCCAAATGCGGAGCTTACCGCCTGCGTCATTACCCAGGG |
| | | CCACATTCTTGGCCAATTGCAAGCCATCAACAAAGCCCGCCAAGAGTTTCT |
| | | GCTACGAAAGGGACGGGGGTTTACTTGGACCCCAGTCCGGCGAGGAG |

-continued

Sequences

| SEQ ID NO: | DESCRIPTION | SEQUENCE |
|---|---|---|
| | | CTCAACCCAATCCCCCCGCCGCCGCAGCCCTATCAGCAGCAGCCGCGGG
CCCTTGCTTCCCAGGATGGCACCCAAAAAGAAGCTGCAGCTGCCGCCGCC
ACCCACGGACGAGGAGGAATACTGGGACAGTCAGGCAGAGGAGGTTTTGG
ACGAGGAGGAGGAGGACATGATGGAAGACTGGGAGAGCCTAGACGAGGA
AGCTTCCGAGGTCGAAGAGGTGTCAGACGAAACACCGTCACCCTCGGTCG
CATTCCCCTCGCCGGCGCCCCAGAAATCGGCAACCGGTTCCAGCATGGCT
ACAACCTCCGCTCCTCAGGCGCCGCCGGCACTGCCCGTTCGCCGACCCAA
CCGTAGATGGGACACCACTGGAACCAGGGCCGGTAAGTCCAAGCAGCCGC
CGCCGTTAGCCCAAGAGCAACAACAGCGCCAAGGCTACCGCTCATGGCGC
GGGCACAAGAACGCCATAGTTGCTTGCTTGCAAGACTGTGGGGGCAACAT
CTCCTTCGCCCGCCGCTTTCTTCTCTACCATCACGGCGTGGCCTTCCCCCG
TAACATCCTGCATTACTACCGTCATCTCTACAGCCCATACTGCACCGGCGG
CAGCGGCAGCGGCAGCAACAGCAGCGGCCACACAGAAGCAAAGGCGACC
GGATAGCAAGACTCTGACAAAGCCCAAGAAATCCACAGCGGCGGCAGCAG
CAGGAGGAGGAGCGCTGCGTCTGGCGCCCAACGAACCCGTATCGACCCG
CGAGCTTAGAAACAGGATTTTTCCCACTCTGTATGCTATATTTCAACAGAGC
AGGGGCCAAGAACAAGAGCTGAAAATAAAAAACAGGTCTCTGCGATCCCTC
ACCCGCAGCTGCCTGTATCACAAAAGCGAAGATCAGCTTCGGCGCACGCT
GGAAGACGCGGAGGCTCTCTTCAGTAAATACTGCGCGCTGACTCTTAAGGA
CTAGTTTCGCGCCCTTTCTCAAATTTAAGCGCGAAAACTACGTCATCTCCAG
CGGCCACACCCGGCGCCAGCACCTGTCGTCAGCGCCATTATGAGCAAGGA
AATTCCCACGCCCTACATGTGGAGTTACCAGCCACAAATGGGACTTGCGGC
TGGAGCTGCCCAAGACTACTCAACCCGAATAAACTACATGAGCGCGGGAC
CCCACATGATATCCCGGGTCAACGGAATCCGCGCCCACCGAAACCGAATT
CTCTTGGAACAGGCGGCTATTACCACCACACCTCGTAATAACCTTAATCCC
CGTAGTTGGCCCGCTGCCCTGGTGTACCAGGAAAGTCCCGCTCCCACCAC
TGTGGTACTTCCCAGAGACGCCCAGGCCGAAGTTCAGATGACTAACTCAG
GGGCGCAGCTTGCGGGCGGCTTTCGTCACAGGGTGCGGTCGCCCGGGCA
GGGTATAACTCACCTGACAATCAGAGGGCGAGGTATTCAGCTCAACGACGA
GTCGGTGAGCTCCTCGCTTGGTCTCCGTCCGGACGGGACATTTCAGATCG
GCGGCGCCGGCCGCTCTTCATTCACGCCTCGTCAGGCAATCCTAACTCTG
CAGACCTCGTCCTCTGAGCCGCGCTCTGGAGGCATTGGAACTCTGCAATTT
ATTGAGGAGTTTGTGCCATCGGTCTACTTTAACCCCTTCTCGGGACCTCCC
GGCCACTATCCGGATCAATTTATTCCTAACTTTGACGCGGTAAAGGACTCG
GCGGATGGCTACGACTGAATGTTAAGTGGAGAGGCAGAGCAACTGCGCCT
GAAACACCTGGTCCACTGTCGCCGCCACAAGTGCTTTGCCCGCGACTCCG
GTGAGTTTTGCTACTTTGAATTGCCCGAGGATCATATCGAGGGCCCGGCGC
ACGGCGTCCGGCTTACCGCCCAGGGAGAGCTTGCCCGTAGCCTGATTCGG
GAGTTTACCCAGCGCCCCCTGCTAGTTGAGCGGGACAGGGGACCCTGTGT
TCTCACTGTGATTTGCAACTGTCCTAACCCTGGATTACATCAAGATCTTTGT
TGCCATCTCTGTGCTGAGTATAATAAATACAGAAATTAAAATATACTGGGGC
TCCTATCGCCATCCTGTAAACGCCACCGTCTTCACCCGCCCAAGCAAACCA
AGGCGAACCTTACCTGGTACTTTTAACATCTCTCCCTCTGTGATTTACAACA
GTTTCAACCCAGACGGAGTGAGTCTACGAGAGAACCTCTCCGAGCTCAGCT
ACTCCATCAGAAAAAACACCACCCTCCTTACCTGCCGGGAACGTACGACCT
AGGGATAACAGGGTAATAAGCAATTGACTCTATGTGGGATATGCTCCAGCG
CTACAACCTTGAAGTCAGGCTTCCTGGATGTCAGCATCTGACTTTGGCCAG
CACCTGTCCCGCGGATTTGTTCCAGTCCAACTACAGCGACCCACCCTAACA
GAGATGACCAACACAACCAACGCGGCCGCCGCTACCGGACTTACATCTAC
CACAAATACACCCCAAGTTTCTGCCTTTGTCAATAACTGGGATAACTTGGGC
ATGTGGTGGTTCTCCATAGCGCTTATGTTTGTATGCCTTATTATTATGTGGC
TCATCTGCTGCCTAAAGCGCAAACGCGCCCGACCACCCATCTATAGTCCCA
TCATTGTGCTACACCCAAACAATGATGGAATCCATAGATTGGACGGACTGA
AACACATGTTCTTTTCTCTTACAGTATGATTAAATGAGACATGATTCCTCGAG
TTTTTATATTACTGACCCTTGTTGCGCTTTTTTGTGCGTGCTCCACATTGGCT
GCGGTTTCTCACATCGAAGTAGACTGCATTCCAGCCTTCACAGTCTATTTGC
TTTACGGATTTGTCACCCTCACGCTCATCTGCAGCCTCATCACTGTGGTCAT
CGCCTTTATCCAGTGCATTGACTGGGTCTGTGTGCGCTTTGCATATCTCAG
ACACCATCCCCAGTACAGGGACAGGACTATAGCTGAGCTTCTTAGAATTCT
TTAATTATGAAATTTACTGTGACTTTTCTGCTGATTATTTGCACCCTATCTGC
GTTTTGTTCCCCGACCTCCAAGCCTCAAAGACATATATCATGCAGATTCACT
CGTATATGGAATATTCCAAGTTGCTACAATGAAAAAGCGATCTTTCCGAAG
CCTGGTTATATGCAATCATCTCTGTTATGGTGTTCTGCAGTACCATCTTAGC
CCTAGCTATATATCCCTACCTTGACATTGGCTGGAAACGAATAGATGCCATG
AACCACCCAACTTTCCCCGCGCCCGCTATGCTTCCACTGCAACAAGTTGTT
GCCGGCGGCTTTGTCCCAGCCAATCAGCCTCGCCCCACTTCTCCCACCCC
CACTGAAATCAGCTACTTTAATCTAACAGGAGGAGATGACTGACACCCTAG
ATCTAGAAATGGACGGAATTATTACAGAGCAGCGCCTGCTAGAAAGACGCA
GGGCAGCGGCCGAGCAACAGCGCATGAATCAAGAGCTCCAAGACATGGTT
AACTTGCACCAGTGCAAAAGGGGTATCTTTTGTCTGGTAAAGCAGGCCAAA
GTCACCTACGACAGTAATACCACCGGACACCGCCTTAGCTACAAGTTGCCA
ACCAAGCGTCAGAAATTGGTGGTCATGGTGGGAGAAAAGCCCATTACCATA
ACTCAGCACTCGGTAGAAACCGAAGGCTGCATTCACTCACCTTGTCAAGGA
CCTGAGGATCTCTGCACCCTTATTAAGACCCTGTGCGGTCTCAAAGATCTT |

| SEQ ID NO: | DESCRIPTION | SEQUENCE |
|---|---|---|
| | | ATTCCCTTTAACTAATAAAAAAAAATAATAAAGCATCACTTACTTAAAATCAG
TTAGCAAATTTCTGTCCAGTTTATTCAGCAGCACCTCCTTGCCCTCCTCCCA
GCTCTGGTATTGCAGCTTCCTCCTGGCTGCAAACTTTCTCCACAATCTAAAT
GGAATGTCAGTTTCCTCCTGTTCCTGTCCATCCGCACCCACTATCTTCATGT
TGTTGCAGATGAAGCGCGCAAGACCGTCTGAAGATACCTTCAACCCCGTGT
ATCCATATGACACGGAAACCGGTCCTCCAACTGTGCCTTTTCTTACTCCTCC
CTTTGTATCCCCCAATGGGTTTCAAGAGAGTCCCCCTGGGGTACTCTCTTT
GCGCCTATCCGAACCTCTAGTTACCTCCAATGGCATGCTTGCGCTCAAAAT
GGGCAACGGCCTCTCTCTGGACGAGGCCGGCAACCTTACCTCCCAAAATG
TAACCACTGTGAGCCCACCTCTCAAAAAAACCAAGTCAAACATAAACCTGG
AAATATCTGCACCCCTCACAGTTACCTCAGAAGCCCTAACTGTGGCTGCCG
CCGCACCTCTAATGGTCGCGGGCAACACACTCACCATGCAATCACAGGCC
CCGCTAACCGTGCACGACTCCAAACTTAGCATTGCCACCCAAGGACCCCTC
ACAGTGTCAGAAGGAAAGCTAGCCCTGCAAACATCAGGCCCCCTCACCAC
CACCGATAGCAGTACCCTTACTATCACTGCCTCACCCCCTCTAACTACTGC
CACTGGTAGCTTGGGCATTGACTTGAAAGAGCCCATTTATACACAAAATGG
AAAACTAGGACTAAAGTACGGGGCTCCTTTGCATGTAACAGACGACCTAAA
CACTTTGACCGTAGCAACTGGTCCAGGTGTGACTATTAATAATACTTCCTTG
CAAACTAAAGTTACTGGAGCCTTGGGTTTTGATTCACAAGGCAATATGCAAC
TTAATGTAGCAGGAGGACTAAGGATTGATTCTCAAAACAGACGCCTTATACT
TGATGTTAGTTATCCGTTTGATGCTCAAAACCAACTAAATCTAAGACTAGGA
CAGGGCCCTCTTTTTATAAACTCAGCCCACAACTTGGATATTAACTACAACA
AAGGCCTTTACTTGTTTACAGCTTCAAACAATTCCAAAAAGCTTGAGGTTAA
CCTAAGCACTGCCAAGGGGTTGATGTTTGACGCTACAGCCATAGCCATTAA
TGCAGGAGATGGGCTTGAATTTGGTTCACCTAATGCACCAAACACAAATCC
CCTCAAAACAAAAATTGGCCATGGCCTAGAATTTGATTCAAACAAGGCTATG
GTTCCTAAACTAGGAACTGGCCTTAGTTTTGACAGCACAGGTGCCATTACA
GTAGGAAACAAAAATAATGATAAGCTAACCCTATGGACAGGTCCAAAACCA
GAAGCCAACTGCATAATTGAATACGGGAAACAAAACCCAGATAGCAAACTA
ACTTTAATCCTTGTAAAAAATGGAGGAATTGTTAATGGATATGTAACGCTAAT
GGGAGCCTCAGACTACGTTAACACCTTATTTAAAAACAAAAATGTCTCCATT
AATGTAGAACTATACTTTGATGCCACTGGTCATATATTACCAGACTCATCTT
CTCTTAAAACAGATCTAGAACTAAAATACAAGCAAACCGCTGACTTTAGTGC
AAGAGGTTTTATGCCAAGTACTACAGCGTATCCATTTGTCCTTCCTAATGCG
GGAACACATAATGAAAATTATATTTTTGGTCAATGCTACTACAAAGCAAGCG
ATGGTGCCCTTTTTCCGTTGGAAGTTACTGTTATGCTTAATAAACGCCTGCC
AGATAGTCGCACATCCTATGTTATGACTTTTTTATGGTCCTTGAATGCTGGT
CTAGCTCCAGAAACTACTCAGGCAACCCTCATAACCTCCCCATTTACCTTTT
CCTATATTAGAGAAGATGACTAATAAACTCTAAAGAATCGTTTGTGTTATGTT
TCAACGTGTTTATTTTTCAATTGCAGAAAATTTCAAGTCATTTTTCATTCAGT
AGTATAGCCCCACCACCACATAGCTTATACAGATCACCGTACCTTAATCAAA
CTCACAGAACCCTAGTATTCAACCTGCCACCTCCCTCCCAACACACAGAGT
ACACAGTCCTTTCTCCCCGGCTGGCCTTAAAAAGCATCATATCATGGGTAA
CAGACATATTCTTAGGTGTTATATTCCACACGGTTTCCTGTCGAGCCAAACG
CTCATCAGTGATATTAATAAACTCCCCGGGCAGCTCACTTAAGTTCATGTCG
CTGTCCAGCTGCTGAGCCACAGGCTGCTGTCCAACTTGCGGTTGCTTAACG
GGCGGCGAAGGAGAAGTCCACGCCTACATGGGGGTAGAGTCATAATCGTG
CATCAGGATAGGGCGGTGGTGCTGCAGCAGCGCGCGAATAAACTGCTGCC
GCCGCCGCTCCGTCCTGCAGGAATACAACATGGCAGTGGTCTCCTCAGCG
ATGATTCGCACCGCCCGCAGCATAAGGCGCCTTGTCCTCCGGGCACAGCA
GCGCACCCTGATCTCACTTAAATCAGCACAGTAACTGCAGCACAGCACCAC
AATATTGTTCAAAATCCCACAGTGCAAGGCGCTGTATCCAAAGCTCATGGC
GGGGACCACAGAACCCACGTGGCCATCATACCACAAGCGCAGGTAGATTA
AGTGGCGACCCCTCATAAACACGCTGGACATAAACATTACCTCTTTTGGCA
TGTTGTAATTCACCACCTCCCGGTACCATATAAACCTCTGATTAAACATGGC
GCCATCCACCACCATCCTAAACCAGCTGGCCAAAACCTGCCCGCCGGCTA
TACACTGCAGGGAACCGGGACTGGAACAATGACAGTGGAGAGCCCAGGAC
TCGTAACCATGGATCATCATGCTCGTCATGATATCAATGTTGGCACAACACA
GGCACACGTGCATACACTTCCTCAGGATTACAAGCTCCTCCCGCGTTAGAA
CCATATCCCAGGGAACAACCCATTCCTGAATCAGCGTAAATCCCACACTGC
AGGGAAGACCTCGCACGTAACTCACGTTGTGCATTGTCAAAGTGTTACATT
CGGGCAGCAGCGGATGATCCTCCAGTATGGTAGCGCGGGTTTCTGTCTCA
AAAGGAGGTAGACGATCCCTACTGTACGGAGTGCGCCGAGACAACCGAGA
TCGTGTTGGTCGTAGTGTCATGCCAAATGGAACGCCGGACGTAGTCATATT
TCCTGAAGCAAAACCAGGTGCGGGCGTGACAAACAGATCTGCGTCTCCGG
TCTCGCCGCTTAGATCGCTCTGTGTAGTAGTTGTAGTATATCCACTCTCTCA
AAGCATCCAGGCGCCCCTGGCTTCGGGTTCTATGTAAACTCCTTCATGCG
CCGCTGCCCTGATAACATCCACCACCGCAGAATAAGCCACACCCAGCCAA
CCTACACATTCGTTCTGCGAGTCACACACGGGAGGAGCGGGAAGAGCTGG
AAGAACCATGTTTTTTTTTTATTCCAAAAGATTATCCAAAACCTCAAAATGA
AGATCTATTAAGTGAACGCGCTCCCCTCCGGTGGCGTGGTCAAACTCTACA
GCCAAAGAACAGATAATGGCATTTGTAAGATGTTGCACAATGGCTTCCAAAA
GGCAAACGGCCCTCACGTCCAAGTGGACGTAAAGGCTAAACCCTTCAGGG
TGAATCTCCTCTATAAACATTCCAGCACCTTCAACCATGCCCAAATAATTCT |

| SEQ ID NO: | DESCRIPTION | SEQUENCE |
|---|---|---|
| | | CATCTCGCCACCTTCTCAATATATCTCTAAGCAAATCCCGAATATTAAGTCC<br>GGCCATTGTAAAAATCTGCTCCAGAGCGCCCTCCACCTTCAGCCTCAAGCA<br>GCGAATCATGATTGCAAAAATTCAGGTTCCTCACAGACCTGTATAAGATTCA<br>AAAGCGGAACATTAACAAAAATACCGCGATCCCGTAGGTCCCTTCGCAGGG<br>CCAGCTGAACATAATCGTGCAGGTCTGCACGGACCAGCGCGGCCACTTCC<br>CCGCCAGGAACCTTGACAAAGAACCCACACTGATTATGACACGCATACTC<br>GGAGCTATGCTAACCAGCGTAGCCCCGATGTAAGCTTTGTTGCATGGGCG<br>GCGATATAAAATGCAAGGTGCTGCTCAAAAAATCAGGCAAAGCCTCGCGCA<br>AAAAAGAAAGCACATCGTAGTCATGCTCATGCAGATAAAGGCAGGTAAGCT<br>CCGGAACCACCACAGAAAAAGACACCATTTTTCTCTCAAACATGTCTGCGG<br>GTTTCTGCATAAACACAAAATAAAATAACAAAAAAACATTTAAACATTAGAAG<br>CCTGTCTTACAACAGGAAAAACAACCCTTATAAGCATAAGACGGACTACGG<br>CCATGCCGGCGTGACCGTAAAAAAACTGGTCACCGTGATTAAAAAGCACCA<br>CCGACAGCTCCTCGGTCATGTCCGGAGTCATAATGTAAGACTCGGTAAACA<br>CATCAGGTTGATTCATCGGTCAGTGCTAAAAAGCGACCGAAATAGCCCGGG<br>GGAATACATACCCGCAGGCGTAGAGACAACATTACAGCCCCCATAGGAGG<br>TATAACAAAATTAATAGGAGAGAAAAACACATAAACACCTGAAAAACCCTCC<br>TGCCTAGGCAAAATAGCACCCTCCCGCTCCAGAACAACATACAGCGCTTCA<br>CAGCGGCAGCCTAACAGTCAGCCTTACCAGTAAAAAAGAAAACCTATTAAA<br>AAAACACCACTCGACACGGCACCAGCTCAATCAGTCACAGTGTAAAAAAGG<br>GCCAAGTGCAGAGCGAGTATATATAGGACTAAAAAATGACGTAACGGTTAA<br>AGTCCACAAAAAACACCCAGAAAACCGCACGCGAACCTACGCCCAGAAAC<br>GAAAGCCAAAAAACCCACAACTTCCTCAAATCGTCACTTCCGTTTTCCCACG<br>TTACGTAACTTCCCATTTTAAGAAAACTACAATTCCCAACACATACAAGTTAC<br>TCCGCCCTAAAACCTACGTCACCCGCCCCGTTCCCACGCCCCGCGCCACG<br>TCACAAACTCCACCCCCTCATTATCATATTGGCTTCAATCCAAAATAAGGTA<br>TATTATTGATGATGTTAAT |
| 56 | HER2(A3)-CD28TM, ICD-CD3Z CAR | MTRAMDWIWRILFLVGAATGAHSEVQLVQSGTEVKKPGASVRVSCKSSGYTF<br>TSYYIHWVRQAPGQGLEWMAIINPGNGDTNYAQRFQGRVTMTRDTSTSTVYM<br>ELRSLRSDDTAVYFCAREIASYSGSYYDYWGQGTLVTVSSGGGGSGGGGSG<br>GGGSQAVVLQEPSLSVSPGGTVTLTCGLSSGSVSTGHYASWYQQTPGQAPR<br>TLFYNTNTRSSGVPDRFSGSIVGNKAALTITGAQADDESDYYCVLYVGDGIWVF<br>GGGTKLTVLEPKSCDKTHTCPTRFWVLVVVGGVLACYSLLVTVAFIIFWVRSKR<br>SRLLHSDYMNMTPRRPGPTRKHYQPYAPPRDFAAYRSRVKFSRSADAPAYQ<br>QGQNQLYNELNLGRREEYDVLDKRRGRDPEMGGKPQRRKNPQEGLYNELQK<br>DKMAEAYSEIGMKGERRRGKGHDGLYQGLSTATKDTYDALHMQALPPR |
| 57 | HER2(A3) LC-CDR1 | GLSSGSVSTGHYAS |
| 58 | HER2(A3) LC-CDR2 | NTNTRSS |
| 59 | HER2(A3) LC-CDR3 | VLYVGDGIWV |
| 60 | HER2(A3) HC-CDR1 | SYYIHWVRQA |
| 61 | HER2(A3) HC-CDR2 | IINPGNGDTNYAQRFQG |
| 62 | HER2(A3) HC-CDR3 | EIASYSGSYYDY |
| 63 | HER2(A3) VL | QAVVLQEPSLSVSPGGTVTLTCGLSSGSVSTGHYASWYQQTPGQAPRTLFYN<br>TNTRSSGVPDRFSGSIVGNKAALTITGAQADDESDYYCVLYVGDGIWVFGGGT<br>KLTVL |
| 64 | HER2(A3) VH | EVQLVQSGTEVKKPGASVRVSCKSSGYTFTSYYIHWVRQAPGQGLEWMAIINP<br>GNGDTNYAQRFQGRVTMTRDTSTSTVYMELRSLRSDDTAVYFCAREIASYSG<br>SYYDYWGQGTLVTVSS |

The disclosure includes the combination of the aspects and preferred features described except where such a combination is clearly impermissible or expressly avoided.

The section headings used herein are for organizational purposes only and are not to be construed as limiting the subject matter described.

Aspects and embodiments of the present disclosure will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where a nucleic acid sequence in disclosed the reverse complement thereof is also expressly contemplated.

BRIEF DESCRIPTION OF THE FIGURES

Embodiments and studies illustrating the principles of the disclosure will now be discussed with reference to the accompanying figures.

FIG. 1A shows schematic representations of examples of HER2-specific CAR constructs. FIG. 1B shows a schematic of an example of a protocol for transducing T cells to produce HER2-specific CAR-T.

FIG. 4A is a bar chart showing in vitro cell killing of MDA cells (which do not express HER2 at the cell surface; negative control), MDA-HER2 cells (which express HER2 at the cell surface; positive control), FaDu and SCC47 cells by anti-HER2 clone C5, E4 and F1 CAR-T cells (or non-transduced (NT) cells), as determined by $^{51}$Cr release assay. FIG. 4B shows graphs indicating expression of HER2 on MDA-HER2 cells, FaDu and SCC47 cells but not on MDA cells, as determined by flow cytometry.

FIG. 6 shows a schematic representation of the sequences of an example of an ICOSTAT oncolytic adenovirus construct.

FIG. 10A is a schematic representation of the HDAdIL-12_TK_PDL1 construct. FIG. 10B is a bar chart showing production of IL-12p70 by cells transfected with the indicated helper-dependent adenovirus (HDAd) constructs. FIG. 10C is a photograph of a western blot showing production of anti-PD-L1 minibody by cells transfected with the HDAd constructs. FIG. 10D is a photograph of a wells demonstrating HSV thymidine kinase production by cells transfected with the HDAd constructs.

FIGS. 15A to 15C. Images and graph showing the results of in vivo analysis of the anticancer activity of adoptively-transferred luciferase-expressing T cells in an orthotopic FaDu cell-derived model of squamous cell head and neck carcinoma. FIGS. 15A and 15B show the number and location of luciferase-expressing non-transduced T cells (NT), and cells expressing luciferase-expressing T cells expressing C5, F1 or A3 HER2-specific CARs within mice at the indicated number of days after infusion of the cells. FIG. 15C shows the percentage of surviving subjects in the different treatment groups at the inciated number of days after infusion of the cells. A negative control condition wherein mice were not administered with T cells is also shown (-).

FIG. 16A shows the number and location of luciferase-expressing non-transduced T cells (NT), and cells expressing luciferase-expressing T cells expressing C5, F1 or A3 HER2-specific CARs within mice at the indicated number of days after infusion of the cells. FIG. 16B shows measurements for total flux (in photons per second; p/s) of ventral surface for mice of the different groups at the indicated number of days after infusion of the cells. FIG. 16C shows the weights of mice in the different treatment groups at the indicated number of days after infusion of the cells, expressed as a percentage of body weight at day 0.

HER2-specific CAR T cells used in experiments for in vivo analysis of the anti-cancer activity of the combination of CAdtrio and adoptively-transferred T cells. FIG. 17A shows the percentages of CD4+ T cells and CD8+ T cells within the F1.CAR-T population. FIG. 17B shows the percentage cells expressing HER2 CAR at the cell surface. FIG. 17C shows the percentages of cells within the F1.CAR-T population expressing CCR7 and/or CD45RO.

FIG. 18A shows the number and location of luciferase-expressing non-transduced T cells (NT), and cells expressing luciferase-expressing T cells expressing F1 HER2-specific CAR within mice at the indicated number of days after infusion of the cells Top right figure (Y-axis is labelled as Total Flux) is "Days post-injection of CAR T-cells". Bottom 2 figures are "Days post-injection of CAdtrio. FIG. 18B shows measurements for total flux (in photons per second; p/s) of ventral surface for mice of the different groups at the indicated number of days after administration of CAdtrio. FIG. 18C shows the weights of mice in the different treatment groups at the indicated number of days after administration of CAdtrio, expressed as a percentage of body weight at day 0. FIG. 18D shows the percentage of surviving subjects in the different treatment groups at the inciated number of days after administration of CAdtrio. A negative control condition wherein mice were not administered with CAdtrio or T cells is also shown (-).

FIG. 19A shows the number and location of luciferase-expressing FaDu cells within mice at the indicated number of days after administration of CAdtrio. FIG. 19B shows measurements for total flux (in photons per second; p/s) of ventral surface for mice of the different groups at the indicated number of days after administration of CAdtrio. FIG. 19C shows the weights of mice in the different treatment groups at the indicated number of days after administration of CAdtrio, expressed as a percentage of body weight at day 0.

FIGS. 20A and 20B show the GAPDH-normalised copy number of (FIG. 20A) Onc5/3Ad2E1Δ24 and (FIG. 20B) HDAdIL-12_TK_PD-L1 in tumors of mice administered with the combination of Onc5/3Ad2E1Δ24 and HDAdIL-12_TK_PD-L1 (CAdtrio) at 22 days post infection, with or without GCV treatment. FIG. 20C shows tumor volume in mm³ of mice administered with the combination of Onc5/3Ad2E1Δ24 and HDAdIL-12_TK_PD-L1 (CAdtrio) at the indicated number of days post-injection of CAdtrio, with or without GCV treatment. FIG. 20D shows IL-12 levels detected by ELISA analysis of blood samples obtained at the indicated number of days post-injection of CAdtrio, with or without GCV treatment.

FIG. 21A shows the level of IL-12 in cell culture supernatant as determined by ELISA. FIG. 21B shows anti-PD-L1 minibody detected in cell culture supernatant by western blot. FIG. 21C shows viable cells detected by Cystal Violet staining at the end of the experiment.

FIG. 22A shows the percentages of CD4+ T cells and CD8+ T cells within the AdVST population. FIG. 22B shows the percentages of cells within the AdVST population expressing CCR7 and/or CD45RO.

FIG. 23A shows the percentages of CD4+ T cells and CD8+ T cells within the transduced population. FIG. 23B shows the percentage cells expressing HER2 CAR at the cell surface. FIG. 23C shows the percentages of cells within the F1.CAR-AdVST population expressing CCR7 and/or CD45RO.

FIG. 24A shows the number and location of luciferase-expressing FaDu cells within mice at the indicated number of days after administration of CAdtrio. FIG. 24B shows measurements for total flux (in photons per second; p/s) of ventral surface for mice of the different groups at the indicated number of days after administration of CAdtrio. FIG. 24C shows the weights of mice in the different treatment groups at the indicated number of days after administration of CAdtrio, expressed as a percentage of body weight at day 0. FIG. 24D shows the percentage of surviving subjects in the different treatment groups at the indicated number of days after administration of CAdtrio. *P<0.04, P<0.07, *P<0.02 for FIG. 24B. *P<0.01, P<0.04, *P<0.02 for 24C. *P=0.03, **P=0.02 for FIG. 24D.

NUMBERED STATEMENTS OF DISCLOSURE

Figure 1A:
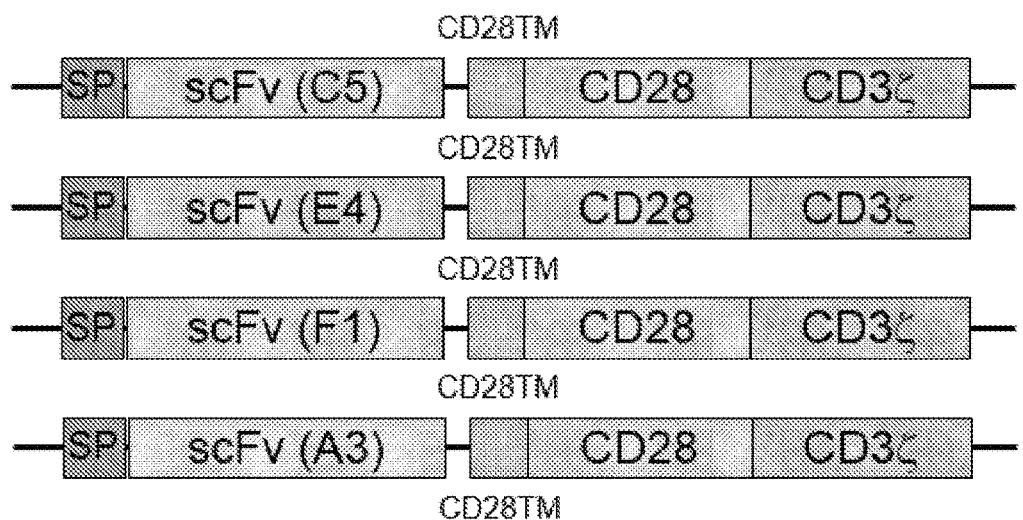
FIGS. 1A and 1B.

Following numbered paragraphs (paras) describe particular aspects and embodiments of the present disclosure:

1. A method of treating a cancer, comprising administering to a subject:
   (i) an oncolytic virus;
   (ii) a virus comprising nucleic acid encoding an immunomodulatory factor; and
   (iii) at least one cell comprising a chimeric antigen receptor (CAR) specific for a cancer cell antigen.

2. The method of para 1, wherein the oncolytic virus is an oncolytic adenovirus (OncAd).

3. The method of para 1 or para 2, wherein the oncolytic virus is derived from adenovirus 5 (Ad5).

4. The method of any one of paras 1 to 3, wherein the oncolytic virus encodes an E1A protein which displays reduced binding to Rb protein as compared to E1A protein encoded by Ad5.

5. The method of any one of paras 1 to 4, wherein the oncolytic virus encodes an E1A protein lacking the amino acid sequence LTCHEACF (SEQ ID NO:52).

6. The method of any one of paras 1 to 5, wherein the oncolytic virus encodes an E1A protein comprising, or consisting of, the amino acid sequence SEQ ID NO:34.

7. The method of any one of paras 1 to 6, wherein the oncolytic virus comprises nucleic acid having one or more binding sites for one or more transcription factors.

8. The method of any one of paras 1 to 7, wherein the oncolytic virus comprises nucleic acid having one or more binding sites for STAT1.

9. The method of any one of paras 1 to 8, wherein the virus comprising nucleic acid encoding an immunomodulatory factor is a helper-dependent adenovirus (HDAd).

10. The method of any one of paras 1 to 9, wherein the immunomodulatory factor is selected from: an agonist of an effector immune response or antagonist of an immunoregulatory response.

11. The method of any one of paras 1 to 10, wherein the virus comprising nucleic acid encoding an immunomodulatory factor comprises nucleic acid encoding IL-12 and/or antagonist anti-PD-L1 antibody.

12. The method of any one of paras 1 to 11, wherein the virus comprising nucleic acid encoding an immunomodulatory factor comprises nucleic acid encoding a thymidine kinase.

13. The method of any one of paras 1 to 12, wherein the at least one cell comprising a CAR specific for a cancer cell antigen is a T cell.

14. The method of any one of paras 1 to 13, wherein the CAR comprises an antigen binding domain capable of specific binding to HER2.

15. The method of any one of paras 1 to 14, wherein the CAR comprises an antigen binding domain comprising:
   a VL domain comprising:
      LC-CRD1: SEQ ID NO:10;
      LC-CRD2: SEQ ID NO:11;
      LC-CRD3: SEQ ID NO:12;
   and a VH domain comprising:
      HC-CRD1: SEQ ID NO:13;
      HC-CRD2: SEQ ID NO:14;
      HC-CRD3: SEQ ID NO:15;
or
   a VL domain comprising:
      LC-CRD1: SEQ ID NO:18;
      LC-CRD2: SEQ ID NO:19;
      LC-CRD3: SEQ ID NO:20;
   and a VH domain comprising:
      HC-CRD1: SEQ ID NO:21;
      HC-CRD2: SEQ ID NO:22;
      HC-CRD3: SEQ ID NO:23;
or
   a VL domain comprising:
      LC-CRD1: SEQ ID NO:26;
      LC-CRD2: SEQ ID NO:27;
      LC-CRD3: SEQ ID NO:28;
   and a VH domain comprising:
      HC-CRD1: SEQ ID NO:29;
      HC-CRD2: SEQ ID NO:30;
      HC-CRD3: SEQ ID NO:31.

16. The method of any one of paras 1 to 15, wherein the CAR comprises an antigen binding domain comprising:
   a VL comprising, or consisting of or consisting essentially of, an amino acid sequence having at least 75% sequence identity to SEQ ID NO:16 and a VH comprising, or consisting of or consisting essentially of, an amino acid sequence having at least 75% sequence identity to SEQ ID NO:17;
or
   a VL comprising, or consisting of or consisting essentially of, an amino acid sequence having at least 75% sequence identity to SEQ ID NO:24 and a VH comprising, or consisting of or consisting essentially of, an amino acid sequence having at least 75% sequence identity to SEQ ID NO:25;
or
   a VL comprising, or consisting of or consisting essentially of, an amino acid sequence having at least 75% sequence identity to SEQ ID NO:32 and a VH comprising, or consisting of or consisting essentially of, an amino acid sequence having at least 75% sequence identity to SEQ ID NO:33.

17. The method of any one of paras 1 to 16, wherein the method additionally comprises:
   (a) isolating at least one cell from a subject;
   (b) modifying the at least one cell to express or comprise a CAR specific for a cancer cell antigen, or a nucleic acid encoding a CAR specific for a cancer cell antigen,
   (c) optionally expanding the modified at least one cell, and;
   (d) administering the modified at least one cell to a subject.

18. The method of any one of paras 1 to 17, wherein the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

19. An oncolytic adenovirus (OncAd) encoding an E1A protein comprising, or consisting of, the amino acid sequence SEQ ID NO:34.

20. An oncolytic adenovirus (OncAd) comprising nucleic acid having one or more binding sites for STAT1.

21. The OncAd according to para 20, wherein the OncAd comprises a nucleic acid sequence having at least 60% sequence identity to SEQ ID NO:51 or an equivalent sequence as a result of codon degeneracy.

22. A helper-dependent adenovirus (HDAd) comprising nucleic acid encoding IL-12 and/or antagonist anti-PD-L1 antibody.

23. The HDAd according to para 22, wherein the HDAd additionally comprises nucleic acid encoding a thymidine kinase.

24. A chimeric antigen receptor (CAR) comprising an antigen binding domain comprising:
   a VL domain comprising:
      LC-CRD1: SEQ ID NO:10;
      LC-CRD2: SEQ ID NO:11;
      LC-CRD3: SEQ ID NO:12;
   and a VH domain comprising:
      HC-CRD1: SEQ ID NO:13;
      HC-CRD2: SEQ ID NO:14;
      HC-CRD3: SEQ ID NO:15;
or
   a VL domain comprising:
      LC-CRD1: SEQ ID NO:18;
      LC-CRD2: SEQ ID NO:19;
      LC-CRD3: SEQ ID NO:20;
   and a VH domain comprising:
      HC-CRD1: SEQ ID NO:21;
      HC-CRD2: SEQ ID NO:22;
      HC-CRD3: SEQ ID NO:23;
or
   a VL domain comprising:
      LC-CRD1: SEQ ID NO:26;
      LC-CRD2: SEQ ID NO:27;
      LC-CRD3: SEQ ID NO:28;
   and a VH domain comprising:
      HC-CRD1: SEQ ID NO:29;
      HC-CRD2: SEQ ID NO:30;
      HC-CRD3: SEQ ID NO:31.

25. The CAR according to para 24, wherein the CAR comprises an antigen binding domain comprising:
- a VL comprising, or consisting of, an amino acid sequence having at least 75% sequence identity to SEQ ID NO:16 and a VH comprising, or consisting of or consisting essentially of, an amino acid sequence having at least 75% sequence identity to SEQ ID NO:17;

or
- a VL comprising, or consisting of or consisting essentially of, an amino acid sequence having at least 75% sequence identity to SEQ ID NO:24 and a VH comprising, or consisting of or consisting essentially of, an amino acid sequence having at least 75% sequence identity to SEQ ID NO:25;

or
- a VL comprising, or consisting of, an amino acid sequence having at least 75% sequence identity to SEQ ID NO:32 and a VH comprising, or consisting of or consisting essentially of, an amino acid sequence having at least 75% sequence identity to SEQ ID NO:33.

26. A nucleic acid, optionally isolated or man-made, encoding the oncolytic adenovirus (OncAd) according to any one of paras 19 to 21, the helper-dependent adenovirus (HDAd) according to para 22 or para 23, or the chimeric antigen receptor (CAR) according to para 24 or para 25.

27. A cell comprising the oncolytic adenovirus (OncAd) according to any one of paras 19 to 21, the helper-dependent adenovirus (HDAd) according to para 22 or para 23, the chimeric antigen receptor (CAR) according to para 24 or para 25, or the nucleic acid according to para 26, optionally wherein the cell is man-made and not found in nature.

28. A pharmaceutical composition comprising the oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26 or the cell according to para 27 and a pharmaceutically acceptable carrier, diluent, excipient or adjuvant.

29. A method of treating cancer comprising administering to a subject the oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26, the cell according to para 27 or the pharmaceutical composition according to para 28.

30. The oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26, the cell according to para 27 or the pharmaceutical composition according to para 28 for use in a method of treating a cancer.

31. Use of the oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26, the cell according to para 27 or the pharmaceutical composition according to para 28 in the manufacture of a medicament for treating a cancer.

32. The method, the use or the use according to any one of paras 29 to 31, wherein the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

33. A kit of parts comprising a predetermined quantity of the oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26, the cell according to para 27 or the pharmaceutical composition according to para 28.

EXAMPLES

In the following Examples, the inventors describe the generation functional characterisation of novel HER-2 specific CARs and CAR-T cells, oncolytic adenoviruses and helper-dependent adenovirus.

Example 1: HER2-Specific CAR-T Cells 1.1 Generation of HER2-Specific CAR Constructs and CAR-T Cells HER2-binding CAR constructs were prepared. Briefly, DNA encoding scFv (i.e. VL domain and VH domain joined by a linker sequence) for the anti-HER2 antibody clone C5, E4, F1 or A3 was cloned into a CAR construct backbone comprising a 5' signal peptide (SP), and CD28 transmembrane (TM) and intracellular domain sequence, with a 3' CD3ζ intracellular domain sequence. The three HER2-binding CAR constructs are represented schematically in FIG. 1A.

Figure 1B:
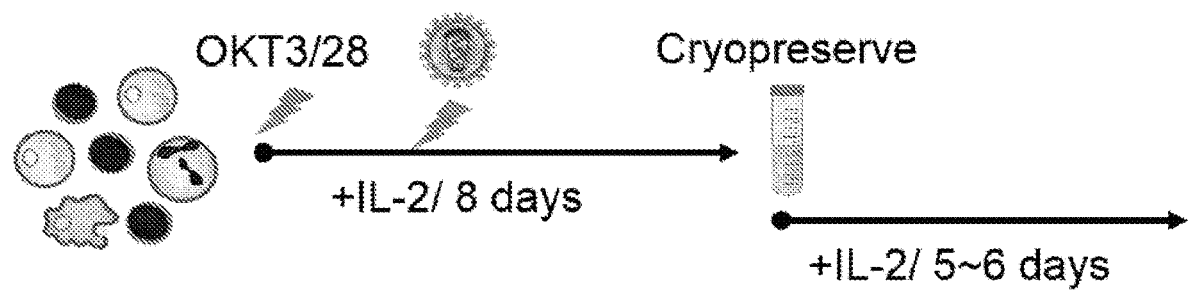
Figure 14:
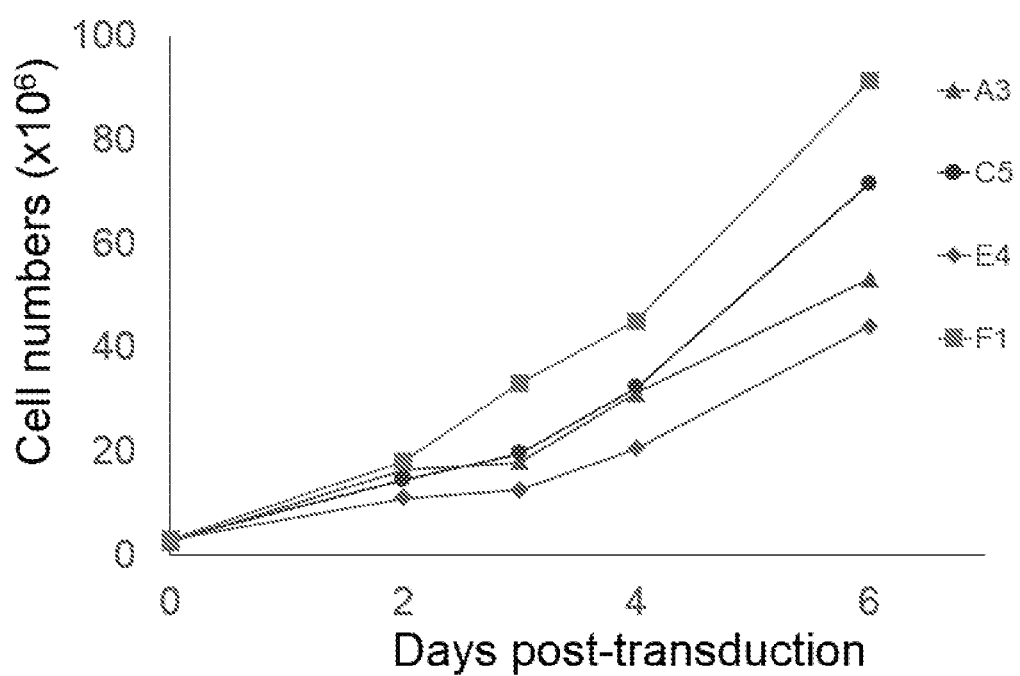
FIG. 14. Graph showing numbers of HER2-specific CAR T cells following the indicated number of days of in vitro cell culture after transuction with the indicated CAR constructs.

HER2 specific CAR-T cells were generated as represented graphically in FIG. 1B. Briefly, human PBMCs were isolated from blood samples by with Ficoll density gradient centrifugation. Cells were treated by stimulation with anti-CD3(OKT3)/anti-CD28 in the presence of IL-2 to promote T cell activation and proliferation, and the cells were transduced with retrovirus encoding the HER2 CAR constructs. T-cells were expanded by culture in the presence of 100 IU/mL recombinant human IL-2, and were frozen at 6 days post-transduction. The HER2-specific CAR construct-transduced T cells were readily expanded by culture in vitro (see e.g. FIG. 14). T-cells were thawed and expanded in the presence of 100 IU/mL of recombinant human IL-2 for 5 days and used for in vitro/in vivo experiments and phenotypic analysis.

1.2 Characterisation of the HER2-Specific CAR-T Cells 1.2.1 Expression of Surface Markers and HER2 CARs T cells transduced with HER2 CAR construct encoding scFv for anti-HER2 antibody clone E4 were characterised by flow cytometry for expression of different cell surface molecules. Expanded HER2 specific CAR T-cells were stained with fluorescently-labelled monoclonal antibodies for 30 minutes at 4° C. Discrimination of live/dead cells was achieved by including 7AAD in stainings (BD Pharmingen). Stained cells were analyzed using a Gallios flow cytometer and Kaluza software (BD Bioscience), according to manufacturer's instructions.

Figure 2:
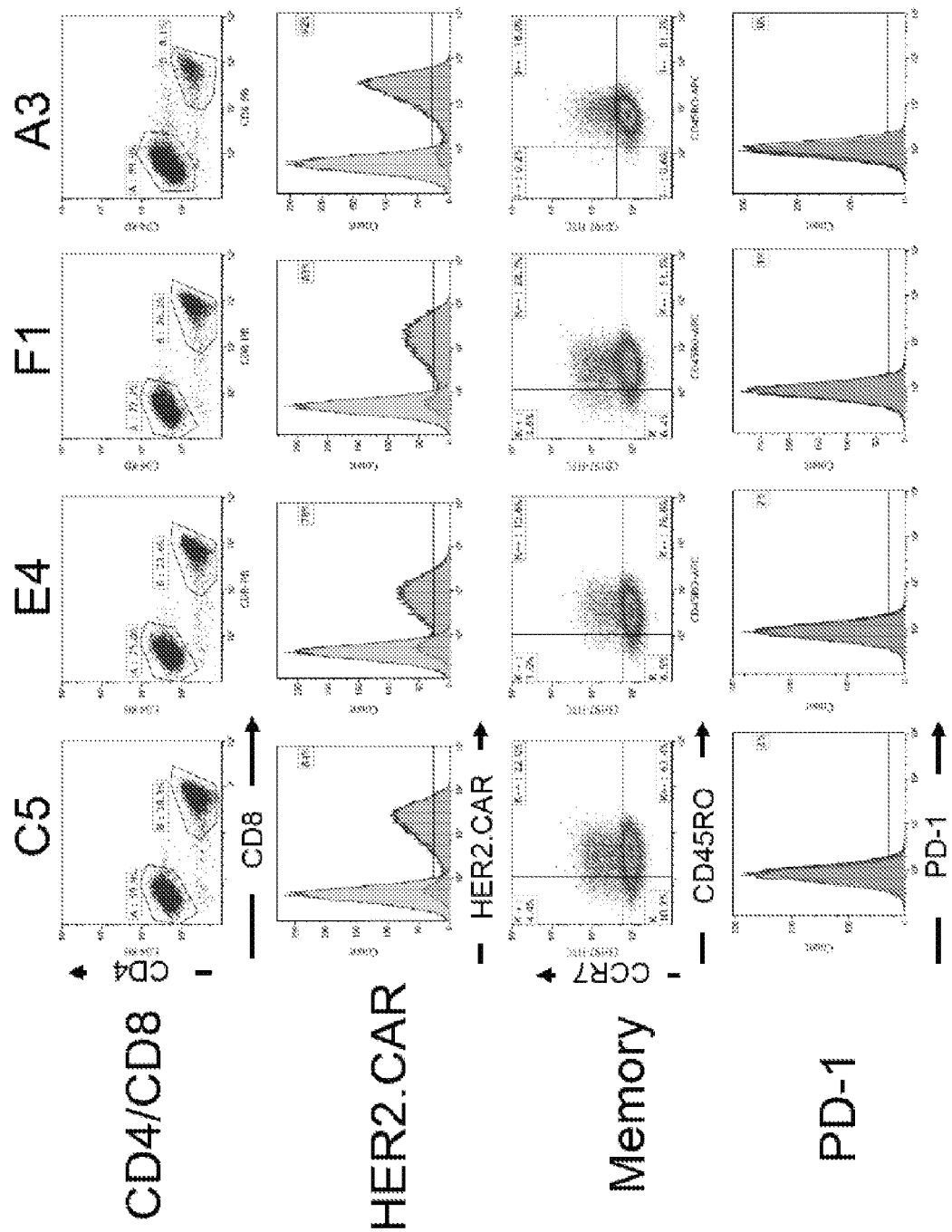
FIG. 2. Graphs showing expression of the HER2-CARs, CCR7, CD45RO and PD-1 on T cells transduced with the indicated HER2-CAR constructs, as determined by flow cytometry.
Figure 3:
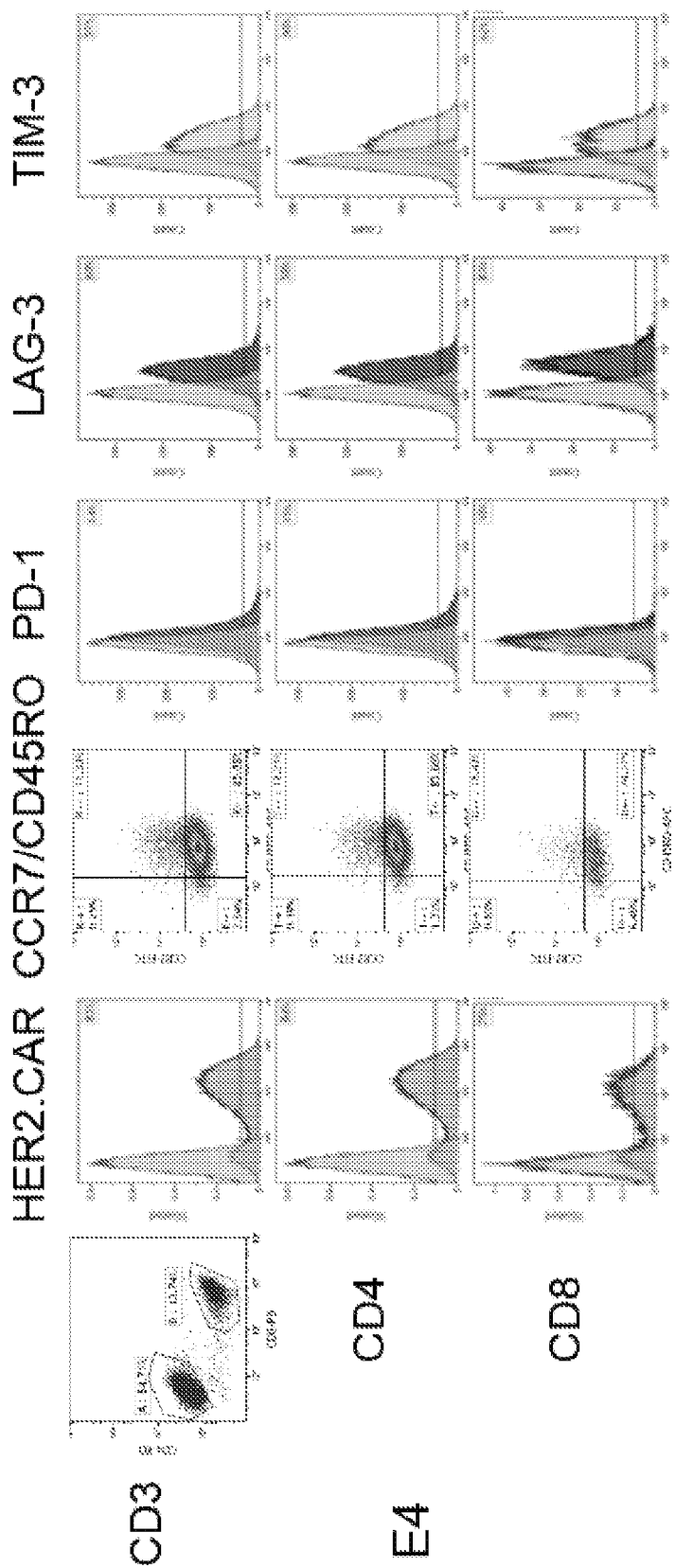
FIG. 3. Graphs showing expression of HER2-CAR, CCR7, CD45RO, PD-1, LAG-3 and TIM-3 on CD4 and CD8 T cells following transduction with anti-HER2 clone E4 CAR construct, as determined by flow cytometry.

The results are shown in FIGS. 2 and 3. Strong surface expression of the HER2-CARs was detected on the transduced cells (FIG. 2).

FIG. 3 shows the results of characterisation of T cells transduced with HER2(E4)-CAR. CD3+ cells, CD4+ cells and CD8+ cells expressing HER2(E4)-CAR were shown to have increased expression of PD-1, LAG-3 and TIM-3, and to have reduced level of expression of CCR7 as compared to non-transduced cells (FIG. 3).

1.2.2 Cell Killing Activity

The HER2-CAR-T cells were analysed for their ability to kill HER2 expressing cancer cells in vitro in cell killing assays.

Figure 4A:
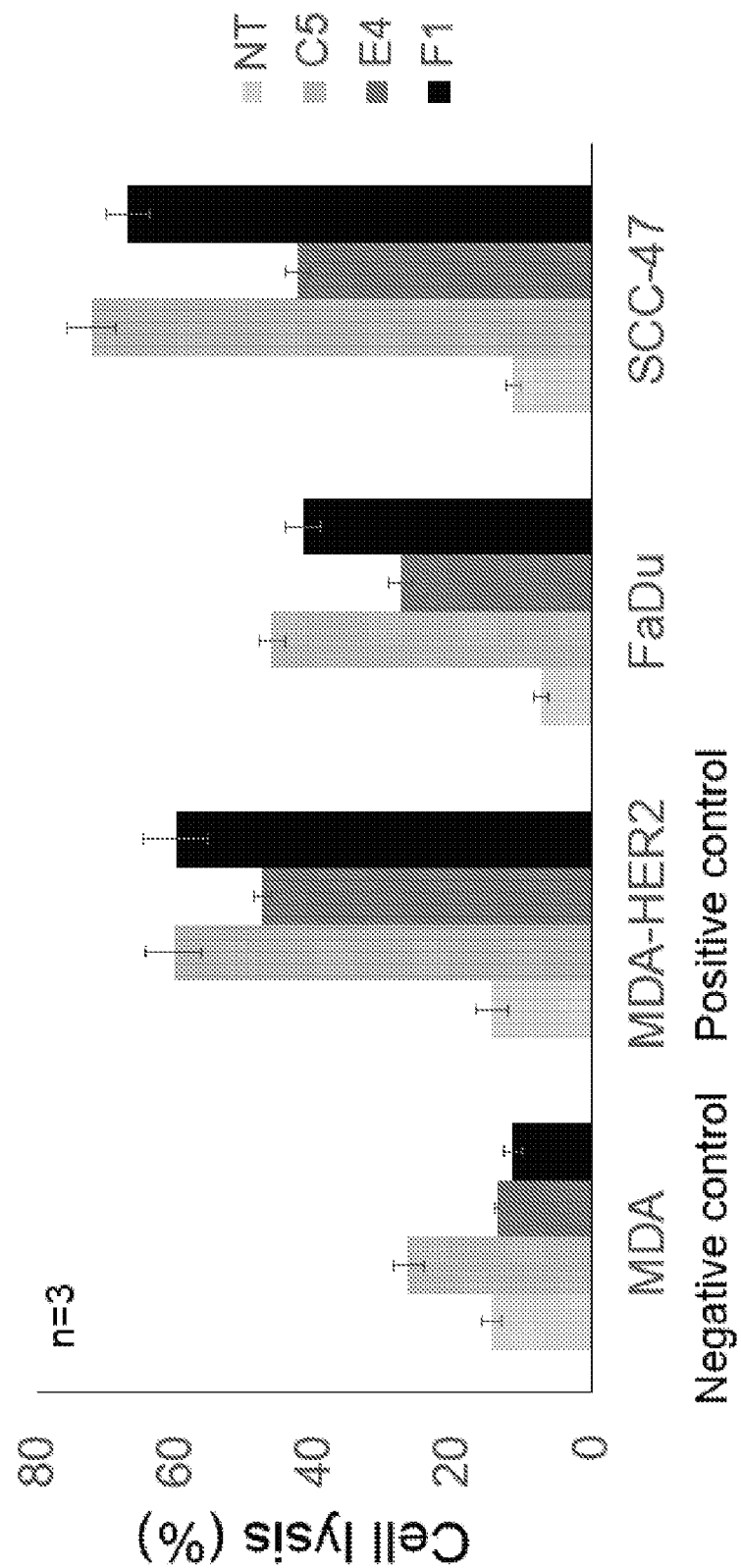
FIGS. 4A and 4B.

In a first experiment, cells of the HER2 negative MDA cell line (negative control), MDA cells stably expressing HER2 (MDA-HER2; positive control), pharynx squamous cell carcinoma cell line FaDu or the head and neck squamous carcinoma cell line SCC47 cells were labelled with Chromium-51 ($^{51}$Cr) and co-cultured with non-transduced T-cells (NT) or the HER2-CAR-T cells expressing the indicated CARs at an effector:target cell ratio of 20:1 for 4 hours. After centrifugation, $^{51}$Cr levels in the cell culture media were counted using a liquid scintillation counter. The results are shown in FIG. 4A; the HER2-CAR-T cells were shown to kill HER2-expressing cancer cells. Similar results were obtained when the experiments were performed using an effector:target cell ratio of 10:1.

Figure 4B:
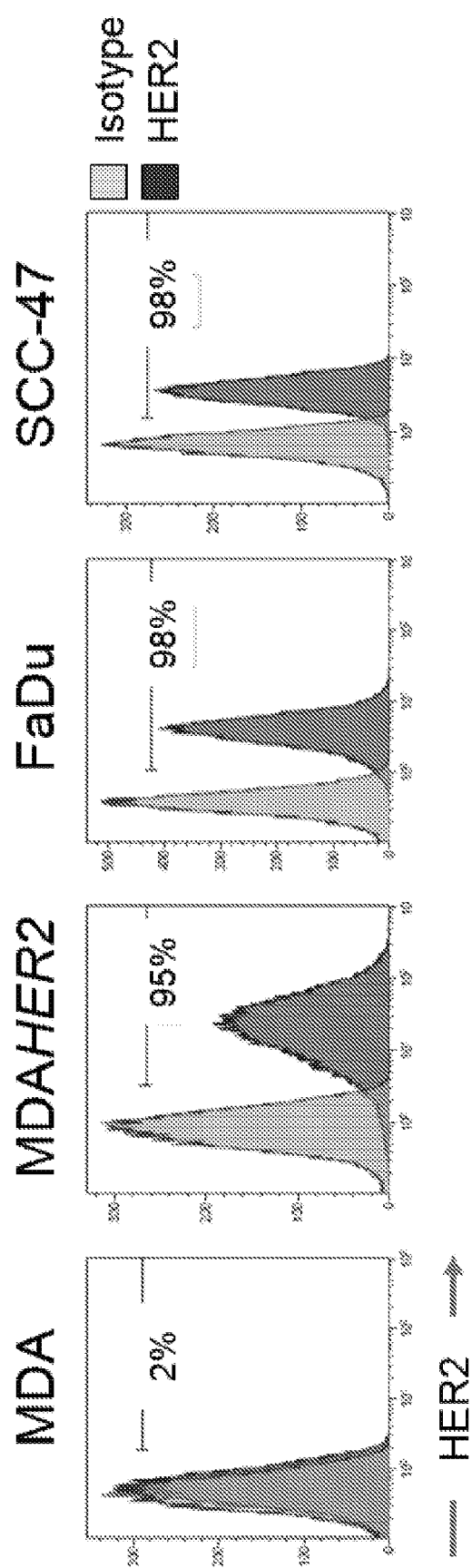

Expression of HER2 on MDA-HER2, FaDu and SCC47 was confirmed by flow cytometry. Briefly, the cells were were stained with fluorescently-labelled monoclonal anti-HER2 antibody or isotype control antibody for 30 minutes at 4° C. Discrimination of live/dead cells was achieved by including 7AAD in stainings (BD Pharmingen). Stained cells were analyzed using a Gallios flow cytometer and Kaluza software (BD Bioscience), according to manufacturer's instructions. The results are shown in FIG. 4B; MDA cells were confirmed not to express HER2, whilst MDA-HER2, FaDu and SCC47 express HER2.

Figure 5:
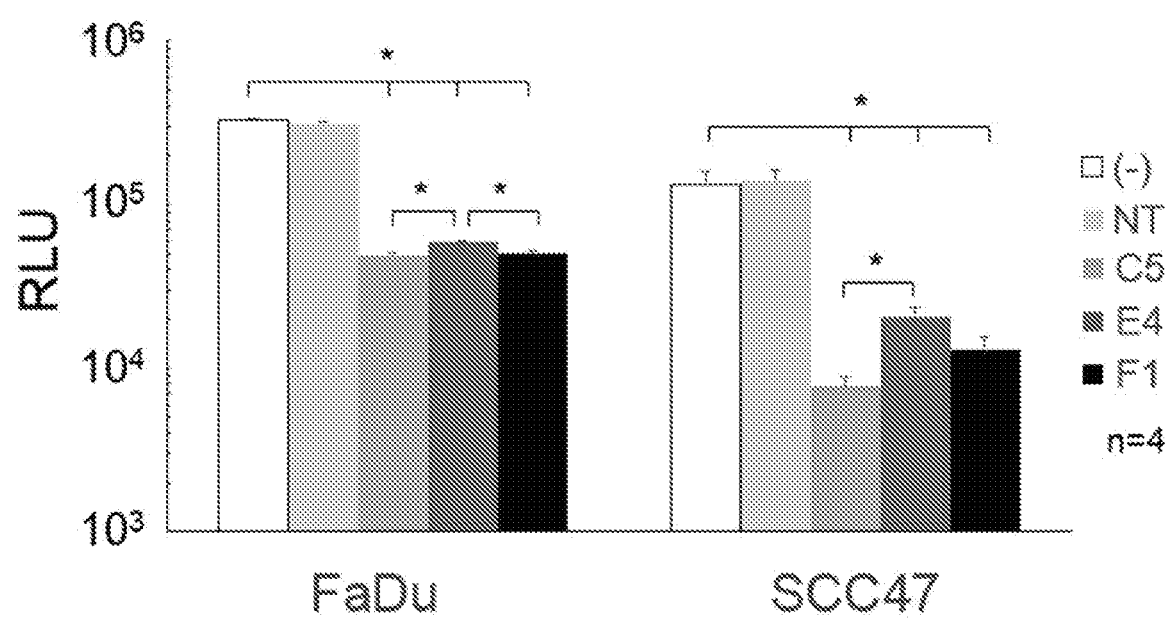
FIG. 5. Bar chart showing in vitro cell killing of FaDu and SCC47 cells genetically modified to express firefly luciferase (ffLuc) by anti-HER2 clone C5, E4 and F1 CAR-T cells (or non-transduced (NT) cells), as determined by ffLuc activity assay. Data are presented as mean±SD (n=4). *P<0.001.

In a separate experiment, FaDu and SCC47 cells genetically modified to express firefly luciferase (ffLuc) were seeded in wells of 24-well plates, and co-cultured with HER2(C5)-CAR-T cells, HER2(E4)-CAR-T cells, or HER2 (F1)-CAR-T cells at an effector:target cell ratio of 1:5 for 3 days, and ffLuc activity was measured using a plate reader (Life Technologies). The results are shown in FIG. 5; the HER2-CAR-T cells were shown to kill HER2-expressing cancer cells, as evidenced by a reduction in ffLuc activity (relative light units, RLU). Similar results were obtained when the experiment was performed using an effector:target cell ratio of 1:20.

Example 2: OncAd Constructs 2.1 Generation of OncAd Constructs

Novel constructs encoding oncolytic adenovirus are prepared using recombinant DNA techniques. In particular embodiments, an OncAd is produced upon modification of a known virus. For example, a region encoding E1A protein from adenovirus 5, such as one lacking the sequence LTCHEACF (SEQ ID NO:52) involved in binding the Rb protein, is replaced with sequence encoding E1A protein from adenovirus 2, similarly lacking the sequence LTCHEACF (SEQ ID NO:52).

Figure 6:
FIG. 6.

ICOSTAT shown in FIG. 6 was produced from ICO-VIR15 disclosed e.g. in Rojas et al. 2010 Mol Ther 18 1960-1971. Briefly, the region of ICOVIR15 encoding eight copies of a binding site for the transcription factor E2F was replaced with a region encoding eight tandem copies of a binding site for the transcription factor STAT1. The sequence of ICOSTAT is shown in SEQ ID NO:51.

Figure 12A:
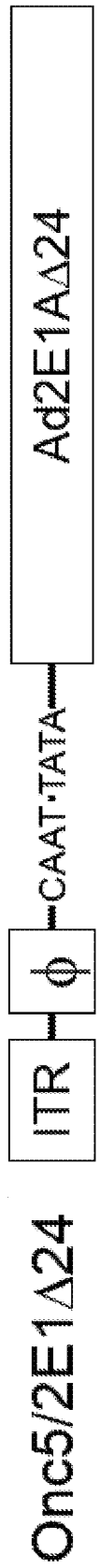
FIGS. 12A and 12B. Schematic representations of the sequences of (FIG. 12A) an example of an Onc5/2E1Δ24 oncolytic adenovirus construct, and (FIG. 12B) a plasmid encoding an Onc5/2E1Δ24 oncolytic adenovirus construct.
Figure 12B:
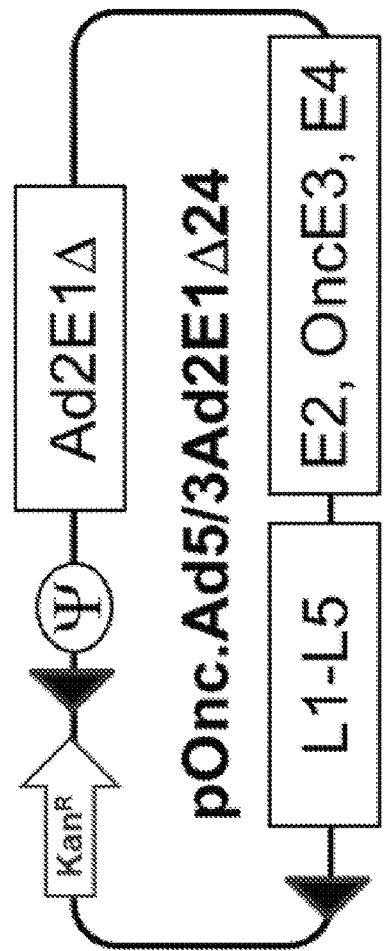

Onc5/3Ad2E1Δ24 (also referred to herein as "Onc5/2E1Δ24") shown in SEQ ID NO:55 and represented schematically in FIG. 12 was also prepared by using recombinant DNA techniques. Onc5/3Ad2E1Δ24 has a similar structure as Onc5Δ24 disclosed e.g. in Fueyo et al. 2000 Oncogene 19:2-12 (hereby incorporated by reference in its entirety; Onc5Δ24 is also referred to in Fueyo et al. as "Δ24"), but differs in that Onc5/3Ad2E1Δ24 encodes E1A protein from adenovirus type 2 (Ad2) lacking the sequence LTCHEACF (SEQ ID NO:52), rather than E1A protein from adenovirus type 5 (Ad5) lacking the sequence LTCHEACF (SEQ ID NO:52).

2.2 Cell Killing Activity

The ability of an oncolytic adenovirus of choice or ICOSTAT as generated in Example 2.1 to kill cancer cells may be analysed for example by MTS assay. Briefly, cells of the human alveolar basal epithelial adenocarcinoma cell line A549 cells, FaDu cells, SCC47 cells, or non-cancerous WI-38 human lung fibroblasts or ARPE-19 human retinal pigmented epithelial cells were seeded in wells of 96-well plates and infected with different amounts of a helper-dependent, non-replicating adenovirus (HDAd; as a negative control), an oncolytic adenovirus of choice (e.g. Onc5/3Ad2E1Δ24 described in Example 2.1), or ICOSTAT described in Example 2.1 above.

Cells may be cultured for 4 days, for example, and then MTS reagents (Promega) may be added to each well, with cells being incubated at 37° C. for 2 hours. Live cells may be analyzed by measuring the absorbance at 490 nm with a plate reader. Readings may be normalized using the readings for untreated cells of each type (i.e. untreated cells=100% cell viability), and wells lacking cells would be considered 0%.

In particular embodiments, the oncolytic virus of choice is able to kill cancer cells in a dose-dependent manner. The oncolytic virus of choice also exhibits a lower level of cell killing of non-cancerous cells, such as WI-38 and ARPE-19 cells as compared to the level of killing by the virus of cancerous cells, in specific embodiments.

Figure 7A:
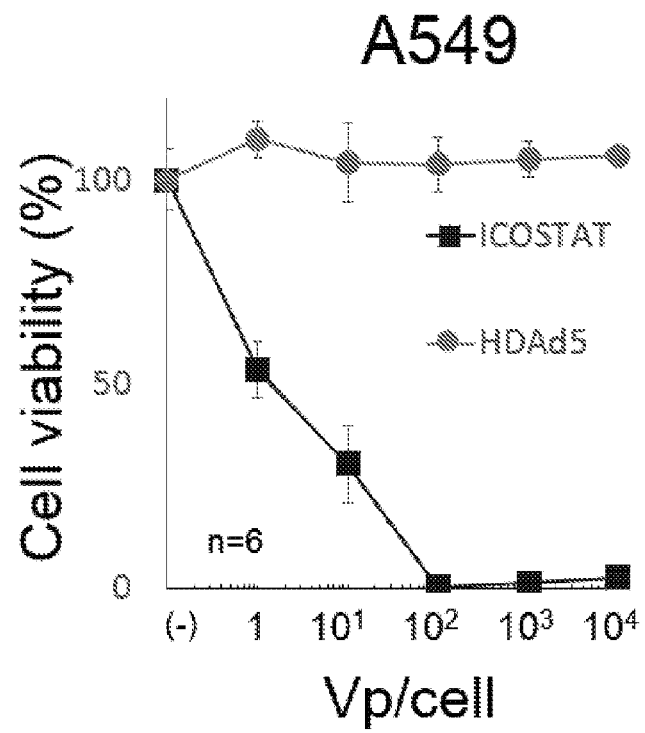
FIGS. 7A to 7F. Graphs showing the ability of ICOSTAT oncolytic adenovirus to kill A549 cells (FIGS. 7A and 7F), FaDu cells (FIG. 7B), SCC47 cells (FIG. 7C), WI-38 cells (FIG. 7D) and ARPE-19 cells (FIG. 7E) following infection with the indicated concentration of viral particles (Vp), as determined by MTS viability assay. Helper-dependent adenovirus (HDAd) is included as a control condition.
Figure 7B:
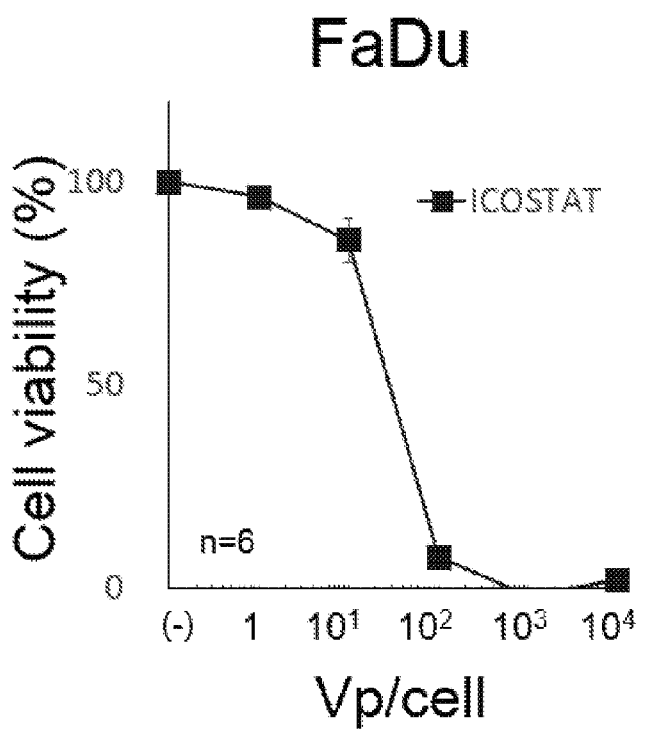
Figure 7C:
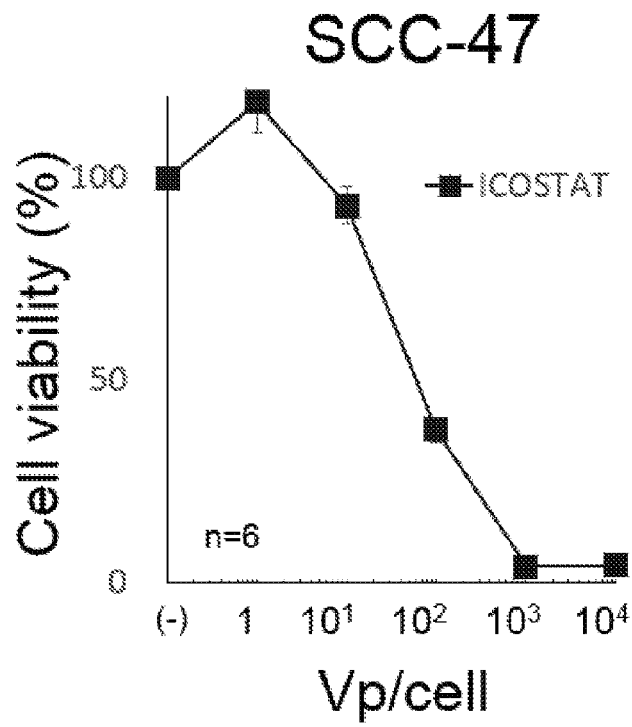
Figure 7D:
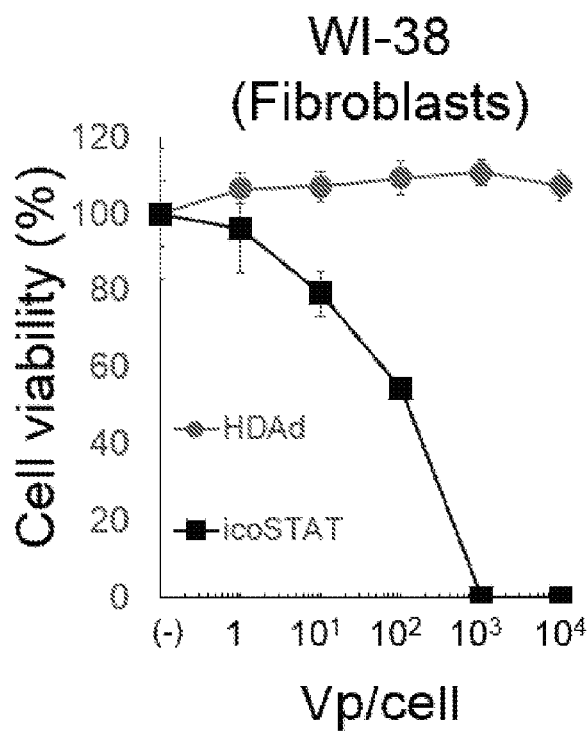
Figure 7E:
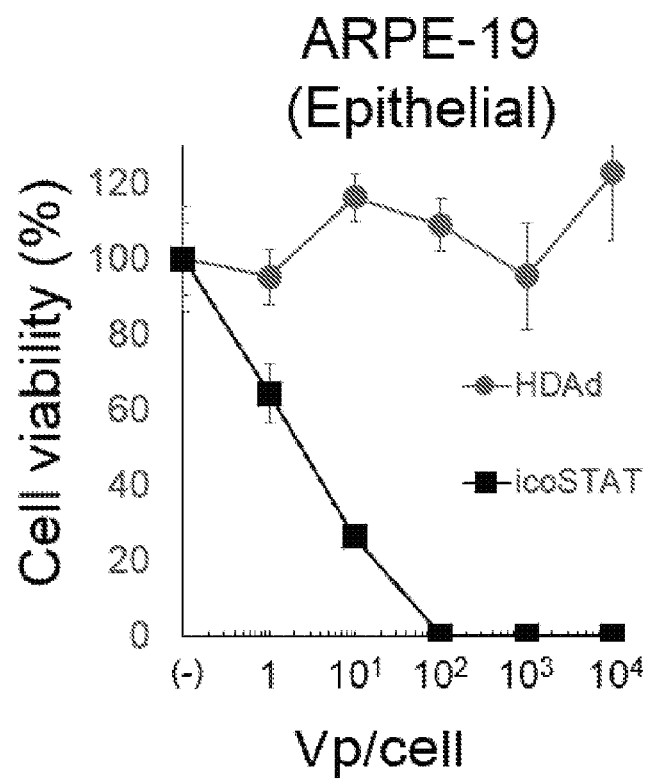
Figure 7F:
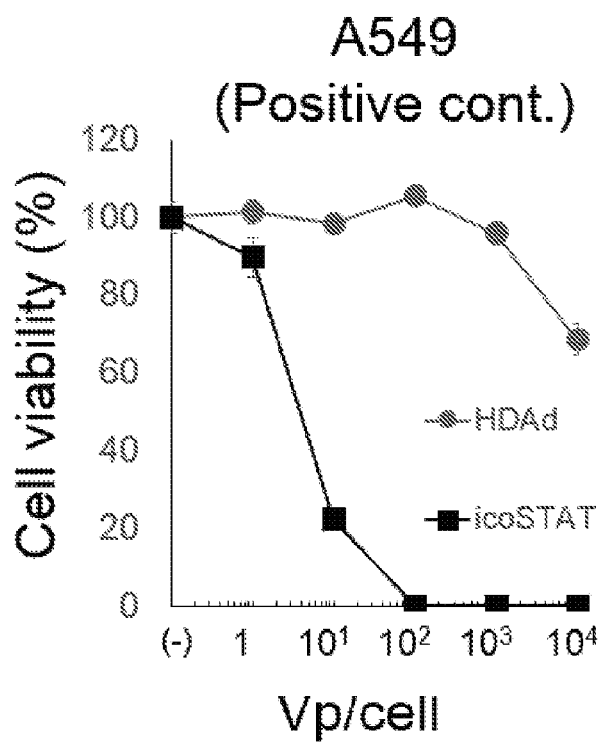

FIGS. 7A to 7F show that ICOSTAT is able to kill cancer cells (i.e. A549, FaDu and SCC47 cells) in a dose-dependent manner (FIGS. 7A to 7C and 7F), and exhibits a lower level of cell killing of non-cancerous cells WI-38 and ARPE-19 cells as compared to the level of killing of the cancerous cells (FIGS. 7D and 7E).

Figure 13A:
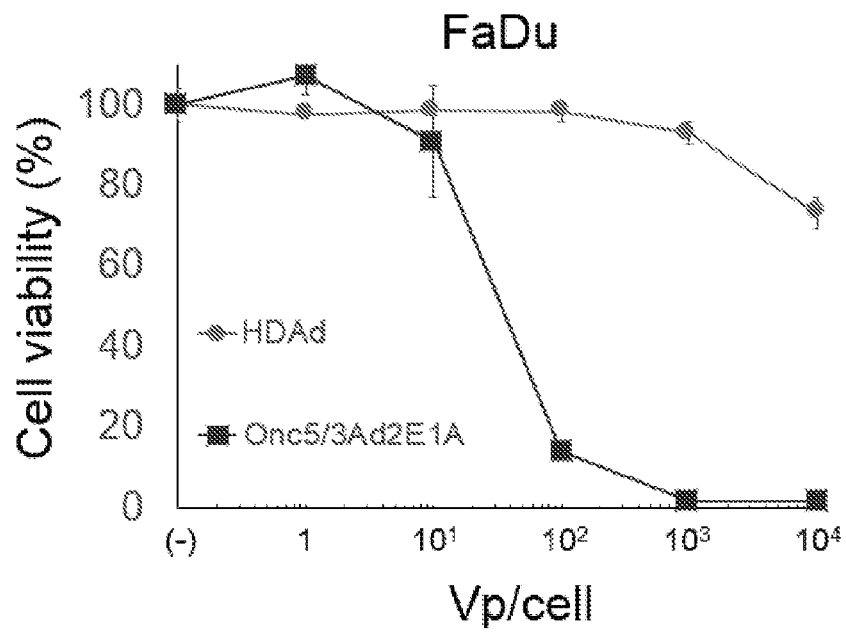
FIGS. 13A to 13D. Graphs showing the ability of Onc5/3Ad2E1A oncolytic adenovirus to kill FaDu cells (FIG. 13A), SCC47 cells (FIG. 13B), WI-38 cells (FIG. 13C) and ARPE-19 cells (FIG. 13D) following infection with the indicated concentration of viral particles (Vp), as determined by MTS viability assay. Helper-dependent adenovirus (HDAd) is included as a control condition.
Figure 13B:
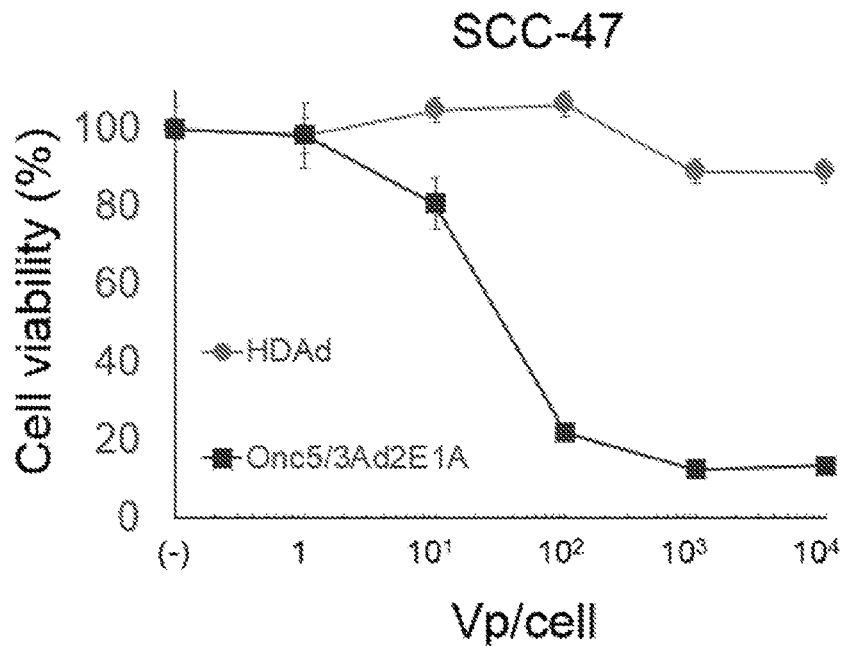
Figure 13C:
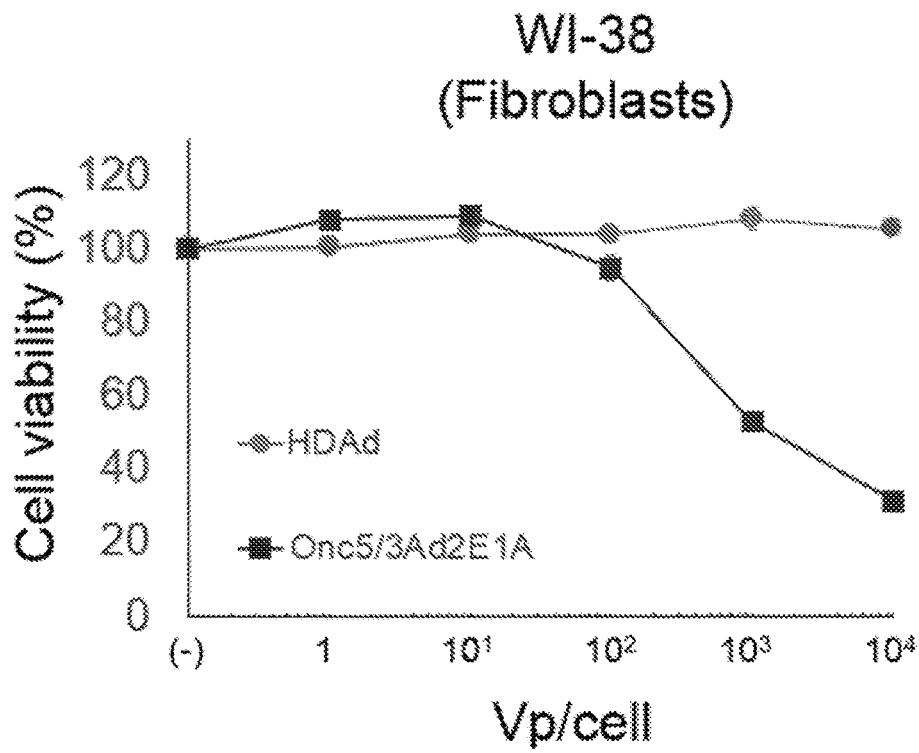
Figure 13D:
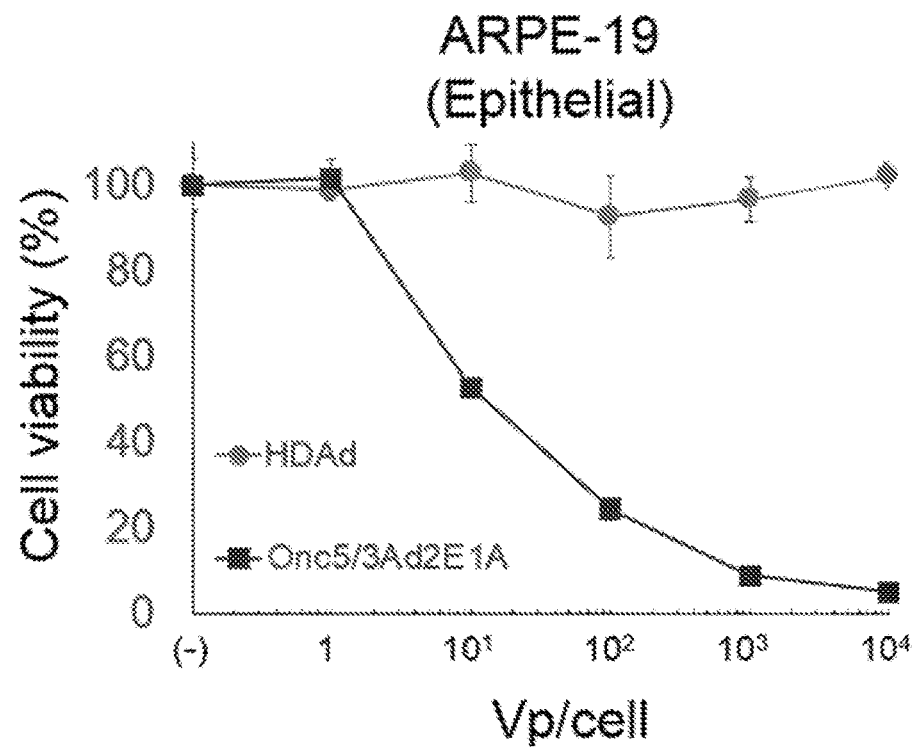

FIGS. 13A to 13D show that Onc5/3Ad2E1Δ24 is able to kill cancer cells (i.e. FaDu and SCC47 cells) in a dose-dependent manner (FIGS. 13A and 13B), and exhibits a lower level of cell killing of non-cancerous WI-38 and ARPE-19 cells as compared to the level of killing of the cancerous cells (FIGS. 13C and 13D).

2.3 Ability to Help Helper-Dependent Adenovirus (HDAd)

The ability of an oncolytic adenovirus of choice or ICOSTAT as generated in Example 2.1 to assist replication of a helper-dependent adenovirus (HDAd) may be analysed by co-infecting cancer cells with the OncoAd and HDAd, and determining virus copy number. Briefly, FaDu or SCC47 cells are plated in 24-well plates and infected with 10 viral particles per cell of HDAd alone, or OncAd+HDAd (at an OncAd:HDAd ratio of 1:10). Cells are harvested at 48 hours post-infection, DNA is extracted and both HDAd and Onc.Ad vector copies are analyzed by quantitative real-time PCR (10 min at 95° C. and then 45 cycles of 10 s at 95° C., 15 s at 60° C., and 30 s at 72° C.) using a Bio-Rad iQ5 real-time PCR detection system (Bio-Rad), and Applied Biosystems SYBR green PCR master mix (Life Technologies). Copy number is normalized using copy number detected for GAPDH.

In particular embodiments, the oncolytic virus of choice is able to replicate itself and the HDAd sufficiently.

Figure 8A:
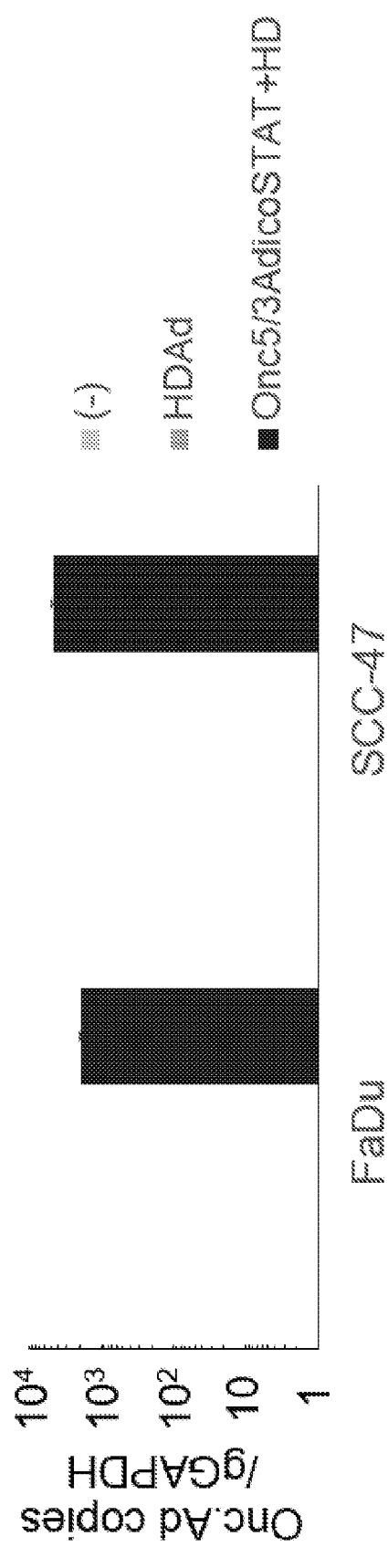
FIGS. 8A and 8B. Bar charts showing ability of ICOSTAT oncolytic adenovirus to replicate and act as helper for replication of helper-dependent adenovirus (HDAd), as determined by copy number analysis by quantitative real-time PCR. The virus designated "Onc5/3AdicoSTAT" is ICOSTAT. "+HD" indicates co-infection of ICOSTAT with HDAd.
Figure 8B:
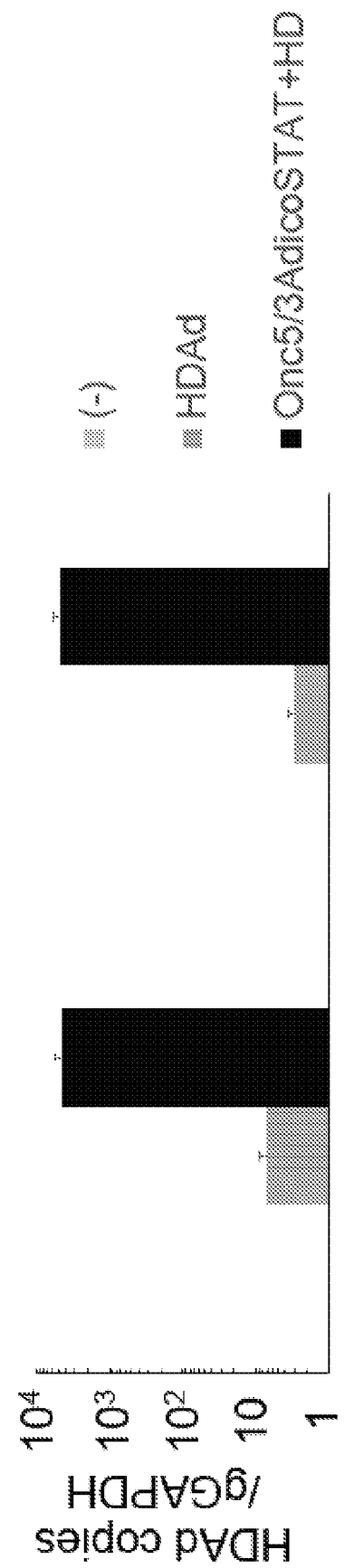

FIGS. 8A and 8B show that ICOSTAT (designated "Onc5/3AdicoSTAT" in the figures) was found to be able to replicate itself (FIG. 8A) and the HDAd (FIG. 8B).

2.4 Effect of IFNγ on Replication of ICOSTAT in Cancer Cells

The effect of IFNγ treatment on replication of ICOSTAT OncAd was analysed. Briefly, FaDu and SCC47 cells are plated in 24-well plates, and the cells are infected with 10 vp/cell of the oncolytic virus of choice or icoSTAT 3 hours post-infection cell culture medium is replaced with medium containing, or not containing, 10 ng/mL recombinant IFNγ at 3 hours post-infection, and cell culture media are replaced with fresh media with/without 10 ng/mL recombinant IFNγ again at 24 and 48 hours post-infection. Cells are harvested at 3, 24, 48 and 72 hours post-infection, DNA is extracted from the cells, viral copy numbers are analysed by quantitative real-time PCR and normalized using copy number detected for GAPDH.

Figure 9A:
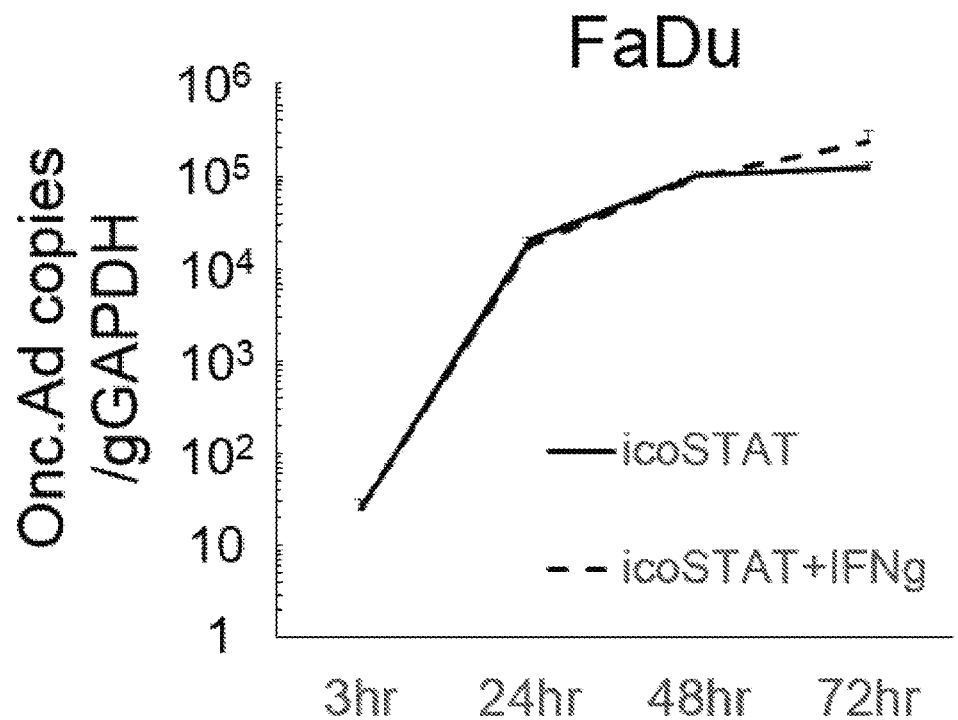
FIGS. 9A and 9B. Graphs showing the replication of ICOSTAT oncolytic adenovirus in FaDu cells (FIG. 9A) and SCC47 cells (FIG. 9B), in the presence or absence of 10 ng/ml IFNγ in the cell culture media.
Figure 9B:
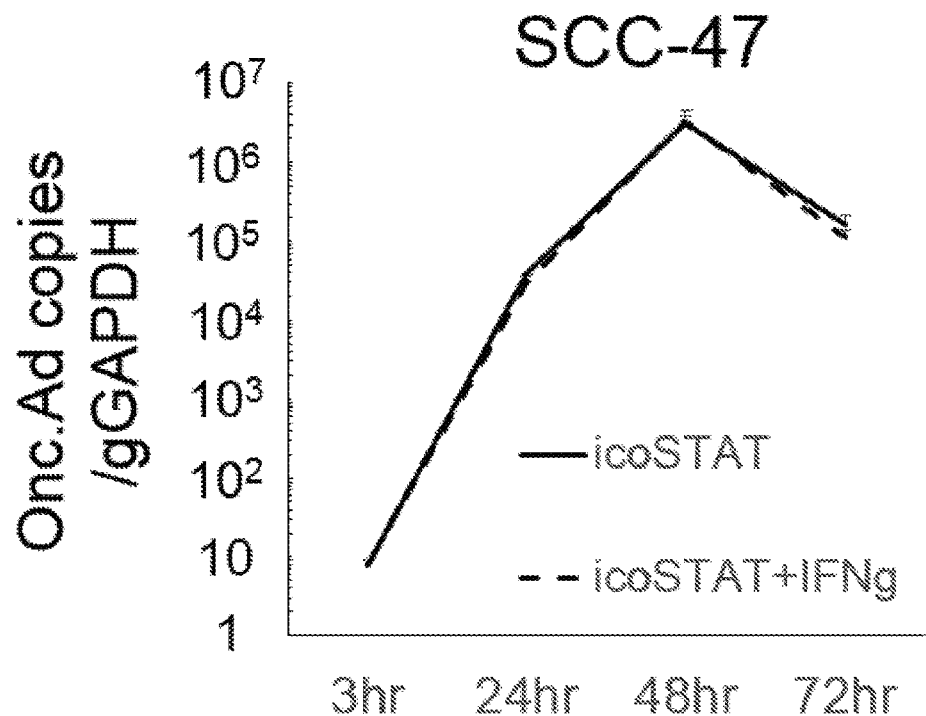

FIGS. 9A and 9B show that ICOSTAT was able to replicate in FaDu cells and SCC47 cells, in the presence or absence of IFNγ.

Figure 10A:
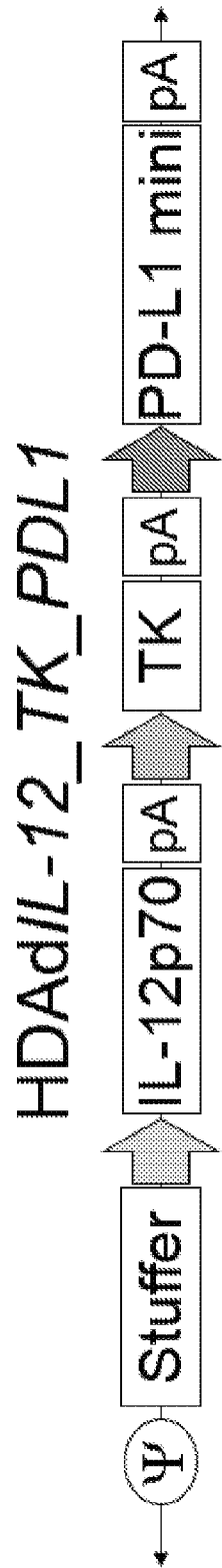
FIGS. 10A to 10D.

Example 3: Helper-Dependent Ad (HDAd) Constructs 3.1 HDAd Constructs and Production A novel construct encoding a helper-dependent adenovirus was prepared using recombinant DNA techniques. The coding sequence of the resulting construct designated HDAdIL-12_TK_PD-L1 is represented schematically in FIG. 10A. HDAdIL-12_TK_PD-L1 contains sequence encoding expression cassettes for (i) human IL-12p70 (sequence encoding alpha and beta chains), (ii) HSV-1 thymidine kinase, and (iii) an anti-PD-L1 minibody (comprising the CDRs of anti-PD-L1 clone H12_gl described e.g. in WO 2016111645 A1) including a HA tag. The three coding sequences each have their own polyA signal sequences.

The HDAd HDΔ28E4EGFP construct containing an EGFP transgene driven by the CMV promoter (HDAdeGFP) was produced as described in Farzad et al. Oncolytics 2014 1: 14008.

The HDAd "HDIL12_PDL1" contains sequence encoding human IL-12p70 protein and anti-PD-L1 minibody derived from YW243.55.S70 (atezolizumab). The anti-PD-L1 minibody of this construct consists of scFv for YW243.55.S70 fused with a hinge, CH2 and CH3 regions of human IgG1 and a C-terminal HA tag (as described e.g. in Tanoue et al. Cancer Res. (2017) 77(8):2040-2051).

3.2 Expression of Encoded Proteins

Cancer cells were transfected with plasmid HDAd vectors, and medium samples were collected to analyze IL-12p70 and anti-PD-L1 minibody levels in the cell culture media of the transfected cells at 48 hours post-transfection.

Figure 10B:
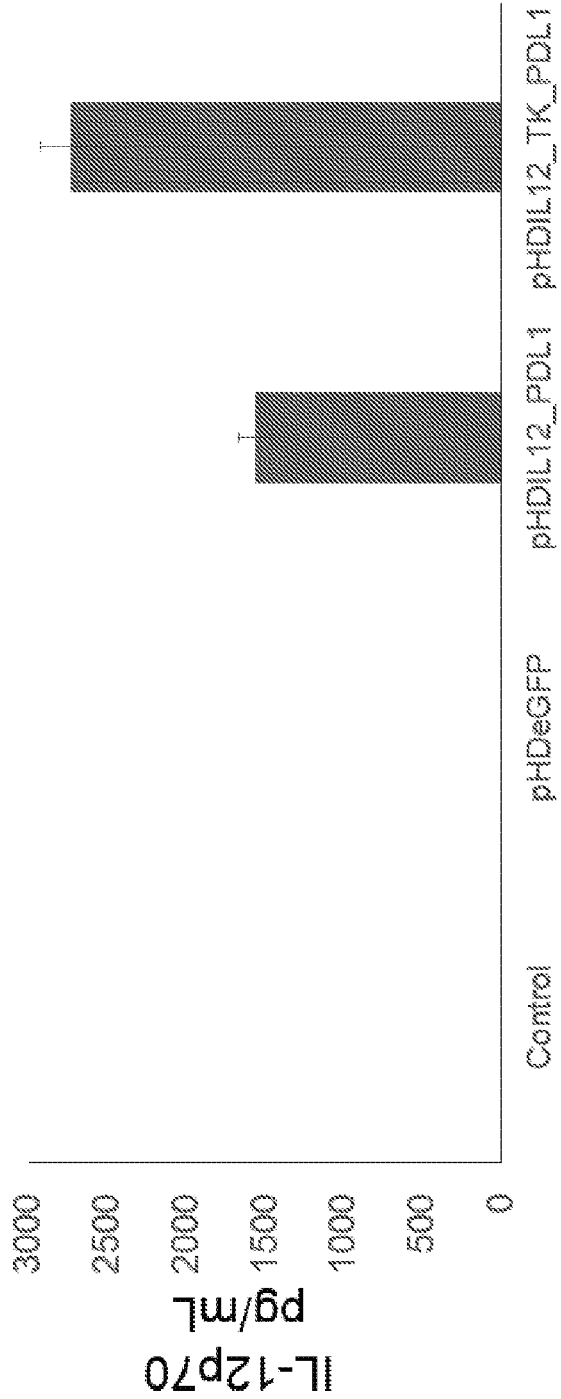

IL-12p70 levels in media were measured using the BD cytokine multiplex bead array system (BD Biosciences), according to manufacturer's instructions. The results are shown in FIG. 10B. Cells transfected with the HDAdIL-12_TK_PD-L1 construct were found to produce higher levels of IL-12p70 than cells transfected with the HDIL-12_PD-L1 construct.

Figure 10C:
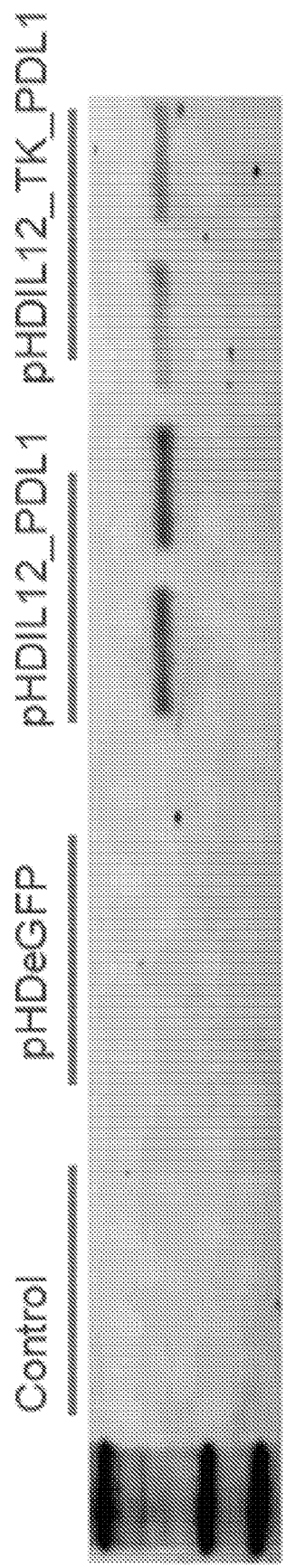

Secretion of anti-PD-L1 minibodies into the cell culture medium was detected by western blot analysis, using an anti-HA antibody (to detect the HA-tagged minibodies). FIG. 10C shows that cells transfected with the HDAdIL-12_TK_PD-L1 construct secreted the anti-PD-L1 minibody into the cell culture medium.

In another experiment, cells were transfected with the different constructs and at 8 hours post-transfection the cell culture media was replaced with medium containing 10 ng/ml Ganciclovir (GCV). Cell culture medium was then replaced with medium containing 10 ng/ml every 24 hours, and after 7 days, the wells were stained with Crystal Violet solution to reveal viable cells.

Figure 10D:
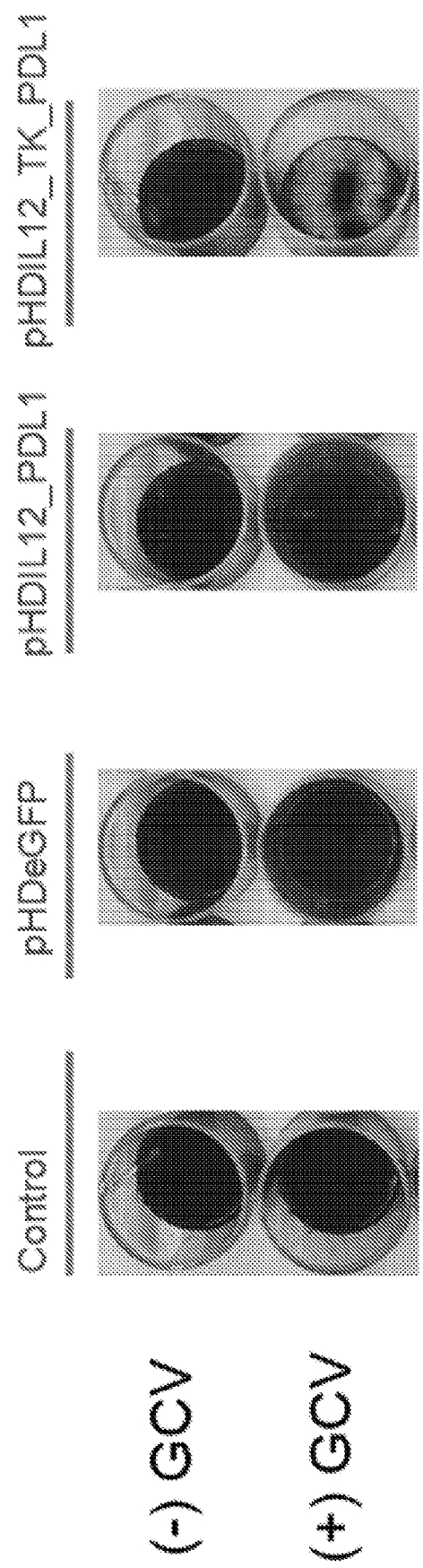

The results are shown in FIG. 10D, and confirm that cells transfected with the HDAdIL-12_TK_PD-L1 construct express thymidine kinase.

In further experiments A549, FaDu or SCC47 cells (n=4 wells per condition) were infected in vitro with HDAdIL-12_TK_PD-L1, HDAd_PD-L1 (see e.g. Tanoue et al., supra), or a control HDAd encoding eGFP (see Farzad et al., supra). The cells were either cultured for 48 hours in the absence of ganciclovir, or medium was changed at 8 hours post-infection and every 24 hours thereafter with medium containing 10 ng/ml ganciclovir.

Secretion of IL-12 into the cell culture supernatant was analysed by ELISA, and secretion of anti-PD-L1 minibody was analysed by western blot using an anti-HA antibody (the anti-PD-L1 minibody comprises a C-terminal HA-tag). At the end of the experiment wells were stained with Crystal Violet solution to reveal viable cells.

Figure 21A:
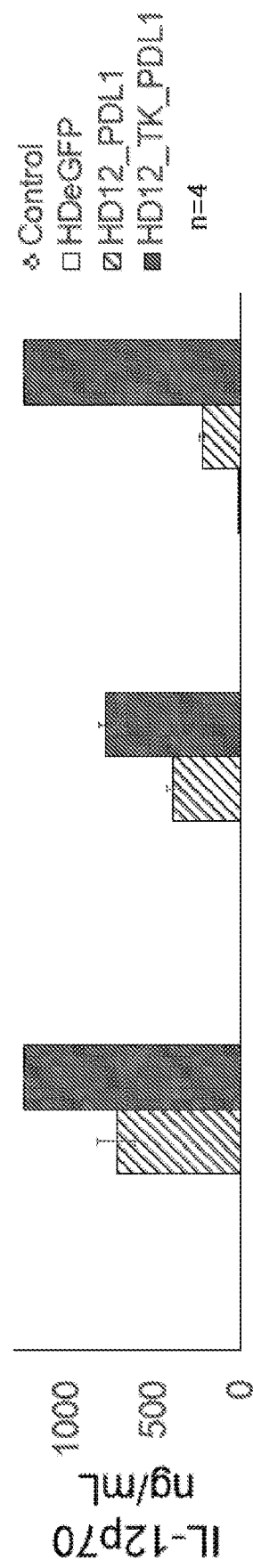
FIGS. 21A to 21C. Bar chart and images showing the results of analysis of transgene expression in cancer cell lines infected with different HDAd viruses, cultured in the presence or absence of ganciclovir (GCV).
Figure 21B:
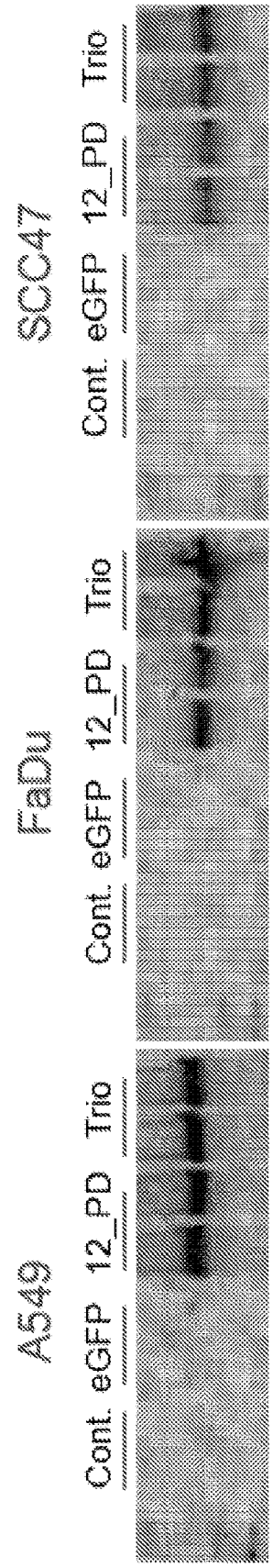
Figure 21C:
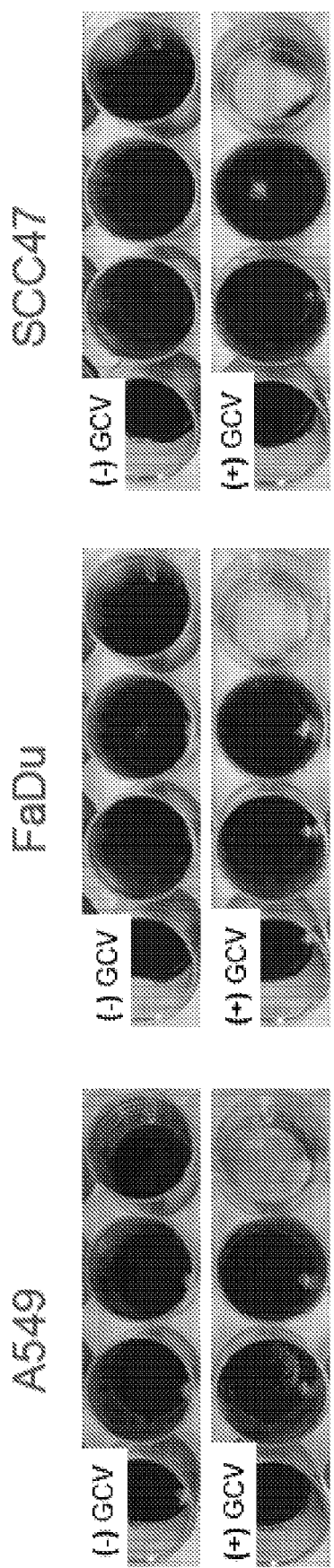
Figure 22A:
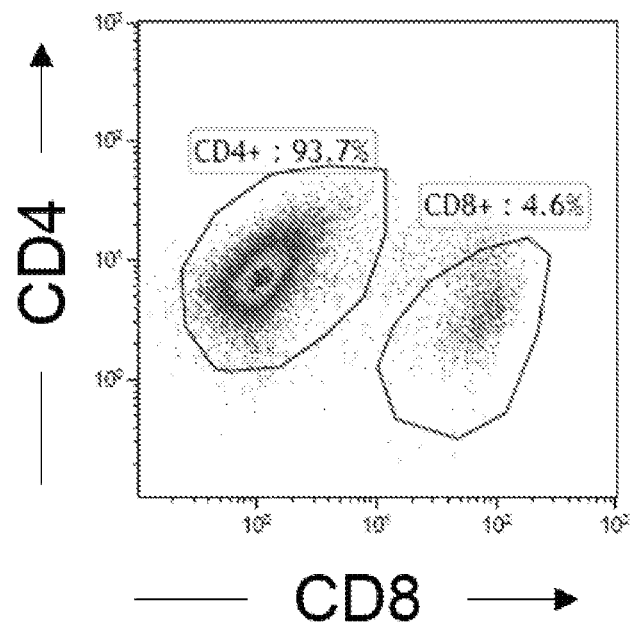
FIGS. 22A and 22B. Scatterplots showing the results of characterisation by flow cytometry of Adenovirus-specific T cells (AdVSTs) used in experiments of Example 9.
Figure 22B:
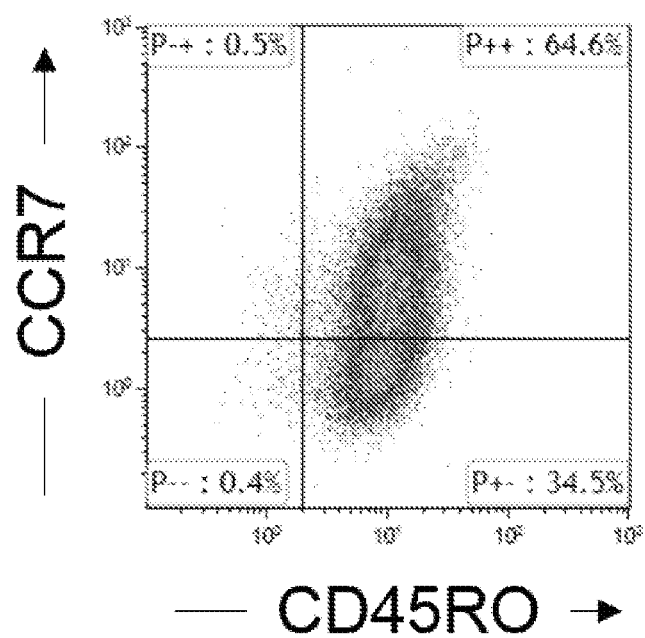
Figure 23A:
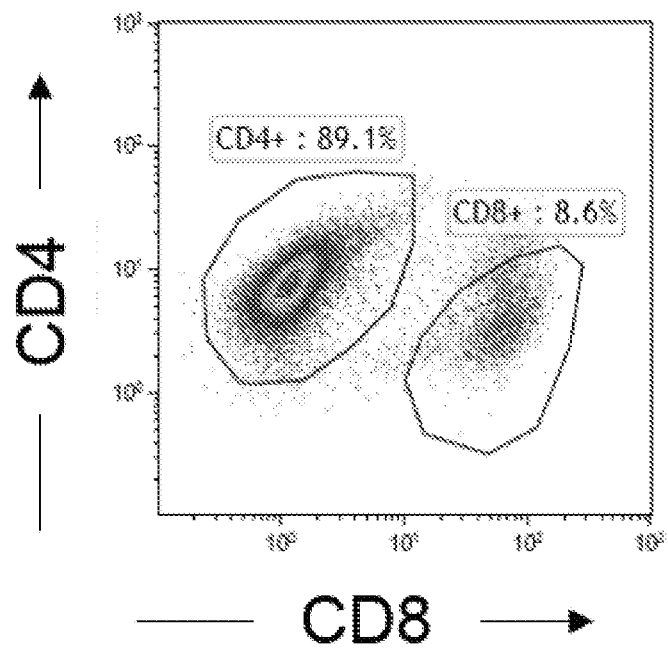
FIGS. 23A to 23C. Scatterplots and histograms showing the results of characterisation by flow cytometry F1.CAR-transduced AdVSTs used in experiments of Example 9.
Figure 23B:
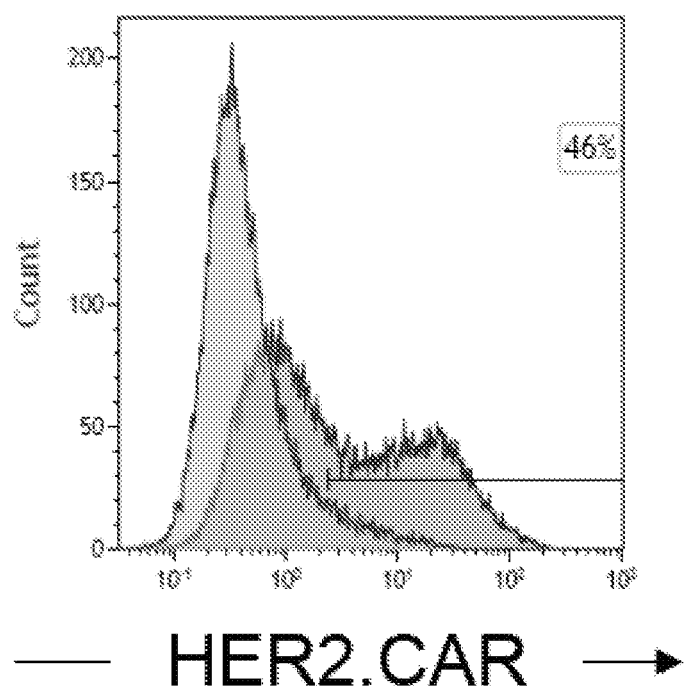
Figure 23C:
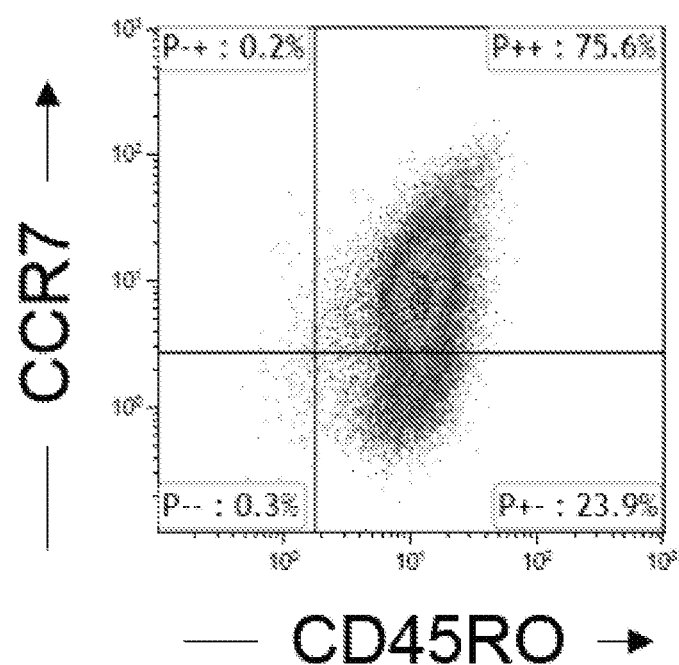
Figure 24A:
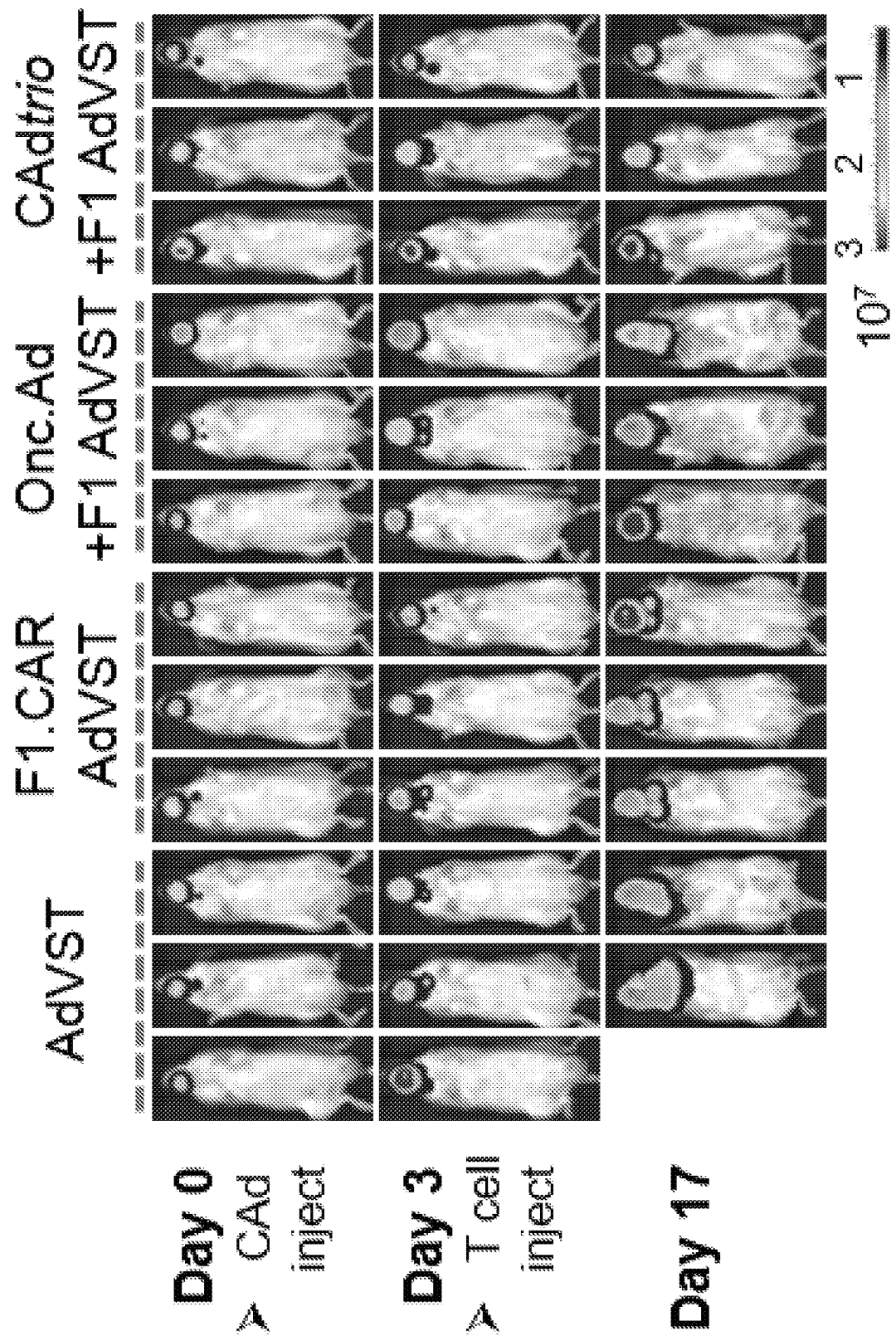
FIGS. 24A to 24D. Images and graphs showing the results of in vivo analysis of the anti-cancer activity of Adenovirus-specific T cells (AdVSTs), F1.CAR-transduced AdVSTs, the combination of F1.CAR-transduced AdVSTs with Onc5/3Ad2E1Δ24, and the combination of F1.CAR-transduced AdVSTs with Onc5/3Ad2E1Δ24+HDAdIL-12_TK_PD-L1 ("CAdtrio").
Figure 24B:
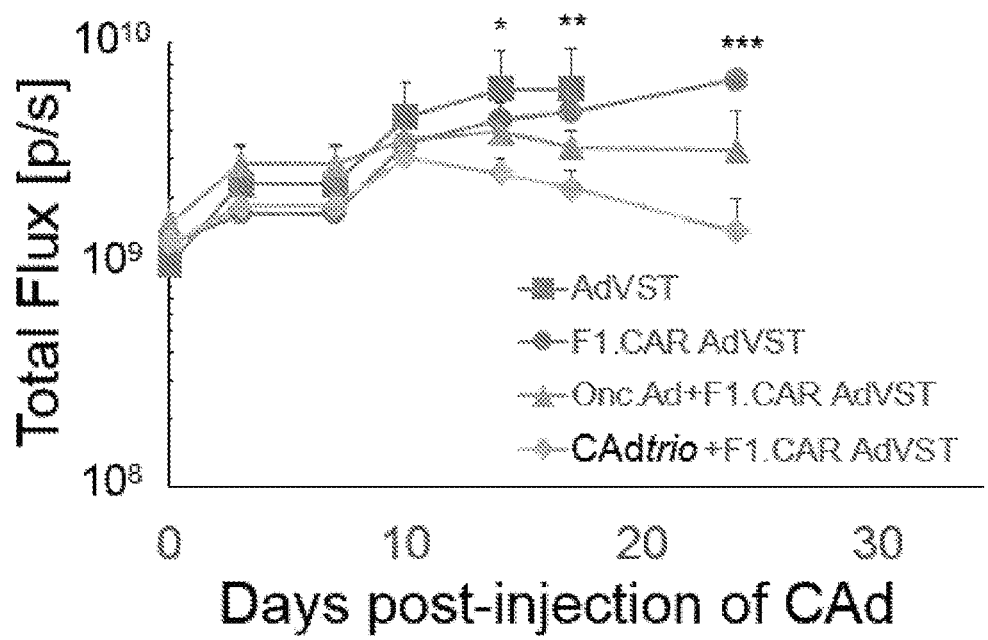
Figure 24C:
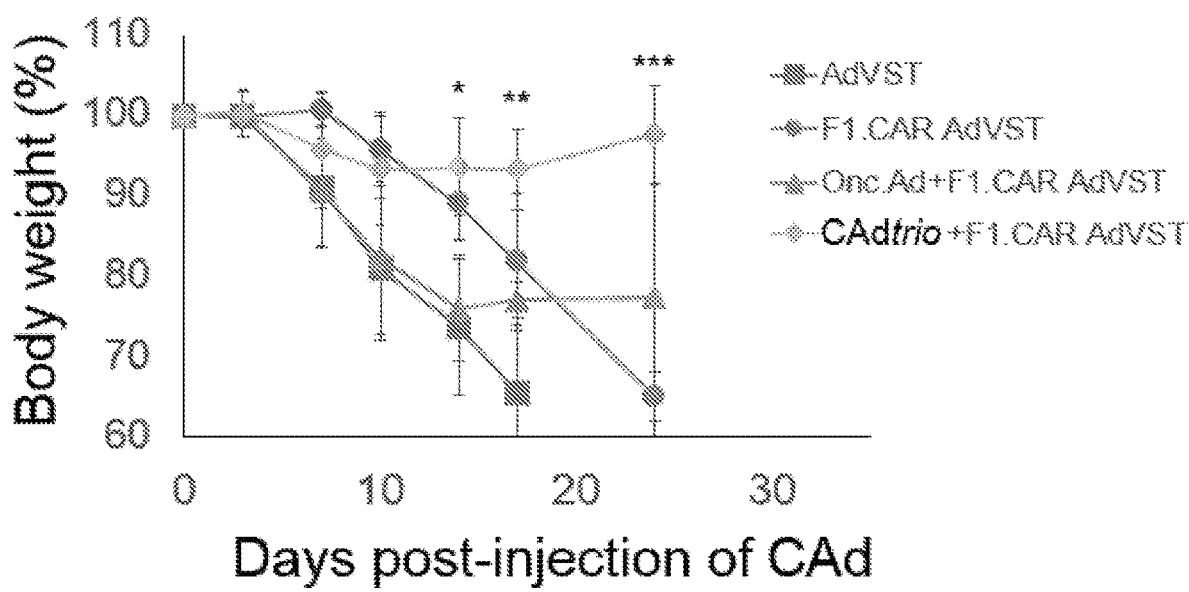
Figure 24D:
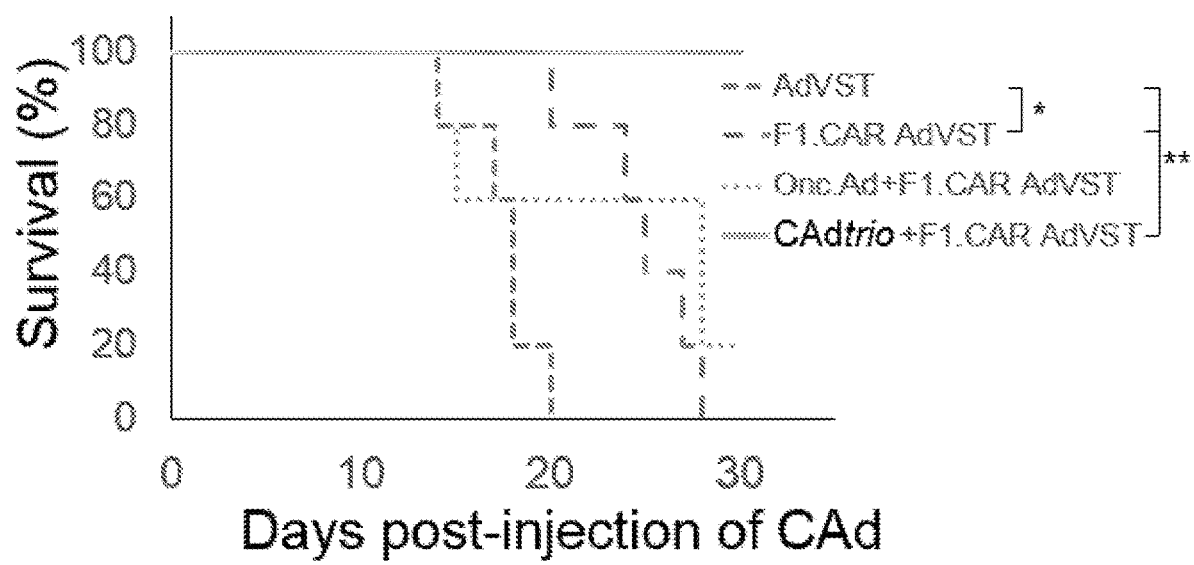

The results are shown in FIGS. 21A to 21C, and confirmed expression of the transgenes encoded by the HDAds in the different cancer cell lines analysed.

3.3 Confirmation of Anti-PD-L1 Minibody Binding to PD-L1

The ability of the anti-PD-L1 minibody encoded by HDAdIL-12_TK_PD-L1 to bind to PD-L1 was analysed by ELISA.

Briefly, Immulon 2 high binding 96-well plates (VWR) were coated with 500 ng/well of recombinant human PD-L1 (BioVision). After blocking plate with PBS-T containing 3% BSA, serially diluted cell culture media of A549 cells which had been transfected with plasmid encoding GFP (pGFP; negative control), plasmid encoding the anti-PD-L1 minibody described in Tanoue et al. supra, (pPDL1 mini Tanoue) or plasmid encoding the anti-PD-L1 minibody encoded by HDAdIL-12_TK_PD-L1 (pPDL1 mini) were added and incubated at 4° C. for 24 hours. Serially diluted anti-human PD-L1 antibody starting from 10 μg/well (BioLegend) was used as a positive control (PDL1 IgG). After washing plate with PBS-T, HRP-labeled anti-human IgG (for PD-L1 mini and PDL1 mini Tanoue) or HRP-labeled anti-mouse IgG (BioRad; for PD-L1 IgG and Iso IgG) were added for detection, and incubated at room temperature for 1 hour. The plate was then developed, and absorbance at 450 nm was measured using Tecan reader (TECAN).

Figure 11:
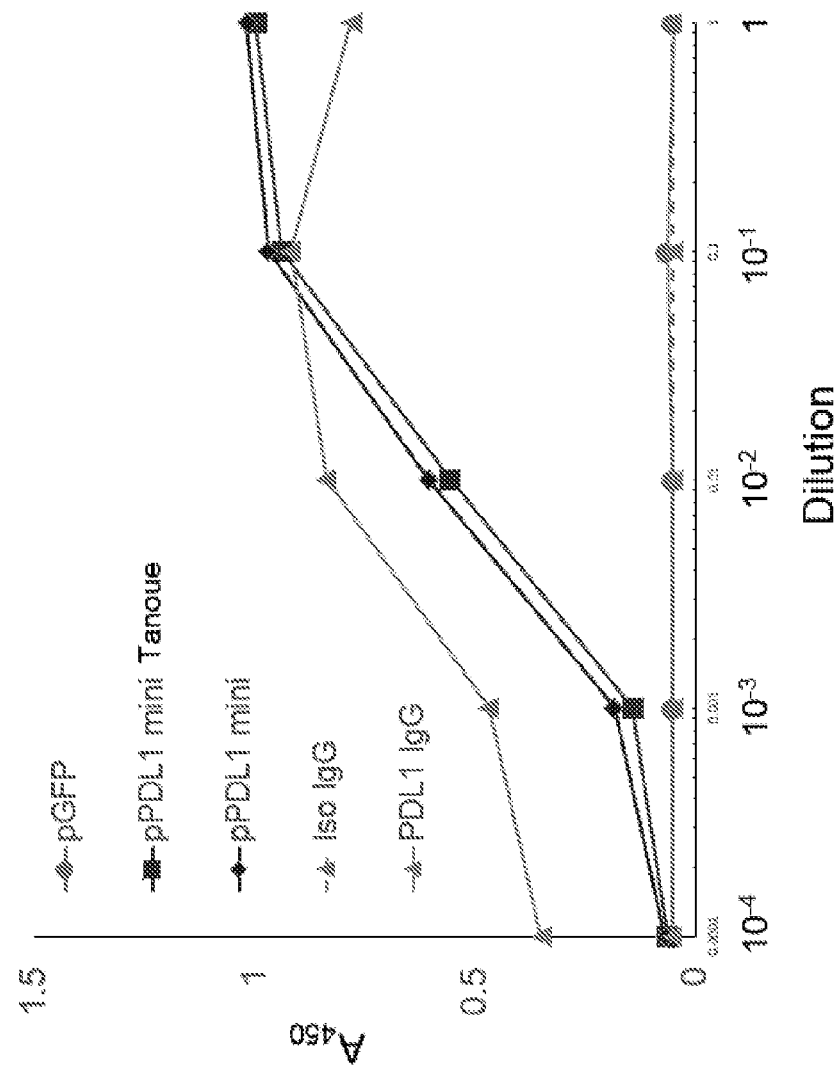
FIG. 11. Graph showing ELISA analysis of PD-L1 minibody avidity to recombinant human PD-L1, using serially diluted cell culture media of A549 cells which had been transfected with plasmid encoding GFP (pGFP; negative control), plasmid encoding the anti-PD-L1 minibody described in Tanoue et al. supra, (pPDL1 mini Tanoue) or plasmid encoding the anti-PD-L1 minibody encoded by HDAdIL-12_TK_PD-L1 (pPDL1 mini). Serially diluted anti-human PD-L1 antibody was used as a positive control (PDL1 IgG).

The results are shown in FIG. 11. The anti-PD-L1 minibody comprising the CDRs of anti-PD-L1 antibody clone H12 was found to bind to human PD-L1 in a dose-dependent fashion, with comparable (or greater) avidity as compared to the avidity of binding by anti-PD-L1 minibody described in Tanoue et al. supra.

Example 4: Analysis of Treatment of Cancer In Vivo

The anticancer effect of treatment with the combination of (1) an oncolytic virus of choice+HDAdIL-12_TK_PD-L1+HER2-CAR-T and (2) ICOSTAT+HDAdIL-12_TK_PD-L1+HER2-CAR-T is demonstrated in vivo in mouse xenograft tumour models.

In a first experiment, $1 \times 10^6$ FaDu cells are injected subcutaneously in PBS into NSG male mice. After 12 days, $1 \times 10^8$ viral particles (1) oncolytic virus and HDAdIL-12_TK_PD-L1 or (2) ICOSTAT+HDAdIL-12_TK_PD-L1 are injected intratumorally at an OncAd:HDAd ratio of 1:20.

In a second experiment, 0.5×10⁶ FaDu cells are injected orthotopically into NSG male mice. After 6 days, 1×10⁸ viral particles (1) oncolytic virus and HDAdIL-12_TK_PD-L1 or (2) ICOSTAT+HDAdIL-12_TK_PD-L1 are injected intratumorally at an OncAd:HDAd ratio of 1:20.

In both experiments, 3 days after administration of the viral particles, 1×10⁶ HER2-CAR T cells are administered intravenously.

In both experiments, control conditions are included as follows:

| Condition | OncAd | HDAd | CAR T |
|---|---|---|---|
| 1 (test condition) | Of choice | HDAdIL-12_TK_PD-L1 | HER2 CAR-T |
| 2 (test condition) | ICOSTAT | HDAdIL-12_TK_PD-L1 | HER2 CAR-T |
| 3 | — | HDAdIL-12_TK_PD-L1 | HER2 CAR-T |
| 4 | Of choice | — | HER2 CAR-T |
| 5 | ICOSTAT | — | HER2 CAR-T |
| 6 | Of choice | HDAdIL-12_TK_PD-L1 | — |
| 7 | ICOSTAT | HDAdIL-12_TK_PD-L1 | — |
| 8 | Of choice | — | — |
| 9 | ICOSTAT | — | — |
| 10 | — | HDAdIL-12_TK_PD-L1 | — |
| 11 | — | — | HER2 CAR-T |

Tumor size is monitored and tumour volumes are calculated using the formula: Width²×Length×0.5.

The use of the combination of oncolytic virus, HDAdIL-12_TK_PD-L1 and HER2 CAR-T (test condition 1) is found to have an improved antitumour effect as compared to the use of any of the agents alone (conditions 8, 10 or 11), or compared to the use of two of the three agents (conditions 3, 4 and 6).

Similarly, the use of the combination of ICOSTAT, HDAdIL-12_TK_PD-L1 and HER2 CAR-T (test condition 2) is found to have an improved antitumour effect as compared to the use of any of the agents alone (conditions 9, 10 or 11), or compared to the use of two of the three agents (conditions 3, 5 and 7).

Similar results are observed when xenograft tumours are established using SCC47 cells and A549 cells.

Example 5: Analysis of the Anti-Cancer Activity of the HER2-Specific CAR-T Cells In Vivo The anti-cancer activity of the HER2-specific CAR-T cells (see Example 1 above) was investigated in vivo in a FaDu cell-derived xenograft model of squamous cell head and neck cancer.

Briefly, 0.5×10⁶ FaDu cells were injected orthotopically into NSG male mice. After 9 days, mice were injected via the tail vein with 1×10⁶ T cells genetically modified to express firefly luciferase, which had not been transduced with a HER2-CAR construct, or with 1×10⁶ firefly luciferase-expressing T cells which had been transduced with the C5, F1 or A3 CAR constructs. A control condition was included in the experiment in which mice were not injected with T cells at day 9.

Luciferase activity (and thus number and distribution of the administered T cells), body weight, survival of the mice was monitored over time. Luciferase activity was monitored by intraperitoneal injection of D-Luciferin (1.5 mg per mouse), and imaging of the mice 10 min later using an IVIS imager (Xenogen).

Figure 15B:
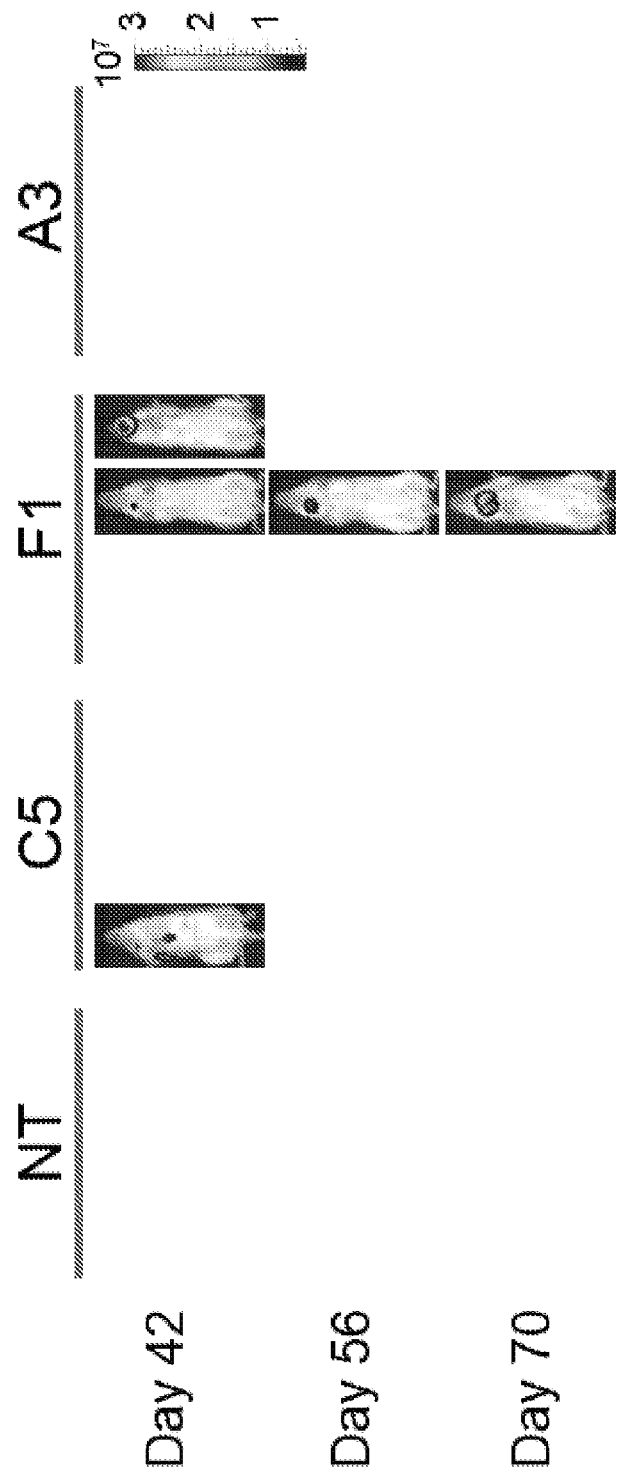

FIGS. 15A and 15B show the images acquired on days 0, 4, 7, 14, 28, 42, 56 and 70 following injection of the luciferase-expressing T cells (i.e. the non-transduced T cells or HER2-specific CAR-T cells) (days refer to days after ffLuc T cell injection). The systemically infused T cells were shown to migrate to the site of the orthotopic tumors. The T cells which had not been modified to express HER2-specific CARs were undetectable after 7 days. By contrast, the HER2-specific CAR-T cells persisted and remained detectable throughout the experiment.

Figure 15C:
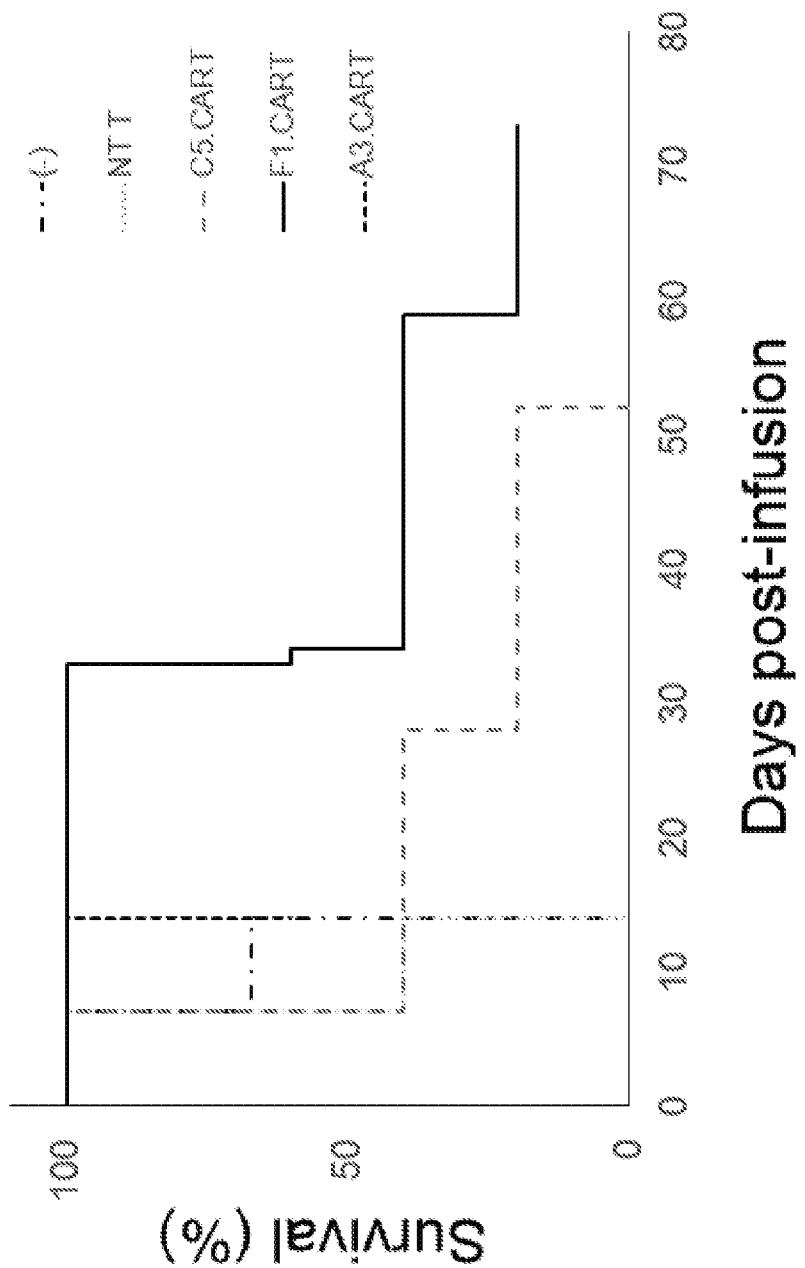

FIG. 15C shows percentage survival of mice subjected to the different treatments over the course of the experiment. Administration of HER2-specific CAR-T cells was found to increase survival.

In a separate experiment NOD scid gamma (NSG) mice were injected via the tail vein with 1×10⁶ firefly luciferase-expressing T cells which had not been transduced with a HER2-CAR construct, or with 1×10⁶ firefly luciferase-expressing T cells which had been transduced with the C5, F1 or A3 CAR construct. Luciferase activity was monitored as described above, and body weight of the mice was also monitored over time.

Figure 16A:
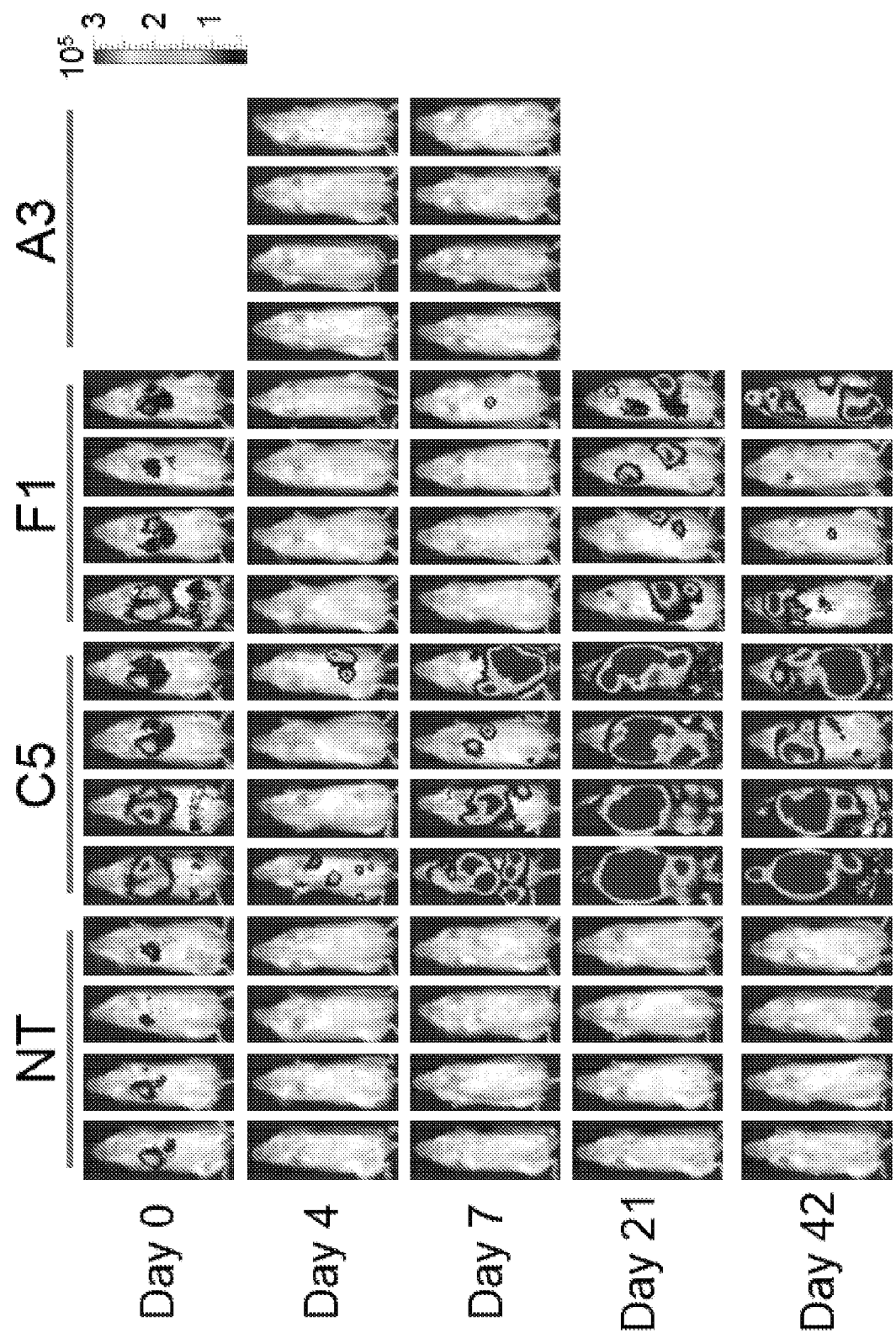
FIGS. 16A to 16C. Images and graphs showing the results of in vivo analysis of adoptively-transferred T cells in NSG mice.
Figure 16B:
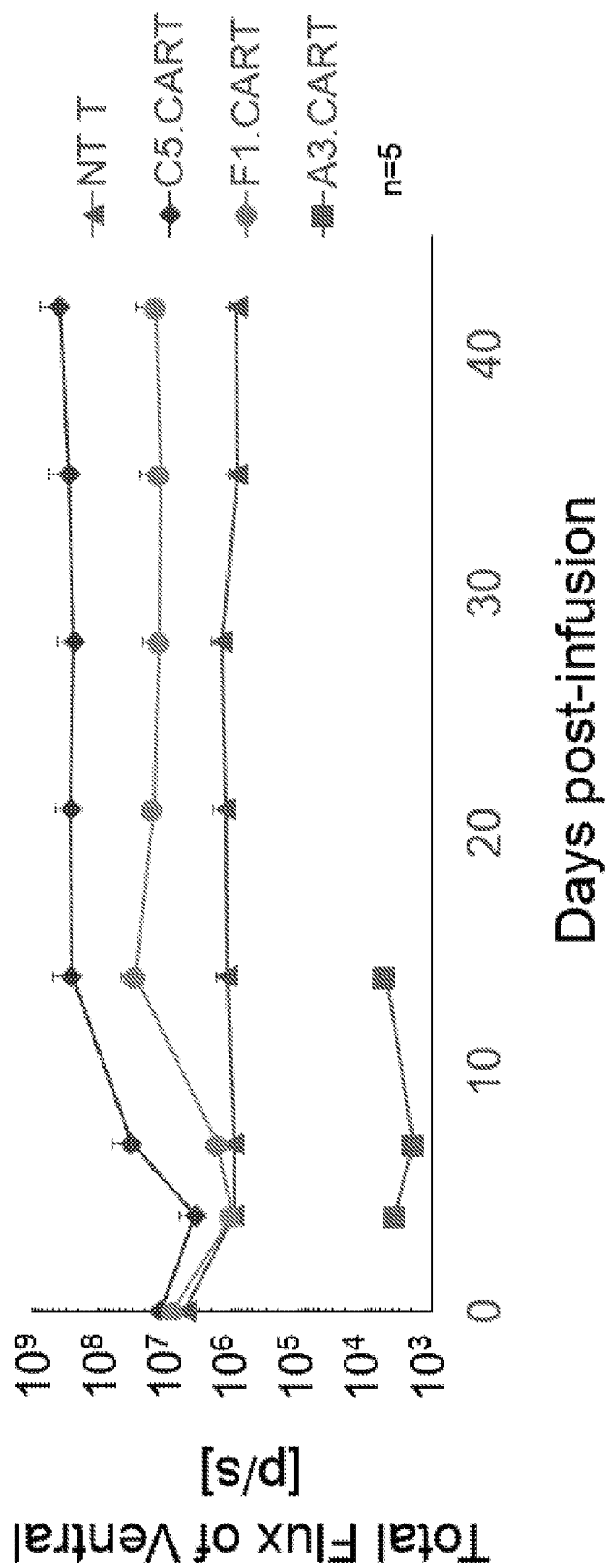
Figure 16C:
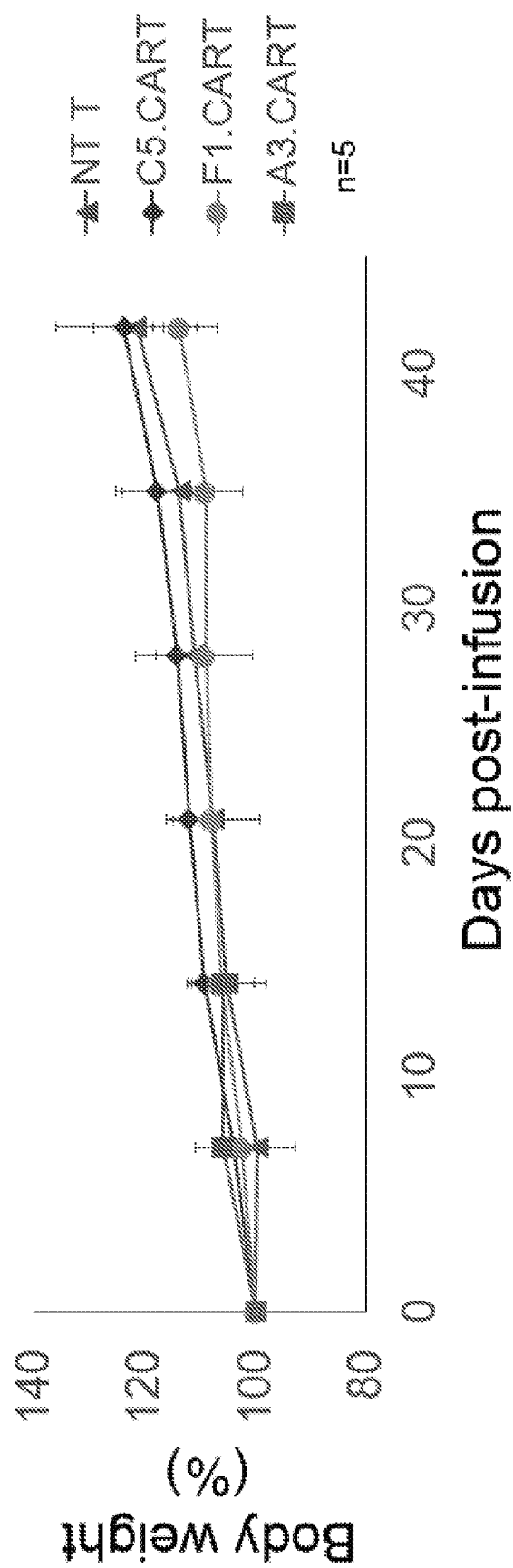

The results of the experiment are shown in FIGS. 16A to 16C. The C5 CAR-T cells were found to expand non-specifically in NSG mice (FIG. 16A). No significant weight loss was observed in NSG mice administered with the HER2-specific CAR-T cells (FIG. 16C).

Example 6: Analysis of of the Anti-Cancer Activity of the Combination of Oncolytic Virus, HDAd Virus and HER2-Specific CAR-T Cells In Vivo The anti-cancer activity of a combination of oncolytic virus, HdAd and HER-specific CAR-T cell therapy was investigated in vivo in a FaDu cell-derived xenograft model of squamous cell head and neck cancer.

Briefly, 0.5×10⁶ FaDu cells were injected orthotopically into NSG male mice. After 6 days, one group of mice was then injected intratumorally with a combination of Onc5/3Ad2E1Δ24 (described in Example 2.1) and HDAdIL-12_TK_PD-L1 described in Example 3.1 (this combination of OncAd and HdAd is referred to herein as "CAdtrio"). A total of 1×10⁷ viral particles were administered, at a 1:10 ratio of Onc5/3Ad2E1Δ24:HDAdIL-12_TK_PD-L1.

Three days later, mice were injected via the tail vein with 1×10⁶ T cells engineered to express firefly luciferase, which had been transduced with the HER2-specific CAR construct corresponding to clone F1. A control group of mice which had not been administered with CAdtrio was injected via the tail vein with 1×10⁶ firefly luciferase-expressing T cells which had not been transduced with a HER2-CAR construct, and a further control group of mice was not administered with CAdtrio nor injected with T cells. Luciferase activity, body weight and survival of the mice was monitored over time.

Figure 17A:
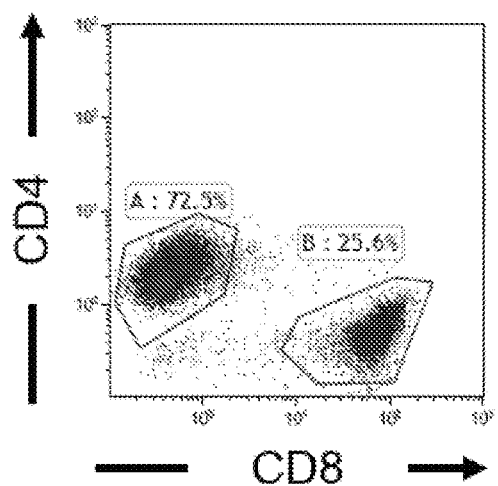
FIGS. 17A to 17C. Scatterplots and histograms showing the results of characterisation by flow cytometry of F1
Figure 17B:
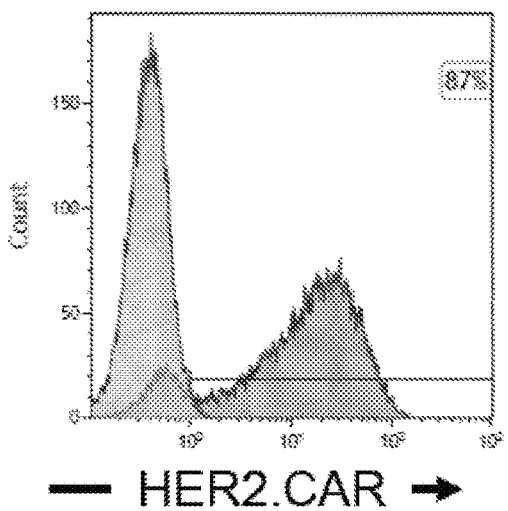
Figure 17C:
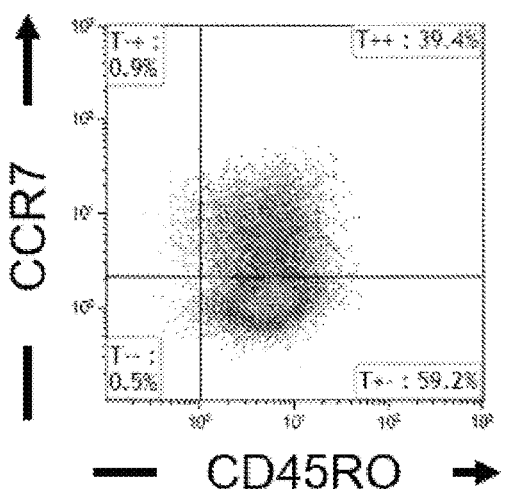
Figure 18A:
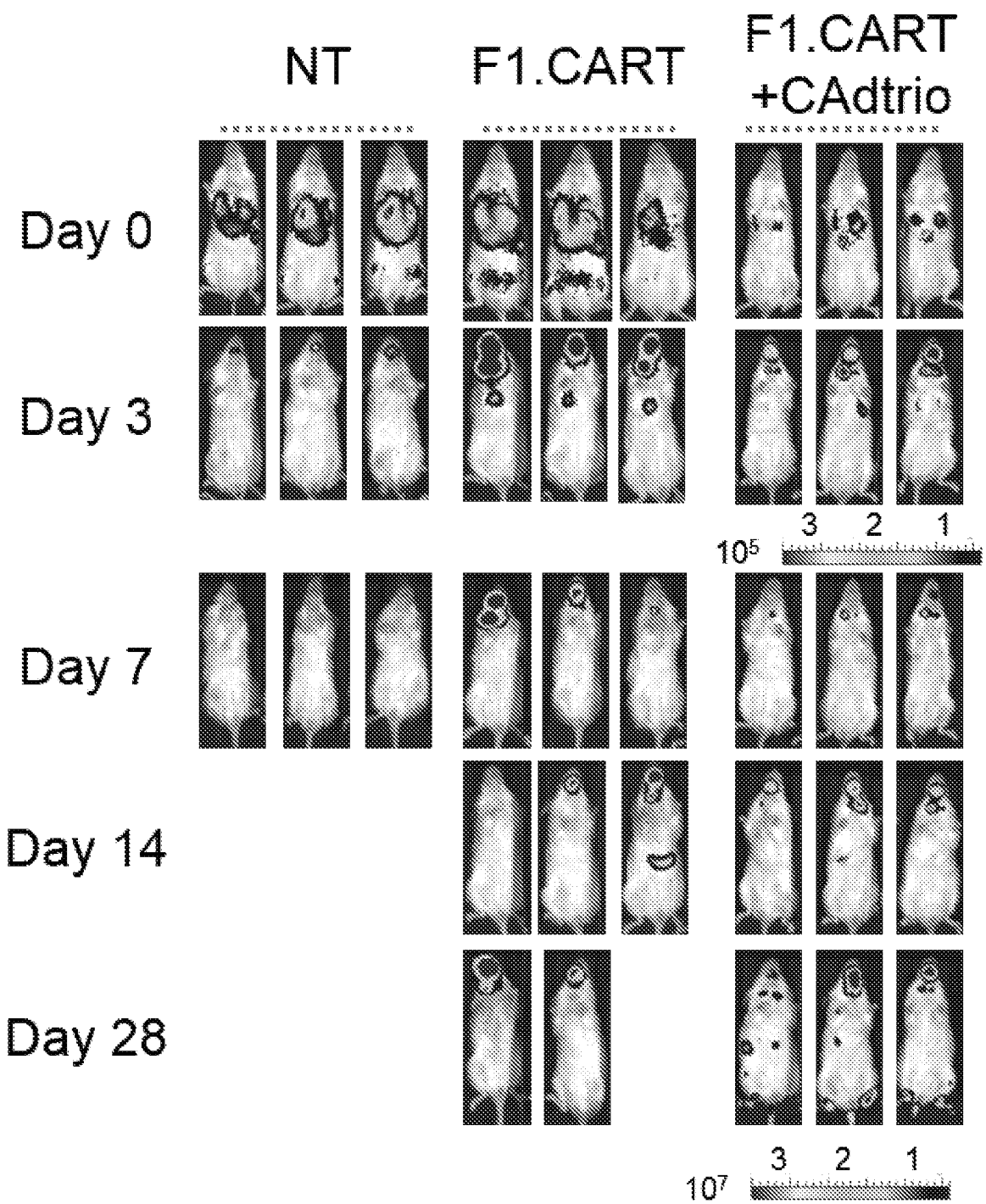
FIGS. 18A to 18D. Images and graphs showing the results of in vivo analysis of the anti-cancer activity of the combination of CAdtrio and adoptively-transferred T cells, in an orthotopic FaDu cell-derived model of squamous cell head and neck carcinoma.
Figure 18B:
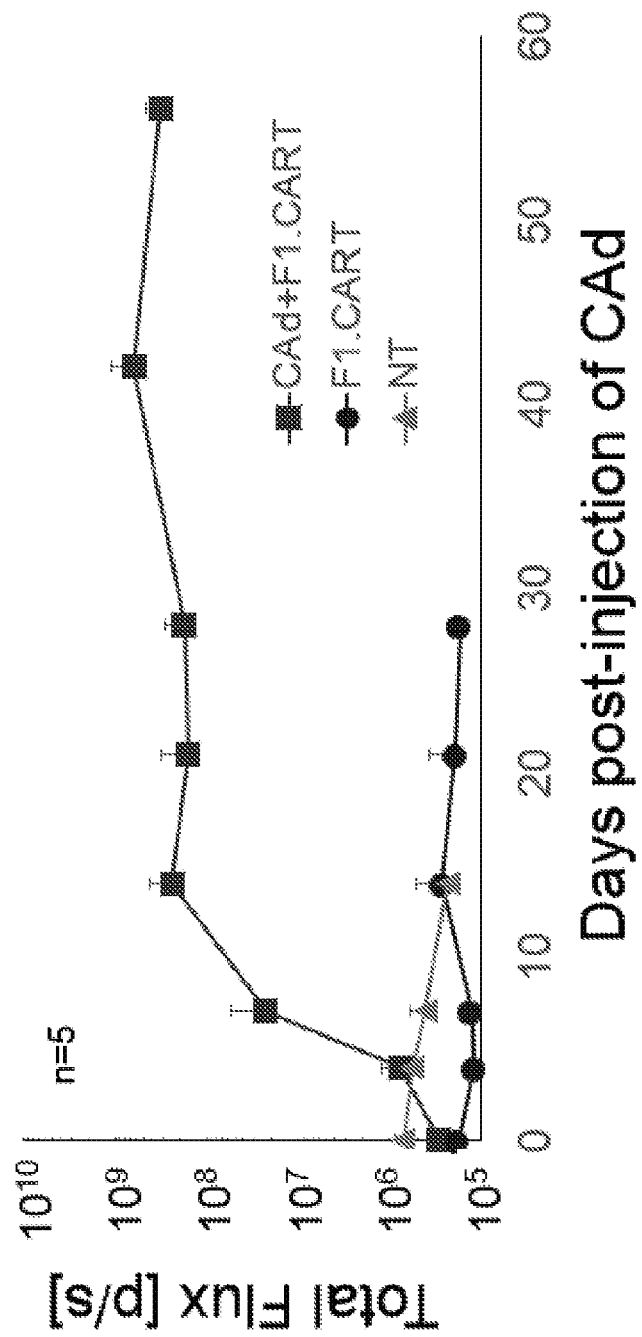
Figure 18C:
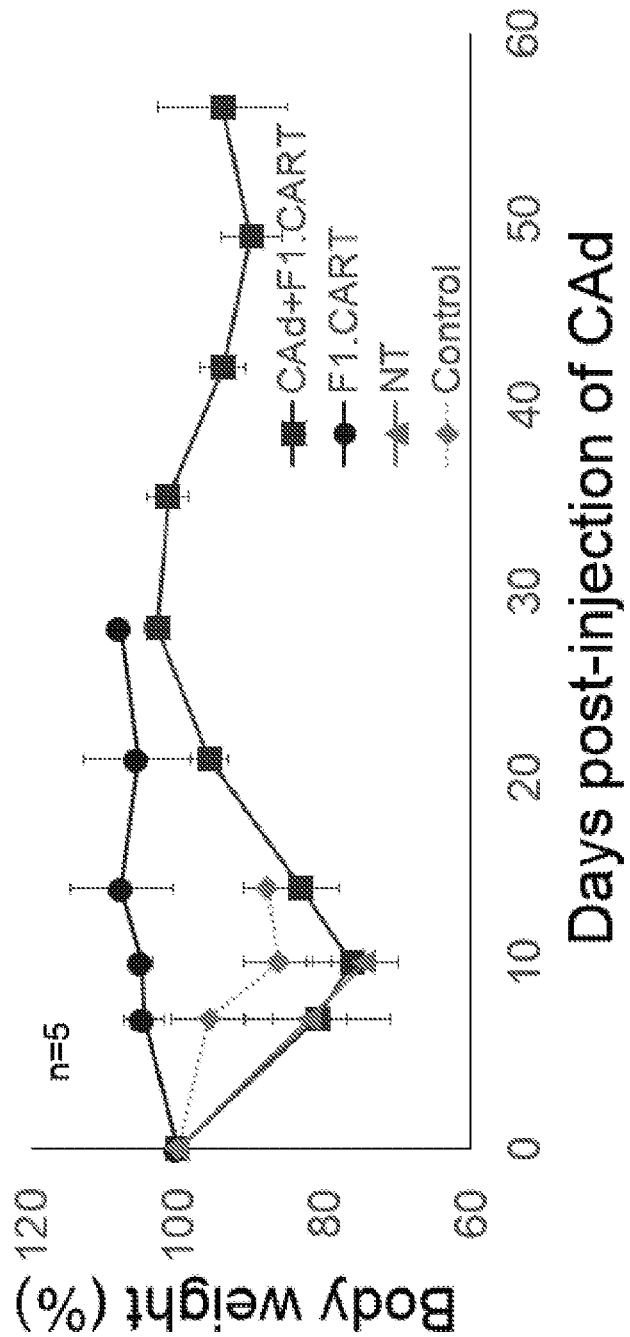
Figure 18D:
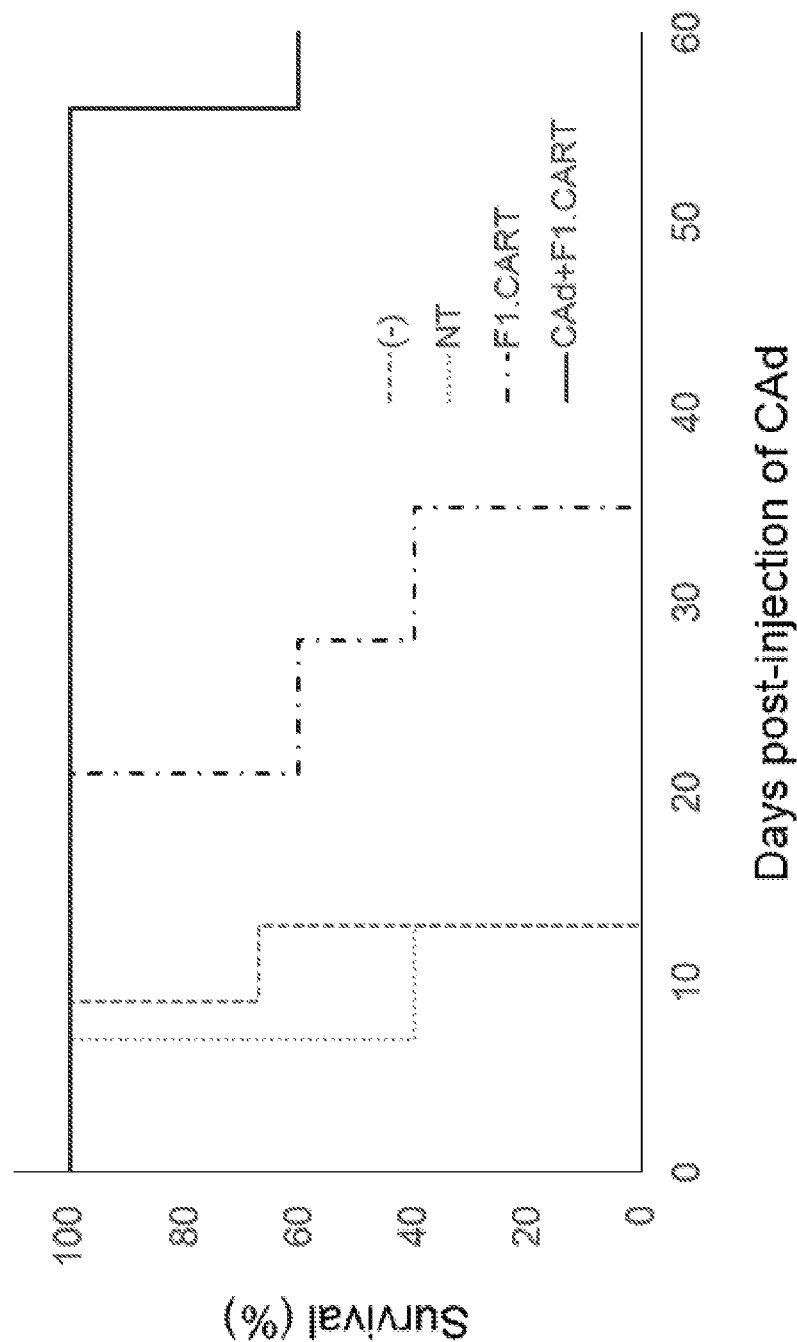

Prior to their use in the experiment the F1.CART cells were characterised flow cytometry, and the results are shown in FIGS. 17A to 17C. The cells were found to comprise 72.5% CD4+ cells and CD8+ cells. 87% of the cells were determined to express HER2 CAR at the cell surface. 39% of the cells were CCDR7+CD45RO+, and 59.2% of the cells were CCR7-CD45RO+.

The results of the experiments analysing the therapeutic efficacy of the combination of oncolytic virus, HDAd virus and HER2-specific CAR-T cells to treat cancer in vivo are shown in FIGS. 18A to 18D. The combination of Onc5/

3Ad2E1Δ24, HDAdIL-12_TK_PD-L1 and F1.CART was found to improve survival over treatment with F1.CART cells alone.

In further experiments two different ratios of Onc5/3Ad2E1Δ24 to HDAdIL-12_TK_PD-L1 were investigated.

Briefly, $0.5 \times 10^6$ FaDu cells modified to express firefly luciferase were injected orthotopically into NSG male mice. After 6 days, mice were injected intratumorally with:
  (i) $1 \times 10^7$ viral particles of CAdtrio, at a ratio of Onc5/3Ad2E1Δ24:HDAdIL-12_TK_PD-L1 of 1:10;
  (ii) $1 \times 10^7$ viral particles of CAdtrio, at a ratio of Onc5/3Ad2E1Δ24:HDAdIL-12_TK_PD-L1 of 1:20;
  (iii) $1 \times 10^8$ viral particles of CAdtrio, at a ratio of Onc5/3Ad2E1Δ24:HDAdIL-12_TK_PD-L1 of 1:10; or
  (iv) $1 \times 10^8$ viral particles of CAdtrio, at a ratio of Onc5/3Ad2E1Δ24:HDAdIL-12_TK_PD-L1 of 1:20.

Three days later, mice were injected via the tail vein with $1 \times 10^6$ T cells which had been transduced with the F1 CAR construct (not expressing firefly luciferase). The cancer was monitored over time by analysis of luciferase activity as described above, and the body weight of the mice was also monitored.

Figure 19A:
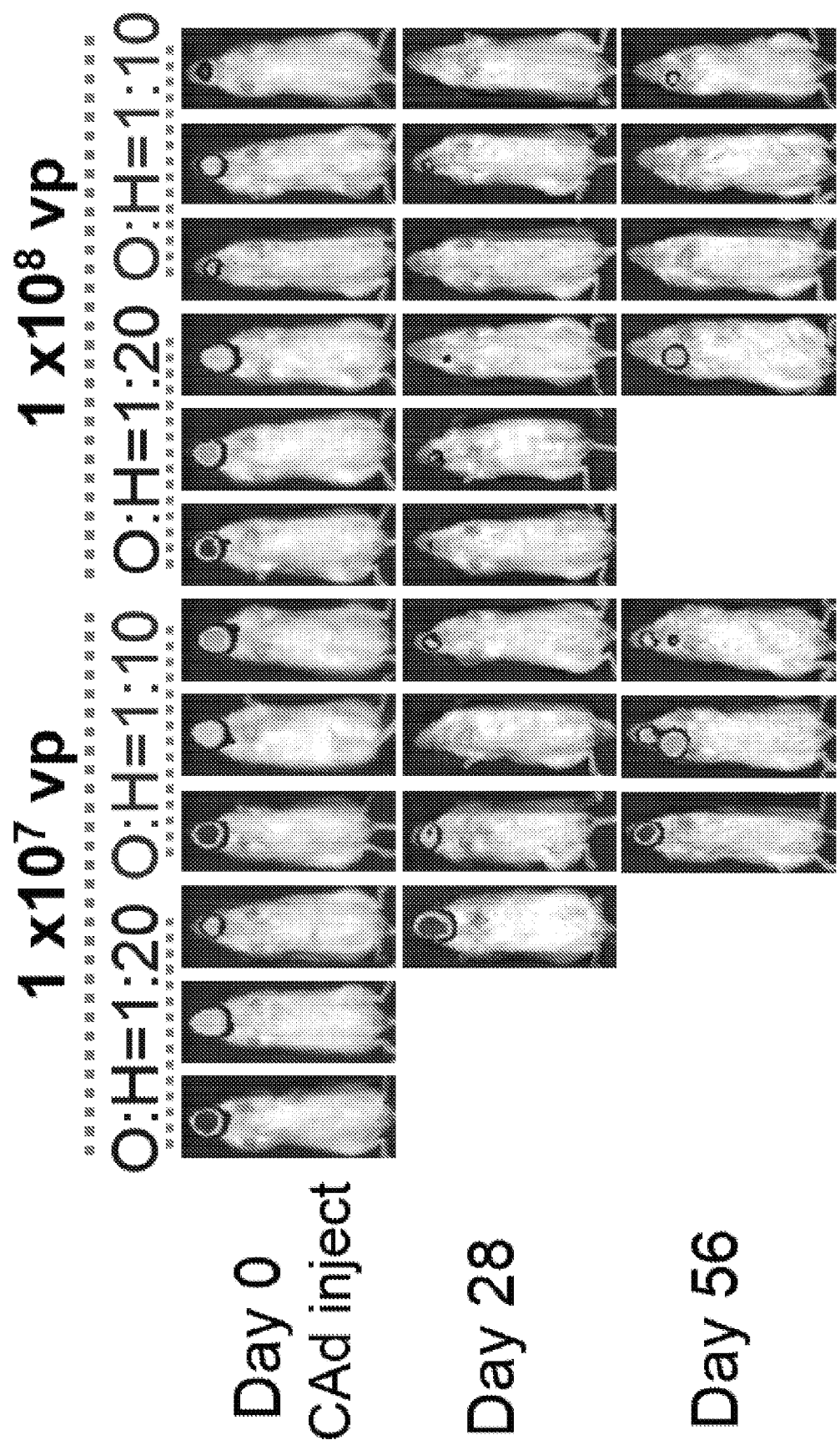
FIGS. 19A to 19C. Images and graphs showing the results of in vivo analysis of the anti-cancer activity of the combination of different ratios of Onc5/3Ad2E1Δ24:HDAdIL-12_TK_PD-L1 and adoptively-transferred HER2-specific CAR T cells, in an orthotopic FaDu cell-derived model of squamous cell head and neck carcinoma.
Figure 19B:
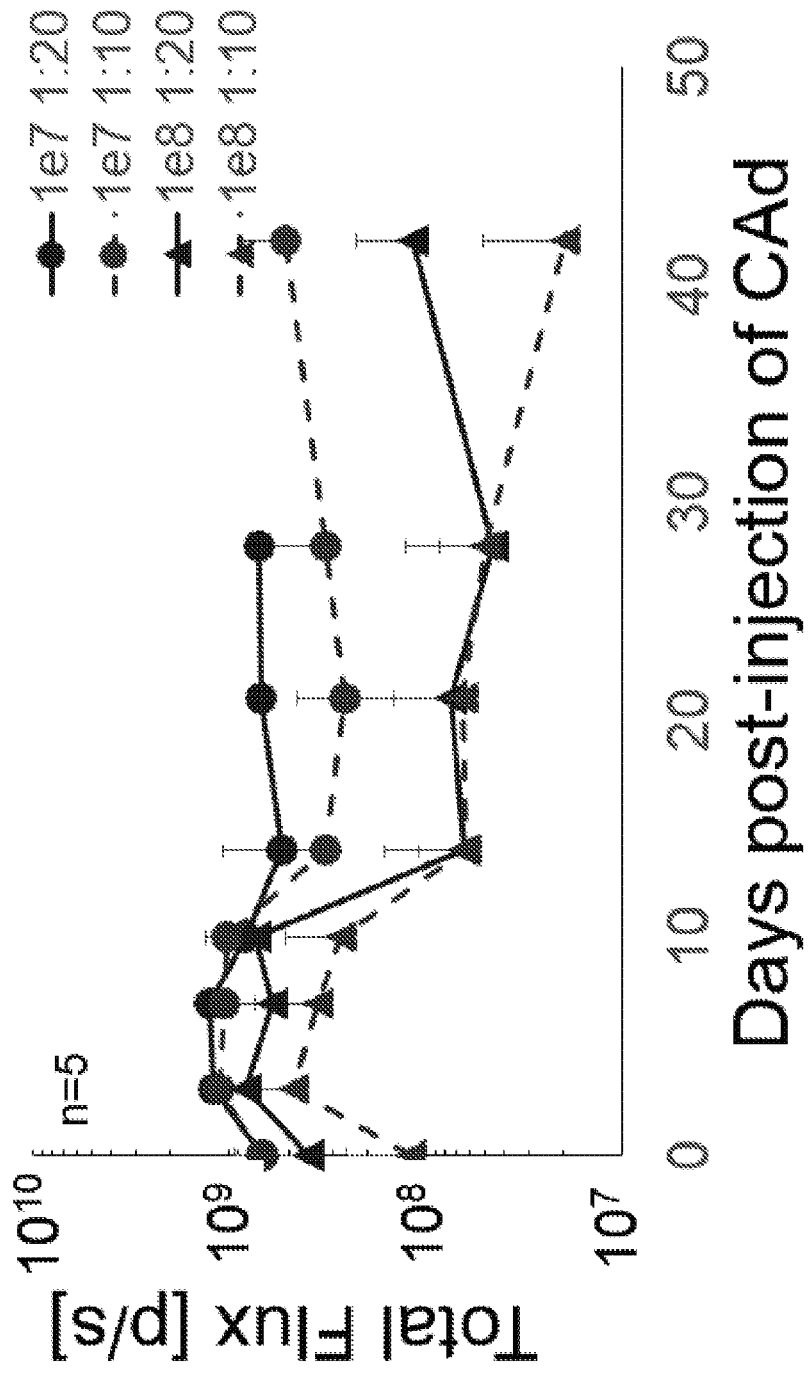
Figure 19C:
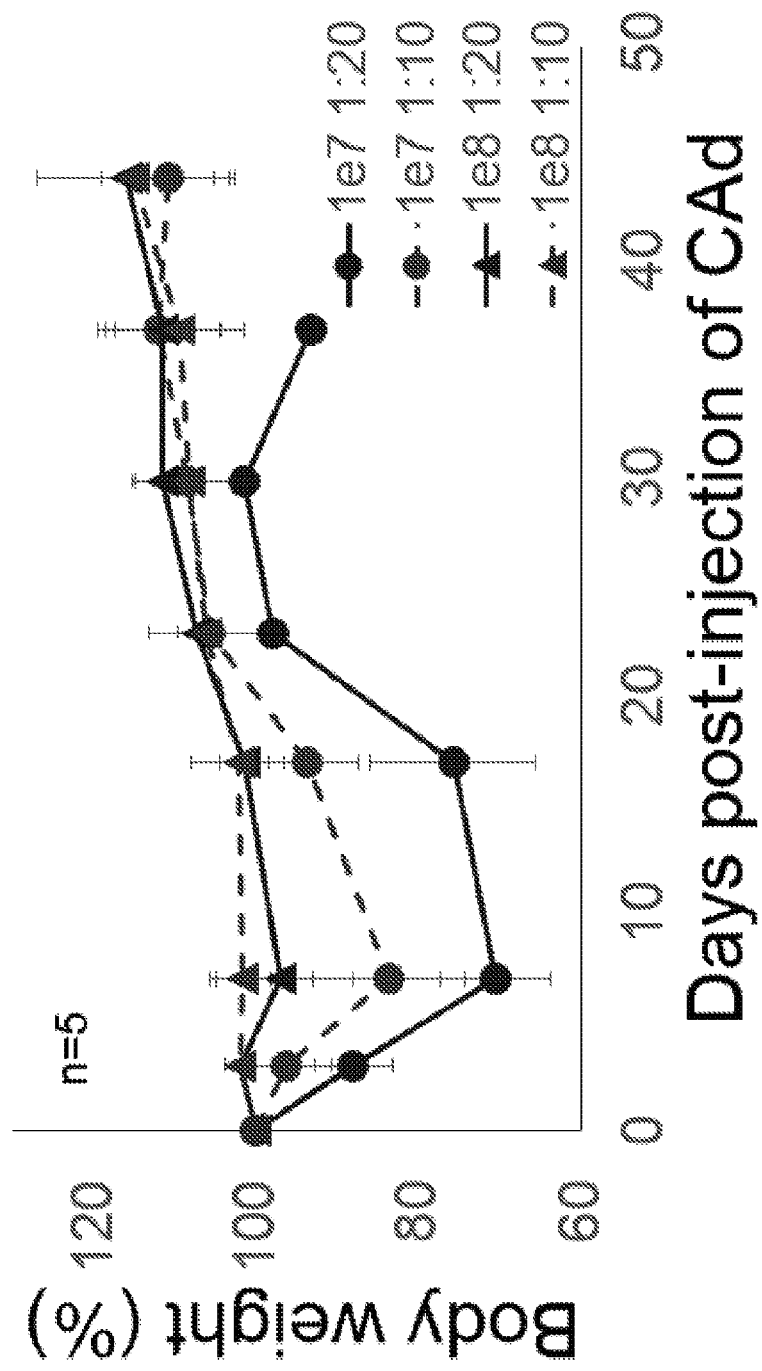

The results of the experiments are shown in FIGS. 19A to 19C. Mice administered with a 1:10 ratio of Onc5/3Ad2E1Δ24:HDAd IL-12_TK_PD-L1 generally had fewer luciferase-expressing FaDu cells than those administered with a 1:20 ratio of Onc5/3Ad2E1Δ24:HDAdIL-12_TK_PD-L1, and mice administered with $1 \times 10^8$ viral particles of CAdtrio generally had fewer luciferase-expressing FaDu cells than those administered with $1 \times 10^7$ viral particles of CAdtrio (FIG. 19B).

Example 7: Analysis of the Anti-Cancer Activity of the Combination of Oncolytic Virus, HDAd Virus and Ganciclovir (GCV) In Vivo The anti-cancer activity of a combination of oncolytic virus and HdAd (encoding thymidine kinase) (l,e, CAdtrio) in conjunction with ganciclovir (GCV) was investigated in vivo in a FaDu cell-derived xenograft model of squamous cell head and neck cancer.

Ectopic FaDu tumors were established by subcutaneous injection of FaDu cells into the flanks of mice. The mice were subsequently injected intratumorally with $1 \times 10^8$ viral particles of CAdtrio, at a ratio of Onc5/3Ad2E1Δ24:HDAdIL-12_TK_PD-L1 of 1:10. One group of mice (n=5) was then injected intraperitoneally on days 2, 3, 4, 5, 7, 10, 14, 17 and 21 days after CAdtrio injection with 10 mg/kg of ganciclovir.

Blood samples were collected from the mice on days 2, 7, 14 and 21 and analysed by ELISA for IL-12 expression. Tumor volumes were monitored throughout the experiment. At day 22 Onc.Ad and HDAd vector copy numbers were determined in DNA extracted from the tumors by quantitative real-time PCR analysis, and normalised using the copy number detected for GAPDH.

Figure 20A:
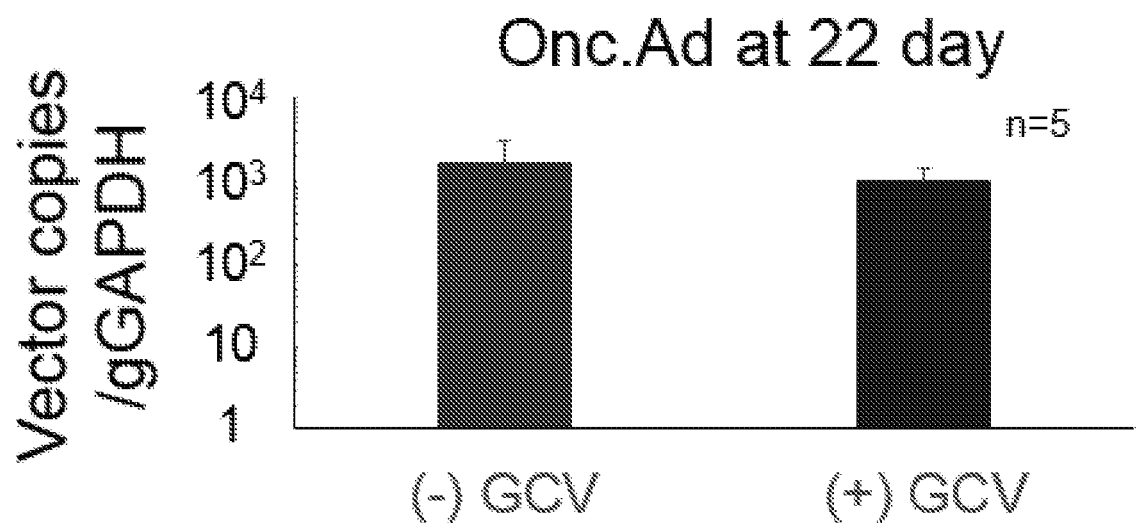
FIGS. 20A to 20D. Bar charts and graphs showing the results of in vivo analysis of the combination of Onc5/3Ad2E1Δ24 and HDAdIL-12_TK_PD-L1 and ganciclovir (GCV), in an ectoptic FaDu cell-derived model of squamous cell head and neck carcinoma.
Figure 20B:
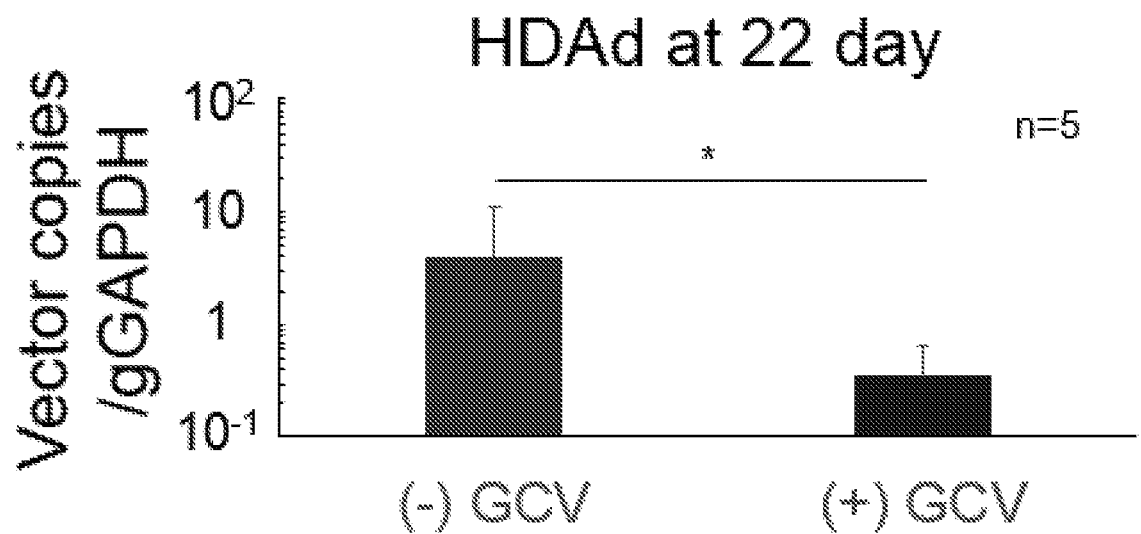
Figure 20C:
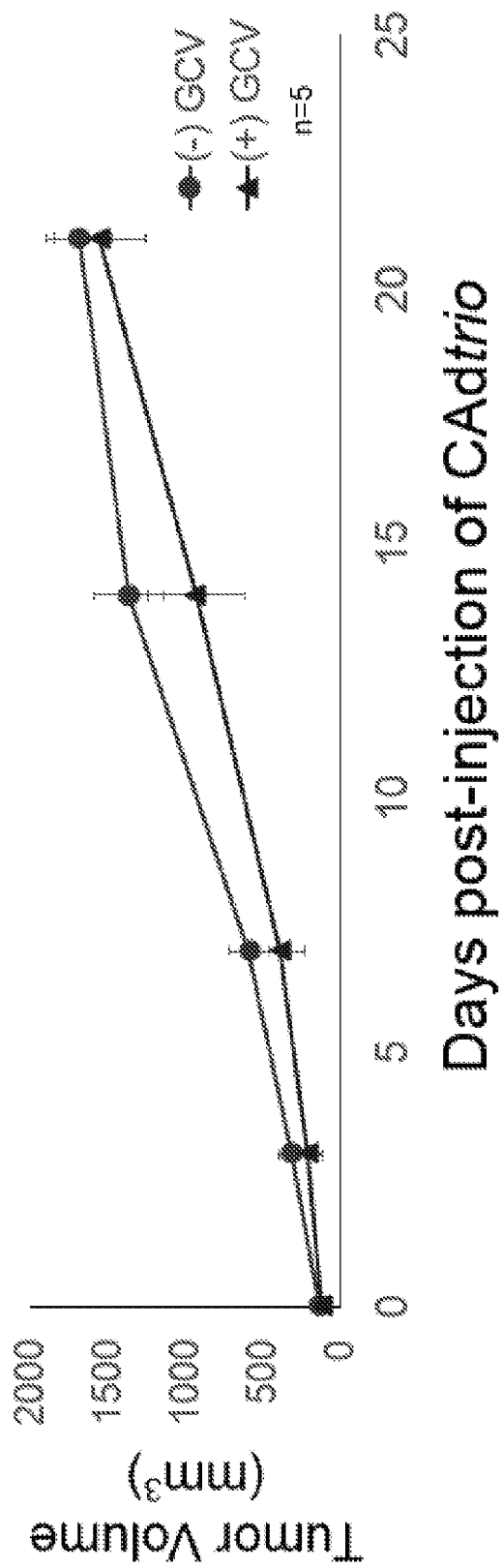
Figure 20D:
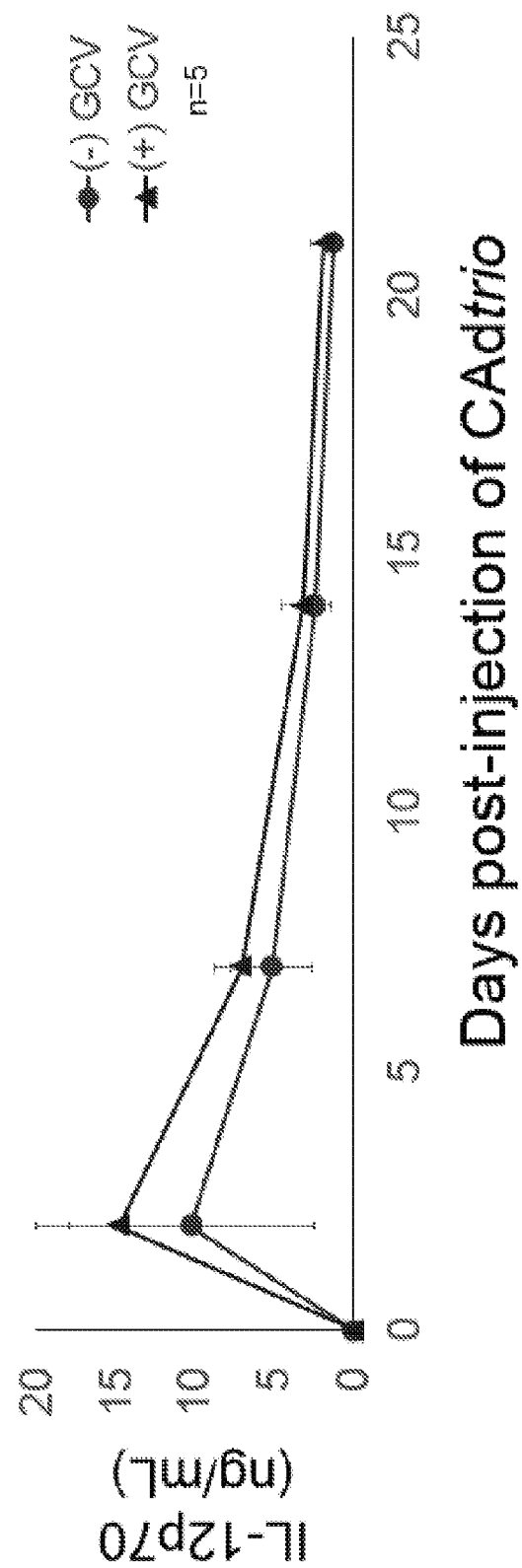

The results of the experiments are shown in FIGS. 20A to 20D. Ganciclovir (GCV) treatment did not significantly influence Onc.Ad vector copy number at day 22 (FIG. 20A), but significantly decreased HDAd vector copy number (FIG. 20B). GCV treatment was also found to improve tumor control (FIG. 20C), but did not significantly influence the levels of IL-12 in the blood (FIG. 20D).

Example 8: Generation of Oncolytic Virus-Specific T Cells and HER-Specific CAR-Expressing Oncolytic Virus-Specific T Cells

8.1 Generation and Characterisation of Oncolytic Virus-Specific T Cells

Adenovirus-specific T cells (AdVSTs) and activated T cells (ATCs) were prepared as follows.

Anti-CD3 (clone OKT3) and anti-CD28 agonist antibodies were coated onto wells of tissue culture plates by addition of 0.5 ml of 1:1000 dilution of 1 mg/ml antibodies, and incubation for 2-4 hr at 37° C., or at 4° C. overnight.

PBMCs were isolated from blood samples obtained from healthy donors according to the standard Ficoll-Paque method.

ATCs:

$1 \times 10^6$ PBMCs (in 2 ml of cell culture medium) were stimulated by culture on the anti-CD3/CD28 agonist antibody-coated plates in CTL cell culture medium (containing 50% Advanced RPMI, 50% Click's medium, 10% FBS, 1% GlutaMax, 1% Pen/Strep) supplemented with 10 ng/ml IL-7 and 5 ng/ml IL-15. The cells were maintained at 37° C. in a 5% $CO_2$ atmosphere. The next day, 1 ml of the cell culture medium was replaced with fresh CTL medium containing 20 ng/ml IL-7 and 10 ng/ml IL-15.

ATCs were maintained in culture, and subsequently harvested and used in experiments or cryopreserved between days 5-7.

AdVSTs:

$1 \times 10^6$ PBMCs (in 2 ml of cell culture medium) were stimulated by culture on the anti-CD3/CD28 agonist antibody-coated plates in CTL cell culture medium supplemented with 10 ng/ml IL-7 and 100 ng/ml IL-15.

20 μl of a 200-fold dilution of Adenovirus-specific Hexon Pepmix (JPT Cat #PM-HAdV3) or Penton PepMix (JPT Cat #PM-HAdV5) was added to the wells. The cells were maintained at 37° C. in a 5% $CO_2$ atmosphere. After 48 hours cells were fed with CTL medium, with added IL-7 and IL-15 to a final concentration of 10 ng/ml IL-7 and 100 ng/ml IL-15.

8.2 Generation of CAR-Expressing, Oncolytic Virus-Specific T Cells

On day 3, AdVSTs were resuspended at a concentration of $0.125 \times 10^6$ cells/ml in CTL cell culture medium containing 10 ng/ml IL-7 and 100 ng/ml IL-15.

Retronectin coated plates were prepared by incubation of RetroNectin (Clontech) diluted 1:100 in PBS for 2-4 hr at 37° C., or at 4° C. overnight. The wells were washed with CTL medium, 1 ml of retroviral supernatant of HER2-specific CAR retrovirus was added to wells, and plates were centrifuged at 2000 g for 1.5 hr. At the end of the centrifugation step retroviral supernatant was aspirated, and 2 ml of AdVST suspension (i.e. $0.25 \times 10^6$ cells) was added to wells of the plate. Plates were centrifuged at 400 g for 5 min, and incubated at 37° C. in a 5% $CO_2$ atmosphere.

After 48 hrs (i.e. on day 6) the cell culture medium was aspirated and replaced with CTL cell culture medium containing 10 ng/ml IL-7 and 100 ng/ml IL-15.

On day 9 cells were harvested and used in experiments or cryopreserved, or subjected to a second stimulation to expand CAR-expressing AdVSTs (see Example 8.3).

8.3 Expansion of AdVSTs and CAR-AdVSTs

AdVSTs and CAR-expressing AdVSTs were expanded by further stimulations as desired, as follows.

Pepmix-pulsed autologous ATCs were used as APCs, and K562cs cells (see e.g. Ngo et al., J Immunother. (2014) 37(4):193-203) were used as costimulatory cells. The final ratio of AdVSTs or CAR-AdVSTs:ATCs:K562cs cells in the stimulation cultures was 1:1:3-5.

AdVSTs or CAR-AdVSTs were resuspended to a concentration of $0.2 \times 10^6$ cells/ml in CTL medium.

$1 \times 10^6$ ATCs were incubated with 10 μl of 200-fold dilution of Adenovirus-specific Hexon Pepmix (JPT Cat

PM-HAdV3) or Penton PepMix (JPT Cat #PM-HAdV5) at 37° C. for 30 min. The ATCs were subsequently irradiated at 30Gy and harvested. 3-5×10⁶ K562cs cells were irradiated at 100Gy.

The ATCs and K562cs cells were then mixed in a total volume of 5 ml CTL medium, and 20 ng/ml IL-7 and 200 ng/ml IL-15 was added, 1 ml of this mixture was added to wells of a 24 well plate, and 1 ml of AdVST suspension or CAR-AdVST suspension was added to the wells.

Cells were maintained at 37° C. in a 5% $CO_2$ atmosphere. After 3-4 days cell culture medium was added as necessary, and after 6-7 days cells the expanded AdVSTs or CAR-AdVSTs were harvested for use in experiments.

Example 9: Analysis of the Anti-Cancer Activity of Combinations of Oncolytic Virus, HDAd, Oncolytic Virus-Specific T Cells and CAR-Expressing Oncolytic Virus-Specific T Cells In Vivo The anti-cancer activity of different combinations of oncolytic virus, HDAd, oncolytic virus-specific T cells and CAR-expressing oncolytic virus-specific T cells was investigated in vivo in a FaDu cell-derived xenograft model of squamous cell head and neck cancer.

Briefly, 0.5×10⁶ FaDu cells engineered to express firefly luciferase were injected orthotopically into NSG male mice. After 6 days groups of mice were injected intratumorally with:

(i) 1×10⁷ viral particles of CAdtrio, at a ratio of Onc5/3Ad2E1Δ24:HDAdIL-12_TK_PD-L1 of 1:10; or (ii) 1×10⁷ viral particles of Onc5/3Ad2E1Δ24.

Three days later, mice were injected via the tail vein with:

(a) 1×10⁶ AdVSTs, or (b) 1×10⁶ AdVSTs transduced with anti-HER2 CAR clone F1 (prepared as described in Example 8).

Prior to their use in the experiment the AdVSTs and F1.CAR-AdVSTs were characterised by flow cytometry, and the results of the analysis are shown in FIGS. 22A and 22B, and FIGS. 23A to 23C.

The cancer was monitored over time by analysis of luciferase activity as described above, and the body weight of the mice was also monitored.

The results of the experiments are shown in FIGS. 24A to 24D. The greatest level of tumor control was observed in mice treated with a combination of CAdtrio+HER2-specific CAR-expressing AdVSTs (i.e. treatment group (i)(b)).

---

The invention claimed is:

1. A method of treating a cancer, comprising administering to a subject:
   (i) an oncolytic virus;
   (ii) a helper dependent adenovirus (HDAd) comprising a nucleic acid encoding IL-12 and an antagonist anti-PD-L1 antibody; and
   (iii) at least one cell comprising a chimeric antigen receptor (CAR), wherein the CAR comprises an antigen binding domain capable of specific binding to HER2;
   wherein the cancer comprises cells expressing HER2.

2. The method according to claim 1, wherein the oncolytic virus is an oncolytic adenovirus (OncAd).

3. The method according to claim 1, wherein the oncolytic virus is derived from adenovirus 5 (Ad5).

4. The method according to claim 1, wherein the oncolytic virus encodes an E1A protein which displays reduced binding to Rb protein as compared to E1A protein encoded by Ad5.

5. The method according to claim 1, wherein the oncolytic virus encodes an E1A protein lacking the amino acid sequence LTCHEACF (SEQ ID NO:52).

6. The method according to claim 1, wherein the oncolytic virus encodes an E1A protein comprising, or consisting of, the amino acid sequence SEQ ID NO:34.

7. The method according to claim 1, wherein the at least one cell comprising a CAR is a T cell.

8. The method according to claim 1, wherein the CAR comprises an antigen binding domain comprising:

a VL domain comprising:
    LC-CDR1: SEQ ID NO:10;
    LC-CDR2: SEQ ID NO:11;
    LC-CDR3: SEQ ID NO:12;
and a VH domain comprising:
    HC-CDR1: SEQ ID NO:13;
    HC-CDR2: SEQ ID NO:14;
    HC-CDR3: SEQ ID NO:15;
or
a VL domain comprising:
    LC-CDR1: SEQ ID NO:18;
    LC-CDR2: SEQ ID NO:19;
    LC-CDR3: SEQ ID NO:20;
and a VH domain comprising:
    HC-CDR1: SEQ ID NO:21;
    HC-CDR2: SEQ ID NO:22;
    HC-CDR3: SEQ ID NO:23;
or
a VL domain comprising:
    LC-CDR1: SEQ ID NO:26;
    LC-CDR2: SEQ ID NO:27;
    LC-CDR3: SEQ ID NO:28;
and a VH domain comprising:
    HC-CDR1: SEQ ID NO:29;
    HC-CDR2: SEQ ID NO:30;
    HC-CDR3: SEQ ID NO:31;
or
a VL domain comprising:
    LC-CDR1: SEQ ID NO:57;
    LC-CDR2: SEQ ID NO:58;
    LC-CDR3: SEQ ID NO:59;

and a VH domain comprising:
HC-CDR1: SEQ ID NO:60;
HC-CDR2: SEQ ID NO:61;
HC-CDR3: SEQ ID NO:62.

9. The method according to claim 1, wherein the CAR comprises an antigen binding domain comprising:
- a VL comprising, or consisting of, an amino acid sequence having at least 75% sequence identity to SEQ ID NO:16 and a VH comprising, or consisting of, an amino acid sequence having at least 75% sequence identity to SEQ ID NO:17, and further wherein the VL comprises LC-CDR1: SEQ ID NO:10; LC-CDR2: SEQ ID NO:11; and LC-CDR3: SEQ ID NO:12; and the VH comprises HC-CDR1: SEQ ID NO:13; HC-CDR2: SEQ ID NO:14; and HC-CDR3: SEQ ID NO:15;

or
- a VL comprising, or consisting of, an amino acid sequence having at least 75% sequence identity to SEQ ID NO:24 and a VH comprising, or consisting of, an amino acid sequence having at least 75% sequence identity to SEQ ID NO:25, and further wherein the VL comprises LC-CDR1: SEQ ID NO:18; LC-CDR2: SEQ ID NO:19; and LC-CDR3: SEQ ID NO:20; and the VH comprises HC-CDR1: SEQ ID NO:21; HC-CDR2: SEQ ID NO:22; and HC-CDR3: SEQ ID NO:23;

or
- a VL comprising, or consisting of, an amino acid sequence having at least 75% sequence identity to SEQ ID NO:32 and a VH comprising, or consisting of, an amino acid sequence having at least 75% sequence identity to SEQ ID NO:33, and further wherein the VL comprises LC-CDR1: SEQ ID NO:26; LC-CDR2: SEQ ID NO:27; and LC-CDR3: SEQ ID NO:28; and the VH comprises HC-CDR1: SEQ ID NO:29; HC-CDR2: SEQ ID NO:30; and HC-CDR3: SEQ ID NO:31;

or
- a VL comprising, or consisting of, an amino acid sequence having at least 75% sequence identity to SEQ ID NO:63 and a VH comprising, or consisting of, an amino acid sequence having at least 75% sequence identity to SEQ ID NO:64, and further wherein the VL comprises LC-CDR: SEQ ID NO:57; LC-CDR2: SEQ ID NO:58; and LC-CDR3: SEQ ID NO:59; and the VH comprises HC-CDR1: SEQ ID NO:60; HC-CDR2: SEQ ID NO:61; and HC-CDR3: SEQ ID NO:62.

10. The method according to claim 1, wherein the helper dependent adenovirus comprises a nucleic acid encoding an enzyme capable of catalysing conversion of a non-toxic factor to a cytotoxic form.

11. The method according to claim 10, wherein the enzyme is selected from: thymidine kinase, cytosine deaminase, nitroreductase, cytochrome P450, carboxypeptidase G2, purine nucleoside phosphorylase, horseradish peroxidase and carboxylesterase.

12. The method according to claim 1, wherein the method of treating a cancer comprises:
  (a) isolating at least one cell from a subject;
  (b) modifying the at least one cell to express or comprise a CAR specific for a cancer cell antigen, or a nucleic acid encoding a CAR specific for a cancer cell antigen, wherein the CAR comprises an antigen binding domain capable of specific binding to HER2;
  (c) optionally expanding the modified at least one cell, and;
  (d) administering the modified at least one cell to a subject.

13. The method according to claim 1, wherein the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

* * * * *